US012188086B2

(12) United States Patent
Ju et al.

(10) Patent No.: US 12,188,086 B2
(45) Date of Patent: Jan. 7, 2025

(54) NUCLEOTIDE ANALOGUES AND USE THEREOF FOR NUCLEIC ACID SEQUENCING AND ANALYSIS PRELIMINARY CLASS

(71) Applicant: The Trustees of Columbia University in the City of New York, New York, NY (US)

(72) Inventors: Jingyue Ju, Englewood Cliffs, NJ (US); Xiaoxu Li, New York, NY (US); Shiv Kumar, Belle Mead, NJ (US); Xin Chen, Hunan (CN); James J. Russo, New York, NY (US); Minchen Chien, Tenafly, NJ (US); Steffen Jockusch, New York, NY (US); Chuanjuan Tao, Fort Lee, NJ (US); Xuanting Wang, Braintree, MA (US); Sergey Kalachikov, Bronx, NY (US); Irina Morozova, Bronx, NY (US); Shundi Shi, Ozone Park, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 238 days.

(21) Appl. No.: 16/980,708

(22) PCT Filed: Mar. 14, 2019

(86) PCT No.: PCT/US2019/022326
§ 371 (c)(1),
(2) Date: Sep. 14, 2020

(87) PCT Pub. No.: WO2019/178393
PCT Pub. Date: Sep. 19, 2019

(65) Prior Publication Data
US 2021/0139976 A1    May 13, 2021

Related U.S. Application Data

(60) Provisional application No. 62/643,633, filed on Mar. 15, 2018.

(51) Int. Cl.
*C12Q 1/68* (2018.01)
*C07H 19/00* (2006.01)
*C07H 21/04* (2006.01)
*C12Q 1/6874* (2018.01)
*C12Q 1/6876* (2018.01)

(52) U.S. Cl.
CPC .......... *C12Q 1/6874* (2013.01); *C07H 19/00* (2013.01); *C07H 21/04* (2013.01); *C12Q 1/6876* (2013.01); *C12Q 2563/107* (2013.01)

(58) Field of Classification Search
CPC .. C12Q 1/6869; C12Q 1/6874; C12Q 1/6876; C12Q 2563/107; C07H 19/00; C07H 21/04

See application file for complete search history.

(56) References Cited

U.S. PATENT DOCUMENTS

| | | |
|---|---|---|
| 5,034,036 A | 7/1991 | Summerton |
| 5,235,033 A | 8/1993 | Summerton |
| 5,804,386 A | 9/1998 | Ju |
| 5,814,454 A | 9/1998 | Ju |
| 5,876,936 A | 3/1999 | Ju |
| 5,952,180 A | 9/1999 | Ju |
| 6,046,005 A | 4/2000 | Ju et al. |
| 6,485,944 B1 | 11/2002 | Church |
| 6,627,748 B1 | 9/2003 | Ju et al. |
| 6,664,079 B2 | 12/2003 | Ju et al. |
| 7,074,597 B2 | 7/2006 | Ju |
| 7,279,563 B2 | 10/2007 | Kwiatkowski |
| 7,345,159 B2 | 3/2008 | Ju et al. |
| 7,414,116 B2 | 8/2008 | Milton |
| 7,541,444 B2 | 6/2009 | Milton |
| 7,566,537 B2 | 7/2009 | Barnes |
| 7,622,279 B2 | 11/2009 | Ju |
| 7,635,578 B2 | 12/2009 | Ju et al. |
| 7,713,698 B2 | 5/2010 | Ju et al. |
| 7,771,973 B2 | 8/2010 | Milton |
| 7,790,869 B2 | 9/2010 | Ju et al. |
| 7,883,869 B2 | 2/2011 | Ju et al. |
| 7,982,029 B2 | 7/2011 | Ju et al. |
| 8,071,739 B2 | 12/2011 | Milton |
| 8,088,575 B2 | 1/2012 | Ju et al. |
| 8,114,973 B2 | 2/2012 | Siddiqi |
| 8,298,792 B2 | 10/2012 | Ju et al. |
| 8,399,188 B2 | 3/2013 | Zhao |
| 8,597,881 B2 | 12/2013 | Milton |
| 8,796,432 B2 | 8/2014 | Ju et al. |
| 8,889,348 B2 | 11/2014 | Ju |

(Continued)

FOREIGN PATENT DOCUMENTS

| | | |
|---|---|---|
| CN | 109476694 A | 3/2019 |
| EP | 2876166 | 5/2015 |

(Continued)

OTHER PUBLICATIONS

International Search Report issued Aug. 22, 2019 in connection with PCT International Application No. PCT/US2019/022326.
Notification of Transmittal of the International Search Report and the Written Opinion of the International Searching Authority, or the Declaration issued Aug. 22, 2019 in connection with PCT International Application No. PCT/US2019/022326.
Written Opinion (form PCT/ISA/237) issued Aug. 22, 2019 in connection with PCT International Application No. PCT/US2019/022326.

(Continued)

*Primary Examiner* — Jezia Riley
(74) *Attorney, Agent, or Firm* — Gary J. Gershik

(57) ABSTRACT

The invention provides various orthogonal nucleotide analogues and methods for using combinations of said various orthogonal nucleotide analogues for sequencing by synthesis.

21 Claims, 246 Drawing Sheets

Specification includes a Sequence Listing.

(56) References Cited

U.S. PATENT DOCUMENTS

| | | |
|---|---|---|
| 8,900,810 B2 | 12/2014 | Gordon et al. |
| 9,115,163 B2 | 8/2015 | Ju et al. |
| 9,121,060 B2 | 9/2015 | Milton |
| 9,121,062 B2 | 9/2015 | Balasubramanian |
| 9,133,511 B2 | 9/2015 | Ju et al. |
| 9,169,510 B2 | 10/2015 | Ju et al. |
| 9,175,342 B2 | 11/2015 | Ju et al. |
| 9,255,292 B2 | 2/2016 | Ju et al. |
| 9,297,042 B2 | 3/2016 | Ju et al. |
| 9,388,464 B2 | 7/2016 | Milton |
| 9,410,200 B2 | 8/2016 | Balasubramanian |
| 9,453,258 B2 | 9/2016 | Kain et al. |
| 9,528,151 B2 | 12/2016 | Ju et al. |
| 9,593,373 B2 | 3/2017 | Liu |
| 9,624,539 B2 | 4/2017 | Ju et al. |
| 9,670,539 B2 | 6/2017 | Ju et al. |
| 9,708,358 B2 | 7/2017 | Ju et al. |
| 9,718,852 B2 | 8/2017 | Ju et al. |
| 9,719,139 B2 | 8/2017 | Ju et al. |
| 9,725,480 B2 | 8/2017 | Ju et al. |
| 9,868,985 B2 | 1/2018 | Ju et al. |
| 9,890,426 B2 | 2/2018 | Ju et al. |
| 10,000,801 B2 | 6/2018 | Ju et al. |
| 10,144,961 B2 | 12/2018 | Ju et al. |
| 10,190,157 B2 | 1/2019 | Wu |
| 10,240,195 B2 | 3/2019 | Fuller et al. |
| 10,246,479 B2 | 4/2019 | Ju et al. |
| 10,260,094 B2 | 4/2019 | Ju et al. |
| 10,273,539 B2 | 4/2019 | Marma et al. |
| 10,301,346 B2 | 5/2019 | Marma et al. |
| 10,336,785 B2 | 7/2019 | Marma et al. |
| 11,085,076 B2 | 8/2021 | Ju et al. |
| 11,089,353 B1 | 8/2021 | Morris |
| 11,266,673 B2 | 3/2022 | Ju et al. |
| 2002/0015961 A1 | 2/2002 | Kwiatkowski |
| 2003/0027140 A1 | 2/2003 | Ju et al. |
| 2006/0003383 A1 | 1/2006 | Graham |
| 2006/0057565 A1 | 3/2006 | Ju et al. |
| 2006/0188901 A1 | 8/2006 | Barnes et al. |
| 2006/0252038 A1 | 11/2006 | Ju |
| 2007/0009980 A1 | 1/2007 | Graham |
| 2007/0219367 A1 | 9/2007 | Shchepinov |
| 2009/0047699 A1 | 2/2009 | Graham |
| 2011/0014611 A1 | 1/2011 | Ju |
| 2012/0142006 A1 | 6/2012 | Ju et al. |
| 2012/0156671 A1 | 6/2012 | Liu |
| 2012/0156680 A1 | 6/2012 | Ju et al. |
| 2013/0264207 A1 | 10/2013 | Ju et al. |
| 2013/0280700 A1 | 10/2013 | Ju et al. |
| 2015/0037678 A1 | 2/2015 | Ju |
| 2015/0080232 A1 | 3/2015 | Ju |
| 2015/0140561 A1 | 5/2015 | Bergmann et al. |
| 2015/0197800 A1 | 7/2015 | Ju et al. |
| 2015/0368710 A1 | 12/2015 | Fuller |
| 2016/0002721 A1 | 1/2016 | Liu |
| 2016/0024570 A1 | 1/2016 | Ju et al. |
| 2016/0041179 A1 | 2/2016 | Ju et al. |
| 2016/0108382 A1 | 4/2016 | Efcavitch |
| 2016/0208313 A1 | 7/2016 | Ju et al. |
| 2016/0264612 A1 | 9/2016 | Ju et al. |
| 2016/0265048 A1 | 9/2016 | Ju et al. |
| 2016/0355541 A1 | 12/2016 | Jain |
| 2016/0369336 A1 | 12/2016 | Stupi |
| 2017/0002407 A1 | 1/2017 | Balasubramanian et al. |
| 2017/0058335 A1 | 3/2017 | Tao et al. |
| 2017/0101675 A1 | 4/2017 | Ju |
| 2017/0137869 A1 | 5/2017 | Marma et al. |
| 2017/0166961 A1 | 6/2017 | Liu |
| 2017/0211134 A1 | 7/2017 | Marma et al. |
| 2017/0283451 A1 | 10/2017 | Ju et al. |
| 2018/0073071 A1 | 3/2018 | Ju et al. |
| 2018/0112257 A1 | 4/2018 | Ju et al. |
| 2018/0201642 A1 | 7/2018 | Ju et al. |
| 2018/0208774 A1 | 7/2018 | Marma et al. |
| 2018/0274024 A1 | 9/2018 | Ju |
| 2018/0274025 A1 | 9/2018 | Marma et al. |
| 2018/0327828 A1 | 11/2018 | Ju et al. |
| 2019/0031704 A1 | 1/2019 | Ju et al. |
| 2019/0031705 A1 | 1/2019 | Ju et al. |
| 2019/0031706 A1 | 1/2019 | Ju et al. |
| 2019/0085014 A1 | 3/2019 | Ju et al. |
| 2019/0085015 A1 | 3/2019 | Ju et al. |
| 2019/0085016 A1 | 3/2019 | Ju et al. |
| 2019/0085388 A1 | 3/2019 | Ju et al. |
| 2019/0092805 A1 | 3/2019 | Ju et al. |
| 2019/0092806 A1 | 3/2019 | Ju et al. |
| 2019/0112650 A1 | 4/2019 | Ju et al. |
| 2019/0135850 A1 | 5/2019 | Ju et al. |
| 2019/0135851 A1 | 5/2019 | Ju et al. |
| 2019/0136308 A1 | 5/2019 | Ju et al. |
| 2019/0153527 A1 | 5/2019 | Ju et al. |
| 2019/0330693 A1 | 10/2019 | Liu et al. |
| 2021/0381043 A1 | 12/2021 | Ju et al. |

FOREIGN PATENT DOCUMENTS

| | | |
|---|---|---|
| EP | 3356381 A4 | 8/2018 |
| WO | WO 2002/022883 | 3/2002 |
| WO | WO 2002/029003 | 4/2002 |
| WO | WO 2008/037568 A2 | 3/2008 |
| WO | WO 2008/144315 A1 | 11/2008 |
| WO | WO 2009/054922 | 4/2009 |
| WO | WO 2012/083249 | 6/2012 |
| WO | WO 2012/162429 | 11/2012 |
| WO | WO 2013/154999 | 10/2013 |
| WO | WO 2013/191793 | 12/2013 |
| WO | WO 2014/144883 | 9/2014 |
| WO | WO 2014/144898 | 9/2014 |
| WO | WO 2015/123430 | 8/2015 |
| WO | WO 2015/148402 | 10/2015 |
| WO | WO 2016/063059 A1 | 4/2016 |
| WO | WO 2016/144973 | 9/2016 |
| WO | WO 2016/154215 | 9/2016 |
| WO | WO 2017/058953 A1 | 4/2017 |
| WO | WO 2017/079498 | 5/2017 |
| WO | WO 2017/087887 | 5/2017 |
| WO | WO 2017/176677 | 10/2017 |
| WO | WO 2017/176679 | 10/2017 |
| WO | WO 2017/176679 A1 | 10/2017 |
| WO | WO 2017/205336 | 11/2017 |
| WO | WO 2018/183538 | 10/2018 |
| WO | WO 2019/105421 A1 | 6/2019 |

OTHER PUBLICATIONS

International Preliminary Report on Patentability issued Sep. 15, 2020, including Written Opinion of the International Searching Authority issued Aug. 22, 2019, in connection with PCT International Application No. PCT/US2019/022326.

Bentley, D.R. et al. (Nov. 6, 2008). "Accurate whole human genome sequencing using reversible terminator chemistry," Nature 456(7218):53-59.

Bergen, K. et al. (Jun. 17, 2013, e-published Jun. 3, 2013). "Structures of KOD and 9°N DNA polymerases complexed with primer template duplex," Chembiochem 14(9):1058-1062.

Bergseid, M. et al. (Nov. 2000). "Small molecule-based chemical affinity system for the purification of proteins," BioTechniques 29(5):1126-1133.

Binauld, S. et al. (Mar. 14, 2013). "Acid-degradable polymers for drug delivery: a decade of innovation," Chem Commun 49(21):2082-2102.

Blackman, M.L. et al. (Oct. 15, 2008, e-published Sep. 18, 2008). "The Tetrazine ligation: fast bioconjugation based on inverse-electron-demand Diels-Alder reactivity," J Am Chem Soc 130(41):13518-13519.

Debets, M.F. et al. (Oct. 14, 2013, e-published Aug. 23, 2013). "Bioorthogonal labelling of biomolecules: new functional handles and ligation methods," Org Biomol Chem 11(38):6439-6455.

Fuller, C.W. et al. (May 10, 2016, e-published Apr. 18, 2016). "Real-time single-molecule electronic DNA sequencing by synthesis using polymer-tagged nucleotides on a nanopore array," PNAS USA 113(19):5233-5238.

(56) References Cited

OTHER PUBLICATIONS

Guillier, F. et al. (Jun. 14, 2000). "Linkers and cleavage strategies in solid-phase organic synthesis and combinatorial chemistry," Chem Rev 100(6):2091-2158.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," PNAS USA 105(27):9145-9150.

Hutter, D. et al. (Nov. 2010). "Labeled nucleoside triphosphates with reversibly terminating aminoalkoxyl groups," Nucleosides Nucleotides Nucleic Acids 29(11):879-895.

Inoue, T. et al. (Nov. 2015). "Synthesis of trifluoromethyl ethers and difluoro(methylthio)methyl ethers by the reaction of dithiocarbonates with IF5-pyridine-HF," Journal of Fluorine Chemistry 179:48-52.

Jewett, J.C. et al. (Mar. 24, 2010). "Rapid Cu-free click chemistry with readily synthesized biarylazacyclooctynones," J Am Chem Soc 132(11):3688-3690.

Ju, J. et al. (Dec. 26, 2006, e-published Dec. 14, 2006). "Four-color DNA sequencing by synthesis using cleavable fluorescent nucleotide reversible terminators," PNAS USA 103(52):19635-19640.

Kumar, S. et al. (2012, e-published Sep. 21, 2012). "PEG-labeled nucleotides and nanopore detection for single molecule DNA sequencing by synthesis," Sci Rep 2:684.

Leicher, T. et al. (Dec. 25, 1998). "Coexpression of the KCNA3B gene product with Kv1.5 leads to a novel A-type potassium channel," J Biol Chem 273(52):35095-35101.

Leriche, G. et al. (Jul. 2010). "Optimization of the Azobenzene Scaffold for Reductive Cleavage by Dithionite; Development of an Azobenzene Cleavable Linker for Proteomic Applications," Eur J Org Chem 2010(23):4360-4364.

Marcus-Sekura, C.J. et al. (Aug. 1, 1988). "Techniques for using antisense oligodeoxyribonucleotides to study gene expression," Anal Biochem 172(2):289-295.

Needleman, S.B. et al. (Mar. 1970). "A general method applicable to the search for similarities in the amino acid sequence of two proteins," J Mol Biol 48(3):443-453.

Pearson, W.R. et al. (Apr. 1988). "Improved tools for biological sequence comparison," PNAS USA 85(8):2444-2448.

Rathod, K.M. et al. (2013). "Synthesis and Antimicrobial Activity of Azo Compounds Containing m-Cresol Moiety," Chem Sci Trans 2(1): 25-28.

Rosenblum, B.B. et al. (Nov. 15, 1997). "New dye-labeled terminators for improved DNA sequencing patterns," Nucleic Acids Res 25(22):4500-4504.

Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," PNAS USA 102(17):5932-5937.

Shenoi, R.A. et al. (Sep. 12, 2012, e-published Aug. 30, 2012). "Branched multifunctional polyether polyketals: variation of ketal group structure enables unprecedented control over polymer degradation in solution and within cells," J Am Chem Soc 134(36):14945-14957.

Smith T.F. et al. (Dec. 1981). "Comparison of biosequences," Adv Appl Math 2(4):482-489.

Southworth, M.W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," PNAS USA 93(11):5281-5285.

Svagera, Z., Hanzlikova, D., Simek, P., and Husek, P. (2012) Study of disulfide reduction and alkyl chloroformate derivatization of plasma sulfur amino acids using gas chromatography-mass spectrometry. Anal. Bioanal. Chem. 402: 2953-2963.

Tang et al. Synthesis and Application of Four Fluorescence Labeled Nucleotides Through Disulfide as Reversible Terminators in DNA Sequencing by Synthesis. Chem. J. Chinese U. Nov. 2014; 35(11):2346-52, including an English language abstract.

Uhlmann, E. et al. (Jun. 1990). "Antisense oligonucleotides: a new therapeutic principle," Chemical Reviews 90(4):543-584.

Weintraub, H.M. (Jan. 1990). "Antisense RNA and DNA," Sci Am 262(1):40-46.

Wolfram Schumacher, Christof Holliger, Alexander J.B Zehnder, Wilfred R Hagen, Redox chemistry of cobalamin and iron-sulfur cofactors in the tetrachloroethene reductase of Dehalobacter restrictus, FEBS Letters, vol. 409, Issue 3, 1997, pp. 421-425, ISSN 0014-5793.

Wu, J. et al. (Oct. 16, 2007, e-published Oct. 8, 2007). "3'-O-modified nucleotides as reversible terminators for pyrosequencing," PNAS USA 104(42):16462-16467.

Zhu, Z. et al. (Aug. 25, 1994). "Directly labeled DNA probes using fluorescent nucleotides with different length linkers," Nucleic Acids Res 22(16):3418-3422.

Sep. 24, 2021 Office Action issued in connection with counterpart Chinese Application No. 201680069556.3, including English Summary thereof.

Response to Feb. 10, 2021 Communication pursuant to Article 94(3) EPC, filed Aug. 20, 2021 in connection with counterpart European Patent Application No. EP 16852516.0.

Qiu C, Kumar S, Guo J, Yu L, Guo W, Shi S, Russo JJ, Ju J. Design and synthesis of cleavable biotinylated dideoxynucleotides for DNA sequencing by matrix-assisted laser desorption/ionization time-of-flight mass spectrometry. Anal Biochem. Aug. 15, 2012;427(2):193-201. doi: 10.1016/j.ab.2012.04.021. Epub Apr. 25, 2012. PMID: 22543091.

Jul. 10, 2023 Office Action issued in connection with counterpart Chinese Application No. 201980032903.9, and a machine translation thereof. (Exhibit 1).

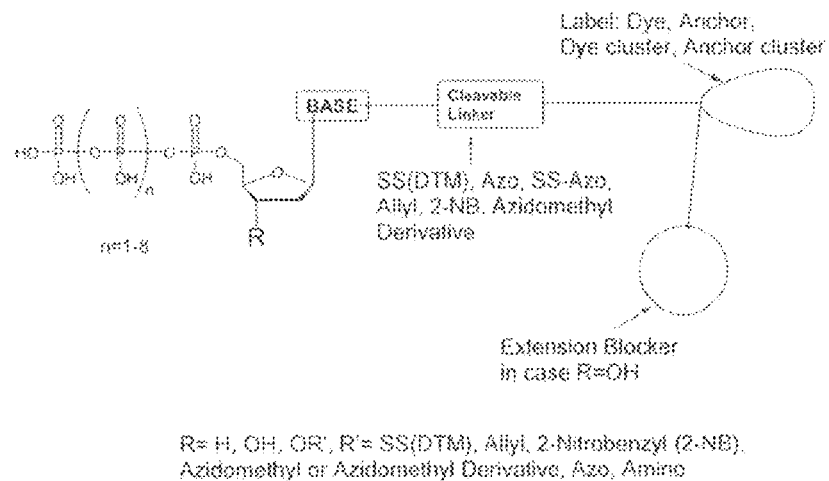
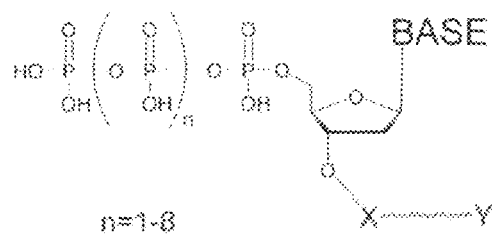
X = Cleavable Linker: SS(DTM), Azo, SS-Azo, Allyl, 2-NB, Azidomethyl Derivative
Y = Label: Dye, Dye cluster, Anchor, Anchor cluster
Fig. 1

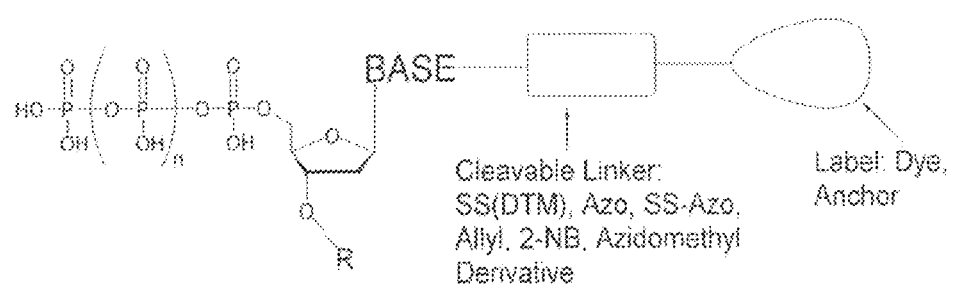
R = SS(DTM), Allyl, 2-Nitrobenzyl, Azidomethyl or Azidomethyl Derivative, Azo, Amino
n = 1-8
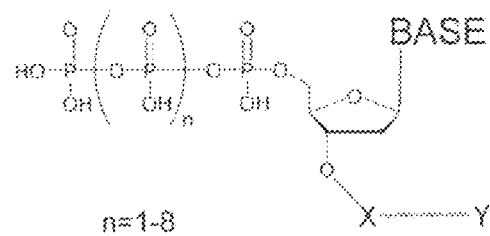
n=1-8
X = Cleavable Linker: SS(DTM), Azo, SS-Azo, Allyl, 2-NB, Azidomethyl Derivative
Y = Label, Dye, Dye cluster, Anchor, Anchor cluster
Fig. 2

X = Cleavable Trigger Moieties: SS(DTM), Azo, SS-Azo, Alkenyl, 2-NB, Azido

Y = Label: Dye, Dye cluster, Anchor, Anchor cluster

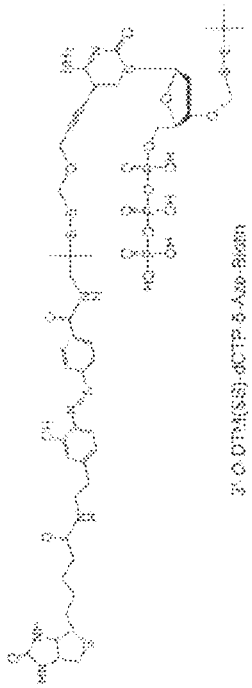
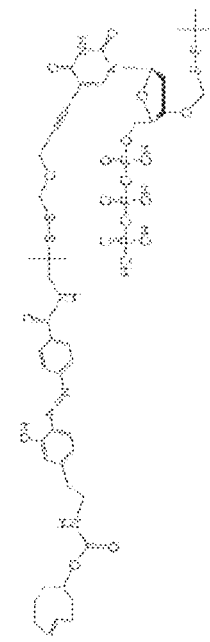
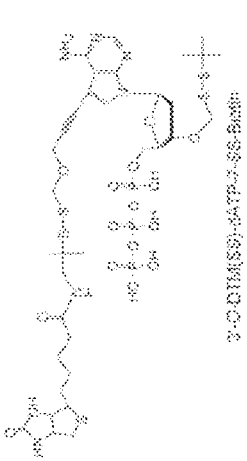
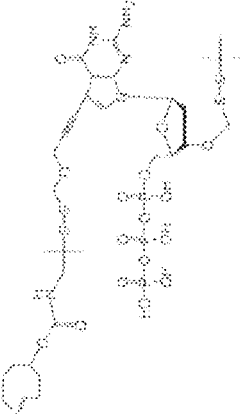
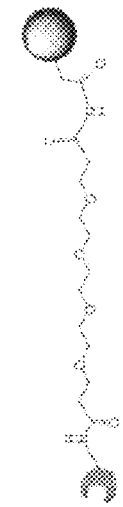
Fig. 10B

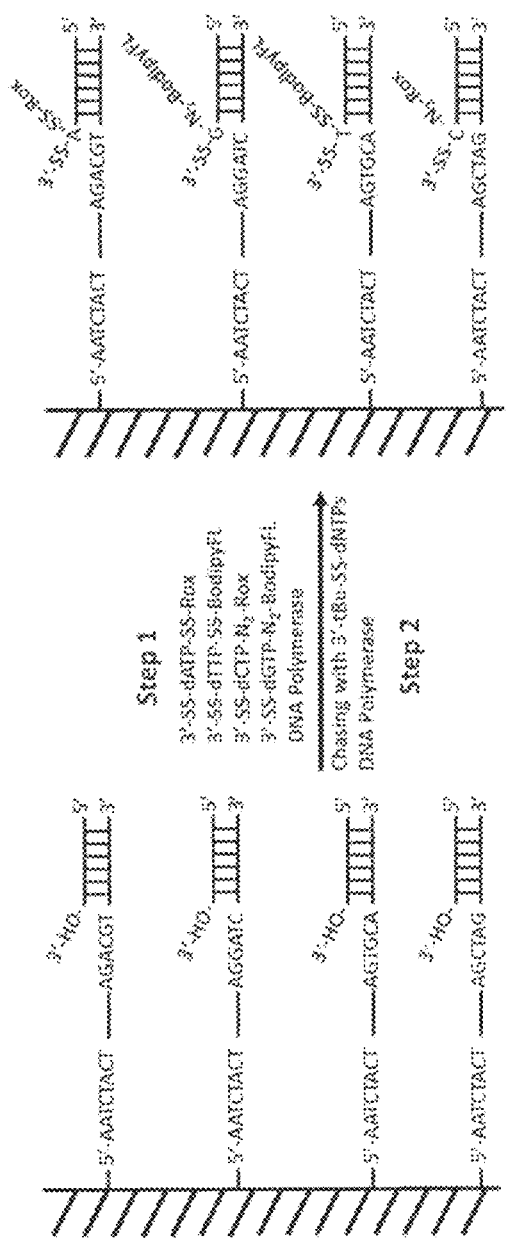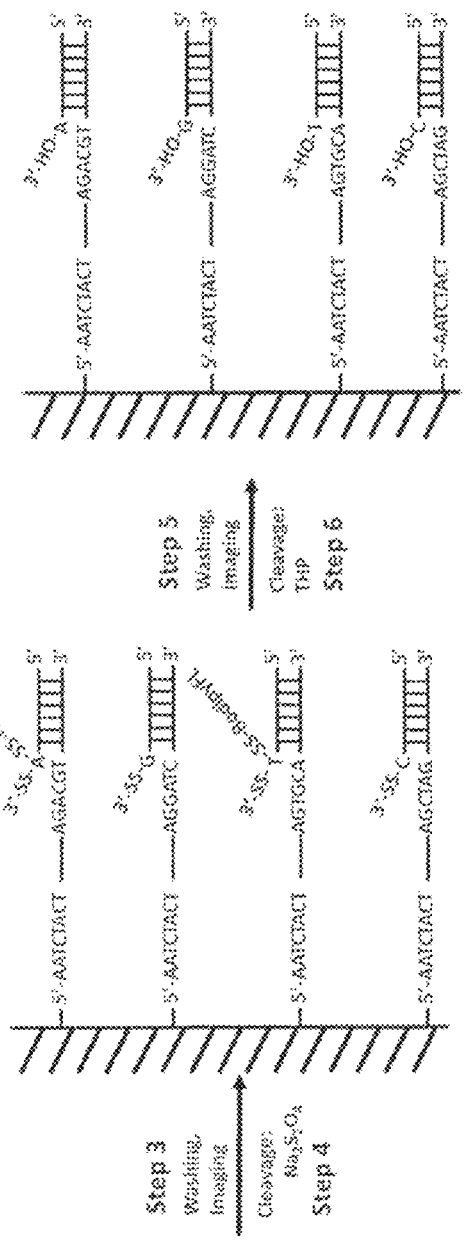
Fig. 31A
Fig. 31B

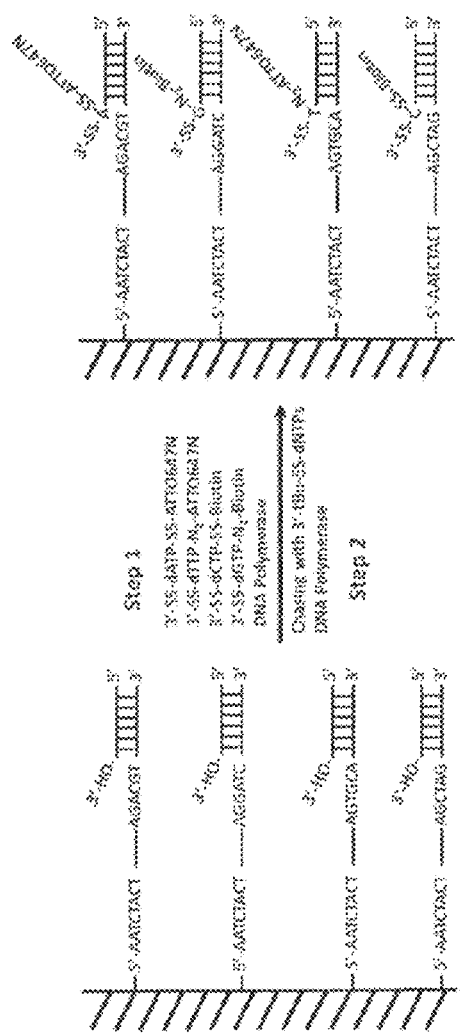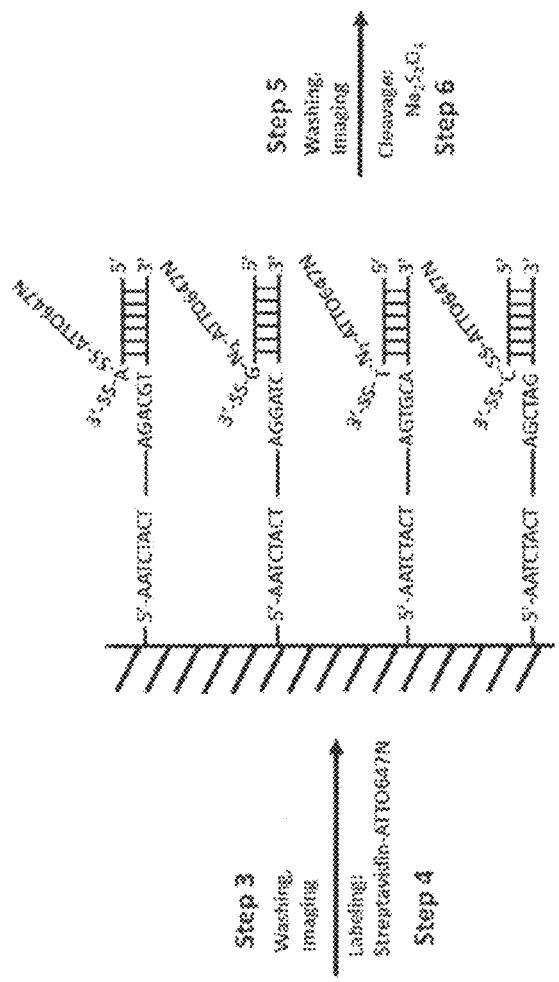
Fig. 32A
Fig. 32B

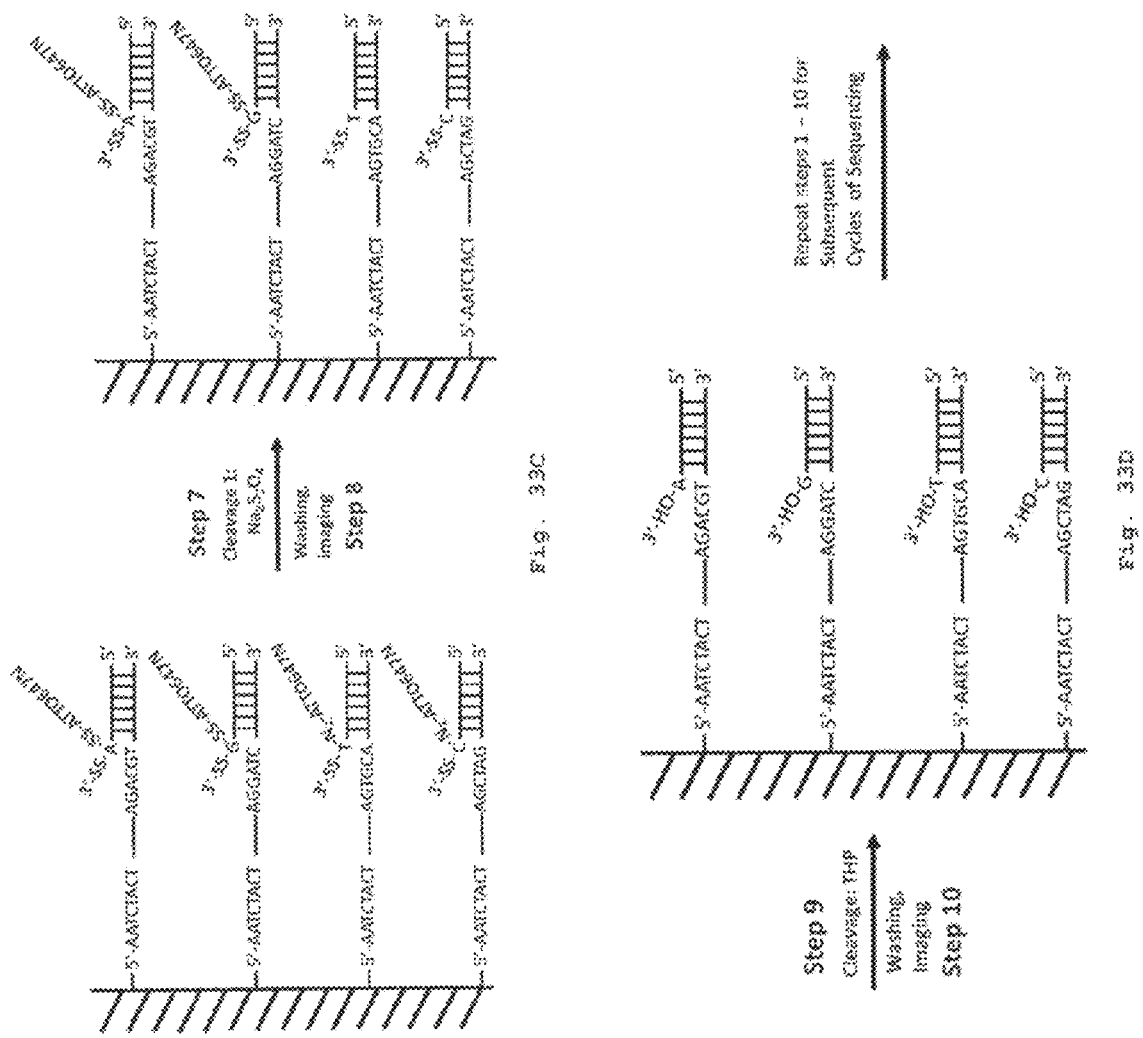

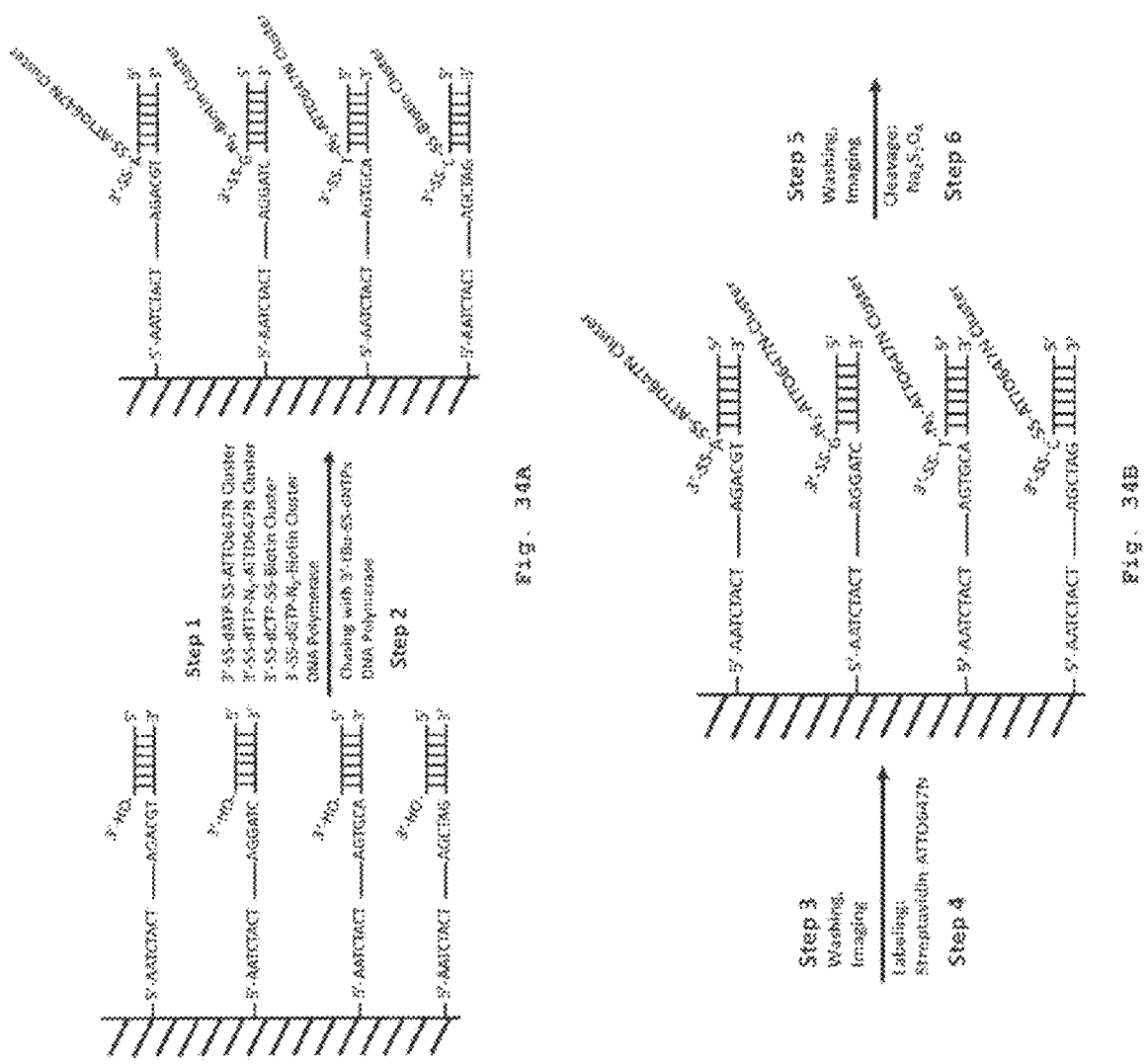

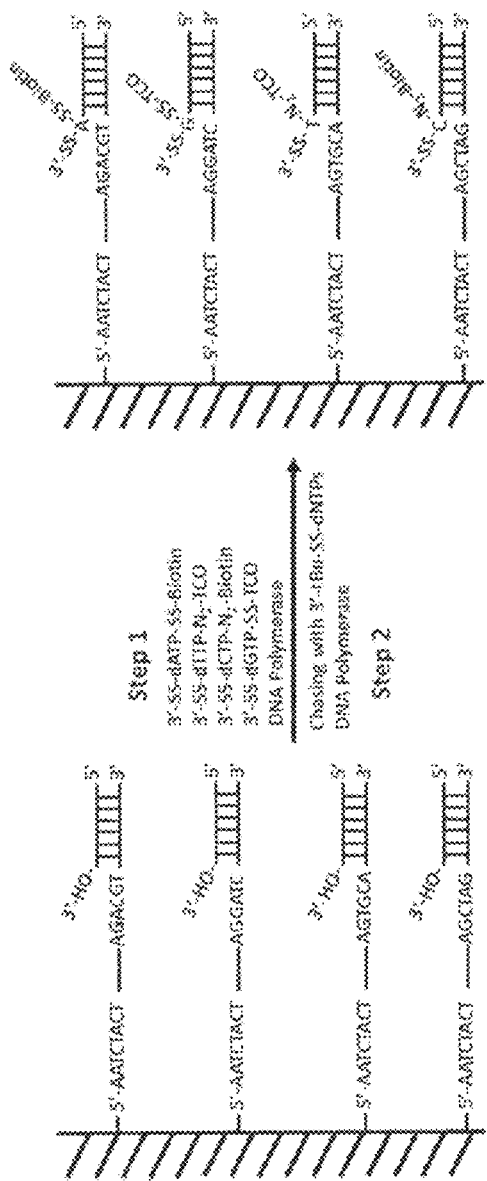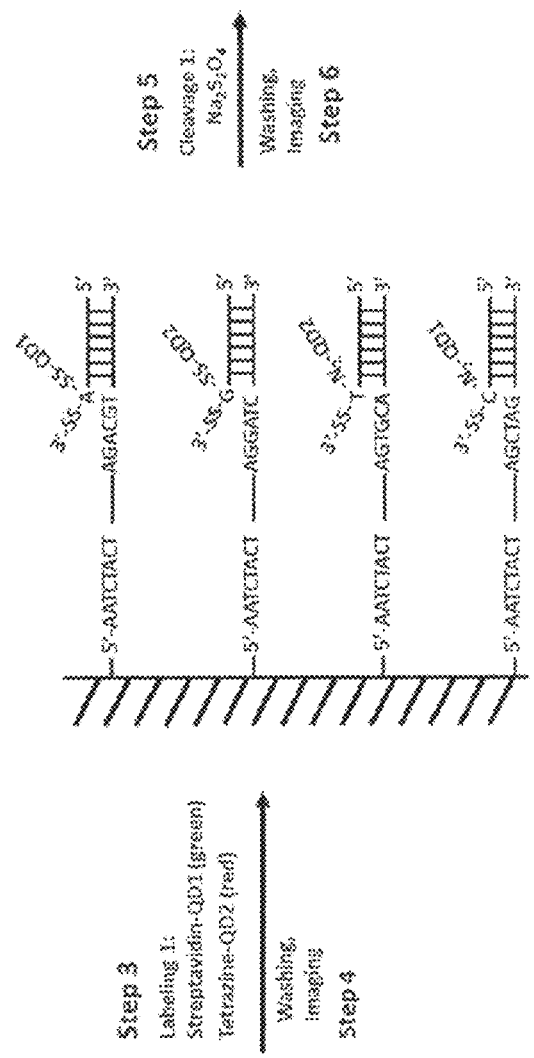
Fig. 37A
Fig. 37B

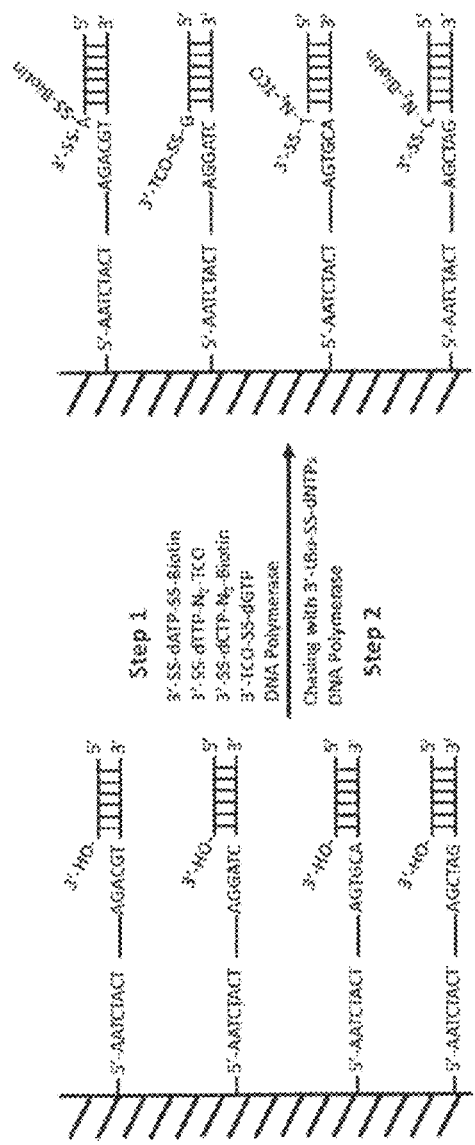
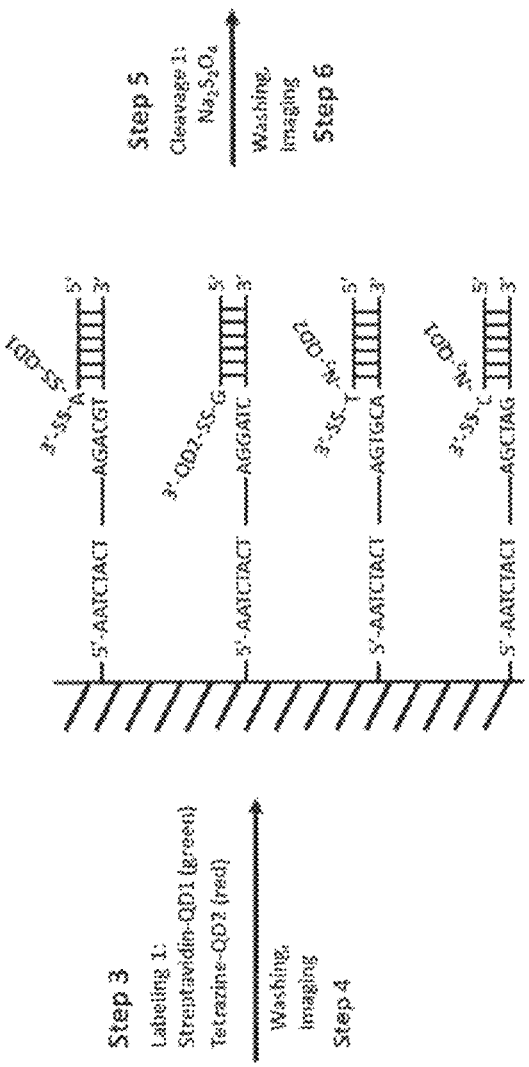
Fig. 39A
Fig. 39B

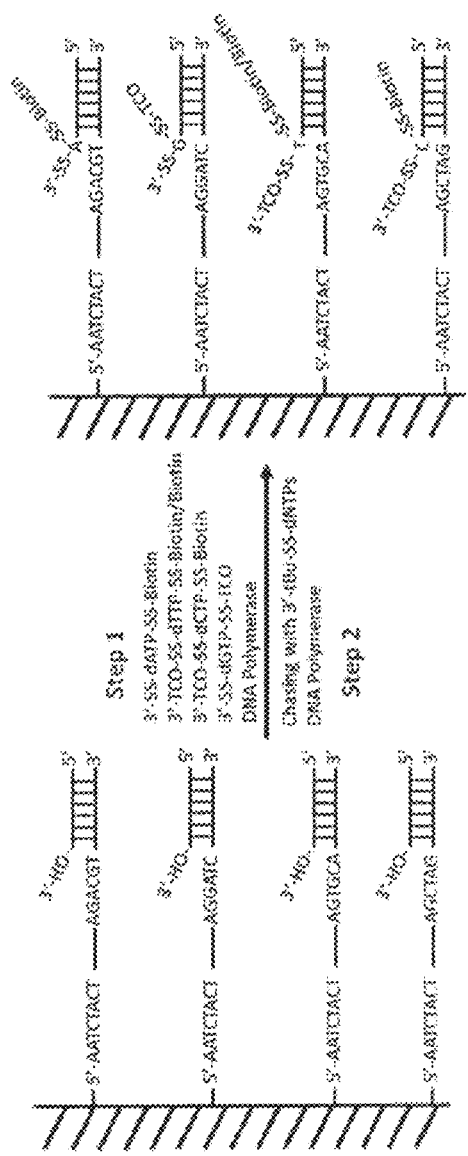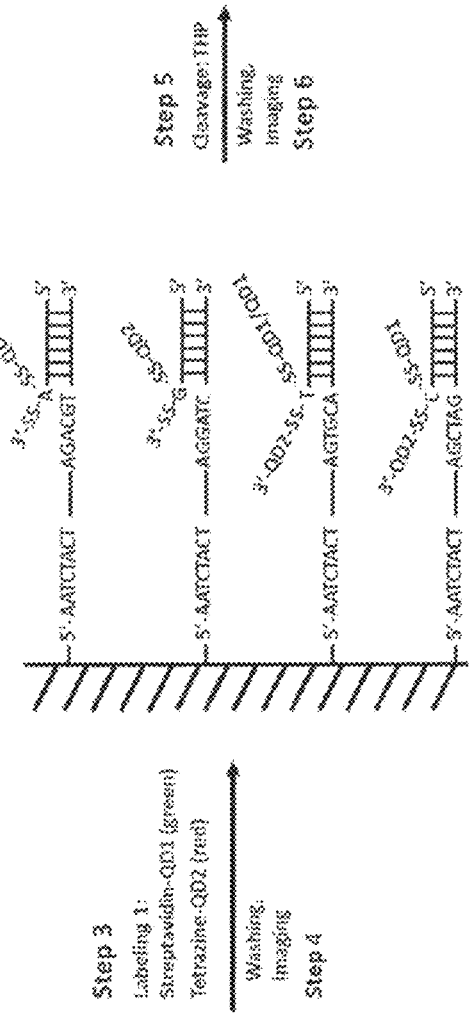
Fig. 40A
Fig. 40B

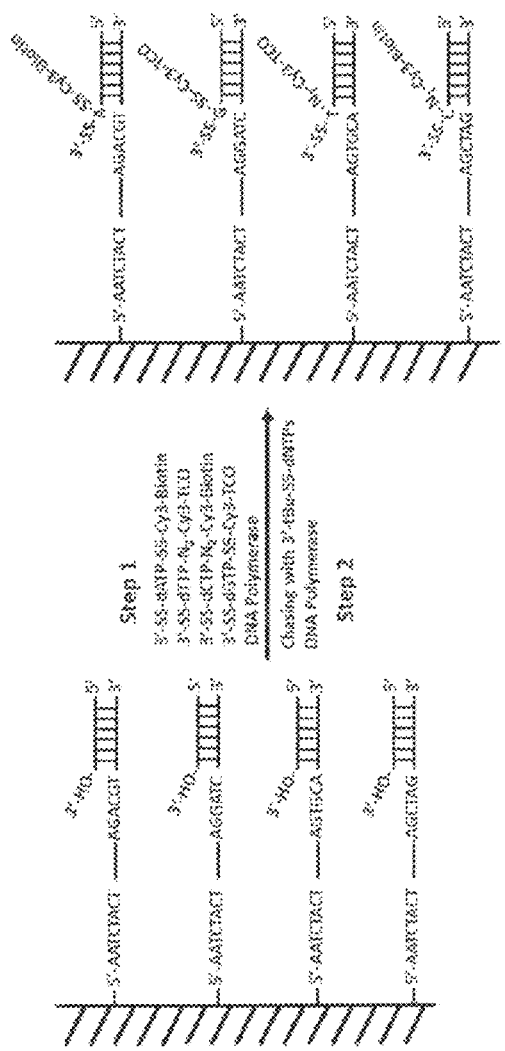
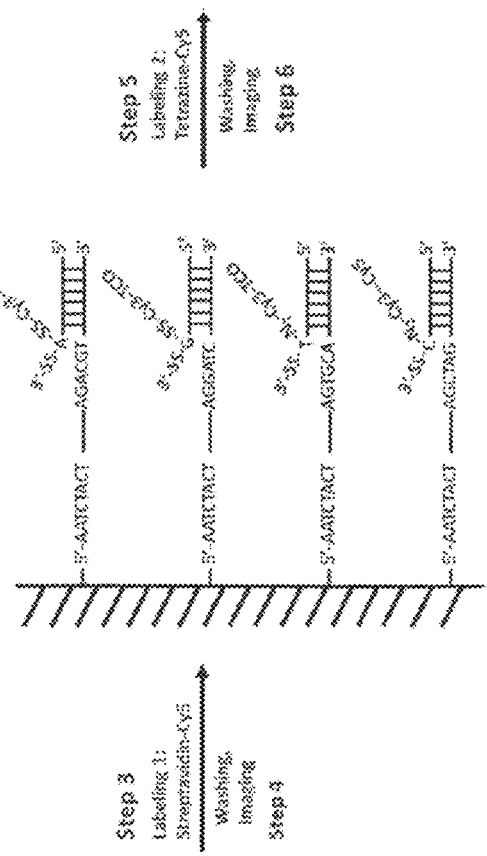
Fig. 41A
Fig. 41B

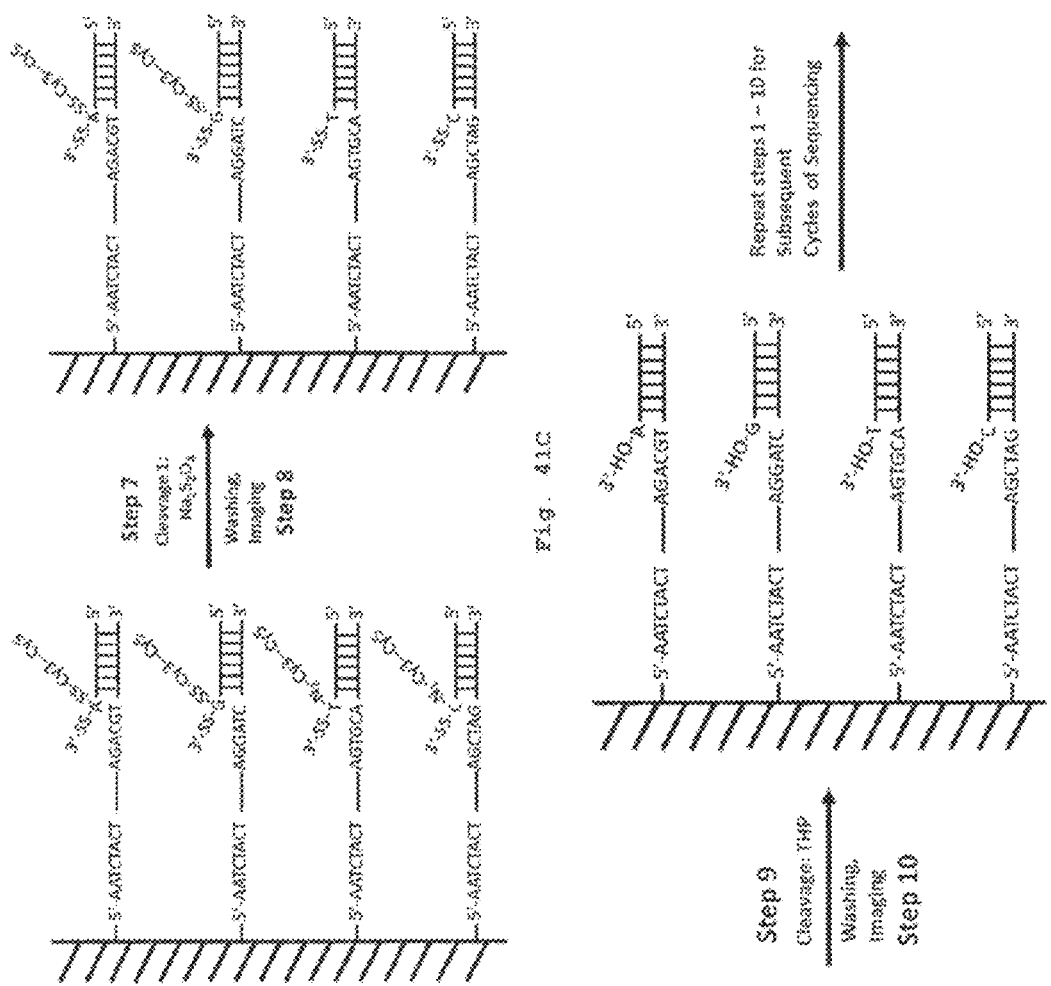

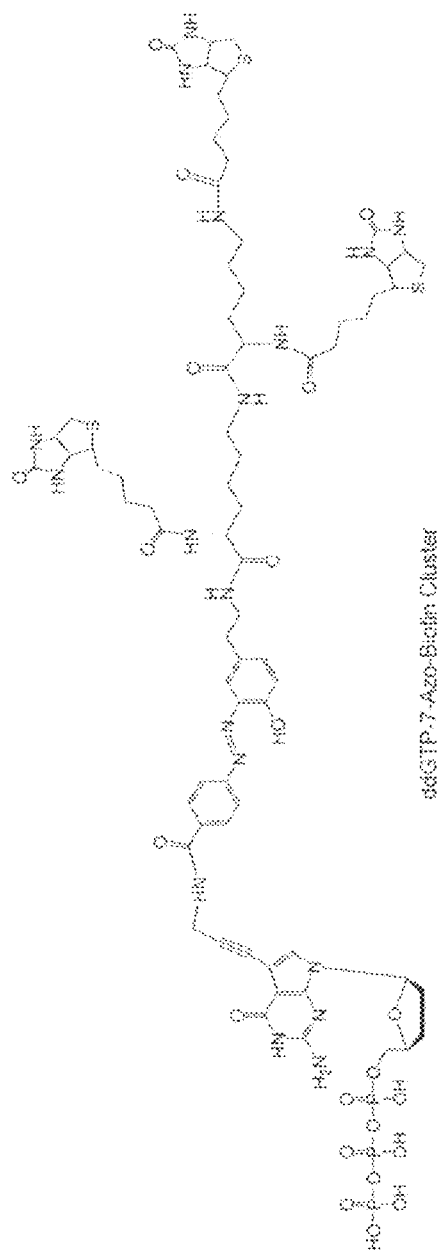
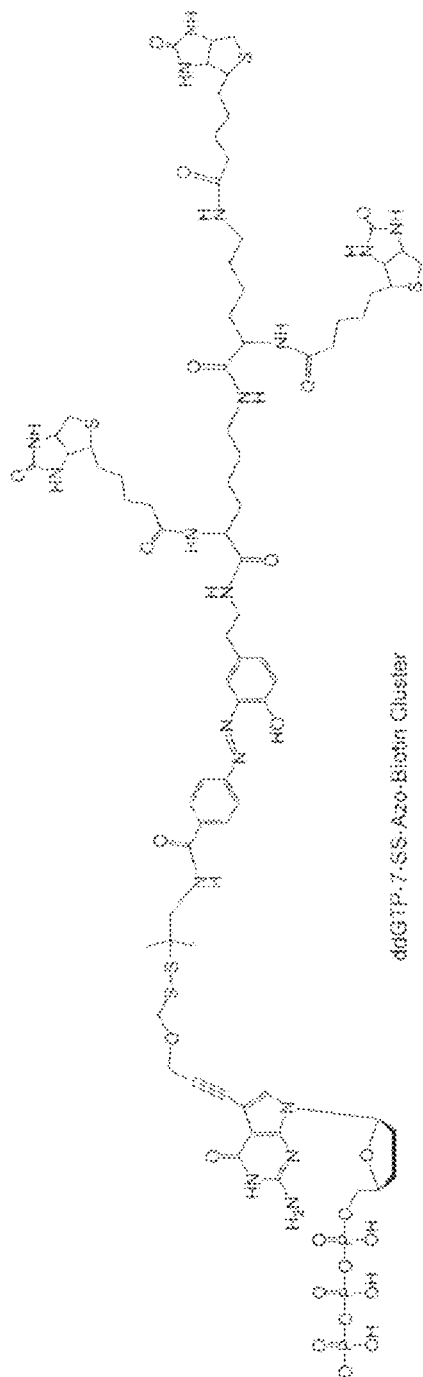
Fig. 45A

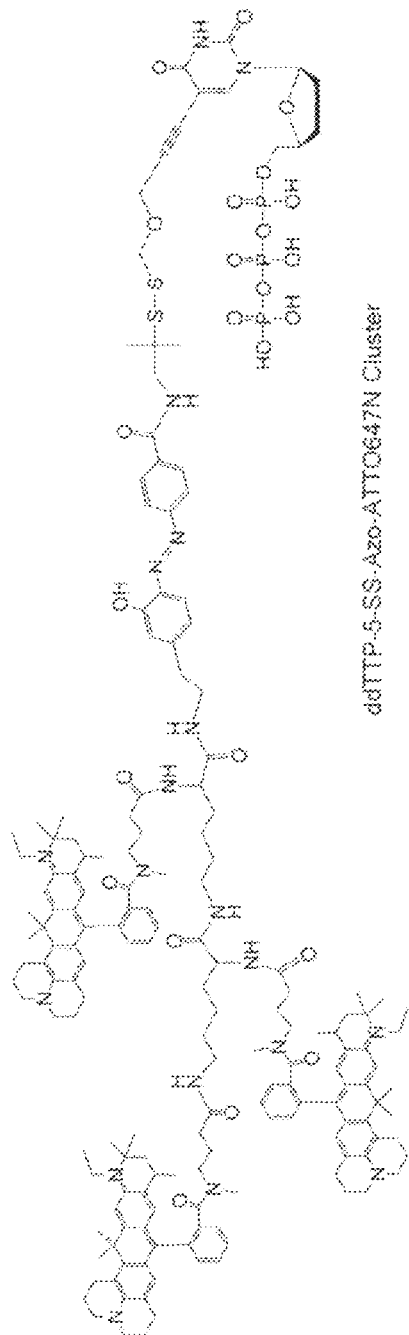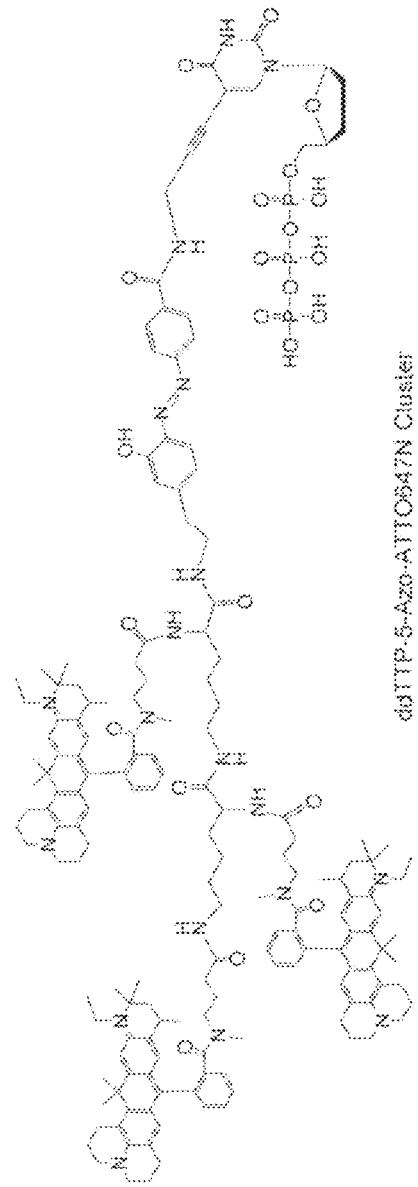
Fig. 45B

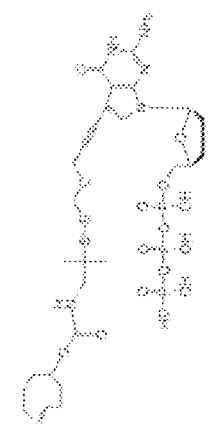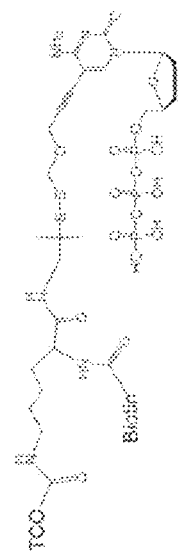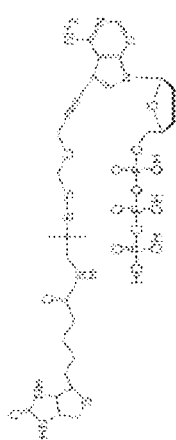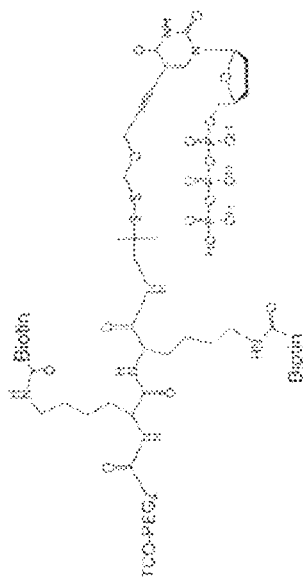
Fig. 49C

Fig. S9

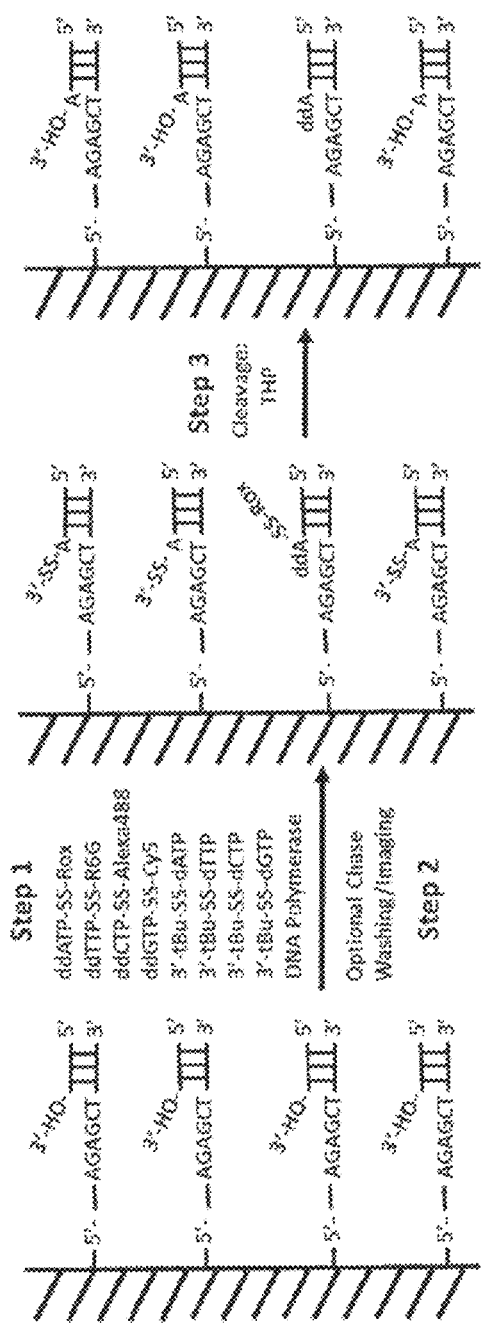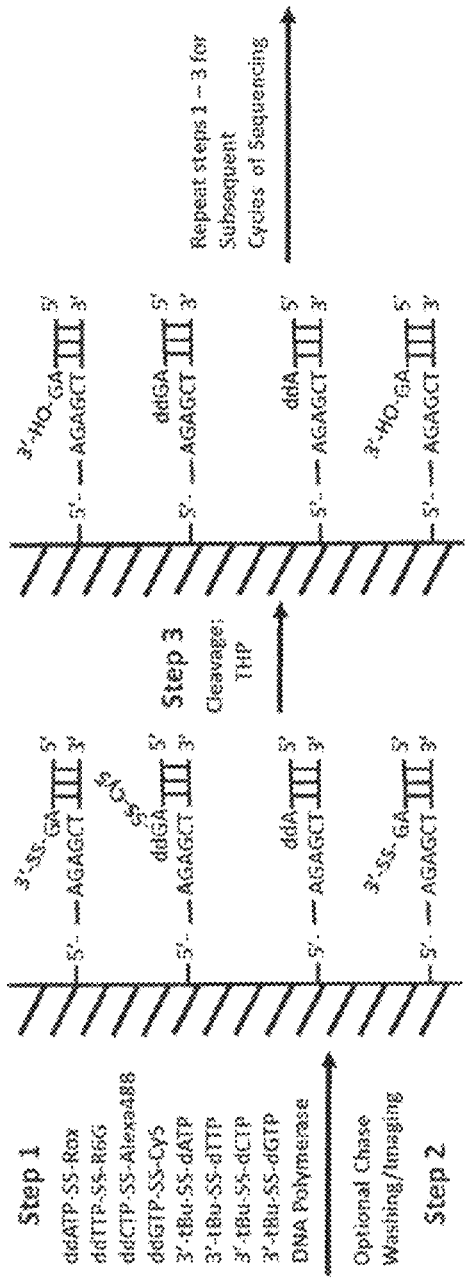
Fig. 66

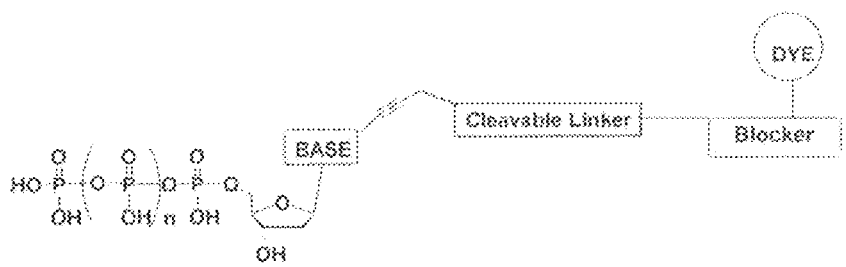

BASE= Adenine, Guanine, Cytosine, Uracil, Thymine, Hypoxanthine or Derivatives thereof Cleavable Linker= azido, disulfide, azo, allyl, or 2-nitrobenzyl Blocker= A nucleotide or a oligonucleotide consisting of 2-30 monomer units of abasic sugars or modified nucleosides or a combination thereof, which is connected to the 5-position of pyrimidines (C or U) and 7-position of deazapurines (A, G, I) via a cleavable linker Dye= A fluorescent dye or dyes attached to the Blocker n= 1-6

Cleavable Linkers:

Azido Linker 

Disulfide Linker 

Azo (N₂) Linker 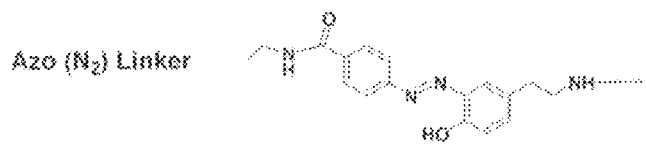

Allyl Linker 

2-Nitrobenzyl (2NB) Linker 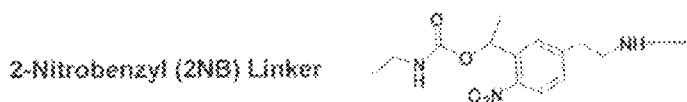

Fig. 7B

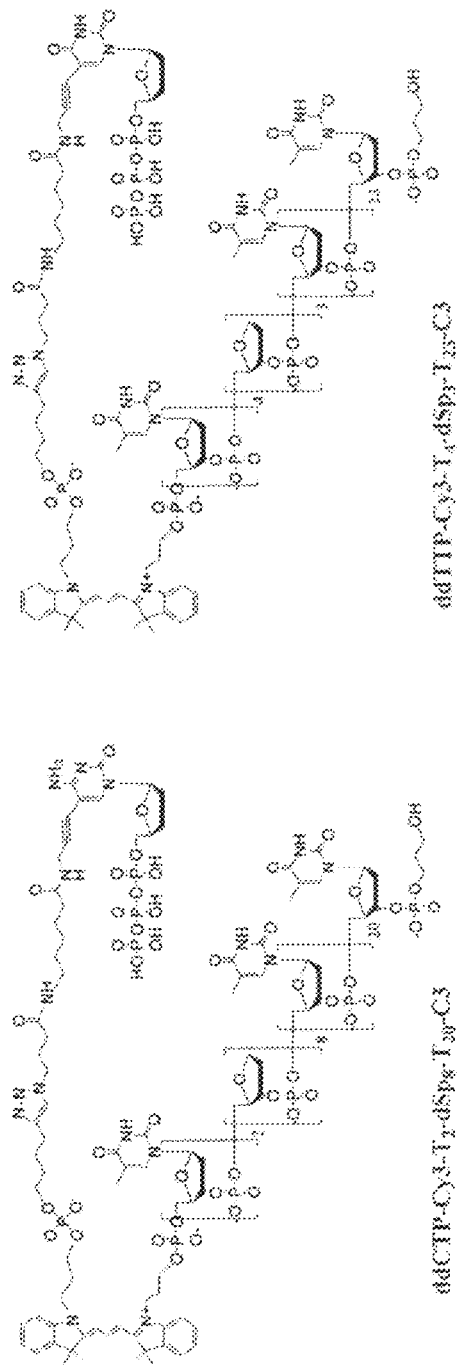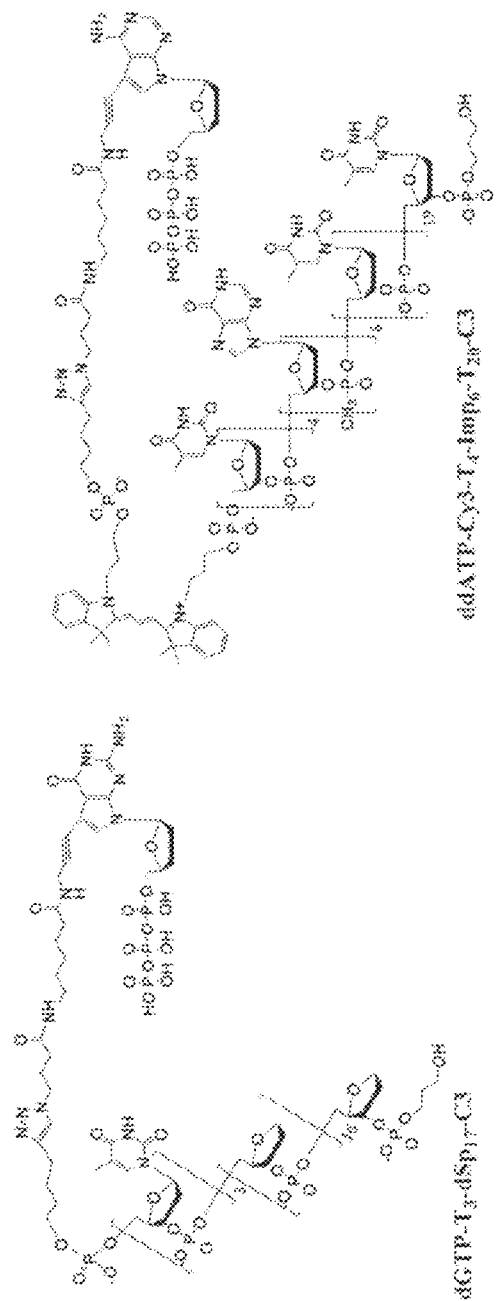
Fig. 79

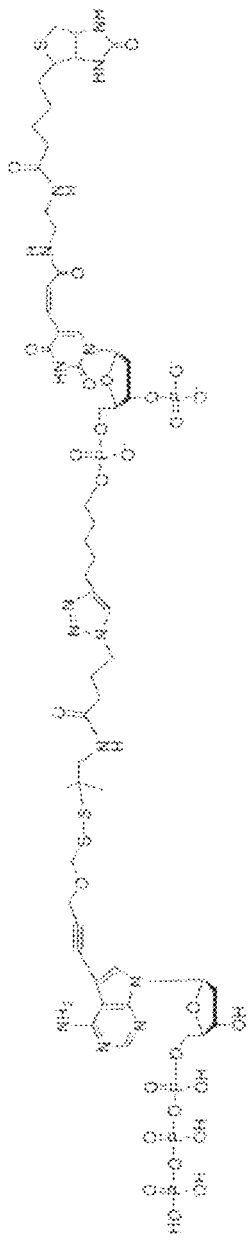
dATP-SS-Blocker-Biotin
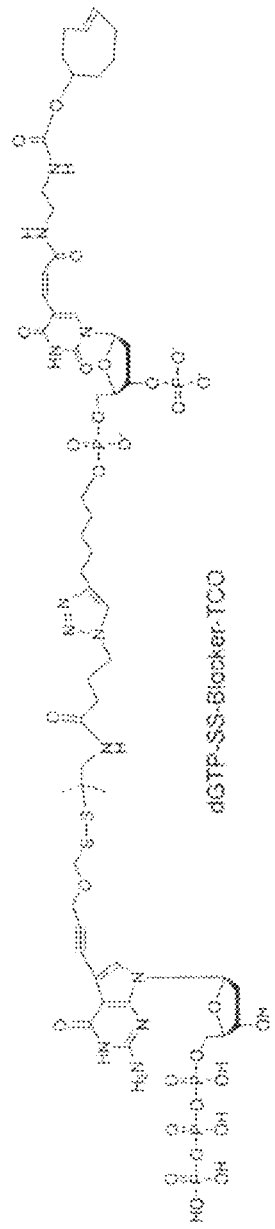
dGTP-SS-Blocker-TCO
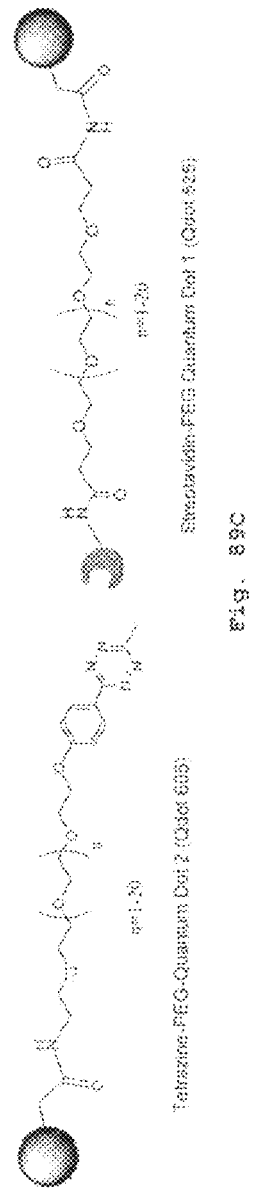
Streptavidin-PEG-Quantum Dot 1 (Qdot 525)
Tetrazine-PEG-Quantum Dot 2 (Qdot 655)
Fig. 89C

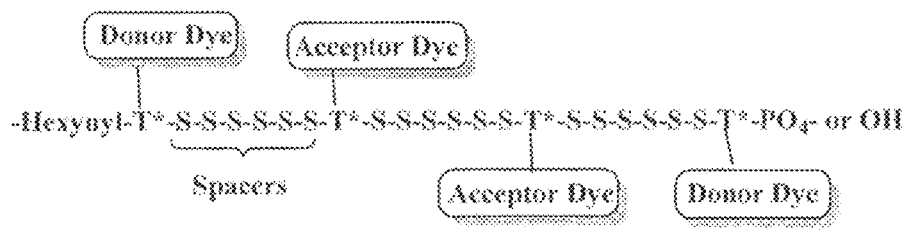
Energy Transfer dye Cassette with more than one donor and acceptor dye synthesized on a DNA synthesizer using standard phosphoramidite chemistry
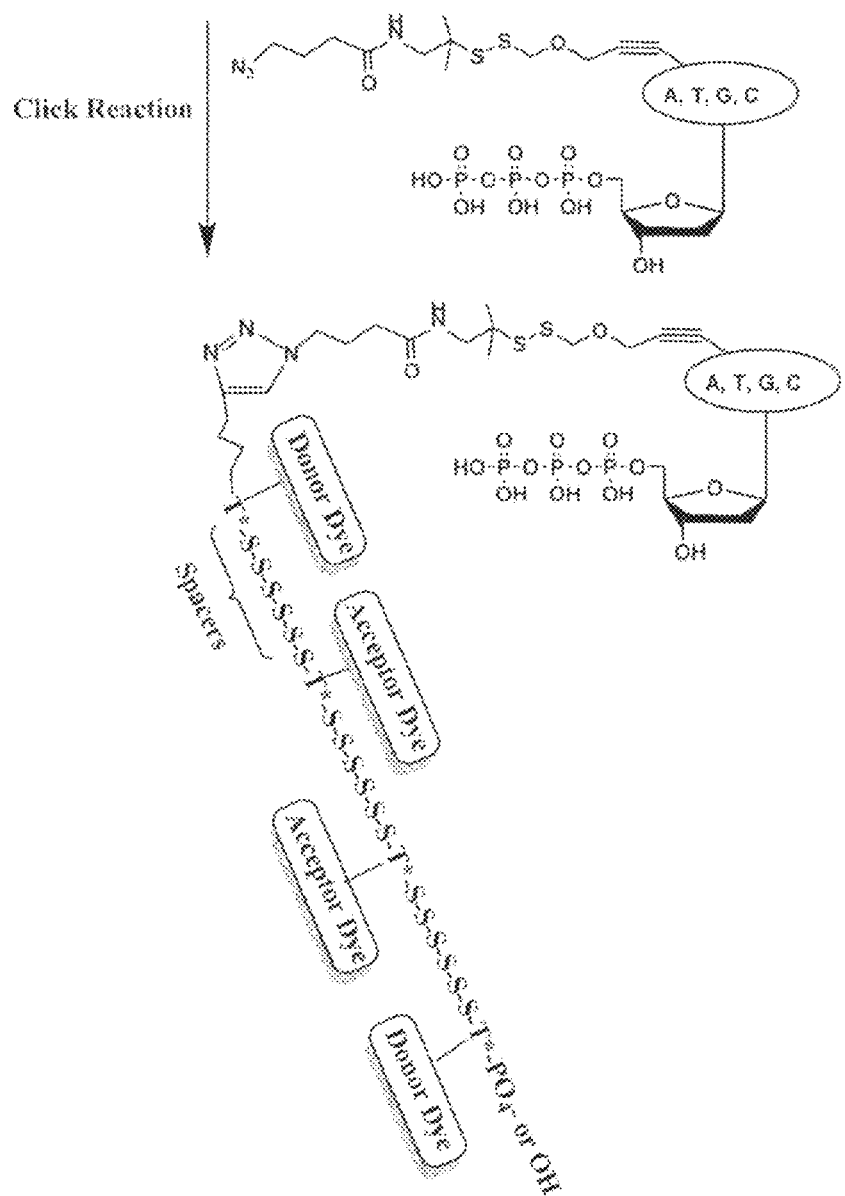
Fig. 96

1-Color / 4-Base SBS

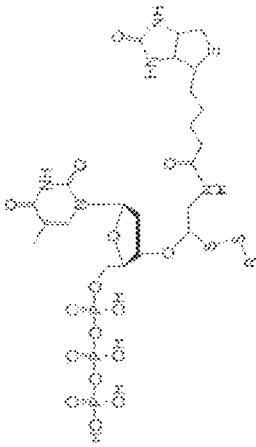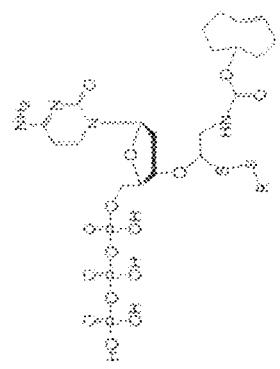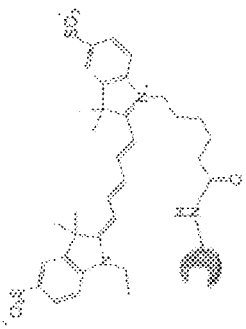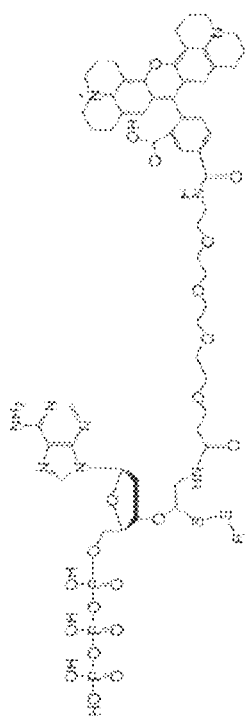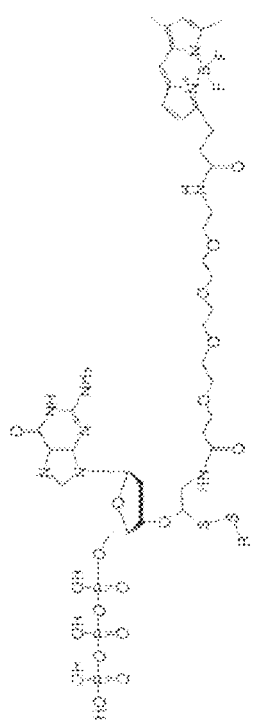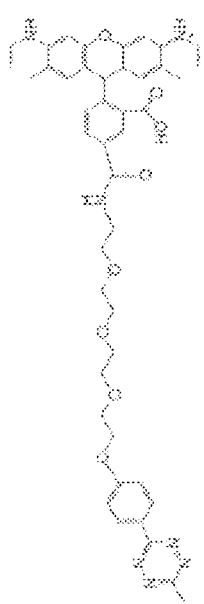
Fig. 105

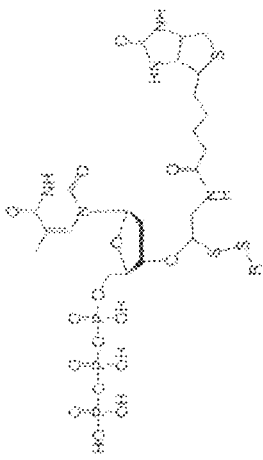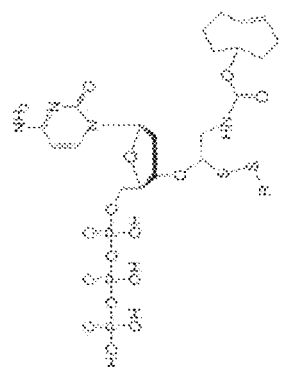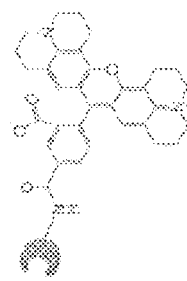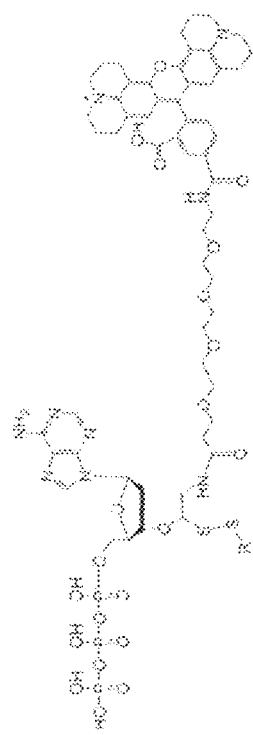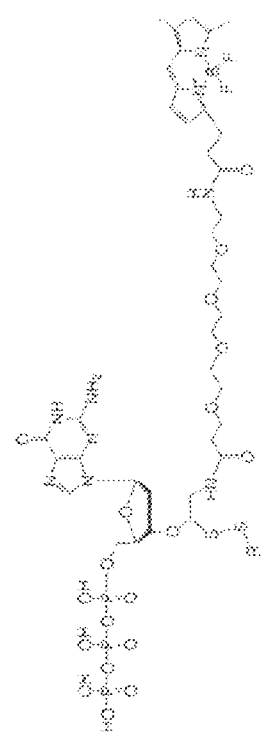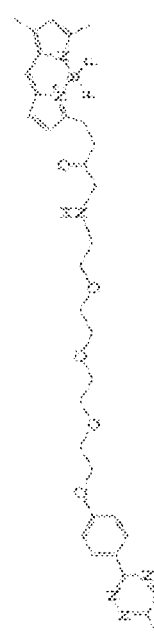
Fig. 106

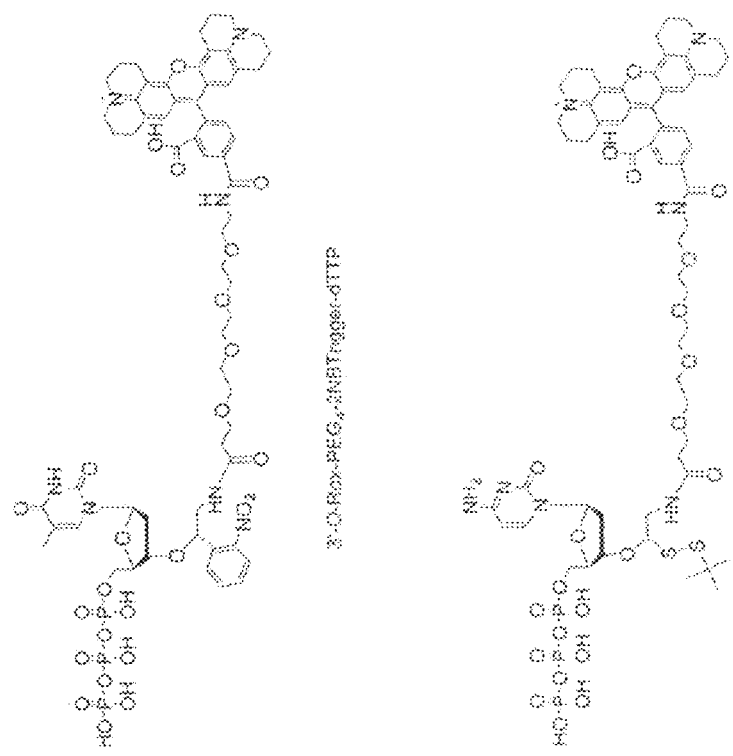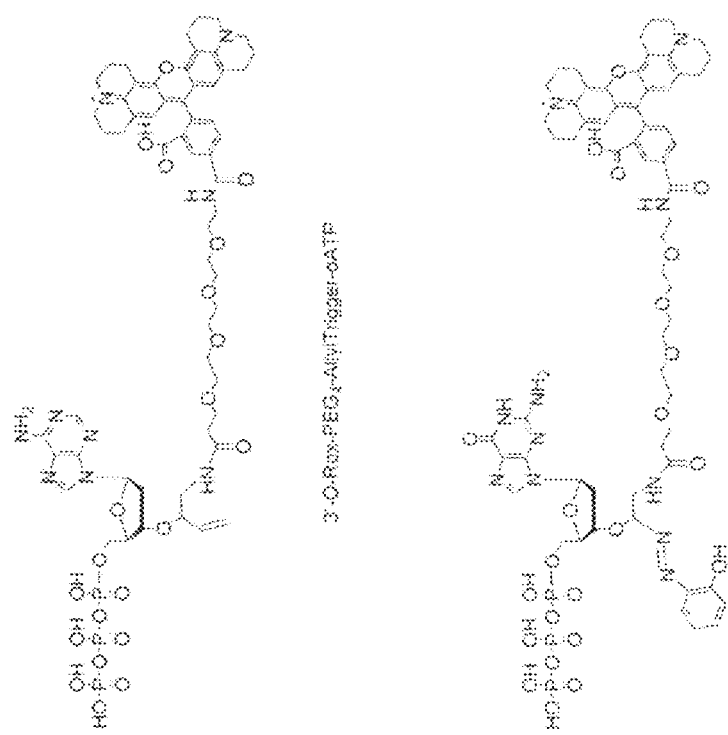
Fig. 108

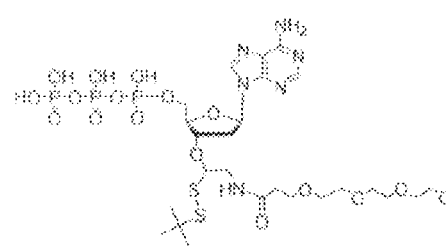
3'-O-Rox-PEG4-SSTrigger-dATP
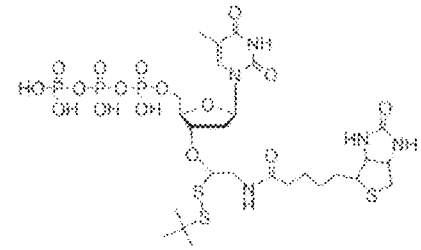
3'-O-Biotin-SSTrigger-dTTP
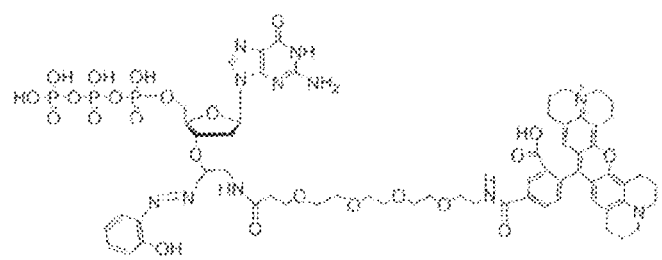
3'-O-Rox-PEG4-AzoTrigger-dGTP
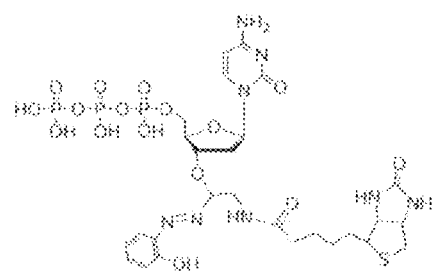
3'-O-Biotin-AzoTrigger-dCTP
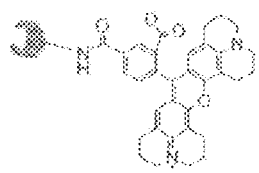
Rox Labeled Streptavidin
Fig. 109

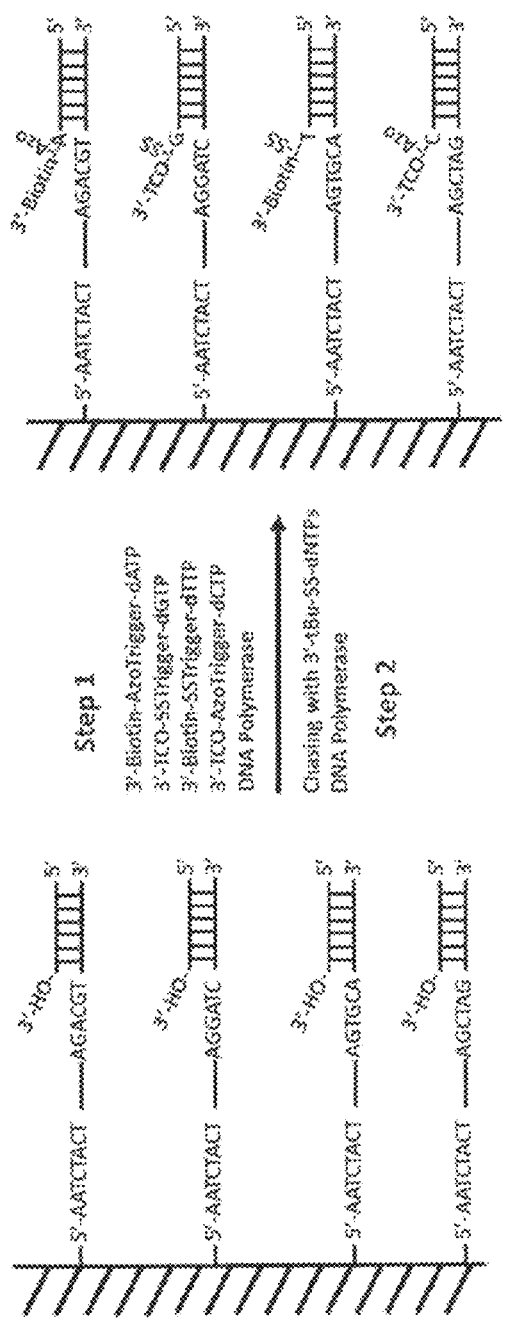
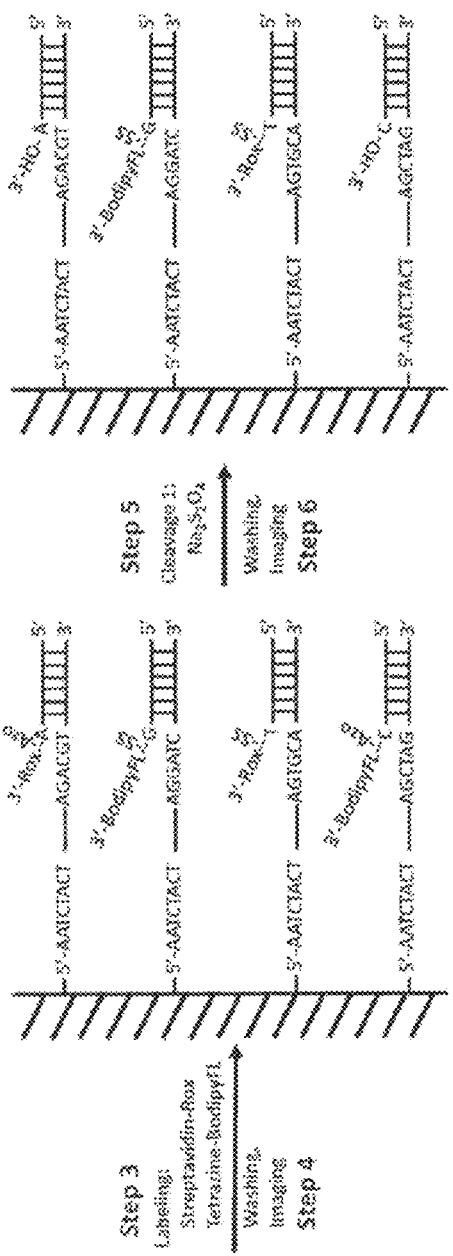
Fig. 121A
Fig. 121B

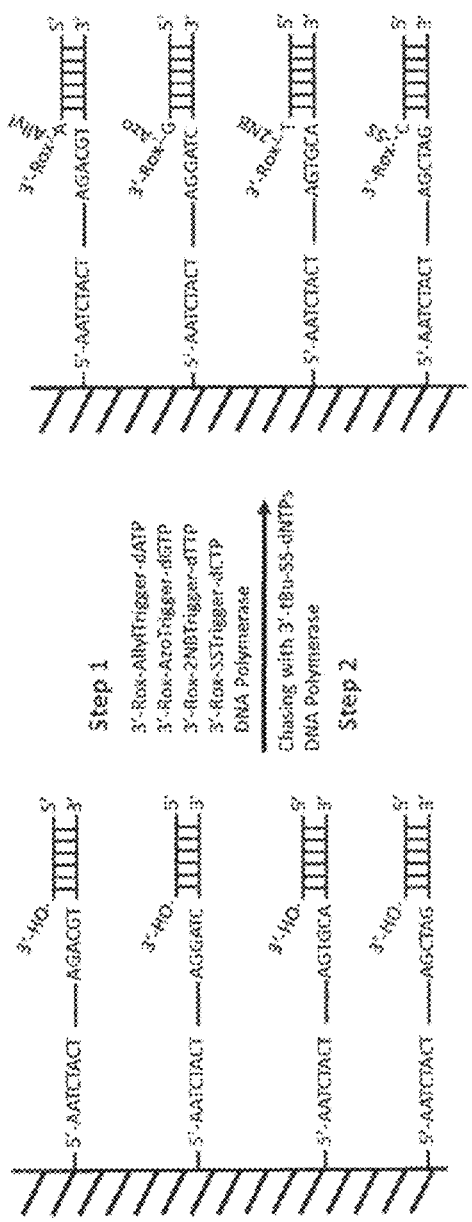
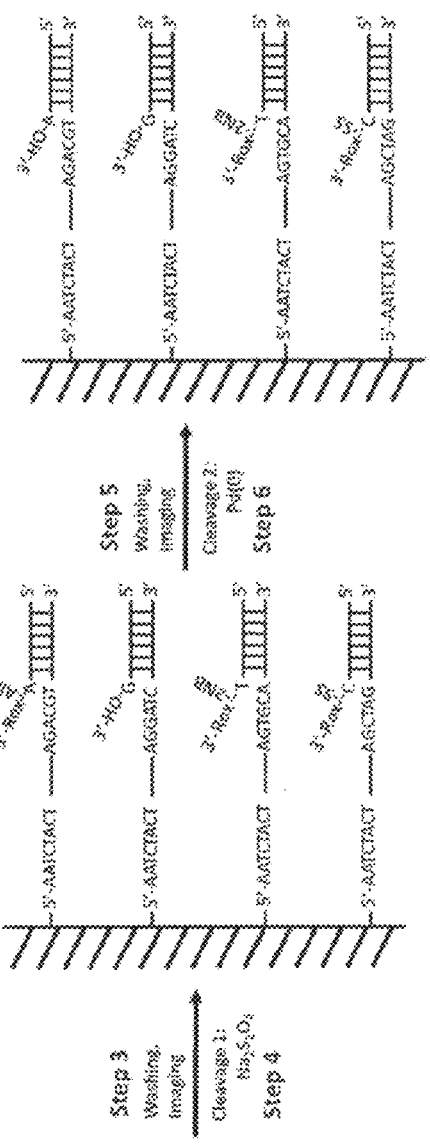
Fig. 122A
Fig. 122B

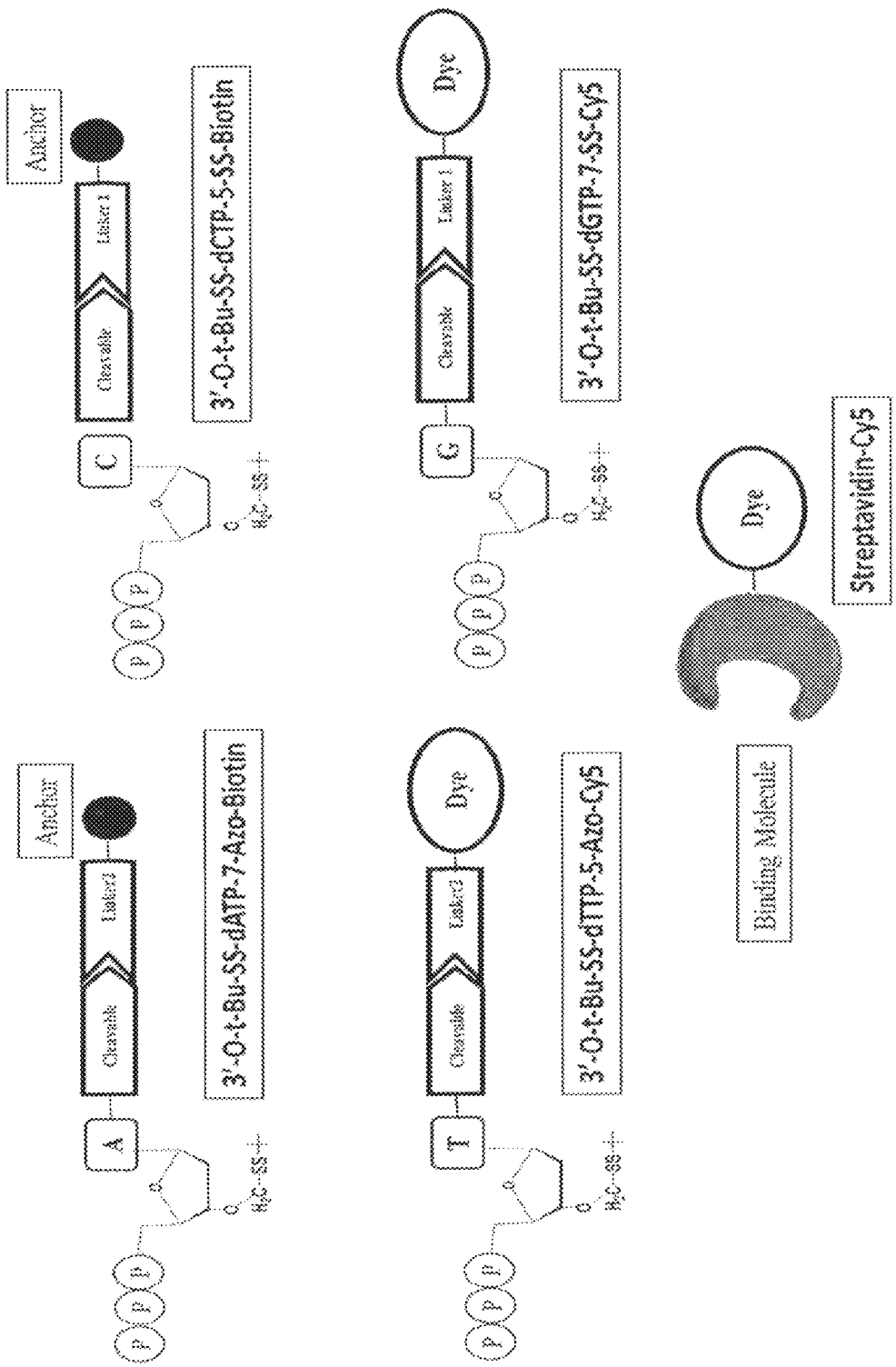

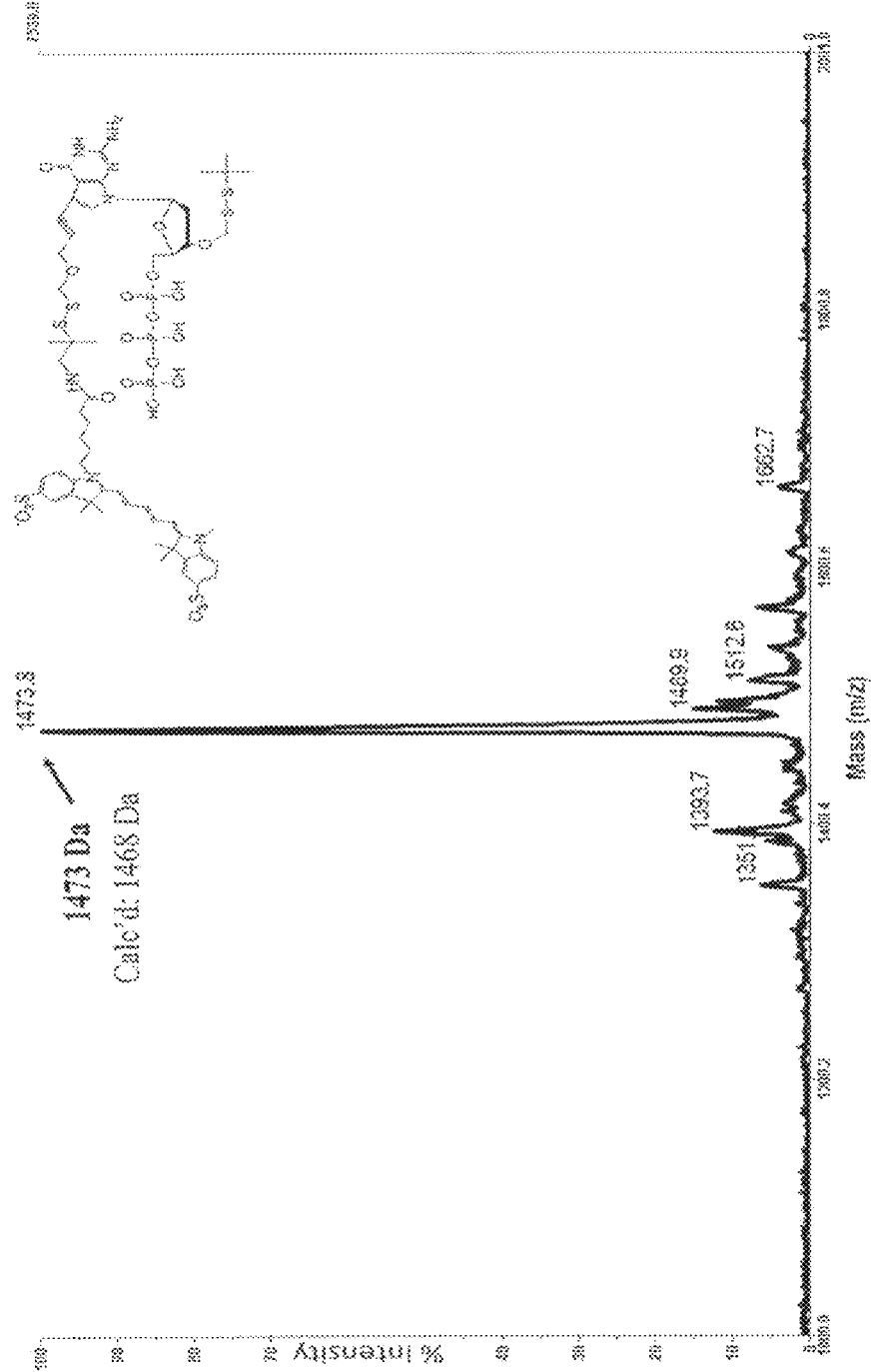

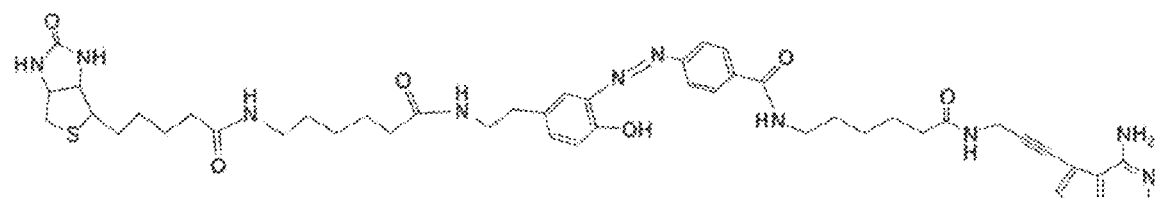
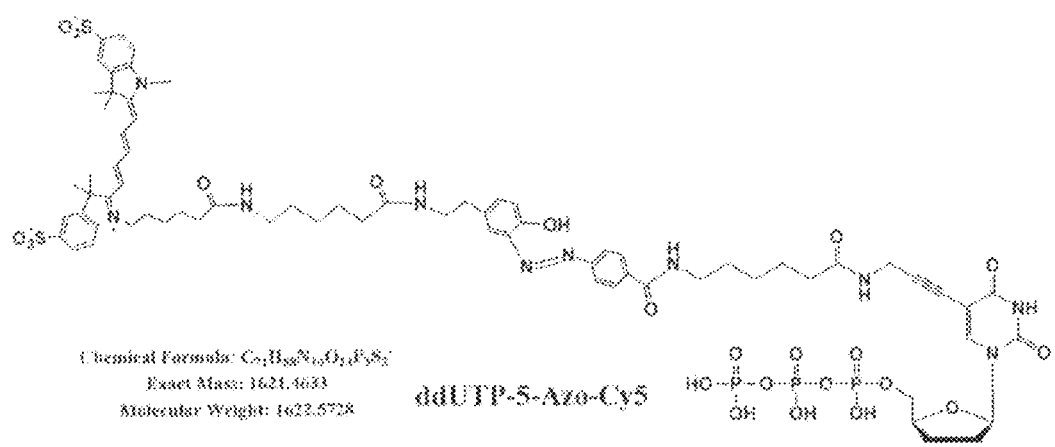
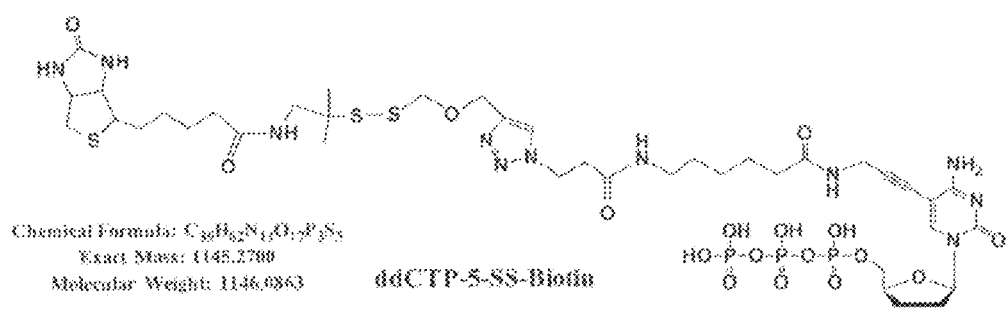
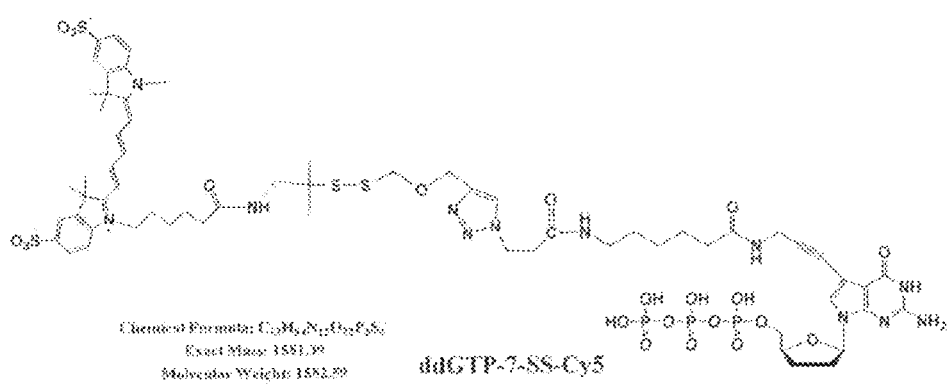
Fig. 147A

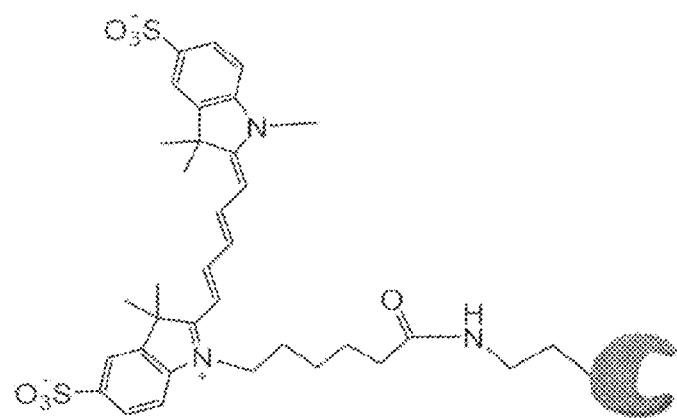
Cy5 Labeled Streptavidin
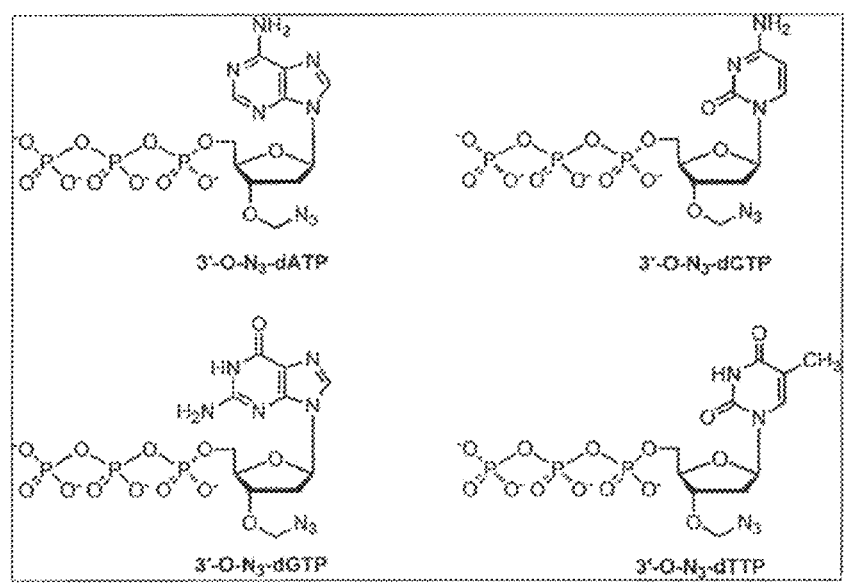
Fig. 147B

Azo-Linker NHS Ester

MALDI-TOF Mass Spectrometry shows extension result using ddCTP-SS-Biotin (M.W. 1146) And cleavage with THP
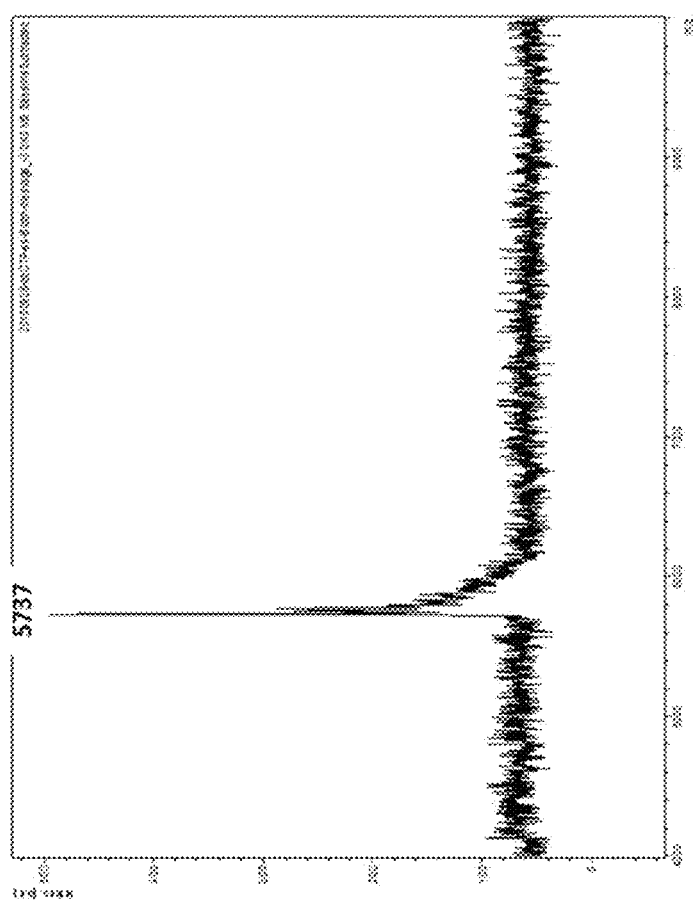
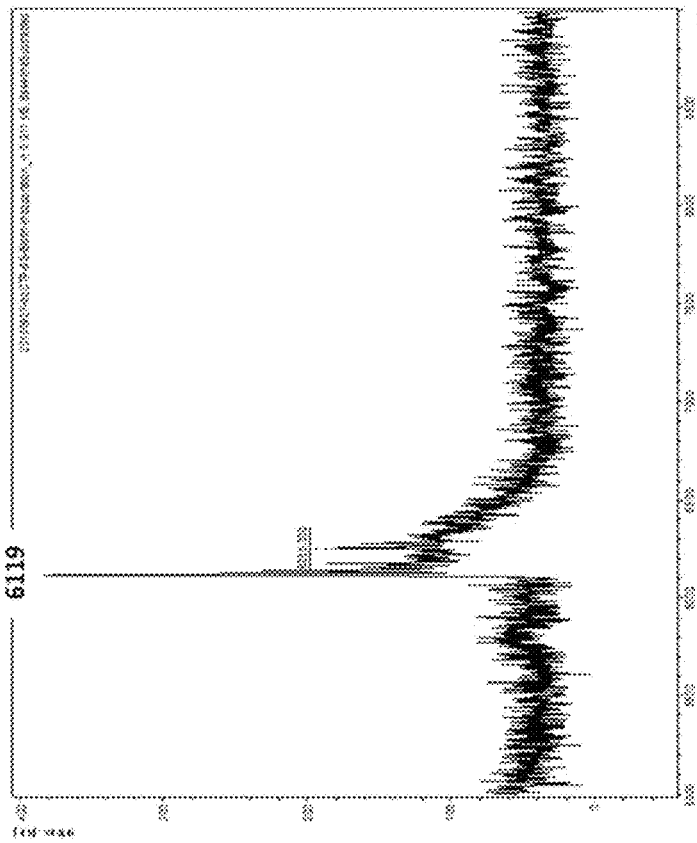
Fig. 161

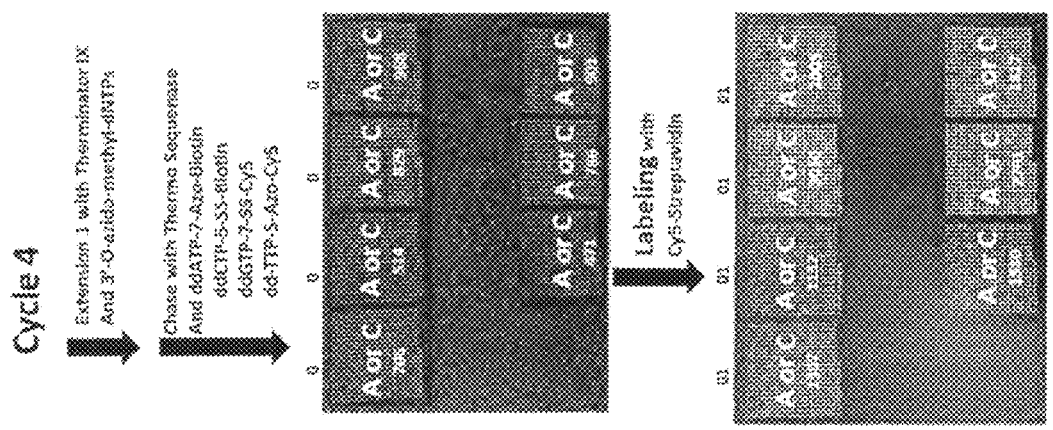
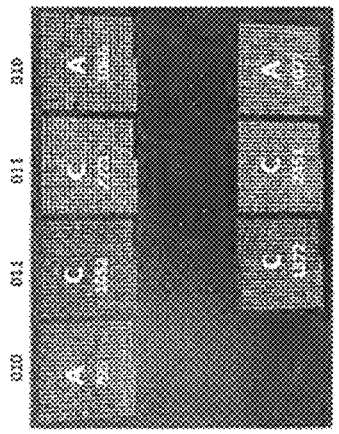
Fig. 16.3D

SEQUENCE LISTING

<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
gataggactc atcacca                                                  17

<210> SEQ ID NO 2
<211> LENGTH: 109
<212> TYPE: DNA
<213> ORGANISM: Artificial Sequence

```
<220> FEATURE:
<223> OTHER INFORMATION: Synthetic DNA Template

<400> SEQUENCE: 2
gaaggagaca cgcggccaga gagggtcctg tccgtgtttg tgcgtggagt tcgacaaggc    60
agggtcatct aatggtgatg agtcctatcc ttttctcttc gttctccgt              109

<210> SEQ ID NO 3
<211> LENGTH: 26
<212> TYPE: DNA
<213> ORGANISM: Artificial Sequence
<220> FEATURE:
<223> OTHER INFORMATION: Synthetic DNA Template

<400> SEQUENCE: 3
cgcggcgcgg ttccgcgccg cgagct                                        26

<210> SEQ ID NO 4
<211> LENGTH: 26
<212> TYPE: DNA
<213> ORGANISM: Artificial Sequence
<220> FEATURE:
<223> OTHER INFORMATION: Synthetic DNA Template

<400> SEQUENCE: 4
cgcggcgcgg ttccgcgccg cggcta                                        26

<210> SEQ ID NO 5
<211> LENGTH: 109
<212> TYPE: DNA
<213> ORGANISM: Artificial Sequence
<220> FEATURE:
<223> OTHER INFORMATION: Synthetic DNA Template

<400> SEQUENCE: 5
gaaggagaca cgcggccaga gagggtcctg tccgtgtttg tgcgtggagt tcgacaaggc    60
agggtcatct aatggtgatg agtcctatcc ttttctcttc gttctccgt              109

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tagatgaccc tgccttgtcg                                               20

<210> SEQ ID NO 7
<211> LENGTH: 17
<212> TYPE: DNA
<213> ORGANISM: Artificial Sequence
<220> FEATURE:
<223> OTHER INFORMATION: Primer

<400> SEQUENCE: 7
tctctggccg cgtgtct                                                  17

<210> SEQ ID NO 8
<211> LENGTH: 17
<212> TYPE: DNA
<213> ORGANISM: Artificial Sequence
<220> FEATURE:
<223> OTHER INFORMATION: Primer
```

```
<400> SEQUENCE: 8
gataggactc atcacca                                               17

<210> SEQ ID NO 9
<211> LENGTH: 100
<212> TYPE: DNA
<213> ORGANISM: Artificial Sequence
<220> FEATURE:
<223> OTHER INFORMATION: Synthetic DNA Template

<400> SEQUENCE: 9
tacccggagg ccaagtacgg cgggtacgtc cttgacaatg tgtacatcaa catcacctac    60
caccatgtca gtctcggttg gatcctctat tgtgtccggg                          100

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gttgatgtac acattgtcaa                                                20
```

NUCLEOTIDE ANALOGUES AND USE THEREOF FOR NUCLEIC ACID SEQUENCING AND ANALYSIS PRELIMINARY CLASS

CROSS-REFERENCE TO RELATED APPLICATIONS

This application is a § 371 national stage of PCT International Application No. PCT/US2019/022326, filed Mar. 14, 2019, claiming the benefit of U.S. Provisional Application No. 62/643,633, filed Mar. 15, 2018, the entire contents of each of which are hereby incorporated by reference into the application.

INCORPORATION BY REFERENCE & SEQUENCE LISTING

Throughout this application, various publications and patents are referenced. Full citations for these references may be found at the end of the specification immediately preceding the claims. The disclosures of these publications and patents in their entirety are hereby incorporated by reference into this application to more fully describe the state of the art to which this invention pertains.

This application incorporates-by-reference nucleotide and/or amino acid sequences which are present in the file named "200914-90419-A-PCT-US_Sequence_Listing_LMO.txt," which is 2.4 kilobytes in size, and which was created Sep. 11, 2020 in the IBM-PC machine format, having an operating system compatibility with MS-Windows, which is contained in the text file filed Sep. 14, 2020 as part of this application.

BACKGROUND OF THE INVENTION

DNA sequencing is a fundamental tool in biological and medical research, and is especially important for the paradigm of personalized medicine. Various new DNA sequencing methods have been investigated with the aim of eventually realizing the goal of the $1,000 genome; the dominant method is sequencing by synthesis (SBS), an approach that determines DNA sequences during the polymerase reaction (Hyman 1988; Ronaghi et al. 1998; Ju et al. 2003; Li 2003; Braslavsky et al. 2003; Ruparel et al. 2005; Margulies et al. 2005; Ju et al. 2006; Wu et al. 2007; Guo et al. 2008; Bentley et al. 2008; Harris et al. 2008; Eid et al. 2009; Rothberg et al. 2011). The currently widely used high-throughput SBS technology (Bentley et al. 2008) uses cleavable fluorescent nucleotide reversible terminator (NRT) sequencing chemistry developed previously (Ju et al. 2003; Ju et al. 2006). These cleavable fluorescent NRTs were designed based on the following rationale: each of the four nucleotides (A, C, G, T) is modified by attaching a unique cleavable fluorophore to the specific location of the base and capping the 3'-OH group with a small reversible moiety so that they are still recognized by DNA polymerase as substrates. Thus, the cleavable fluorescent NRTs involve two site modifications (Ju et al. 2003; Ju et al. 2006): a fluorescent dye to serve as a reporter group on the base and a small chemical moiety to cap the 3'-OH group to temporarily terminate the polymerase reaction after nucleotide incorporation for sequence determination. After incorporation and signal detection, the fluorophore is cleaved and the 3'-OH capping moiety removed to resume the polymerase reaction in the next cycle. These cleavable fluorescent NRTs have proved to be good substrates for reengineered polymerases and have been used extensively in next generation DNA sequencing systems (Ju et al. 2006; Bentley et al. 2008). Moreover, they enable accurate determination of homopolymer sequences, since only one base is identified in each cycle.

An SBS approach using cleavable fluorescent nucleotide analogues as reversible terminators to sequence surface-immobilized DNA has been used (Ju et al. 2003; Li et al. 2003; Ruparel et al. 2005; Ju et al. 2006; Wu et al. 2007; Guo et al. 2008). In this approach, the nucleotides are modified at two specific locations so that they are still recognized by DNA polymerase as substrates: (i) a different fluorophore with a distinct fluorescent emission is linked to the specific location of each of the four bases through a cleavable linker and (ii) the 3'-OH group is capped by a small chemically reversible moiety. DNA polymerase incorporates only a single nucleotide analogue complementary to the base on a DNA template covalently linked to a surface. After incorporation, the unique fluorescence emission detected to identify the incorporated nucleotide. The fluorophore is subsequently removed and 3'-OH group is chemically regenerated, which allows the next cycle of the polymerase reaction to proceed. Because the large surface on a DNA chip can have a high density of different DNA templates spotted, each cycle can identify many bases in parallel, allowing the simultaneous sequencing of a large number of DNA molecules. Previous research efforts have firmly established the molecular level strategy to rationally modify the nucleotides by attaching a cleavable fluorescent dye to the base and reversibly capping the 3'-OH with a small moiety for SBS.

A class of nucleotide analogues with unprotected 3'-OH and a cleavable disulfide linker attached between the base and fluorescent dye has been reported (Turcatti et al. 2008; Mitra et al. 2003). However, after DNA polymerase catalyzed extension reaction on the primer/template and imaging the incorporated base, the cleavage of the disulfide linkage generates a free reactive —SH group which has to be capped with alkylating agent, iodoacetamide as shown below, before the second extension reaction can be carried out. This capping step not only adds an extra step in the process but also limits the addition of multiple nucleotides in a row because of the long remnant tail on the nucleotide base moiety. With this approach the sequencing read length is limited to only 10 bases (Turcatti et al. 2008). Other disulfide-based approaches require a similar capping reaction to render the free SH group unreactive (Mitra et al. 2003).

SUMMARY

This invention provides a method of sequencing nucleic acid comprising:
  a) providing at least one nucleic acid template hybridized to a primer;
  b) extending the primer hybridized to said nucleic acid template with polymerase, and either:
    i) fluorescent labeled nucleotide analogues, wherein said fluorescently labeled nucleotide analogues have the label linked to the base via a cleavable linker and a blocking group on the 3'-hydroxyl group, wherein different nucleotides may have different anchors and different cleavable groups;
    ii) anchor labeled nucleotide analogues, wherein said anchor labeled nucleotide analogues have the anchor attached to the base via a cleavable linker and a blocking group on the 3'-hydroxyl group, wherein different nucleotides may have different anchors and different cleavable groups; or iii) a combination of both fluorescently and anchor labeled nucleotide analogues, wherein said fluorescently or anchor labeled nucleotide analogues have the label linked to the base via a cleavable linker and a blocking group on the 3'-hydroxyl group, wherein different nucleotides may have different cleavable groups;

c) optionally extending any unextended primer with 3' blocked nucleotides without any base modifications, and identifying the fluorescence signal due to incorporation of fluorescently nucleotide analogues;

d) optionally labeling anchor attached primer extension products with fluorescently labeled anchor binding molecules;

e) identifying newly generated fluorescence signals to partially or completely identify the incorporated nucleotides due to the labeling carried out in step d;

f) optionally repeating steps d and e;

g) optionally cleaving the label from fluorescently labeled nucleotides with a specific cleavable agent that cleaves one of the linkers but does not cleave the orthogonal linker;

h) identifying loss of fluorescence due to the cleavage carried out in step f to partially or completely identify the incorporated nucleotide;

i) optionally repeating steps g and h;

j) determining the specific nucleotide analogue incorporated by comparing the results obtained in steps c, e and h;

k) cleaving any remaining labels or anchors from the extended primers, at the same time restoring the 3'-hydroxyl groups; and l) iteratively carrying out steps a to k to obtain the sequence of the nucleic acid template, thereby sequencing the nucleic acid.

This invention also provides a method of sequencing nucleic acid comprising:

a) providing at least one nucleic acid template hybridized to a primer;

b) extending the primer hybridized to said nucleic acid template with polymerase and a set of nucleotide analogues (A, C, G and T) carrying orthogonal sets of labels and anchors, the first nucleotide analogue with a fluorescent label directly attached to the base, the second with a different fluorescent label directly attached to the base, the third with an anchor moiety attached to the base, and the fourth with a different anchor moiety attached to the base, wherein said fluorescent or anchor labeled nucleotide analogues have the label linked to the base via the same type of cleavable linker and a blocking group with the same cleavable moiety on the 3'-hydroxyl position;

c) optionally extending any unextended primer with 3' blocked nucleotides without any base modifications, and identifying the fluorescence signal due to incorporation of fluorescently nucleotide analogues;

d) labeling primer extension products containing anchor moieties with fluorescently labeled anchor binding molecules, wherein the anchor binding molecules for attachment to the two different anchors contain the same two fluorescent labels as the nucleotide analogues in step b;

e) identifying newly generated fluorescence signals due to the labeling carried out in step d to determine the remaining two incorporated nucleotide analogues;

f) cleaving any remaining dyes and anchors from the primer extension products, and restoring the 3'-hydroxyl groups; and iteratively carrying out steps a to f to obtain the sequence of the nucleic acid template.

The invention also provides a method of sequencing nucleic acid comprising:

a) providing a nucleic acid template hybridized to a primer;

b) extending the primer hybridized to said nucleic acid template with polymerase and an orthogonal set of fluorescently labeled nucleotide analogues (A, C, G and T), the first with a fluorescent dye directly attached to the base via a cleavable linker, the second with the same fluorescent dye directly attached to the base via a different type of cleavable linker, the third with a second dye directly attached to the base via the first type of cleavable linker, and the fourth with the second dye directly attached to the base via the second type of cleavable linker, wherein the cleavable moiety in the second cleavable linker can be cleaved under the same conditions as the cleavable blocking moiety at the 3'-hydroxyl position;

c) optionally extending any unextended primer with 3' blocked nucleotides without any base modifications, and identifying the fluorescence signal due to incorporation of fluorescently labeled nucleotide analogues to partially determine incorporation of two of the four nucleotides;

d) cleaving the dyes from fluorescently labeled nucleotides incorporated into the primer with a specific agent that cleaves the first type of linker;

e) identifying loss of fluorescence due to the cleavage carried out in step d;

f) determining the specific nucleotide analogue incorporated by comparing the results obtained in steps c and e;

g) cleaving any remaining dyes from the extended primers, at the same time restoring the 3'-hydroxyl groups; and
iteratively carrying out steps a to g to obtain the sequence of the nucleic acid template.

The invention also provides a method of sequencing nucleic acid comprising:

a) providing at least one nucleic acid template hybridized to a primer;

b) extending the primer hybridized to said nucleic acid template with polymerase and an orthogonal set of anchor labeled nucleotide analogues (A, C, G and T), the first with an anchor moiety directly attached to the base via a first type of cleavable linker, the second with the same anchor moiety directly attached to the base via a second type of cleavable linker, the third with a second anchor moiety directly attached to the base via the first type cleavable linker, and the fourth with the second anchor moiety directly attached to the base via the second type of cleavable linker, wherein the cleavable moiety in the second type of cleavable linker can be cleaved under the same conditions as the cleavable blocking moiety at the 3'-hydroxyl position;

c) optionally extending any unextended primer with 3' blocked nucleotides without any base modifications;

d) labeling primers extended with nucleotide analogues having the first anchor using a fluorescently labeled anchor binding molecule specific for the first anchor;

e) identifying fluorescence signal due to the labeling carried out in step d to partially determine 2 of the 4 incorporated nucleotide analogues;

f) labeling primers extended with nucleotide analogues having the second anchor using a fluorescently labeled anchor binding molecule specific for the second anchor, wherein the fluorescent label is the same label attached to the anchor binding molecule specific for the first anchor;

g) identifying newly generated fluorescence signal due to the labeling carried out in step f to partially determine the other 2 of the 4 incorporated nucleotide analogues;

h) cleaving the dyes and anchors from fluorescently labeled nucleotides with a specific cleavable agent that cleaves the first type of linker;

i) identifying loss of fluorescence due to the cleavage carried out in step h; thereby j) determining the specific nucleotide analogue incorporated into the primer by comparing the results obtained in steps e, g and i;

k) cleaving any remaining dyes or anchors from the extended primers, at the same time restoring the 3'-hydroxyl groups; and iteratively carrying out steps a to i to obtain the sequence of the nucleic acid template.

The invention also provides a method of sequencing nucleic acid comprising:

a) providing at least one nucleic acid template hybridized to a primer;

b) extending the primer hybridized to said nucleic acid template with polymerase and an orthogonal set of anchor labeled nucleotide analogues (A, C, G and T), the first with a dye directly attached to the base via a first type of cleavable linker, the second with the same dye directly attached to the base via a second type of cleavable linker, the third with an anchor moiety directly attached to the base via the first type of cleavable linker, and the fourth with the same anchor moiety directly attached to the base via the second type of cleavable linker, wherein the cleavable moiety in the second type of cleavable linker can be cleaved under the same conditions as the cleavable blocking moiety at the 3'-hydroxyl position;

c) optionally extending any unextended primer with 3' blocked nucleotides without any base modifications, and identifying fluorescence signals to partially determine two of the four nucleotide analogues;

d) labeling primers extended with nucleotide analogues having the anchor using a fluorescently labeled anchor binding molecule specific for that anchor;

e) identifying newly generated fluorescence due to the labeling carried out in step d to partially determine the other two of the four incorporated nucleotides;

f) cleaving the dyes and anchors from fluorescently labeled nucleotides with a specific cleavable agent that cleaves the first type of linker;

g) identifying loss of fluorescence due to the cleavage carried out in step f; thereby h) determining the specific nucleotide analogue incorporated into the primer by comparing the results obtained in steps c, e and g;

i) cleaving any remaining dyes or anchors from the extended primers, at the same time restoring the 3'-hydroxyl groups; and iteratively carrying out steps a to i to obtain the sequence of the nucleic acid template.

The invention also provides a dideoxynucleotide triphosphate (ddNTP) analogue having the structure:

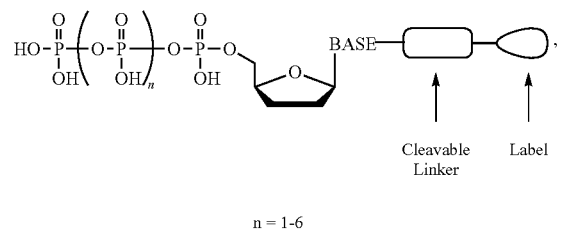

n = 1-6 wherein:

i) BASE comprises adenine, guanine, cytosine, thymine, uracil, hypoxanthine or analog thereof;

ii) cleavable linker an SS(DTM), an azo, an SS-azo, an allyl, a 2-nitrobenzyl, an azidomethyl, or azidomethyl derivative, and is attached to the base via 5 position of pyrimidines (C, U) or 7 position of purines (A, G);

iii) the cleavable linker between BASE and Label comprises polymeric molecule of varying length iv) Label comprises a fluorescent dye, a cluster of fluorescent dyes, an anchor for dye attachment, and/or an anchor cluster for dye attachment The invention also provides a nucleotide analogue having the structure:

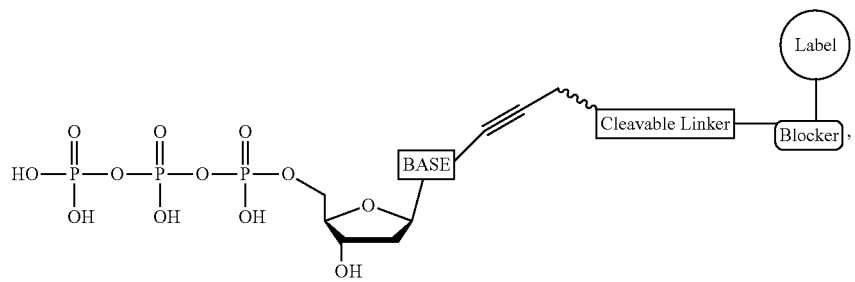

wherein, BASE comprises adenine, guanine, cytosine, thymine, uracil, hypoxanthine or analog thereof; Cleavable Linker comprises an SS(DTM), an azo, an SS-azo, an allyl, a 2-nitrobenzyl, an azidomethyl, or azidomethyl derivative; the attachment between BASE and Label comprises a polymeric molecule; Blocker is a nucleotide or oligonucleotide comprising 2-50 monomer units of abasic sugars or modified nucleosides or a combination thereof; and blocker is connected to the 5-position of pyrimidines (C, U) and 7-position of deazapurines (A, G, I) via a cleavable linker, wherein a Blocker is a molecule that after incorporation of the nucleotide analogue by a nucleotide polymerase, prevents further incorporation of additional nucleotides or nucleotide analogues into a primer strand;

Label comprises a fluorescent dye, a cluster of a fluorescent dye, an anchor for attachment of a fluorescent dye via an anchor binding molecule, or a cluster of an anchor for attachment of fluorescent dyes via anchor binding molecules, wherein Label is attached to the blocker.

The invention also provides a nucleotide analogue having the structure:

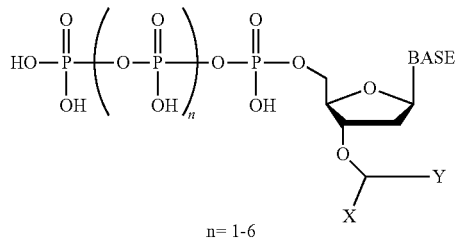

n= 1-6

X=Cleavable Trigger Moiety Y=Label,
wherein, BASE comprises adenine, guanine, cytosine, thymine, uracil, hypoxanthine or analog thereof; X is a cleavable trigger moiety comprising SS(DTM), azo, alkenyl, 2-Nitrobenzyl, or azido; the wavy line to the Label (Y) comprises a polymeric molecule of various lengths; and Y is a Label comprising a fluorescent dye, a cluster of a fluorescent dye, an anchor moiety for binding of a fluorescent dye, or a cluster of an anchor moiety for binding of a fluorescent dye.

The invention also provides a nucleotide analogue having the structure:

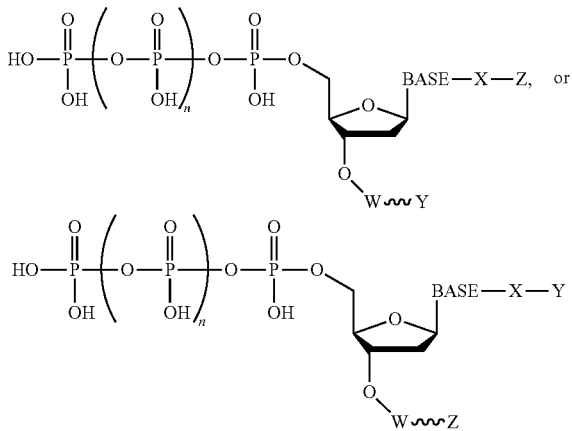

wherein, BASE comprises adenine, guanine, cytosine, thymine, uracil, hypoxanthine or analog thereof; X is a cleavable group comprising SS(DTM), an azo, an SS-azo, an allyl, a 2-nitrobenzyl, an azidomethyl, or azidomethyl derivative; W is a cleavable group comprising SS(DTM), an azo, an SS-azo, an allyl, a 2-nitrobenzyl, an azidomethyl, or azidomethyl derivative; wherein X and W comprise the same or a different cleavable group;

Y is a label comprising a fluorescent dye, a cluster of a fluorescent dye, an anchor moiety for binding of a fluorescent dye, or a cluster of an anchor moiety for binding of a fluorescent dye; and Z is an FRET donor or acceptor dye.

The invention also provides a nucleotide analogue having the structure:

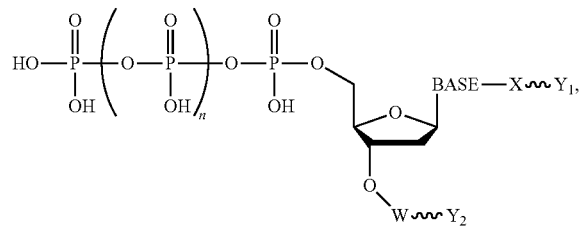

wherein, BASE comprises adenine, guanine, cytosine, thymine, uracil, hypoxanthine or analog thereof; X is a cleavable group comprising SS(DTM), an azo, an SS-azo, an allyl, a 2-nitrobenzyl, an azidomethyl, or azidomethyl derivative; W is a cleavable group comprising SS(DTM), an azo, an SS-azo, an allyl, a 2-nitrobenzyl, an azidomethyl, or azidomethyl derivative;
wherein X and W comprise the same or a different cleavable group; and Y is a Label comprising a fluorescent dye, a cluster of a fluorescent dye, an anchor moiety for binding of a fluorescent dye, or a cluster of an anchor moiety for binding of a fluorescent dye.

BRIEF DESCRIPTION OF THE DRAWINGS

FIG. 1: The two general nucleotide analogue structures that cover most of the variants for Sections I-III.

FIG. 2: The general structures for the key nucleotide analogues used for SBS imaging in Section I.

FIG. 10B: 3'-O-SS(DTM)-dNTP-SS-Anchors (3'-O-SS-dATP-7-SS-Biotin and 3'-O-SS-dGTP-7-SS-TCO), 3'-O-SS(DTM)-dNTP-Azo-Anchors (3'-O-SS-dTTP-5-Azo-TCO and 3'-O-SS-dCTP-5-Azo-Biotin) and the corresponding Quantum Dot Labeled Binding Molecules (Qdot 525 Labeled Streptavidin and Qdot 605 Labeled Tetrazine) for 2-color DNA SBS using approach delineated in Scheme VIB.

FIGS. 31A-31E: A schematic for Scheme I using 3'-O-SS(DTM)-dNTP-SS-Dyes (3'-O-SS-dATP-7-SS-Rox, 3'-O-SS-dTTP-5-SS-BodipyFL) and 3'-O-SS(DTM)-dNTP-Azo-Dyes (3'-O-SS-dCTP-7-Azo-Rox, 3'-O-SS-dGTP-5-Azo-BodipyFL) to perform 2-color DNA SBS.

FIGS. 32A-32D: A schematic for Scheme II using 3'-O-SS(DTM)-dNTP-SS-Dye (3'-O-SS-dATP-7-SS-ATTO647N), 3'-O-SS(DTM)-dNTP-Azo-Dye (3'-O-SS-dTTP-5-Azo-ATTO647N), 3'-O-SS(DTM)-dNTP-SS-Anchor (3'-O-SS-dCTP-5-SS-Biotin), 3'-O-SS(DTM)-dNTP-Azo-Anchor (3'-O-SS-dGTP-7-Azo-Biotin) and the corresponding Dye Labeled Binding Molecule (ATTO647N-labeled Streptavidin) to perform 1-color DNA SBS.

FIGS. 33A-33D: A schematic showing Scheme III using 3'-O-SS(DTM)-dNTP-SS-Anchors (3'-O-SS-dATP-7-SS-Biotin, 3'-O-SS-dGTP-7-SS-TCO), 3'-O-SS(DTM)-dNTP-Azo-Anchors (3'-O-SS-dTTP-5-Azo-TCO, 3'-O-SS-dCTP-5-Azo-Biotin) and the corresponding Dye Labeled Binding Molecules (ATTO647N-labeled Streptavidin and ATTO647N-labeled Tetrazine) to perform 1-color DNA SBS.

FIGS. 34A-34C: A schematic showing Scheme IV using 3'-O-SS(DTM)-dNTP-SS-Dye Cluster (3'-O-SS-dATP-7-SS-ATTO647N Cluster), 3'-O-SS(DTM)-dNTP-Azo-Dye Cluster (3'-O-SS-dTTP-5-Azo-ATTO647N Cluster), 3'-O-SS(DTM)-dNTP-SS-Anchor Cluster (3'-O-SS-dCTP-5-SS-Biotin Cluster), 3'-O-SS(DTM)-dNTP-Azo-Anchor Cluster (3'-O-SS-dGTP-7-Azo-Biotin Cluster) and the corresponding Dye Labeled Binding Molecule (ATTO647N-labeled Streptavidin) to perform 1-color DNA SBS.

FIGS. 37A-37C: A schematic showing Scheme VIB using 3'-O-SS(DTM)-dNTP-SS-Anchors (3'-O-SS-dATP-7-SS-Biotin, 3'-O-SS-dGTP-7-SS-TCO), 3'-O-SS(DTM))-dNTP-Azo-Anchors (3'-O-SS-dTTP-5-Azo-TCO, 3'-O-SS-dCTP-5-Azo-Biotin) and the corresponding Dye Labeled Binding Molecules (Quantum Dot 1 (Green)-labeled Streptavidin and Quantum Dot 2 (Red)-labeled Tetrazine) to perform 2-color DNA SBS.

FIGS. 39A-39C: A schematic showing Scheme VID using 3'-O-SS(DTM)-dNTP-SS-Anchor (3'-O-SS-dATP-7-SS-Biotin), 3'-O-SS(DTM)-dNTP-Azo-Anchors (3'-O-SS-dTTP-5-Azo-TCO, 3'-O-SS-dCTP-5-Azo-Biotin), 3'-O-Anchor-SS(DTM)-dNTP (3'-O-TCO-SS-dGTP), and the corresponding Dye Labeled Binding Molecules (Quantum Dot 1 (Green)-labeled Streptavidin and Quantum Dot 2 (Red)-labeled Tetrazine) to perform 2-color DNA SBS.

FIGS. 40A-40C: A schematic showing Scheme VIE using 3'-O-SS(DTM)-dNTP-SS-Anchors (3'-O-SS-dATP-7-SS-Biotin, 3'-O-SS-dGTP-7-SS-TCO), 3'-O-Anchor-SS(DTM)-dNTP-SS-Anchors (3'-O-TCO-SS-dCTP-5-SS-Biotin, 3'-O-TCO-SS-dTTP-5-SS-Biotin/Biotin) and the corresponding Dye Labeled Binding Molecules (Quantum Dot 1 (Green)- labeled Streptavidin and Quantum Dot 2 (Red)-labeled Tetrazine) to perform 2-color DNA SBS.

FIGS. 41A-41D: A schematic showing Scheme VIIA using 3'-O-SS(DTM)-dNTP-SS-DonorDye-Anchors (3'-O-SS-dATP-7-SS-Cy3-Biotin, 3'-O-SS-dGTP-7-SS-Cy3-TCO), 3'-O-SS(DTM)-dNTP-Azo-DonorDye-Anchors (3'-O-SS-dTTP-5-Azo-Cy3-TCO, 3'-O-SS-dCTP-5-Azo-Cy3-Biotin) and the corresponding Dye Labeled Binding Molecules (Cy5-labeled Streptavidin and Cy5-labeled Tetrazine) to perform 1-color DNA SBS.

Figure 42:
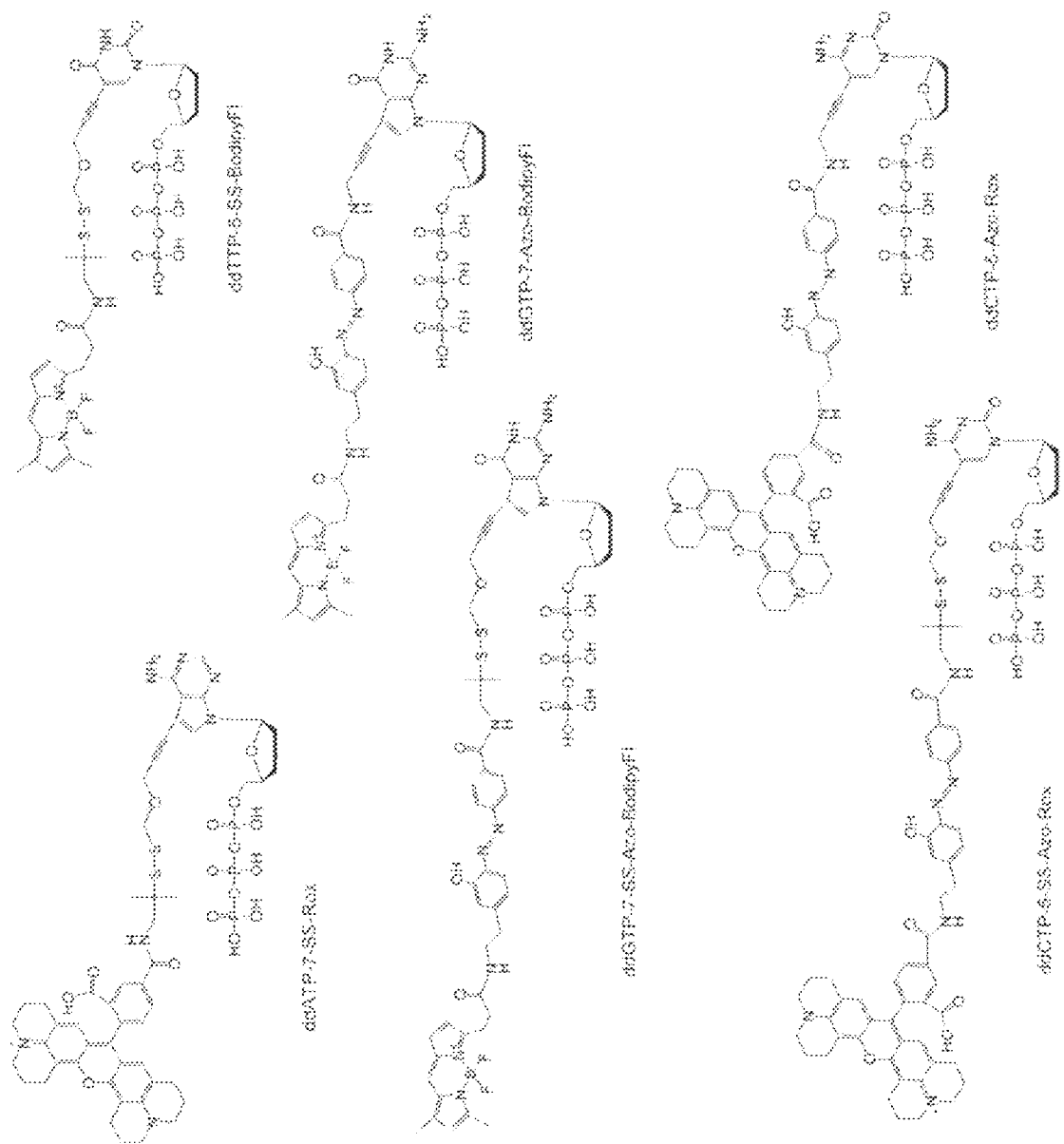

FIG. 42: ddNTP-SS-Dyes (ddATP-7-SS-Rox and ddUTP-5-SS-BodipyFL) and ddNTP-SS-Azo-Dyes (ddCTP-5-Azo-Rox and ddGTP-7-Azo-BodipyFL) for 2-color DNA SBS using approach delineated in Scheme IX. Also shown are the structures of ddCTP-5-SS-Azo-Rox and ddGTP-7-SS-Azo-BodipyFL that have an additional SS linkage between the Azo group and the base. A possible advantage of using such SS-Azo linkers is that after cleavage, an OH rather than an $NH_2$ group remains; the buildup of $NH_2$ reactive groups on primers terminated with such ddNTP analogues may interfere with future extension reactions in their vicinity.

Figure 43:
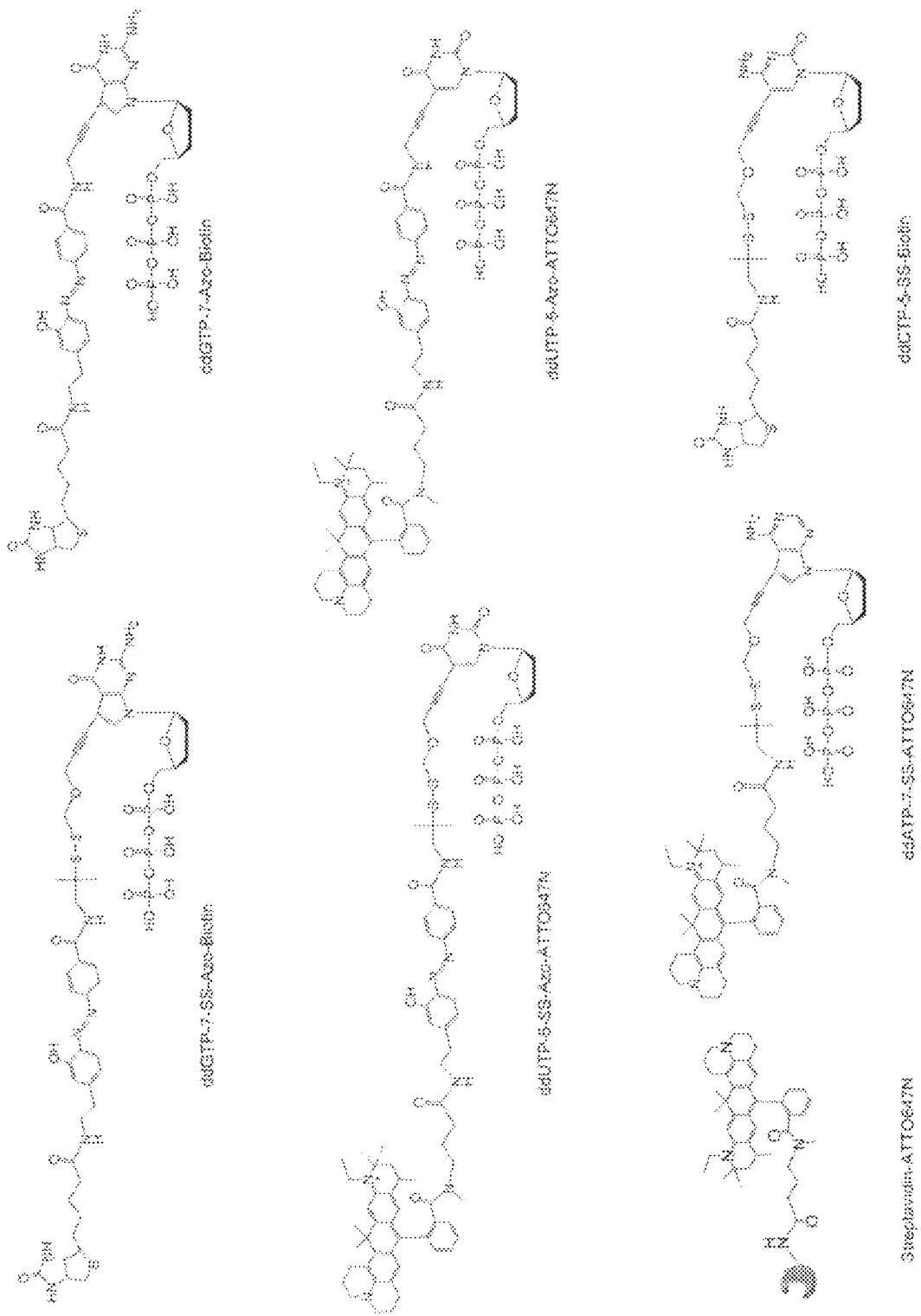

FIG. 43: ddNTP-SS-Dye (ddATP-7-SS-ATTO647N), ddNTP-Azo-Dye (ddTTP-5-Azo-ATTO647N or ddTTP-5-SS-Azo-ATTO647N), ddNTP-SS-Anchor (ddCTP-5-SS-Biotin), ddGTP-7-SS-Azo-Anchor(ddGTP-7-Azo-Biotin or ddGTP-7-SS-Azo-Biotin) and the corresponding Dye Labeled Binding Molecule (ATTO647N Labeled Streptavidin) for 1-color DNA SBS using approach delineated in Scheme X.

Figure 44:
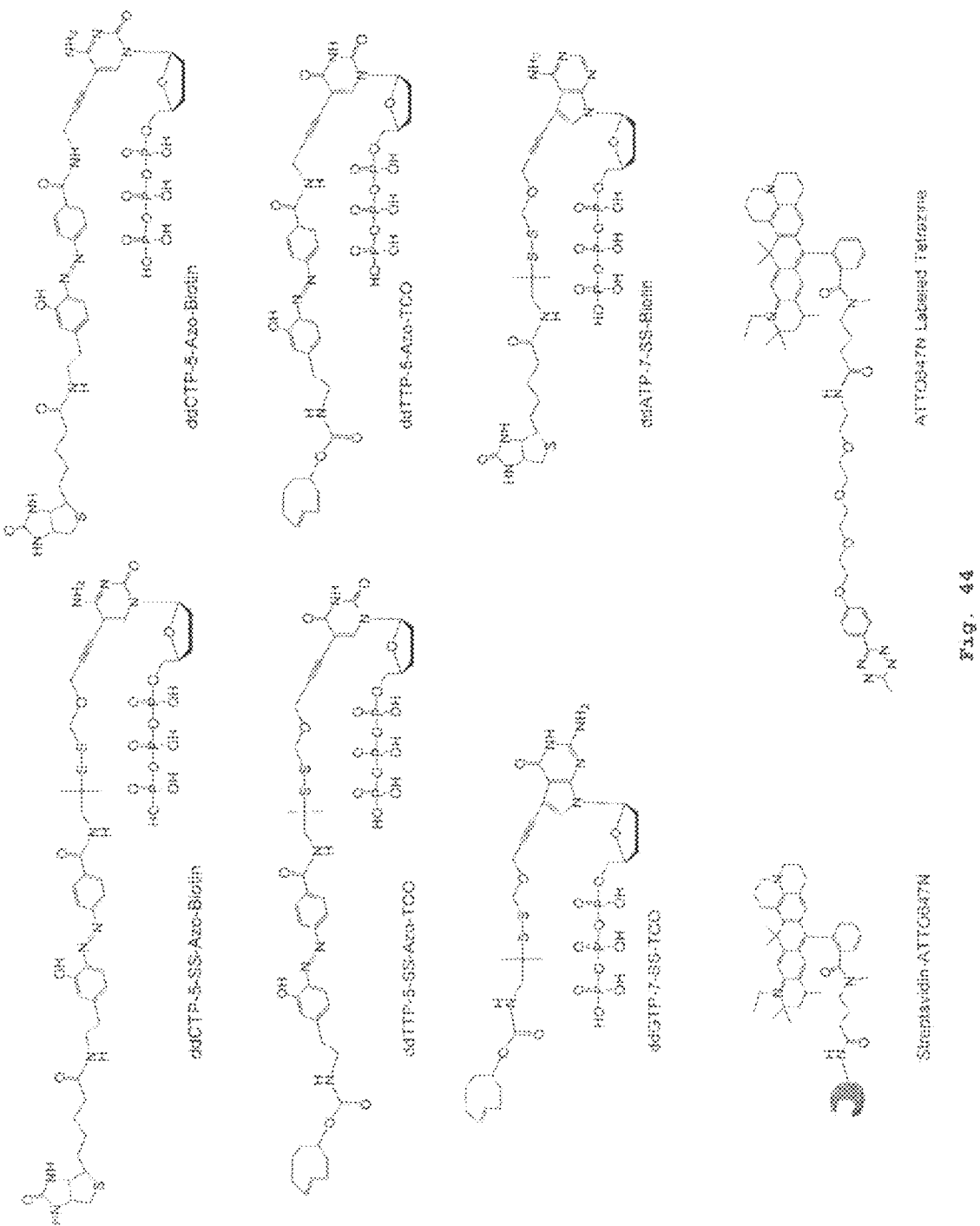
Figure 4S:
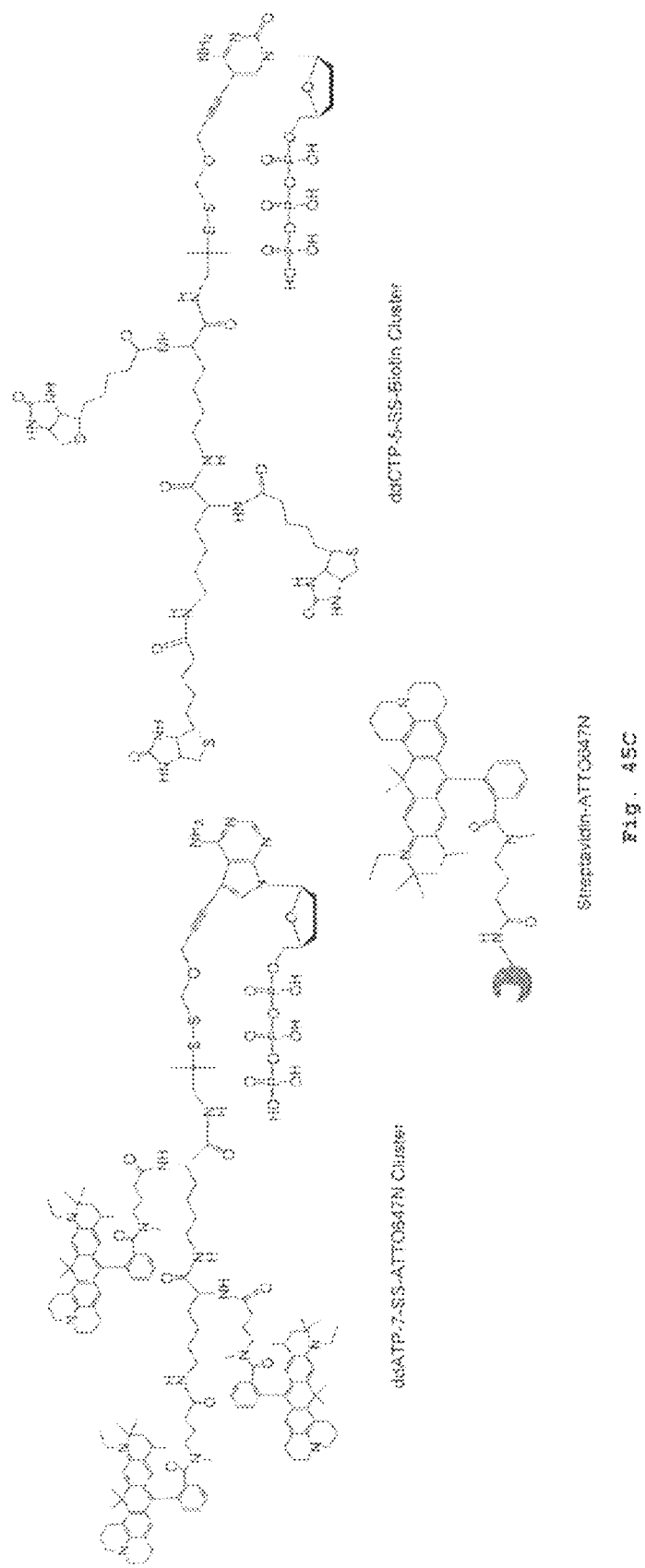

FIG. 44: ddNTP-SS-Anchors (ddATP-7-SS-Biotin and ddGTP-7-SS-TCO), ddNTP-Azo-Anchors (ddCTP-5-Azo-Biotin or ddCTP-5-SS-Azo-Biotin, ddTTP-5-Azo-TCO or ddTTP-5-SS-Azo-TCO) and the corresponding Dye Labeled Binding Molecules (ATTO647N Labeled Streptavidin and ATTO647N Labeled Tetrazine) for 1-color DNA SBS using approach delineated in Scheme XI.

FIGS. 45A-45C: ddNTP-SS-Anchor Cluster (ddCTP-5-SS-Biotin Cluster), ddNTP-Azo-Anchor Cluster (ddGTP-7-Azo-Biotin Cluster or ddGTP-7-SS-Azo-Biotin Cluster), ddNTP-SS-Dye Cluster (ddATP-7-SS-ATTO647N Cluster) and ddNTP-Azo-Dye Cluster (ddTTP-5-Azo-ATTO647N or ddTTP-5-SS-Azo-ATTO647N) and the corresponding Dye Labeled Binding Molecules (ATTO 647N Labeled Streptavidin for 1-color DNA SBS using approach delineated in Scheme XII.

Figure 46A:
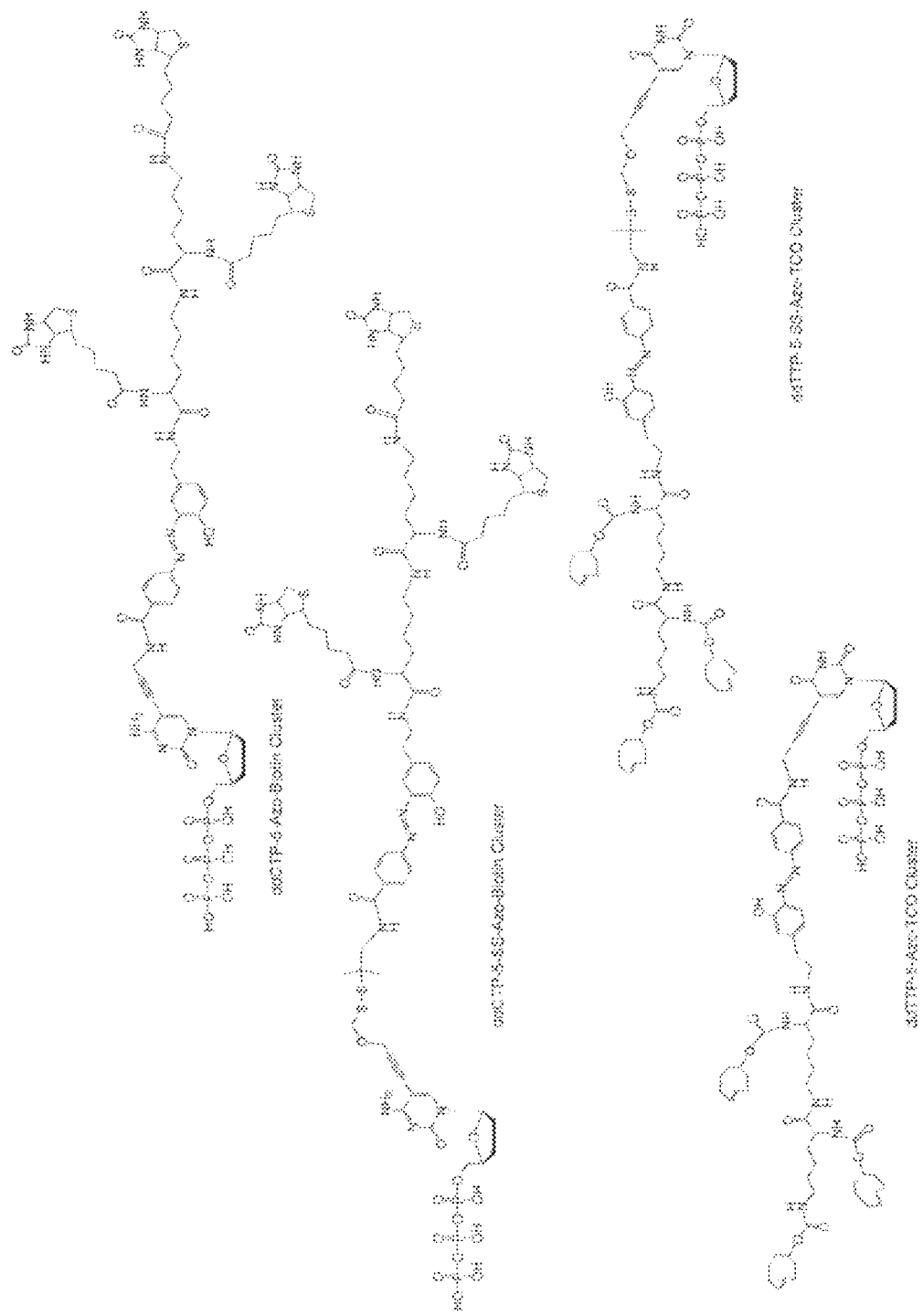
Figure 46B:
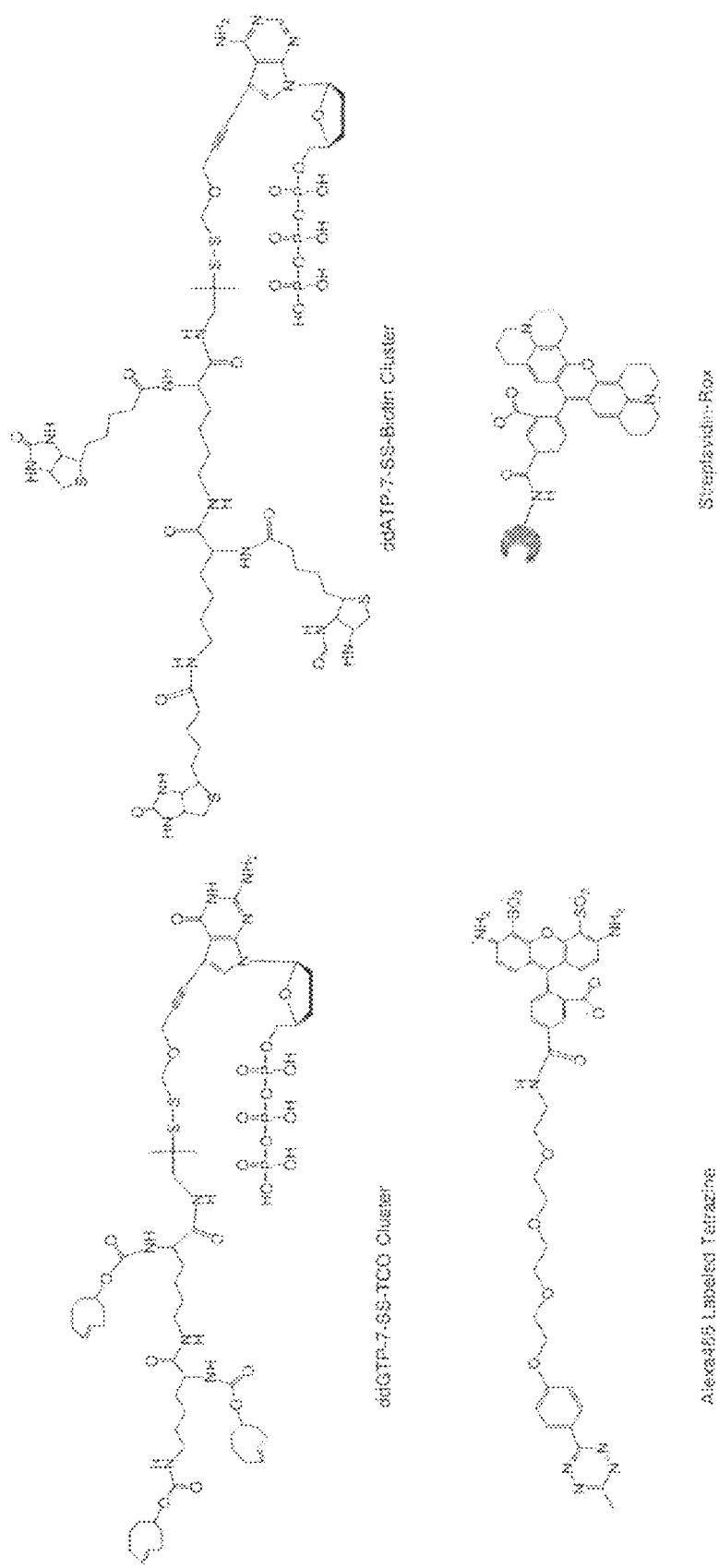

FIGS. 46A-46B: ddNTP-SS-Anchor Cluster (ddATP-7-SS-Biotin Cluster, ddGTP-7-SS-TCO Cluster) and ddNTP-Azo-Anchor Cluster (ddCTP-5-Azo-Biotin Cluster or ddCTP-5-SS-Azo-Biotin Cluster, ddTTP-5-Azo-TCO Cluster or ddTTP-5-SS-Azo-TCO Cluster) and the corresponding Dye Labeled Binding Molecules (Rox Labeled Streptavidin and Alexa488 labeled tetrazine) for 2-color DNA SBS using approach delineated in Scheme XIII.

Figure 47:
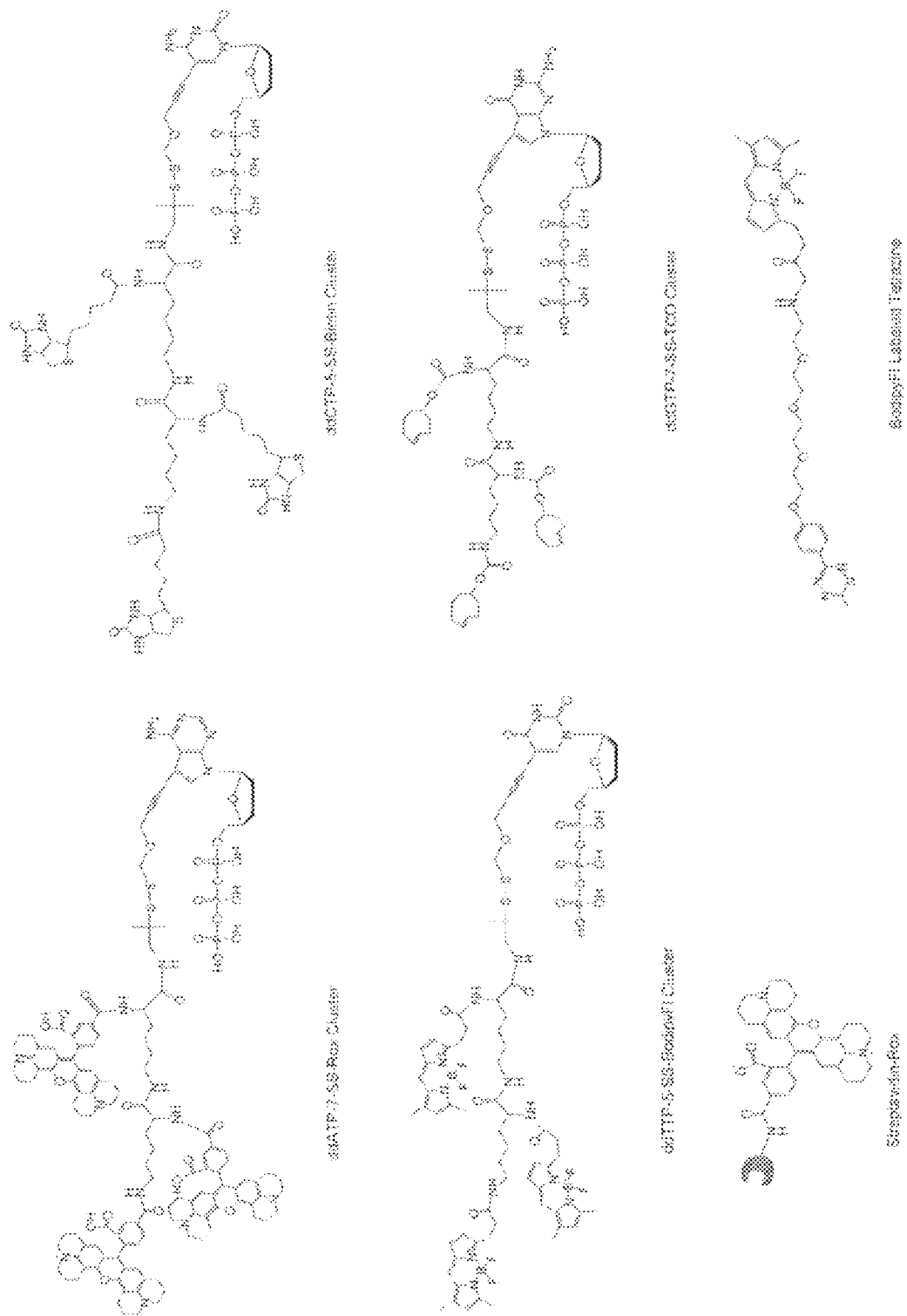

FIG. 47: ddNTP-SS-Dye Cluster (ddATP-7-SS-Rox Cluster, ddTTP-5-SS-BodipyFL Cluster) and ddNTP-SS-Anchor Cluster (ddCTP-5-SS-Biotin Cluster, ddGTP-7-SS-TCO Cluster) and the corresponding Dye Labeled Binding Molecules (Rox Labeled Streptavidin and BodipyFL labeled tetrazine) for 2-color DNA SBS using approach delineated in Scheme XIV.

Figure 48:
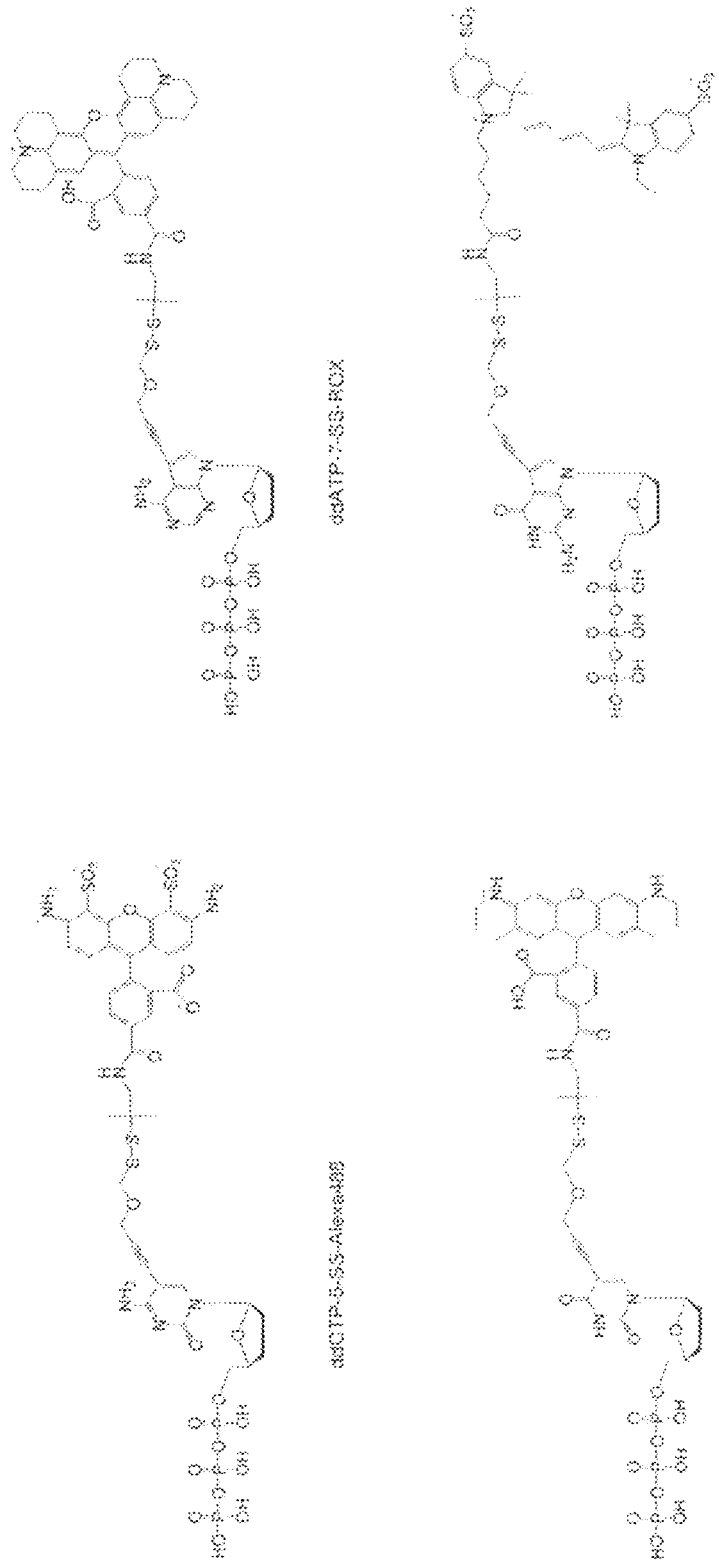

FIG. 48: ddNTP-SS-Dye (ddATP-7-SS-Rox, ddTTP-5-SS-R6G, ddCTP-5-SS-Alexa488 and ddGTP-7-SS-Cy5) for 4-color DNA SBS using approach delineated in Schemes VIII and XV.

Figure 49A:
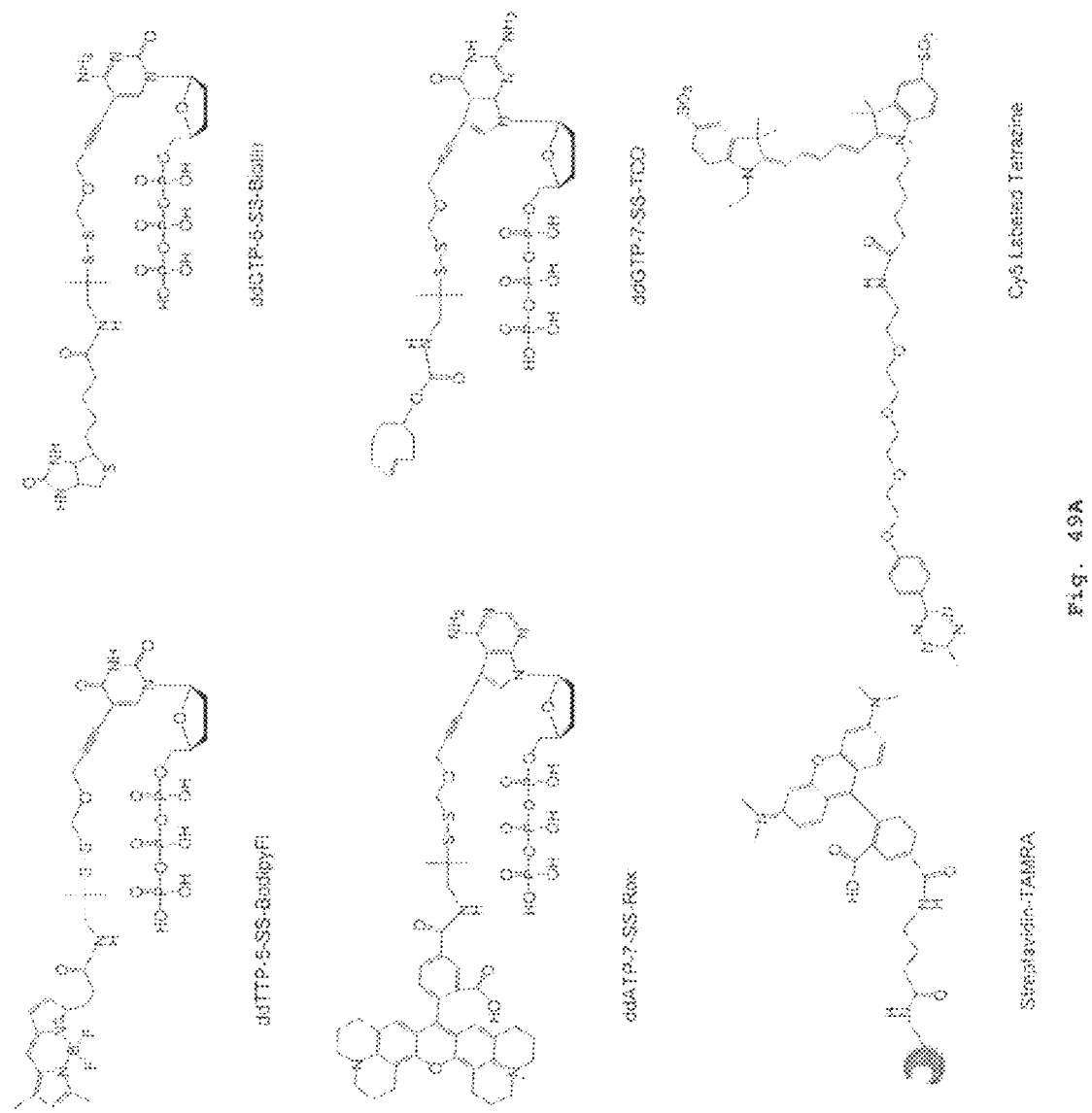

FIG. 49A: ddNTP-SS-Anchors (ddCTP-5-SS-Biotin and ddGTP-7-SS-TCO) and ddNTP-SS-Dyes (ddATP-7-SS-Rox and ddUTP-5-SS-BodipyFl) and the corresponding Dye Labeled Binding Molecules (TAMRA Labeled Streptavidin and Cy5 Labeled Tetrazine) for 4-color DNA SBS using approach delineated in Scheme XVIA.

Figure 49B:
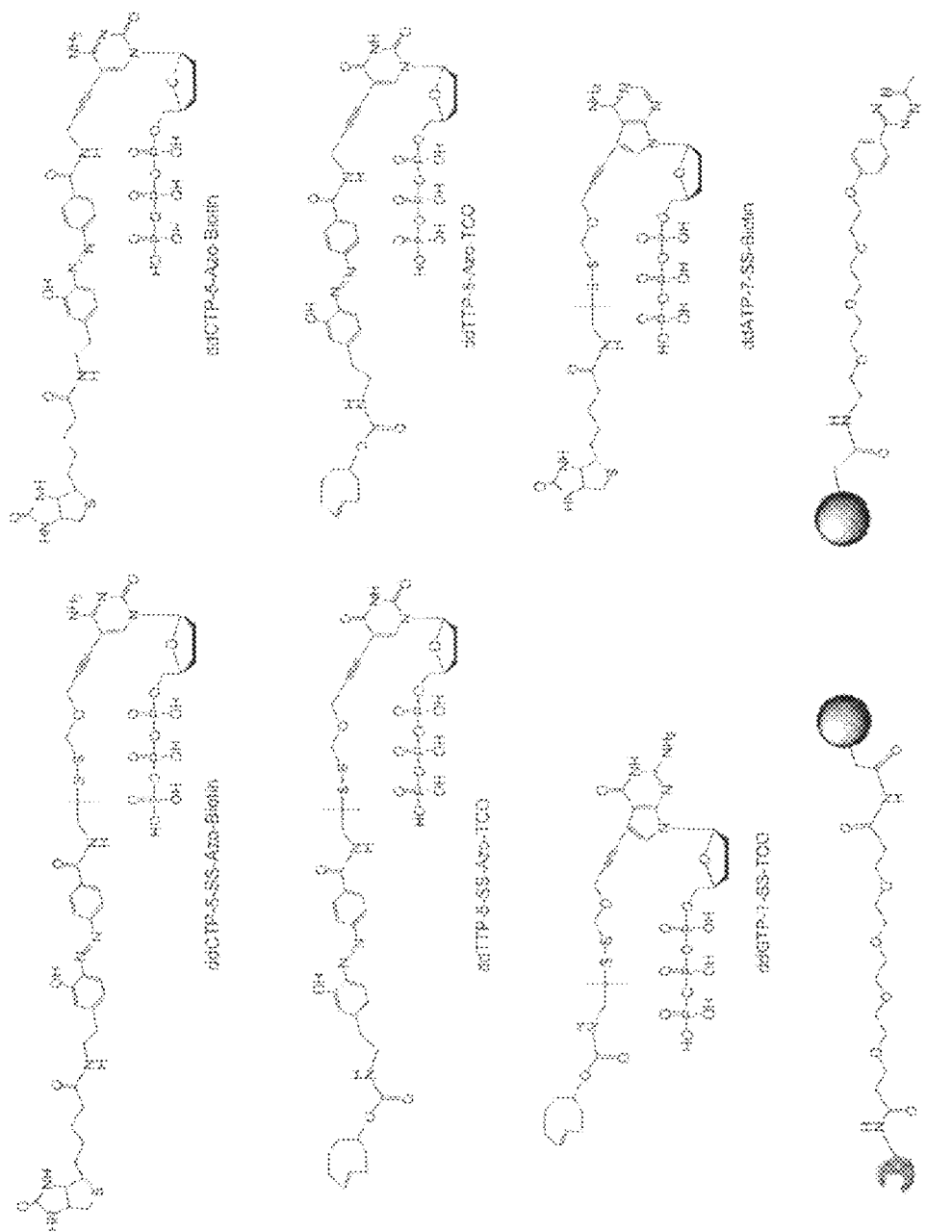

FIG. 49B: ddNTP-SS-Anchors (ddATP-7-SS-Biotin and ddGTP-7-SS-TCO), ddNTP-Azo-Anchors (ddTTP-5-Azo-TCO or ddTTP-5-SS-Azo-TCO and ddCTP-5-Azo-Biotin or ddCTP-5-SS-Azo-Biotin) and the corresponding Quantum Dot Labeled Binding Molecules (Qdot 525 Labeled Streptavidin and Qdot 605 Labeled Tetrazine) for 2-color DNA SBS using approach delineated in Scheme XVIB.

FIG. 49C: ddNTP-SS-Anchors (ddATP-7-SS-Biotin and ddGTP-7-SS-TCO), ddNTP-SS-Anchor-Cluster (ddTTP-5-SS-Biotin-Biotin-TCO and ddCTP-5-SS-Biotin-TCO) and the corresponding Quantum Dot Labeled Binding Molecules (Qdot 525 Labeled Streptavidin and Qdot 605 Labeled Tetrazine) for one laser-2-color DNA SBS using quantum dots approach delineated in Scheme XVIC.

Figure 50:
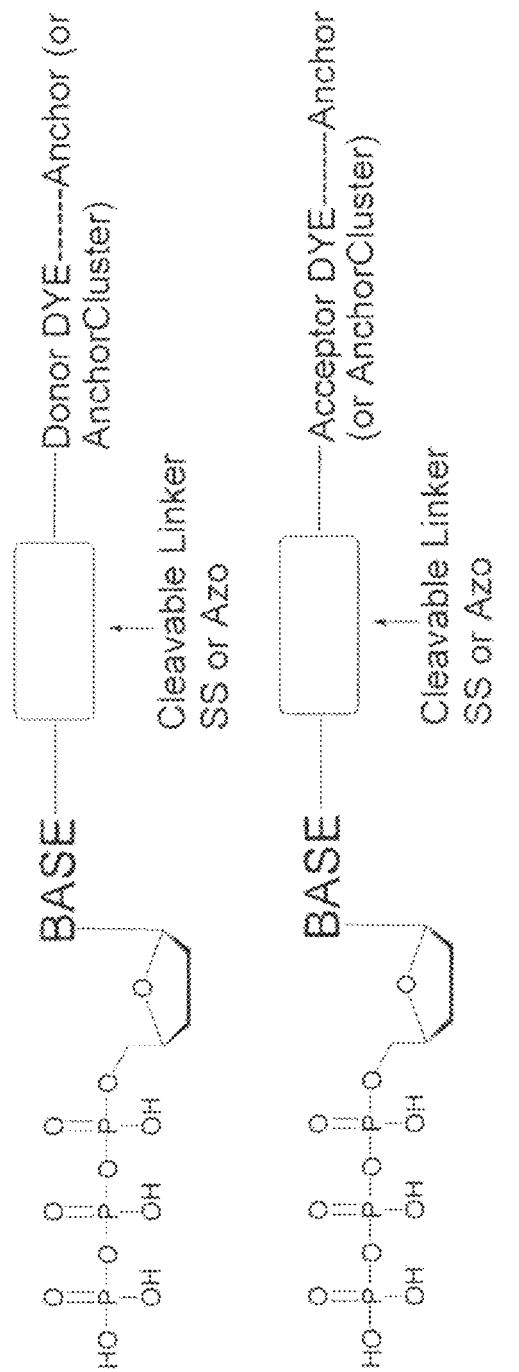

FIG. 50: General structure of ddNTP analogues used for fluorescence resonance energy transfer (FRET) based sequencing by synthesis.

Figure 51A:
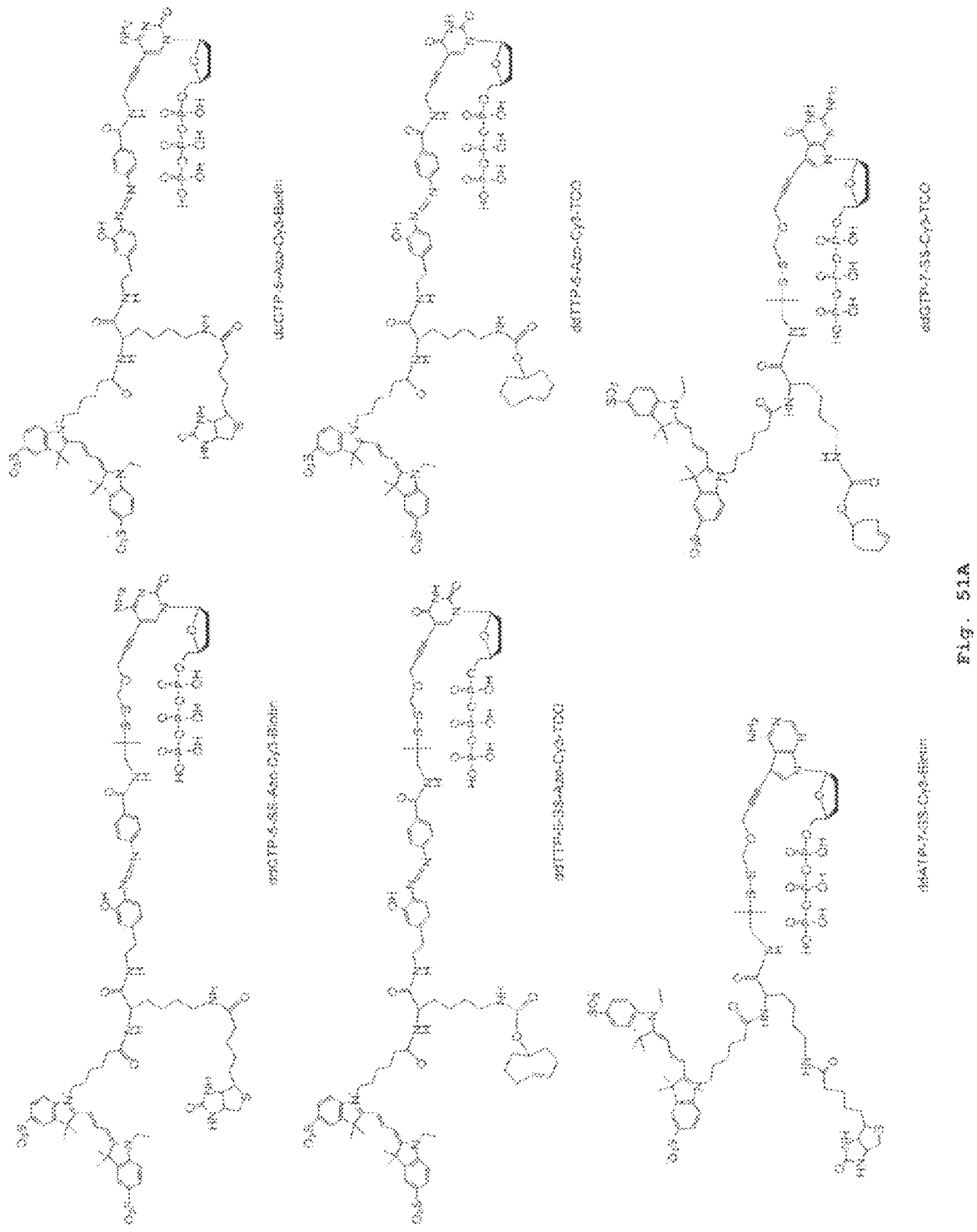
Figure 51B:
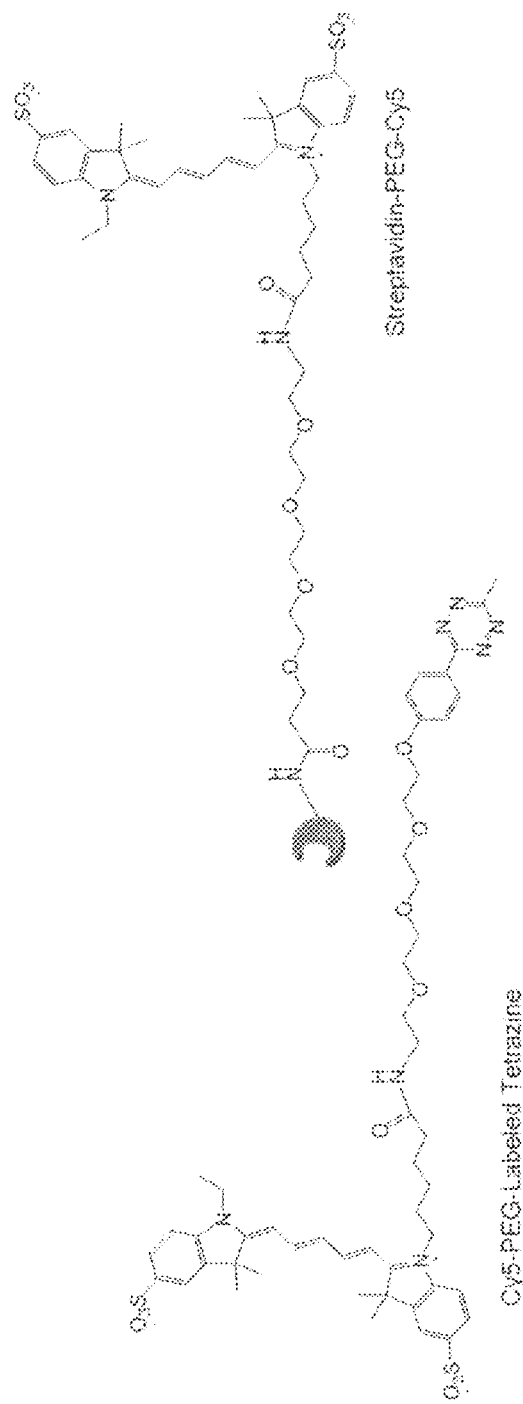

FIGS. 51A-51B: ddNTP-SS-DonorDye-Anchors (ddATP-7-SS-Cy3-Biotin and ddGTP-7-SS-Cy3-TCO), ddNTP-DonorDye-Azo-Anchors (ddTTP-5-Azo-Cy3-TCO or ddTTP-5-SS-Azo-Cy3-TCO and ddCTP-5-Azo-Cy3-Biotin or ddCTP-5-SS-Azo-Cy3-Biotin) and the corresponding Acceptor Dye Labeled Binding Molecules (Cy5 Labeled Streptavidin and Cy5 Labeled Tetrazine) for 1-color DNA SBS using approach delineated in Scheme XVII.

Figure 52:
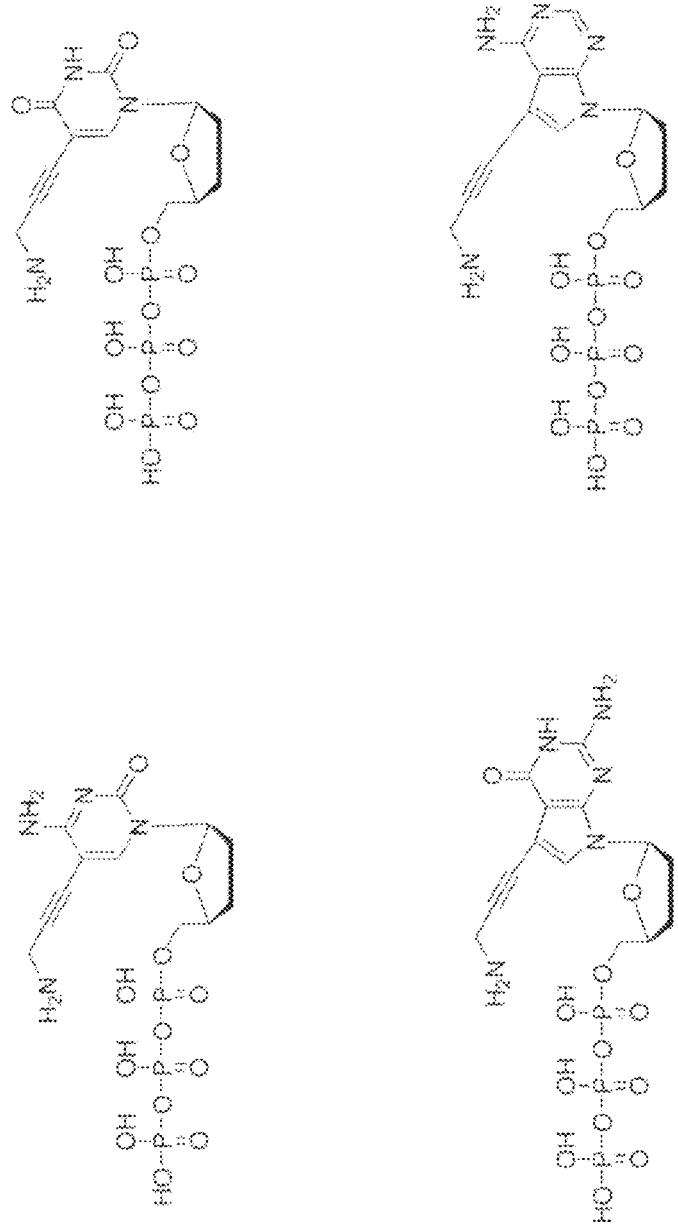

FIG. 52: Structures of ddNTP-PA (ddCTP-5-PA, ddUTP-5-PA, ddGTP-7-PA and ddATP-7-PA) (Guo et al 2008, Ju et al 2016 US 2016/0024574 A1; Hobbs & Trainor 1992 U.S. Pat. No. 5,151,507 A.)

Figure 53:
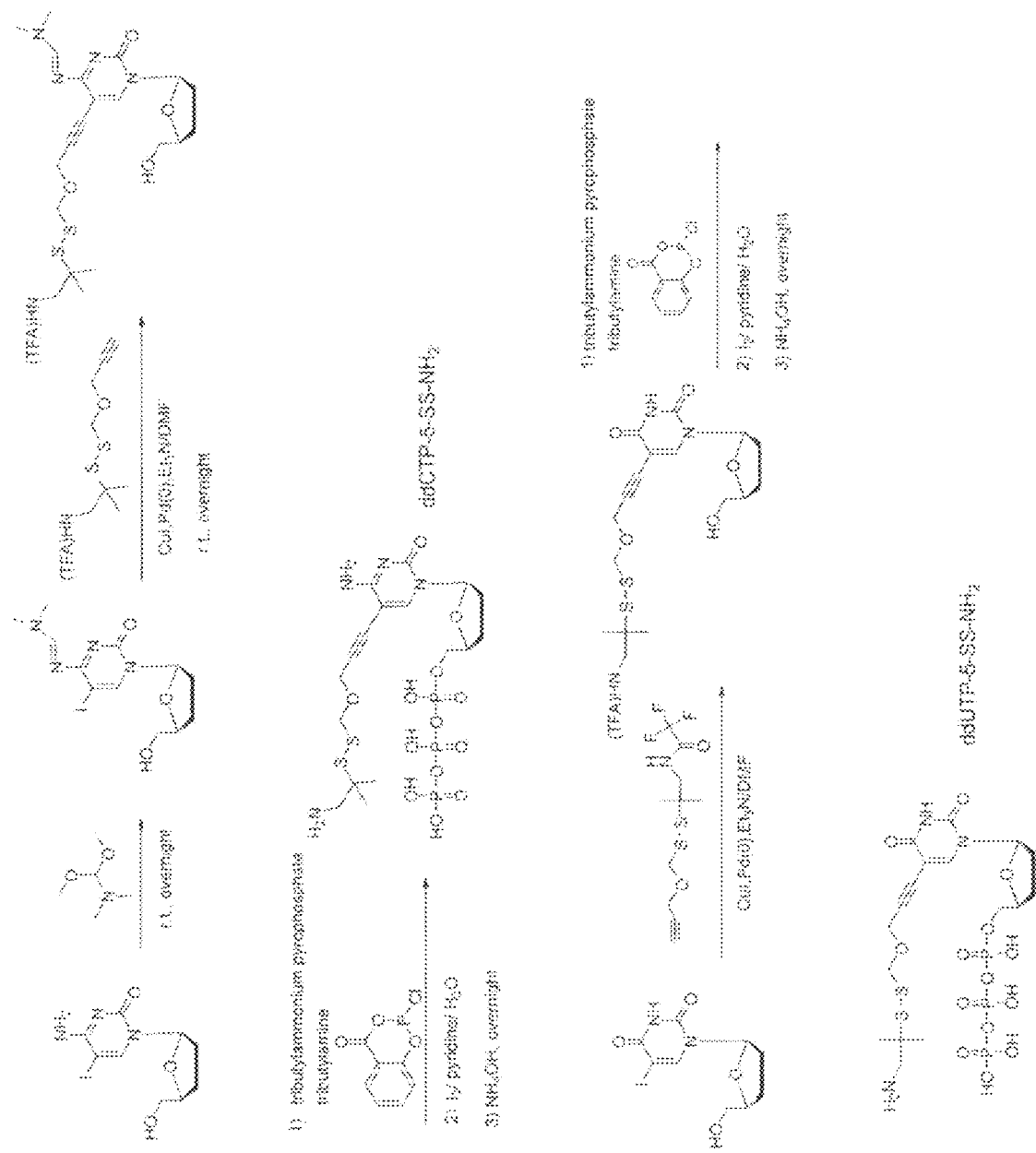

FIG. 53: Synthesis of ddNTP-SS-$NH_2$ (ddCTP-5-SS-$NH_2$ and ddUTP-5-SS-$NH_2$).

Figure 54:
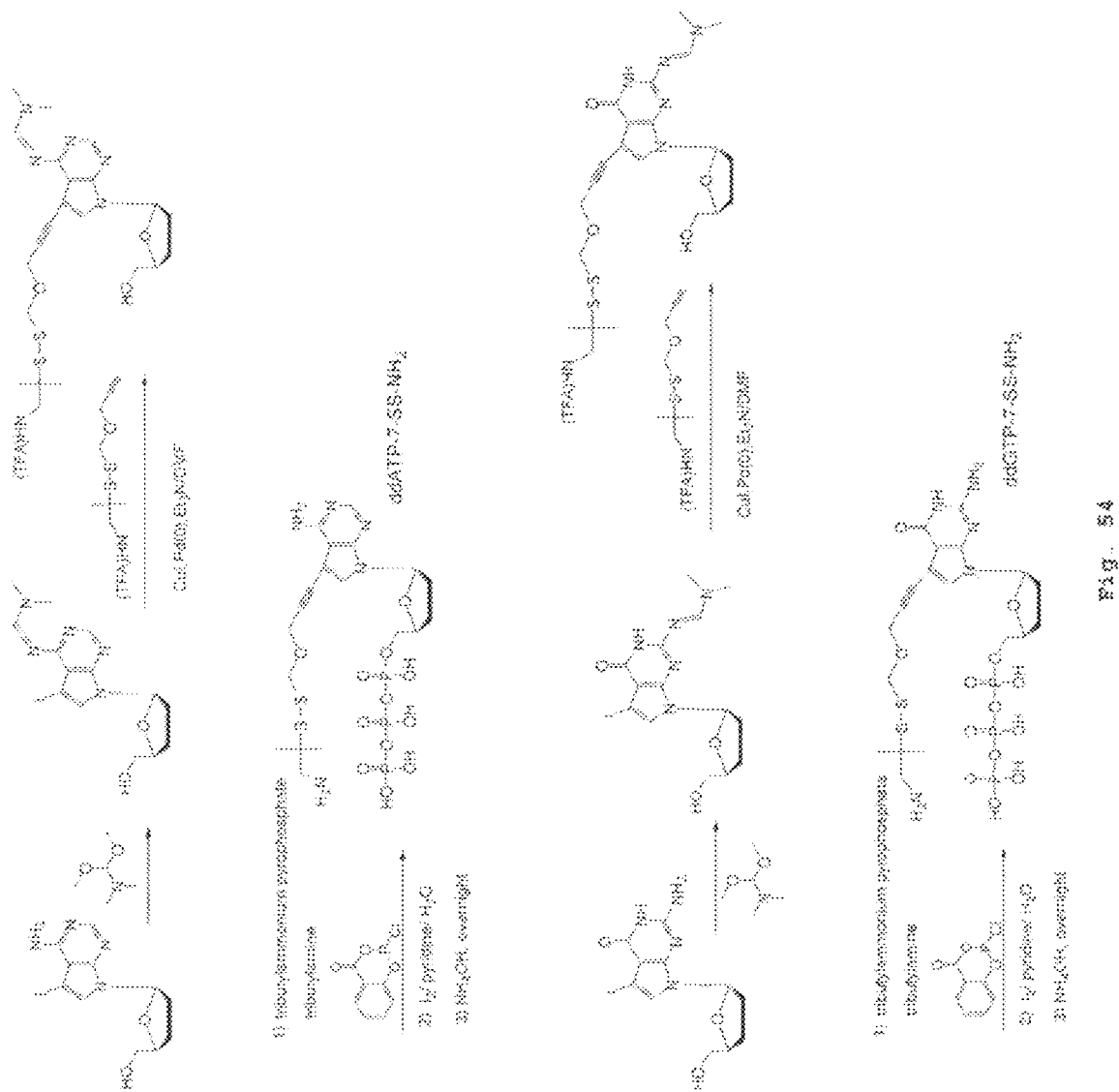

FIG. 54: Synthesis of ddNTP-SS-$NH_2$ (ddGTP-7-SS-$NH_2$ and ddATP-7-SS-$NH_2$).

Figure 55A:
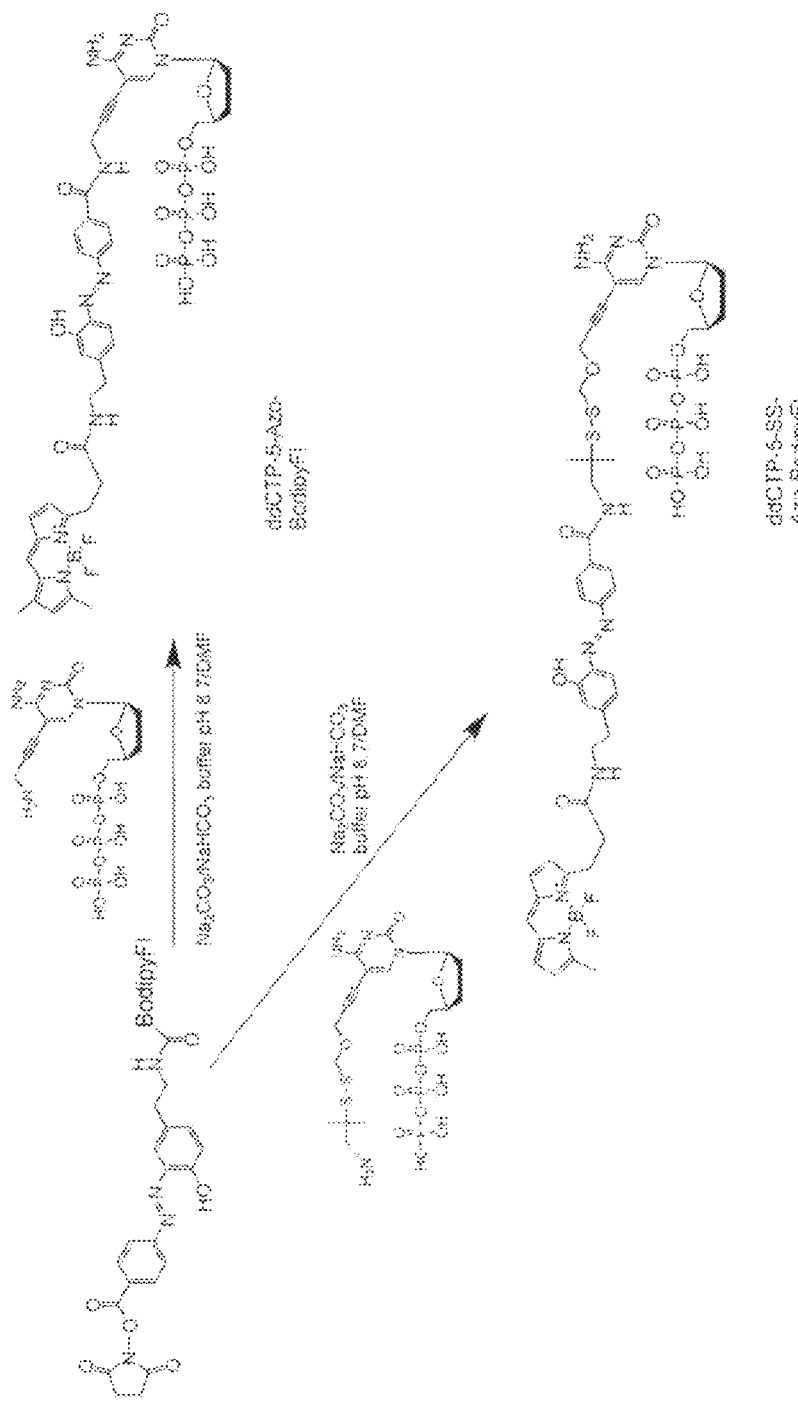
Figure 55B:
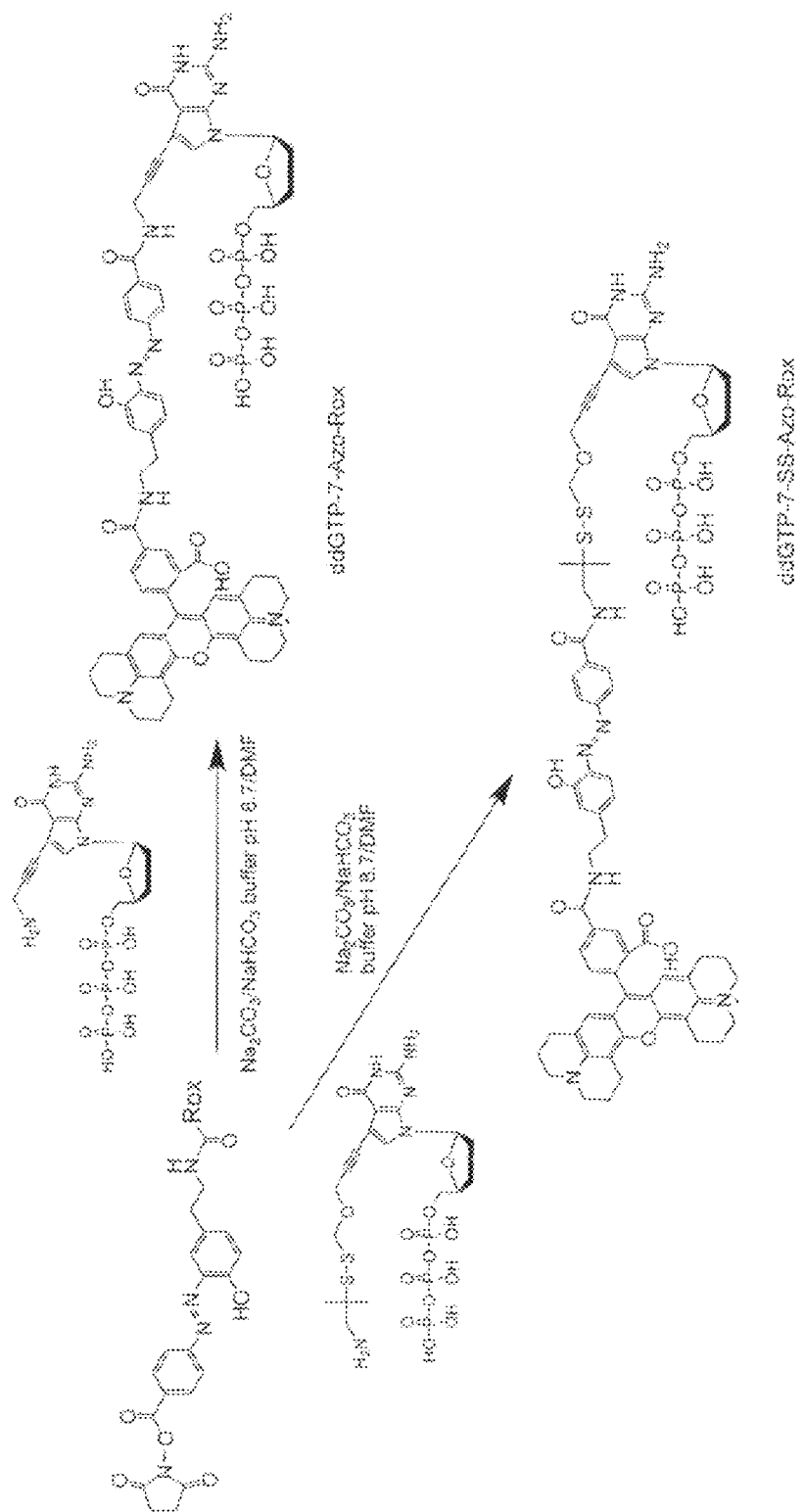

FIGS. 55A-55B: Synthesis of ddNTP-Azo-Dye: ddCTP-5-Azo-BodipyFL and ddGTP-7-Azo-Rox as examples.

Figure 56A:
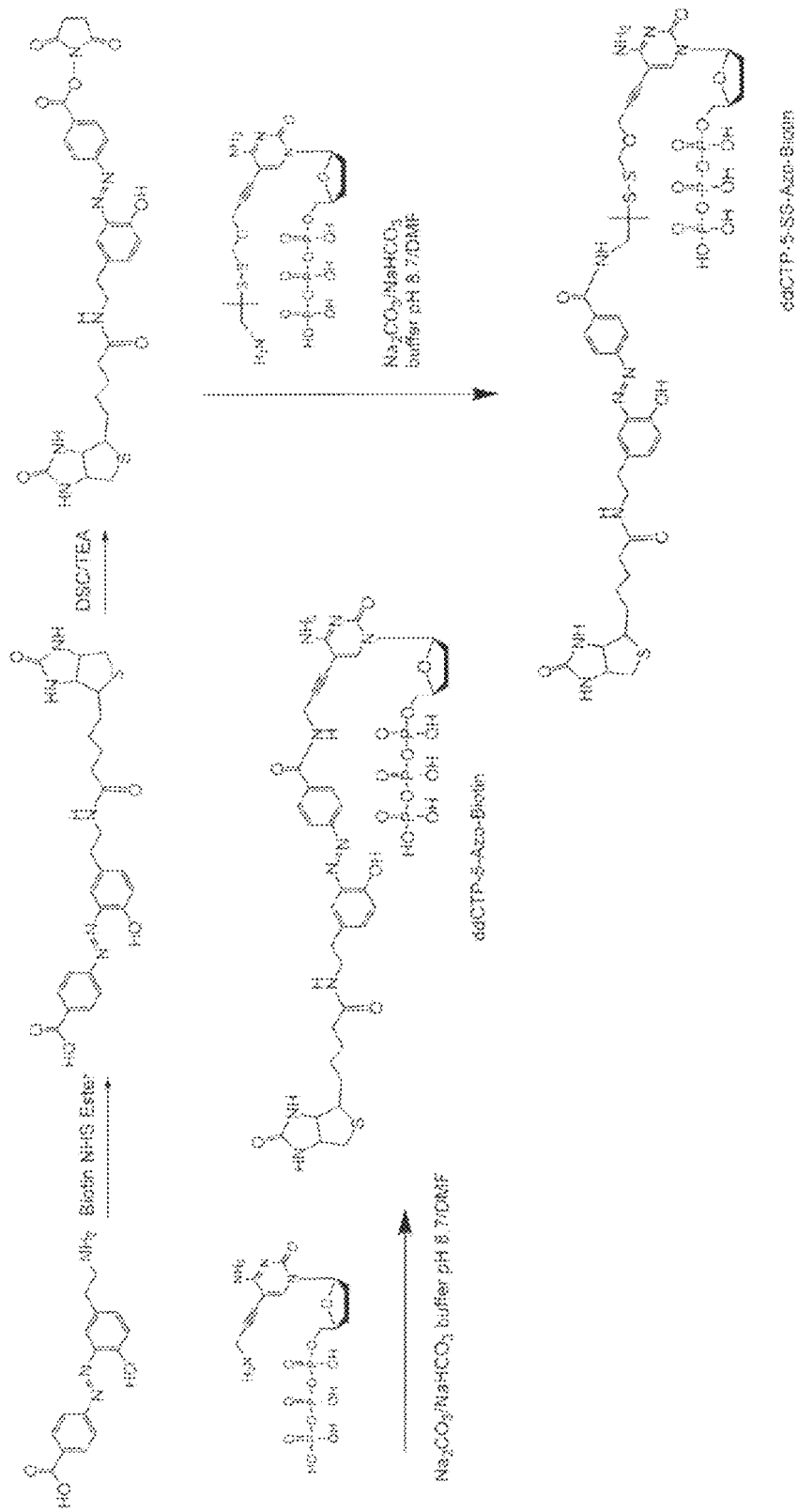
Figure 56B:
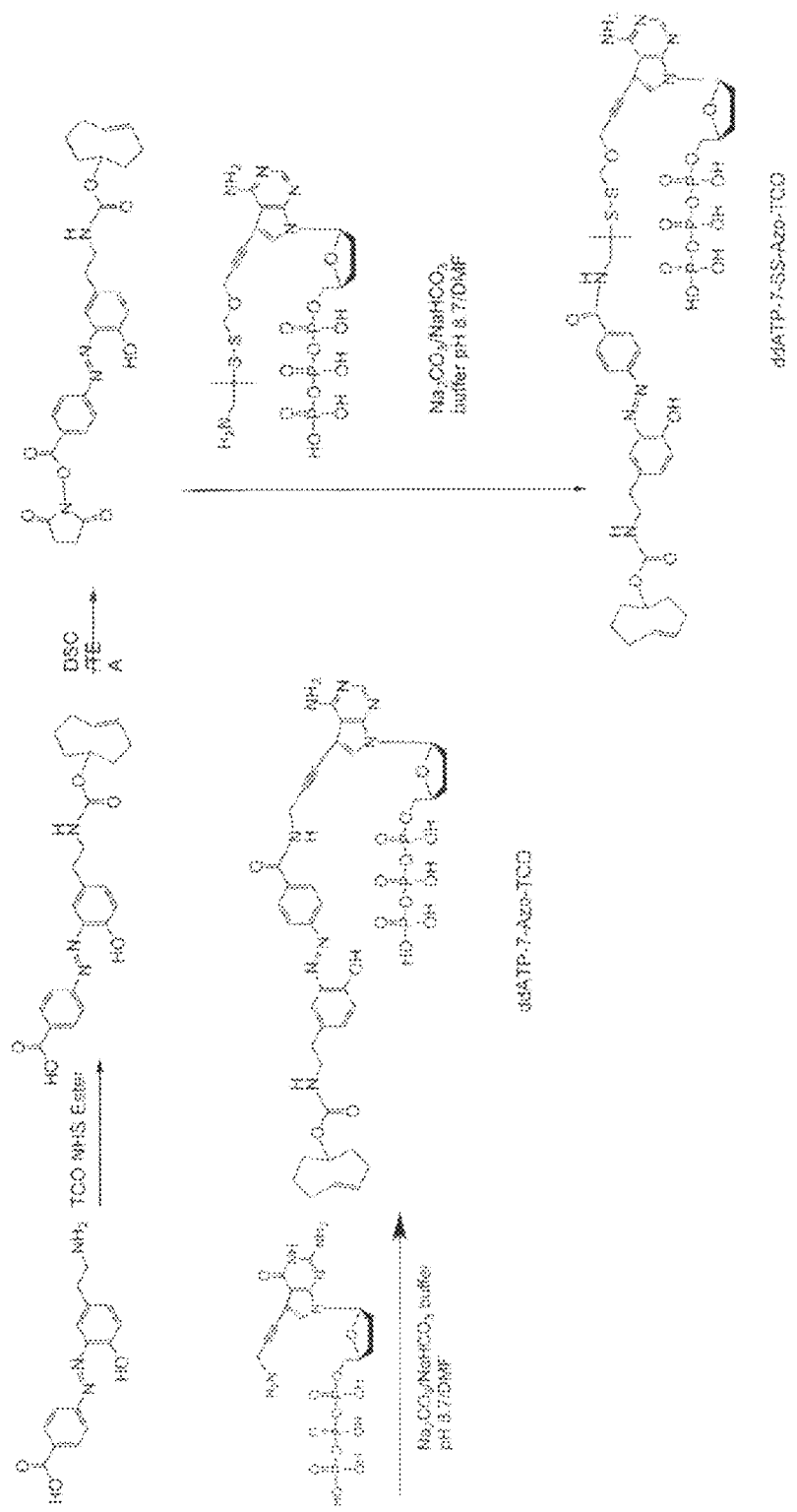

FIGS. 56A-56B: Synthesis of ddNTP-Azo-Anchor: ddCTP-5-Azo-Biotin and ddATP-7-Azo-TCO as examples.

Figure 57:
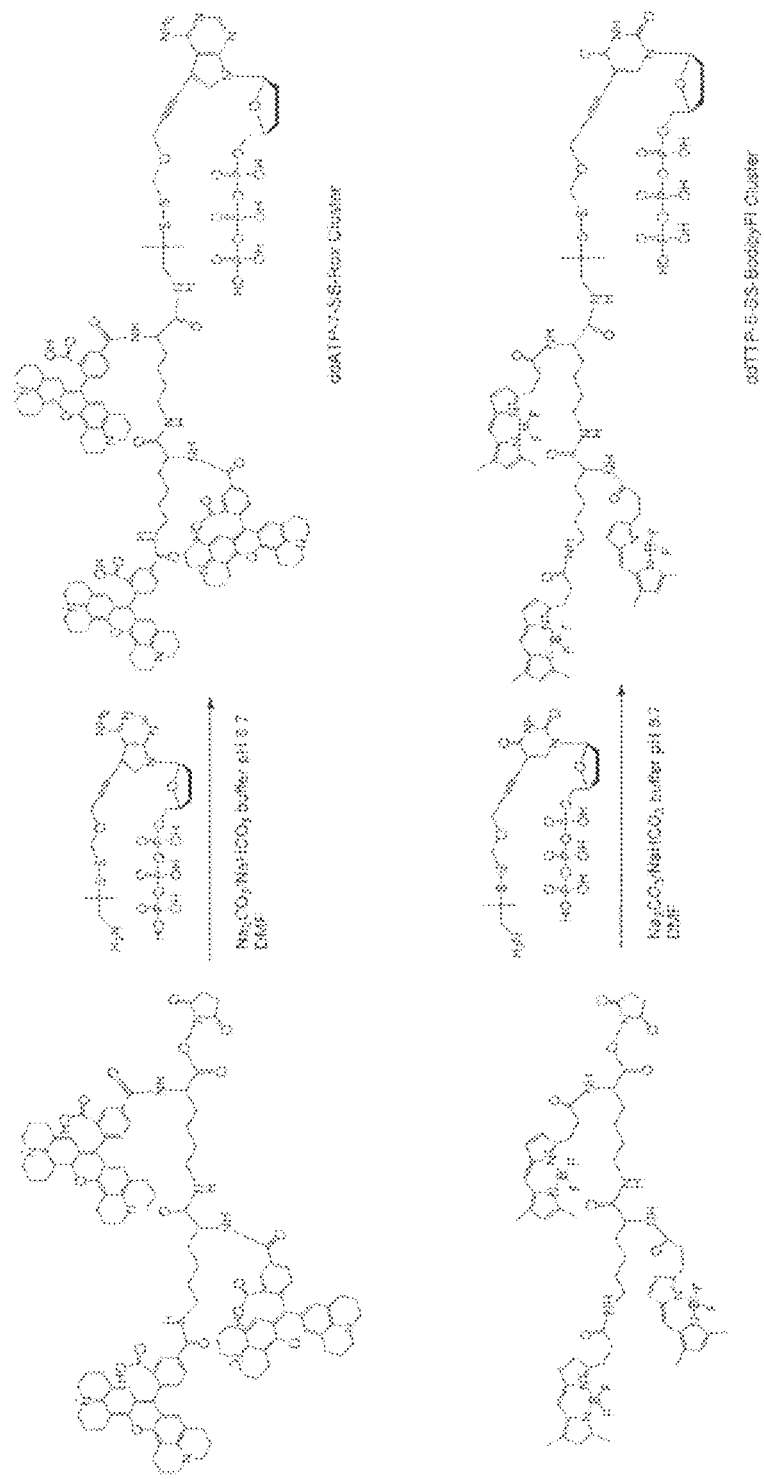

FIG. 57: Synthesis of ddNTP-SS-Dye Cluster: ddATP-7-SS-Rox Cluster and ddTTP-5-SS-BodipyFL Cluster as examples.

Figure 58:
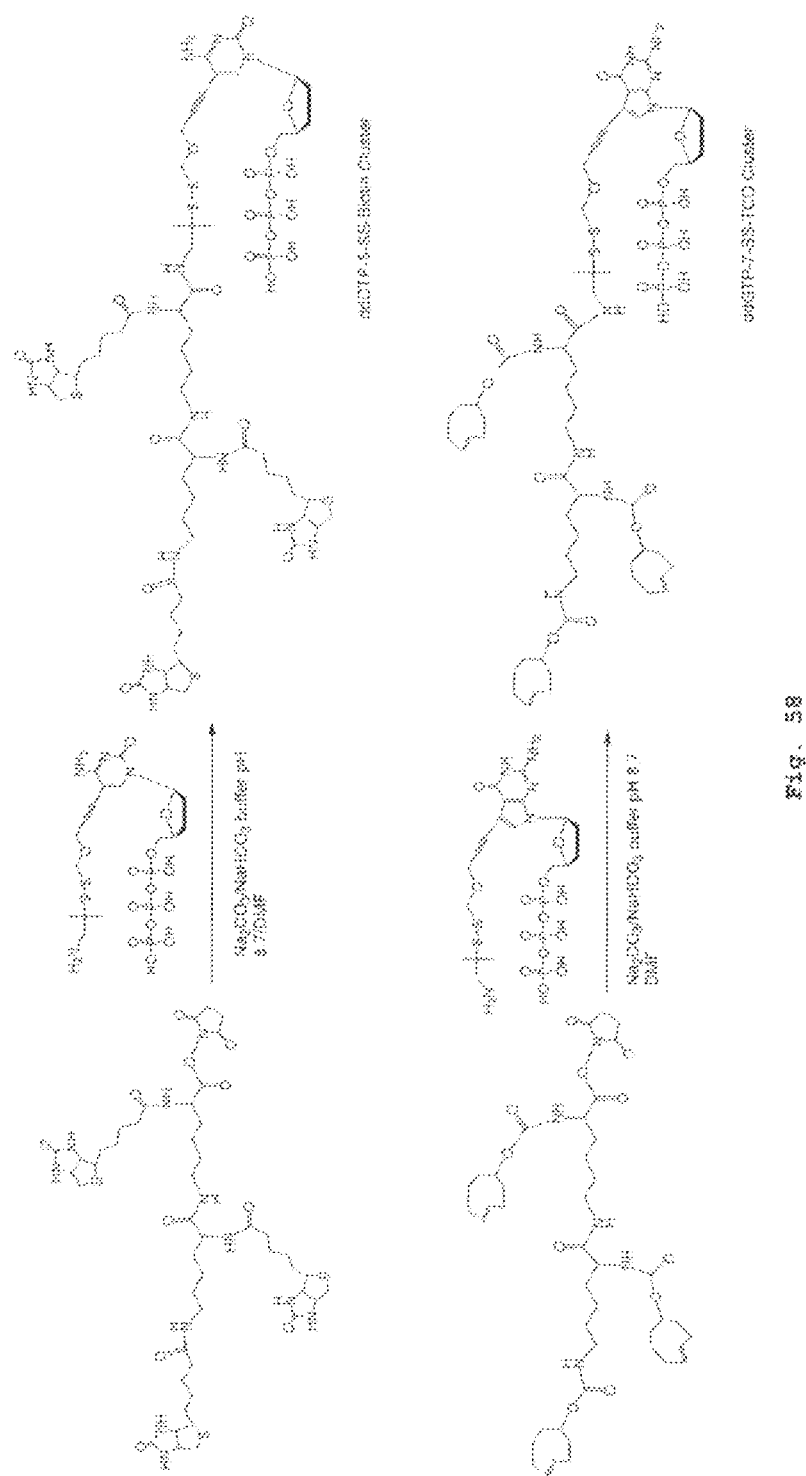

FIG. 58: Synthesis of ddNTP-SS-Anchor Cluster: ddCTP-5-SS-Biotin Cluster and ddGTP-7-SS-TCO Cluster as examples.

Figure 59:
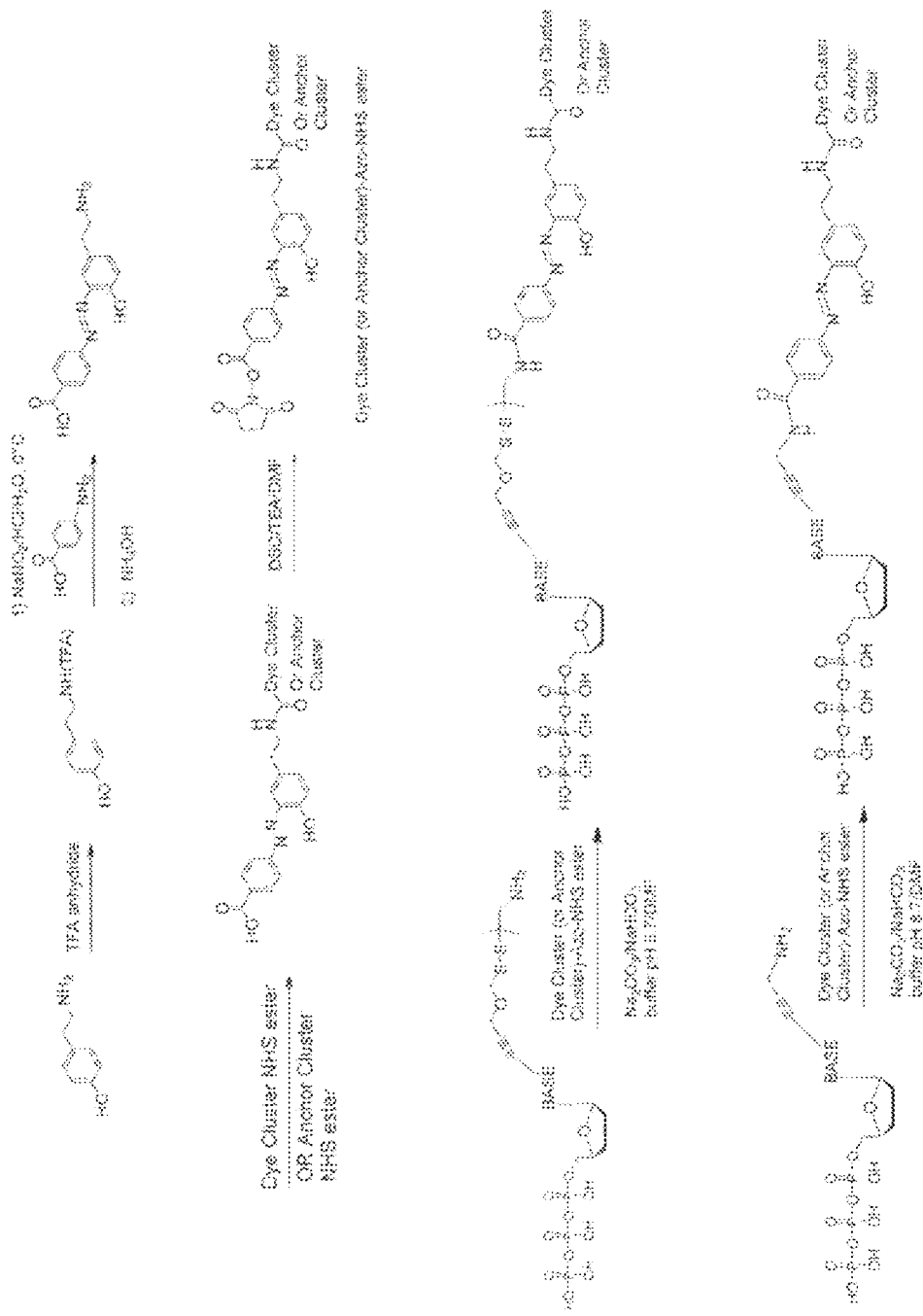

FIG. 59: General synthesis of ddNTP-Azo-Dye or -Anchor Cluster.

Figure 60:
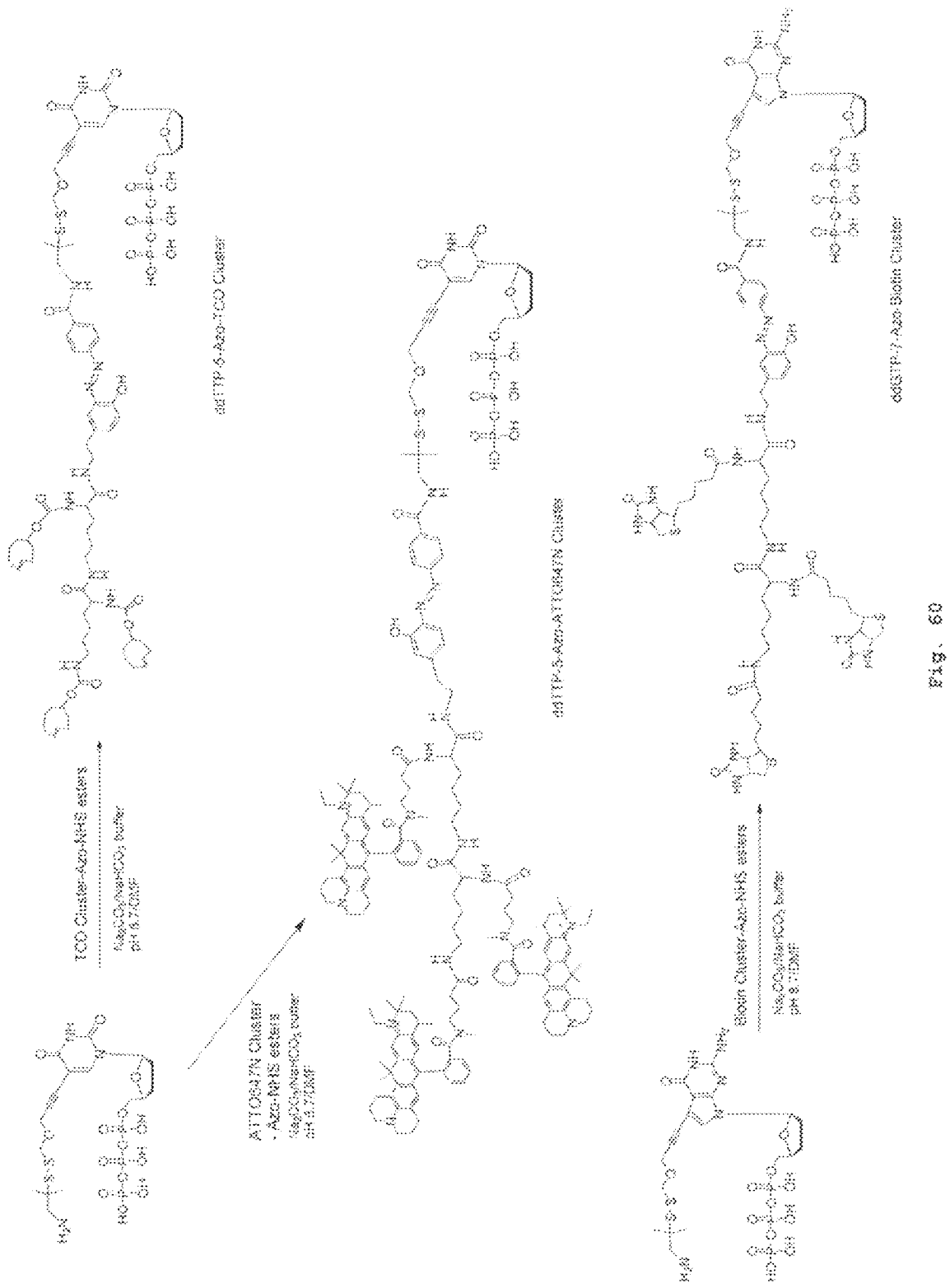

FIG. 60: Synthesis of ddNTP-Azo-Dye or Anchor Cluster: ddTTP-5-Azo-TCO Cluster, ddTTP-5-Azo-ATTO647N Cluster and ddGTP-7-Azo-Biotin Cluster as examples.

Figure 61:
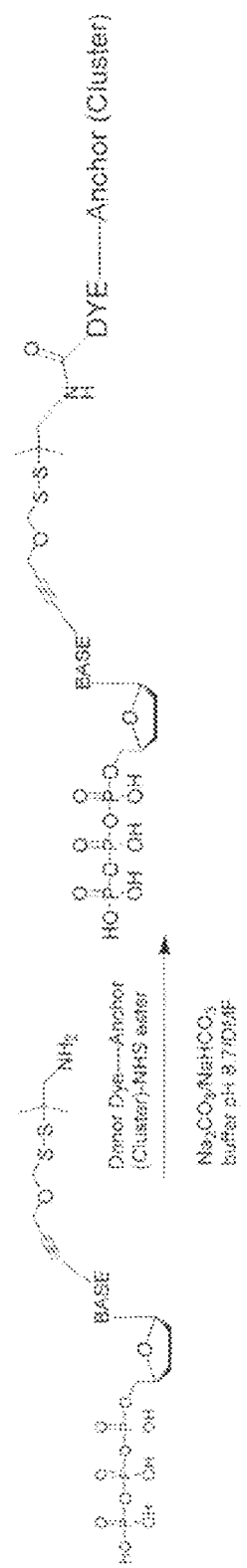
Figure 52:
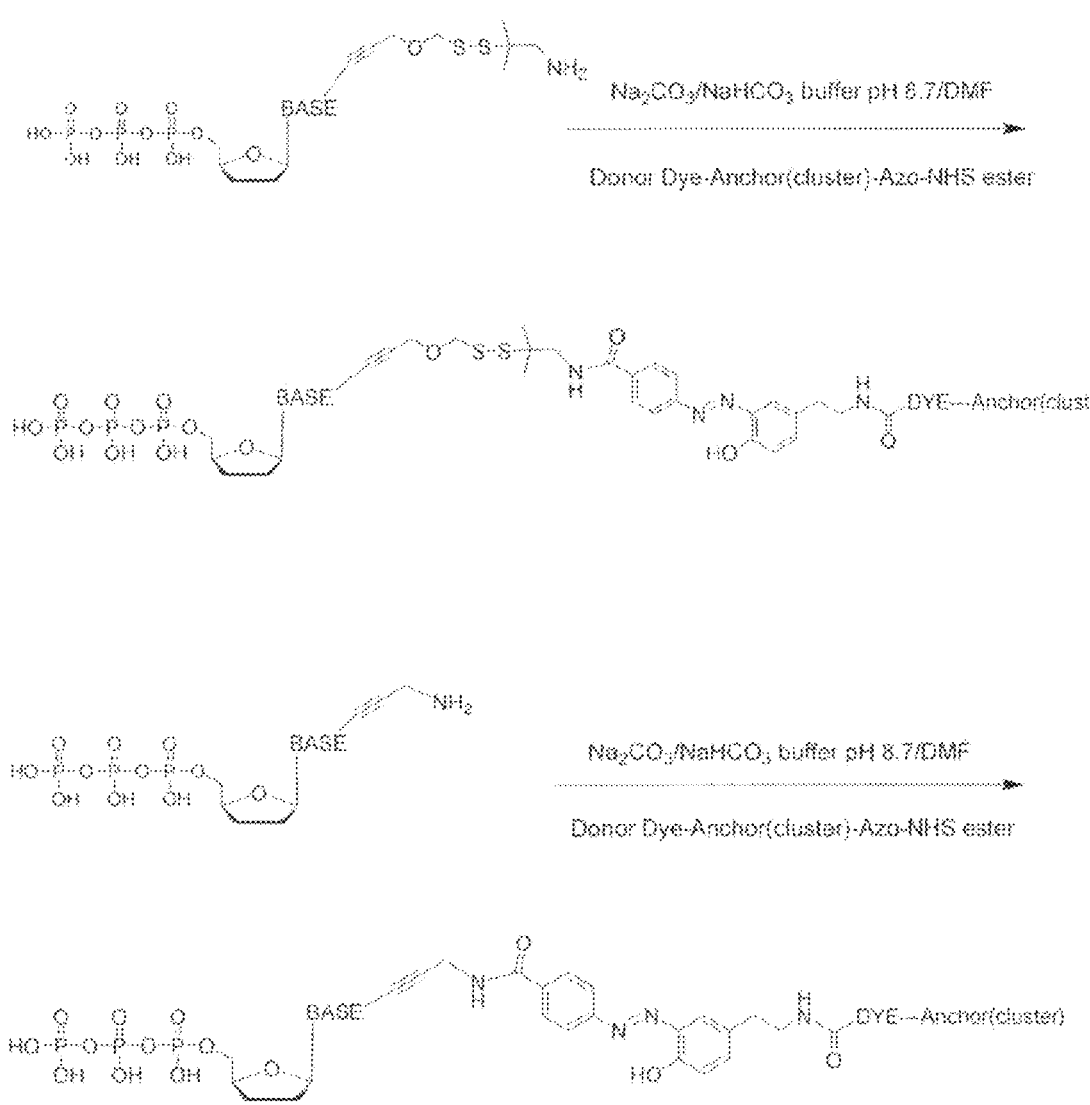

FIG. 61: General synthesis of ddNTP-Donor Dye-Anchor (or Anchor cluster).

FIG. 62: General synthesis of ddNTP-AzoLinker-Donor-Dye-Anchor.

Figure 63:
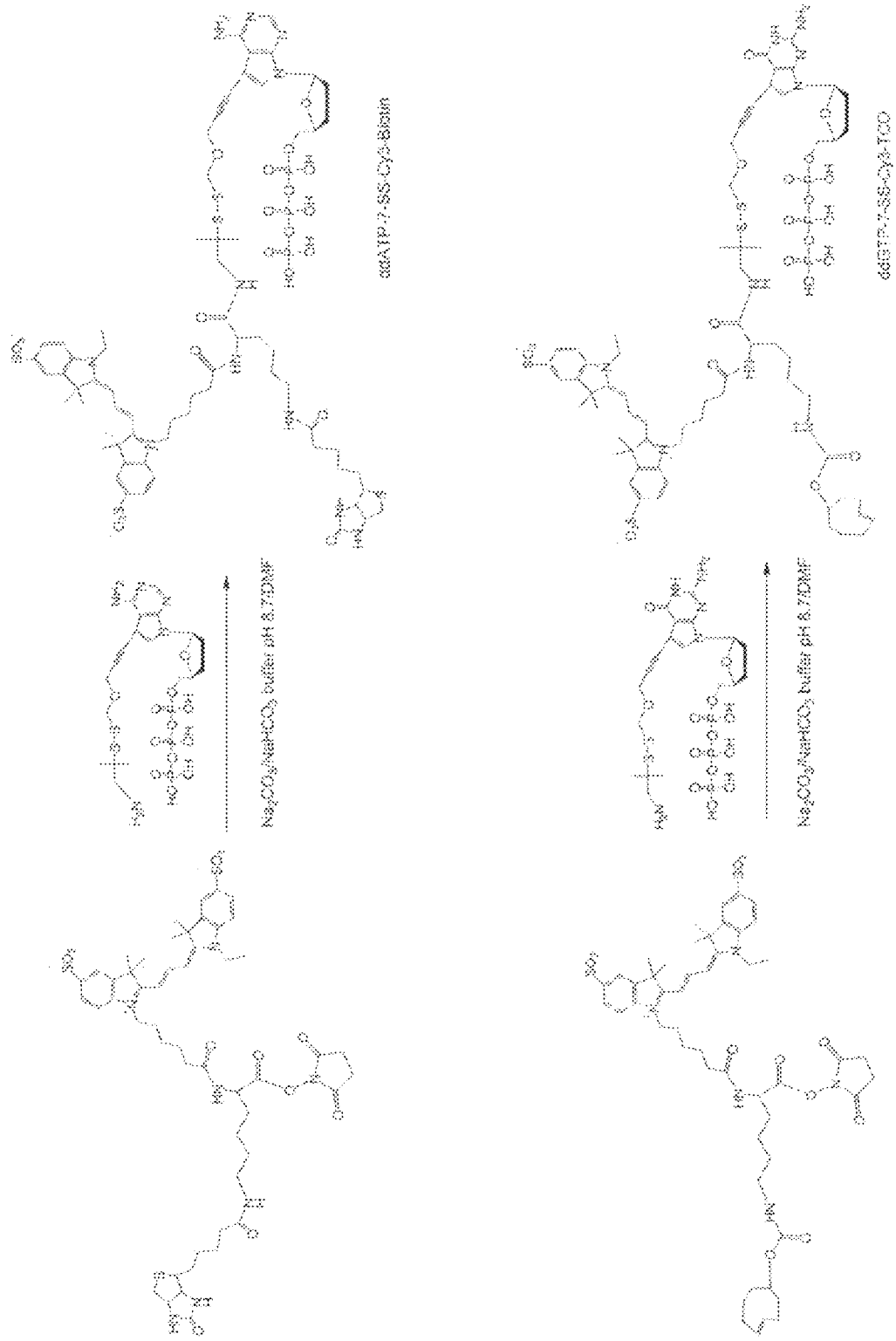

FIG. 63: Synthesis of ddNTP-SS-Dye-Anchor: ddATP-7-SS-Cy3-Biotin and ddGTP-7-SS-Cy3-TCO as examples.

Figure 64A:
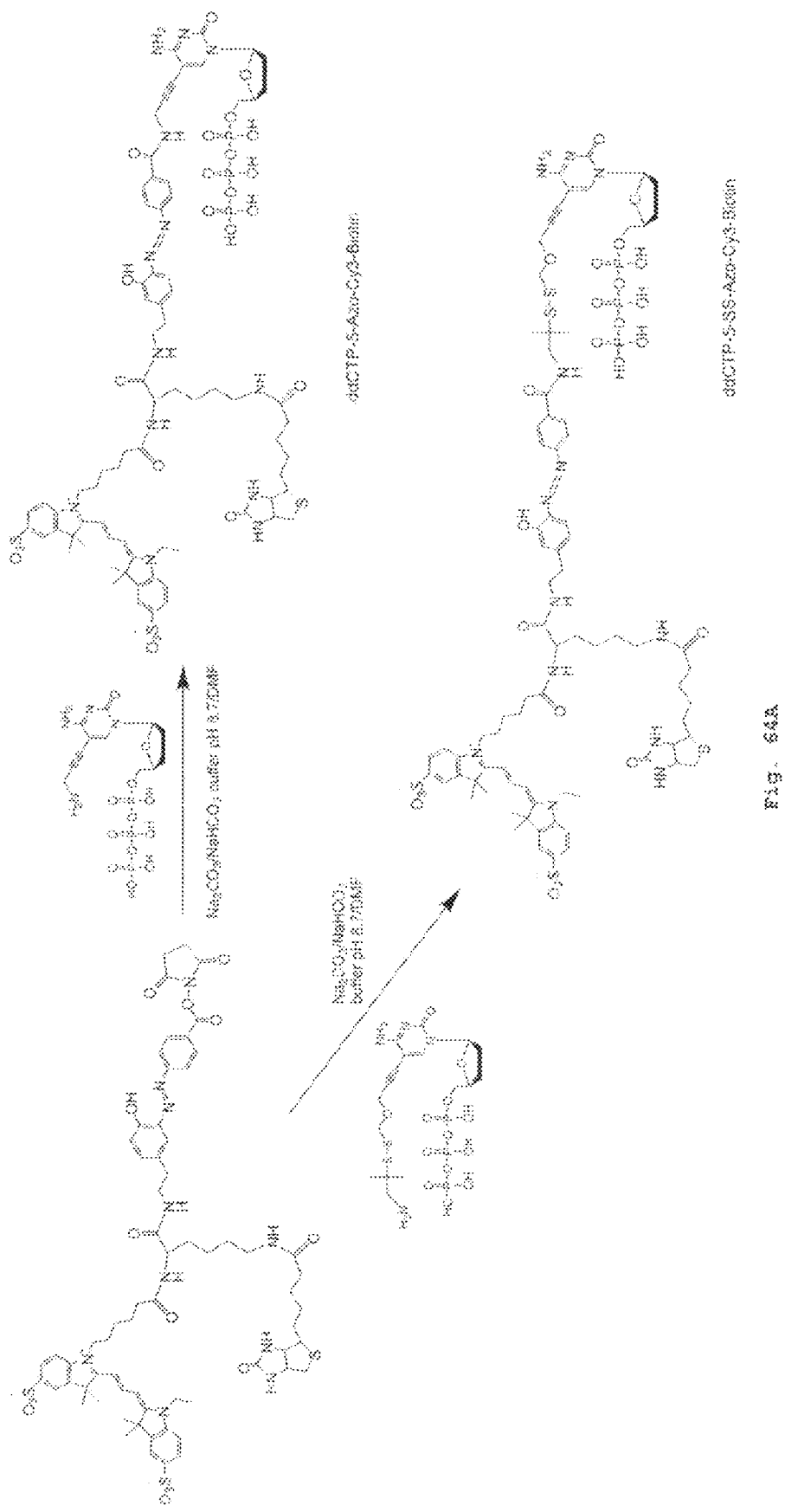
Figure 64B:
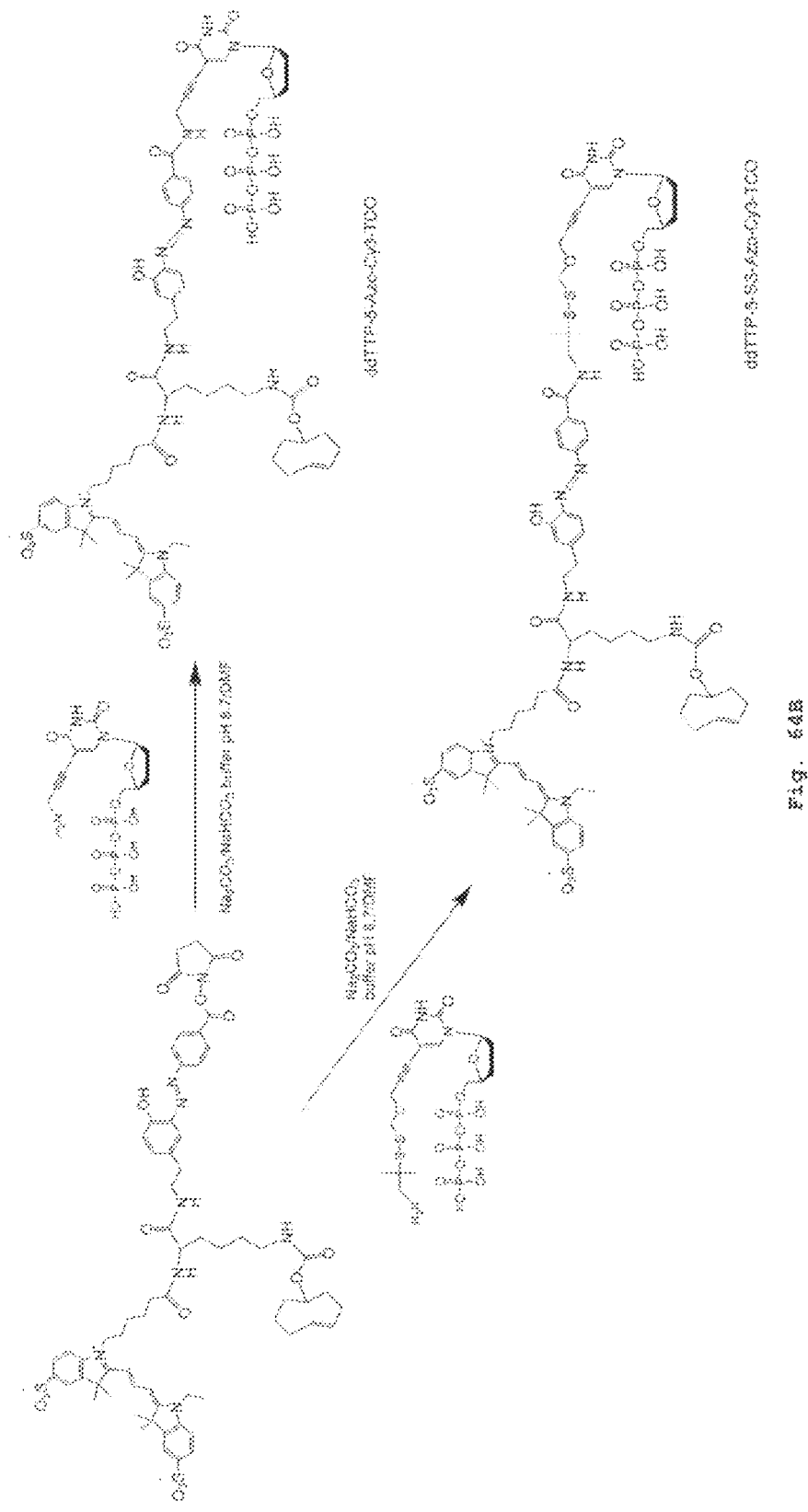

FIGS. 64A-64B: Synthesis of ddNTP-Azo-Dye-Anchor: ddCTP-5-Azo-Cy3-Biotin and ddUTP-5-Azo-Cy3-TCO as examples.

Figure 65A:
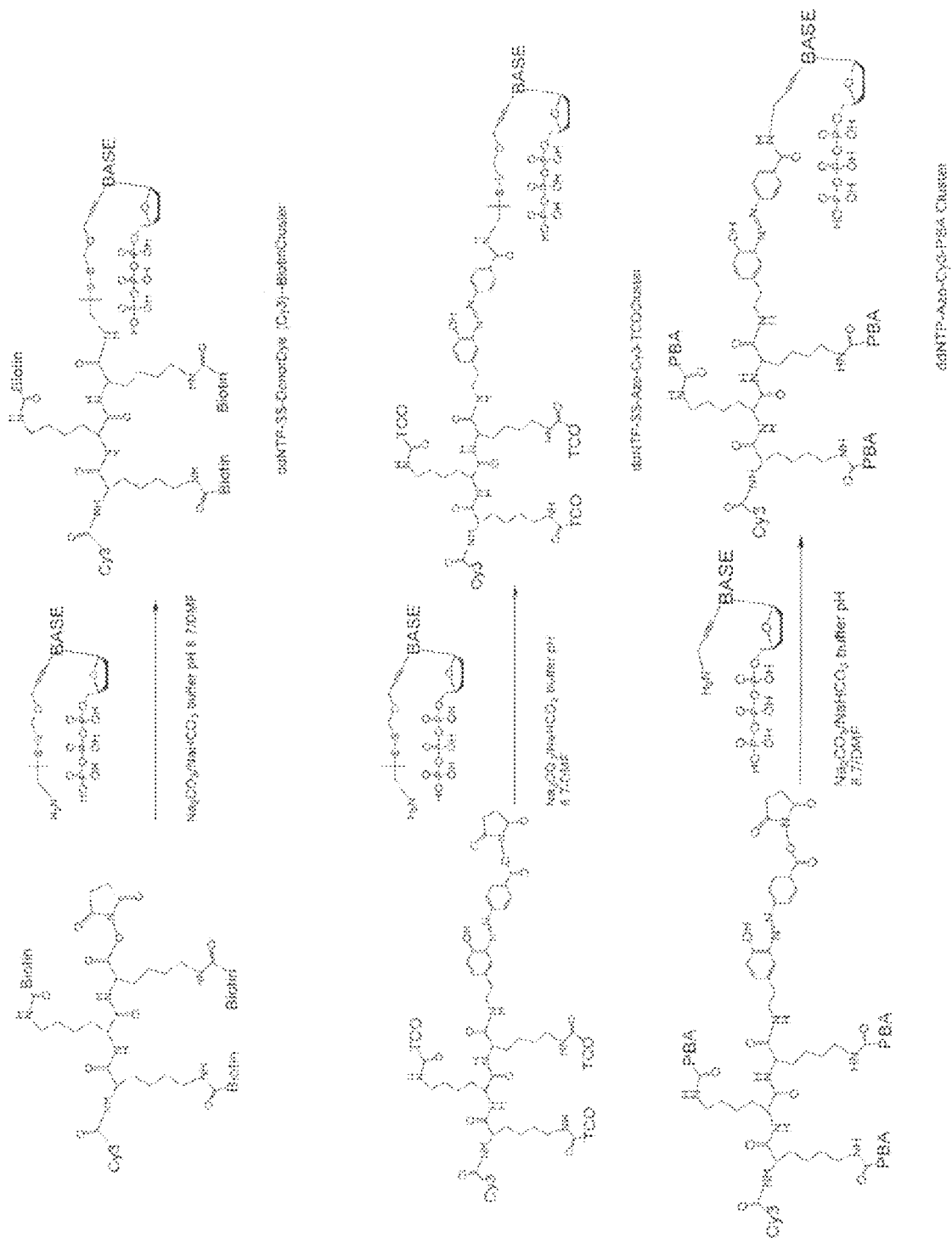

FIG. 65A: Example synthesis of ddNTP-Cleavable Linker (SS or Azo as examples)-Donor Dye (Cy3 as example)-Anchor Clusters (Biotin, TCO or PBA as examples).

Figure 65B:
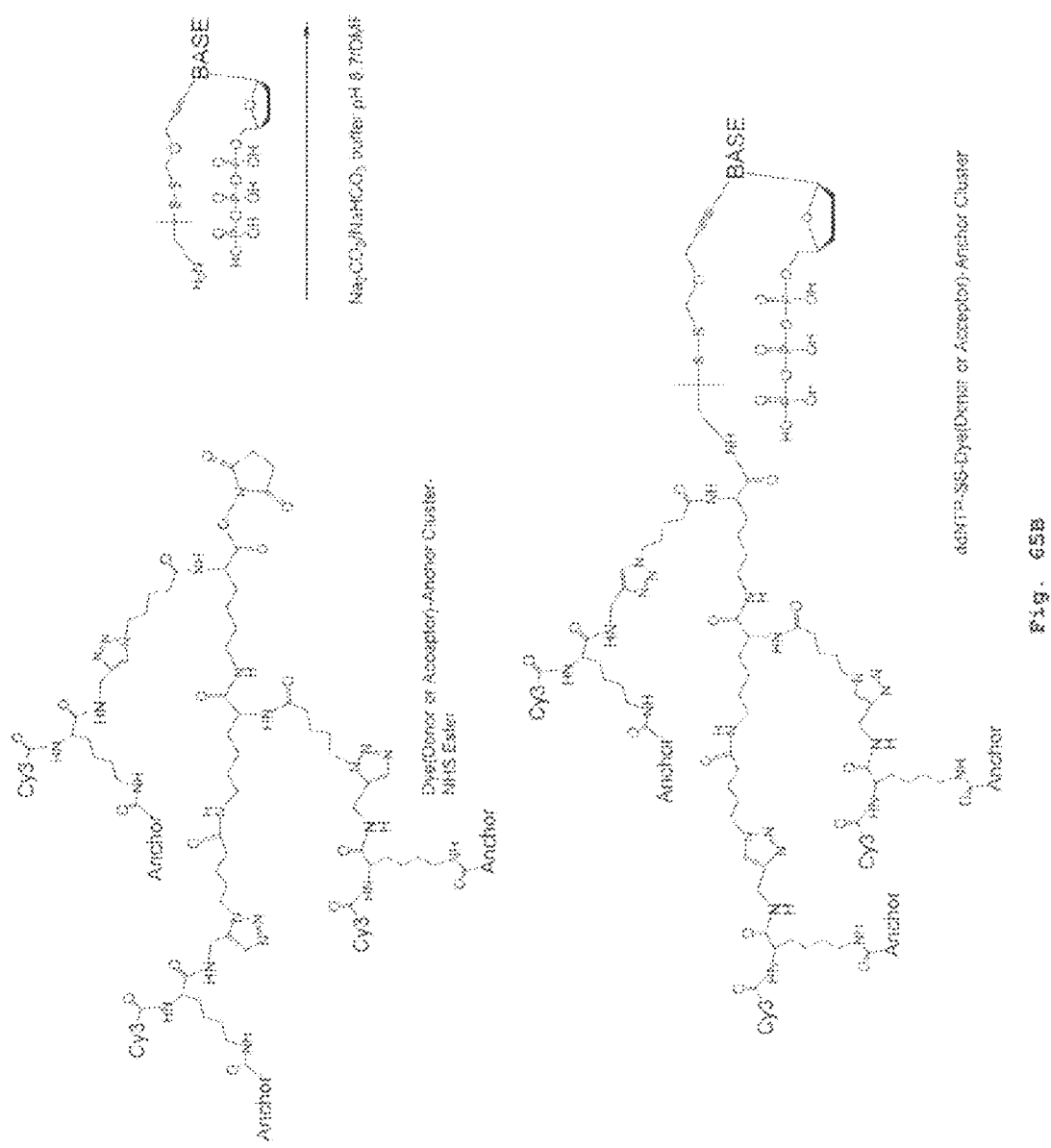

FIG. 65B: General synthesis of ddNTP-SS-Dye (Donor or Acceptor)-Anchor Cluster.

Figure 65C:
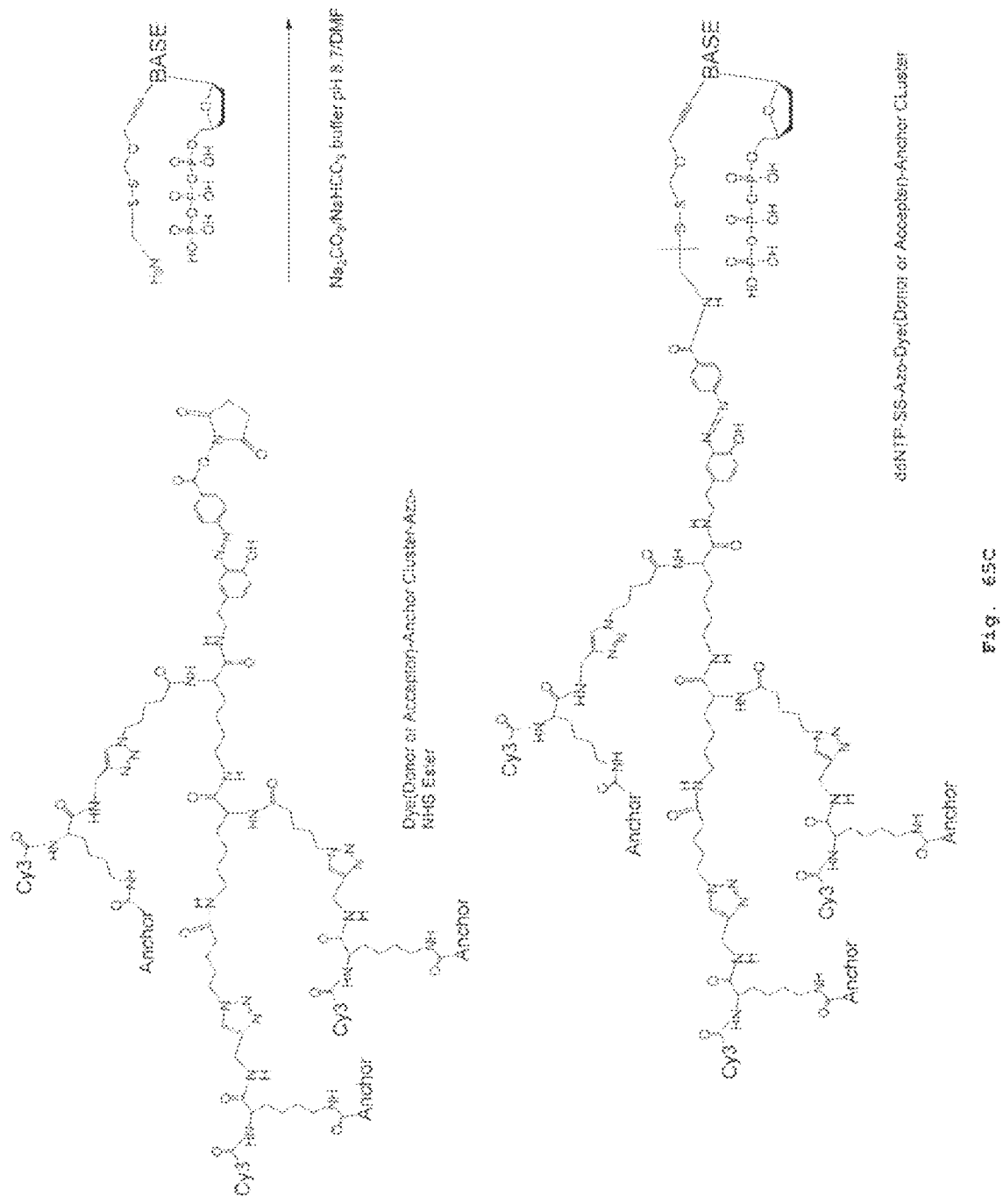

FIG. 65C: General synthesis of ddNTP-SS-Azo-Dye (Donor or Acceptor)-Anchor Cluster.

Figure 65D:
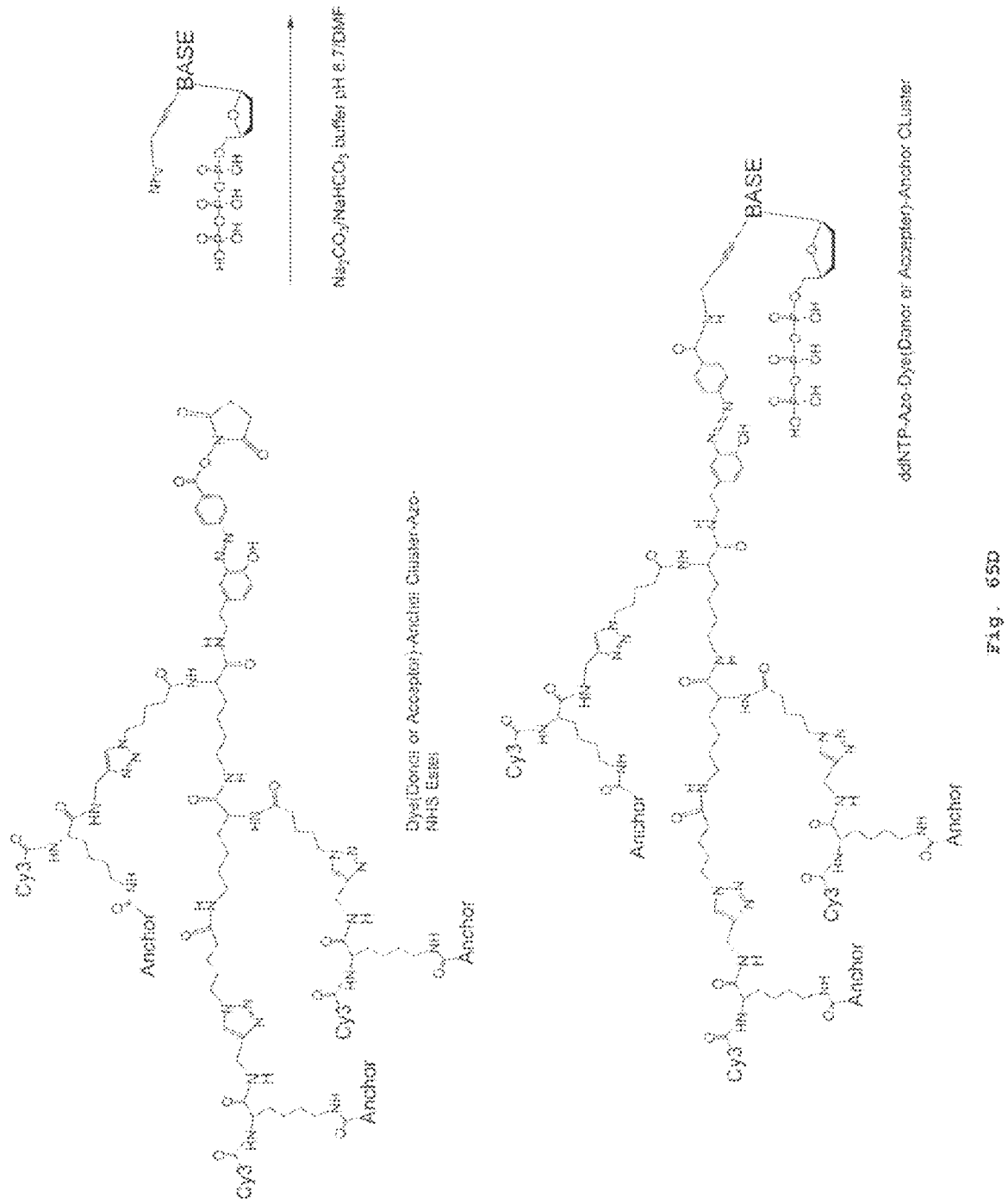

FIG. 65D: General synthesis of ddNTP-Azo-Dye (Donor or Acceptor)-Anchor Cluster.

FIG. 66: A schematic showing the General Scheme VIII for hybrid sequencing using four ddNTP-Cleavable Linker-Dye nucleotide analogues and four nucleotide reversible terminators.

Figure 67A:
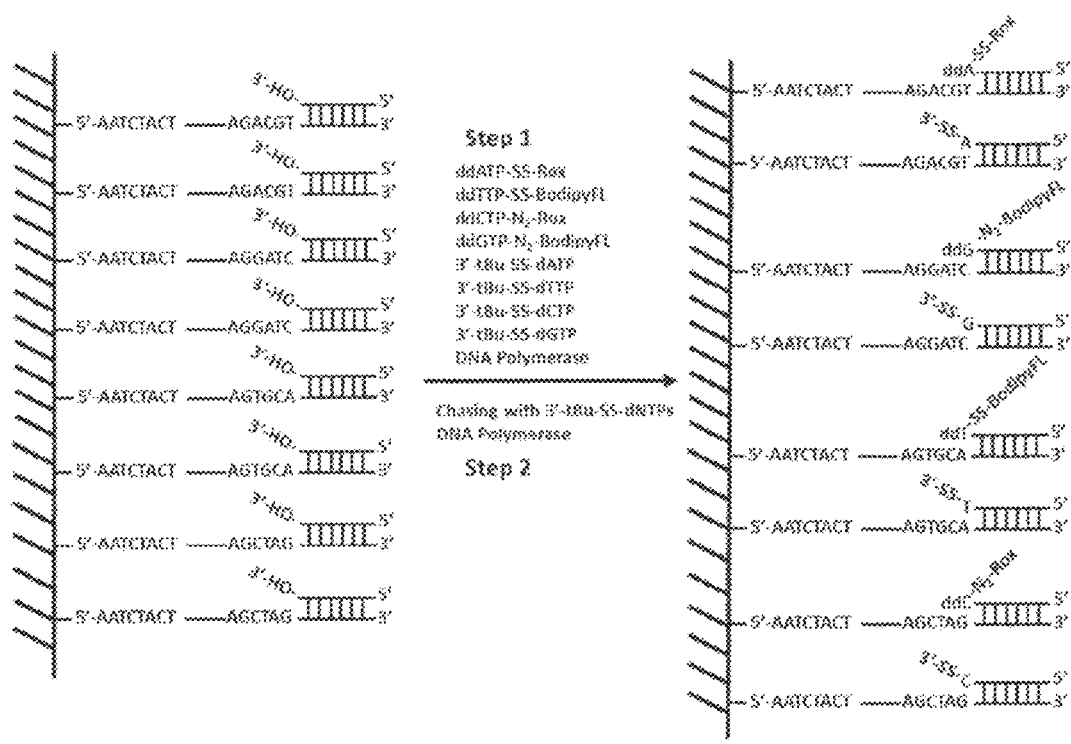
Figure 67B:
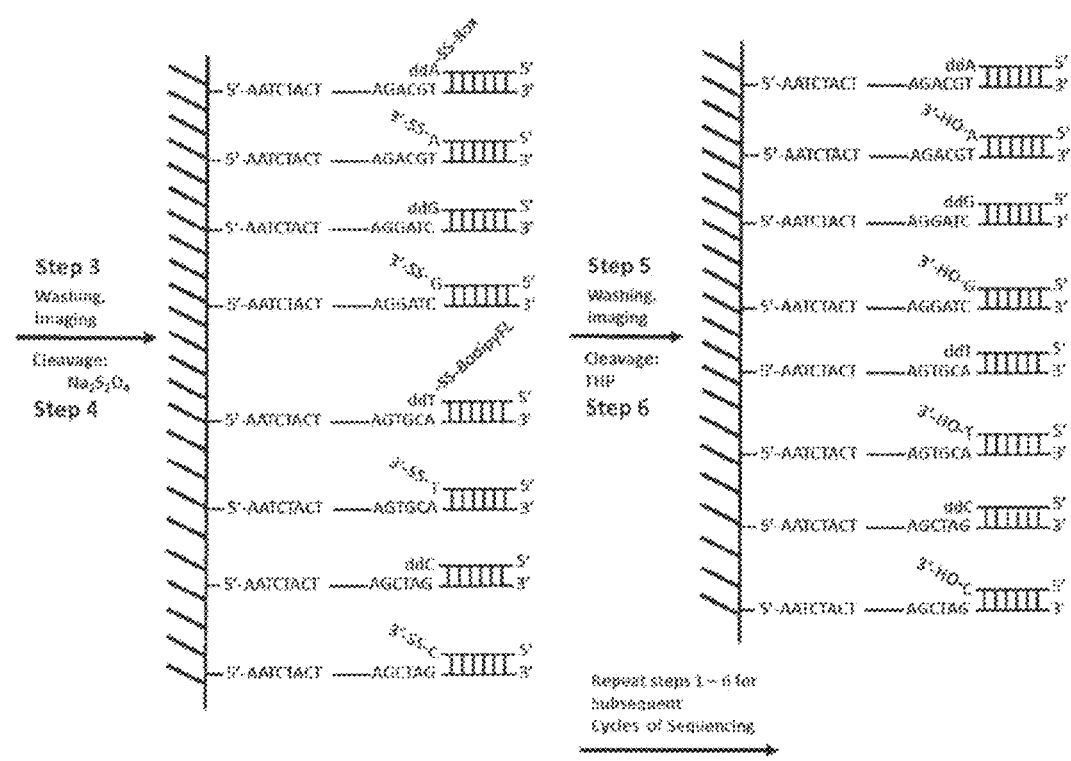

FIGS. 67A-67B: A schematic showing Scheme IX using ddNTP-SS-Dyes (ddATP-7-SS-Rox, ddTTP-5-SS-BodipyFL), ddNTP-Azo-Dyes (ddGTP-7-Azo-BodipyFL, ddCTP-5-Azo-Rox), and 3'-O-SS-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS.

Figure 68A:
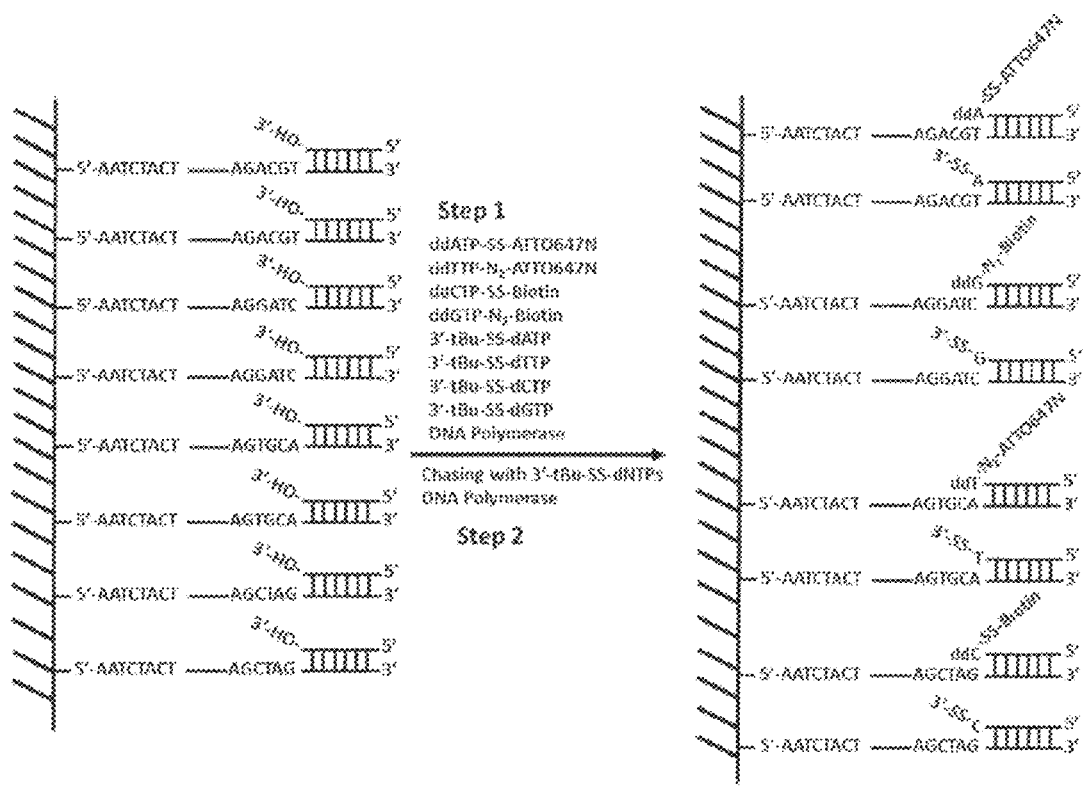
Figure 68B:
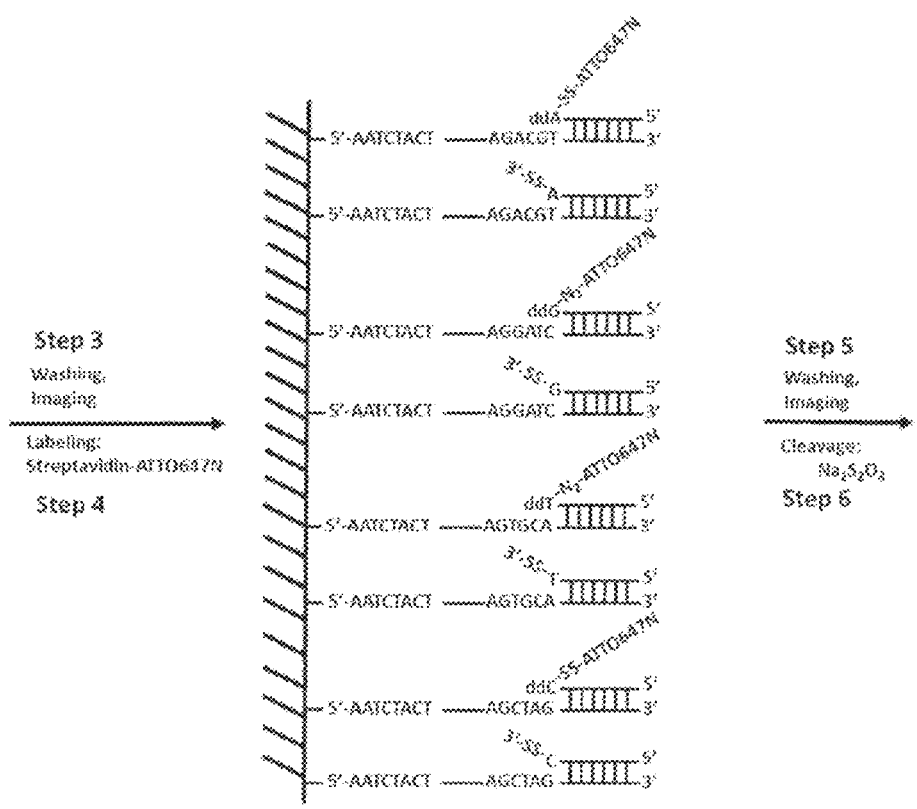
Figure 68C:
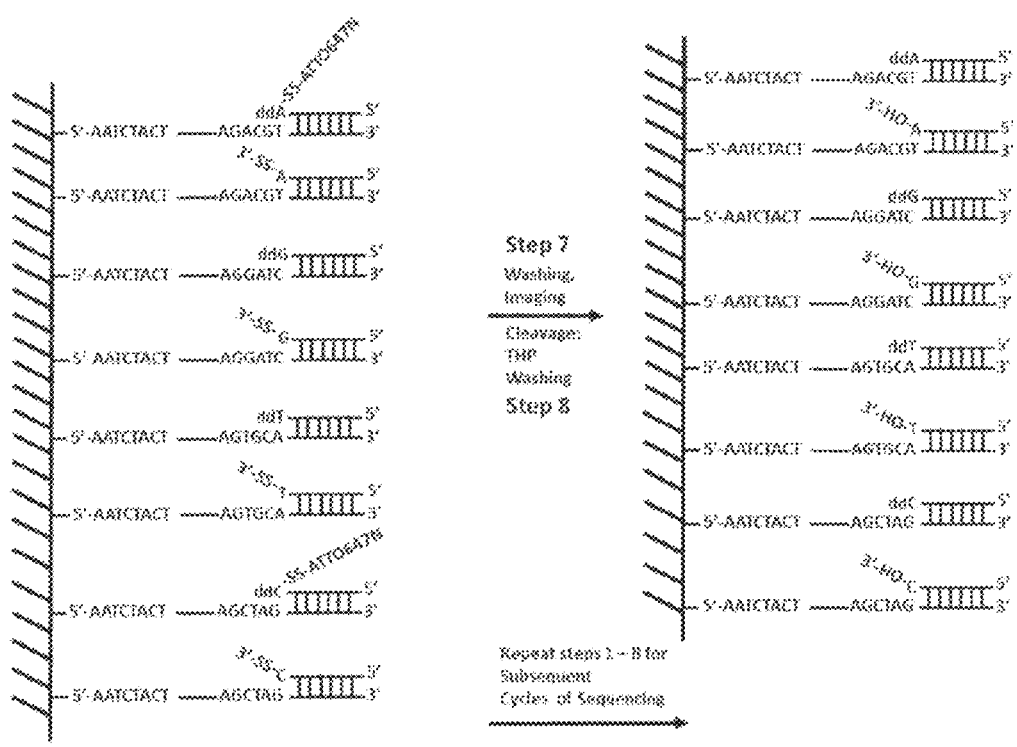
Figure 69A:
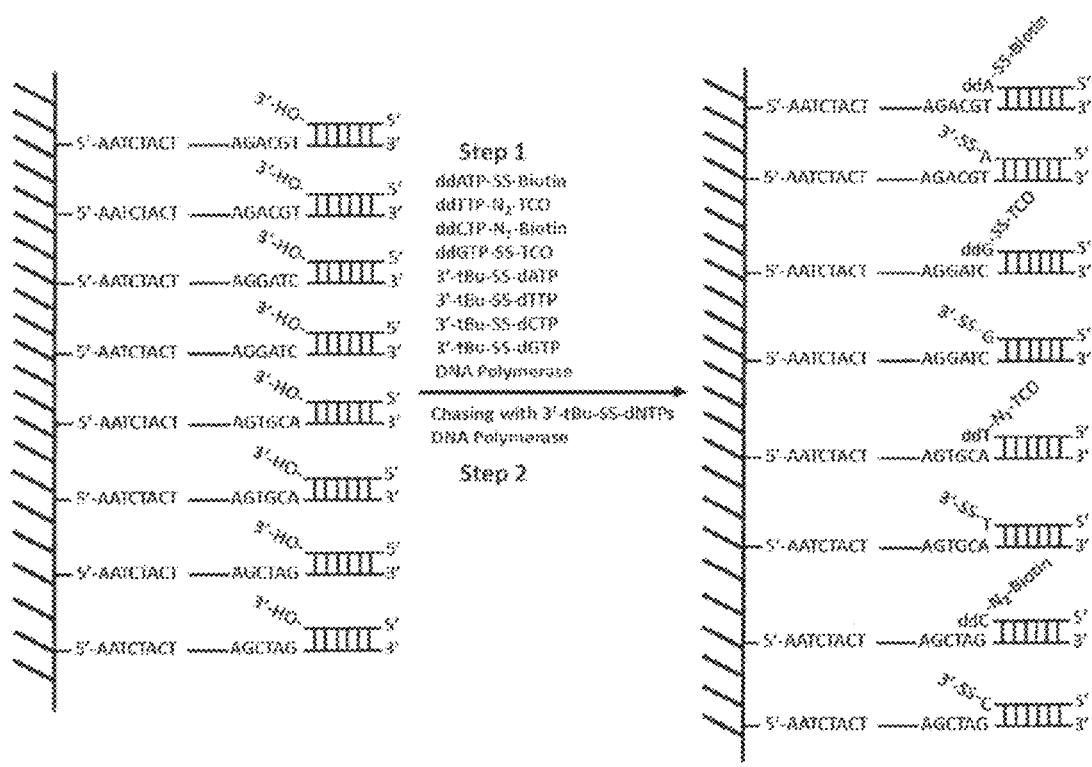
Figure 69B:
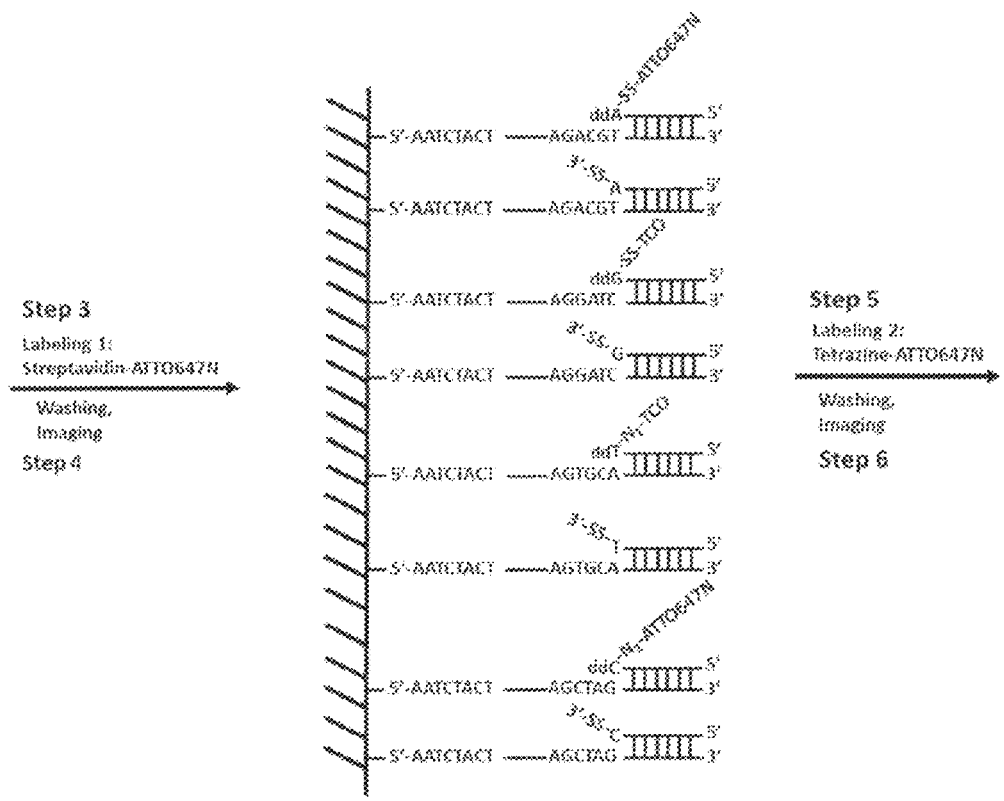
Figure 69C:
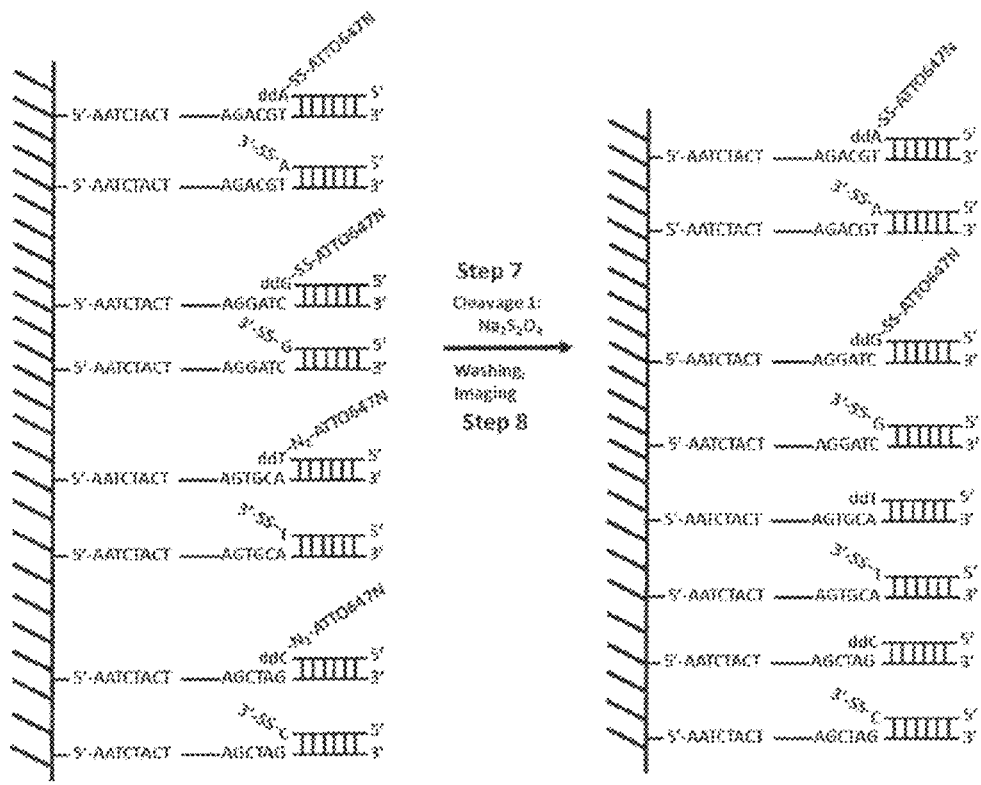
Figure 69D:
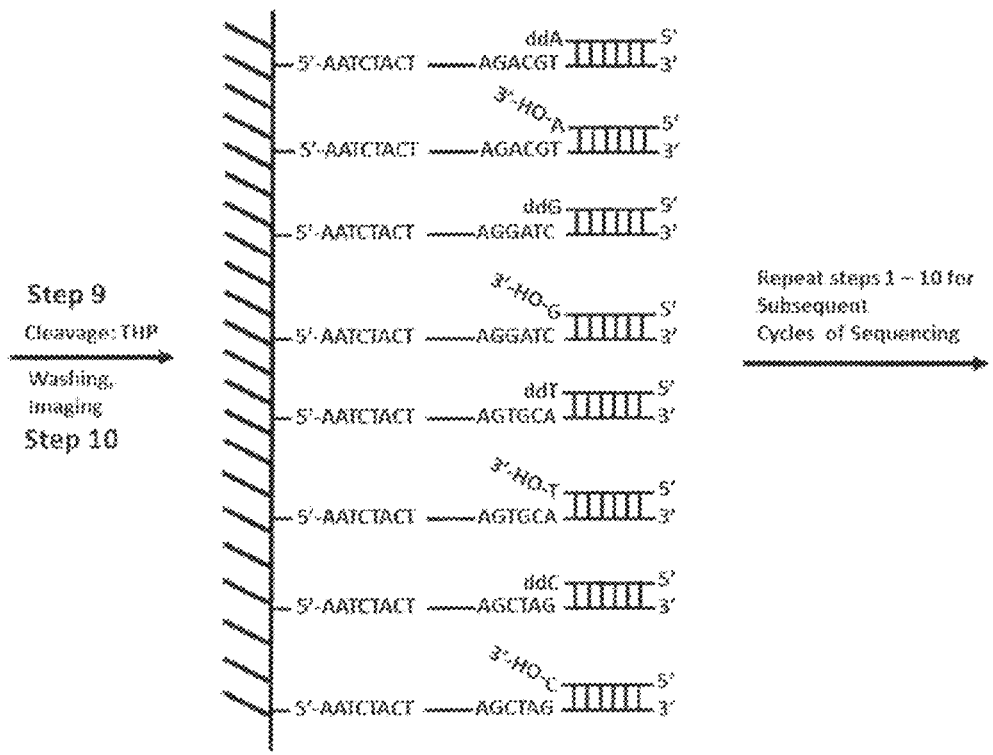

FIGS. 68A-68C: A schematic of Scheme X using ddNTP-SS-Dye (ddATP-7-SS-ATTO647N), ddNTP-Azo-Dye (ddTTP-5-Azo-ATTO647N), ddNTP-SS-Anchor (ddCTP-5-SS-Biotin), ddNTP-Azo-Anchor (3'-O-SS-dGTP-7-Azo-Biotin), the corresponding Dye Labeled Binding Molecule (ATTO647N-labeled Streptavidin), and 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS.

FIGS. 69A-69D: A schematic showing Scheme XI using ddNTP-SS-Anchors (ddATP-7-SS-Biotin, ddGTP-7-SS-TCO), ddNTP-Azo-Anchors (ddTTP-5-Azo-TCO, ddCTP-5-Azo-Biotin), the corresponding Dye Labeled Binding Molecules (ATTO647N-labeled Streptavidin and ATTO647N-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS.

Figure 70A:
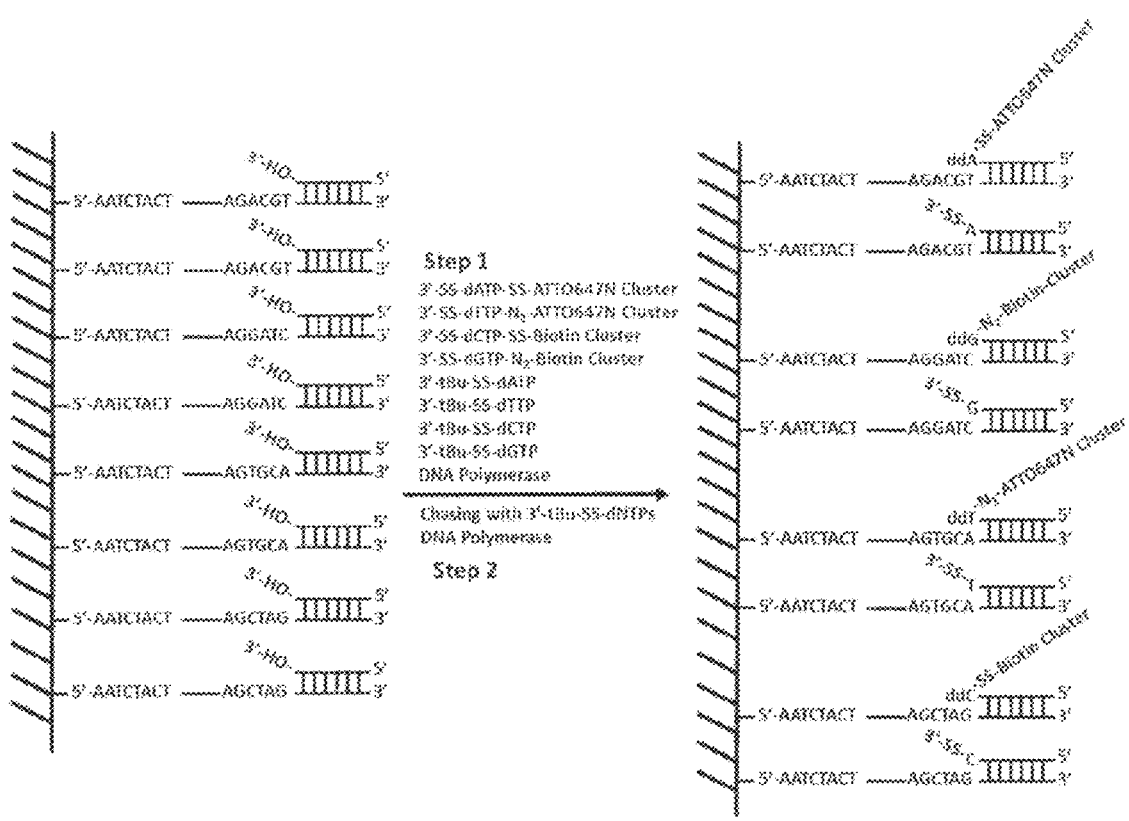
Figure 70B:
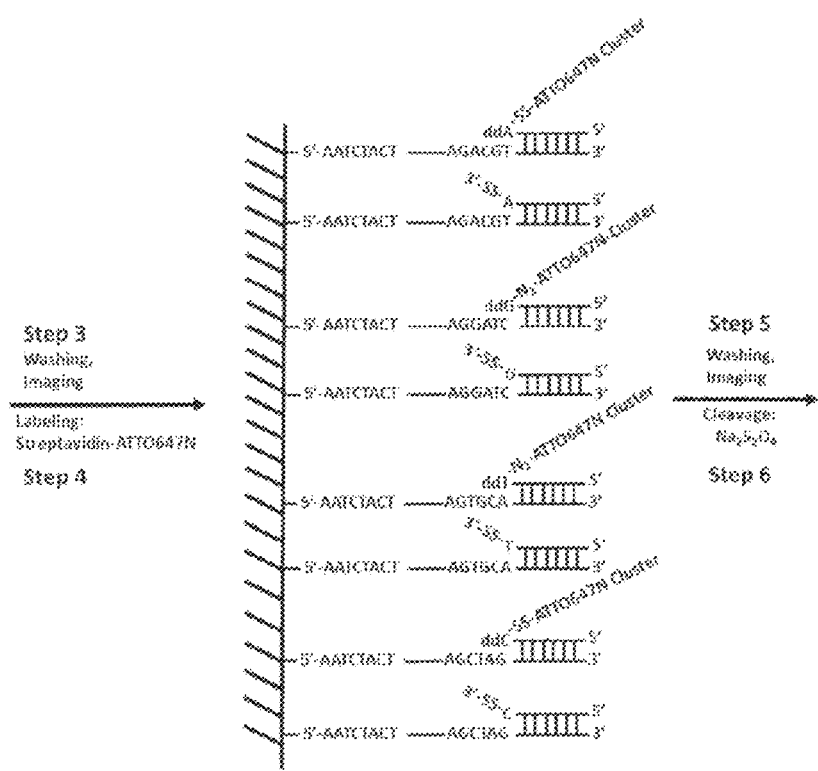
Figure 70C:
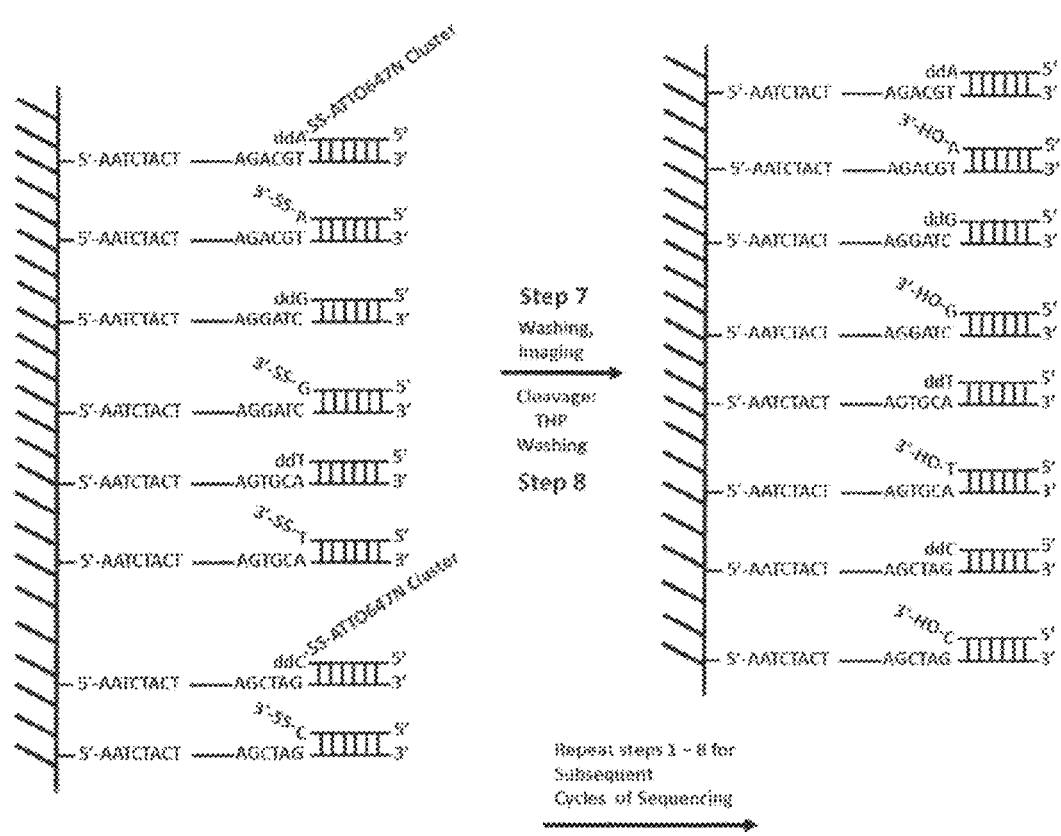
Figure 71A:
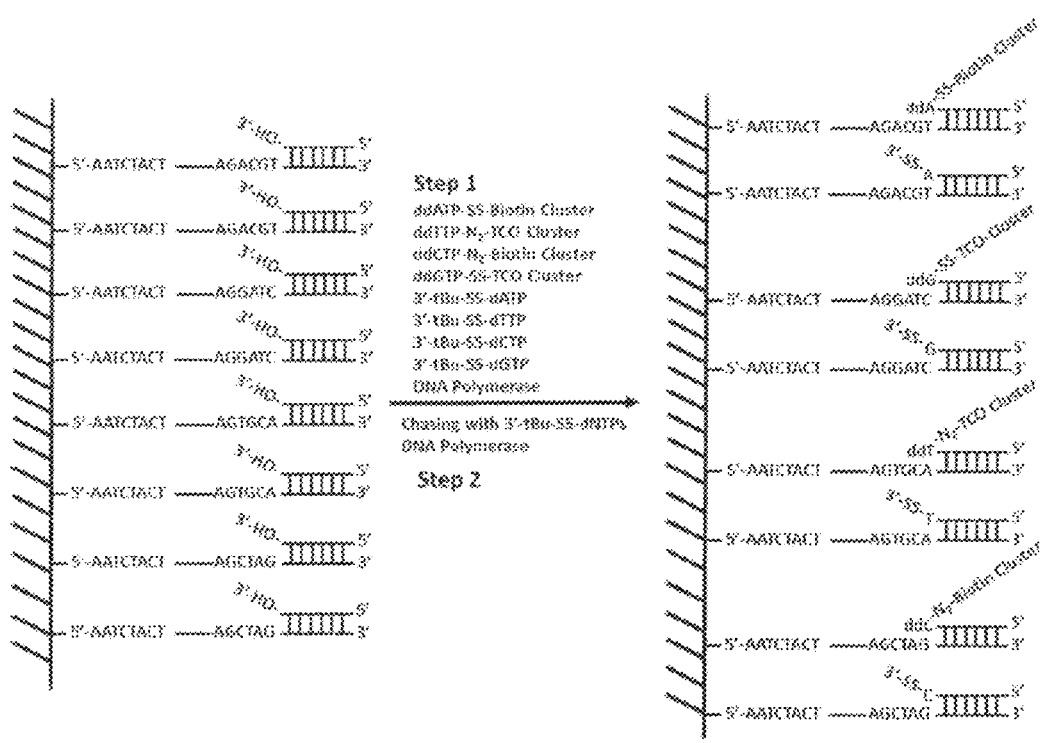
Figure 71B:
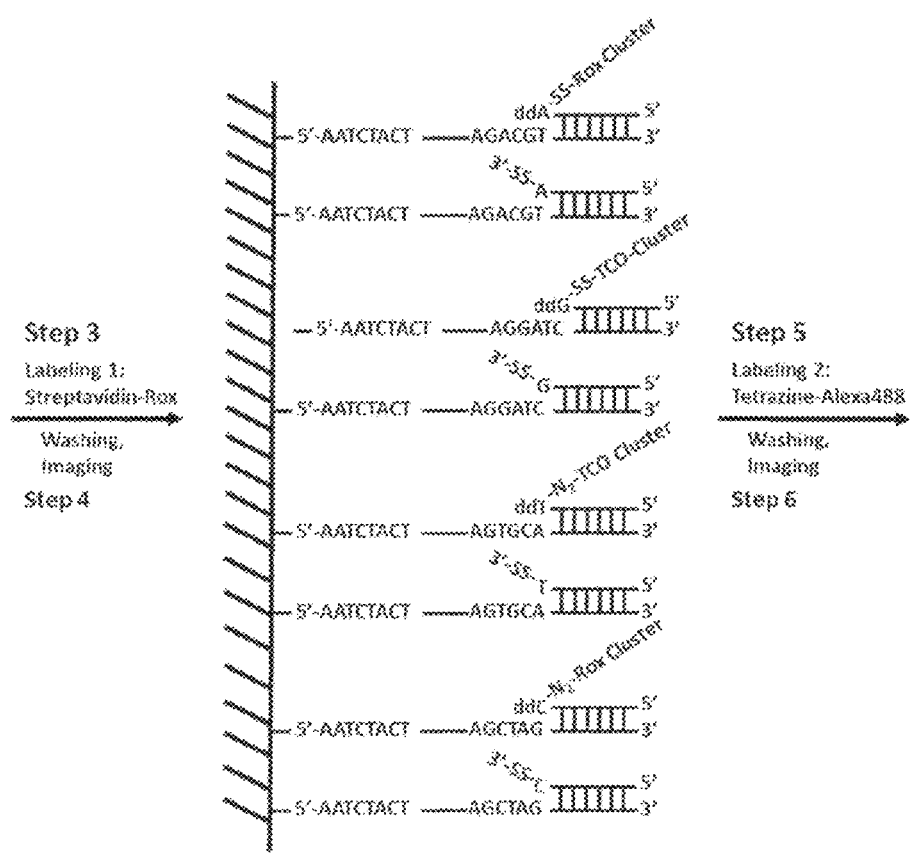
Figure 71C:
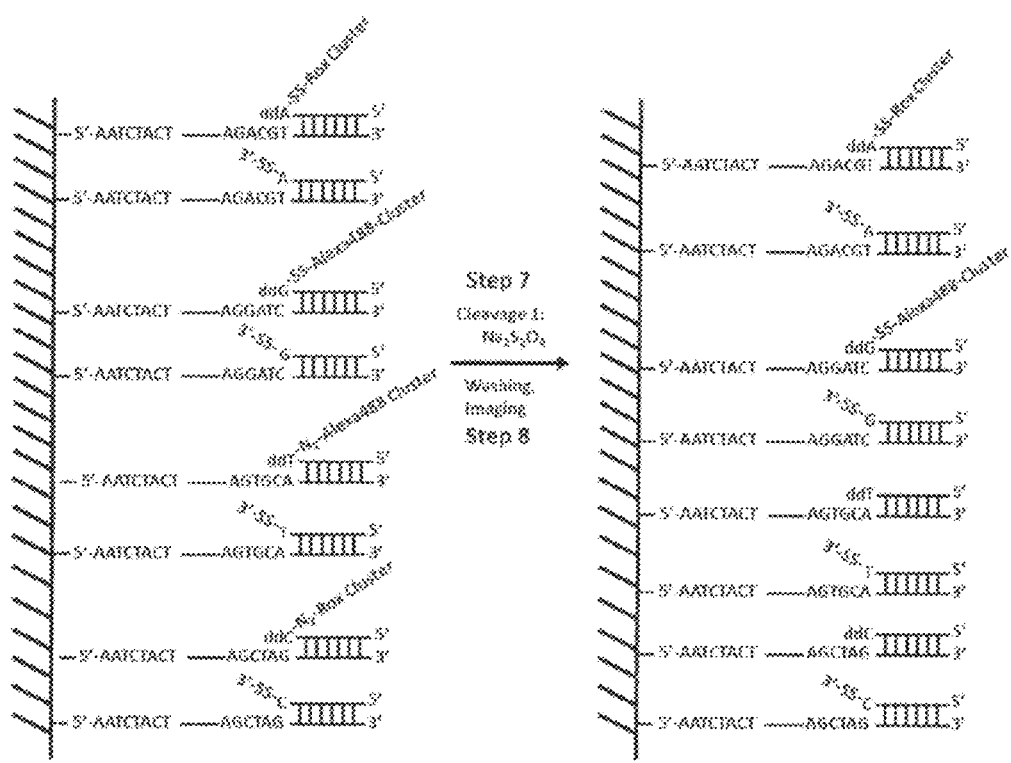
Figure 71D:
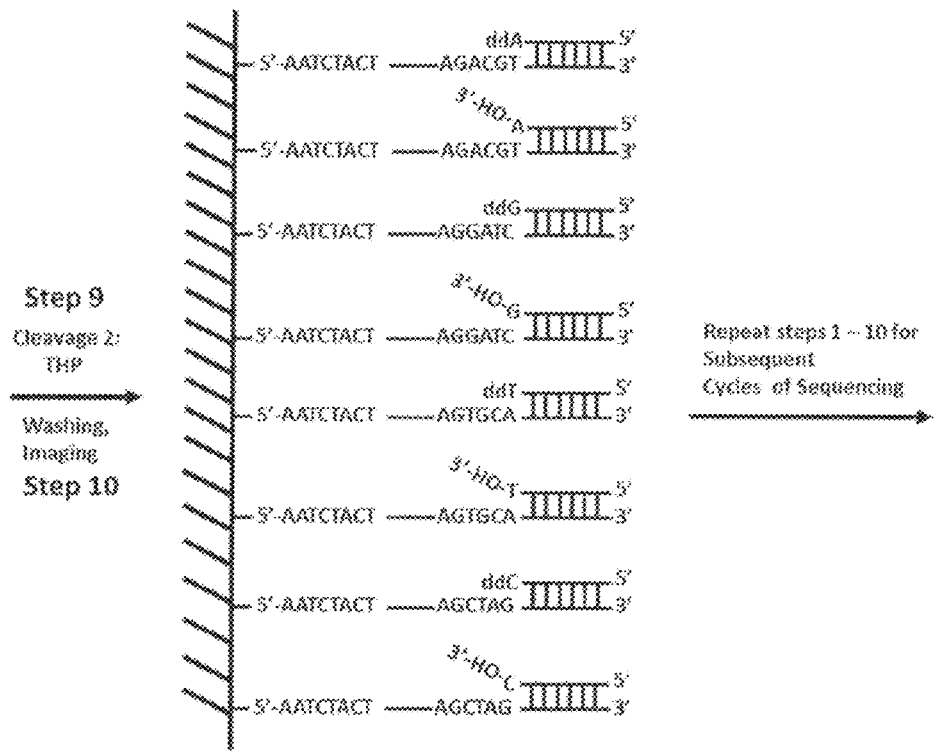

FIGS. 70A-70C: A schematic showing Scheme XII using of ddNTP-SS-Dye Cluster (ddATP-7-SS-ATTO647N Cluster), ddNTP-Azo-Dye Cluster (ddTTP-5-Azo-ATTO647N Cluster), ddNTP-SS-Anchor Cluster (ddCTP-5-SS-Biotin Cluster), ddNTP-Azo-Anchor Cluster (ddGTP-7-Azo-Biotin Cluster), the corresponding Dye Labeled Binding Molecule (ATTO647N-labeled Streptavidin), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS.

FIGS. 71A-71D: A schematic showing Scheme XIII using ddNTP-SS-Anchor Clusters (ddATP-7-SS-Biotin Cluster, ddGTP-7-SS-TCO Cluster), ddNTP-Azo-Anchor Clusters (ddCTP-5-Azo-Biotin Cluster, ddTTP-5-Azo-TCO Cluster), the corresponding Dye Labeled Binding Molecules (Rox-labeled Streptavidin and Alexa488-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS.

Figure 72A:
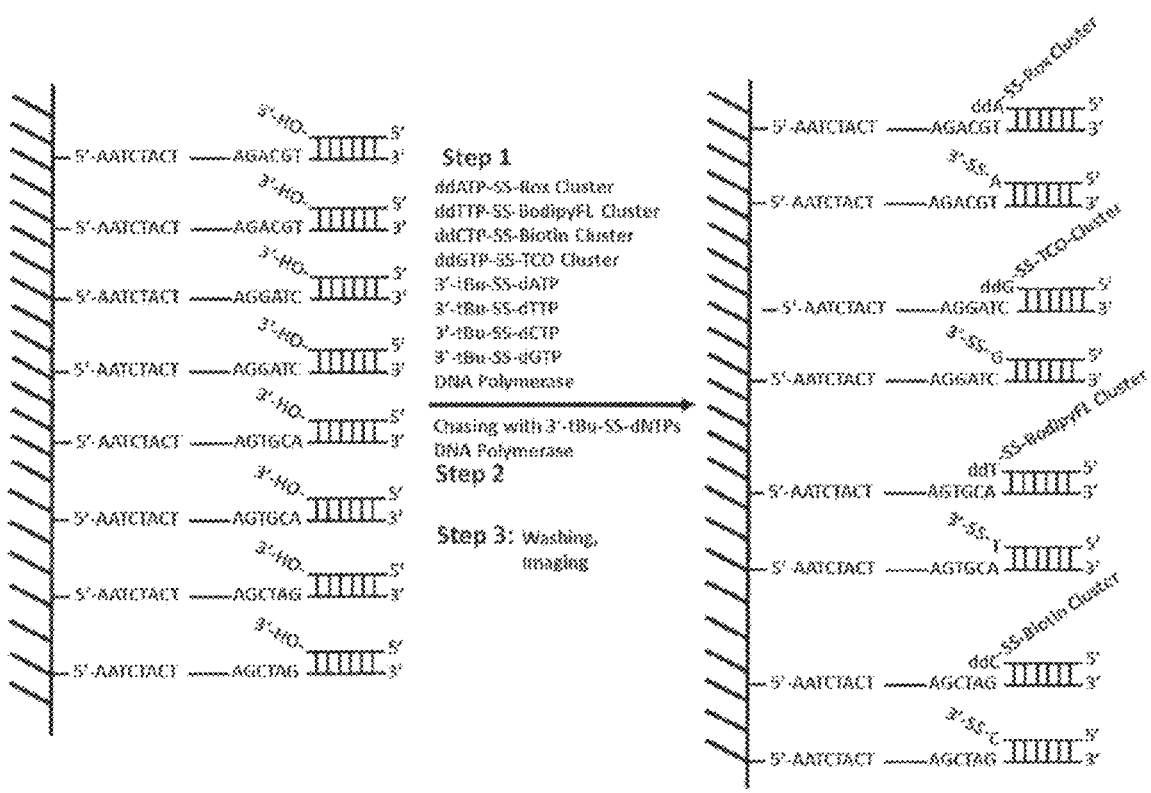
Figure 72B:
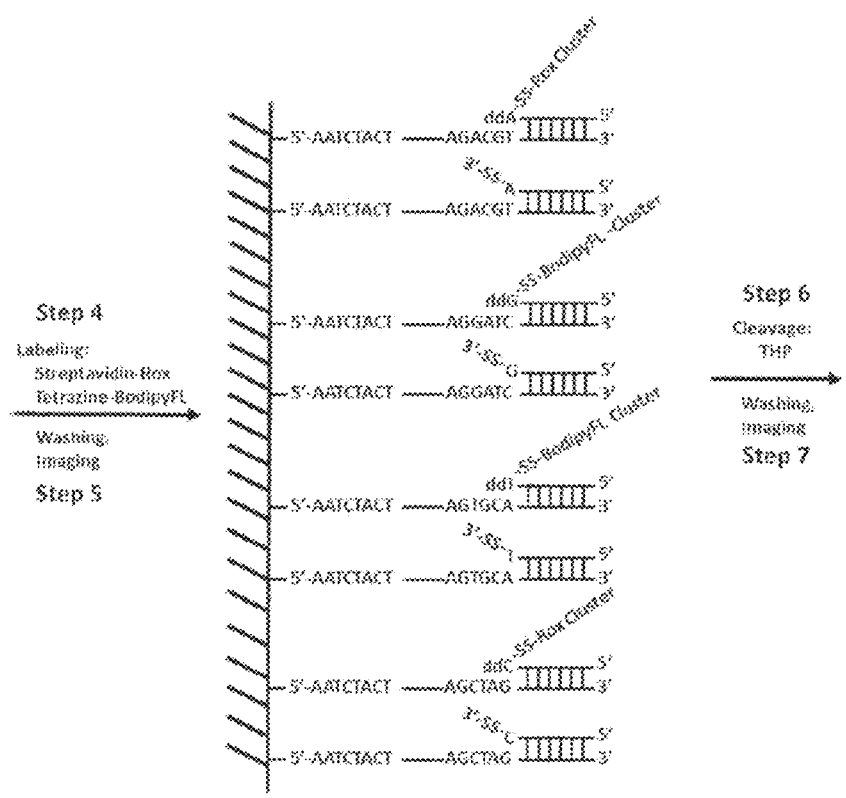
Figure 72C:
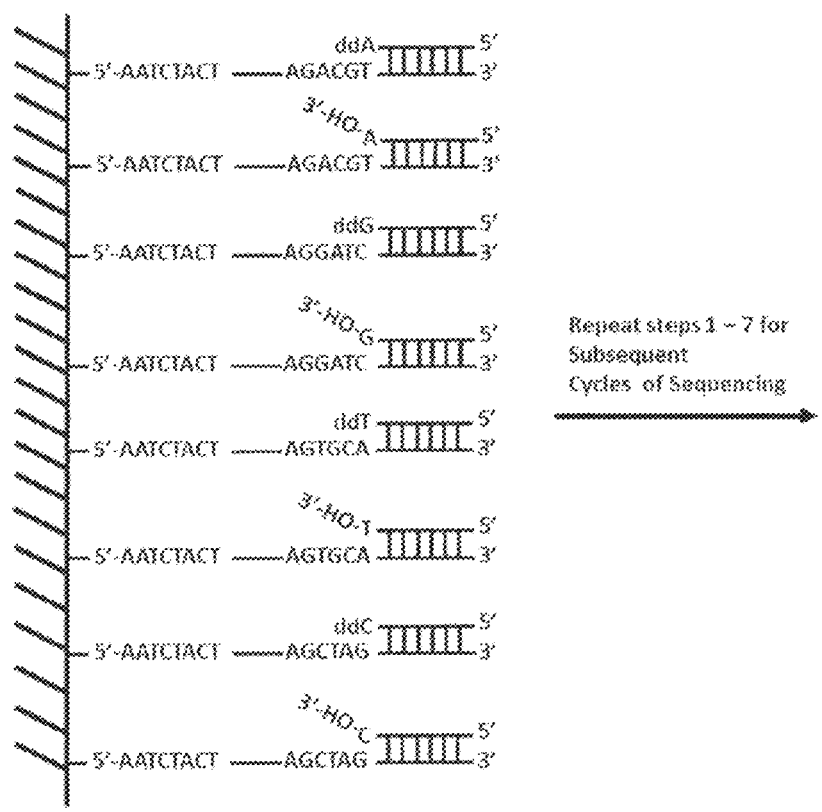

FIGS. 72A-72C: A schematic showing Scheme XIV using ddNTP-SS-Dye Clusters (ddATP-7-SS-Rox Cluster, dTTP-5-SS-BodipyFL Cluster), ddNTP-SS-Anchor Clusters (ddCTP-5-SS-Biotin Cluster, ddGTP-7-SS-TCO Cluster), corresponding dye-labeled anchor binding molecules (Streptavidin-Rox, Tetrazine-BodipyFL), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS.

Figure 73A:
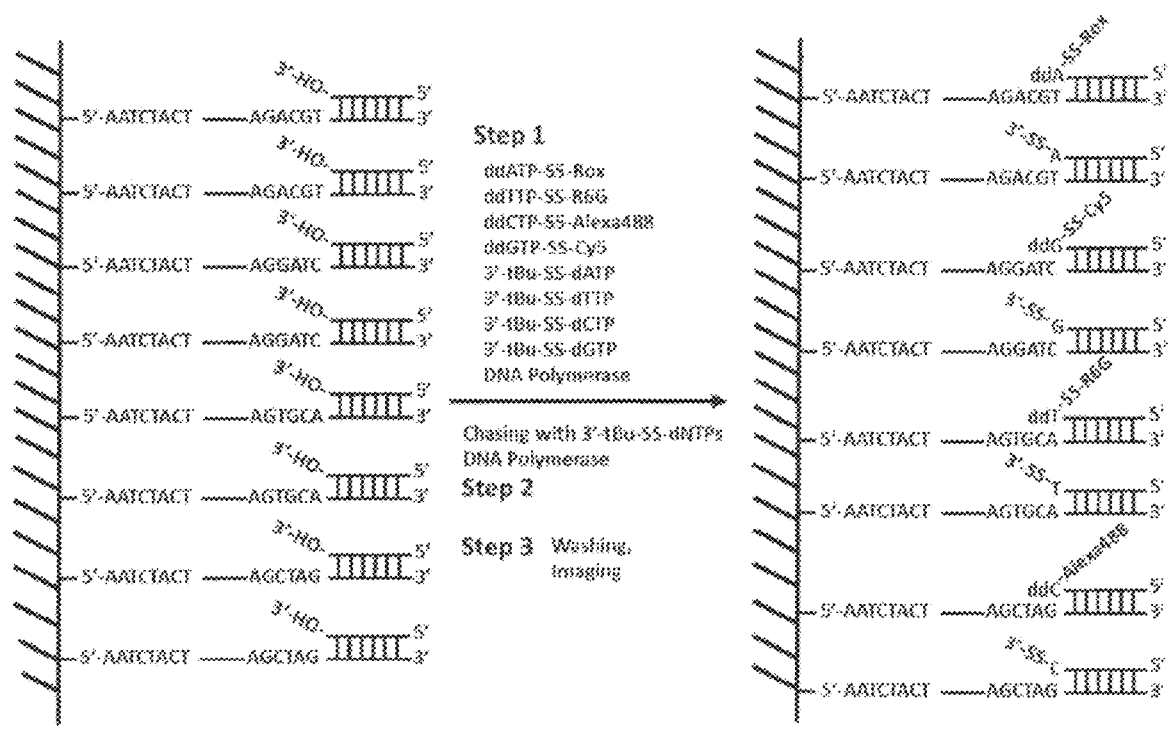
Figure 73B:
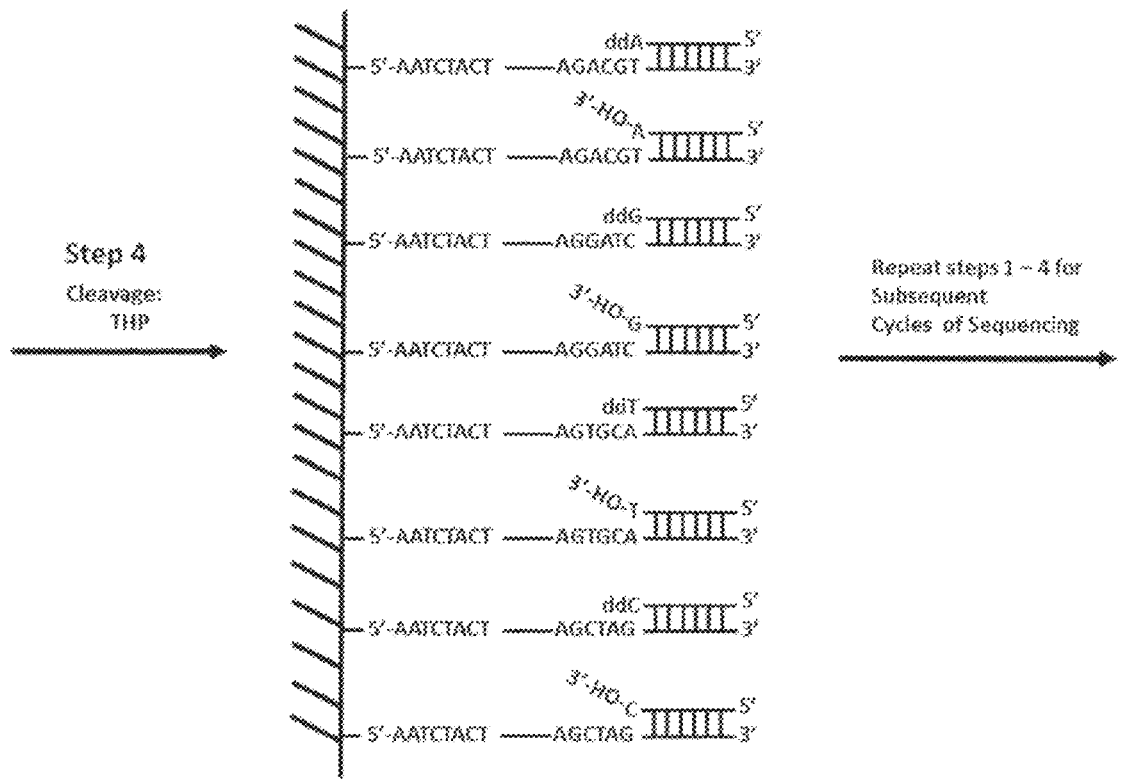

FIGS. 73A-73B: A schematic showing Scheme XV using ddNTP-SS-Dyes (ddATP-7-SS-Rox, dTTP-5-SS-R6G, ddCTP-5-SS-Alexa488, ddGTP-7-SS-Cy5) and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 4-color DNA SBS.

Figure 74A:
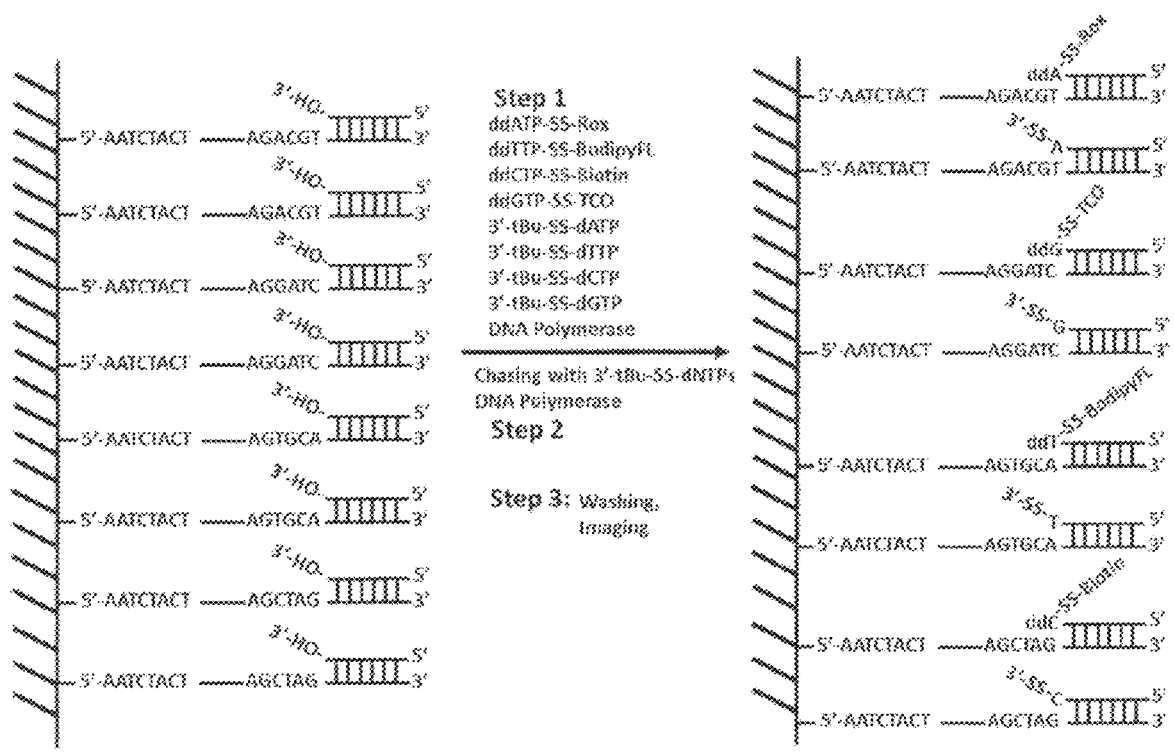
Figure 74B:
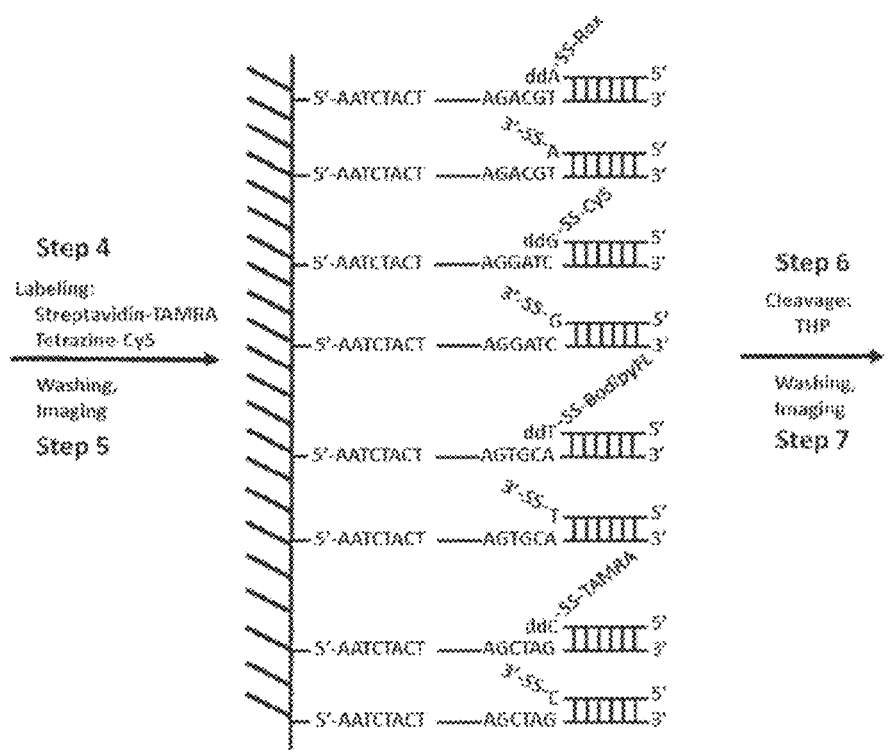
Figure 74C:
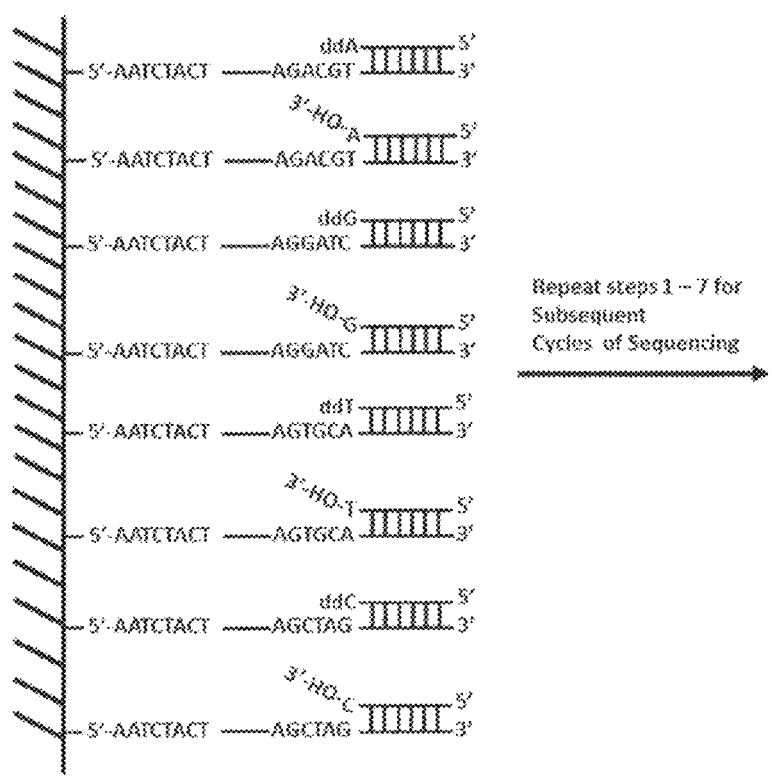

FIG. 74A-74C: A schematic showing Scheme XVIA using ddNTP-SS-Dye (ddATP-7-SS-Rox, dTTP-5-SS-BodipyFL), ddNTP-SS-Anchor (ddCTP-5-SS-Biotin, ddGTP-7-SS-TCO), corresponding dye-labeled anchor binding molecules (Streptavidin-TAMRA, Tetrazine-Cy5), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 4-color DNA SBS.

Figure 75A:
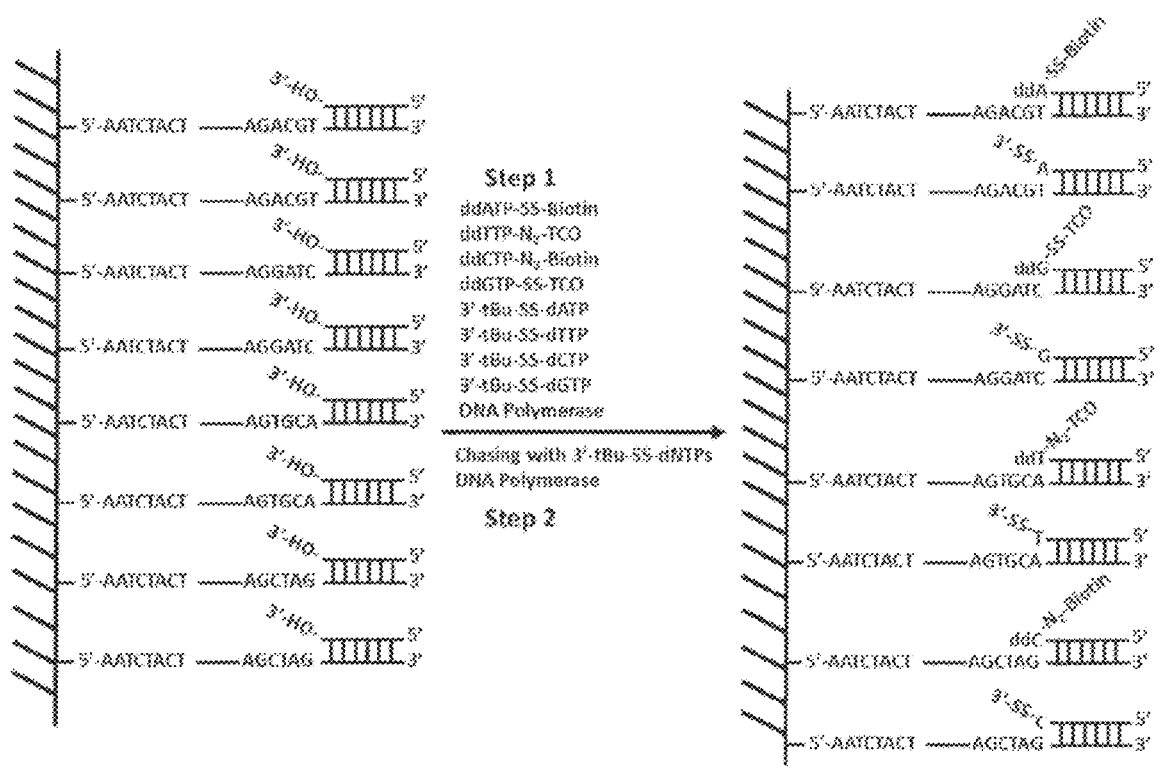
Figure 75B:
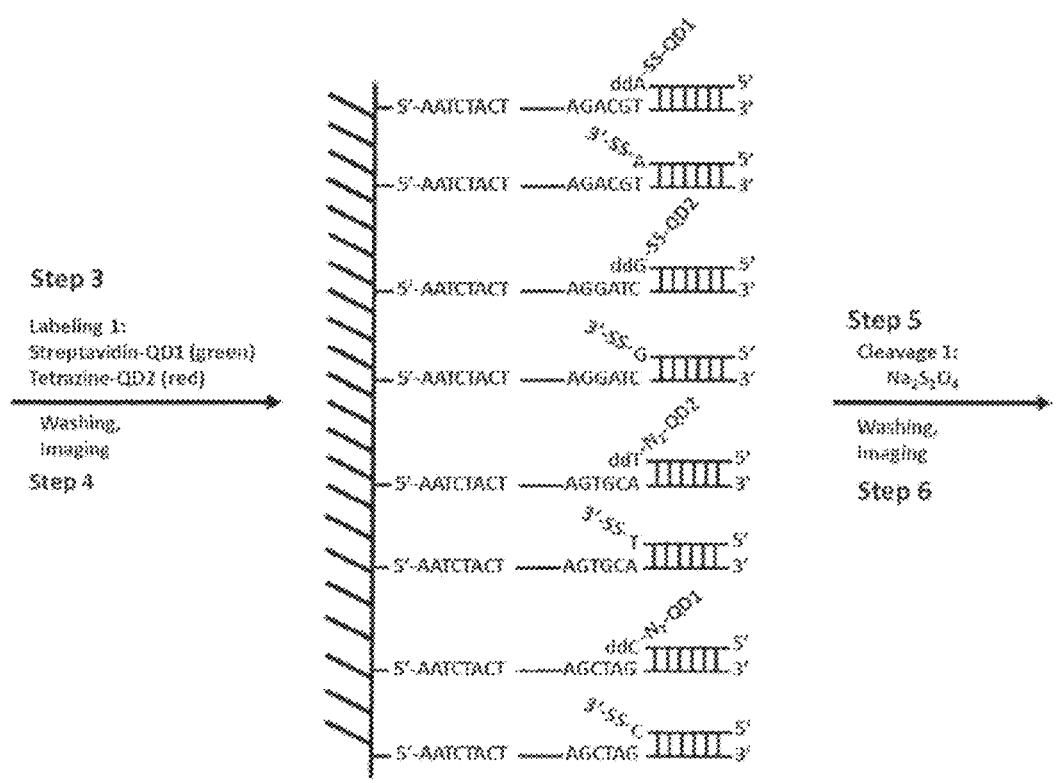
Figure 75C:
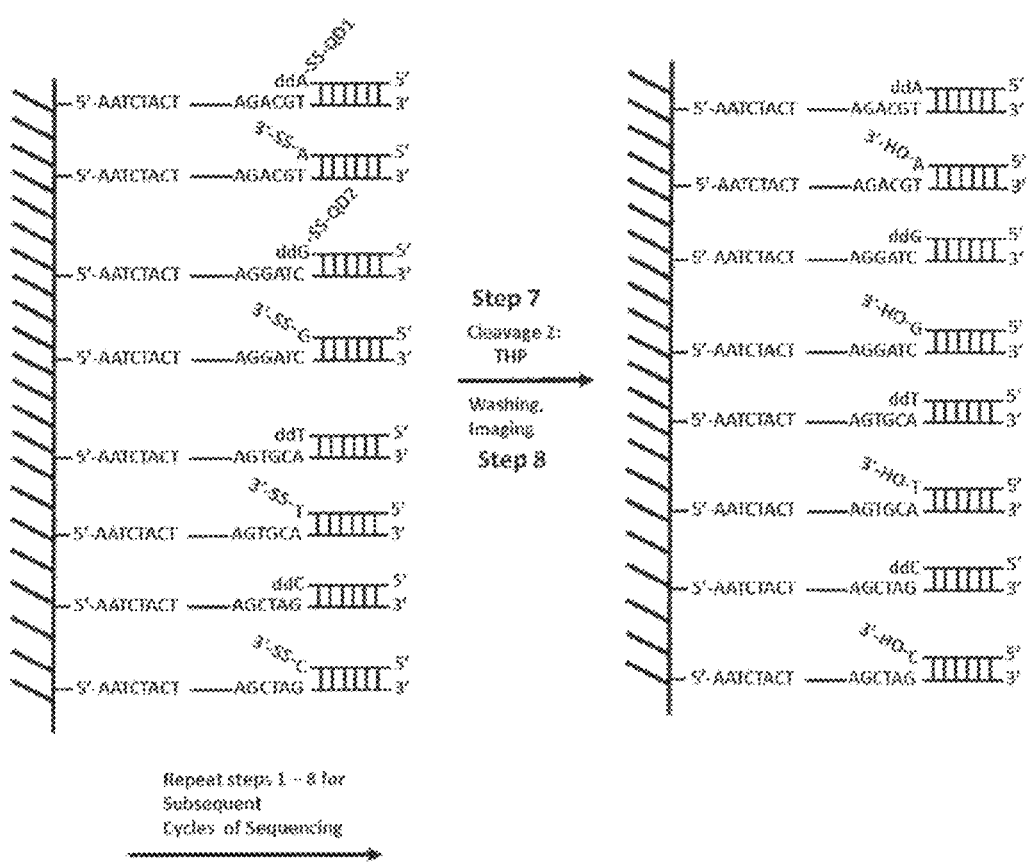

FIGS. 75A-75C: A schematic showing Scheme XVIB using 3'-O-SS(DTM)-dNTP-SS-Anchors (3'-O-SS-dATP-7-SS-Biotin, 3'-O-SS-dGTP-7-SS-TCO), 3'-O-SS(DTM)-dNTP-Azo-Anchors (3'-O-SS-dTTP-5-Azo-TCO, 3'-O-SS-dCTP-5-Azo-Biotin), the corresponding Dye Labeled Binding Molecules (Quantum Dot 1 (Green)-labeled Streptavidin and Quantum Dot 2 (Red)-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS.

Figure 76A:
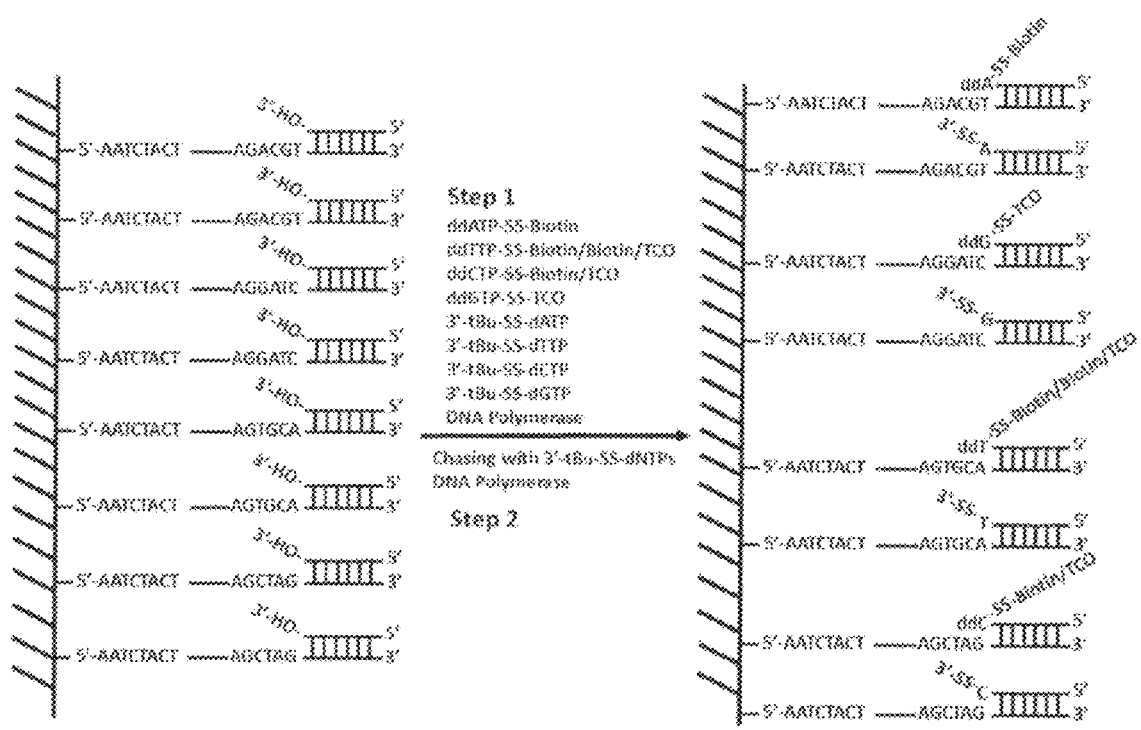
Figure 76B:
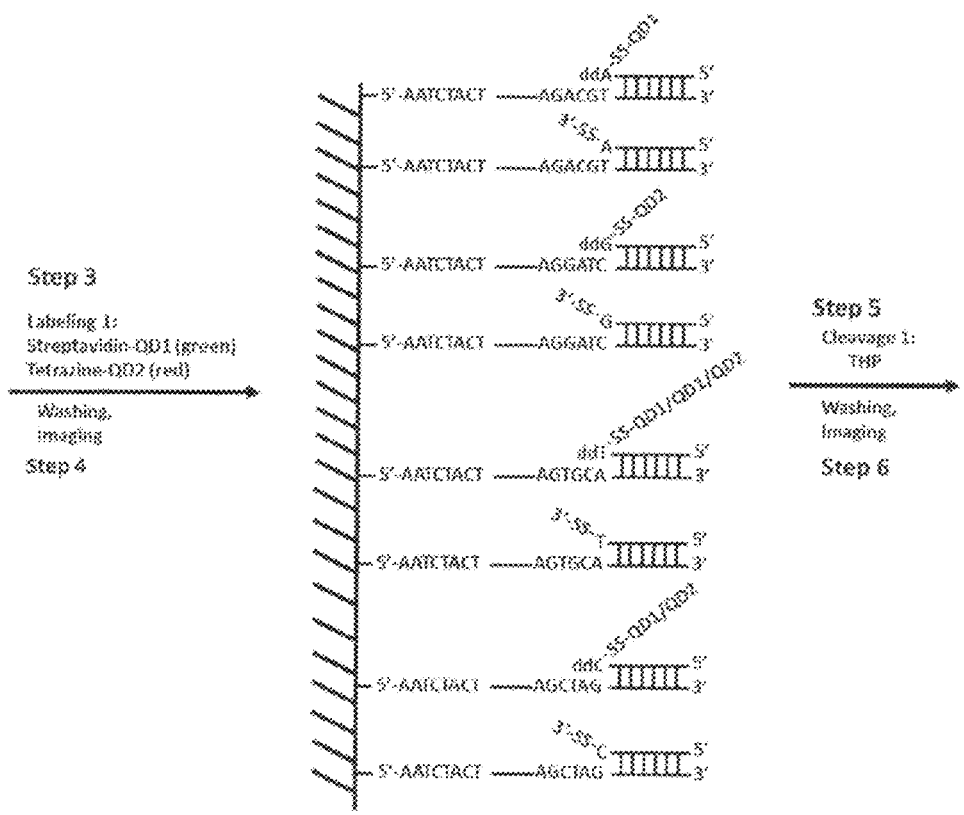
Figure 76C:
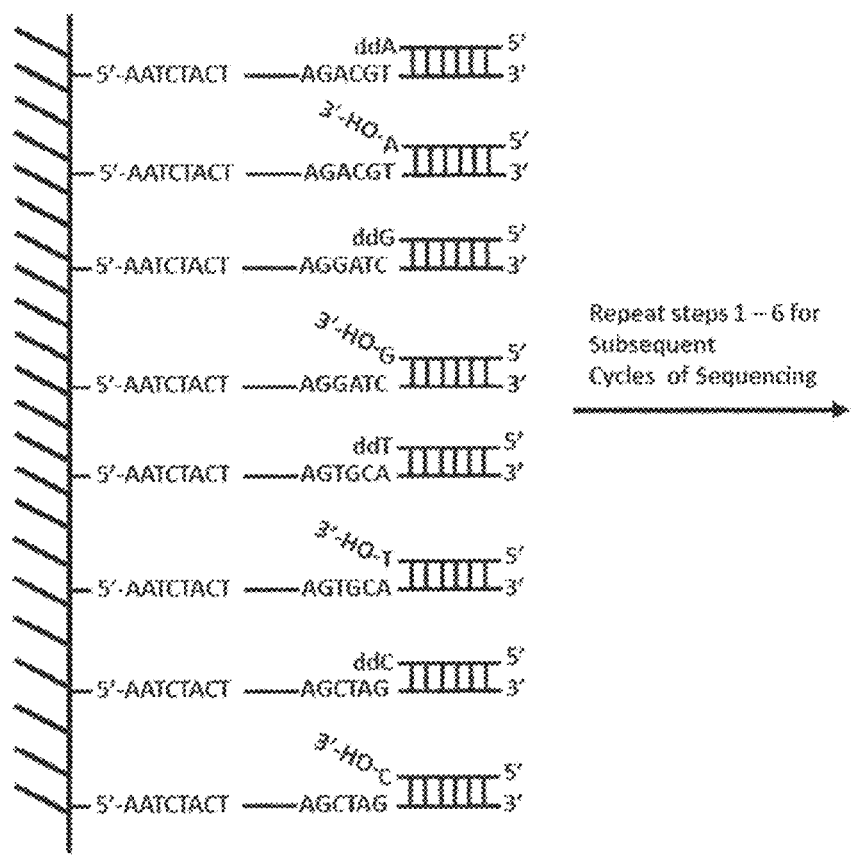
Figure 77A:
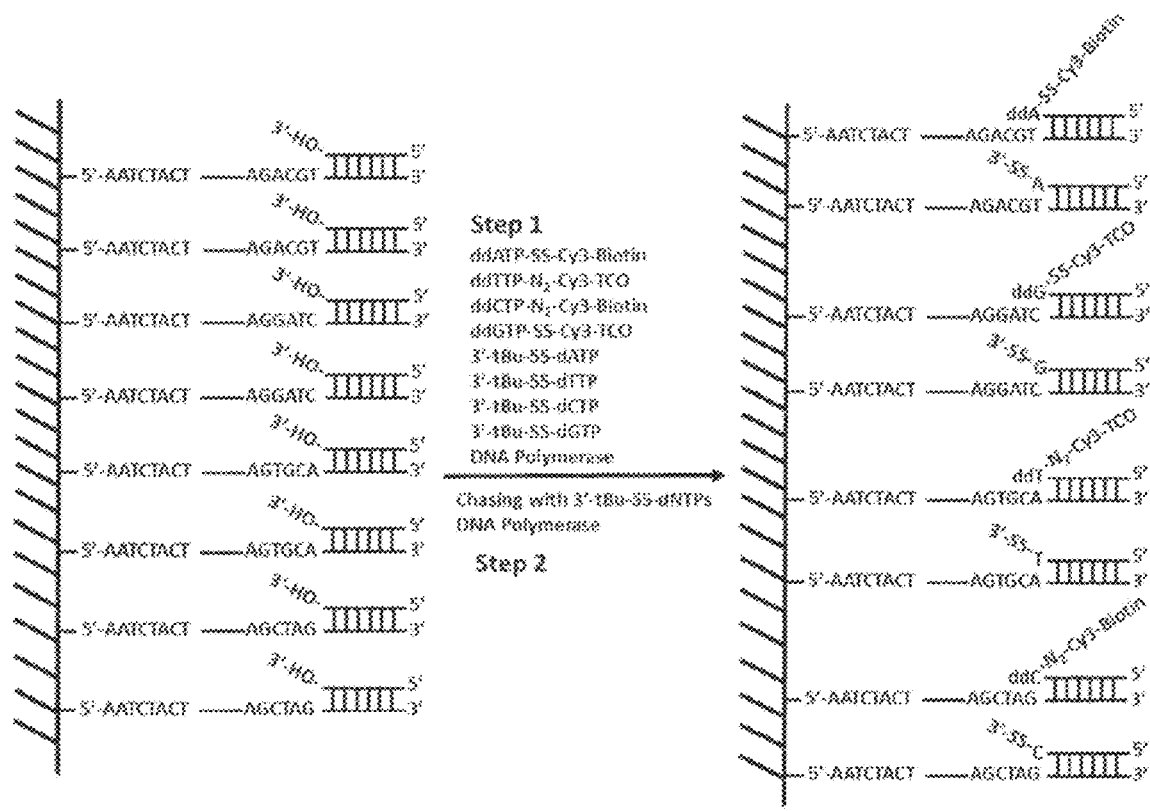
Figure 77B:
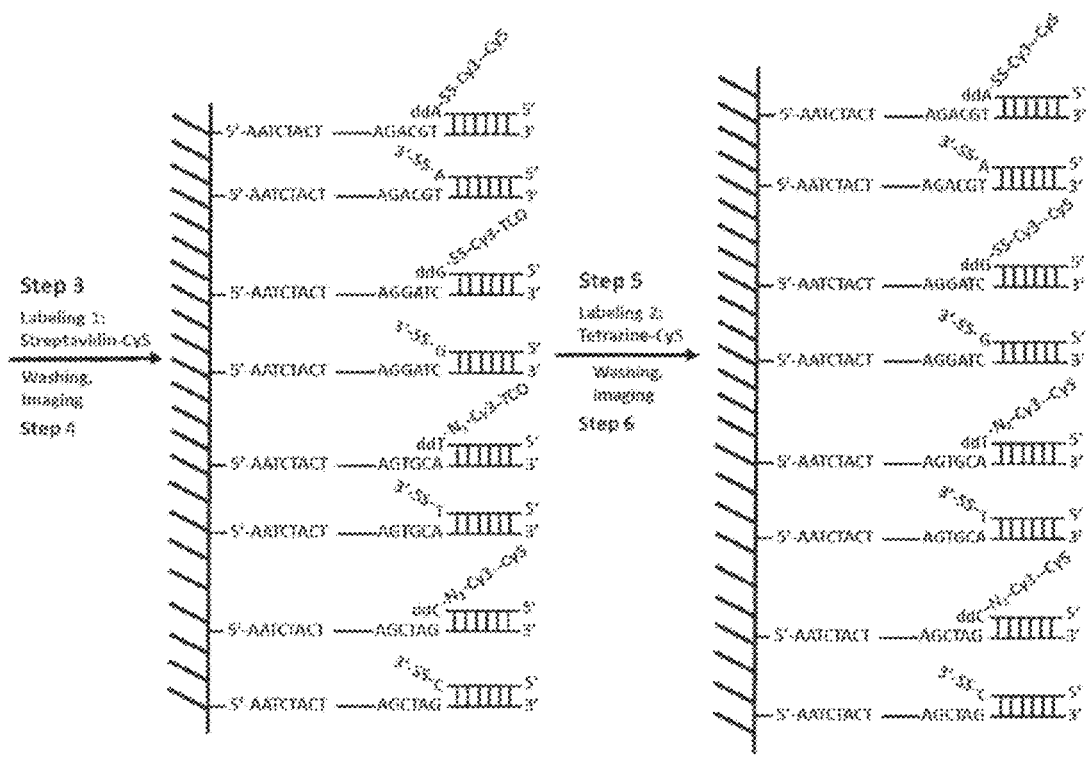
Figure 77C:
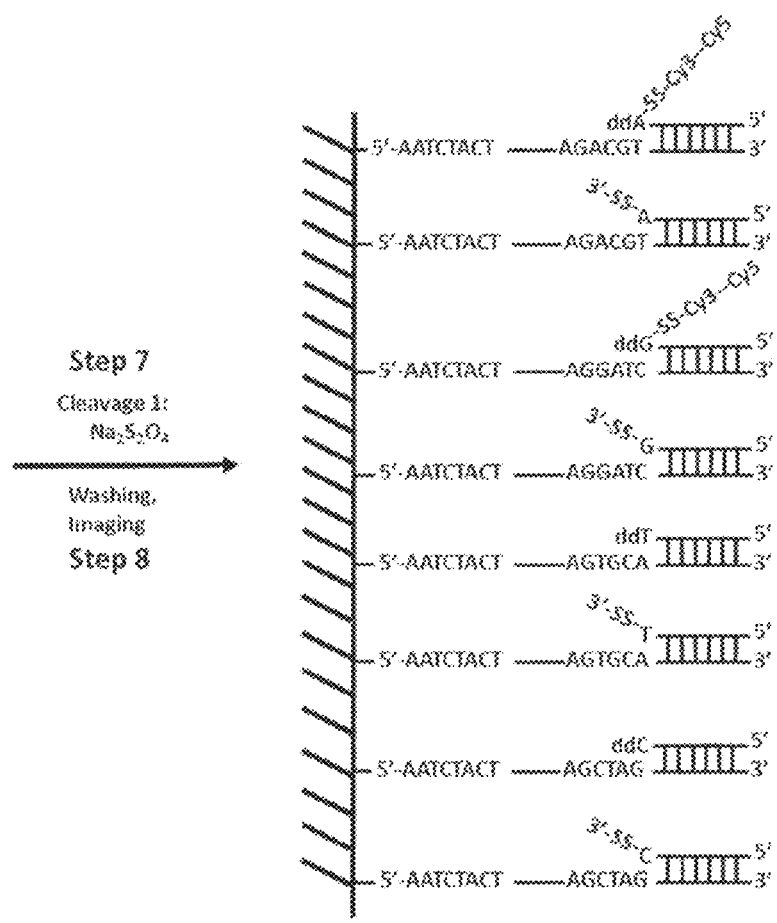
Figure 77D:
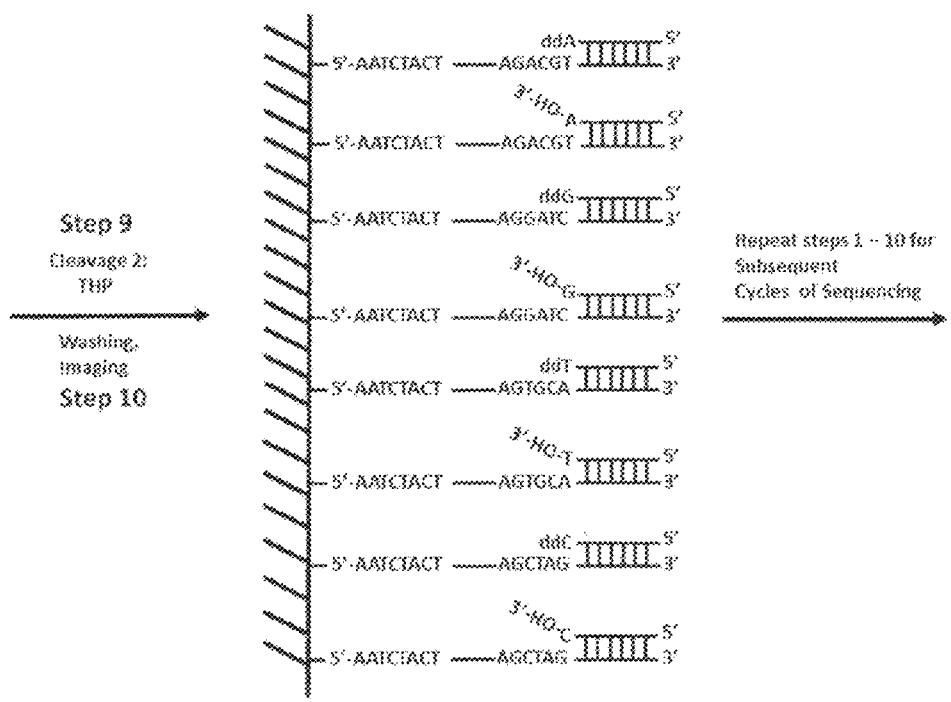

FIGS. 76A-76C: A schematic showing Scheme XVIC using 3'-O-SS(DTM)-dNTP-SS-Anchors (3'-O-SS-dATP-7-SS-Biotin, 3'-O-SS-dGTP-7-SS-TCO, 3'-O-SS-dTTP-5-SS-Biotin/Biotin/TCO, 3'-O-SS-dCTP-5-SS-Biotin/TCO), the corresponding Dye Labeled Binding Molecules (Quantum Dot 1 (Green)-labeled Streptavidin and Quantum Dot 2 (Red)-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS.

FIGS. 77A-77D: A schematic showing Scheme XVII using ddNTP-SS-DonorDye-Anchors (ddATP-7-SS-Cy3-Biotin, ddGTP-7-SS-Cy3-TCO), ddNTP-Azo-Anchors (ddTTP-5-Azo-Cy3-TCO, ddCTP-5-Azo-Cy3-Biotin), the corresponding Dye Labeled Binding Molecules (Cy5-labeled Streptavidin and Cy5-labeled Tetrazine), and the four 3'-O-SS (DTM)-dNTPs (3'-O-t -Butyldithiomethyl (SS)-dATP, 3'-O-t-Butyldithiomethyl (SS)-dCTP, 3'-O -t-Butyldithiomethyl (SS)-dTTP and 3'-O-t-Butyldithiomethyl (SS)-dGTP) to perform 1-color DNA SBS.

FIG. 78: General structures of the nucleotide terminators with unblocked 3'-OH groups. Examples of nucleotides, cleavable linkers (structures shown at bottom), blocking groups and dyes are given.

Figure 97:
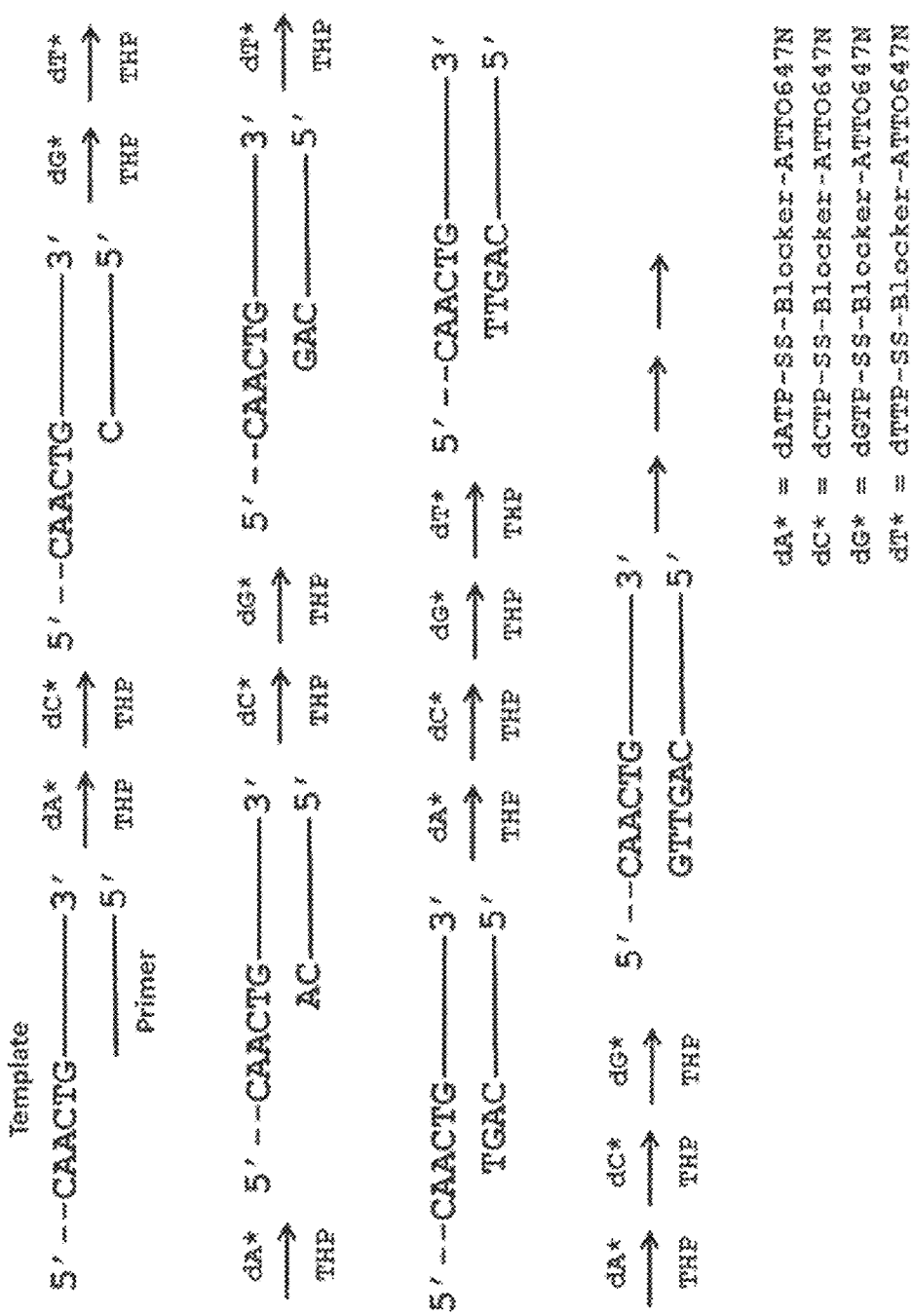
Figure 98:
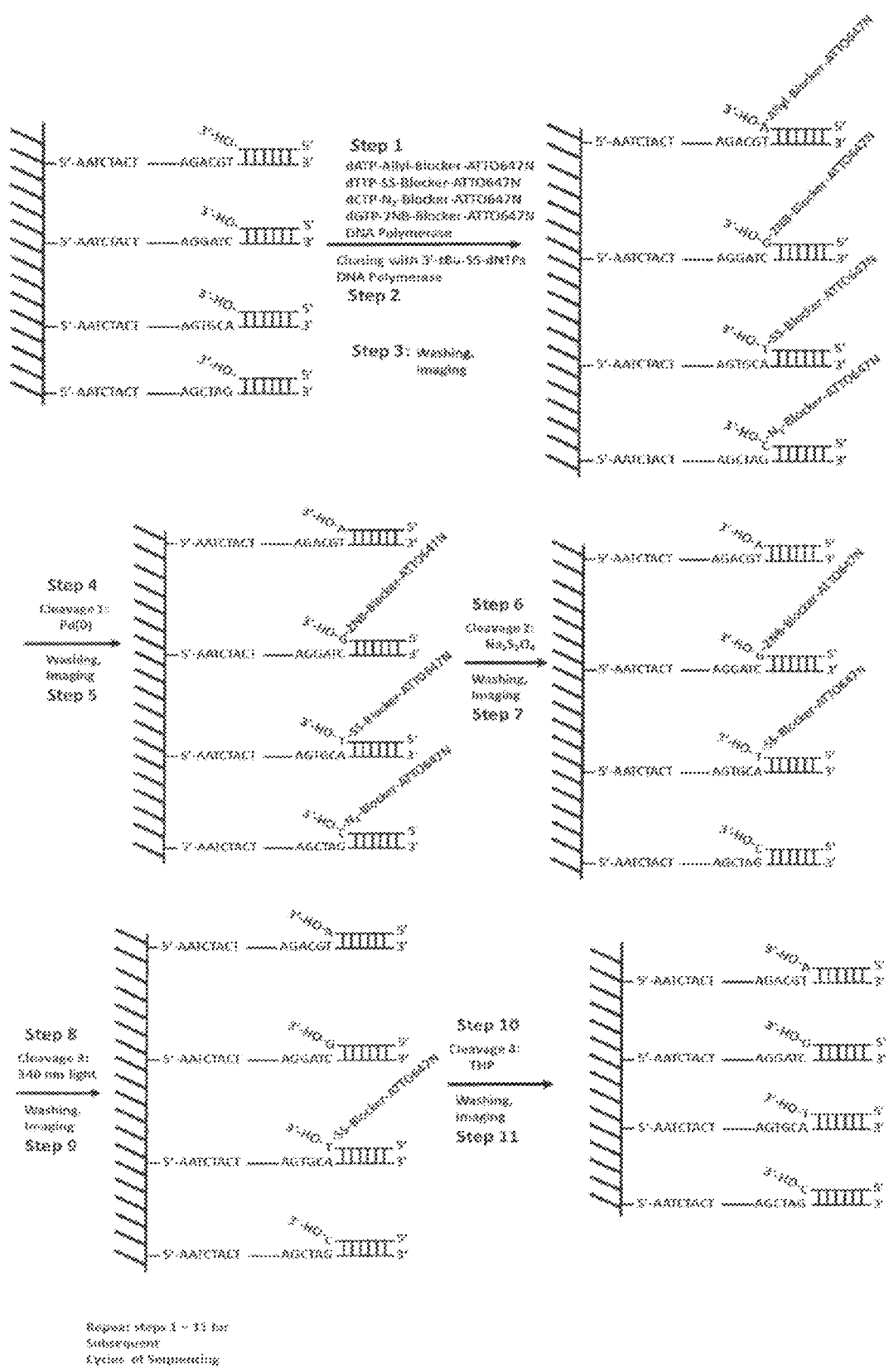

FIG. 79: Dideoxynucleotide analogues with polymer chains attached via a non-cleavable linker to the 5-position of pyrimidines or 7-position of purines. A Cy3 dye is included between the linker and the polymer in all except the ddGTP analogue shown in this figure. Herein described is the ability of these modified ddNTP analogues to be extended by DNA polymerase (FIGS. 97 and 98).

Figure 80:
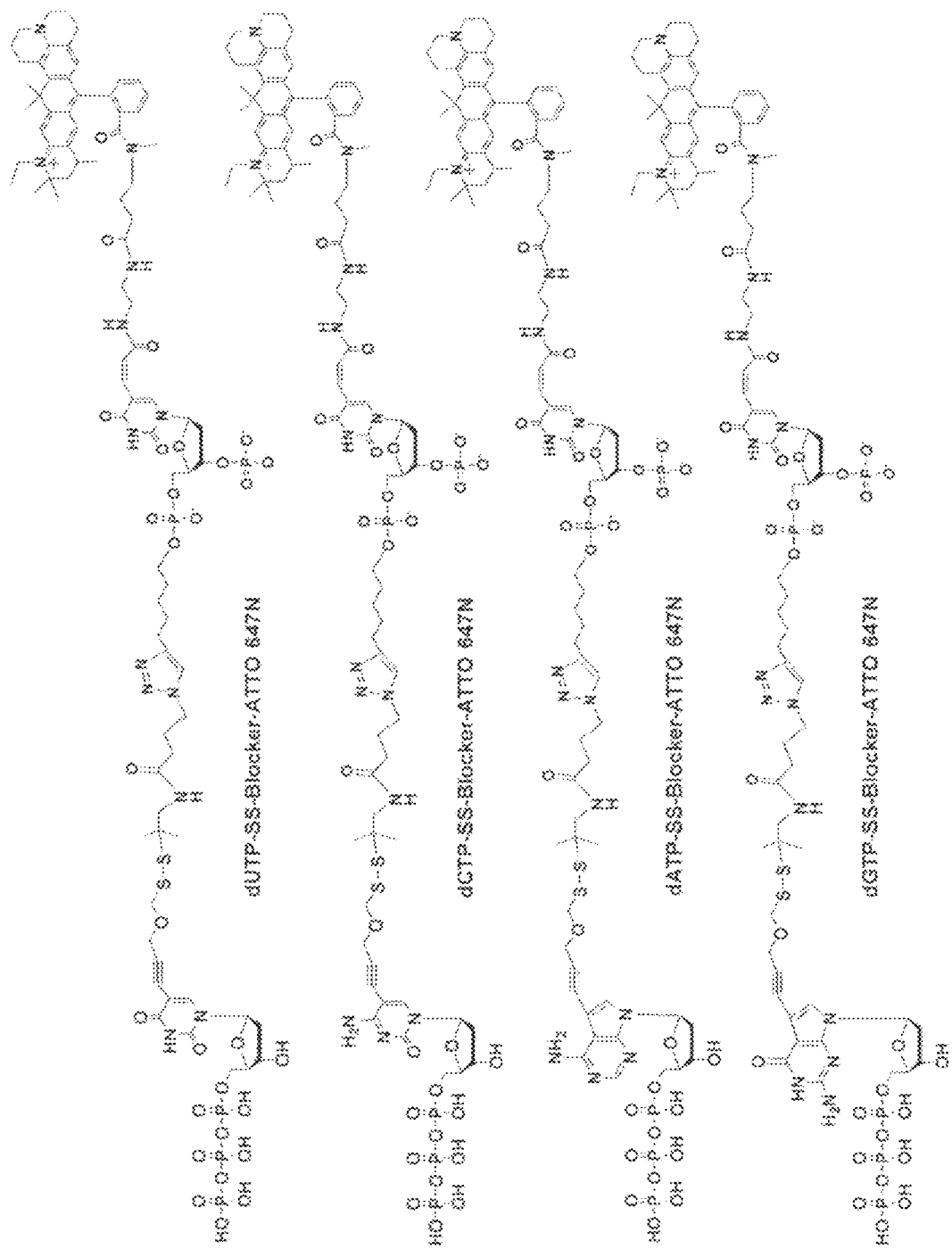

FIG. 80: Examples of 3'-OH containing dNTP-SS-Blocker-Dye molecules for use in stepwise single-color SBS (Scheme XVIII).

Figure 81:
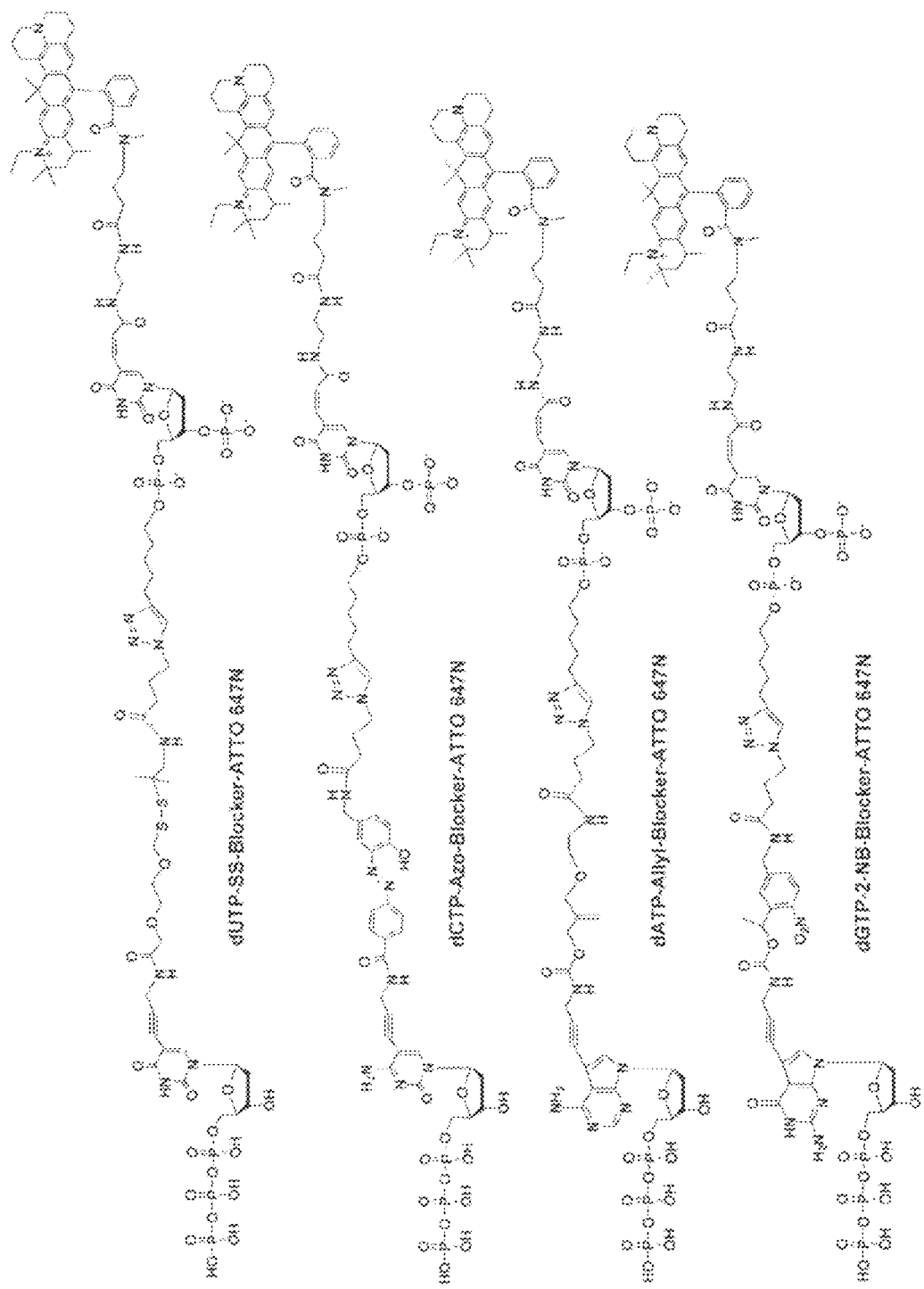

FIG. 81: Examples of 3'-OH containing dNTP-Cleavable Linker-Blocker-Dye molecules for carrying out single-color sequencing by synthesis (Scheme XIX).

Figure 82:
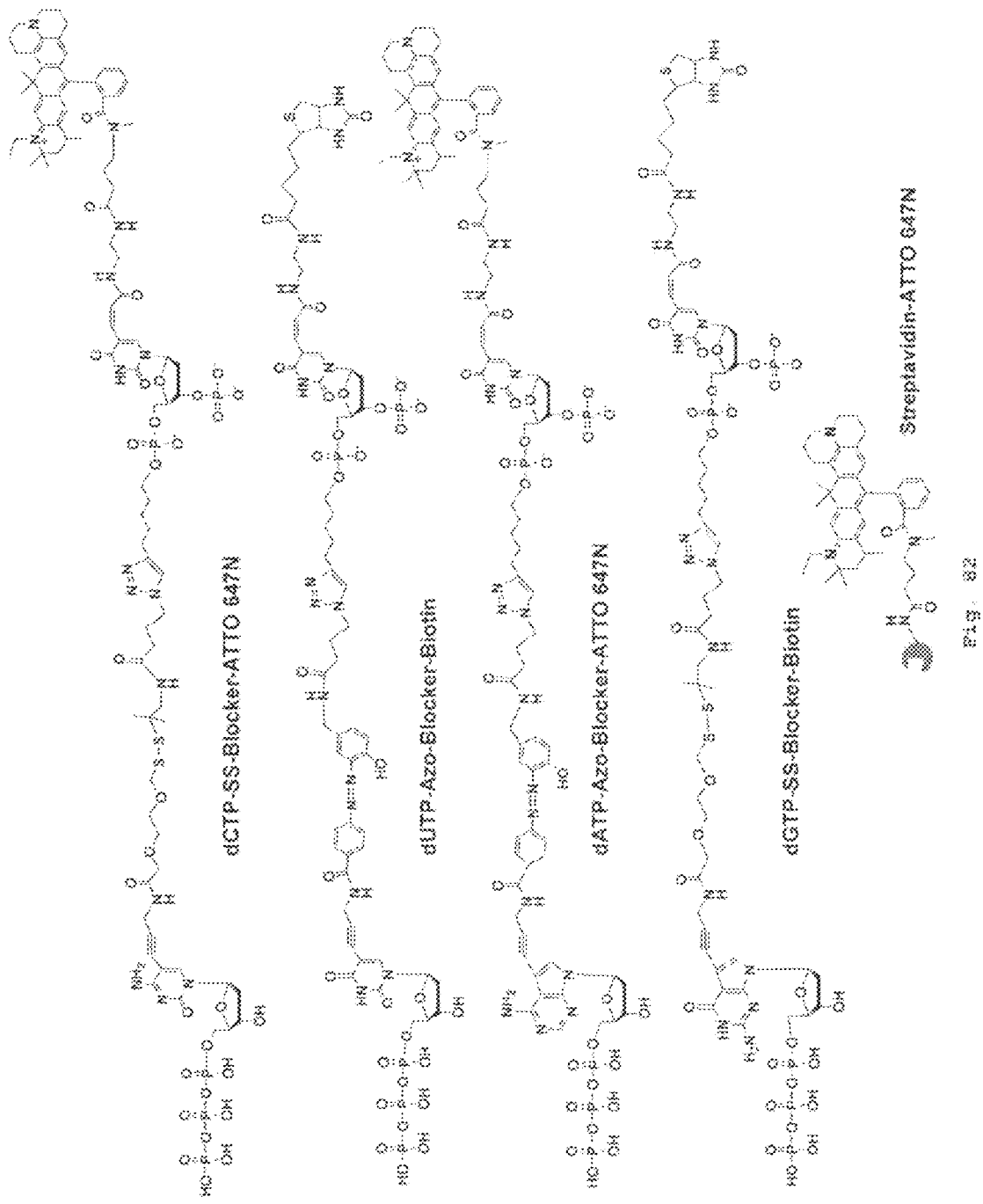

FIG. 82: Examples of 3'-OH containing dNTP-Cleavable Linker-Blocker-Dye, dNTP-Cleavable Linker-Blocker-Anchor, and Dye labeled Anchor Binding molecule used for single-color sequencing by synthesis (Scheme XX).

Figure 83:
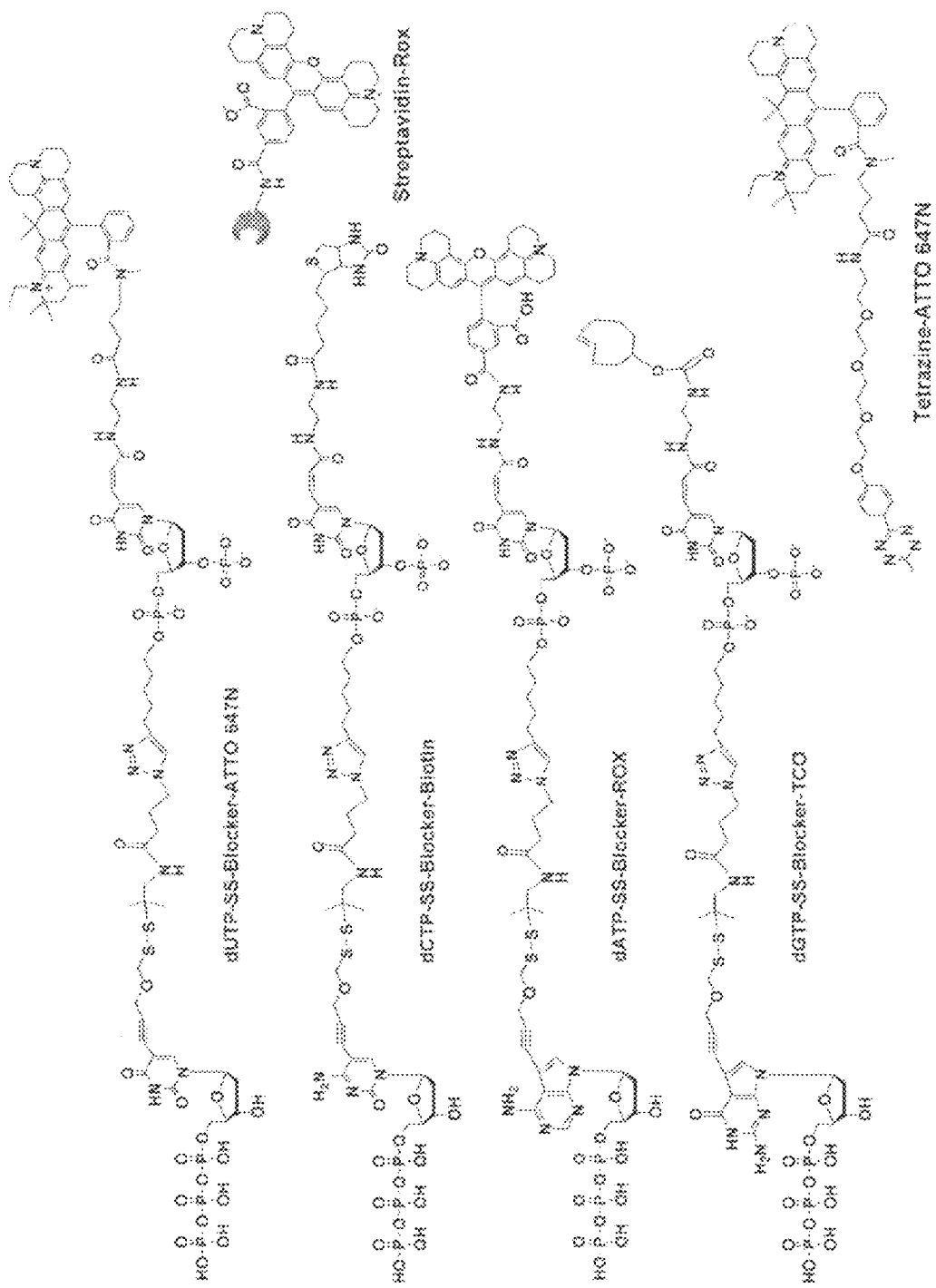
Figure 8A:
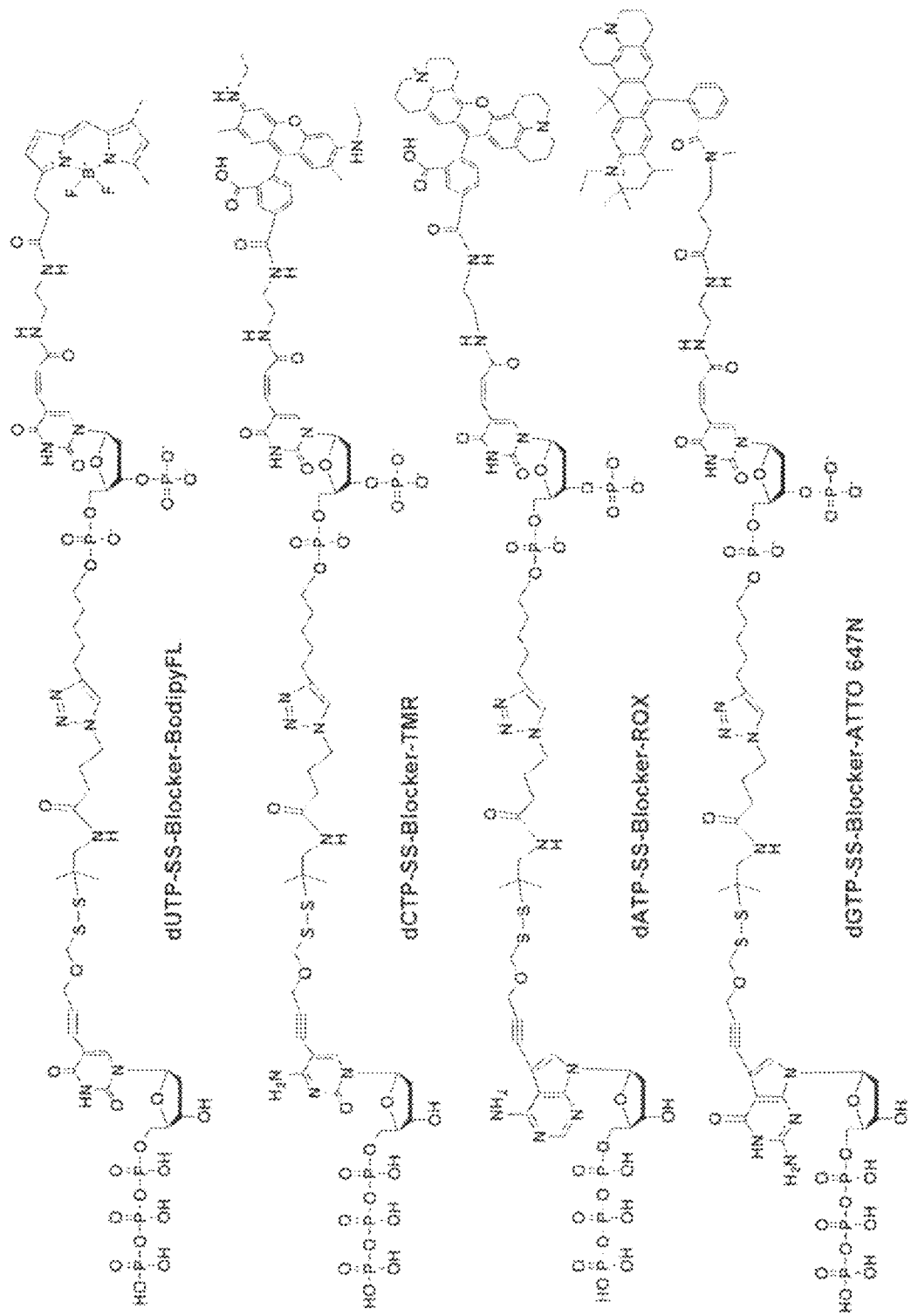

FIG. 83: Examples of 3'-OH containing dNTP-Cleavable Linker-Blocker-Dye, dNTP-Cleavable Linker-Blocker-Anchor, and Dye labeled Anchor Binding molecules used for two-color sequencing by synthesis (Scheme XXI).

FIG. 84: Examples of 3'-OH containing dNTP-SS-Blocker-Dye molecules used for four-color sequencing by synthesis (Scheme XXIIA).

Figure 85:
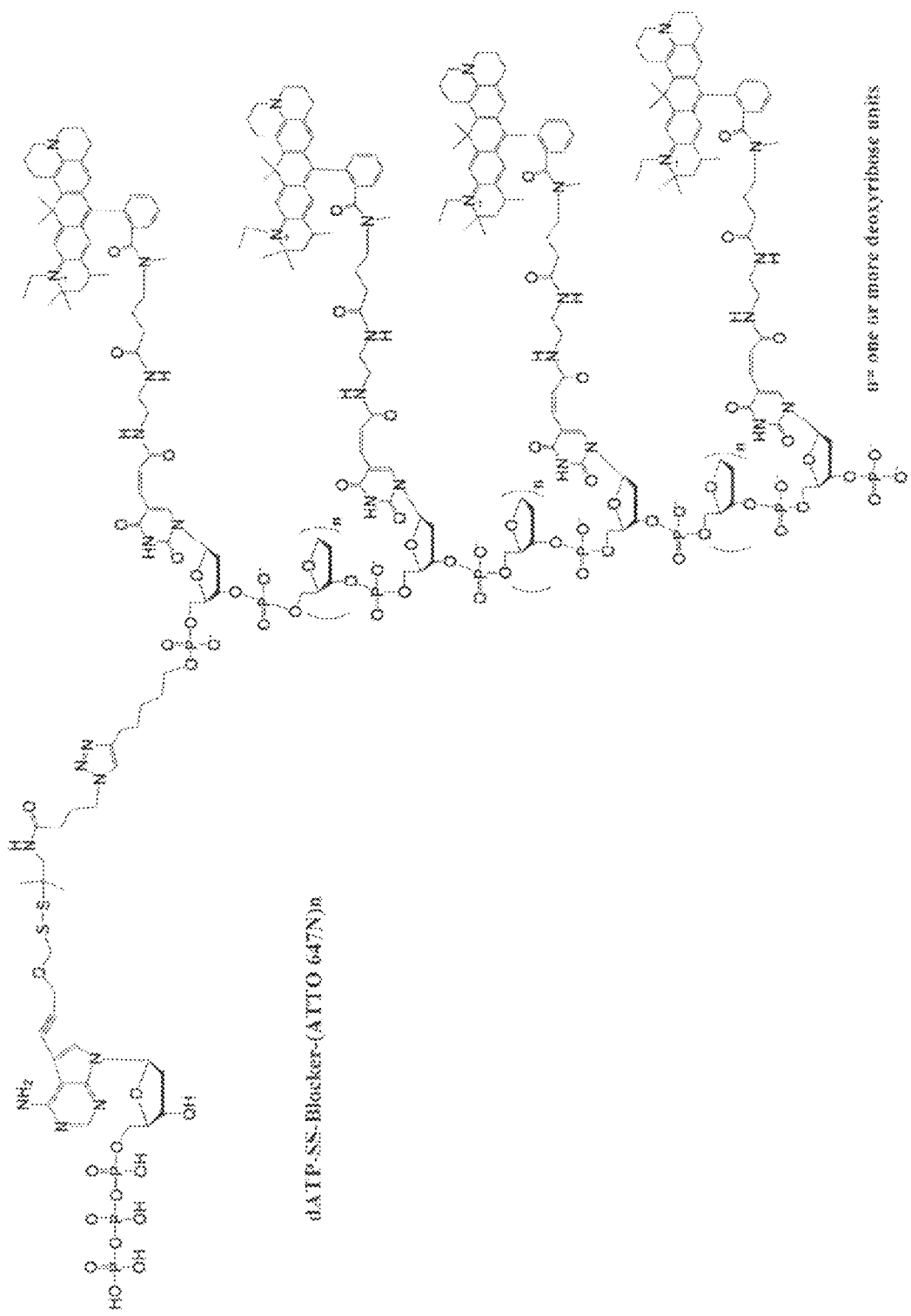

FIG. 85: Example of 3'-OH containing dATP-SS-blocker molecule with a dye cluster on the polynucleotide blocker.

Figure 86:
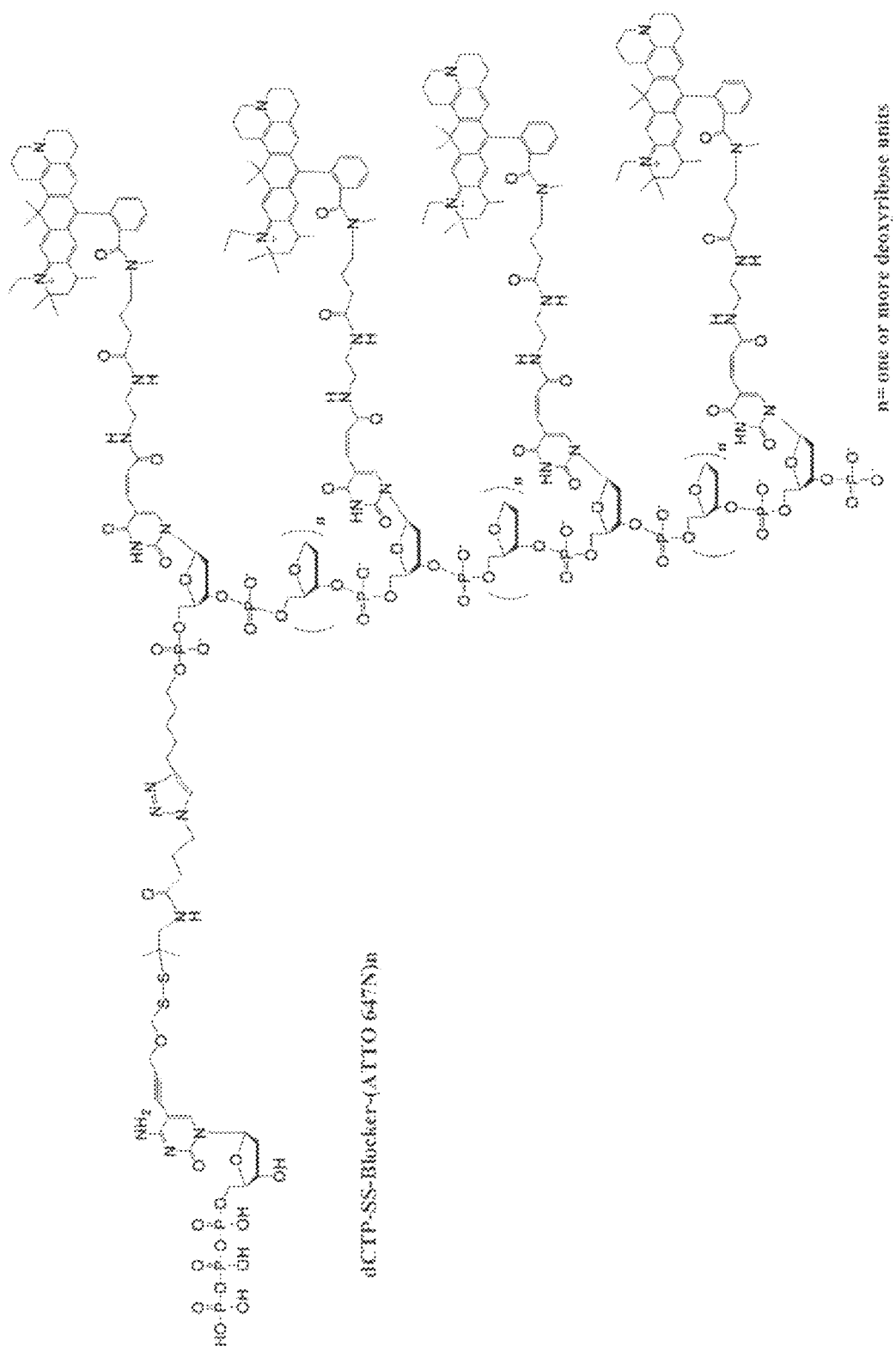

FIG. 86: Example of 3'-OH containing dCTP-SS-blocker molecule with a dye cluster on the polynucleotide blocker.

Figure 87:
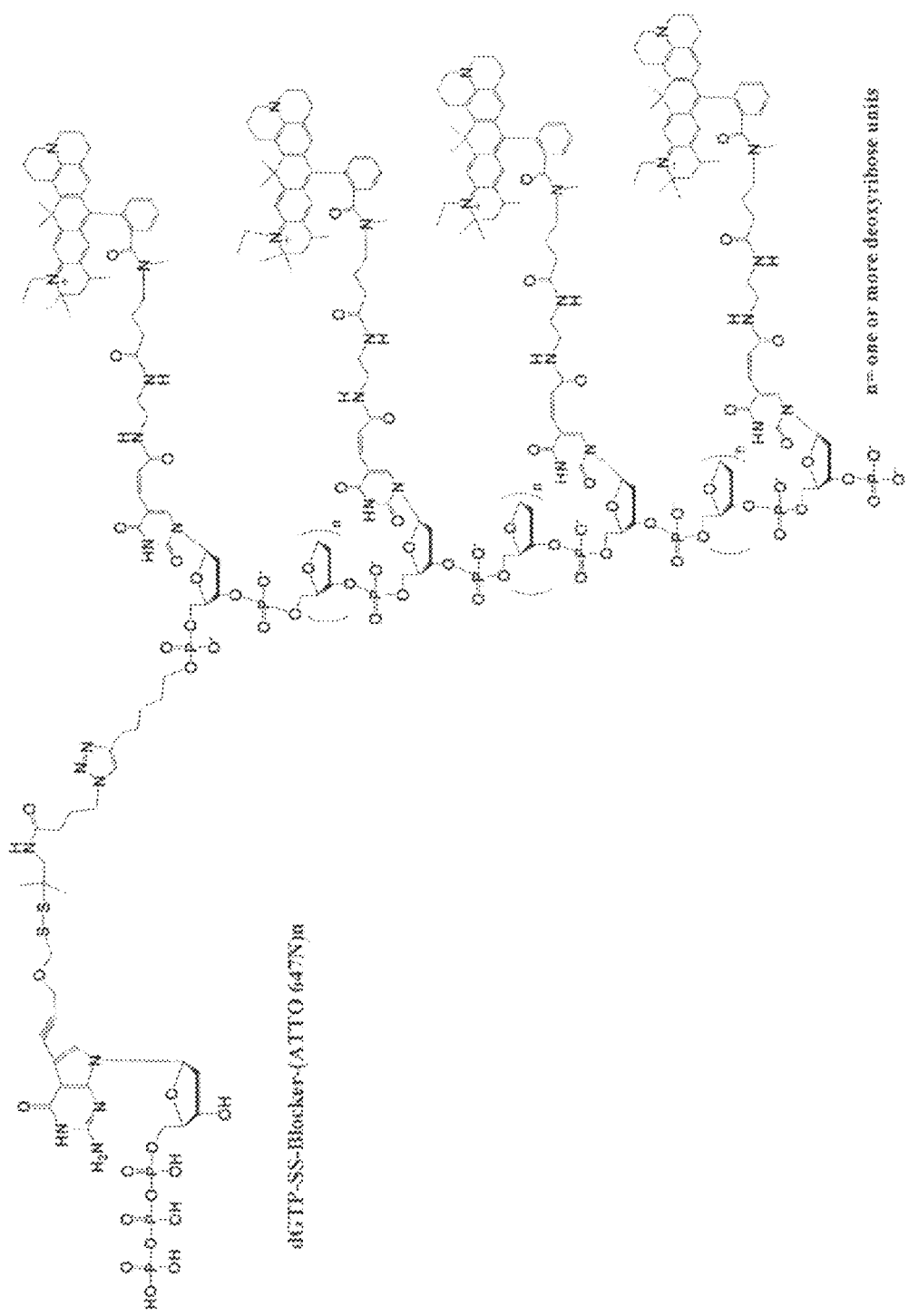

FIG. 87: Example of 3'-OH containing dGTP-SS-blocker molecule with a dye cluster on the polynucleotide blocker.

Figure 88:
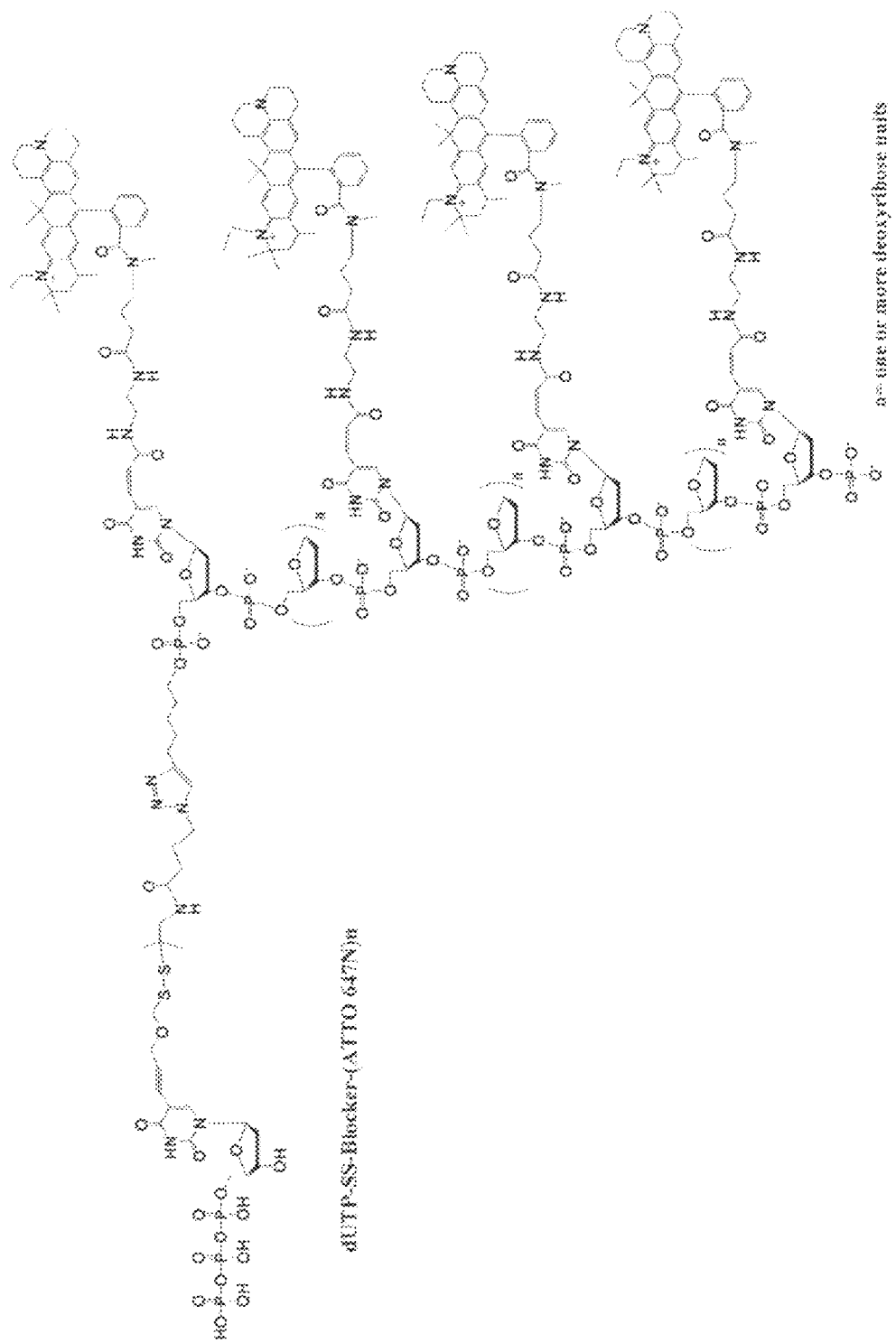
Figure 88A:
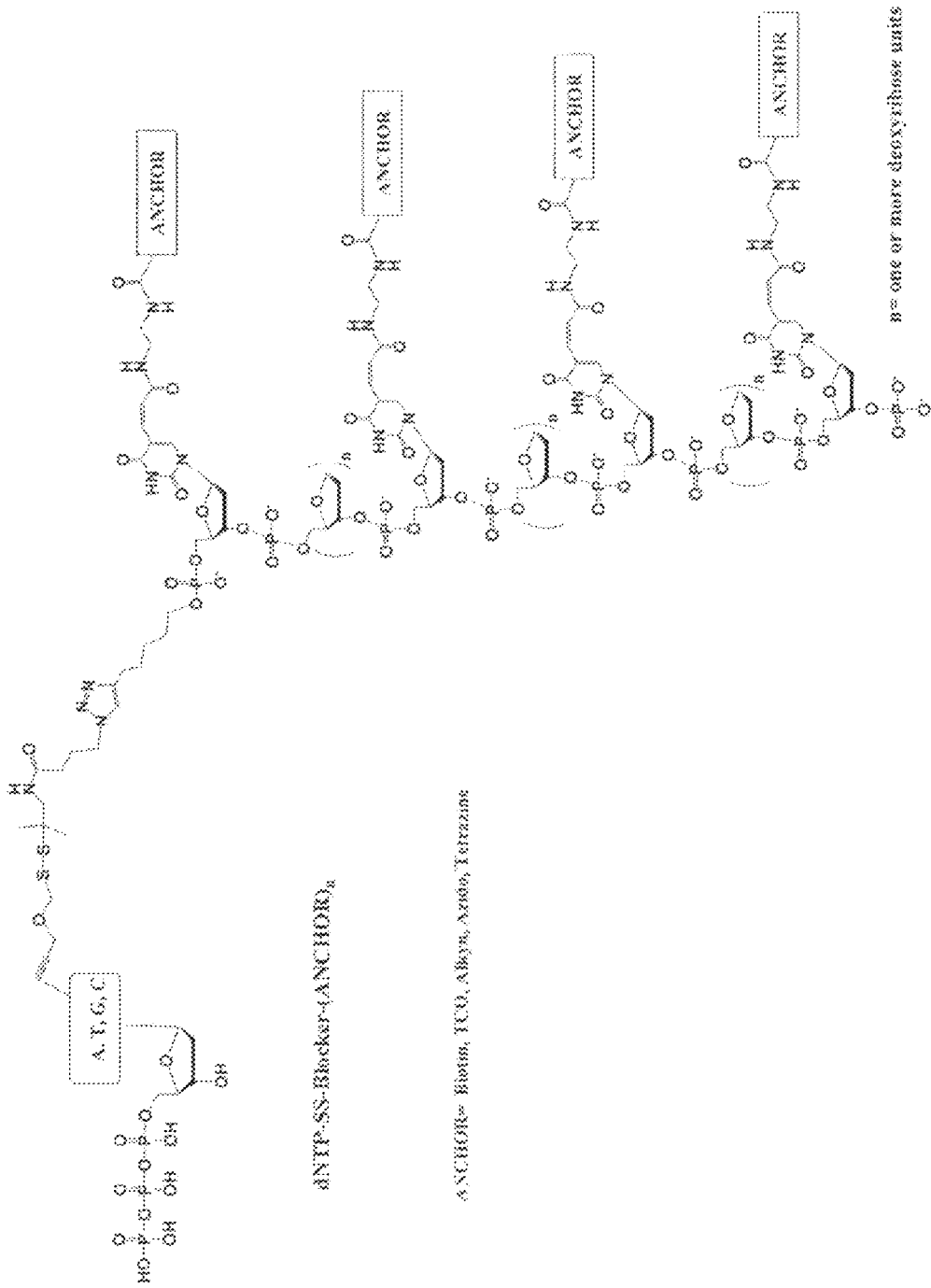

FIG. 88: Example of 3'-OH containing dUTP-SS-blocker molecule with a dye cluster on the polynucleotide blocker.

FIG. 89A: Example of 3'-OH containing dUTP-SS-blocker molecule with an anchor cluster on the polynucleotide blocker. Labeling with the single-dye containing anchor binding molecules results in a dye cluster on these nucleotide analogues.

Figure 89B:
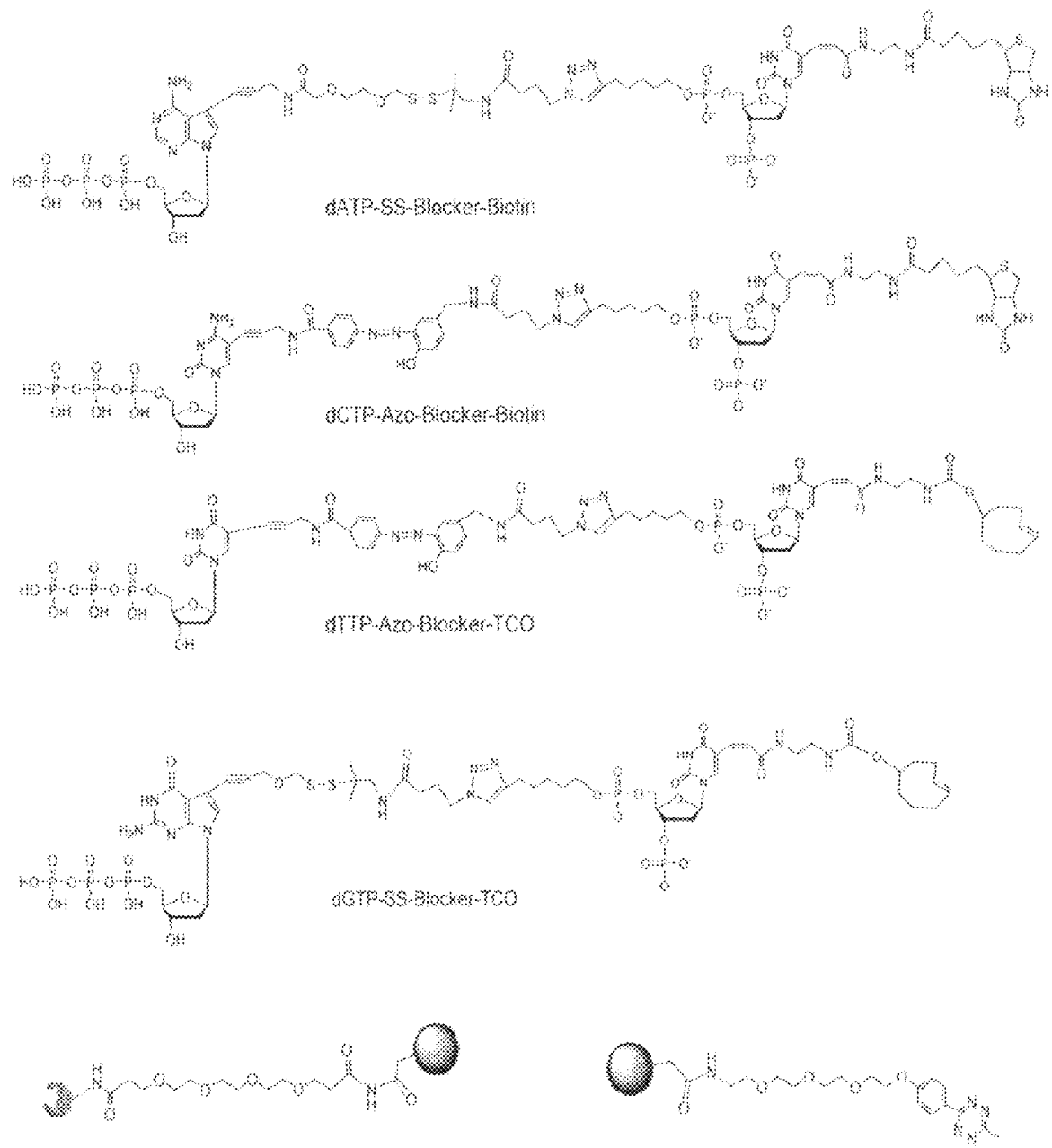

FIG. 89B: Examples of 3'-OH containing dNTP-Cleavable Linker-Blocker-Anchor and Quantum dot labeled Anchor Binding molecule (Qdot 525 Labeled Streptavidin and Qdot 605 Labeled Tetrazine) used for 2-color DNA SBS using approach delineated in Scheme XXIIB.

Figure 89D:
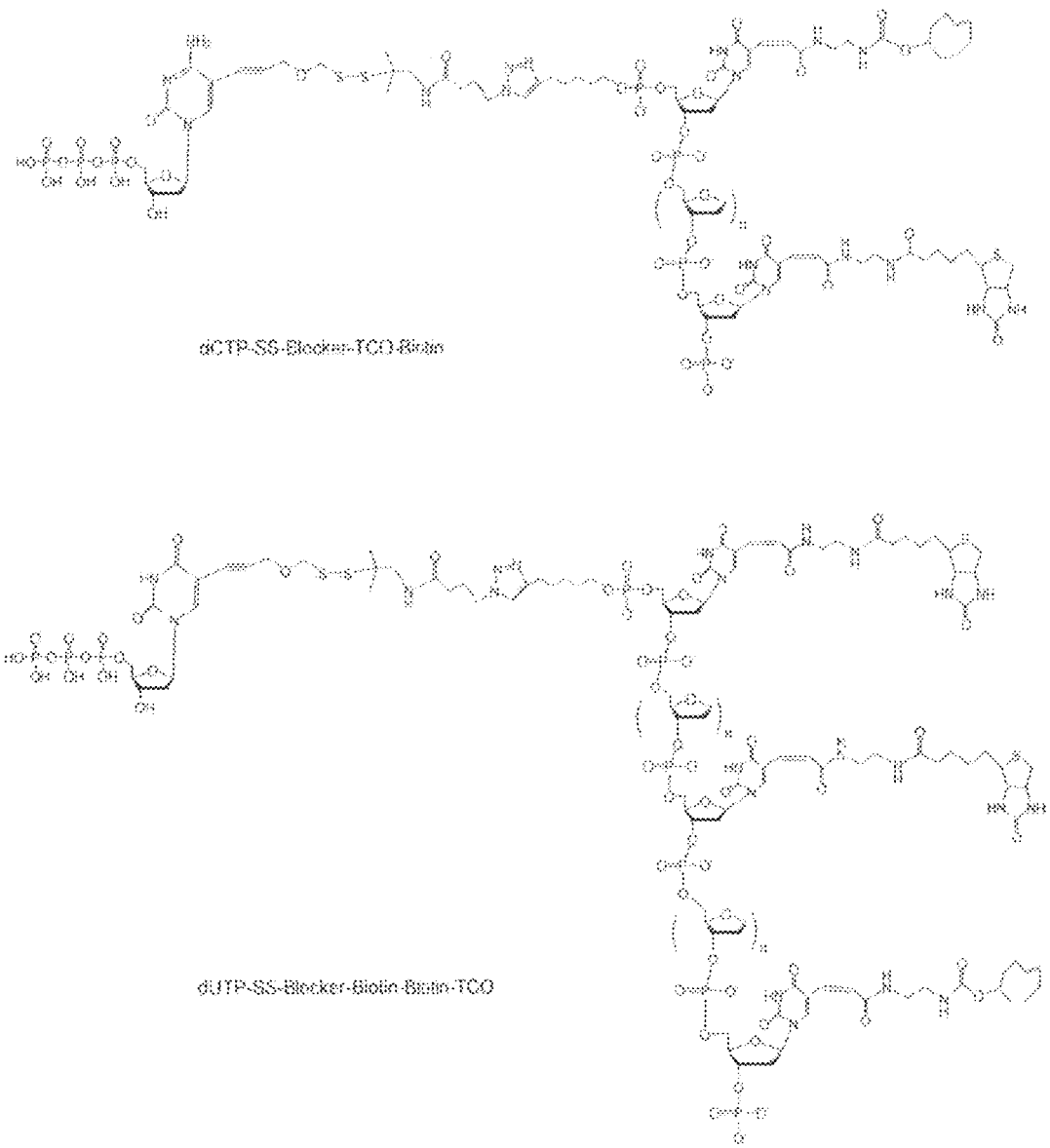

FIGS. 89C-89D: 3'-OH containing dNTP-Cleavable Linker-Blocker-Anchor (dATP-SS-Blocker-Biotin, dGTP-SS-Blocker-TCO, dCTP-SS-Blocker-Biotin-TCO, dTTP-SS-Blocker-Biotin-Biotin-TCO) and Quantum dots labeled Anchor Binding molecule (Qdot 525 Labeled Streptavidin and Qdot 605 Labeled Tetrazine) used for 2-color DNA SBS using approach delineated in Scheme XXIIC.

Figure 90:
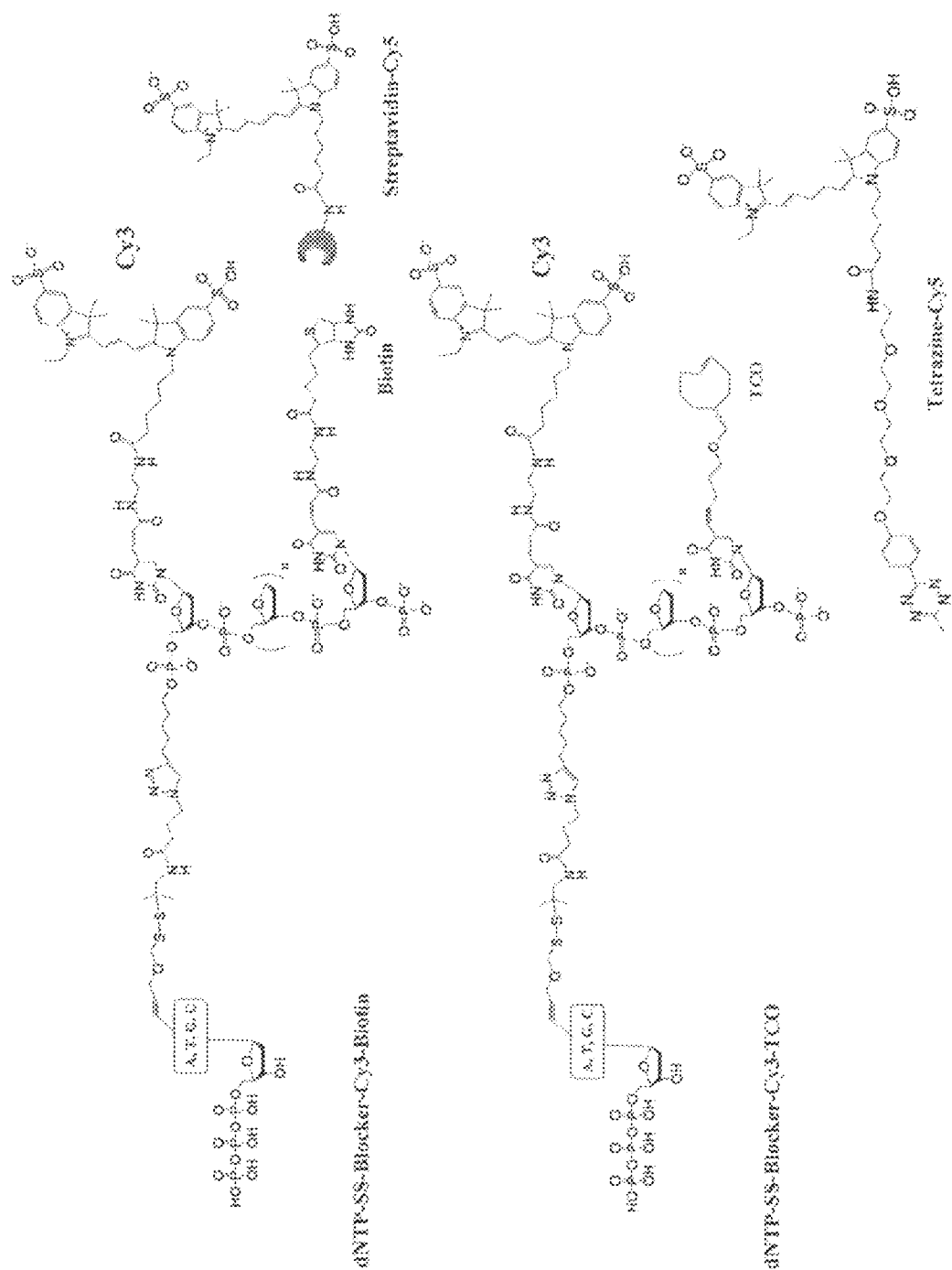

FIG. 90: General structures of dNTP-SS-Blocker-Cy3-Biotin, dNTP-SS-Blocker-Cy3-TCO, Cy5 labeled Streptavidin and Cy5 labeled Tetrazine for use in energy transfer aided SBS.

Figure 91:
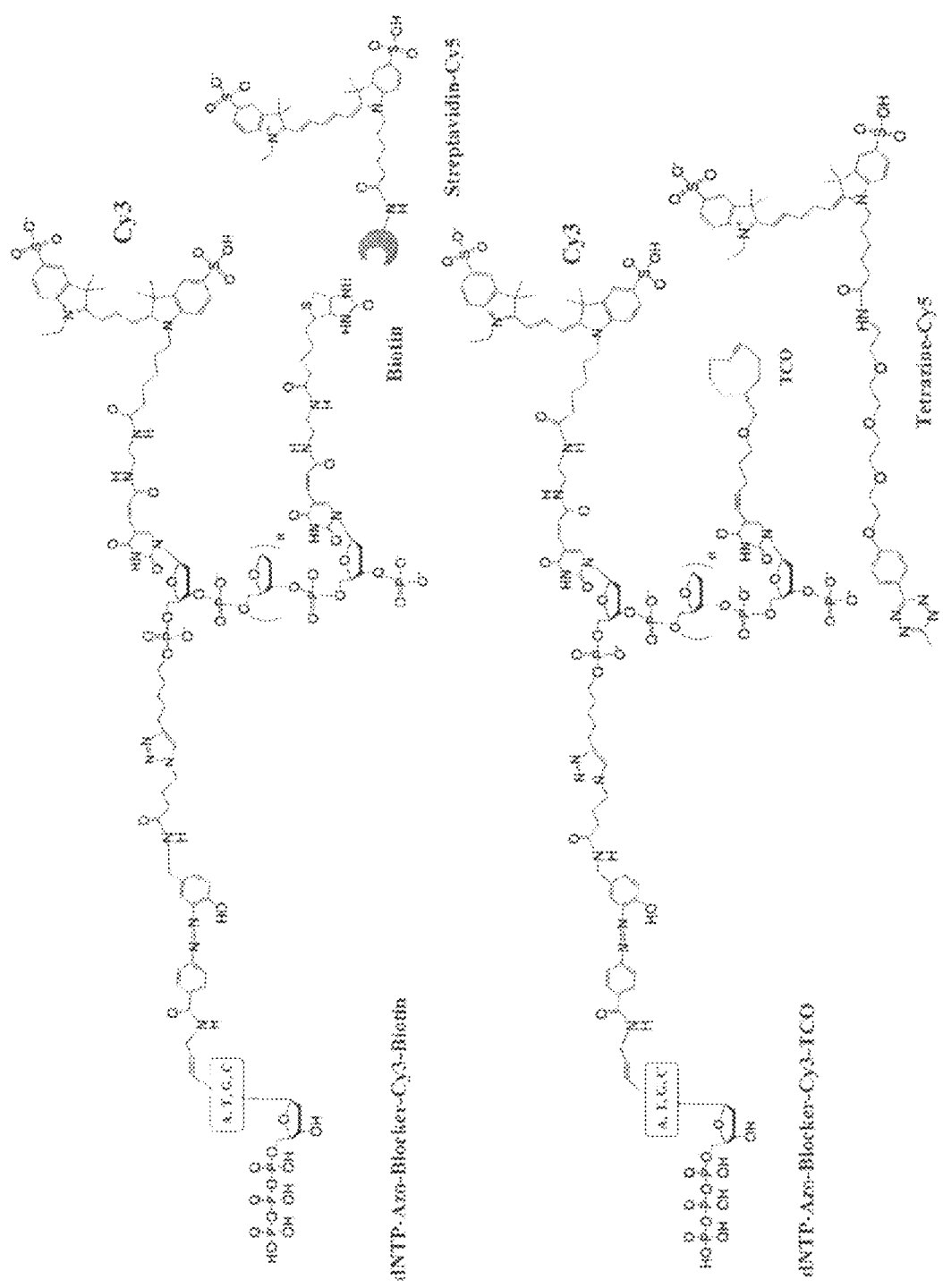

FIG. 91: General structures of dNTP-Azo-Blocker-Cy3-Biotin, dNTP-Azo-Blocker-Cy3-TCO, Cy5 labeled Streptavidin and Cy5 labeled Tetrazine for use in energy transfer aided SBS.

Figure 92A:
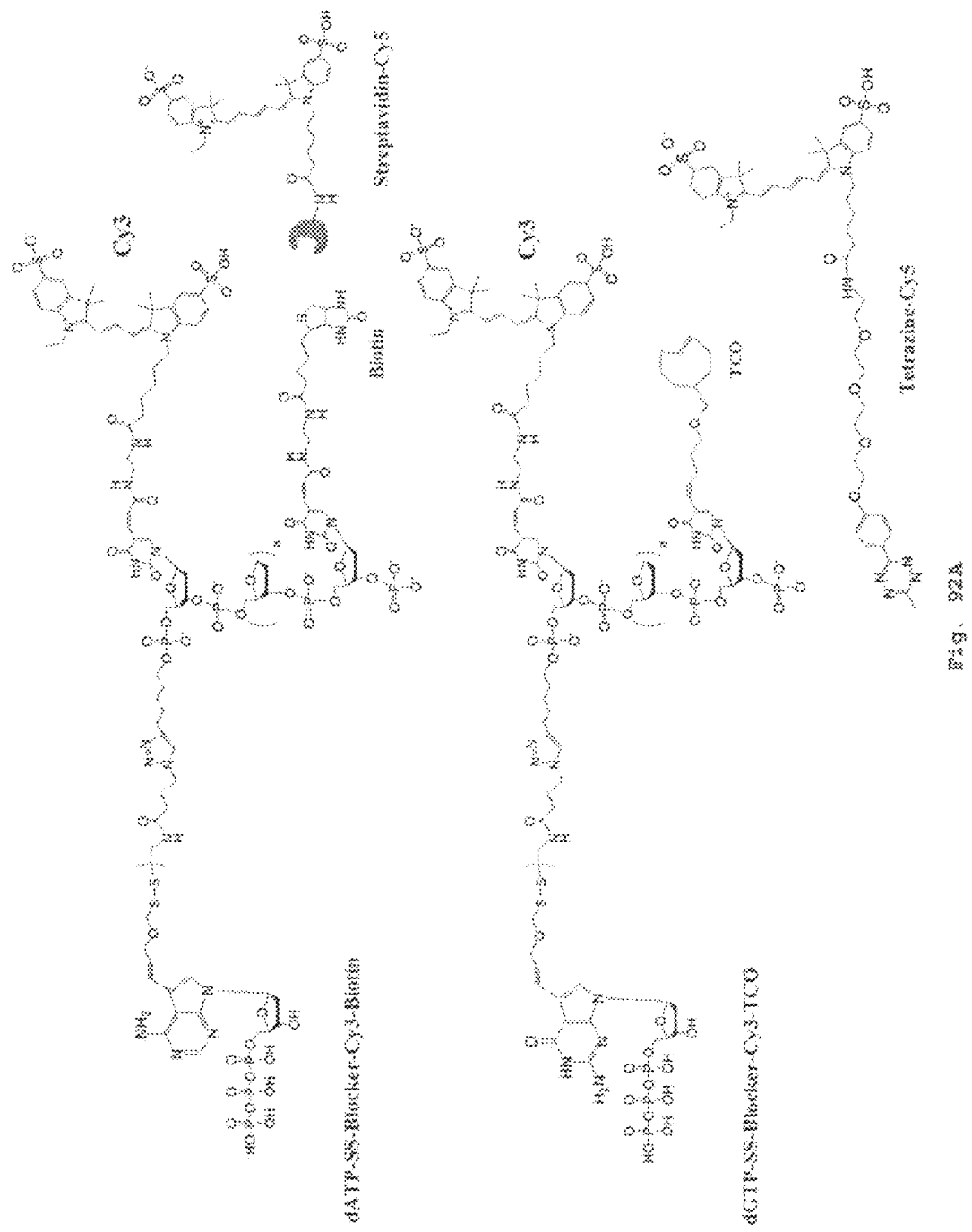
Figure 52B:
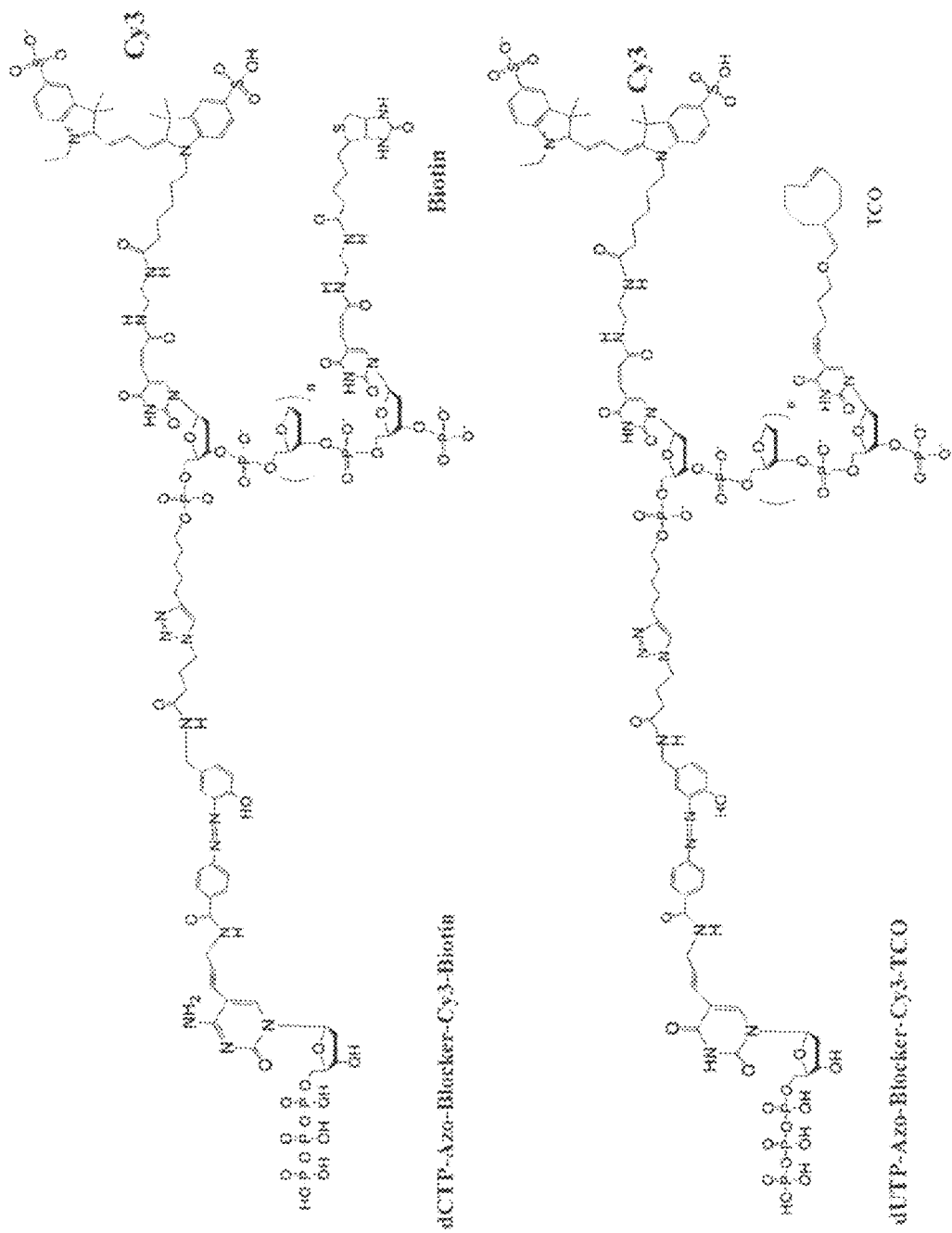

FIGS. 92A-92B: Nucleotide analogues (dATP-SS-Blocker-Cy3-Biotin, dGT-SS-Blocker-Cy3-TCO, dCTP-Azo-Blocker-Cy3-Biotin and dTTP-Azo-Blocker-Cy3-TCO) and labeled binding molecules (Cy5-labeled Tetrazine and Cy5-labeled Streptavidin) for use in single-color SBS (Scheme XXIII).

Figure 93A:
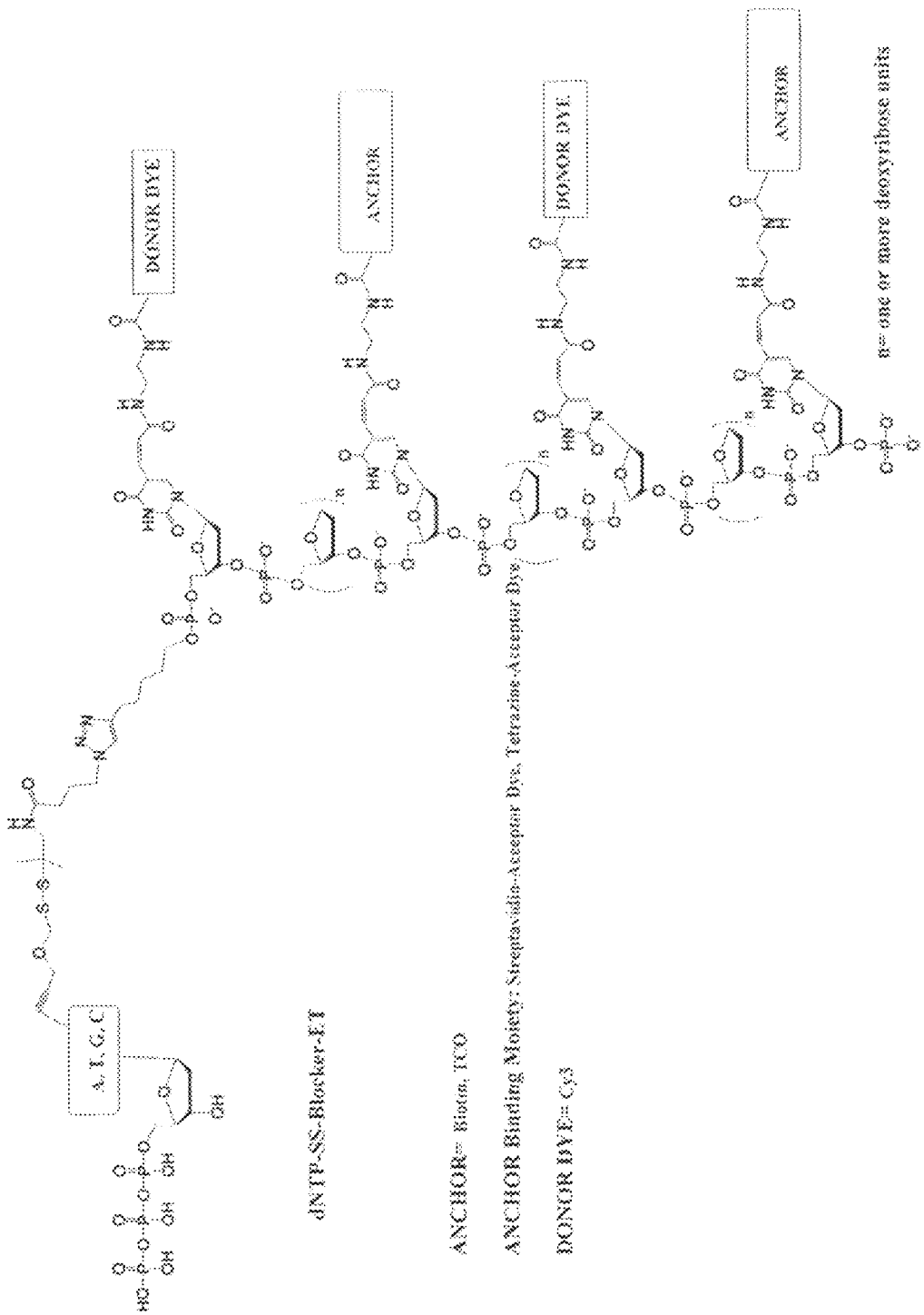

FIG. 93A: General structure of dNTP-SS-Blocker with multiple dyes or multiple anchors for use with FRET-assisted SBS (e.g., in Scheme XXIII). In this example, the structure attached to an SS cleavable linker is a blocker consisting of a linear polymer with 2 iterations of Donor Dye and Acceptor Dye or 2 iterations of Donor Dye and Anchor for binding to Acceptor Dye (e.g., Cy5, Alexa647, ATTO647N). More than two copies can be attached to such a polymer. The key idea is that after conjugation with the Anchor Binding Moiety with the Acceptor Dye, the Donor Dye and Acceptor Dye will be at an ideal distance (close to 5 nm) for maximal energy transfer, while there will be sufficient separation between the repeats to prevent quenching. In addition to the linear arrangement shown here, the donor dyes and anchors/acceptor dyes can be located on different branches of dendrimers. Different cleavable linkers containing Azo, Allyl, 2NB or other moieties can be used.

Figure 93B:
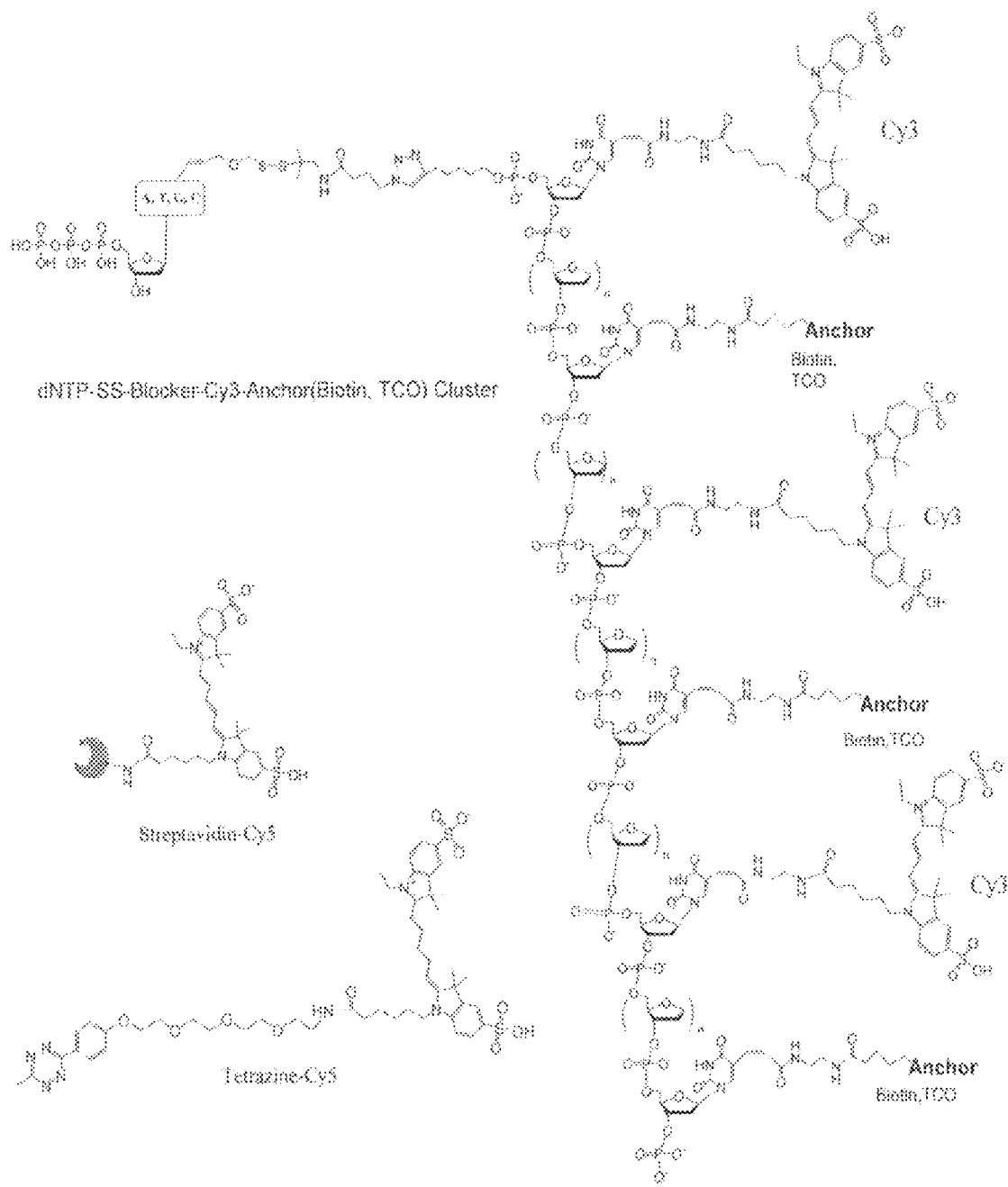

FIG. 93B: General structures of dNTP-SS-Blocker-Anchor (Biotin, TCO) cluster and Cy5 labeled Streptavidin and Cy5 labeled Tetrazine for use in energy transfer aided SBS.

Figure 93C:
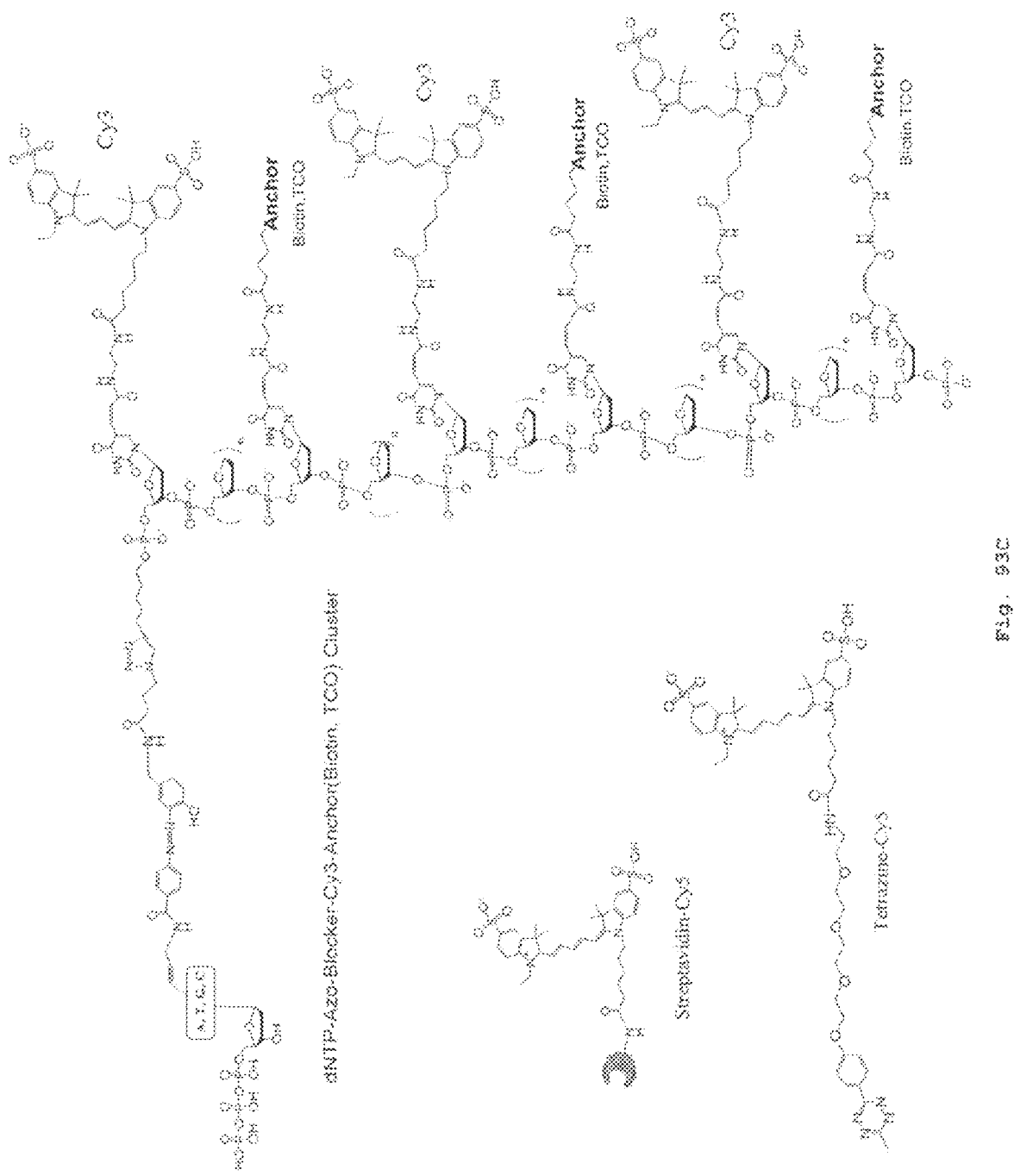

FIG. 93C: General structures of dNTP-SS-Blocker-Cy3-Anchor (Biotin, TCO) cluster and Cy5 labeled Streptavidin and Cy5 labeled Tetrazine for use in energy transfer aided SBS.

Figure 94:
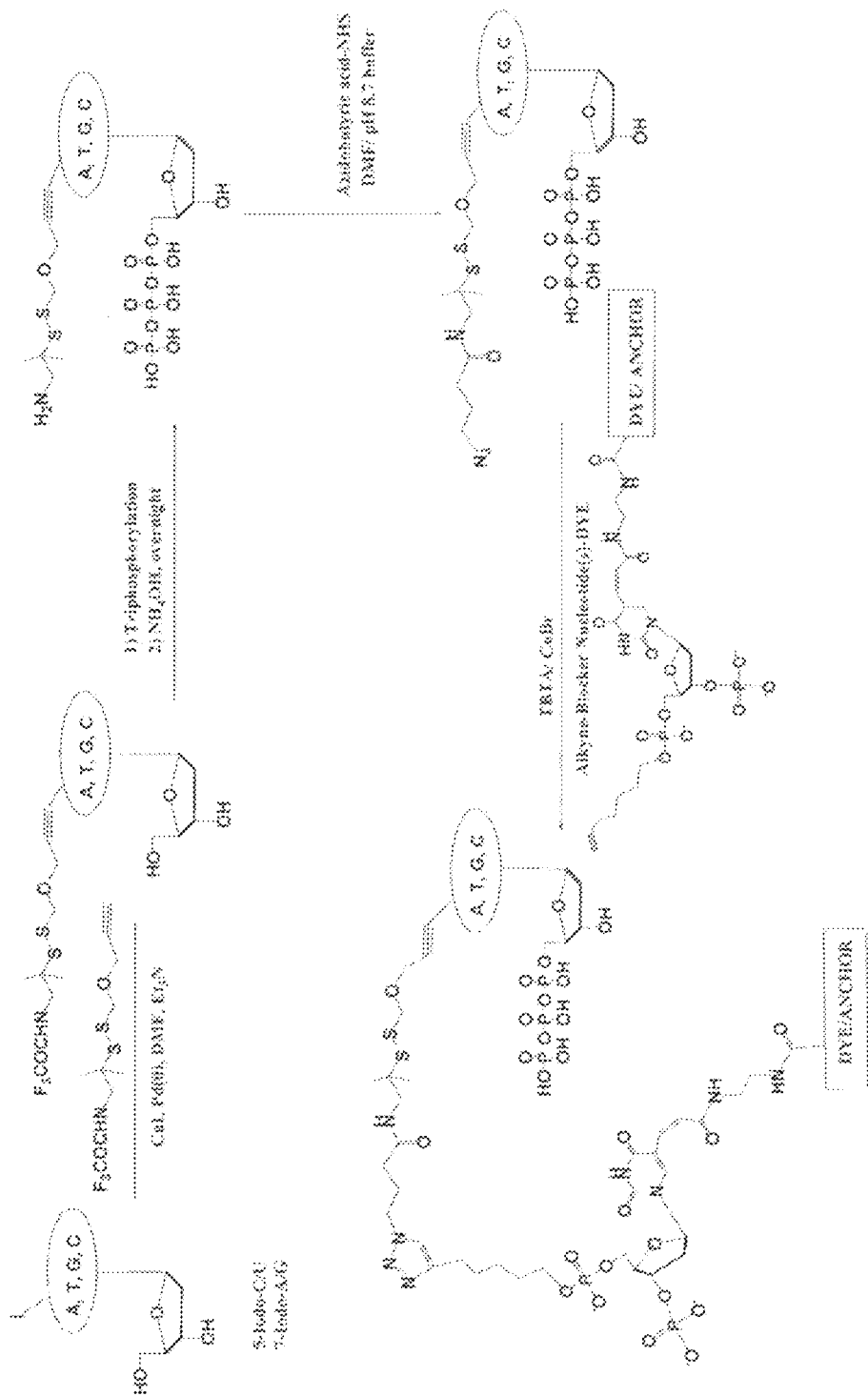

FIG. 94: General scheme for synthesis of 3'-OH containing dNTP-SS-Blocker-Dye/Anchor molecule.

Figure 95:
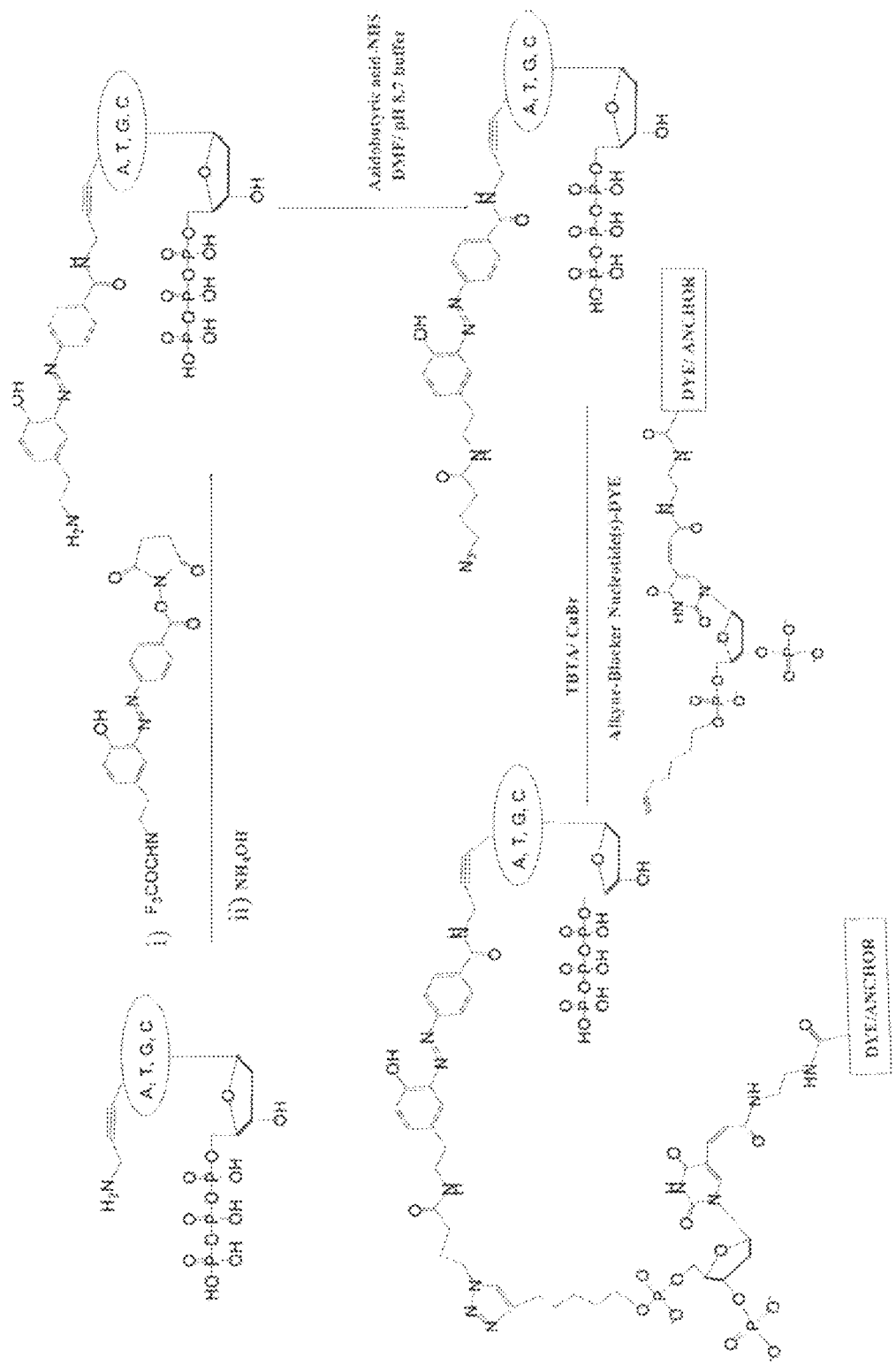

FIG. 95: General scheme for synthesis of 3'-OH containing dNTP-Azo-Blocker-Dye/Anchor molecule.

FIG. 96: Attachment of FRET cassette to dNTP-SS-linker. The same scheme can be used to attach such cassettes to dNTPs, ddNTPs (Section II) or NRTs (Section I) containing different cleavable linkers.

FIG. 97: A schematic showing Scheme XVIII using four dNTP-SS-Blocker-Dye molecules (dATP-SS-Blocker-ATTO647N, dCTP-SS-Blocker-ATTO647N, dGTP-SS-Blocker-ATTO647N, dTTP-SS-Blocker-ATTO647N) for single-color step-by-step sequencing.

FIG. 98: A schematic showing Scheme XIX using dNTP-Cleavable Linker-Blocker-Dyes (dATP-Allyl-Blocker-ATTO647N, dTTP-SS-Blocker-ATTO647N, dCTP-Azo-Blocker-ATTO647N, dGTP-2-Nitrobenzyl-Blocker-ATTO647N) and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS.

FIGS. 99A-99D: A schematic showing Scheme XX using dNTP-Cleavable Linker-Blocker-Dyes (dATP-Azo-Blocker-ATTO647N, dCTP-SS-Blocker-ATTO647N), dNTP-Cleavable Linker-Blocker-Anchors (dTTP-Azo-Blocker-Biotin and dGTP-SS-Blocker-Biotin), the corresponding dye labeled Anchor Binding Molecule (Streptavidin-ATTO647N), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS.

Figure 100A:
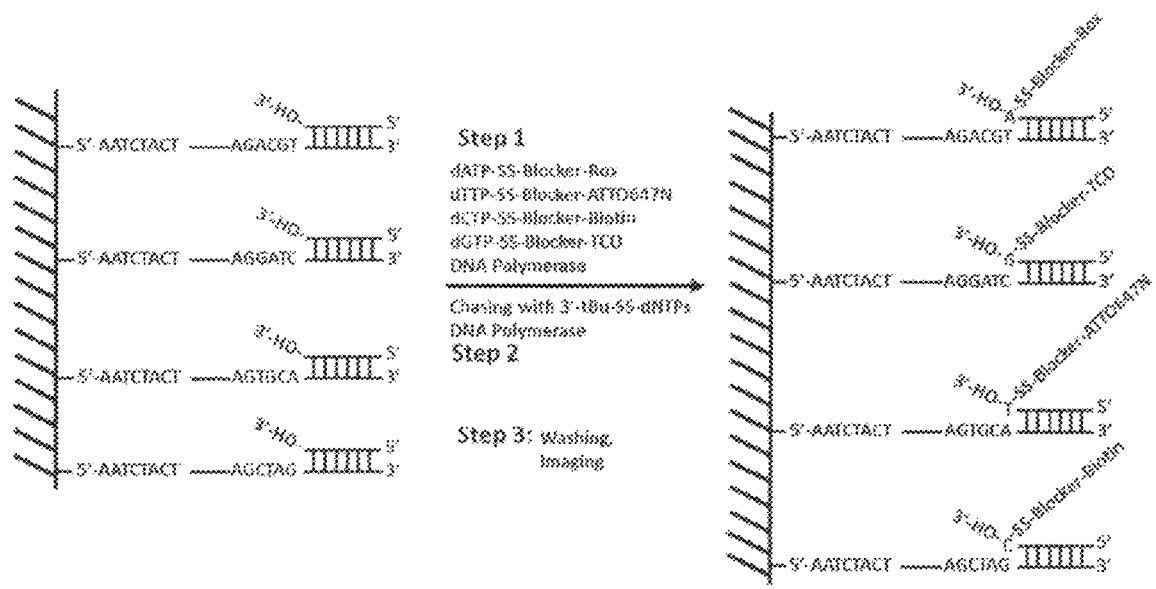
Figure 100B:
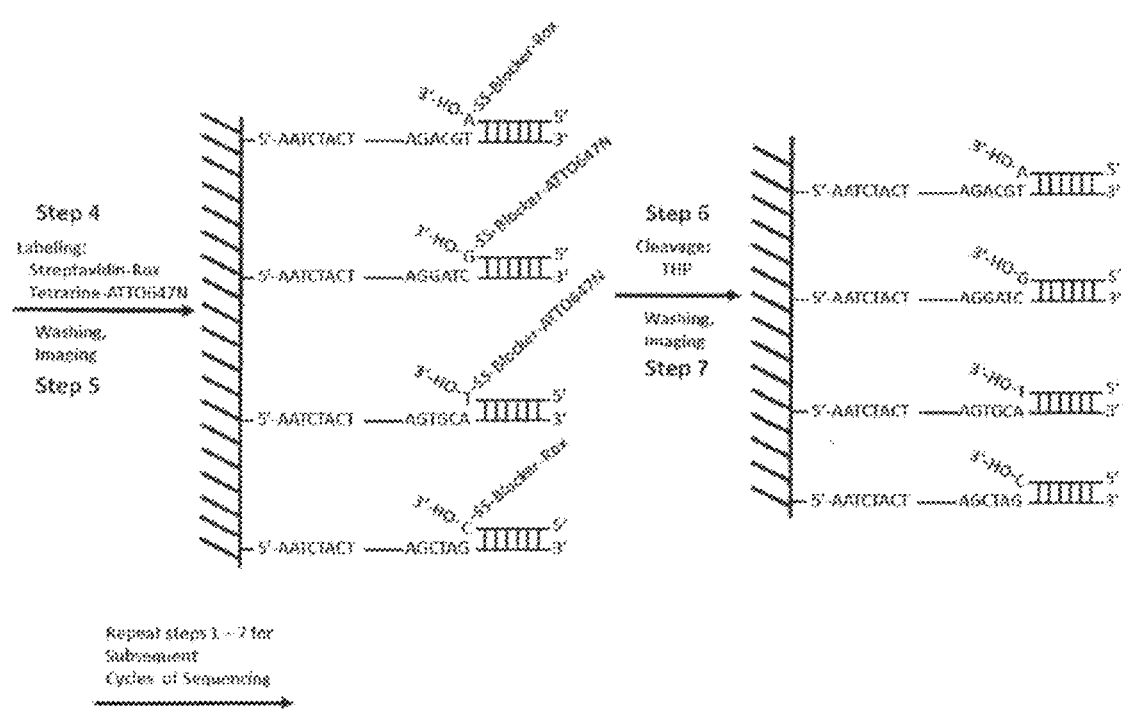
Figure 100C:
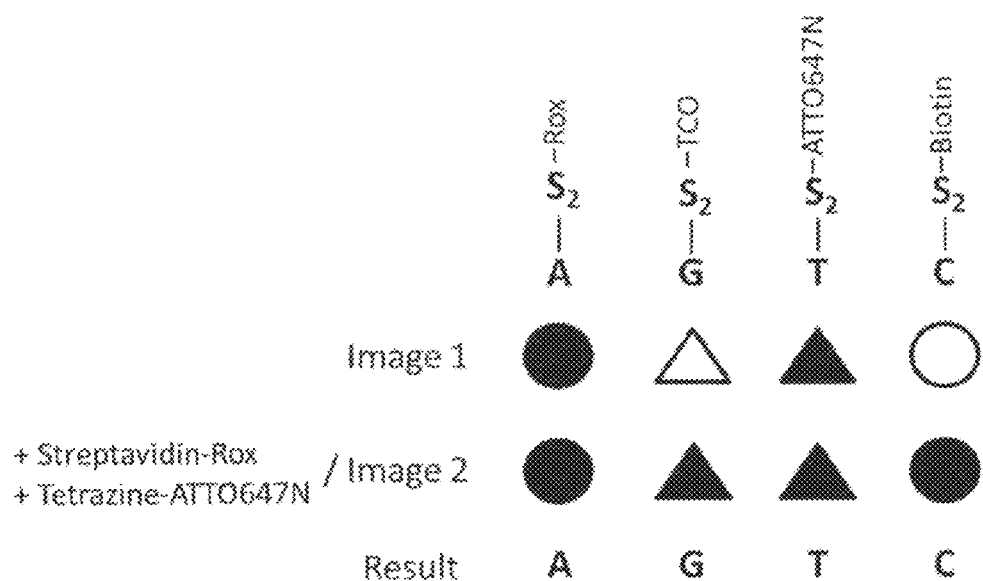

FIGS. 100A-100C: A schematic showing Scheme XXI using dNTP-SS-Blocker-Dyes (dATP-SS-Blocker-Rox, dTTP-SS-Blocker-ATTO647N), dNTP-SS-Blocker-Anchors (dCTP-SS-Blocker-Biotin and dGTP-SS-Blocker-TCO), the corresponding Dye-labeled Anchor Binding Molecules (Streptavidin-Rox and Tetrazine-ATTO647N), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS.

Figure 101:
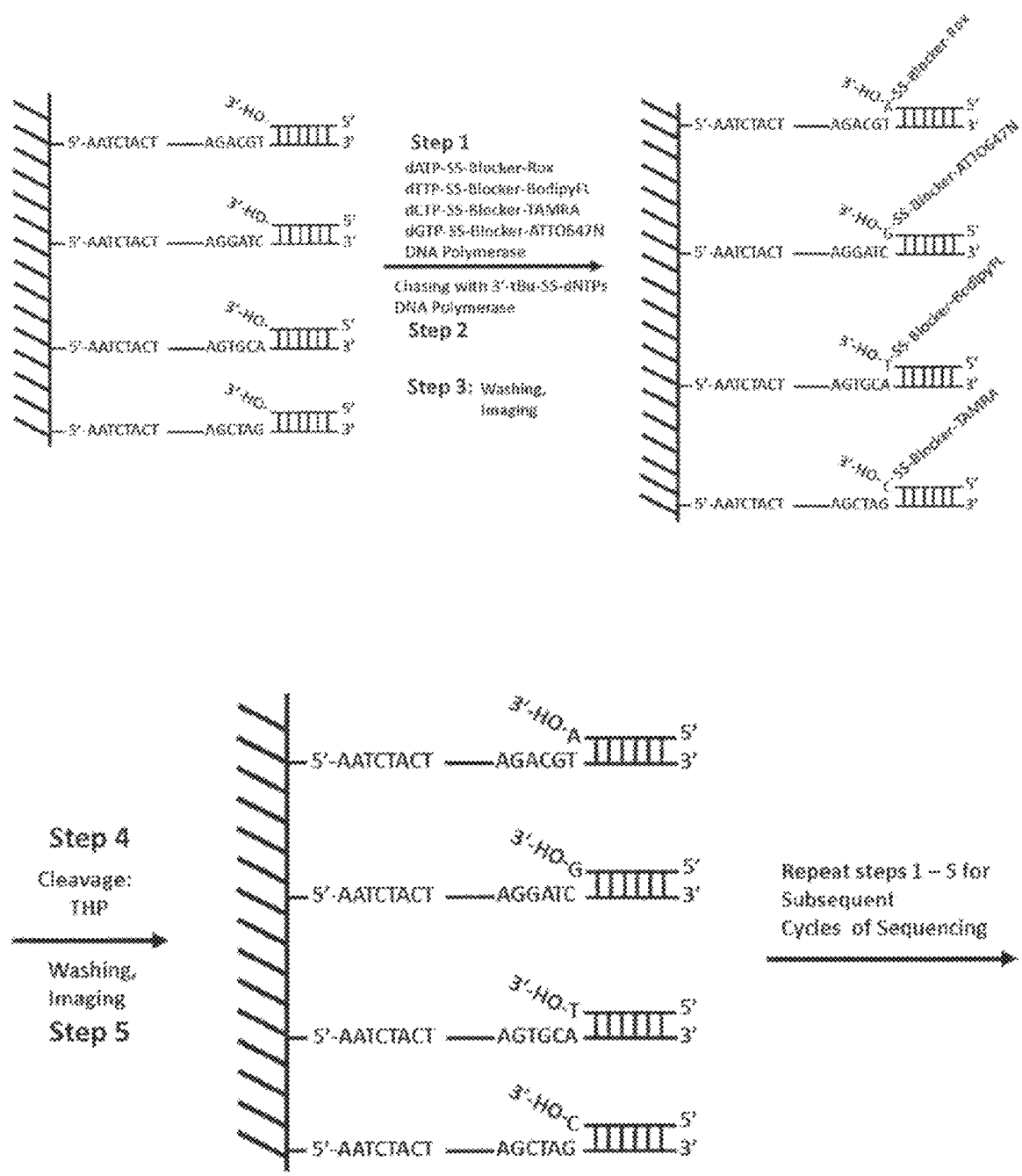

FIG. 101: A schematic showing Scheme XXIIA using dNTP-SS-Blocker-Dyes (dATP-SS-Blocker-Rox, dTTP-SS-Blocker-BodipyFL, dCTP-SS-Blocker-TAMRA and dGTP-SS-Blocker-ATTO647N) and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 4-color DNA SBS.

Figure 102A:
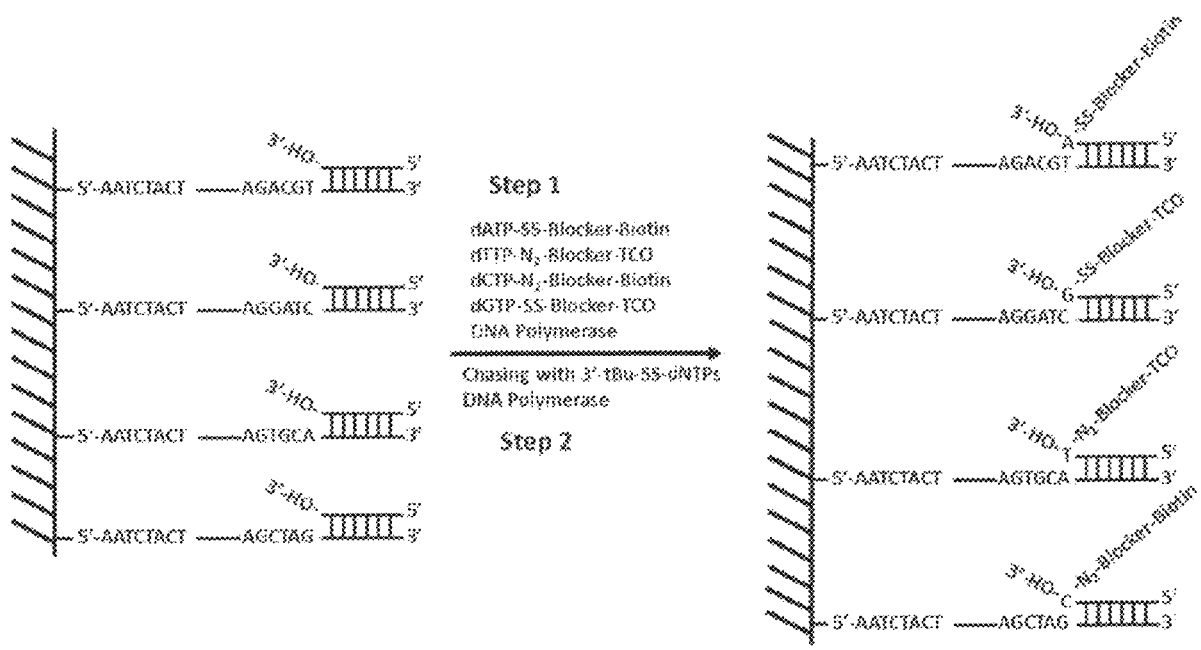
Figure 102B:
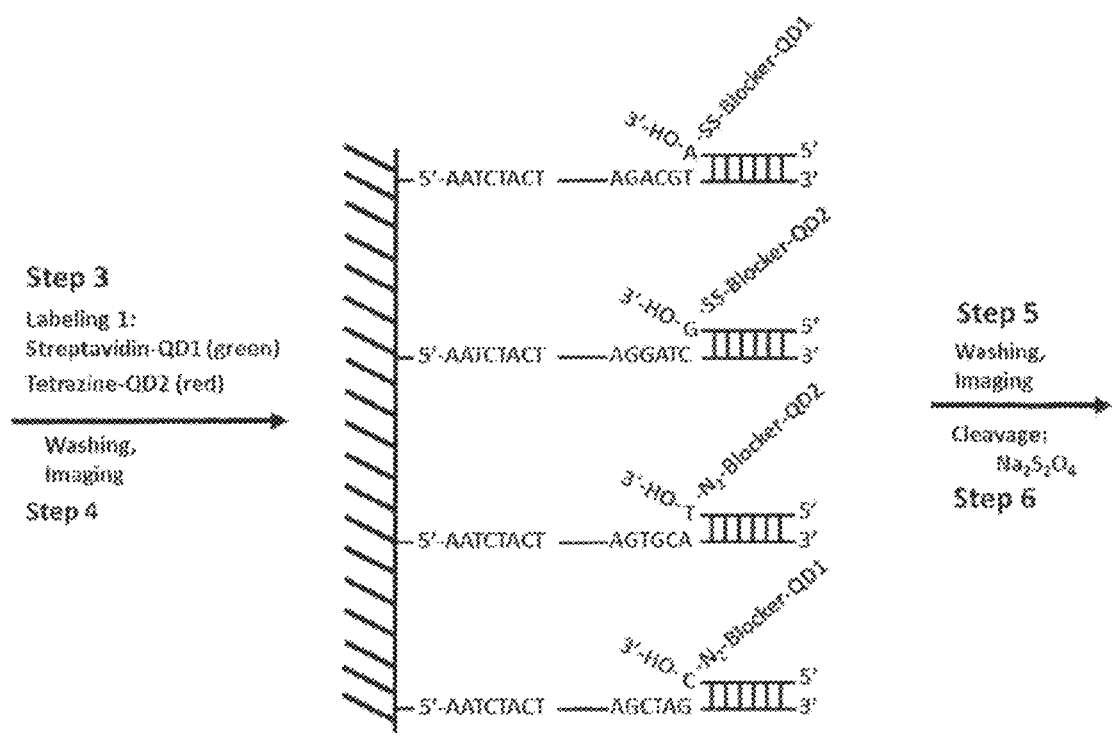
Figure 102C:
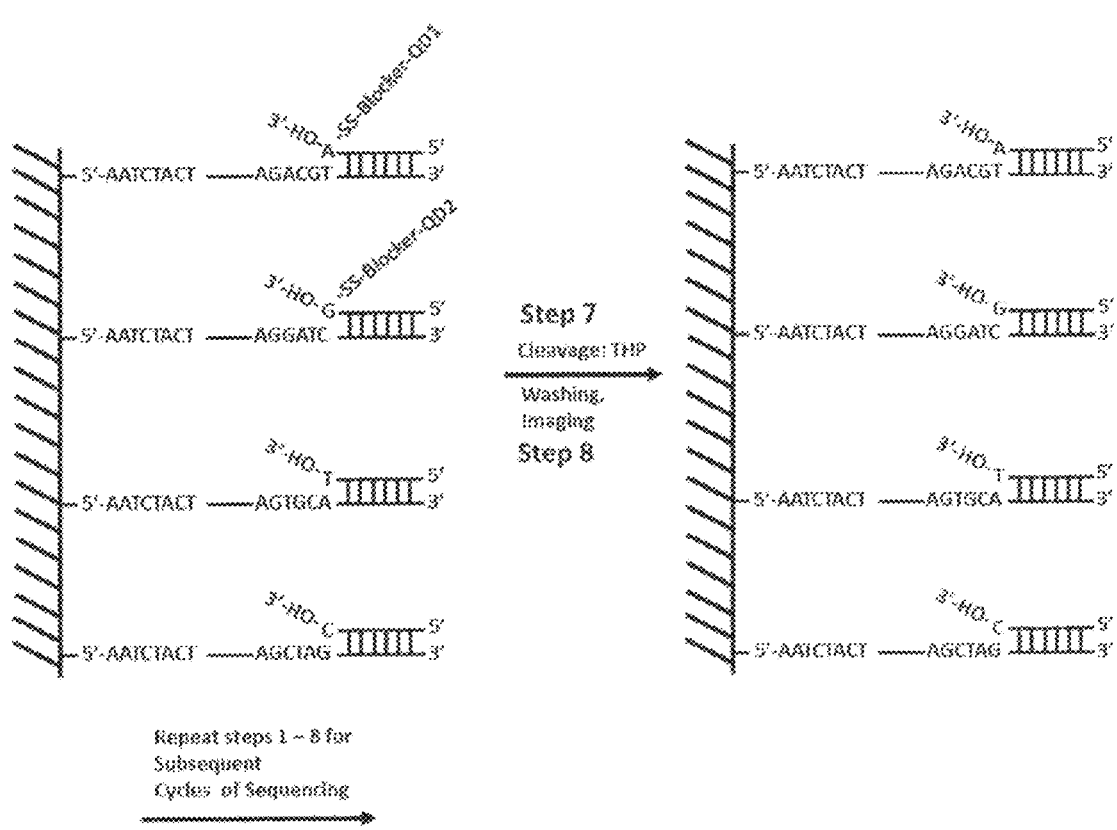

FIGS. 102A-102C: A schematic showing Scheme XXIIB using dNTP-SS-Blocker-Anchors (dATP-SS-Blocker-Biotin, dGTP-SS-Blocker-TCO), dNTP-Azo-Blocker-Anchors (dTTP-Azo-Blocker-TCO, dCTP-Azo-Blocker-Biotin), the corresponding Dye Labeled Binding Molecules (Quantum Dot 1 (Green)-labeled Streptavidin and Quantum Dot 2 (Red)-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS.

Figure 103:
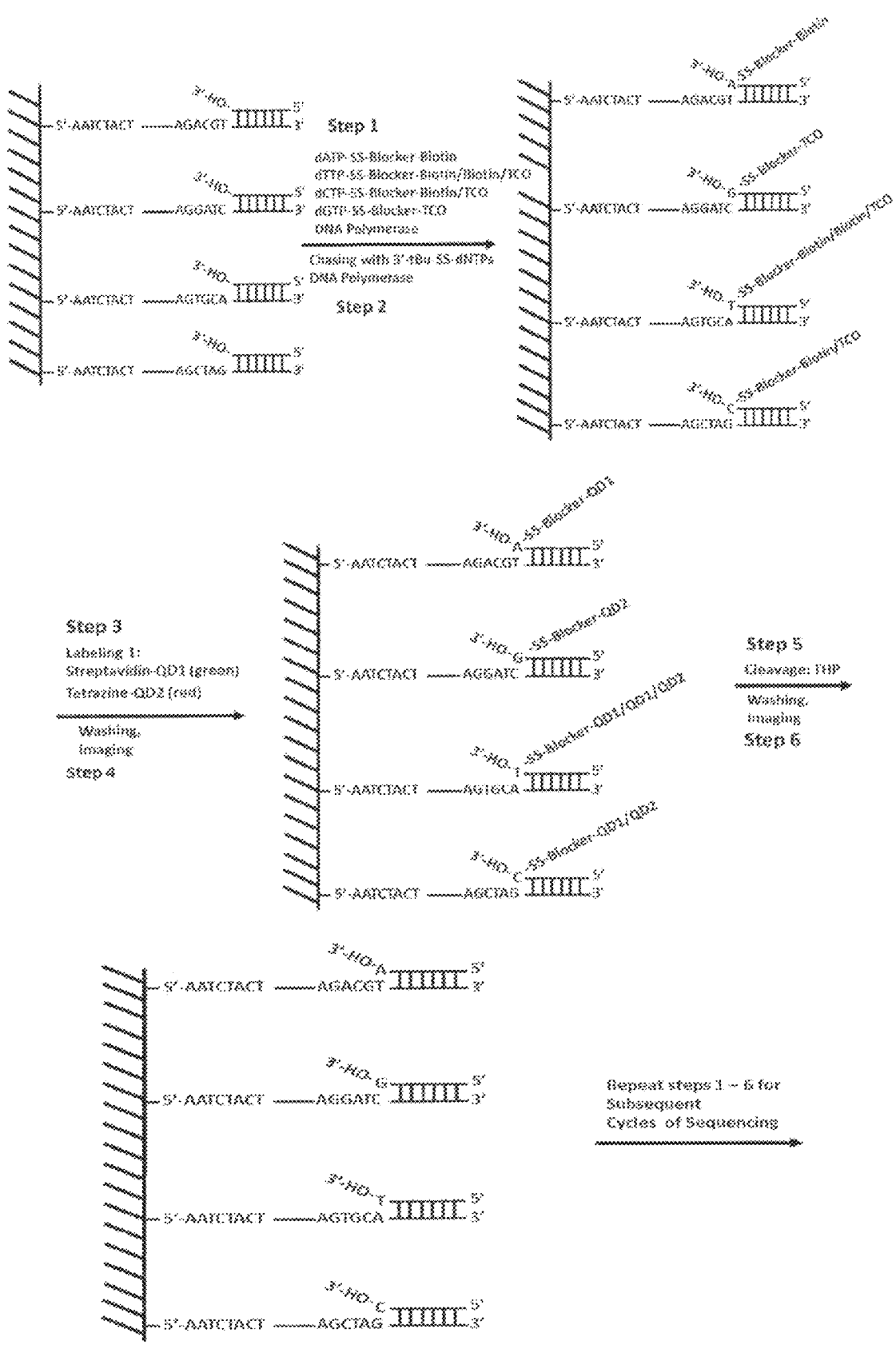
Figure 104A:
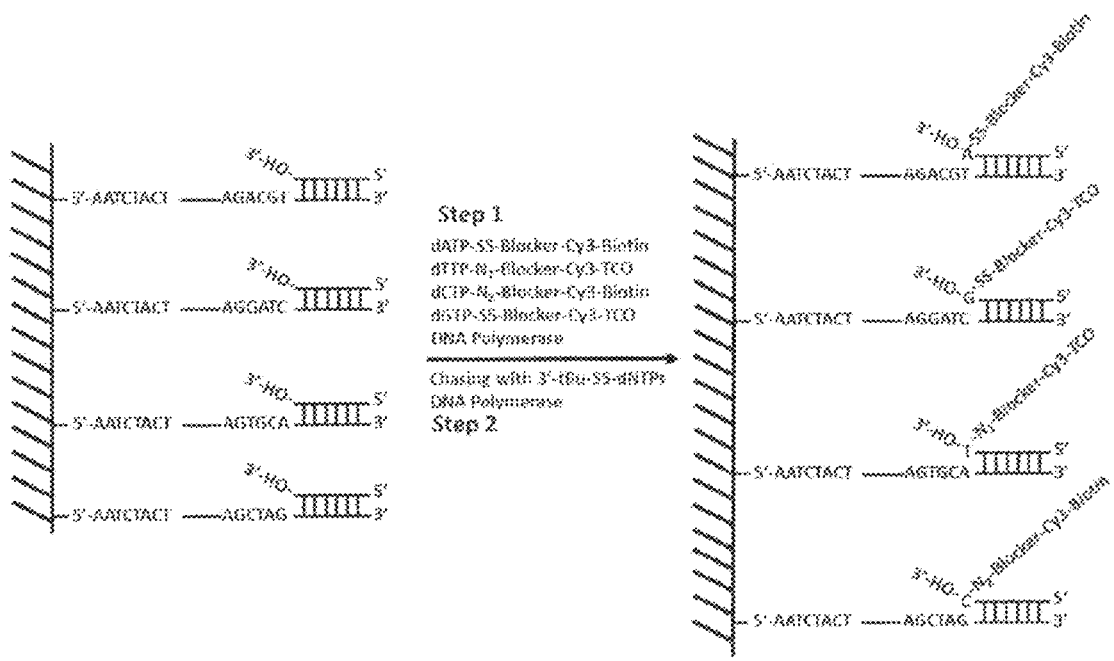
Figure 104B:
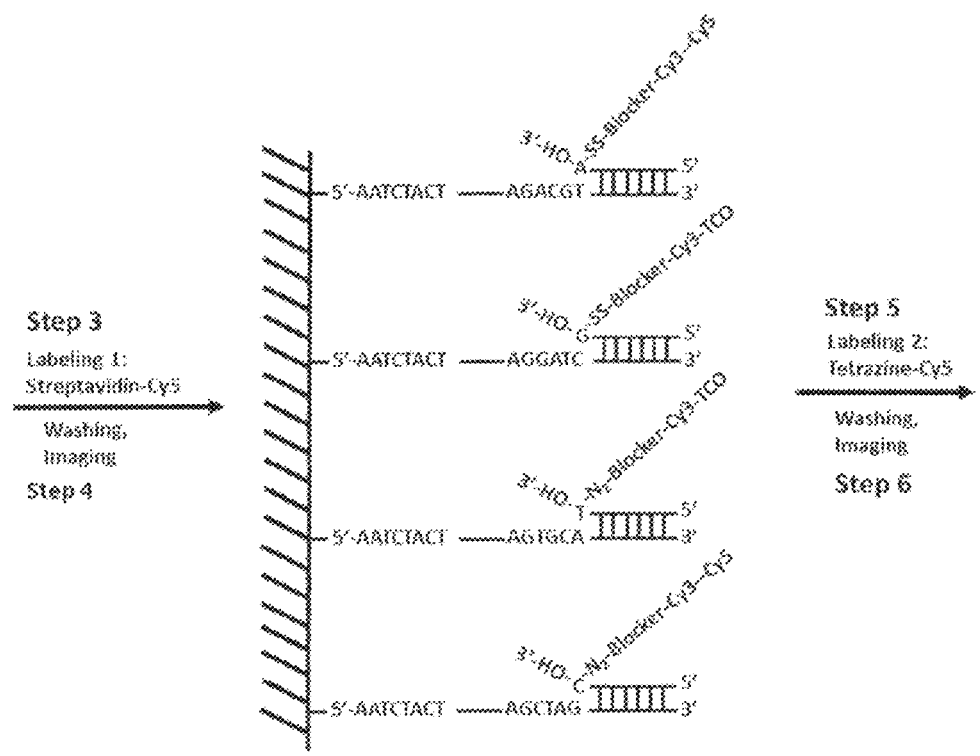
Figure 104C:
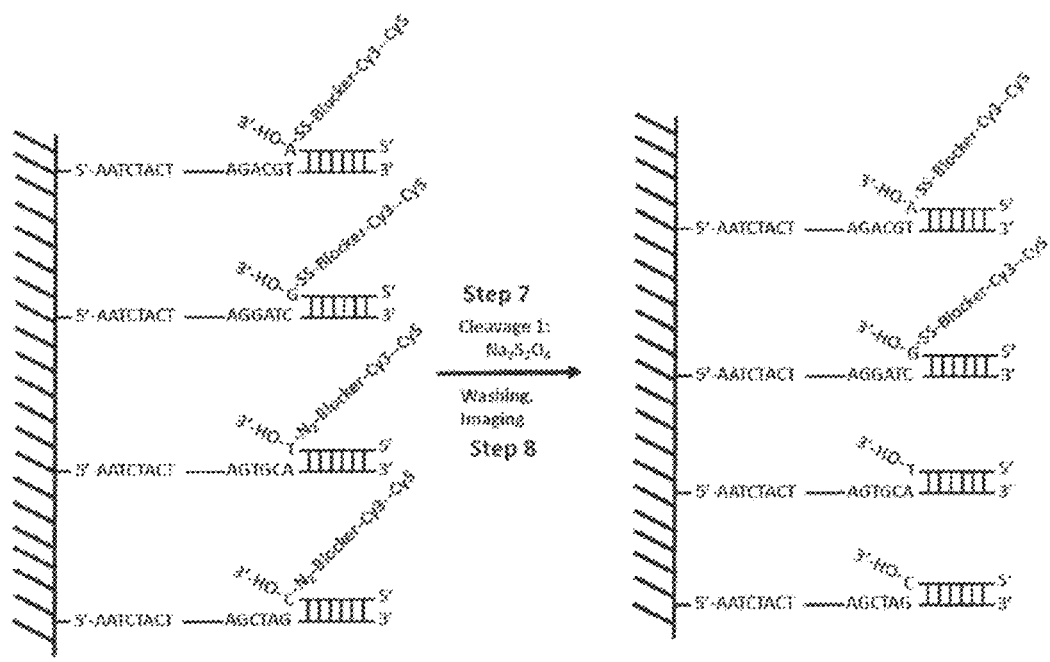
Figure 104D:
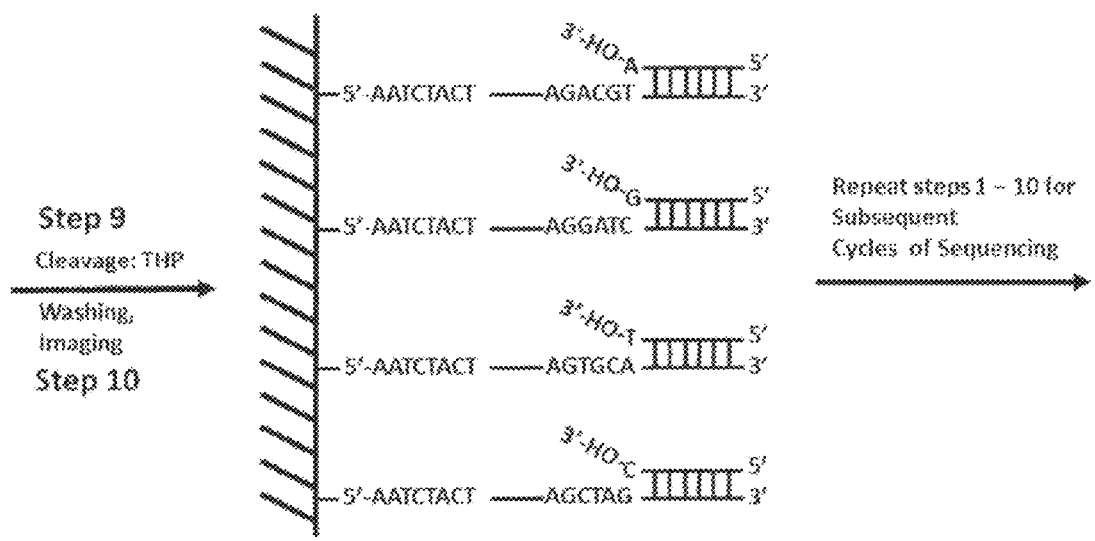

FIG. 103: A schematic showing Scheme XXIIC using dNTP-SS-Blocker-Anchors (dATP-SS-Blocker-Biotin, dGTP-SS-Blocker-TCO, dTTP-SS-Blocker-Biotin/Biotin/TCO, dCTP-SS-Blocker-Biotin/TCO), the corresponding Dye Labeled Binding Molecules (Quantum Dot 1 (Green)-labeled Streptavidin and Quantum Dot 2 (Red)-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS.

FIGS. 104A-104D: A schematic showing Scheme XXIII using dNTP-SS-Blocker-DonorDye-Anchors (3'-O-SS-dATP-7-SS-Blocker-Cy3-Biotin, 3'-O-SS-dGTP-7-SS-Blocker-Cy3-TCO), 3'-O-SS(DTM)-dNTP-Azo-Blocker-Cy3-Anchors (3'-O-SS-dTTP-5-Azo-Blocker-Cy3-TCO, 3'-O-SS-dCTP-5-Azo-Blocker-Cy3-Biotin), the corresponding Dye Labeled Binding Molecules (Cy5-labeled Streptavidin and Cy5-labeled Tetrazine), and the four 3'-O-SS (DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS.

FIG. 105: 3'-O-Dye-SS(DTM)Trigger-dNTPs (3'-O-Rox-PEG$_4$-SS(DTM)Trigger-dATP, 3'-O-BodipyFL-PEG$_4$-SS(DTM)Trigger-dGTP) and 3'-O-Anchor-SS(DTM)Trigger-dNTPs (3'-O-Biotin-SS(DTM)Trigger-dTTP, 3'-O-TCO-SS(DTM)Trigger-dCTP) and the corresponding dye labeled binding molecules (R6G labeled Tetrazine and Cy5 labeled Streptavidin) for 4-color DNA SBS using approach delineated in Scheme XXIV. R-alkyl: methyl, ethyl, propyl, t-butyl.

FIG. 106: 3'-O-Dye-SS(DTM)Trigger-dNTPs (3'-O-Rox-PEG$_4$-SS(DTM)Trigger-dATP, 3'-O-BodipyFL-PEG$_4$-SS(DTM)Trigger-dGTP), 3'-O-Anchor-SS(DTM)Trigger-dNTPs (3'-O-Biotin-SS(DTM)Trigger-dTTP, 3'-O-TCO-SS(DTM)Trigger-dCTP) and associated Dye-labeled Anchor Binding Molecules (Rox-labeled Streptavidin, BodipyFL-labeled Tetrazine) to perform two-color SBS using approach delineated in Scheme XXV. R-alkyl: methyl, ethyl, propyl, t-butyl.

Figure 107:
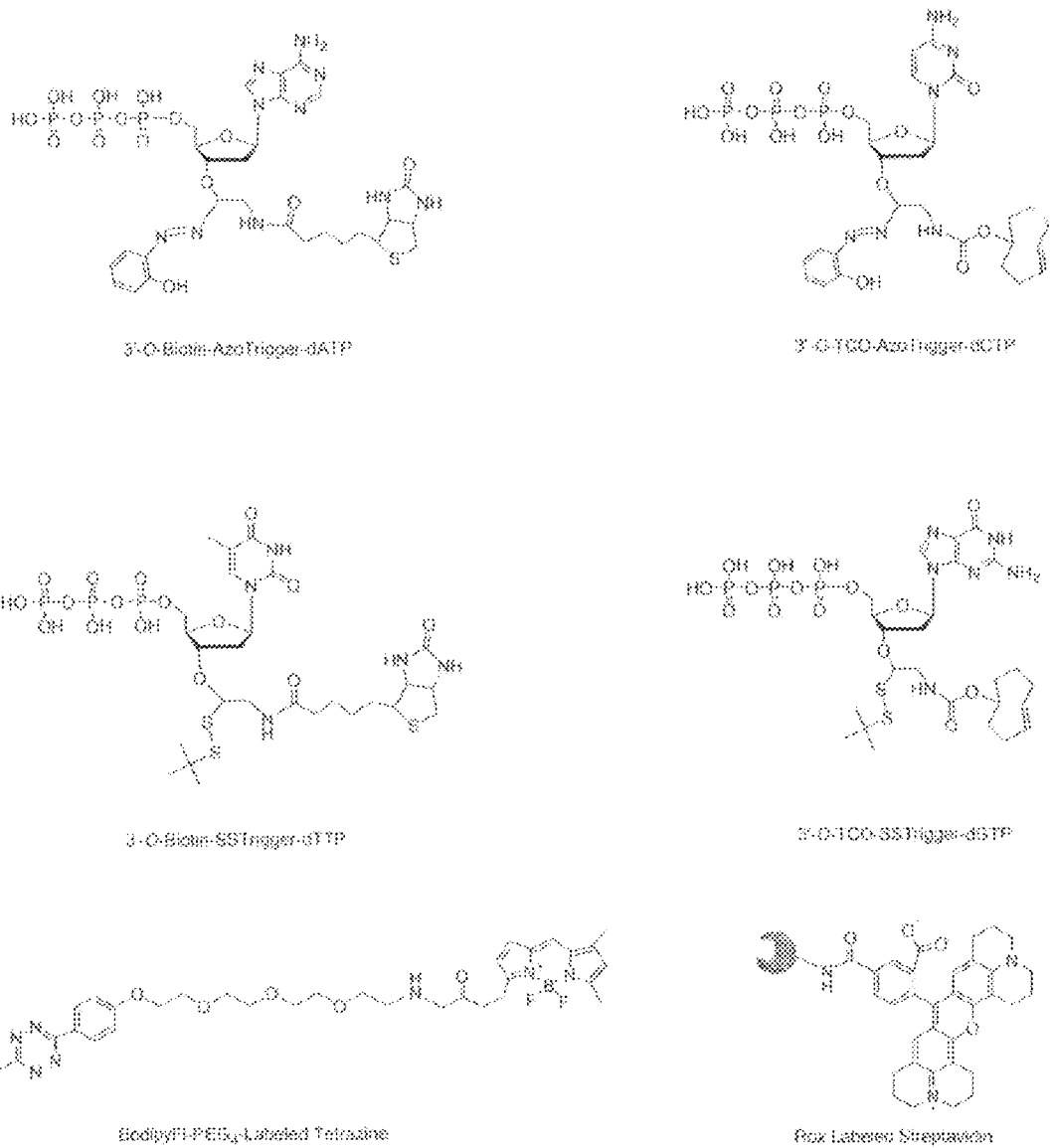

FIG. 107: 3'-O-Anchor-SS(DTM)Trigger-dNTPs (3'-O-Biotin-SS(DTM)Trigger-dTTP, 3'-O-TCO-SS(DTM)Trigger-dGTP), 3'-O-Anchor-AzoTrigger-dNTPs (3'-O-Biotin-AzoTrigger-dATP, 3'-O-TCO-AzoTrigger-dCTP) and associated Dye-labeled Anchor Binding Molecules (Rox-labeled Streptavidin, BodipyFL-PEG$_4$-labeled Tetrazine) to perform two-color SBS using approach delineated in Scheme XXVI.

FIG. 108: 3'-O-Dye-SS(DTM)Trigger-dNTP (3'-O-Rox-PEG$_4$-SS(DTM)Trigger-dCTP), 3'-O-Dye-AzoTrigger-dNTP (3'-O-Rox-PEG$_4$-AzoTrigger-dGTP), 3'-O-Dye-AllylTrigger-dNTP (3'-O-Rox-PEG$_4$-AllylTrigger-dATP), and 3'-O-Dye-2NBTrigger-dNTP (3'-O-Rox-PEG$_4$-2NBTrigger-dTTP) to perform one-color SBS using approach delineated in Scheme XXVII.

FIG. 109: 3'-O-Dye-SS(DTM)Trigger-dNTP (3'-O-Rox-PEG$_4$-SS(DTM)Trigger-dATP), 3'-O-Dye-AzoTrigger-dNTP (3'-O-Rox-PEG$_4$-AzoTrigger-dGTP), 3'-O-Anchor-SS(DTM)Trigger-dNTP (3'-O-Biotin-SS(DTM)Trigger-dTTP), 3'-O-Anchor-AzoTrigger-dNTP (3'-O-Biotin-AzoTrigger-dCTP) and appropriate Dye-labeled Anchor Binding Molecule (Rox-labeled Streptavidin) to perform one-color SBS using approach delineated in Scheme XXVIII.

Figure 110:
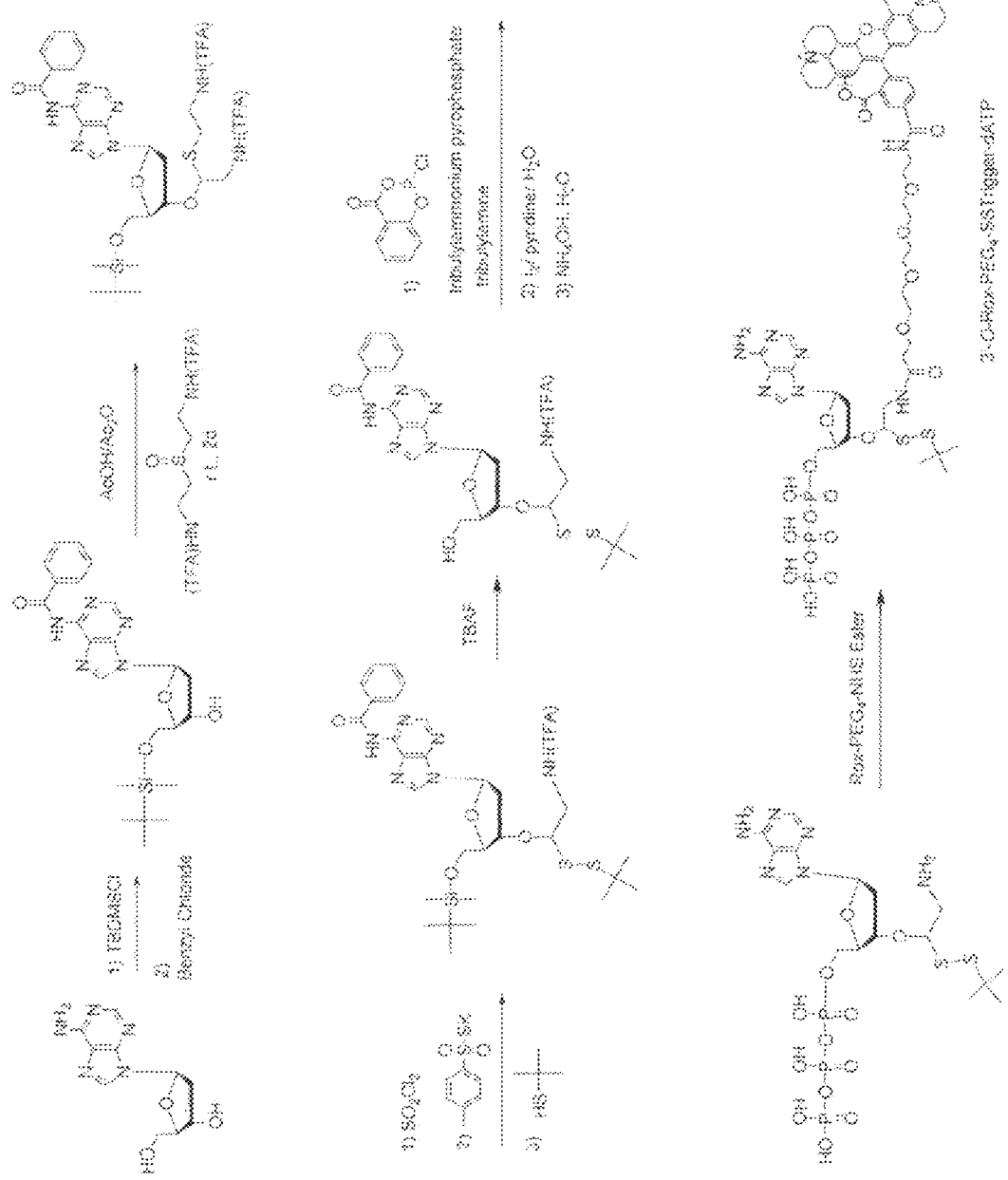

FIG. 110: Synthesis of 3'-O-Dye-SS(DTM)Trigger-dNTP (3'-O-Rox-PEG$_4$-SS(DTM)Trigger-dATP).

Figure 111:
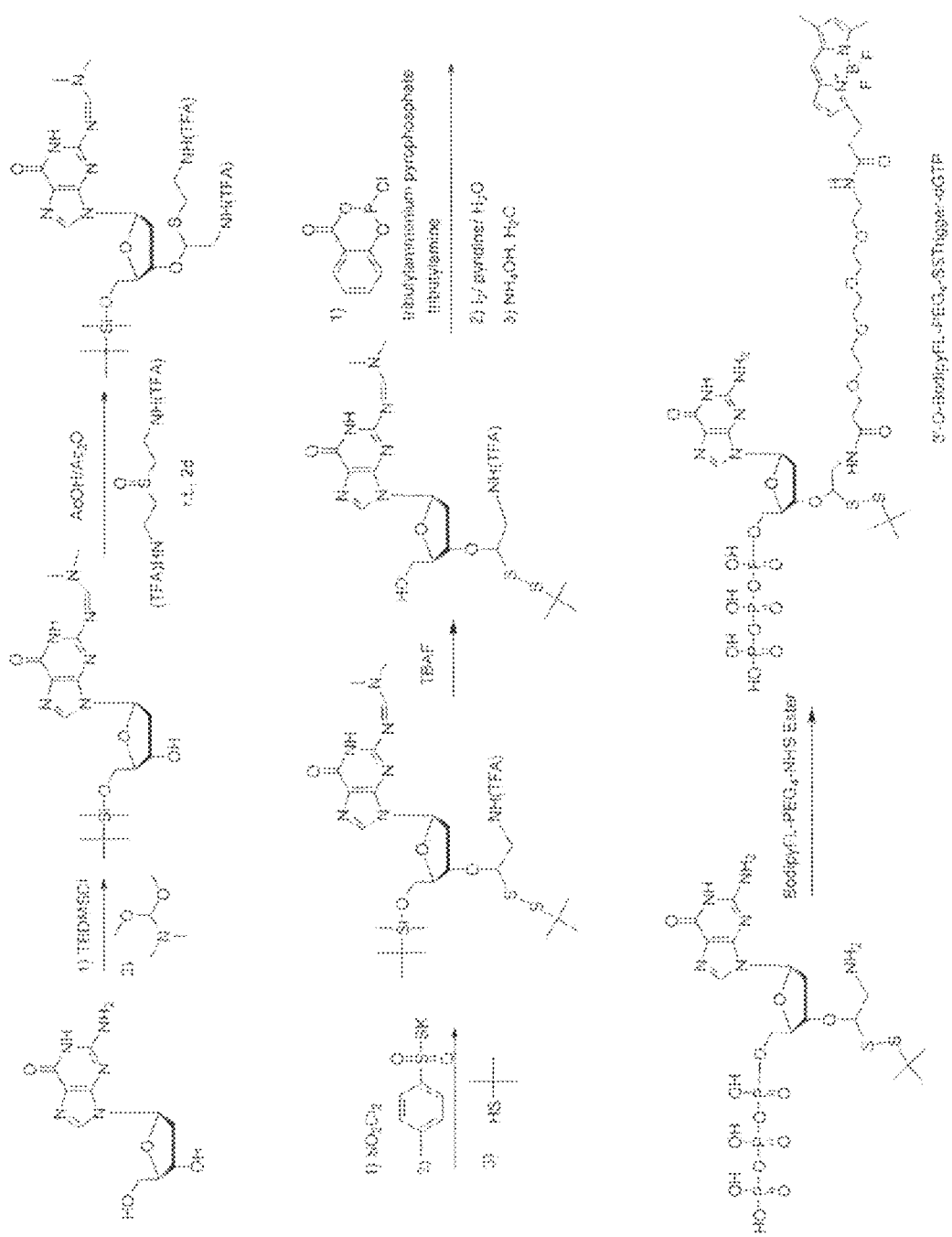

FIG. 111: Synthesis of 3'-O-Dye-SS(DTM)Trigger-dNTP (3'-O-BodipyFL-PEG$_4$-SS(DTM)Trigger-dGTP).

Figure 112:
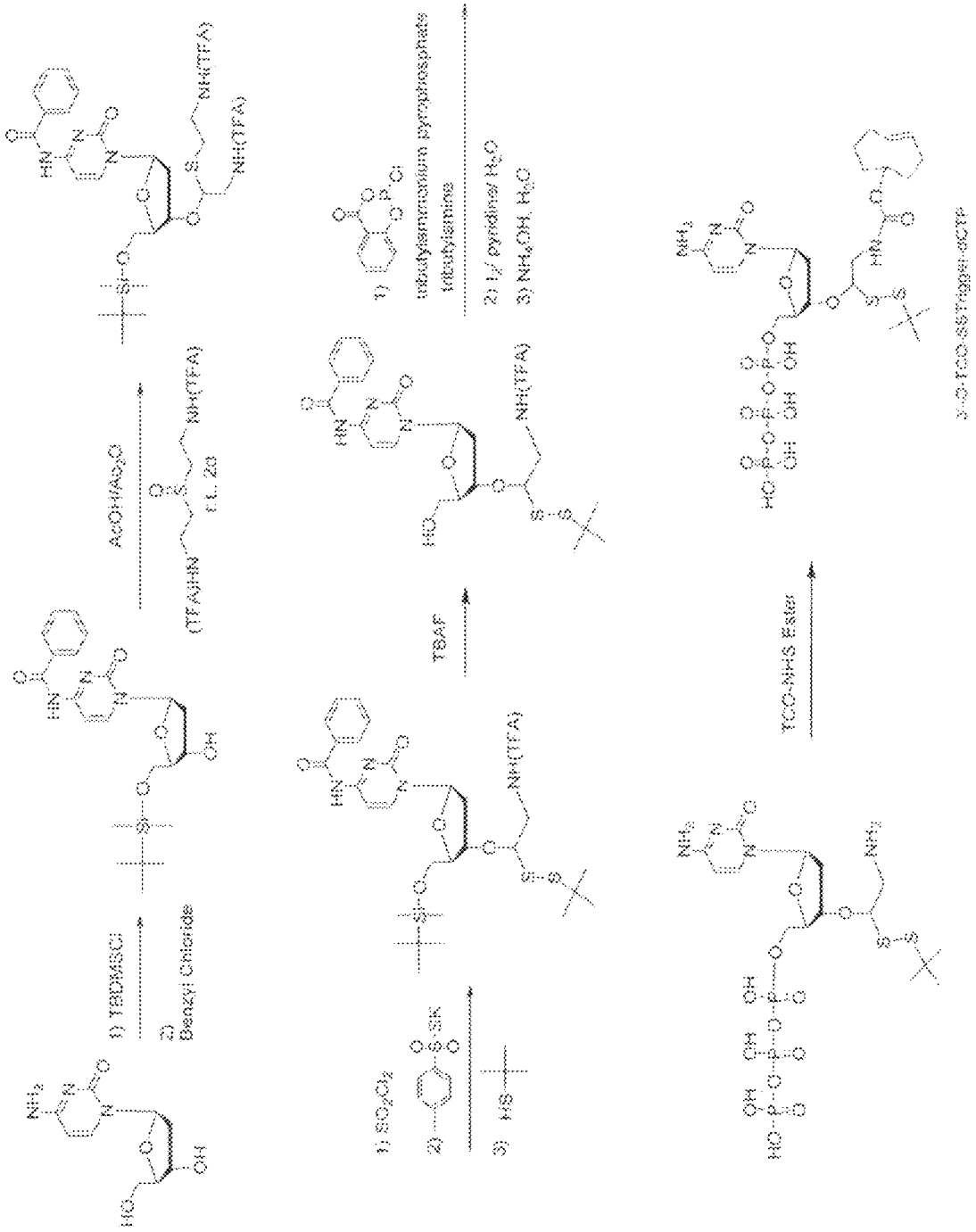

FIG. 112: Synthesis of 3'-O-Anchor-SS(DTM)Trigger-dNTP (3'-O-TCO-SS(DTM)Trigger-dCTP).

Figure 113:
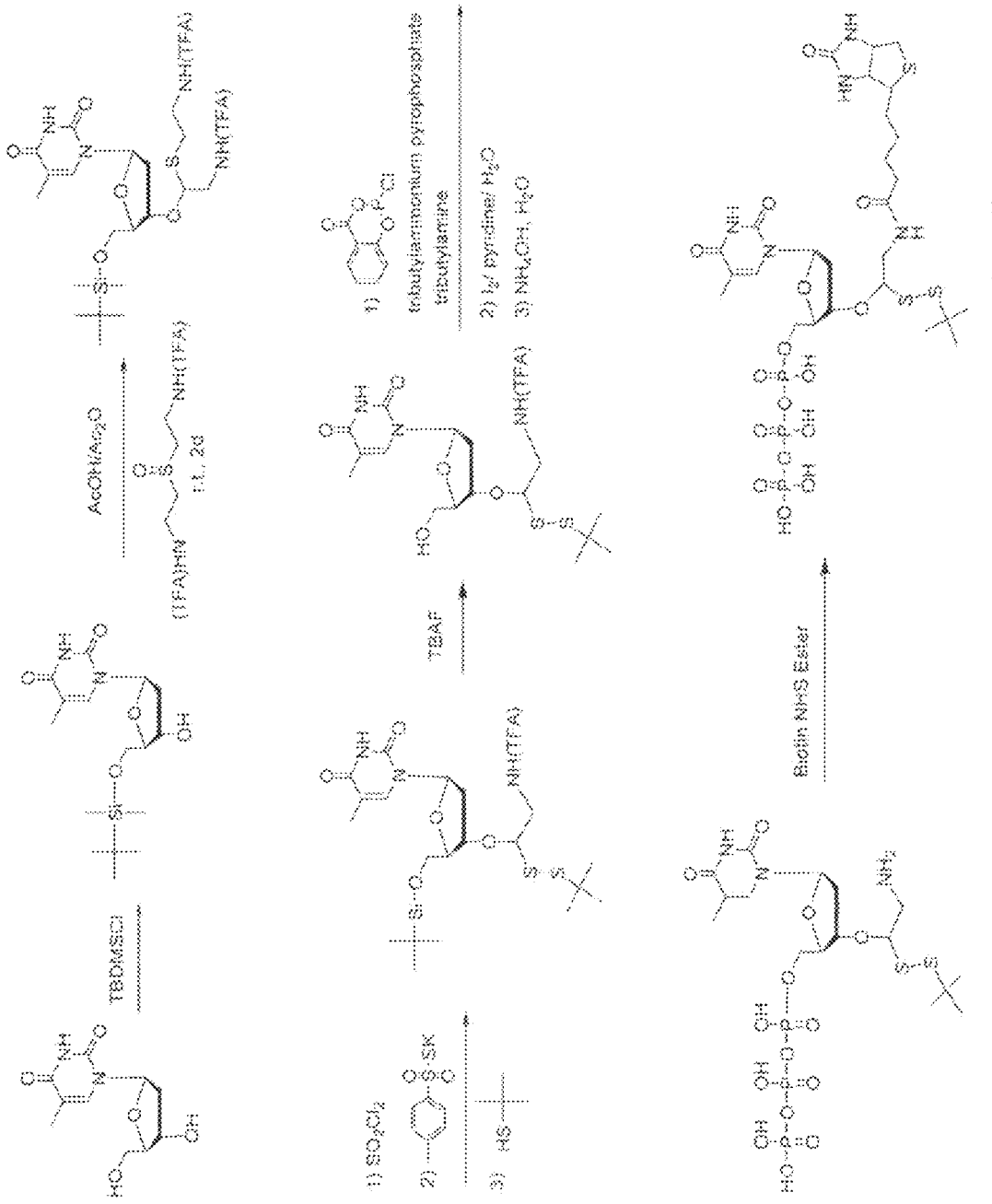

FIG. 113: Synthesis of 3'-O-Anchor-SS(DTM)Trigger-dNTP (3'-O-Biotin-SS(DTM)Trigger-dTTP).

Figure 114:
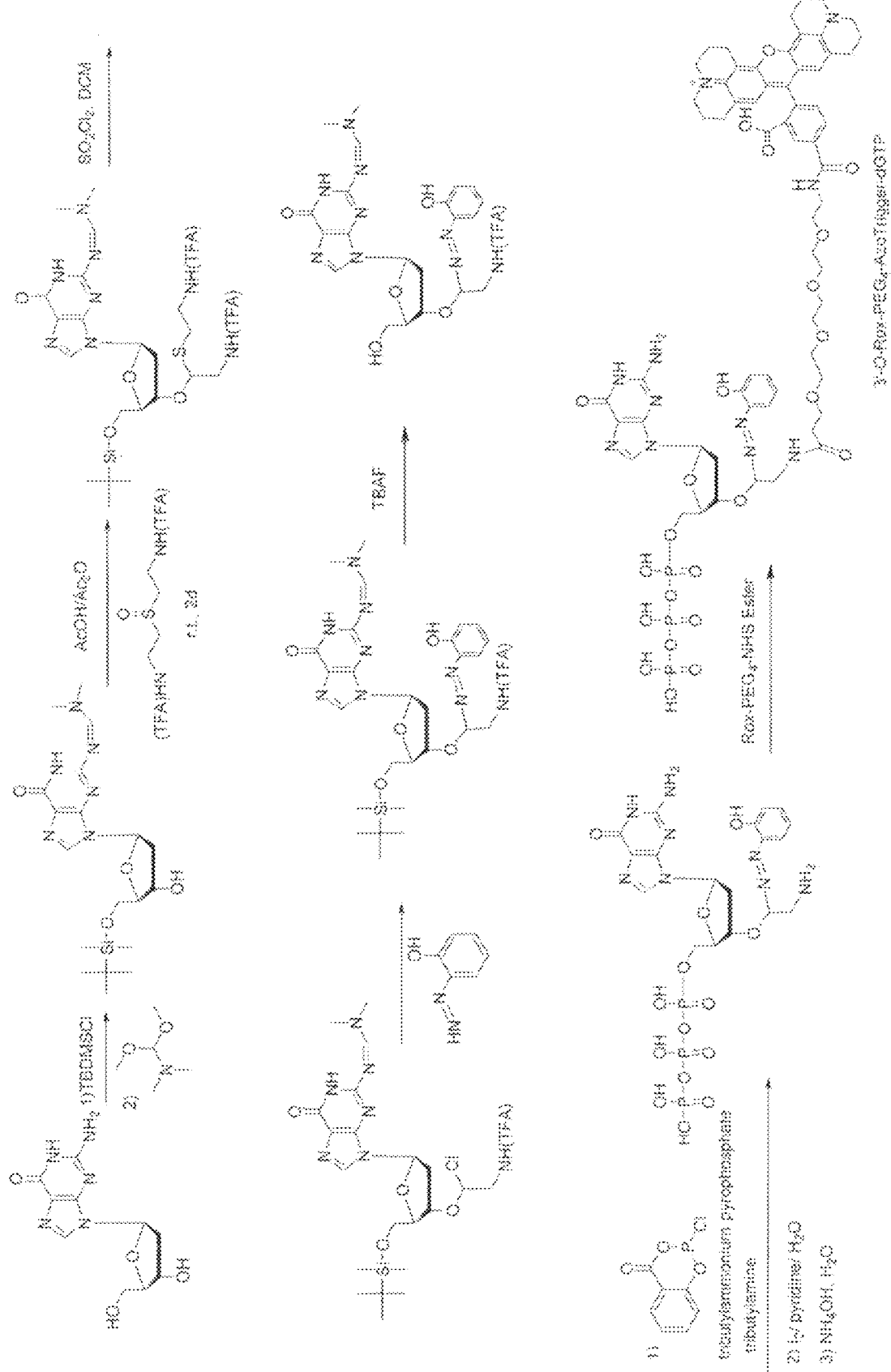

FIG. 114: Synthesis of 3'-O-Dye-AzoTrigger-dNTP (3'-O-Rox-PEG$_4$-AzoTrigger-dGTP).

Figure 115:
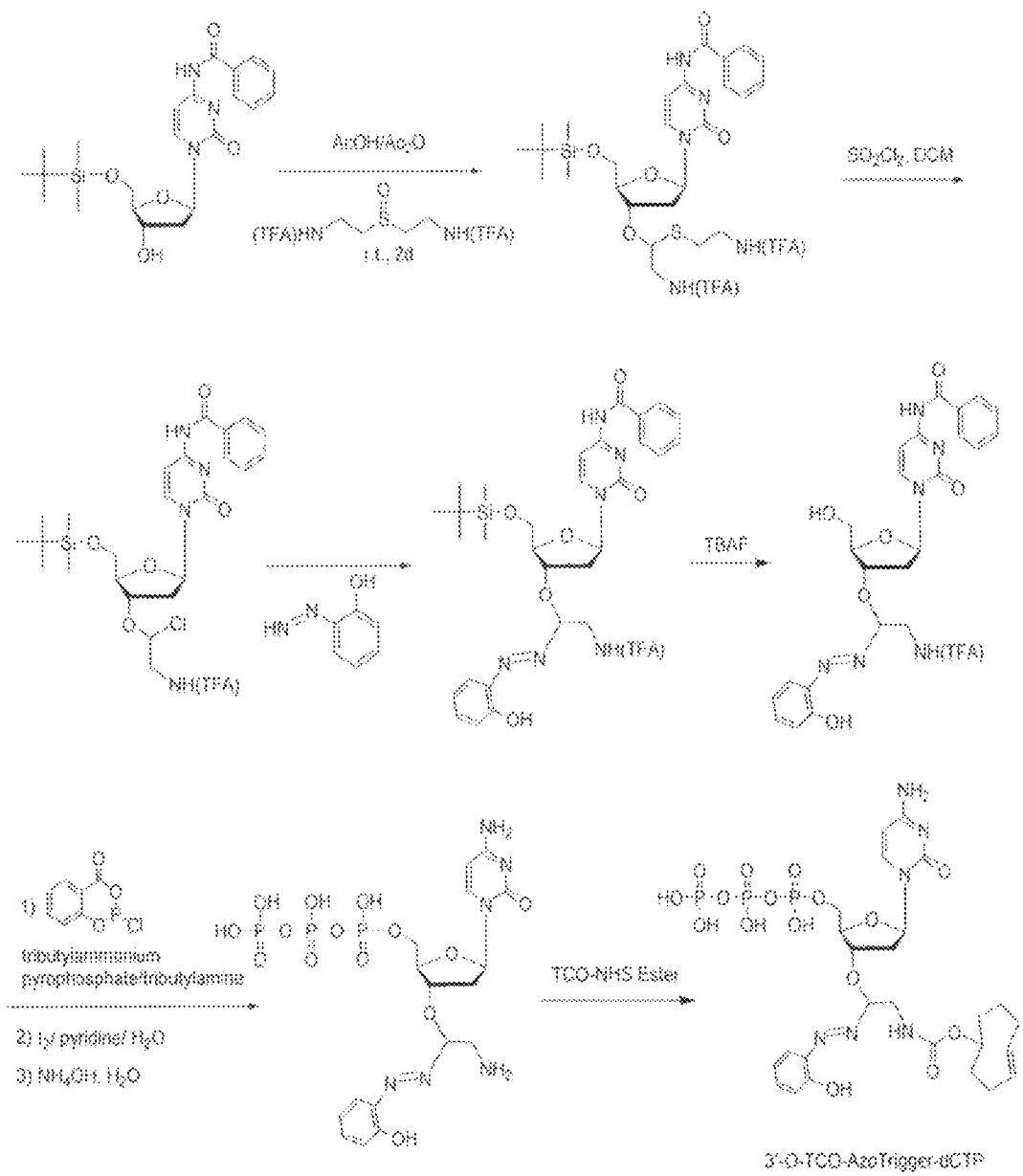

FIG. 115: Synthesis of 3'-O-Anchor-AzoTrigger-dNTP (3'-O-TCO-AzoTrigger-dCTP).

Figure 116:
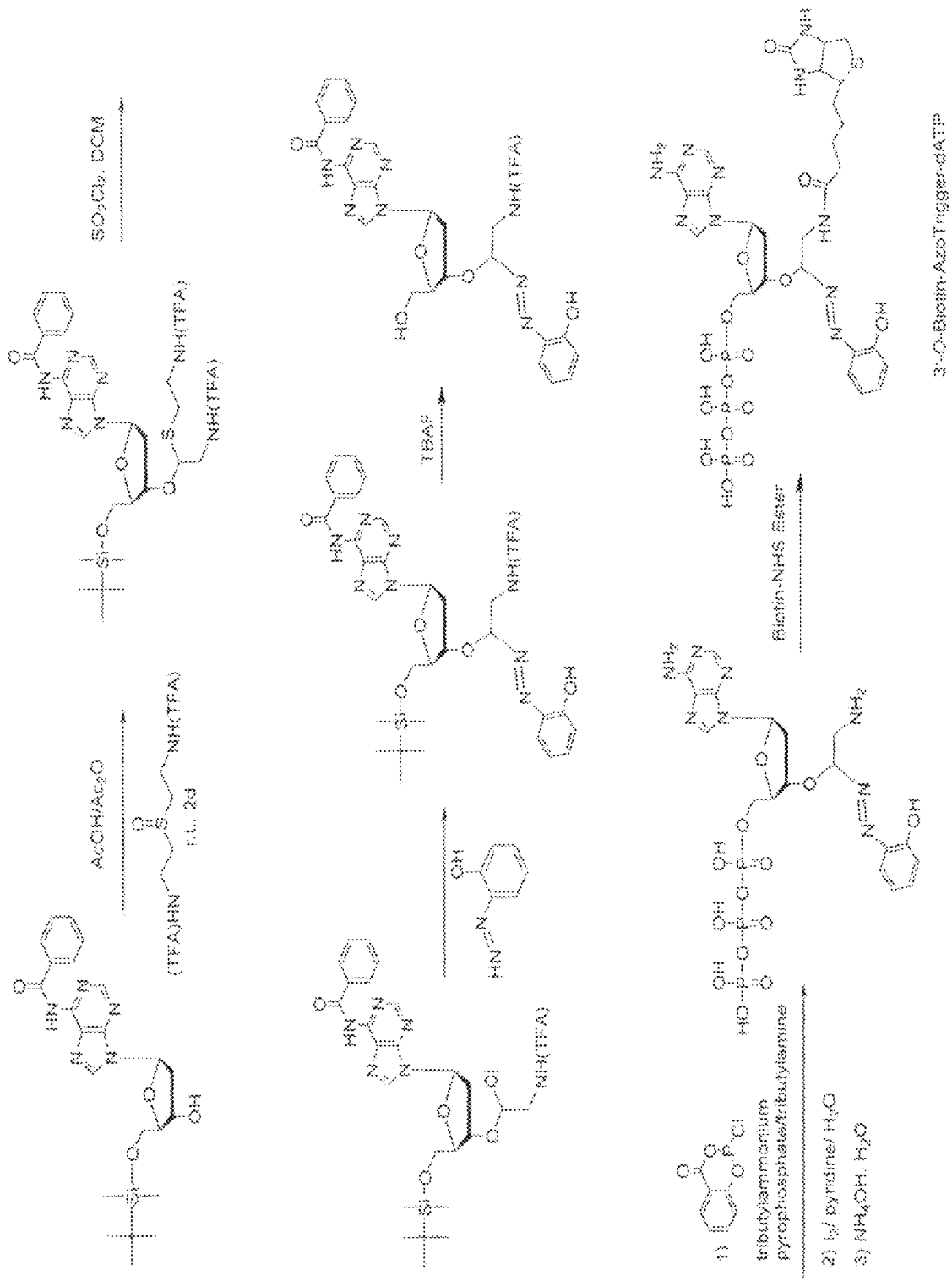

FIG. 116: Synthesis of 3'-O-Anchor-AzoTrigger-dNTP (3'-O-Biotin-AzoTrigger-dATP).

Figure 117:
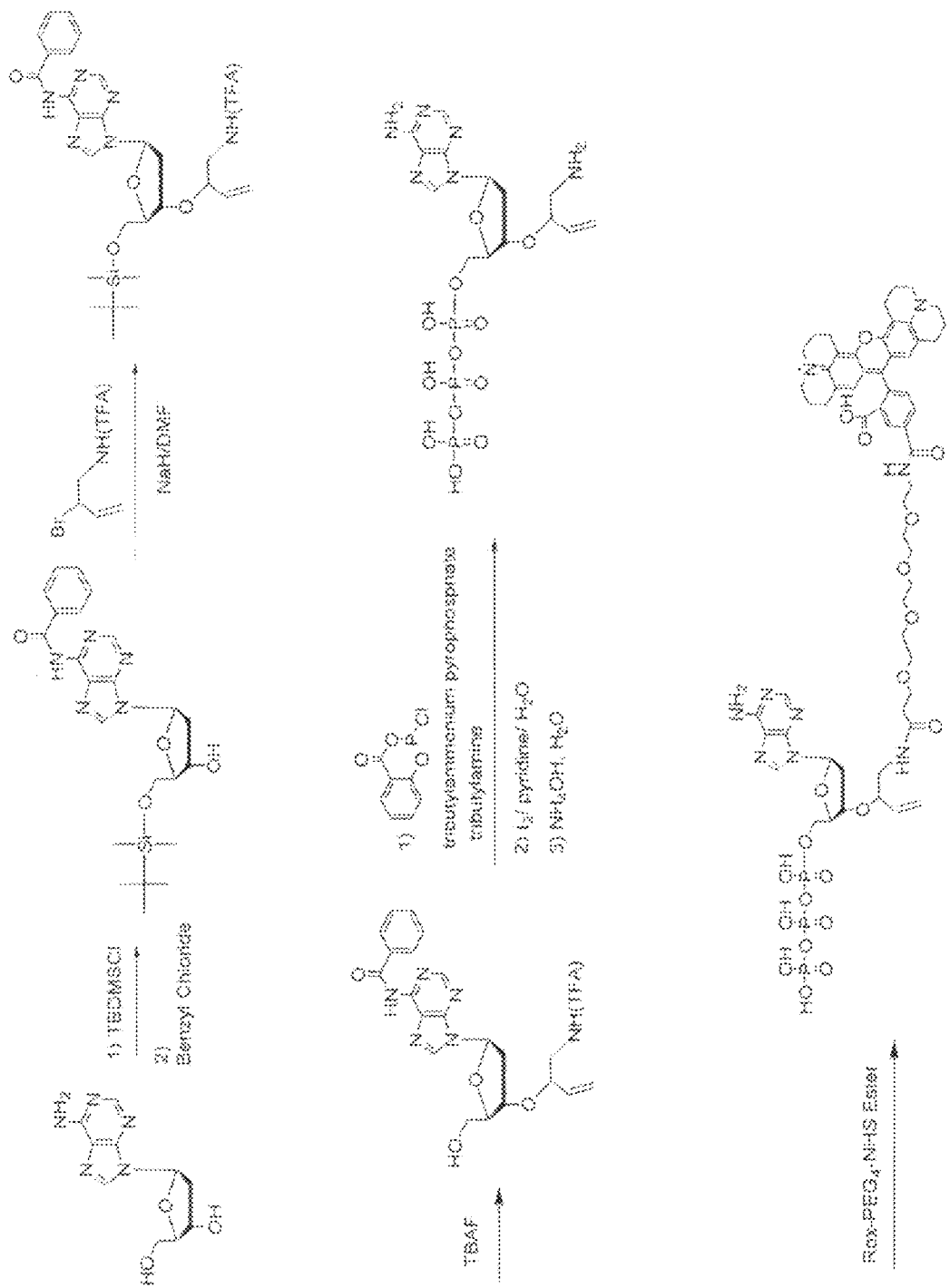

FIG. 117: Synthesis of 3'-O-Dye-AllylTrigger-dNTP (3'-O-Rox-PEG$_4$-AllylTrigger-dATP).

Figure 118:
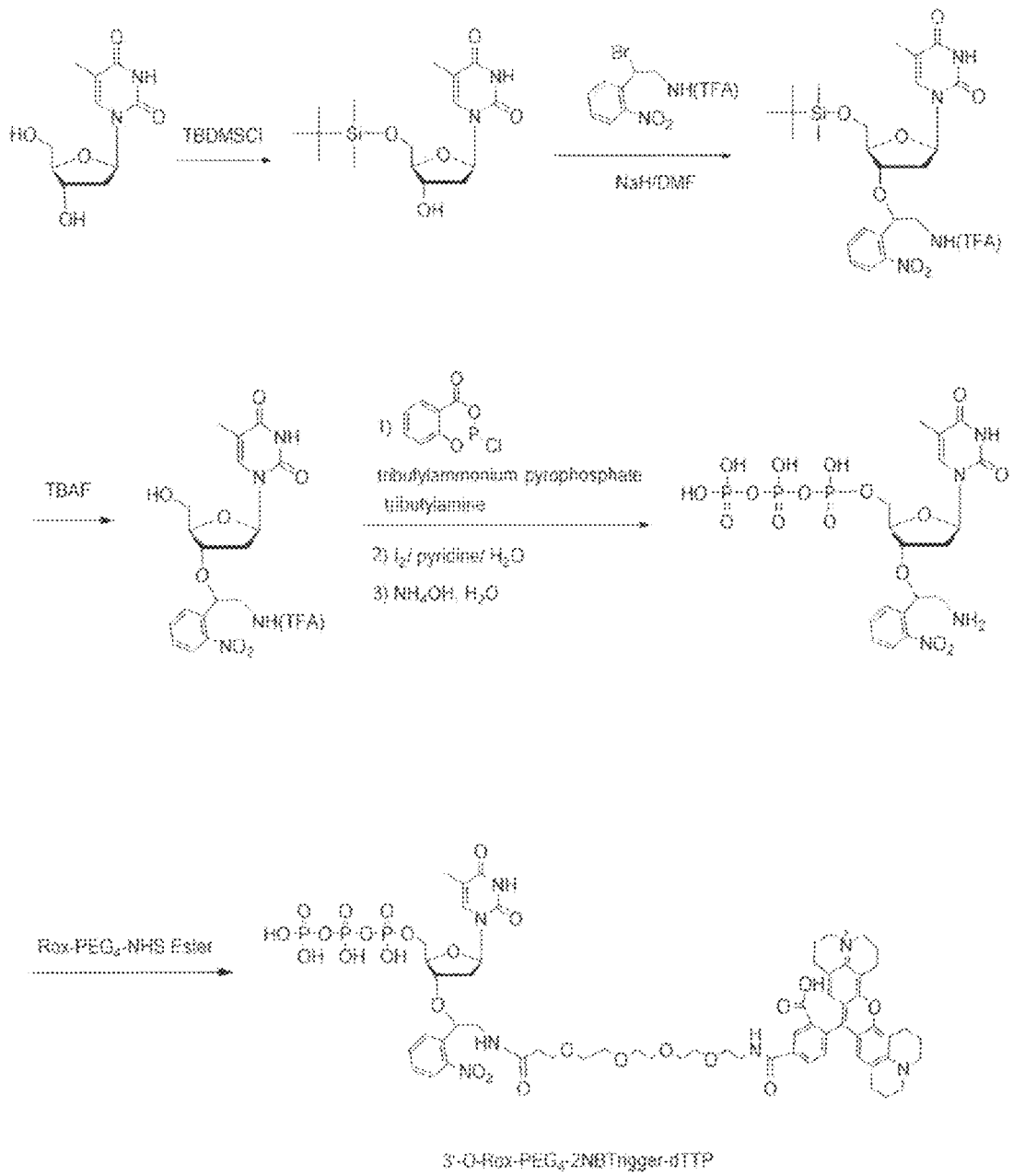

FIG. 118: Synthesis of 3'-O-Dye-2NBTrigger-dNTP (3'-O-Rox-PEG$_4$-2NBTrigger-dTTP).

Figure 119:
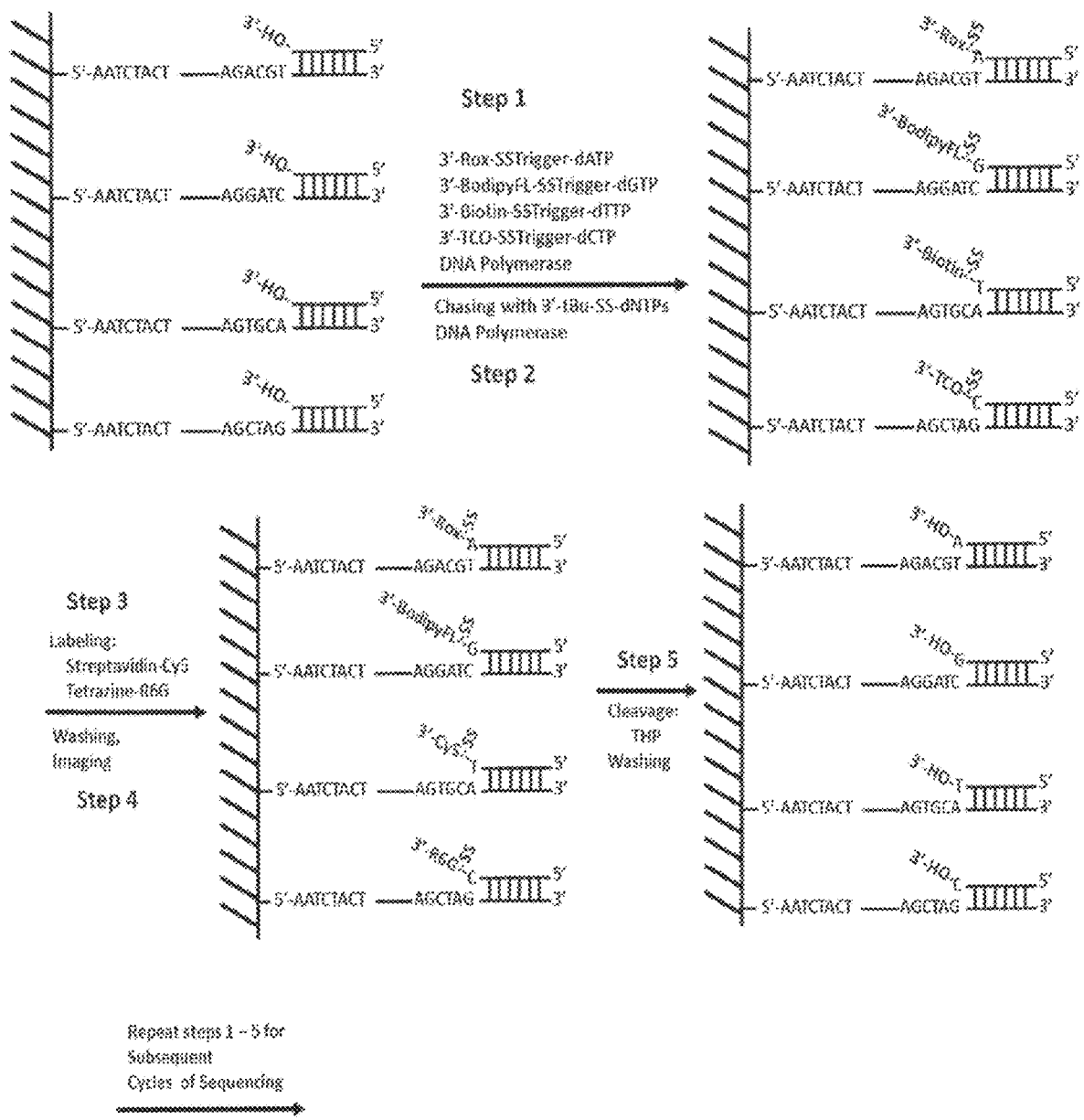

FIG. 119: A schematic showing Scheme XXIV using 3'-O-Dye-SS(DTM)Trigger-dNTPs (3'-O-Rox-PEG$_4$-SS(DTM)Trigger-dATP, 3'-O-BodipyFL-PEG$_4$-SS(DTM)Trigger-dGTP), 3'-O-Anchor-SS(DTM)Trigger-dNTPs (3'-O-Biotin-SS(DTM)Trigger-dTTP, 3'-O-TCO-SS(DTM)Trigger-dCTP) and associated Dye-labeled Anchor Binding Molecules (Cy5-labeled Streptavidin, R6G-labeled Tetrazine) to perform four-color SBS.

Figure 120:
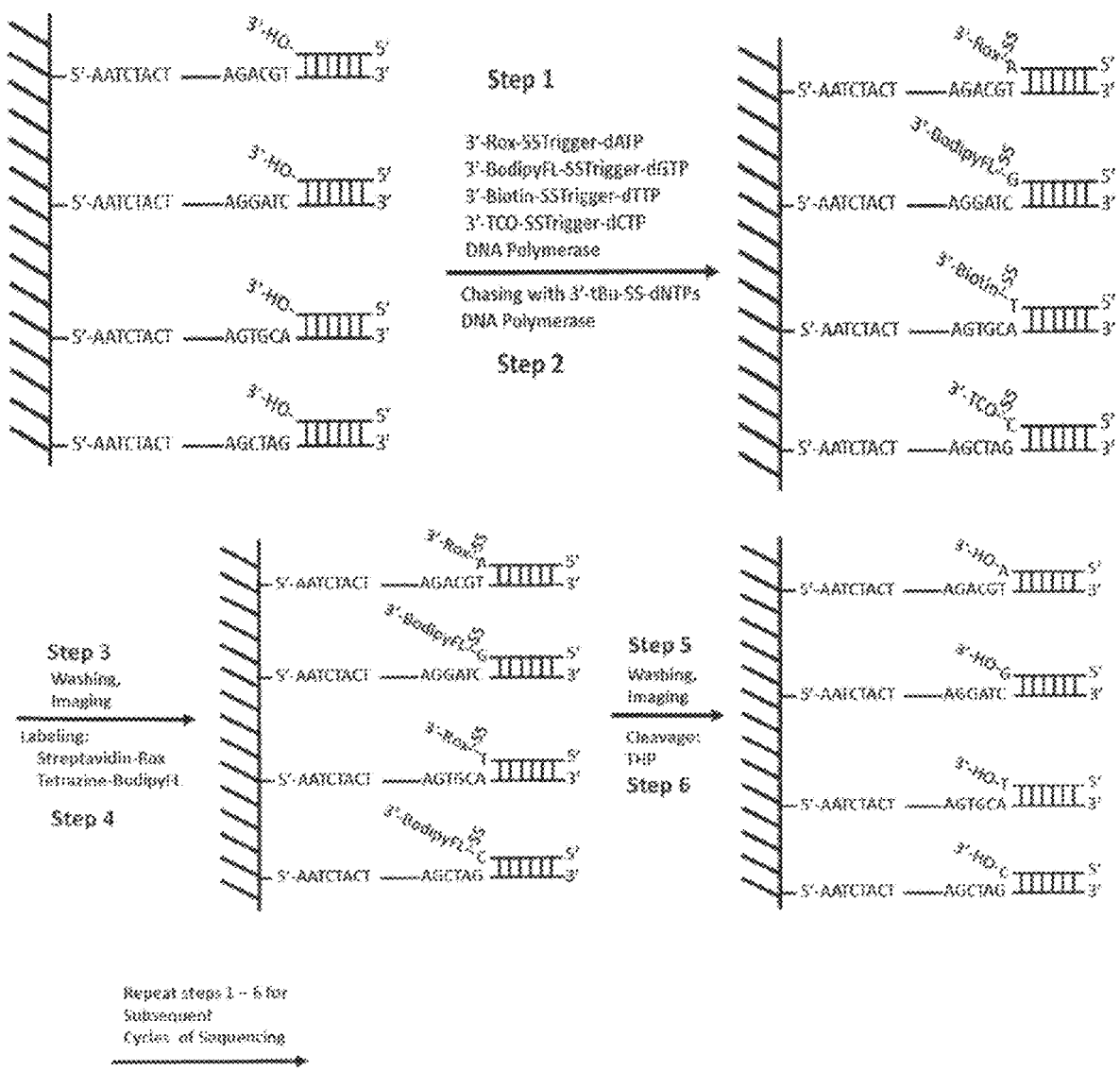

FIG. 120: A schematic showing Scheme XXV using 3'-O-Dye-SS(DTM)Trigger-dNTPs (3'-O-Rox-PEG$_4$-SS(DTM)Trigger-dATP, 3'-O-BodipyFL-PEG$_4$-SS(DTM)Trigger-dGTP), 3'-O-Anchor-SS(DTM)Trigger-dNTPs (3'-O-Biotin-SS(DTM)Trigger-dTTP, 3'-O-TCO-SS(DTM)Trigger-dCTP) and associated Dye-labeled Anchor Binding Molecules (Rox-labeled Streptavidin, BodipyFL-labeled Tetrazine) to perform two-color SBS.

Figure 121C:
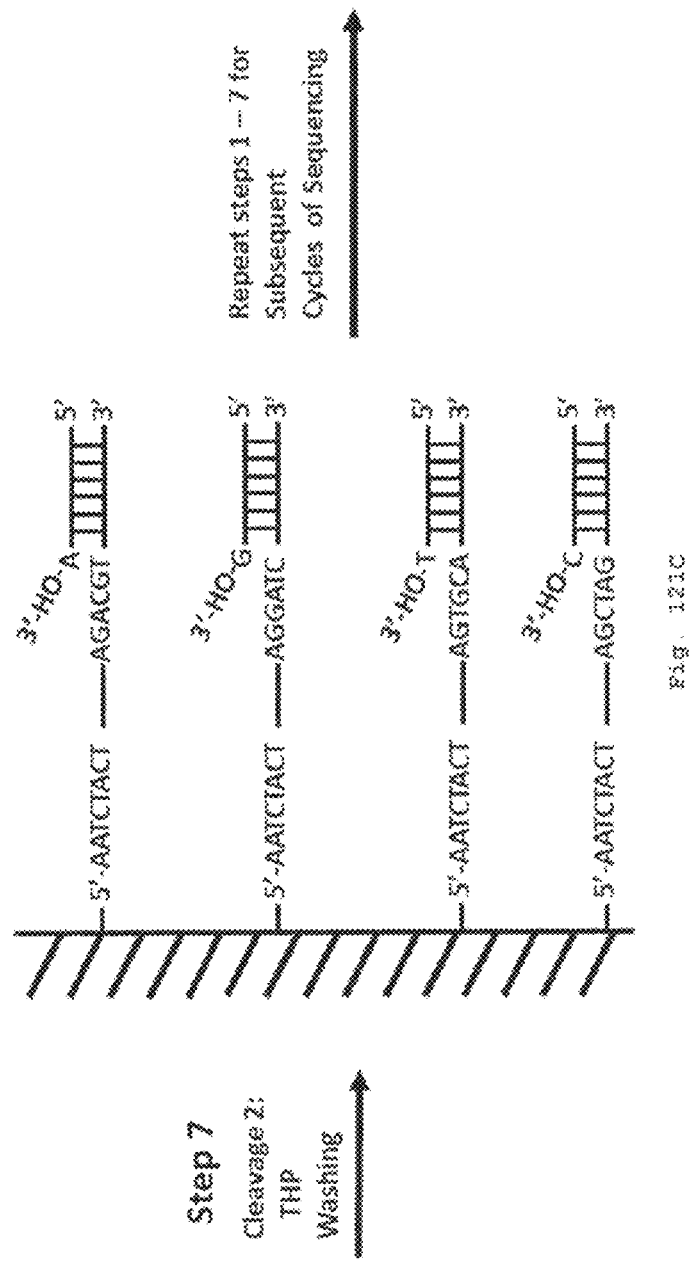

FIGS. 121A-121C: A schematic showing Scheme XXVI using 3'-O-Anchor-SS(DTM)Trigger-dNTPs (3'-O-Biotin-SS(DTM)Trigger-dTTP, 3'-O-TCO-SS(DTM)Trigger-dGTP), 3'-O-Anchor-AzoTrigger-dNTPs (3'-O-Biotin-AzoTrigger-dATP, 3'-O-TCO-AzoTrigger-dCTP) and associated Dye-labeled Anchor Binding Molecules (Rox-labeled Streptavidin, BodipyFL-labeled Tetrazine) to perform two-color SBS.

Figure 122C:
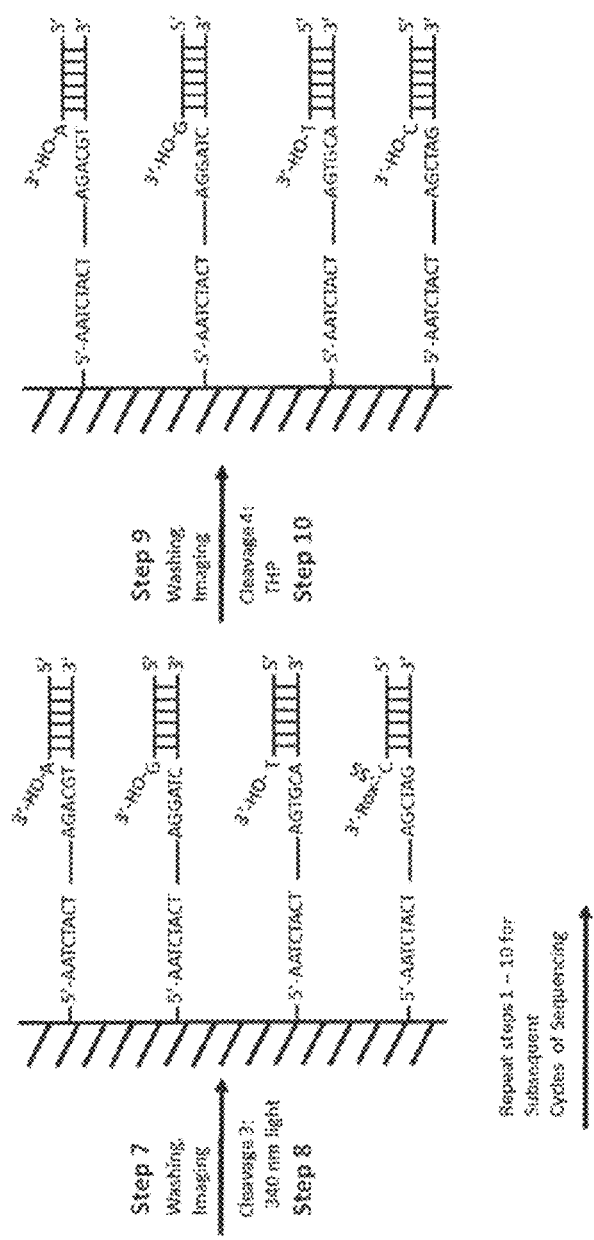

FIGS. 122A-122C: A schematic showing Scheme XXVII using 3'-O-Dye-SS(DTM)Trigger-dNTP (3'-O-Rox-PEG$_4$-SS(DTM)Trigger-dCTP), 3'-O-Dye-AzoTrigger-dNTP (3'-O-Rox-PEG$_4$-AzoTrigger-dGTP), 3'-O-Dye-AllylTrigger-dNTP (3'-O-Rox-PEG$_4$-AllylTrigger-dATP), and 3'-O-Dye-2NBTrigger-dNTP (3'-O-Rox-PEG$_4$-2NBTrigger-dTTP) to perform one-color SBS.

Figure 123A:
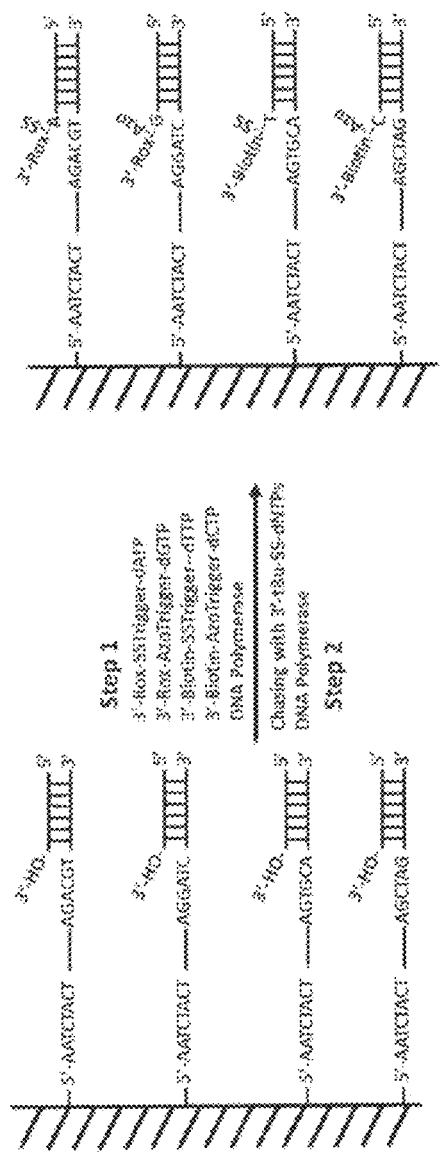
Figure 123B:
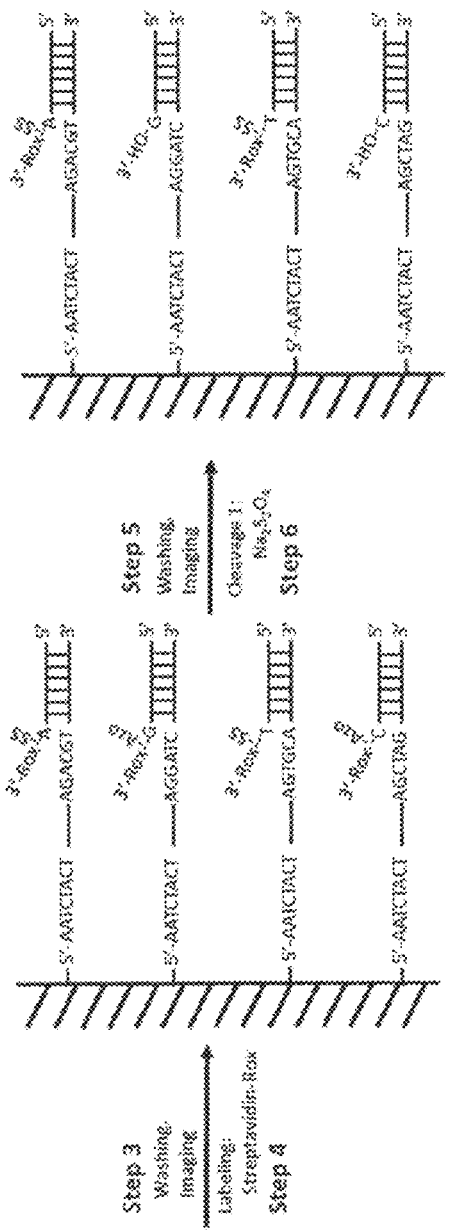
Figure 123C:
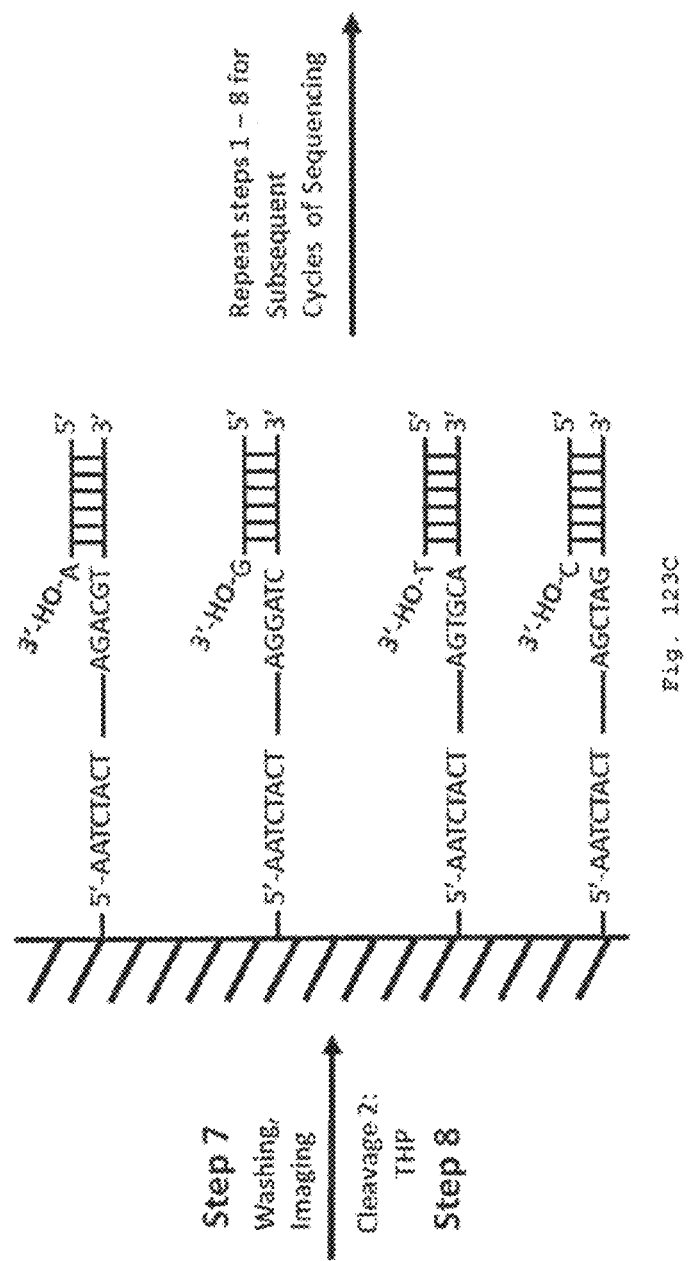

FIGS. 1231-123C: A schematic showing Scheme XXVIII using 3'-O-Dye-SS(DTM)Trigger-dNTP (3'-O-Rox-PEG$_4$-SS(DTM)Trigger-dATP), 3'-O-Dye-AzoTrigger-dNTP (3'-O-Rox-PEG$_4$-AzoTrigger-dGTP), 3'-O-Anchor-SS(DTM)Trigger-dNTP (3'-O-Biotin-SS(DTM)Trigger-dTTP), 3'-O-Anchor-AzoTrigger-dNTP (3'-O-Biotin-AzoTrigger-dCTP) and appropriate Dye-labeled Anchor Binding Molecule (Rox-labeled Streptavidin) to perform one-color SBS.

Figure 124A:
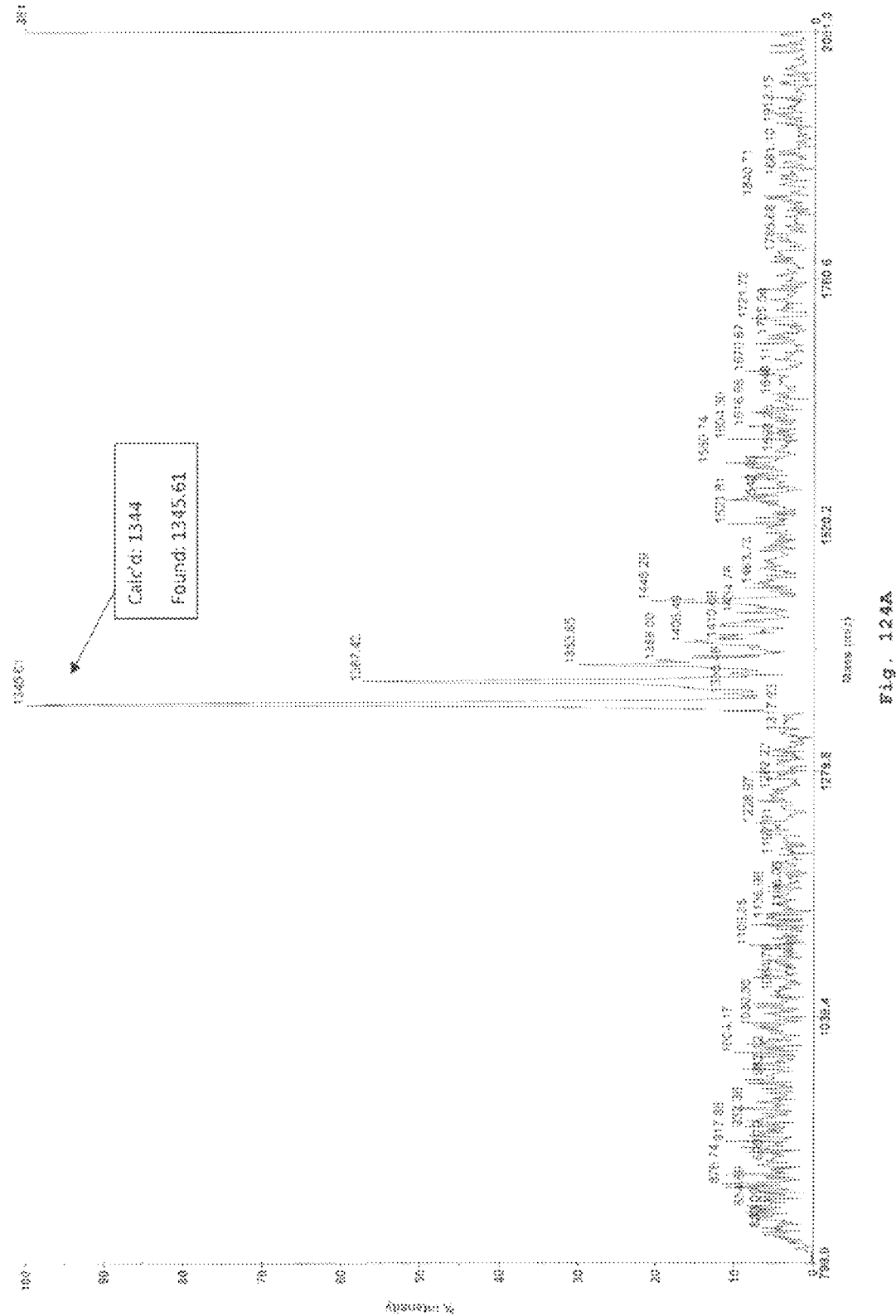
Figure 124B:
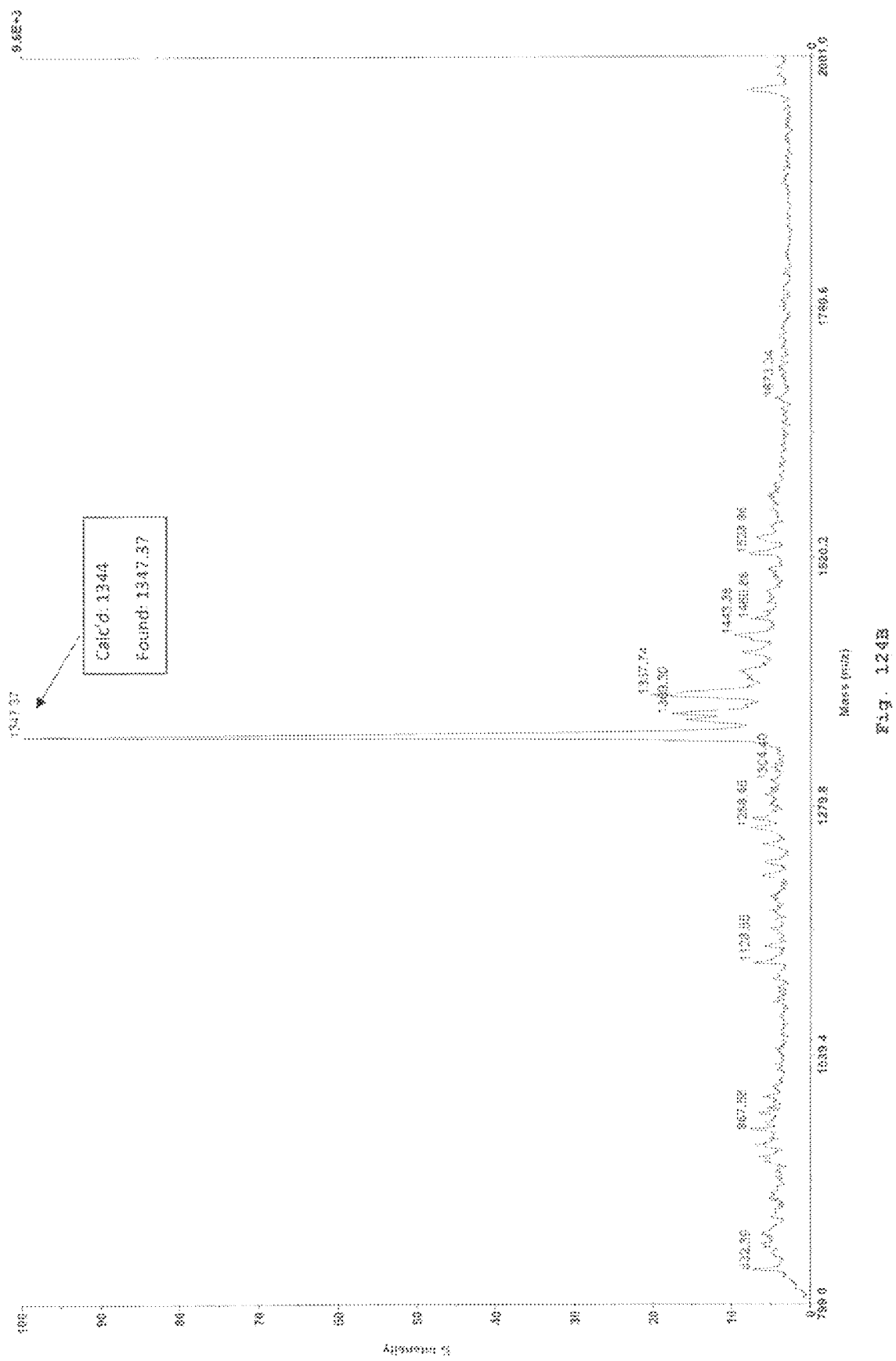

FIGS. 124A-124B: A. MALDI TOF MS spectrum for 3'-O-SS-dATP-SS-Rox. B. MALDI TOF MS spectrum for 3'-O-SS-dATP-SS-Rox after treatment with sodium dithionite.

Figure 125:
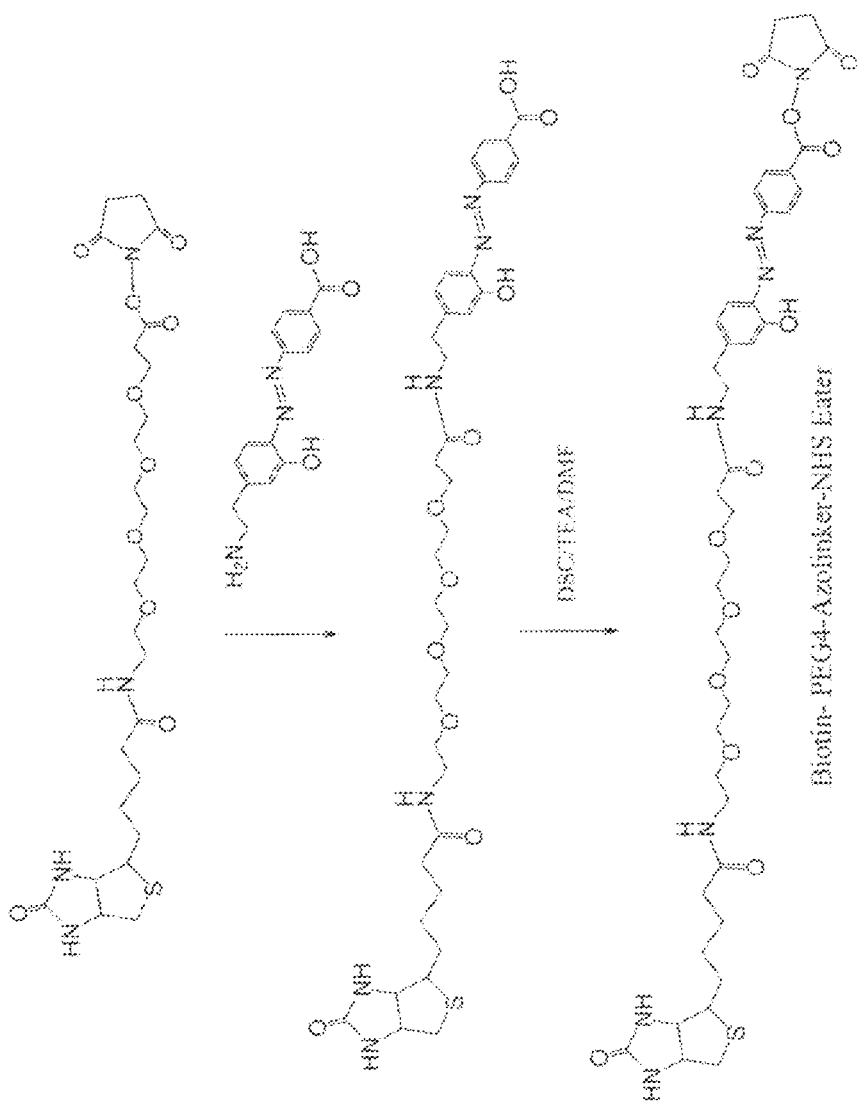

FIG. 125: Synthesis of biotin-PEG4-AzoLinker NHS ester.

Figure 126:
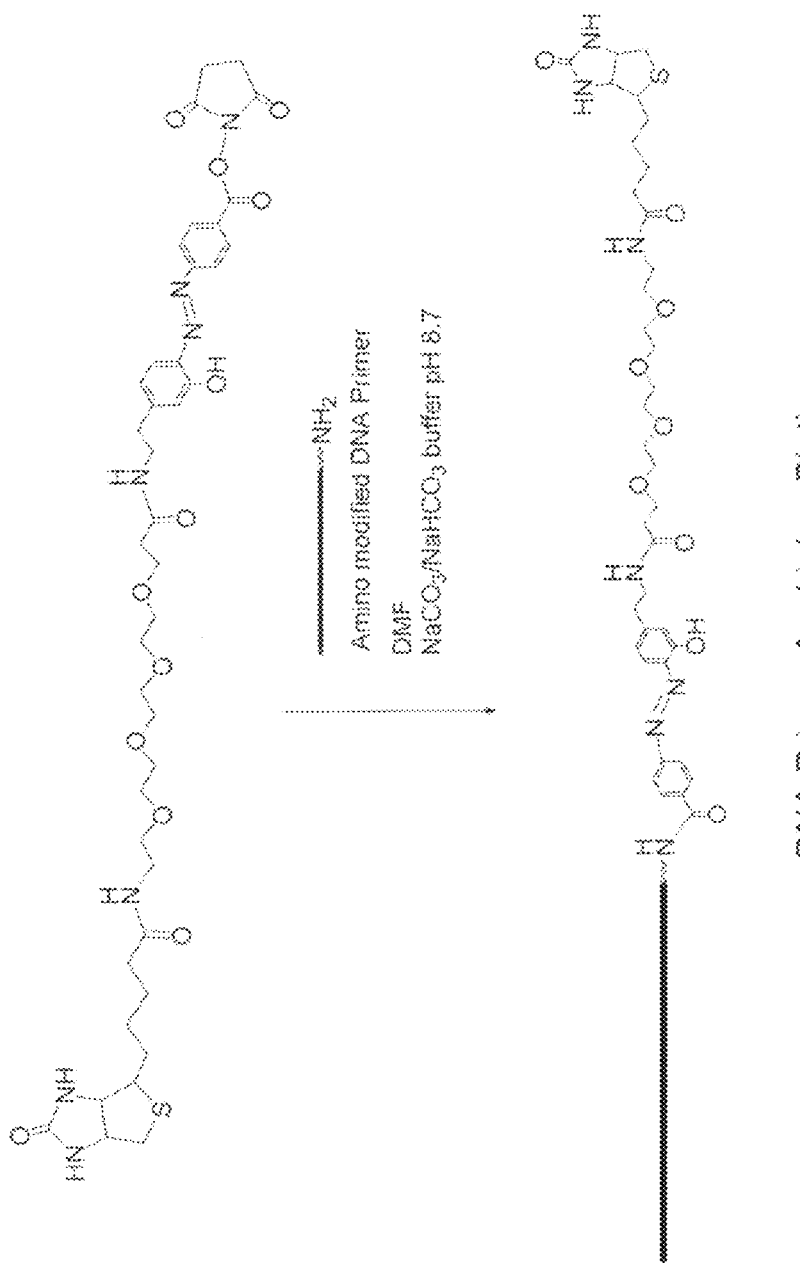

FIG. 126: Synthesis of DNA Primer-AzoLinker-Biotin Conjugate.

Figure 127:
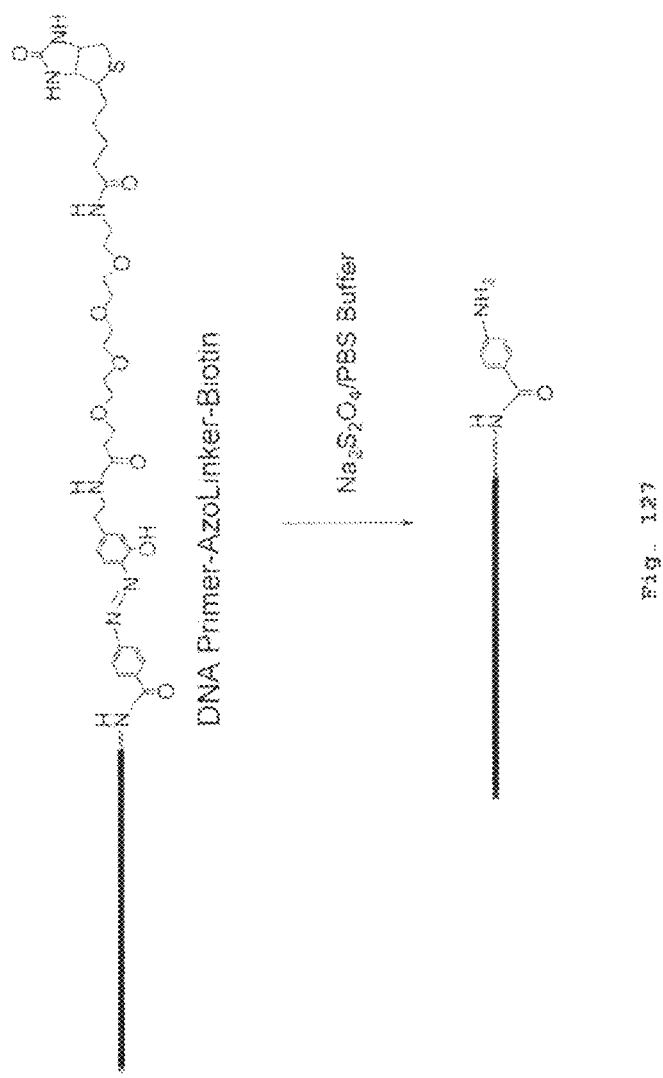

FIG. 127: Cleavage of Azo Linker and Release of DNA Primer by Na$_2$S$_2$O$_4$ Treatment FIG. 128A: HPLC profile prior to cleavage.

Figure 128A:
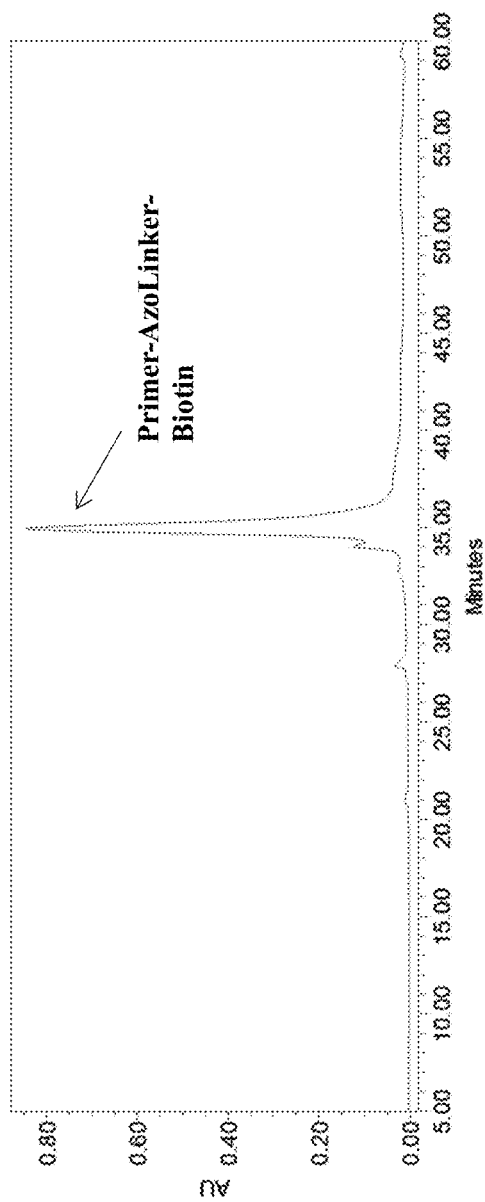
Figure 128B:
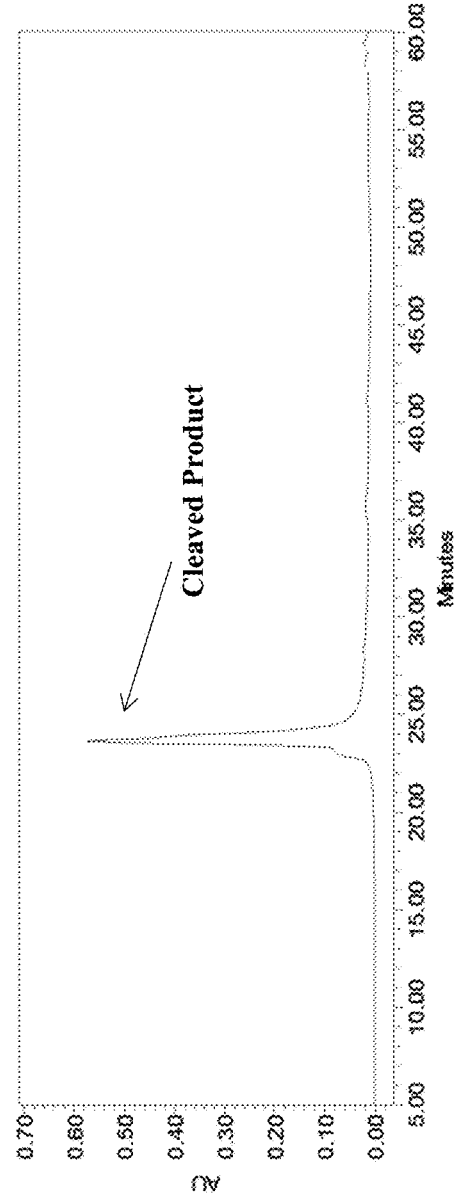

FIG. 128B: indicates the HPLC profile following cleavage.

FIG. 129: Generalized set of dye and anchor labeled orthogonally cleavable 3' blocked nucleotide analogues and labeling reagent for single-color SBS: All the nucleotide analogues have a 3' blocking group (t-Butyl-SS-methyl (—CH2-SS-t-butyl) is shown in the examples herein; other 3' blocking groups can also be used such as: —CH2-SS-CH3; —CH2-SS—CH2CH3; —CH2-N3; —CH2-CH═CH2, etc.). Two have an anchor (e.g., biotin) and two have a dye (e.g., Cy5). For two of these nucleotides, the dye or anchor is attached to the base via cleavable linker 1 (containing an SS group which can be cleaved by THP) and for the other two the dye or anchor is attached to the base via cleavable linker 2 (containing an azo group which can be cleaved by sodium dithionite). The labeling molecule consists of a molecule able to bind specifically to the anchor (streptavidin) and the same dye. Typically, one of the linkers (e.g., SS) can be cleaved by the same agent (e.g., THP) that removes the blocking group (e.g., t-Butyl-SS-methyl or azidomethyl). A set of unlabeled NRTs (e.g., 3'-O-azidomethyl-dNTPs) is added in a chase step.

Figure 130:
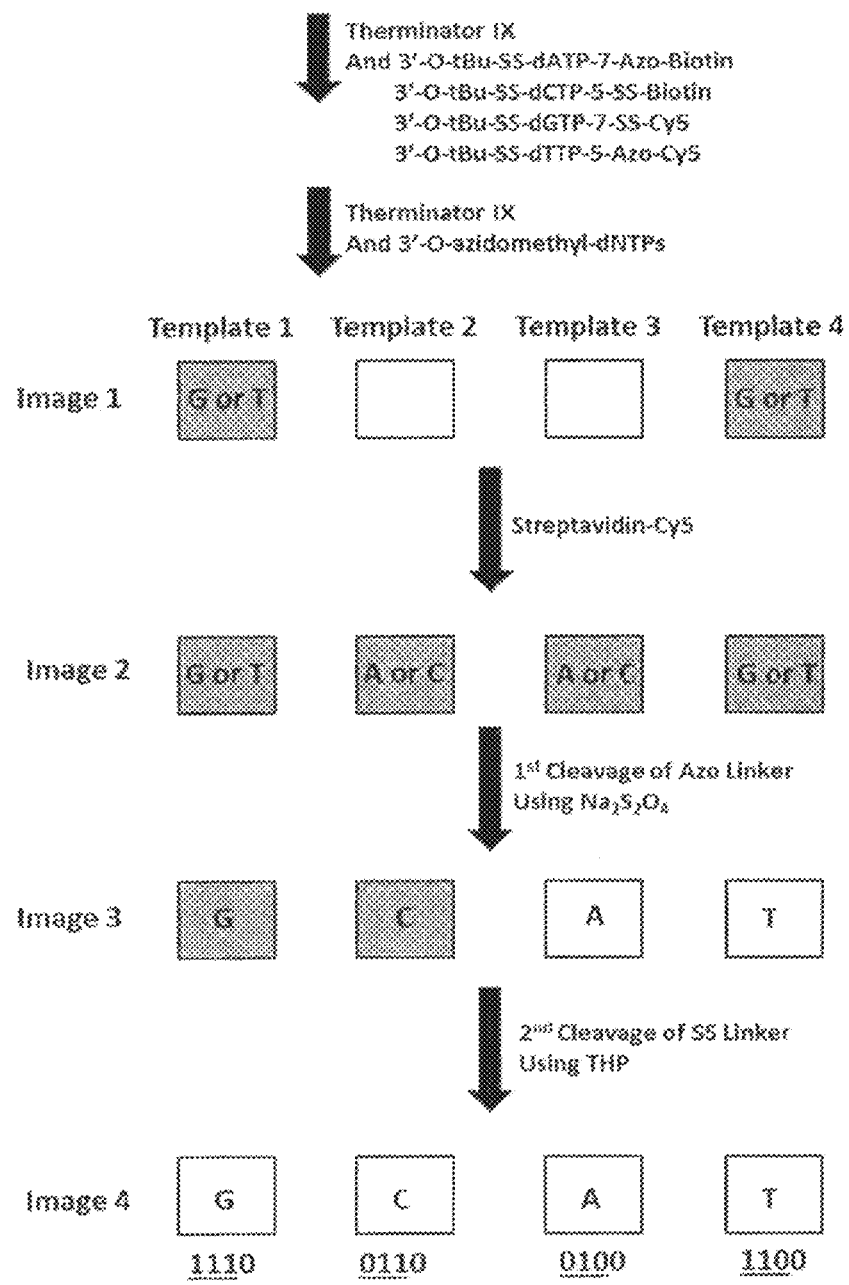

FIG. 130: Simplified presentation of scheme for single-color SBS using orthogonally cleavable nucleotide analogues such as those presented in FIG. 129. Each nucleotide has a different combination of either Cy5 or Biotin and either SS Linker or Azo Linker. The rectangles represent areas containing numerous copies of attached primer-loop-template molecules (though linear primers and attached templates or other template/primer arrangements can be used) in which the next base in the template strand, from left to right is C, G, T or A. After incubation with the four nucleotide analogues and Terminator IX, imaging will reveal a positive signal in the first and fourth areas (representing extension of the primer strand with either G or T) and a negative signal in the second and third areas (extension with A or C). A chase step is carried out with unlabeled NRTs (e.g., 3'-O-azidomethyl-dNTPs) to extend any primers not already extended with the Cy5- or biotin-labeled NRTs. After labeling with Streptavidin-Cy5, imaging of all four areas will reveal a positive signal, confirming the previous possible incorporation events. Imaging after cleavage of the azo linker with sodium dithionite (Na2S2O4) will reveal loss of positive signal in the third and fourth areas, but not the first and second areas. Since the azo group is on the A and T nucleotides, this reveals that in areas 1 through 4, there was incorporation of G, C, A and T respectively. Finally, treatment with THP cleaves the SS linker and removes the t-Butyl-SS-methyl blocker in preparation for the next sequencing cycle. The 5 numeral codes at the bottom represent the signals at each of the five imaging steps (the middle three steps underlined), a positive signal indicated by a 1 and a negative signal indicated by a 0. It is clear that incorporation of each of the four possible nucleotide analogues will be revealed by a unique digital code (010 for A, 011 for C, 111 for G and 110 for T considering just the three middle imaging steps; 00 for A, 01 for C, 11 for G and 10 for T considering just the second and fourth imaging steps).

Figure 131:
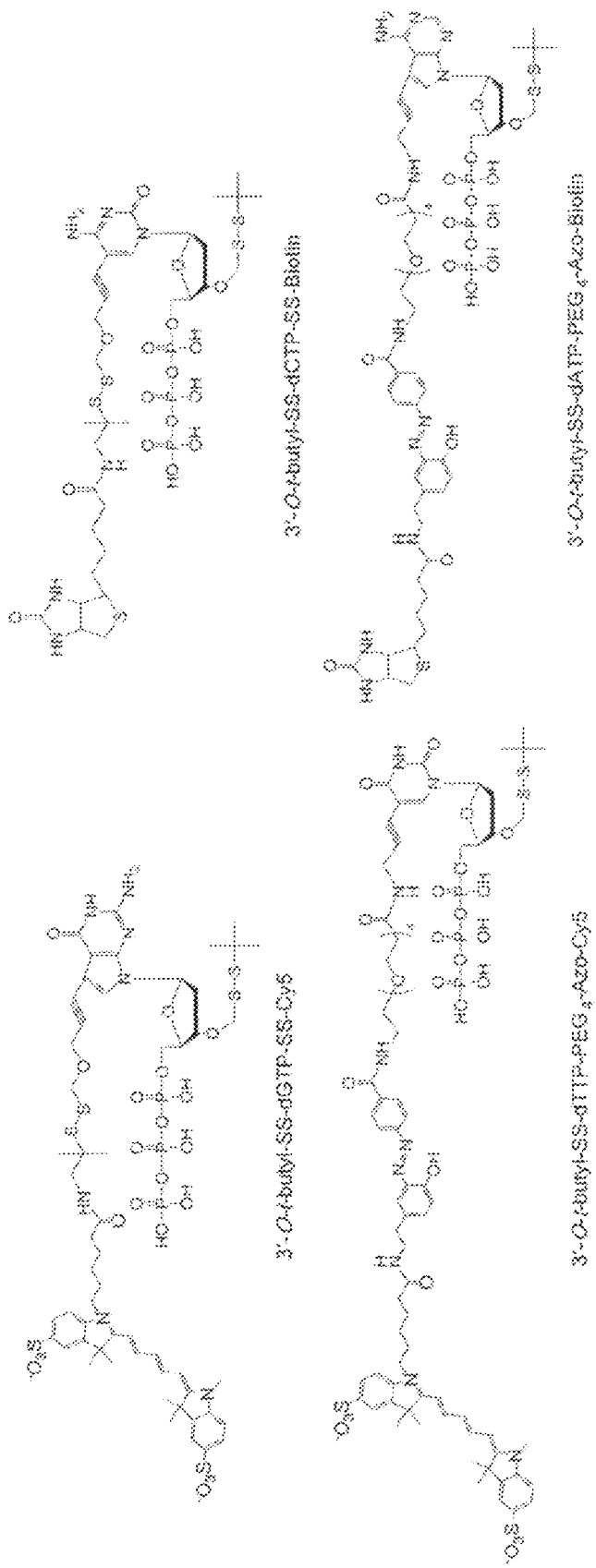

FIG. 131: The four NRT analogues that were synthesized and characterized in Example 3: (1) 3'-O-t-Butyl-SS(DTM)-dTTP-PEG4-Azo-Cy5; (2) 3'-O-t-Butyl-SS(DTM)-dGTP-SS-Cy5; (3) 3'-O-t-Butyl-SS(DTM)-dATP-PEG4-Azo-Biotin; and (4) 3'-O-t-Butyl-SS(DTM)-dCTP-SS-Biotin.

Figure 132:
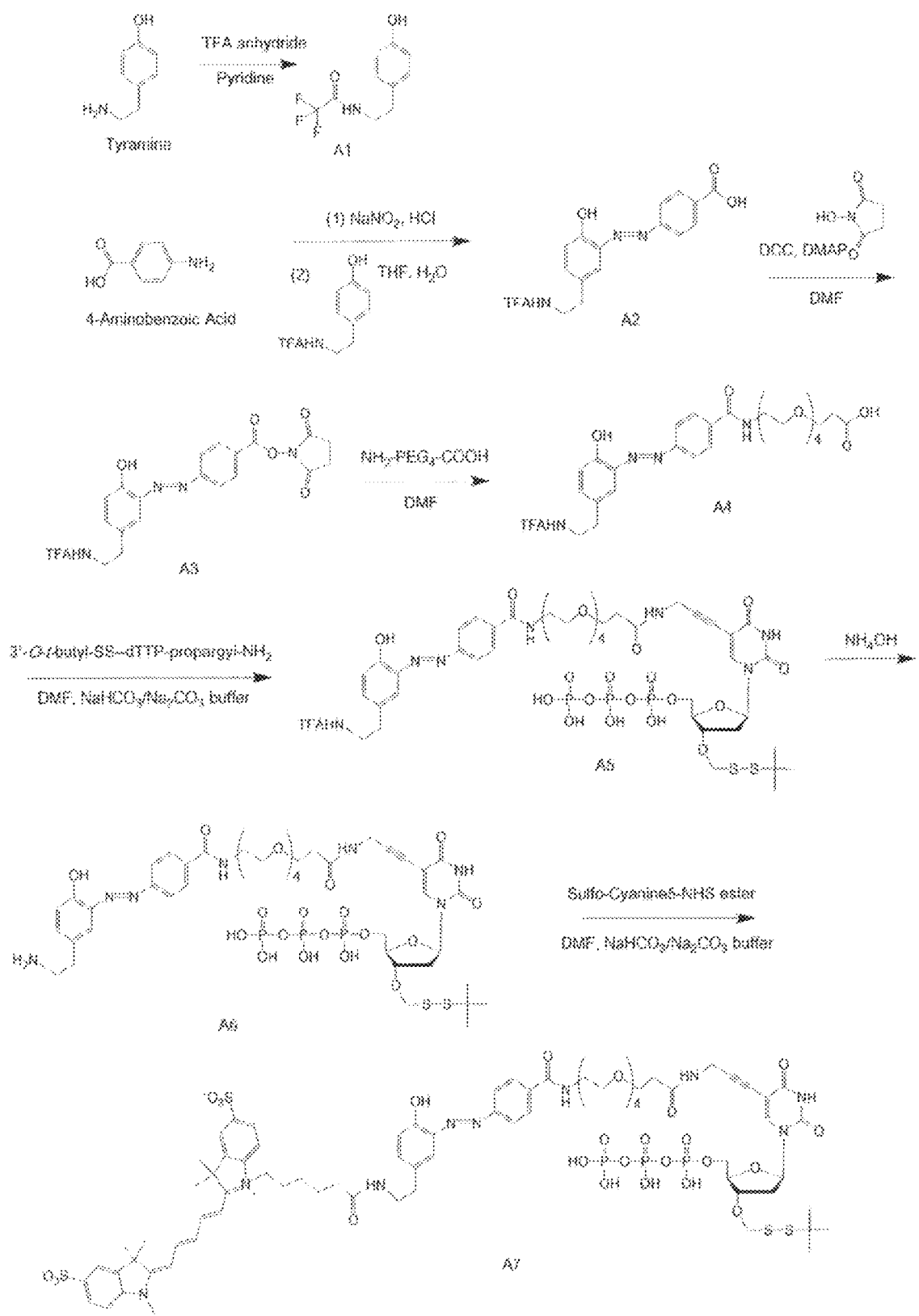

FIG. 132: Synthesis of 3'-O-t-Butyl-SS(DTM)-dTTP-PEG4-Azo-Cy5.

Figure 133:
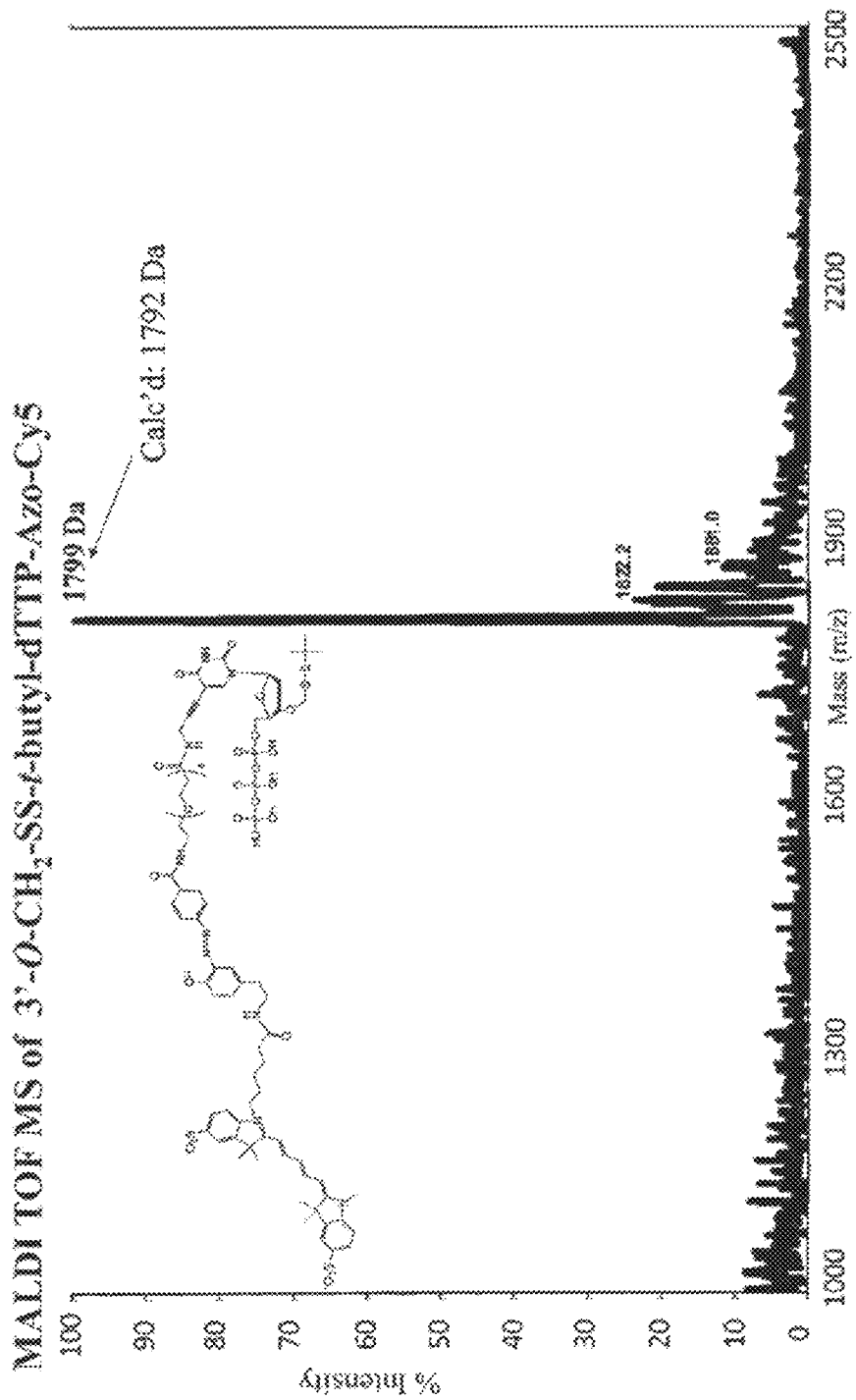

FIG. 133: MALDI-TOF MS characterization of 3'-O-t-butyl-SS-dTTP-PEG4-Azo-Cy5.

Figure 134A:
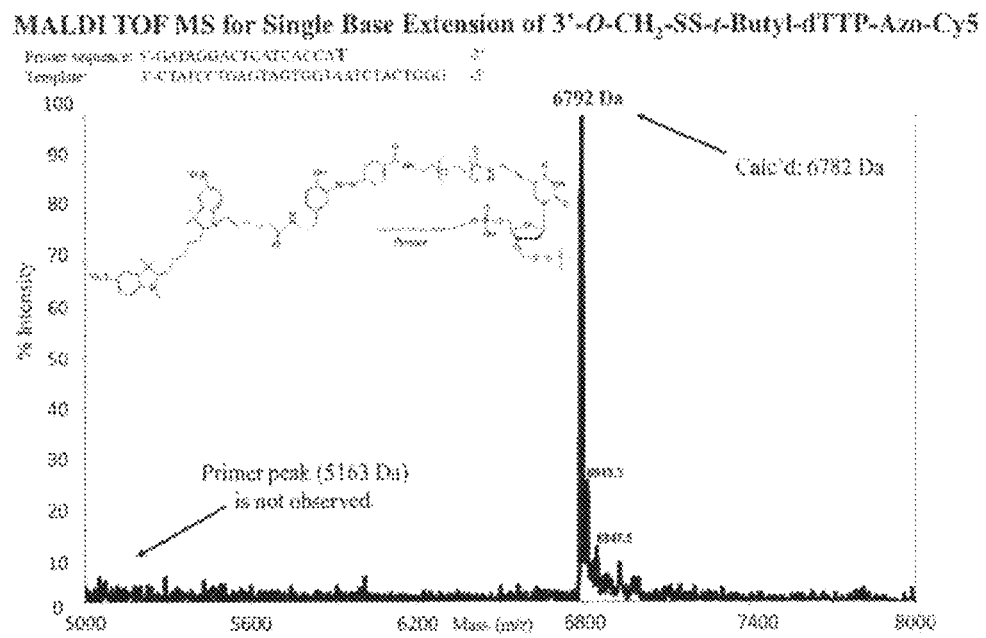
Figure 134B:
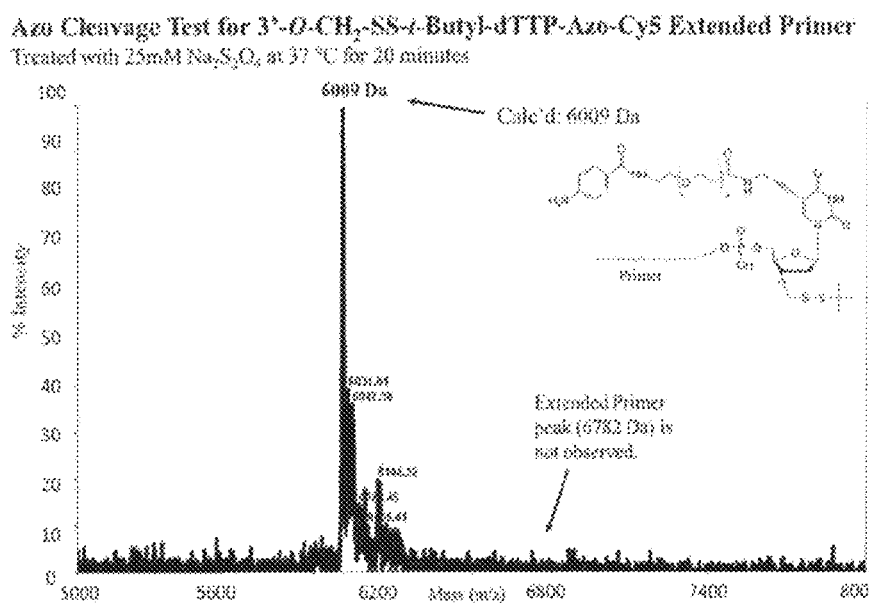

FIGS. 134A-134B: Testing Continuous Incorporation and Cleavage of 3'-O-t-butyl-SS-dTTP-Azo-Cy5. A single base extension reaction was carried out as described in the detailed methods and a MALDI-TOF mass spectrum of the extension product is presented in FIG. 134A. As indicated, essentially complete extension took place with no primer peak visible. Cleavage of the extended product with sodium dithionite to cleave the linker and remove the Cy5 was then performed as described in the detailed methods and the MALDI-TOF mass spectrum indicating complete cleavage is presented in FIG. 134B. Finally, cleavage of the 3' blocking group with THP was carried out, as demonstrated in the MALDI-TOF mass spectrum shown in FIG. 134C. In the figure, only a portion of the template sequence is shown and the bolded T in the primer represents the single base-extended primer sequence.

Figure 135:
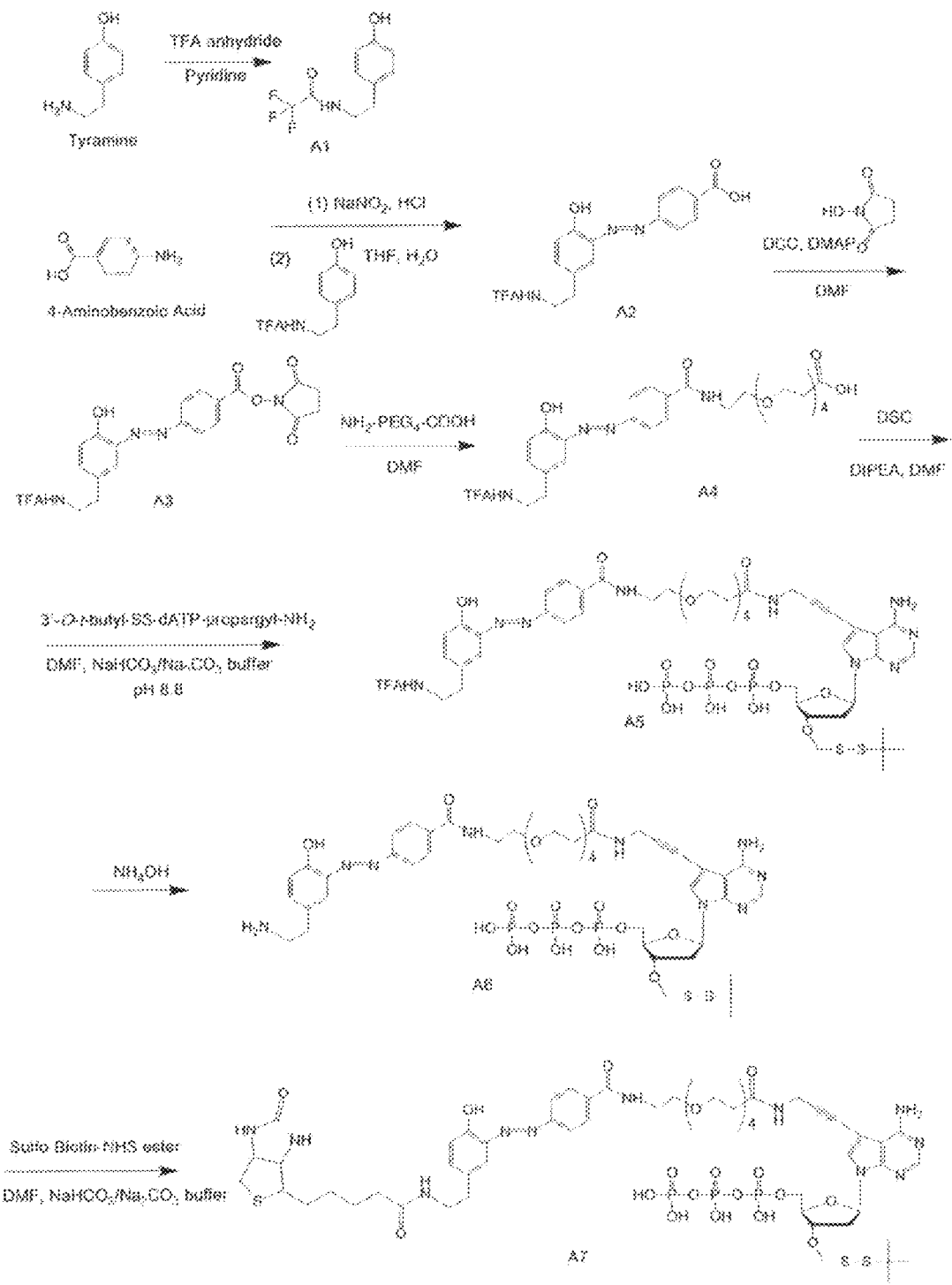

FIG. 135: Synthesis of 3'-O-t-Butyl-SS(DTM)-dATP-PEG4-Azo-Biotin.

Figure 136:
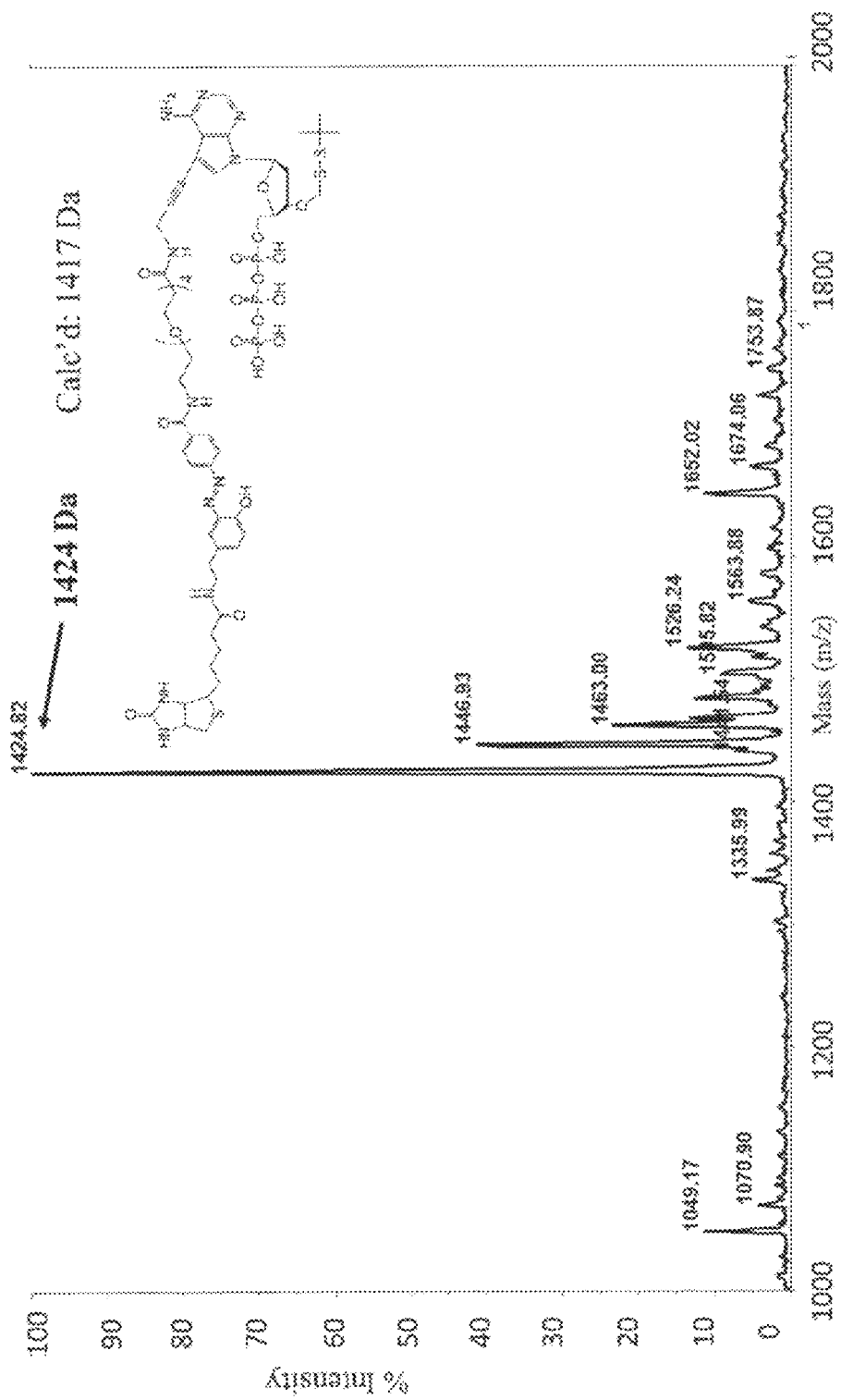

FIG. 136: A MALDI-TOF MS trace to confirm synthesis of 3'-O-t-Butyl-SS(DTM)-dATP-PEG4-Azo-Biotin.

Figure 137A:
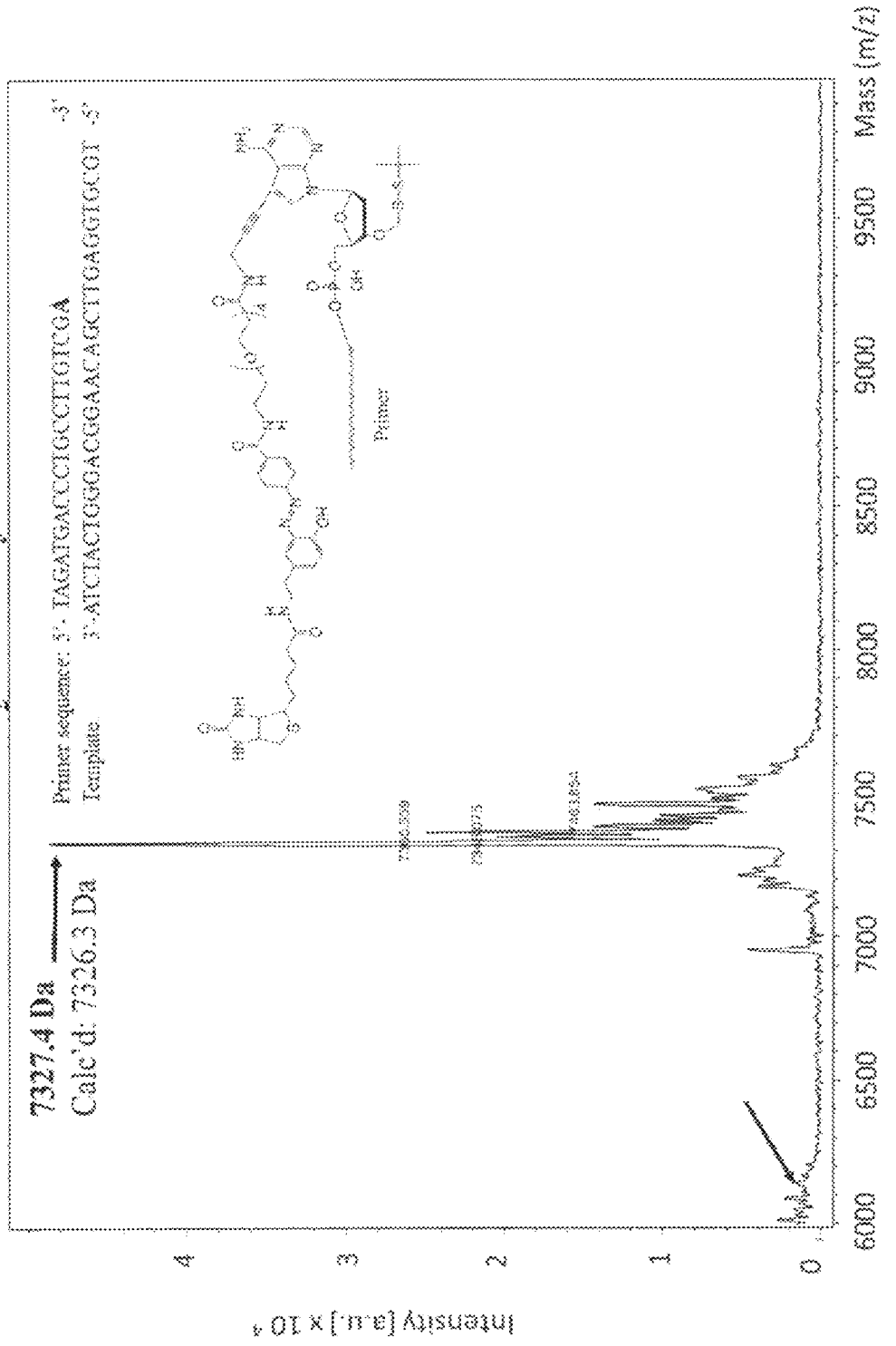
Figure 137B:
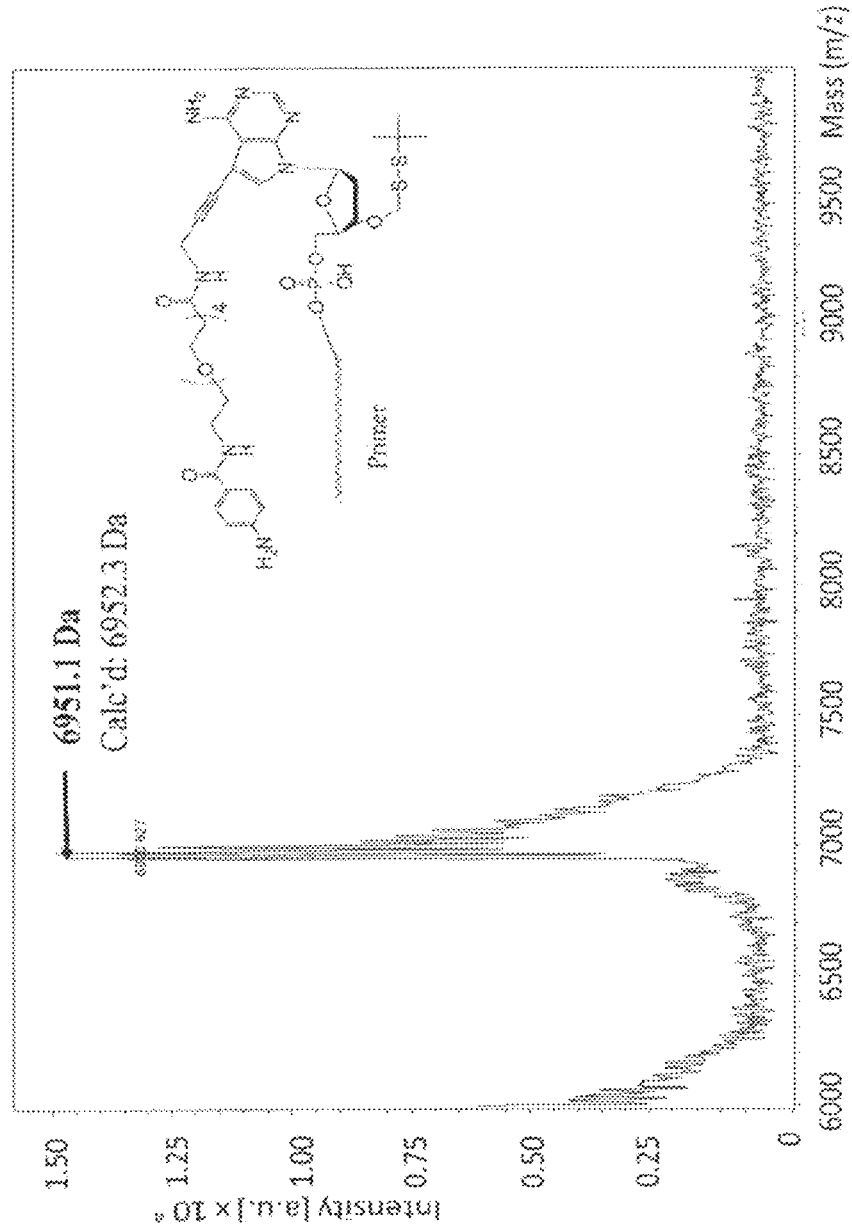

FIGS. 137A-137B: Testing Continuous Incorporation and Cleavage of 3'-O-t-butyl-SS-dATP-Azo-Biotin. A single base extension reaction was carried out as described in the detailed methods and a MALDI-TOF mass spectrum of the extension product is presented in the top panel. As indicated, essentially complete extension took place with no primer peak visible. Cleavage of the extended product with sodium dithionite to cleave the linker and remove the Cy5 was then performed as described in the detailed methods and the MALDI-TOF mass spectrum indicating complete cleavage is presented in the lower panel. In the figure, only a portion of the template sequence is shown and the bolded A in the primer represents the single base-extended primer sequence.

Figure 138:
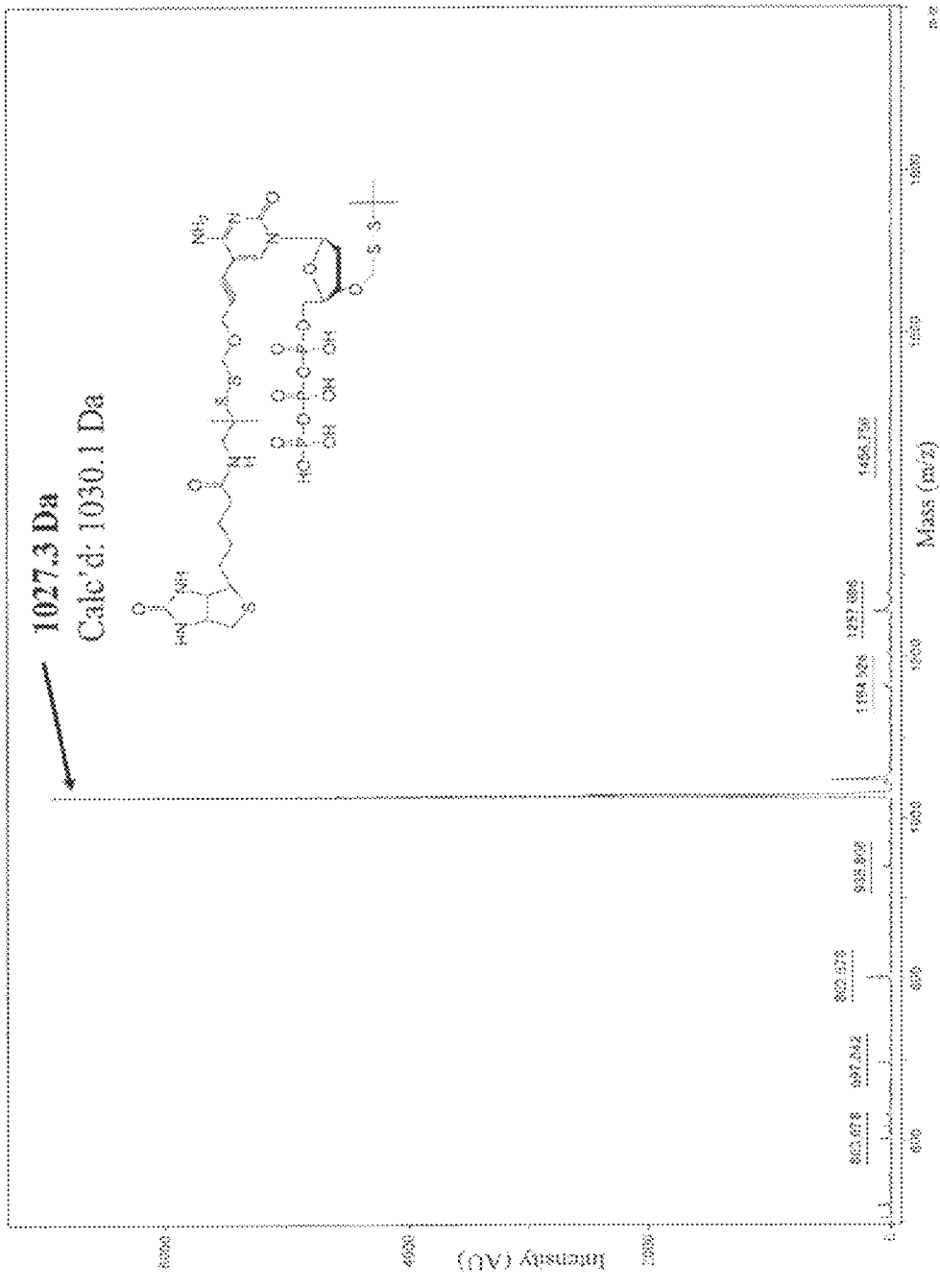

FIG. 138: MALDI-TOF MS characterization of 3'-O-t-butyl-SS-dCTP-SS-Biotin.

FIG. 139: MALDI-TOF MS characterization of 3'-O-t-butyl-SS-dGTP-SS-Cy5.

Figure 140A:
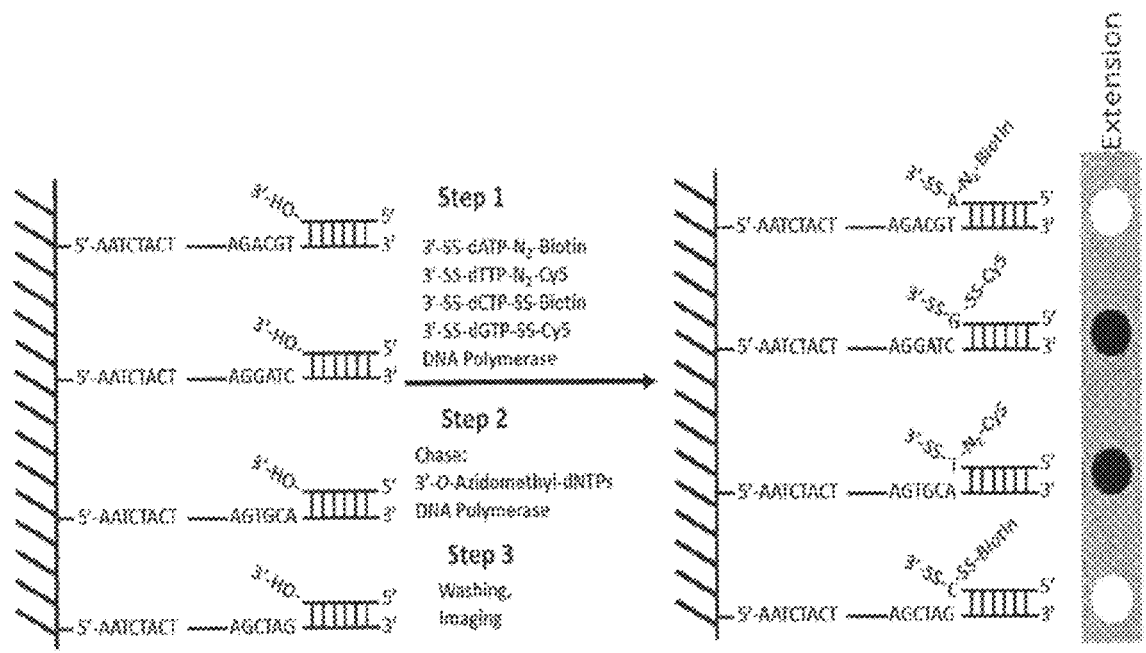
Figure 140B:
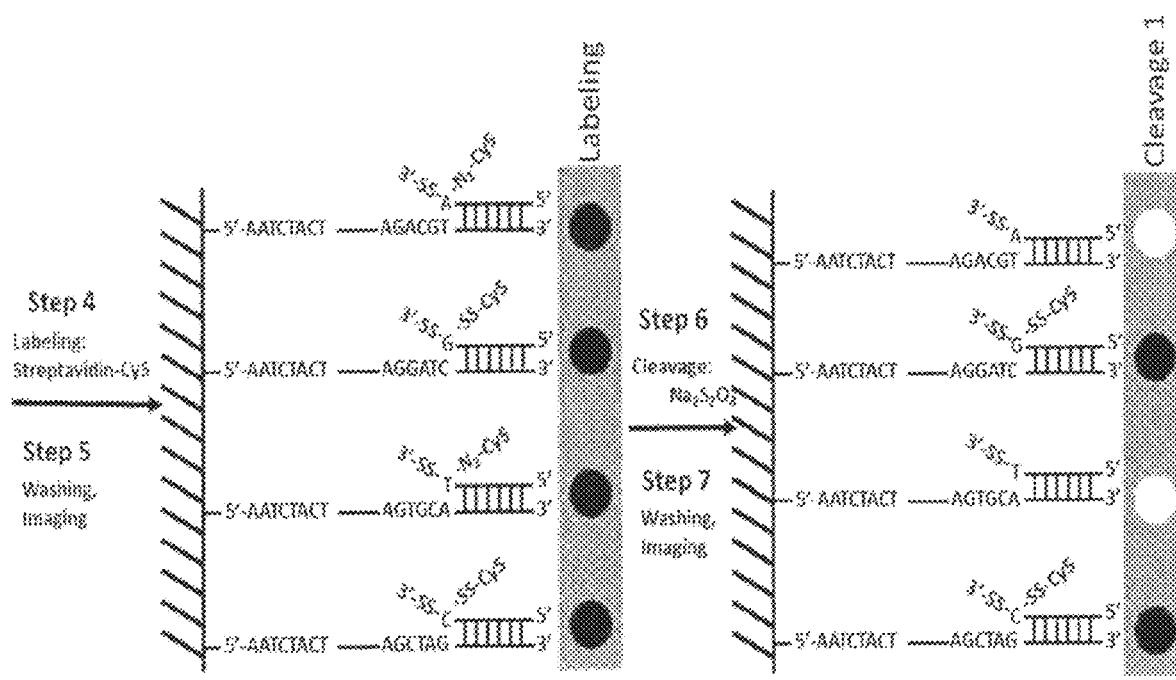
Figure 140C:
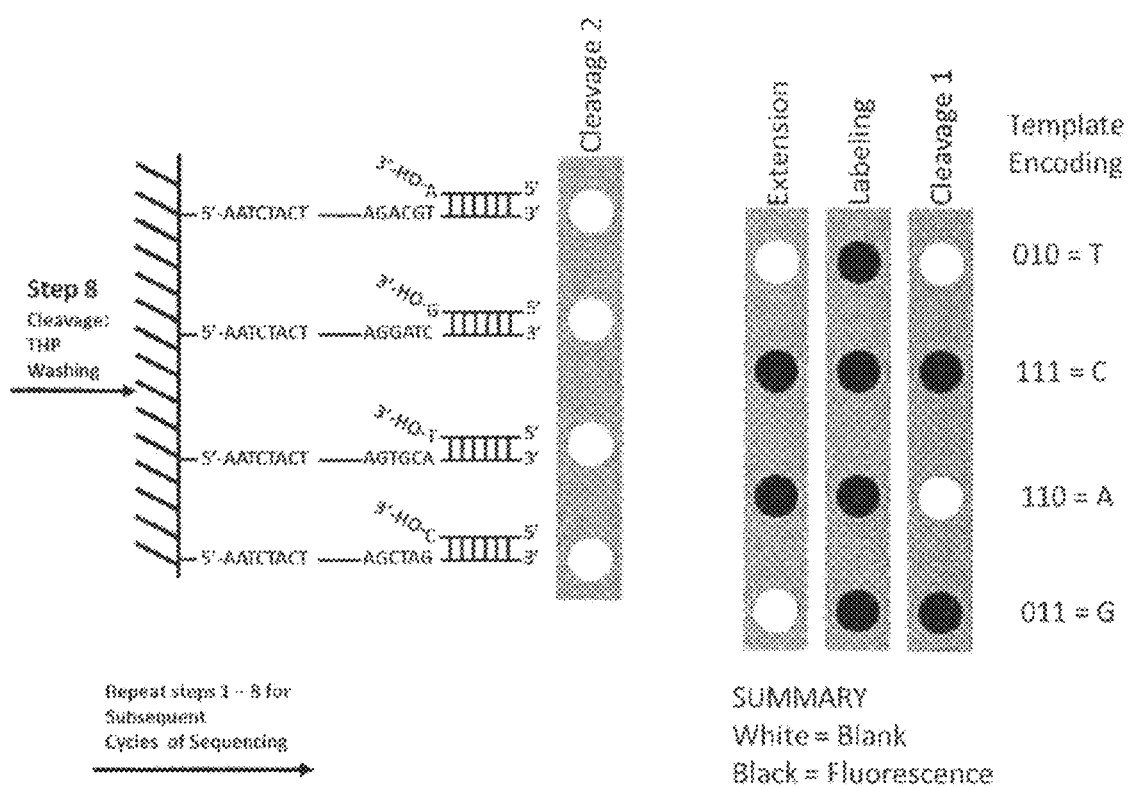

FIGS. 140A-140C: Schematic illustrating Single-color Sequencing by Synthesis Using Orthogonal Set of Nucleotide Reversible Terminators, with All Combinations of Azo and SS Linkers and Biotin and Cy5.

Figure 141:
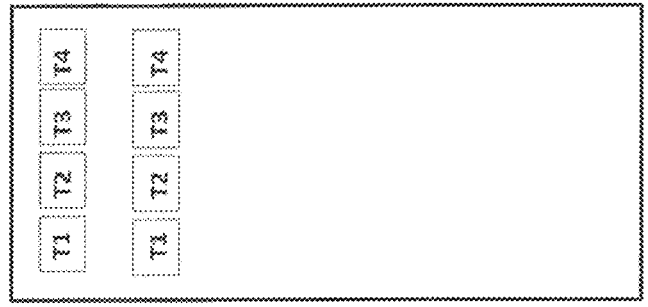

FIG. 141: Attachment of Primer-Loop Template DNA Molecules to Slide. Templates T1, T2, T3 and T4, which are 5'-amino-modified self-priming template DNA, were spotted in the rectangular areas of NHS ester-activated Code-Link slides (Surmodics Inc., MN) as indicated in the figure, 441 (21×21) spots in each rectangular area. The first cycle of sequencing for these four templates will be with nucleotide analogues T, G, C and A, the next cycle will be with nucleotide analogues A, A, A and T, etc.

Figure 142:
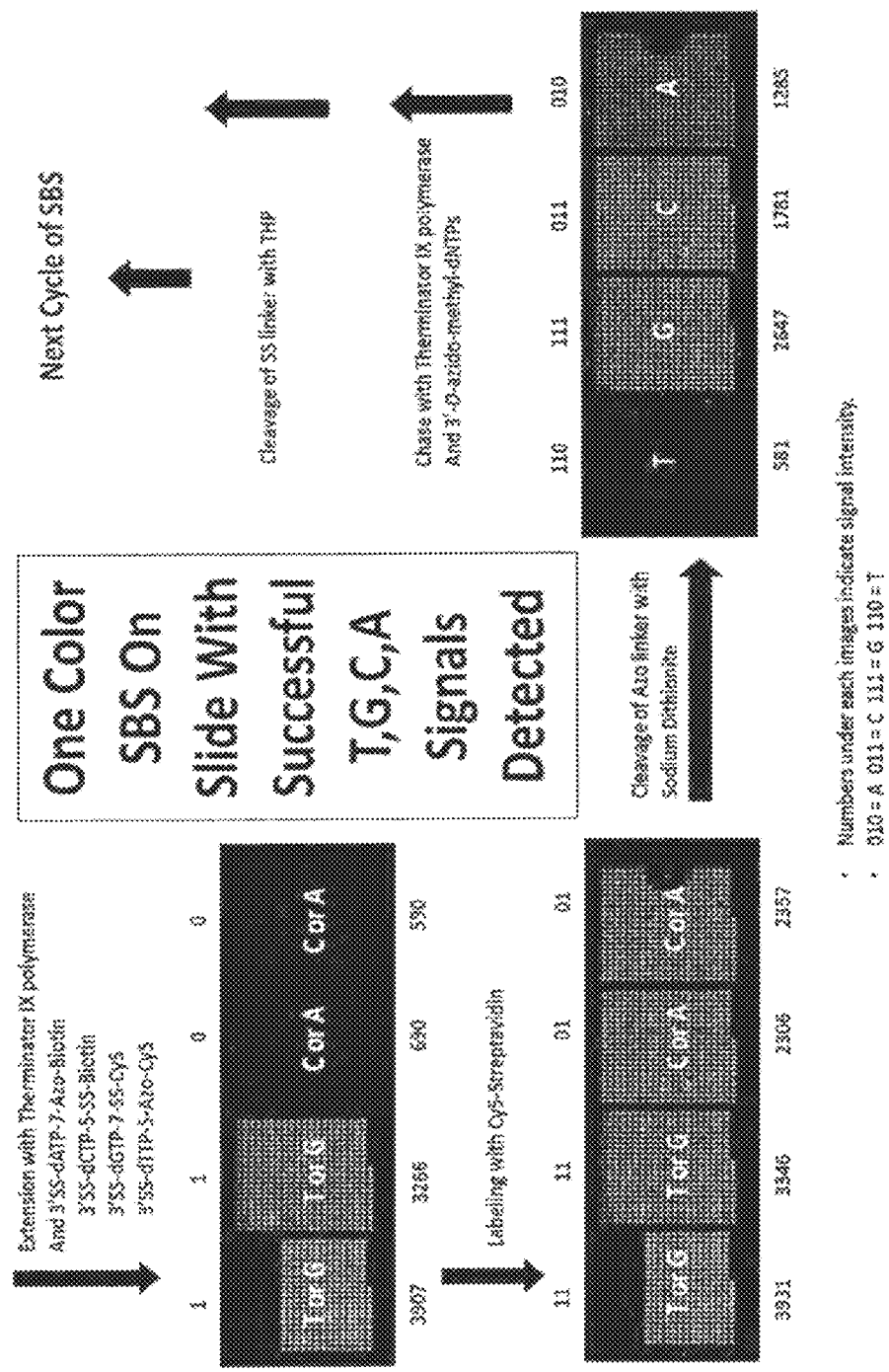

FIG. 142: Results for First Cycle of Single-Color Sequencing by Synthesis with Slide-Immobilized Templates.

Figure 143:
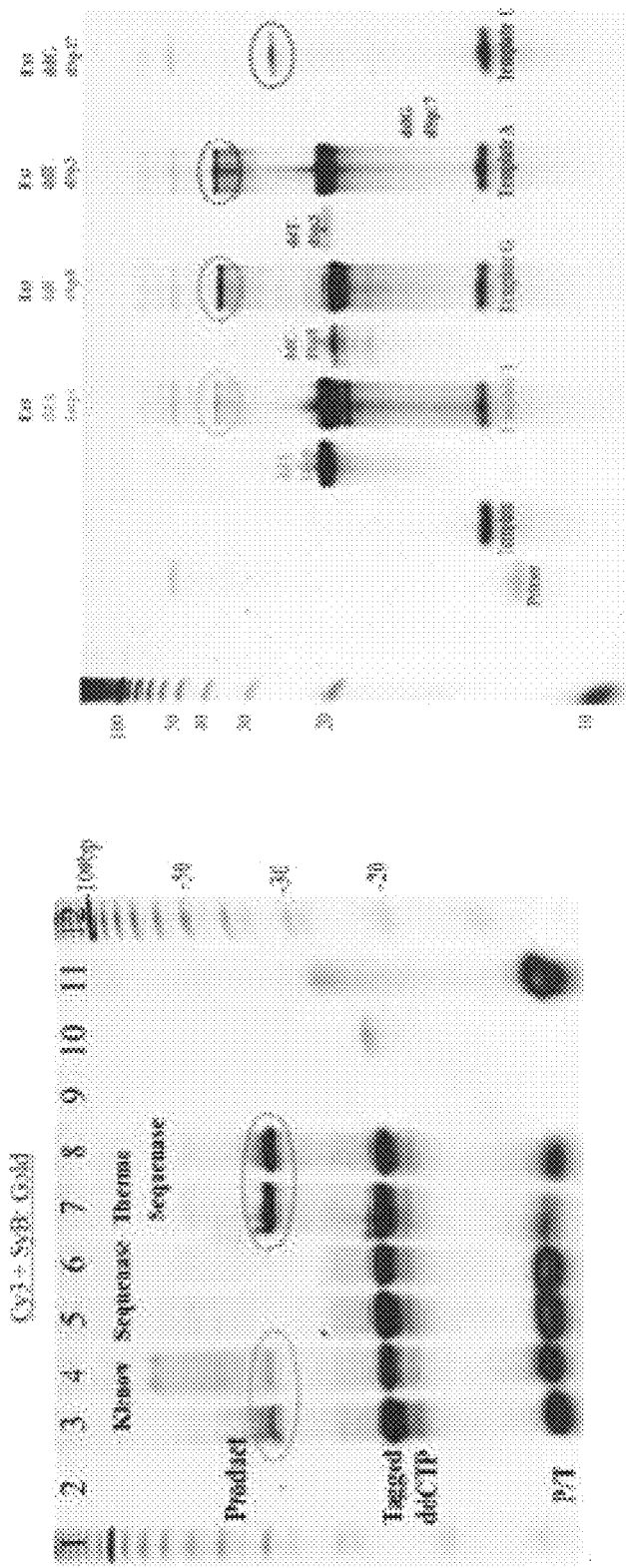

FIG. 143: Screening DNA polymerases for incorporation of the tagged ddCTP shown in FIG. 79. Left: A single base extension reaction was performed with different ratios of a 26-base long self-primed-looped template (1 µM) relative to the tagged ddCTP (20 µM in lanes 3, 5 and 7; 10 µM in lanes 4, 6 and 8). Incubations were carried out in 20 ul reaction volumes for 1 hr at 37 C with either 5 U Klenow (exo-) (NEB), 13 U Sequenase (Affymetrix) or 4 U Thermo Sequenase (Affymetrix). Products were separated on an 8M urea/15% polyacrylamide gel and stained with SybrGold. As shown in lanes 7 and 8, the best incorporation was obtained with Thermo Sequenase. Terminator II and III were also tested, but they showed less complete reactions, similar to Klenow. Right: Results with primer and four different templates specific for each of the four tagged dideoxynucleotides in FIG. 79. The reaction contained 10 pmol biotinylated primer (15 bp), 15 pmol complementary linear template (21 bp), 1 U ThermoSequenase, and 100 pmol dideoxynucleotide analogue. Extension products, visualized on a denaturing gel stained with SybrGold, were obtained with all four nucleotide analogues (lanes 4, 6, 8 and 10). Because the ddG-dSp17 analogue does not contain any purine or pyrimidine bases in the polymer chain, only the SybrGold stained template and extended products are visualized in lane 10. The first lane contains just the primer, the second lane just the template, and lanes 3, 5, 7, and 9 just the respective dideoxynucleotide analogues as controls (again, there is no visible band in lane 9 due to the absence of bases in the polymer tail).

Figure 144:
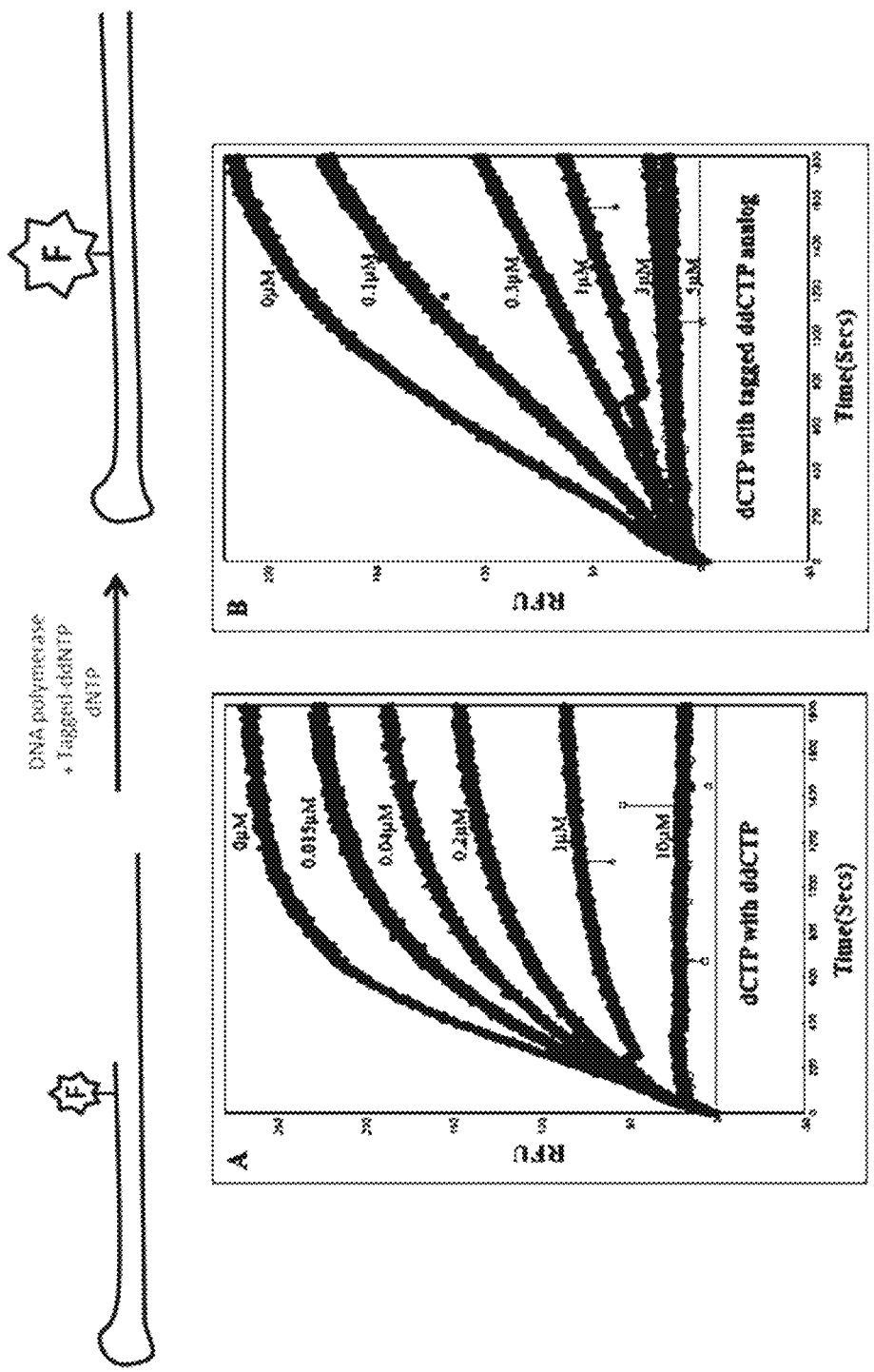

FIG. 144: Fluorescence intensity change vs time using self-primed looped primers having a fluoresceinated dT near their 3' ends. A. Varying concentrations of ddCTP (0 to 10 µM) were added to solutions containing Thermo Sequenase, 0.3 µM single fluorescein labeled self-primed template and 10 pH dCTP. The concentration of unmodified ddCTP that produces the half maximum fluorescent intensity is approximately 0.5 µM. B. The same experiments performed with the tagged ddCTP (0 to 5 µM) shown in FIG. 79 in the presence of the same template and 5 µM dCTP. The result shows that the apparent $IC_{50}$ of polymer tagged ddCTP is approximately 0.25 µM.

Figure 145:
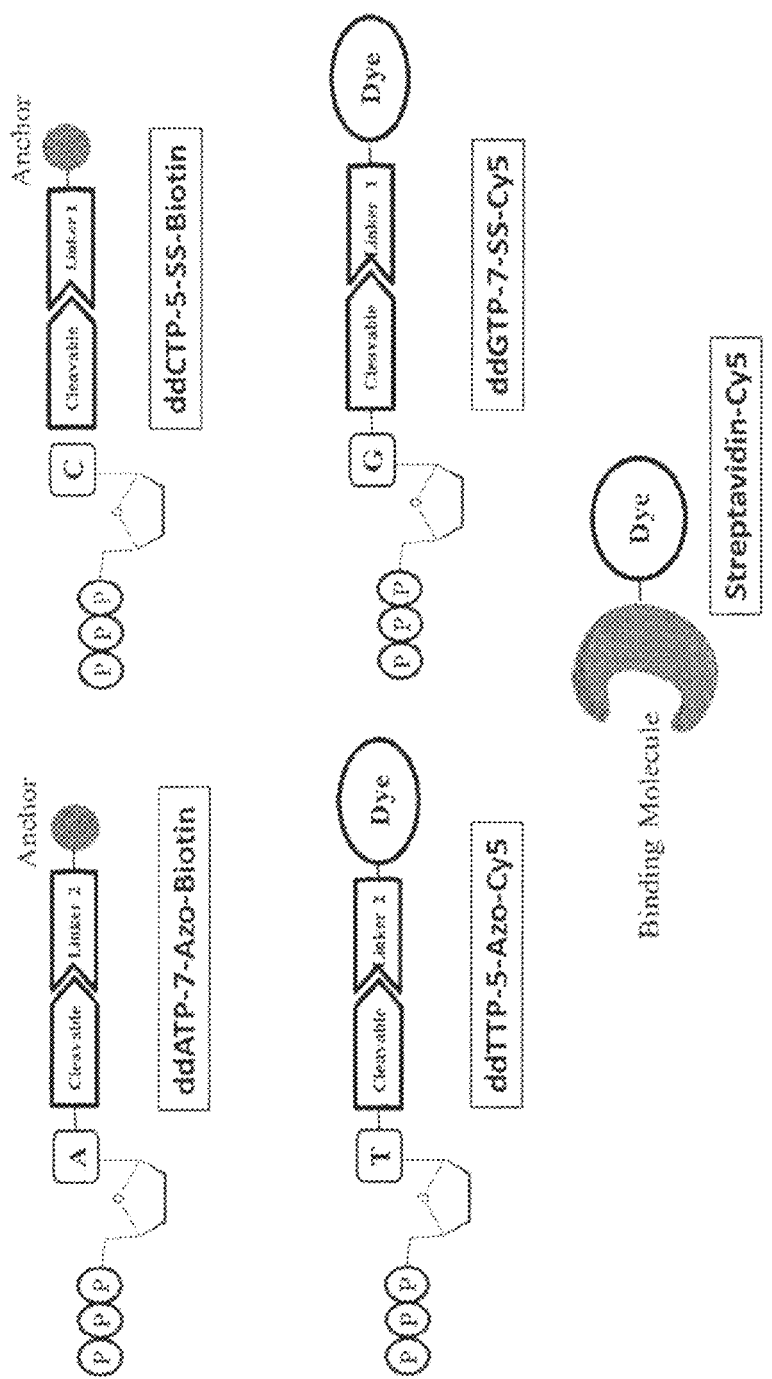

FIG. 145: Generalized set of dye and anchor labeled orthogonally cleavable ddNTP analogues and labeling reagent for single-color SBS: Two of the dideoxynucleotide analogues have an anchor (e.g., biotin) and two have a dye (e.g., Cy5). For two of these nucleotides, the dye or anchor is attached to the base via cleavable linker 1 (containing an SS group which can be cleaved by THP) and for the other two the dye or anchor is attached to the base via cleavable linker 2 (containing an azo group which can be cleaved by sodium dithionite). The labeling molecule consists of a molecule able to bind specifically to the anchor (streptavidin) and the same dye. A requirement of this hybrid SBS method is a separate set of four unlabeled reversible terminators (e.g., azidomethyl dNTPs).

Figure 146:
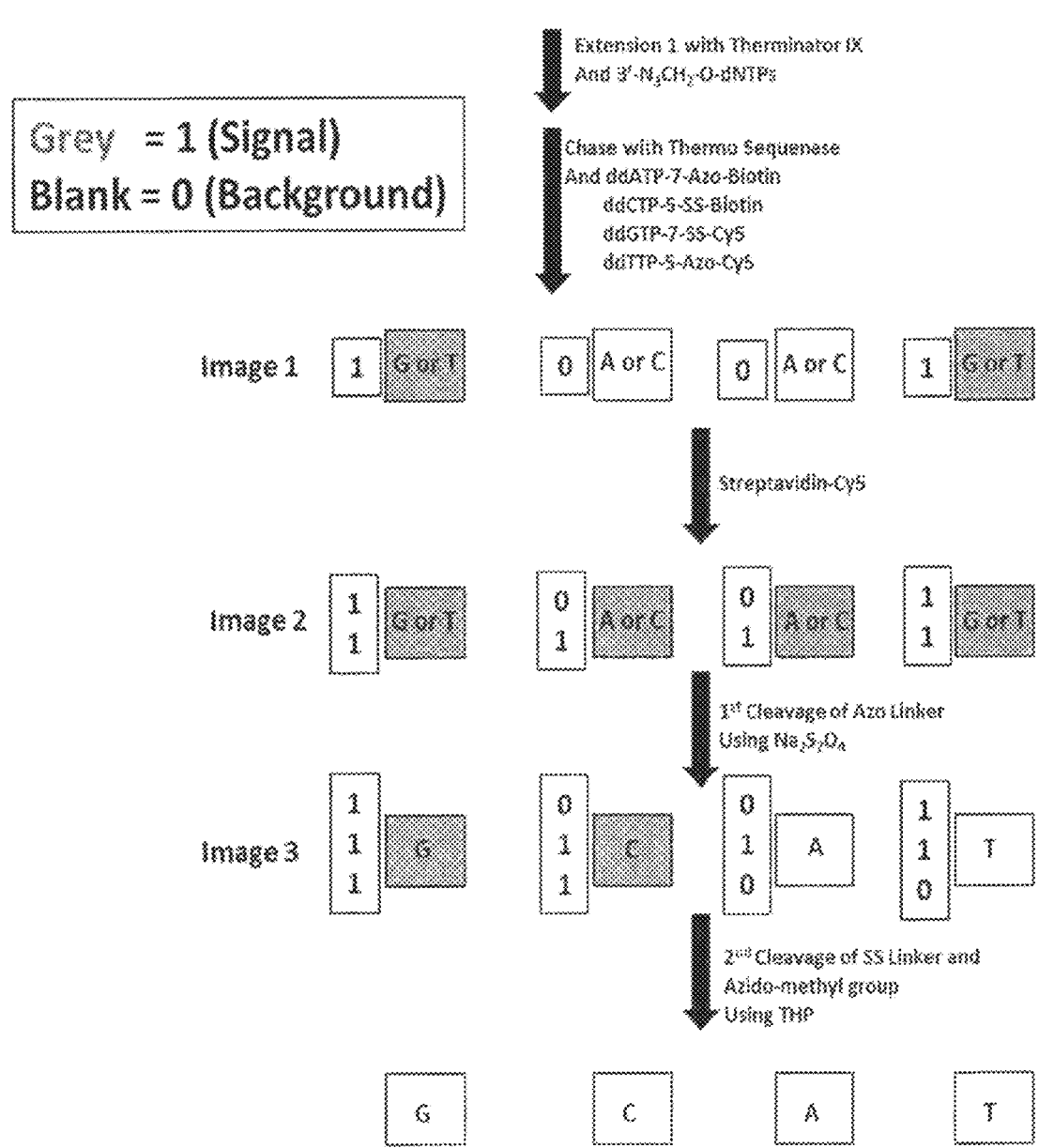

FIG. 146: Simplified presentation of scheme for single-color SBS using orthogonally cleavable nucleotide analogues such as those presented in FIG. 145. Each ddNTP has a different combination of either Cy5 or Biotin and either SS Linker or Azo Linker. The rectangles represent areas containing numerous copies of attached primer-loop-template molecules in which the next base in the template strand, from left to right is C, G, T or A. After incubation with the four unlabeled nucleotide reversible terminators (NRTs, e.g., 3'-azidomethyl dNTPs) and Therminator IX to extend the majority of the primers, incubation with the four labeled ddNTPs and Thermosequenase is performed; imaging will reveal a positive signal in the first and fourth areas (representing extension of the primer strand with either G or T) and a negative signal in the second and third areas (extension with A or C). After labeling with Streptavidin-Cy5, imaging of all four areas will reveal a positive signal, confirming the previous possible incorporation events. Imaging after cleavage of the azo linker with sodium dithionite (Na2S2O4) will reveal loss of positive signal in the third and fourth areas, but not the first and second areas. Since the azo group is on the A and T nucleotides, this reveals that in areas 1 through 4, there was incorporation of G, C, A and T respectively. Finally, treatment with THP cleaves the SS linker and removes the azidomethyl group on any primers extended with NRTs in preparation for the next sequencing cycle. The 1, 2 and 3 numeral codes at the left of each rectangle represent the cumulative signals at each of the three indicated imaging steps, a positive signal indicated by a 1 and a negative signal indicated by a 0. It is clear that incorporation of each of the four possible nucleotide analogues will be revealed by a unique digital code (0101 for A, 011 for C, 111 for G and 110 for T considering all three of these imaging steps; 00 for A, 01 for C, 11 for G and 10 for T considering just the first and third of these imaging steps).

FIGS. 147A-147B: A set of nucleotide analogues for conducting single-color SBS.

Figure 148:
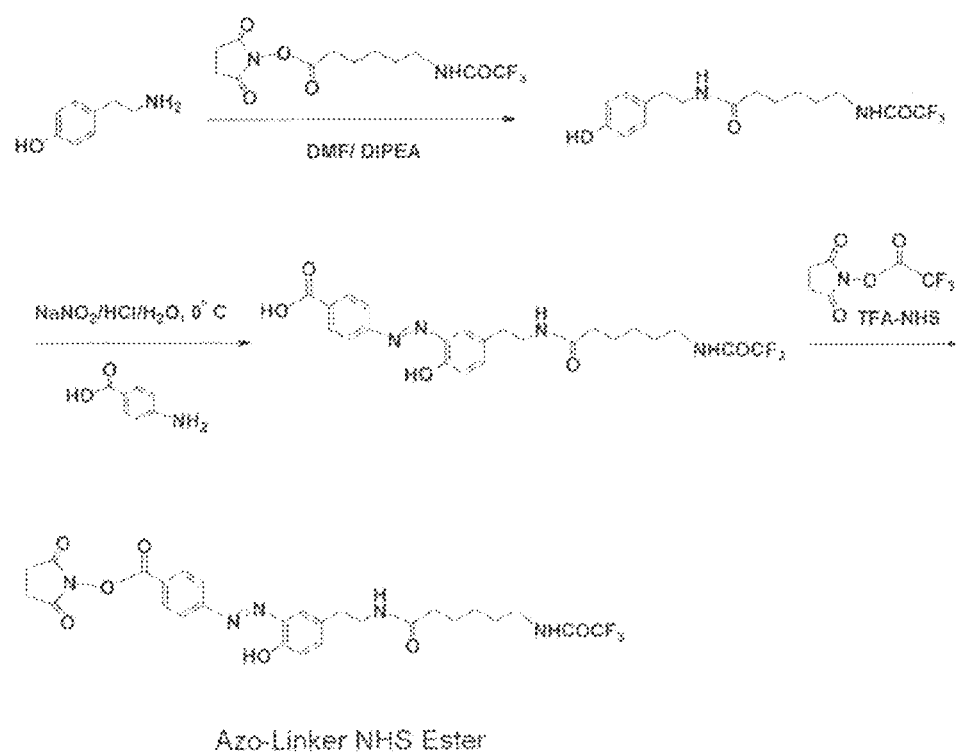

FIG. 148: Synthesis of Azo-Linker NHS Ester.

Figure 149:
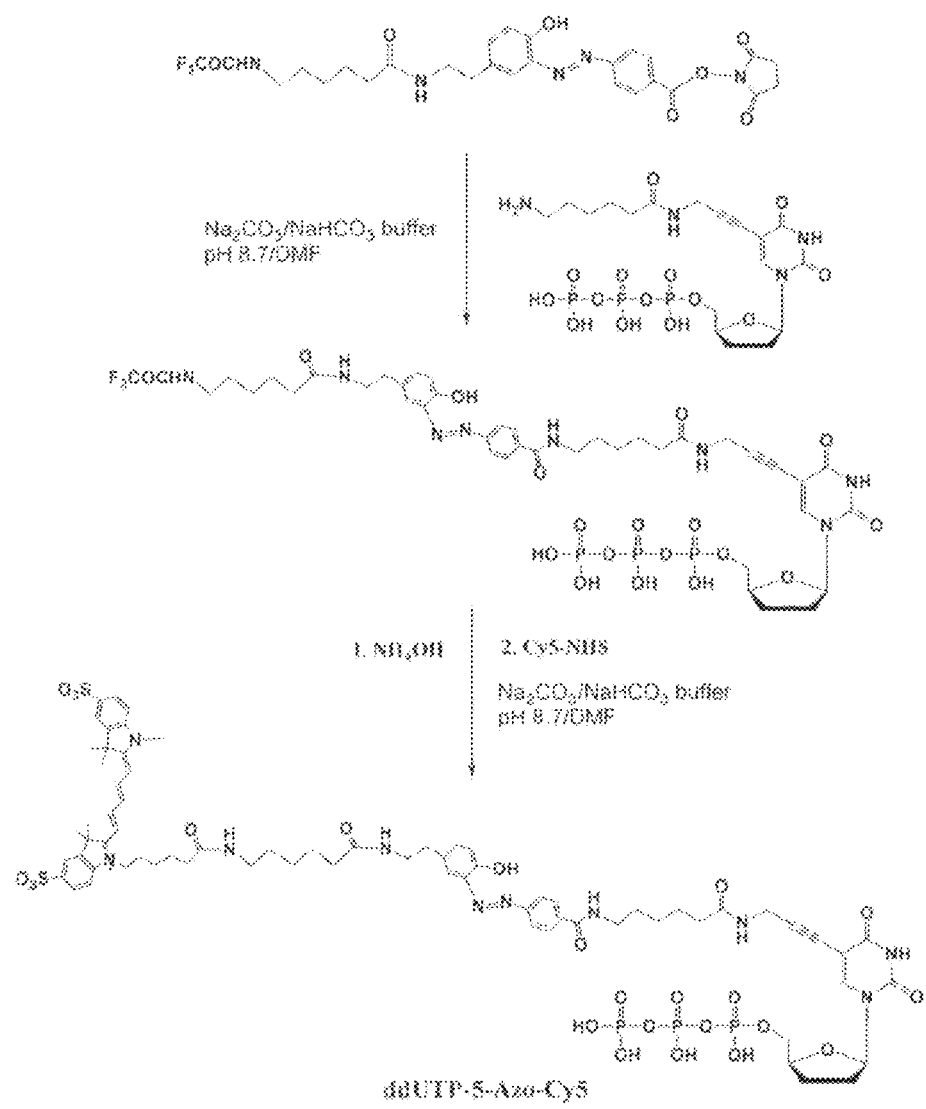

FIG. 149: Synthesis of ddUTP-5-Azo-Cy5.

Figure 150:
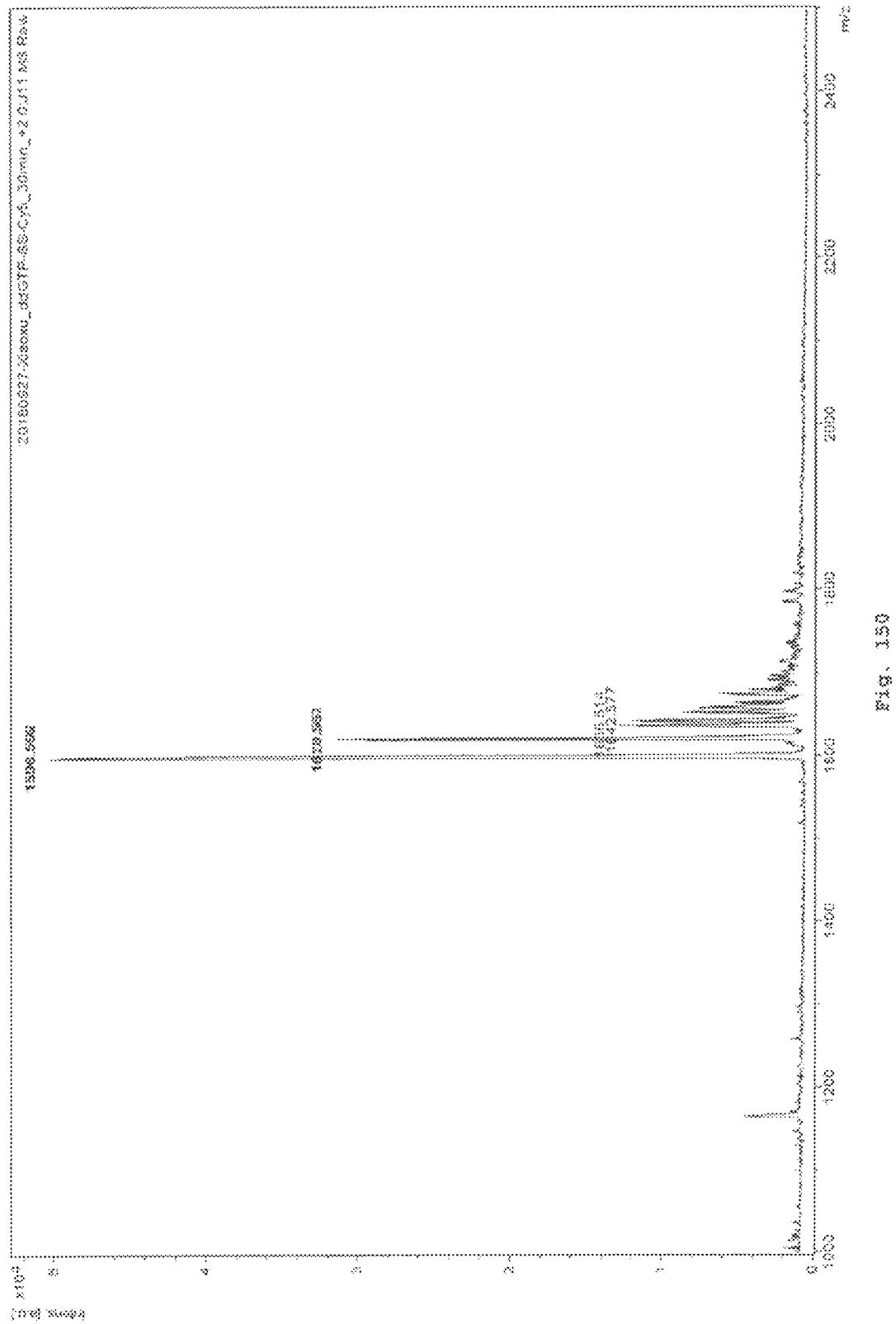

FIG. 150: MALDI-TOF MS traces confirming correct synthesis of ddGTP-7-SS-Cy5.

Figure 151:
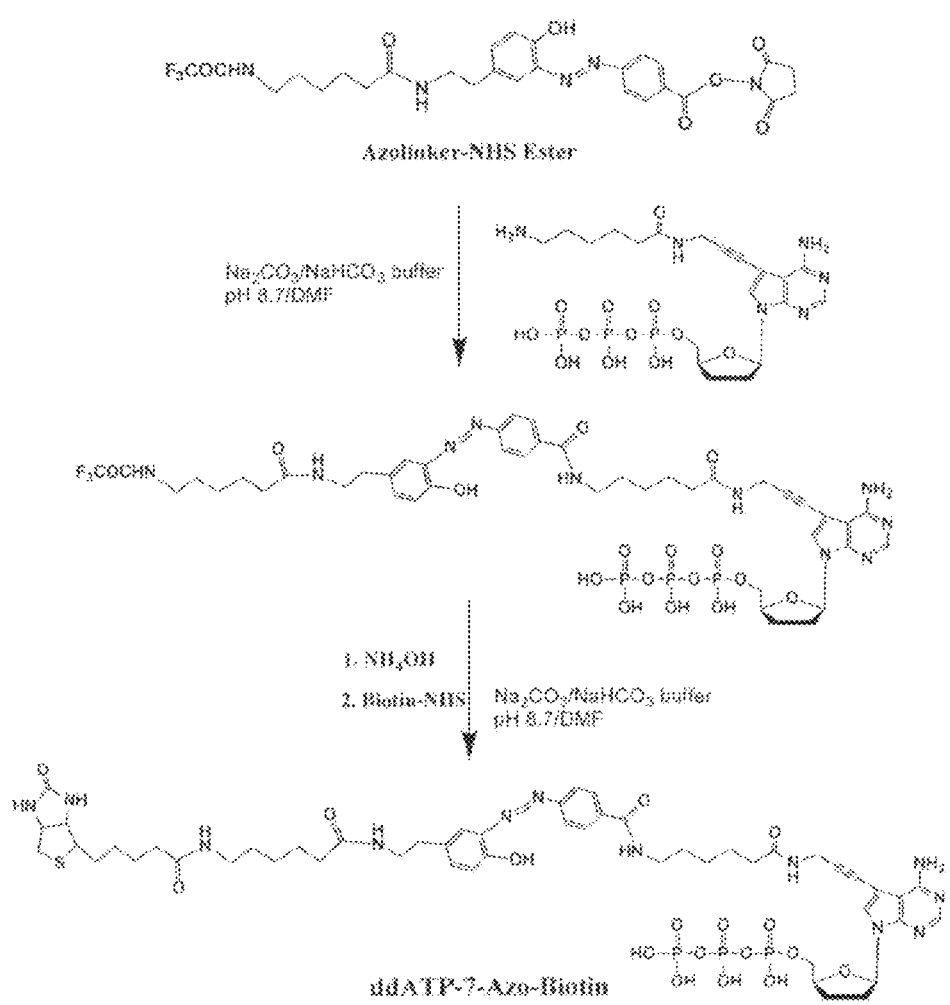

FIG. 151: Synthesis of ddATP-7-Azo-Biotin.

Figure 152:
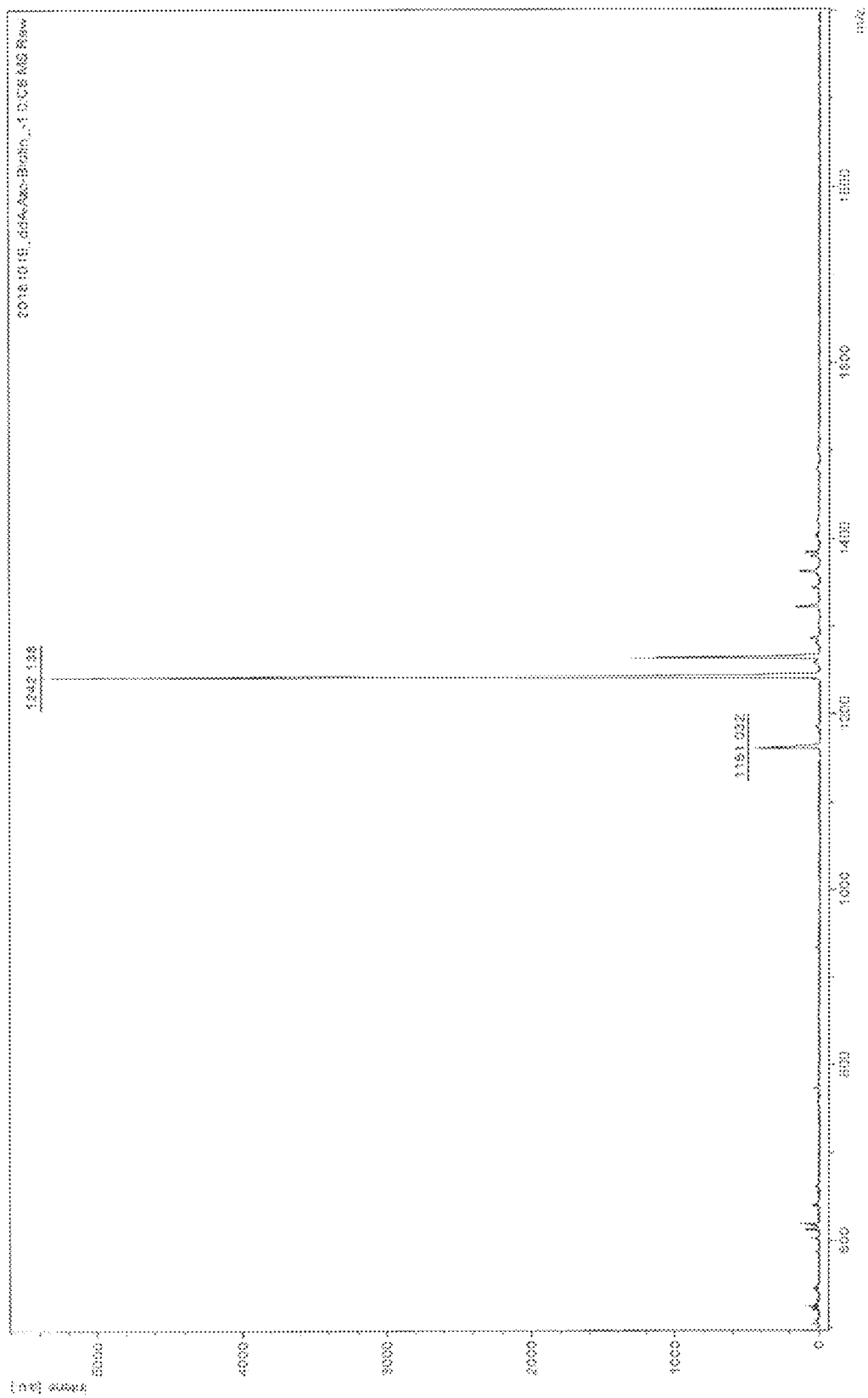

FIG. 152: MALDI-TOF MS traces confirming correct synthesis of ddATP-7-Azo-Biotin.

Figure 153:
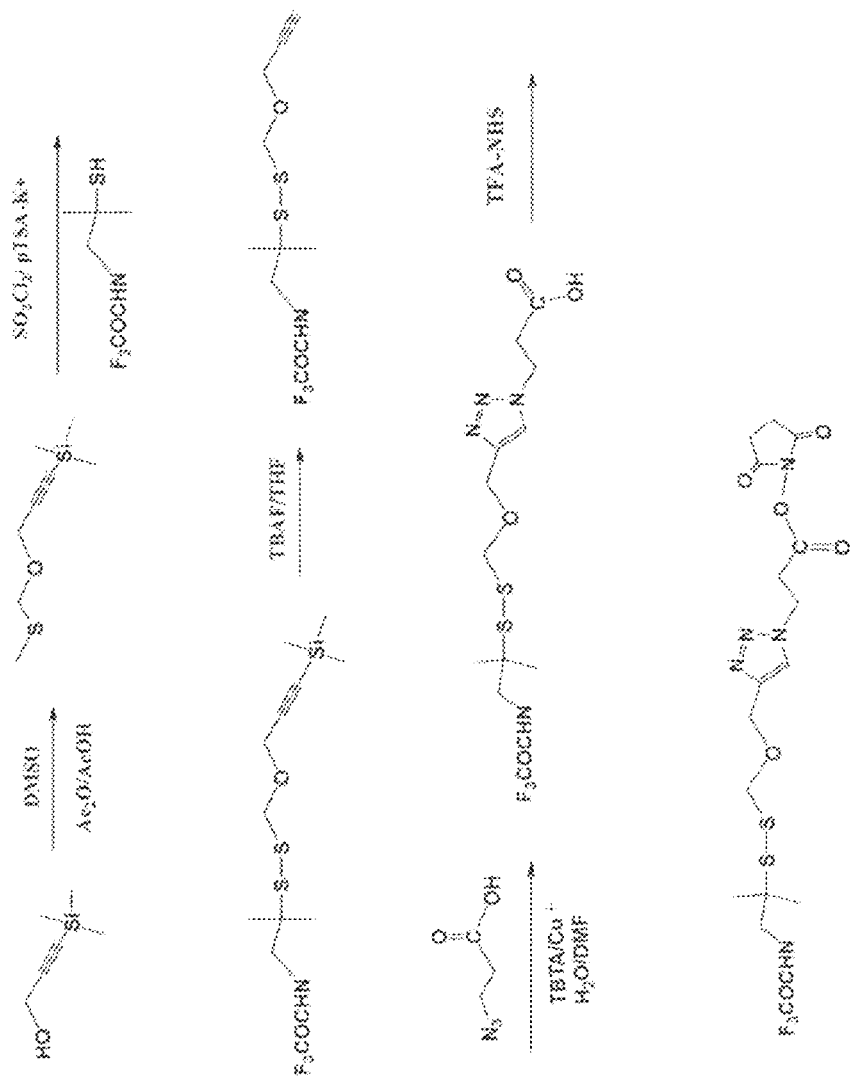

FIG. 153: Synthesis of SS Linker NHS Ester.

Figure 154:
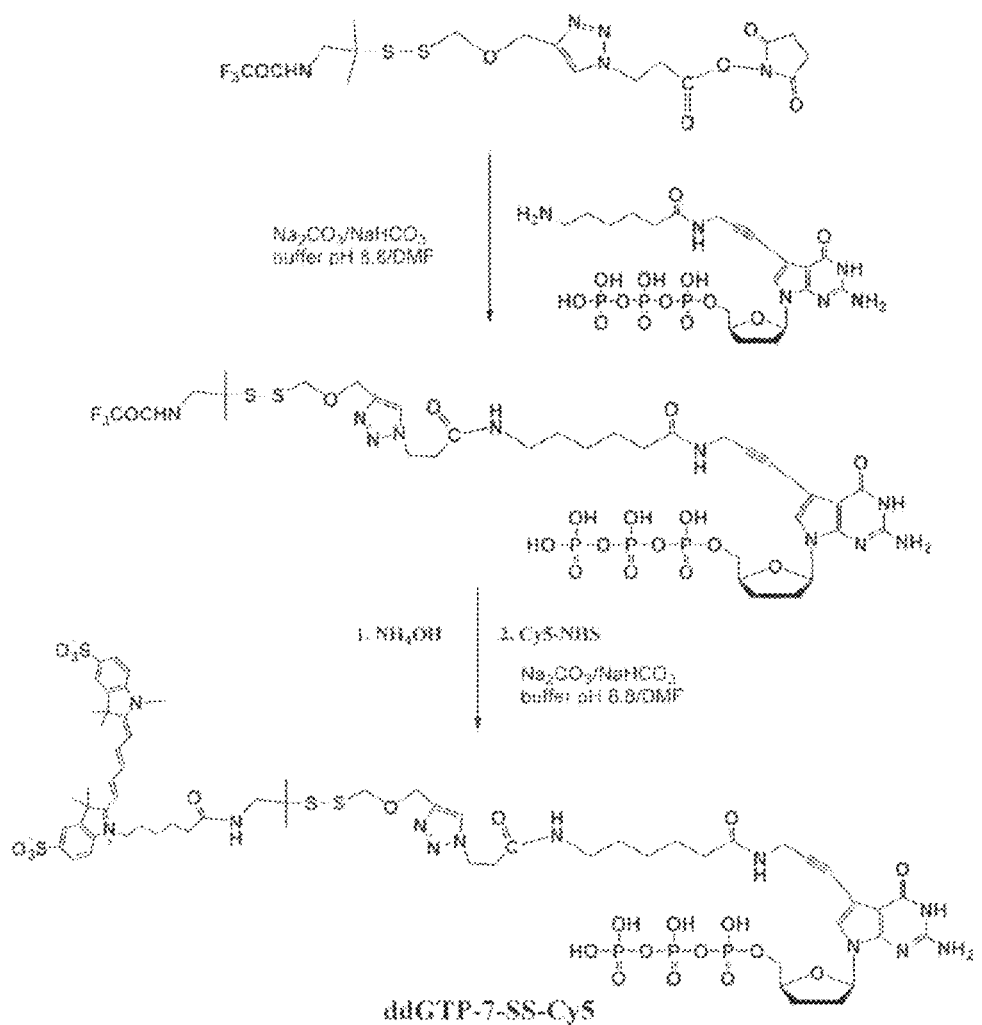

FIG. 154: Synthesis of ddGTP-7-SS-Cy5.

Figure 155:
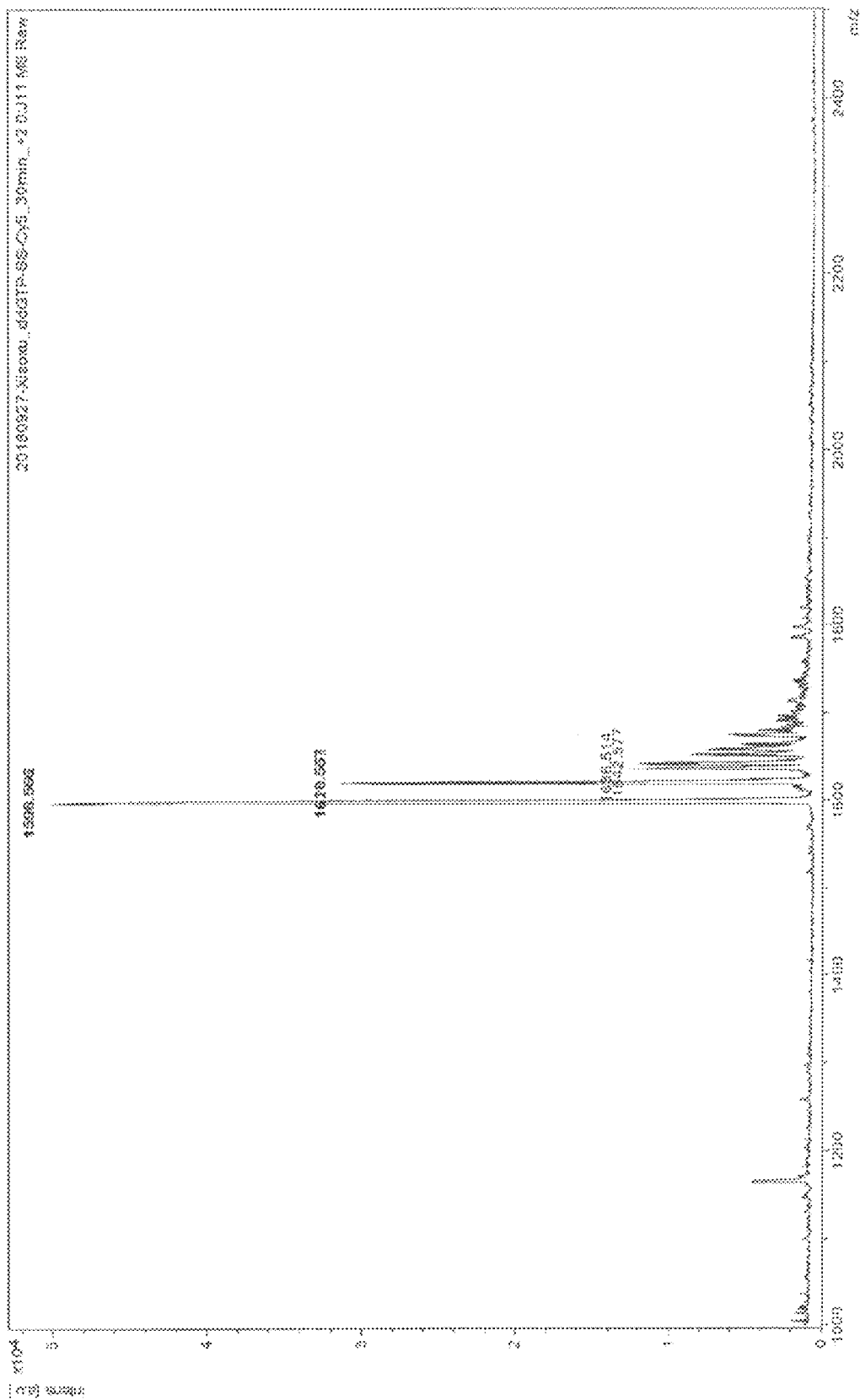

FIG. 155: MALDI-TOF MS traces confirming correct synthesis of ddGTP-7-SS-Cy5.

Figure 156:
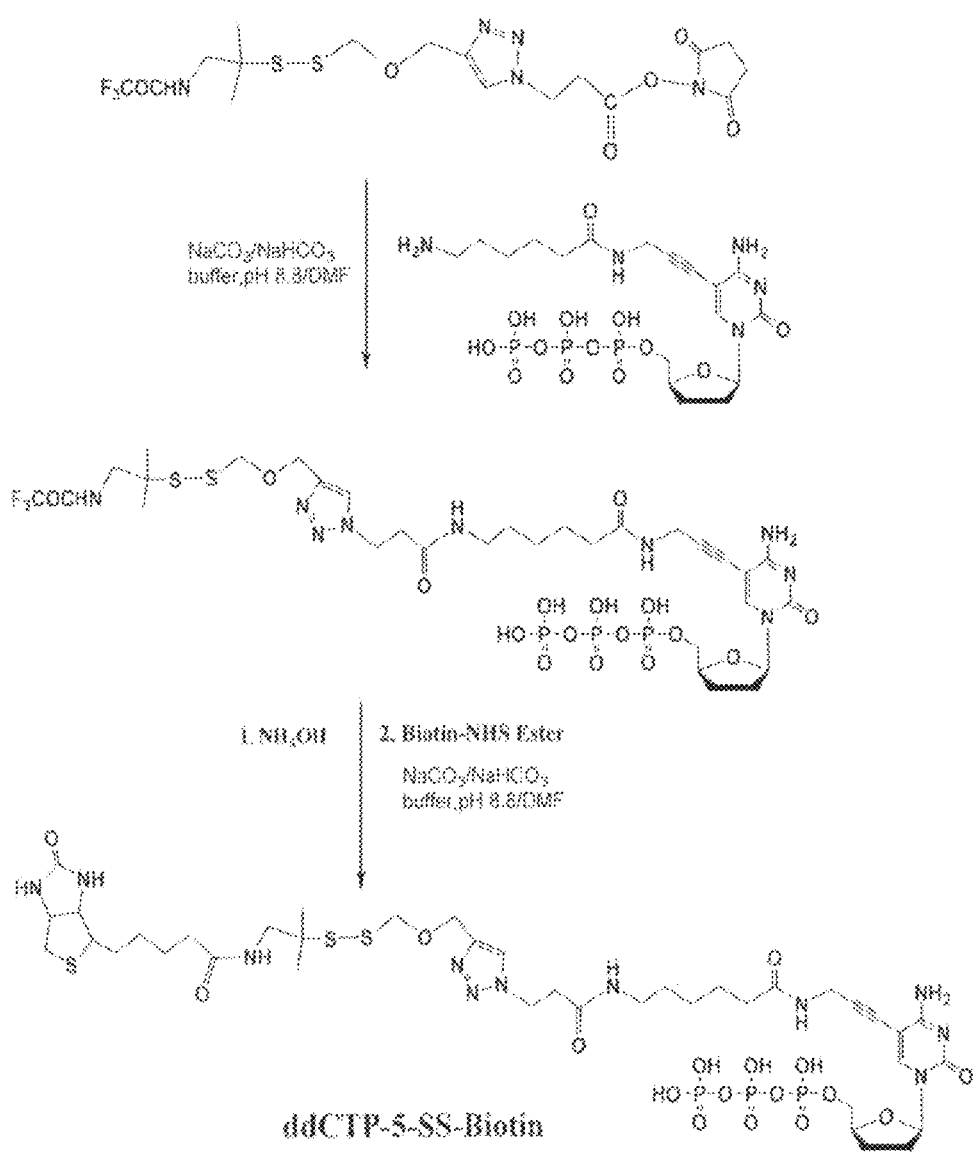

FIG. 156: Synthesis of ddCTP-5-SS-Biotin.

Figure 157:
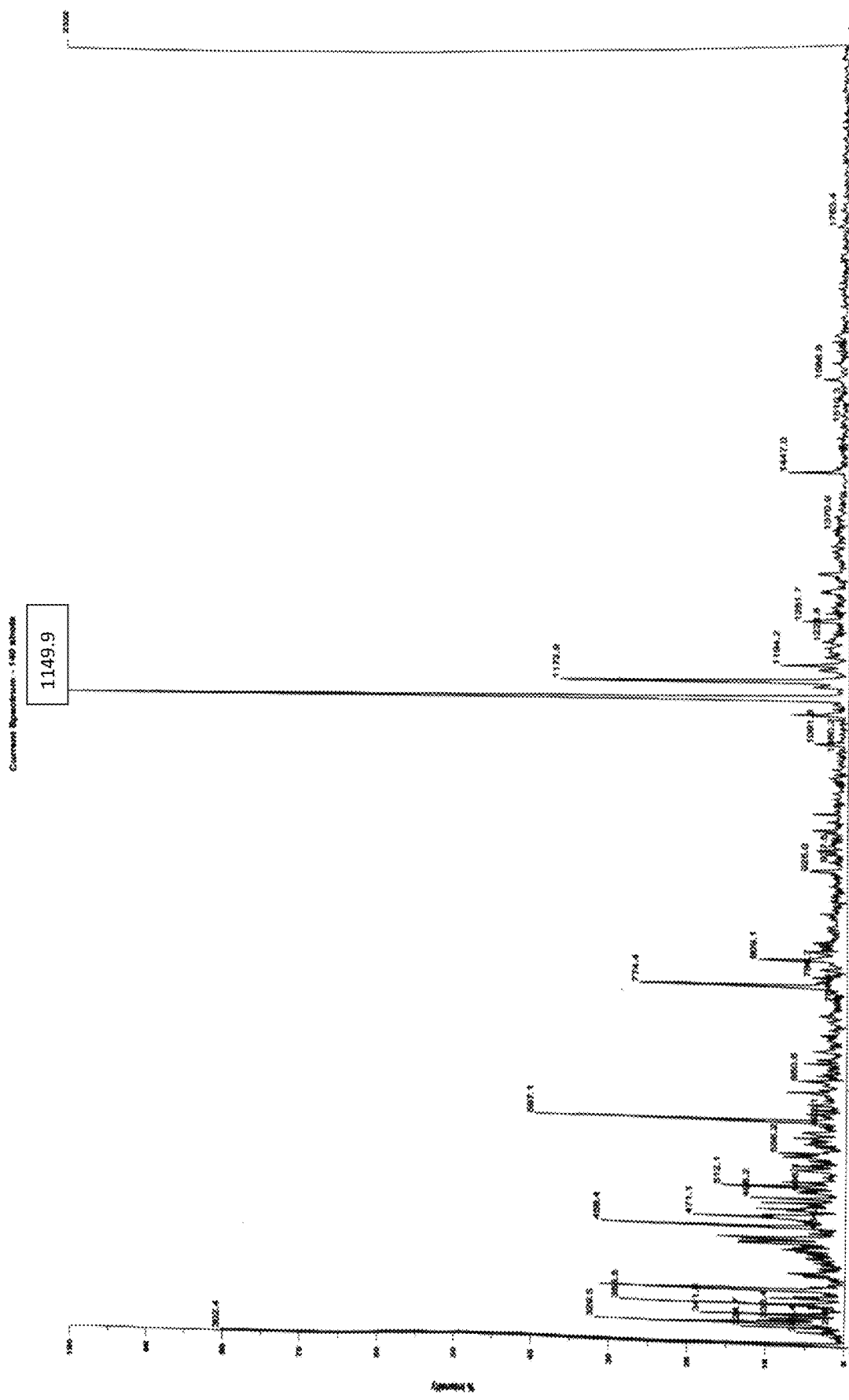

FIG. 157: MALDI-TOF MS traces confirming correct synthesis of ddCTP-5-SS-Biotin.

Figure 158:
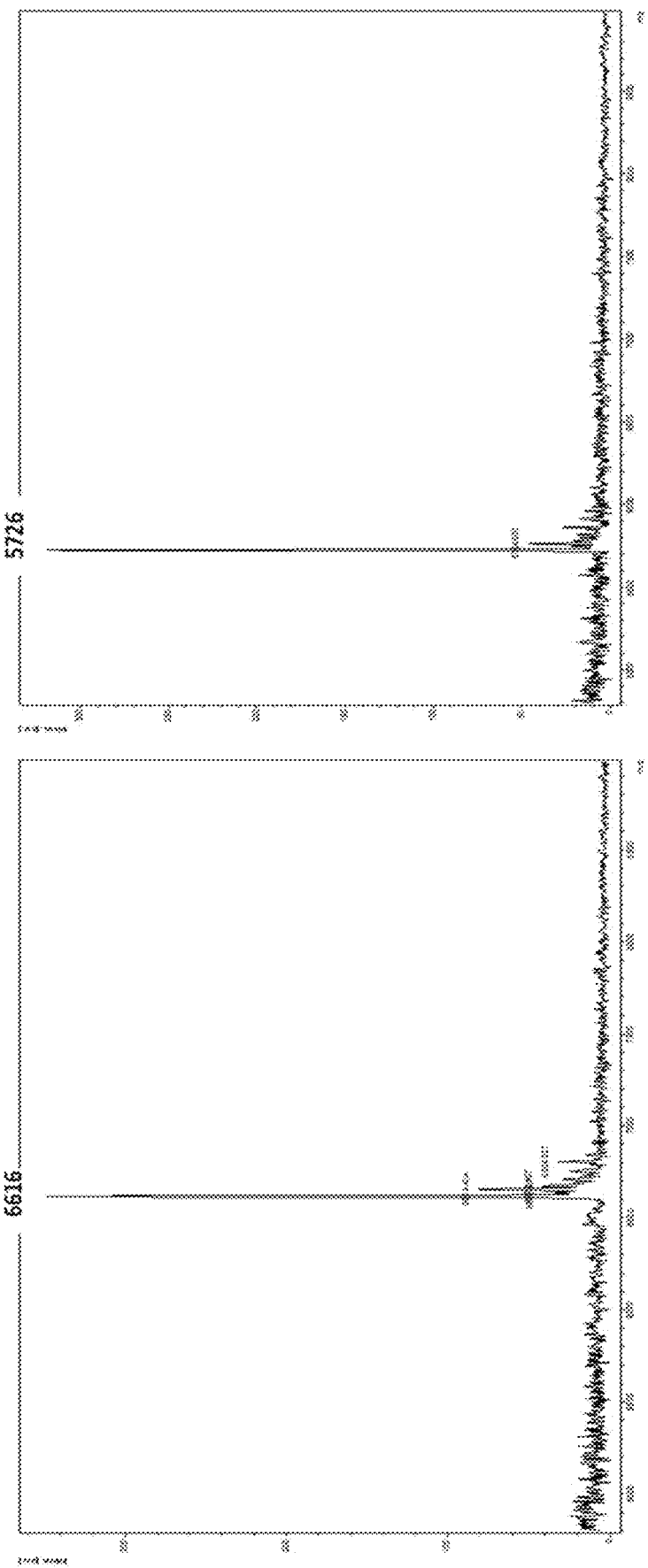

FIG. 158: MALDI-TOF Mass Spectrometry results showing efficient incorporation and cleavage of ddTTP-5-Azo-Cy5.

Figure 159:
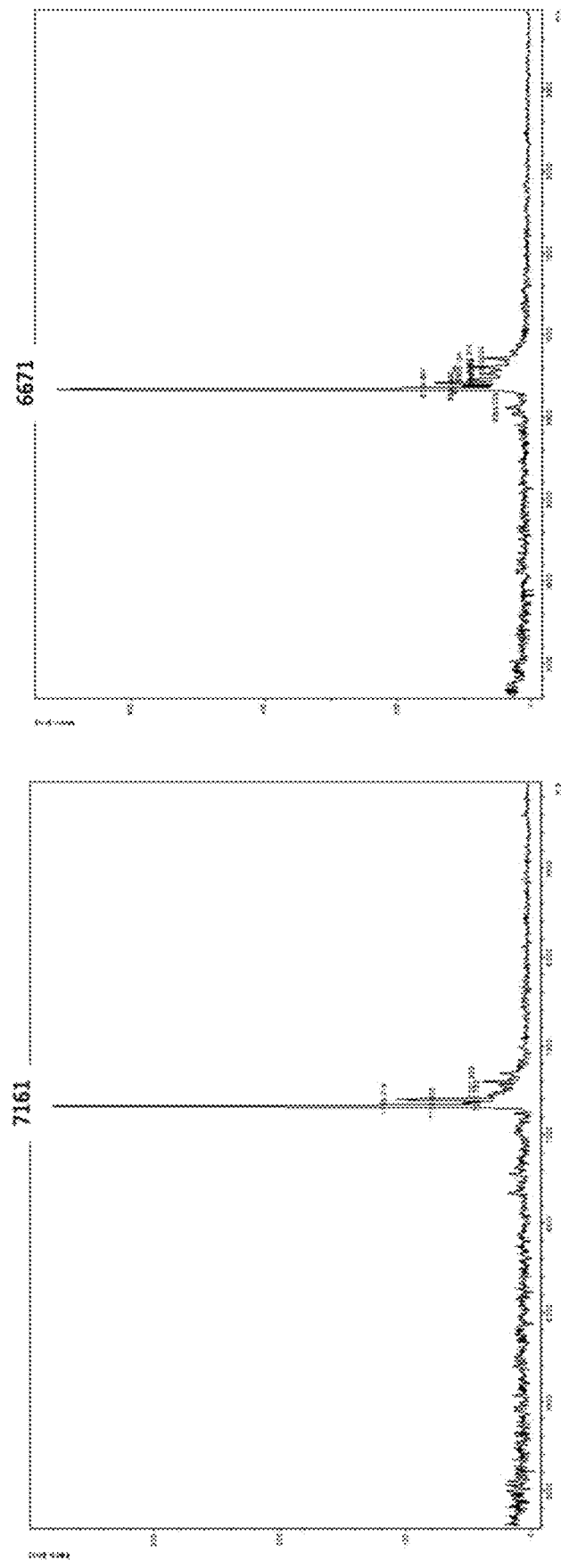

FIG. 159: MALDI-TOF Mass Spectrometry results showing efficient incorporation and cleavage of ddATP-7-Azo-Biotin.

Figure 160:
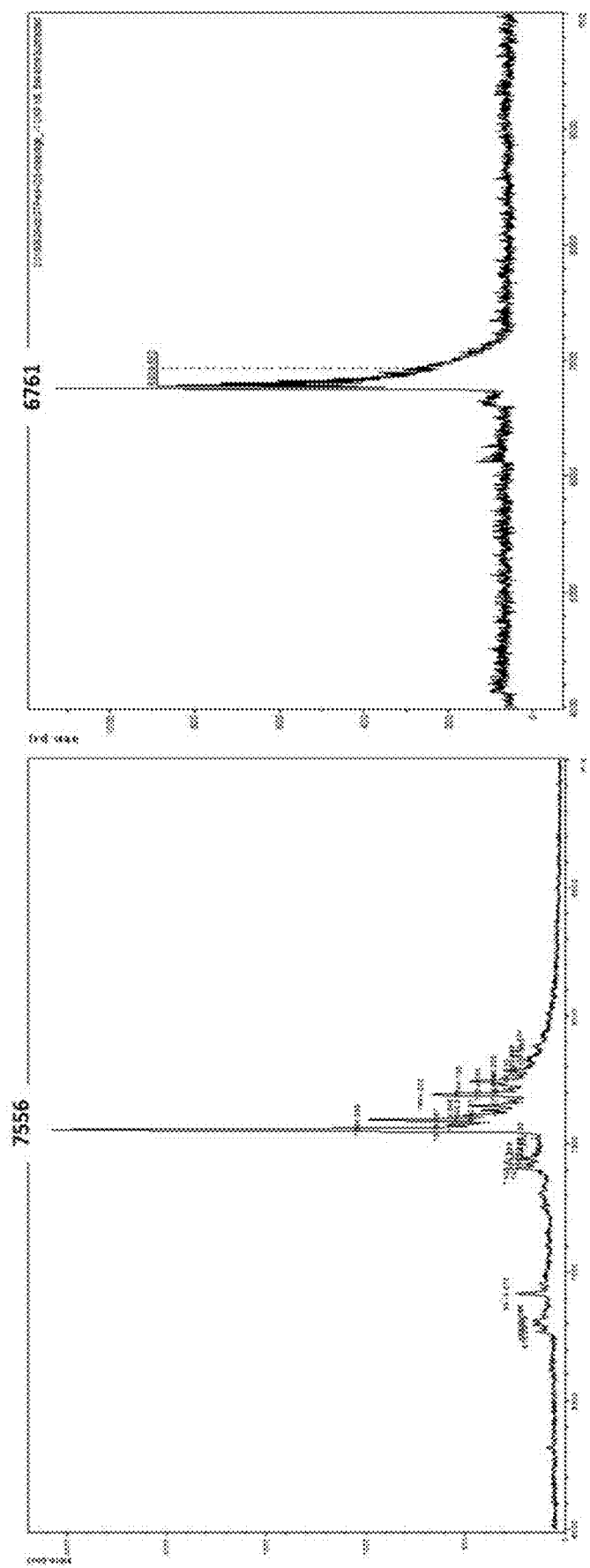

FIG. 160: MALDI-TOF Mass Spectrometry results showing efficient incorporation and cleavage of ddGTP-7-SS-Cy5.

FIG. 161: MALDI-TOF Mass Spectrometry results showing efficient incorporation and cleavage of ddCTP-5-SS-Biotin.

Figure 162A:
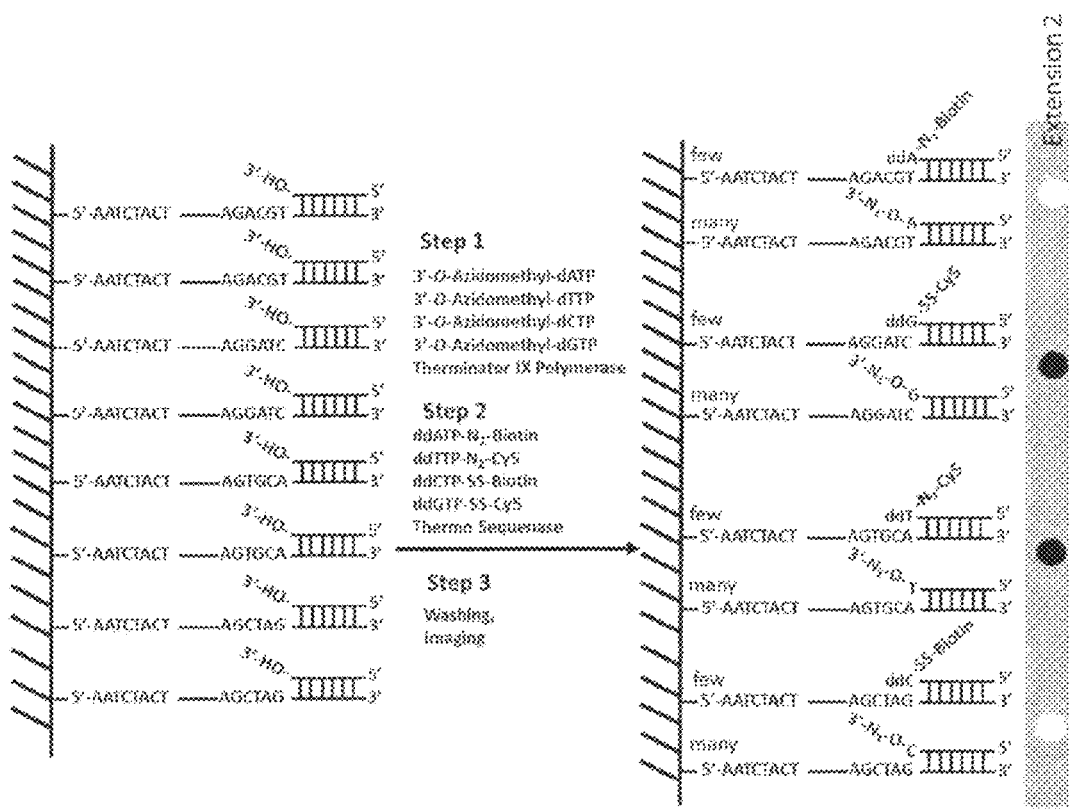
Figure 162B:
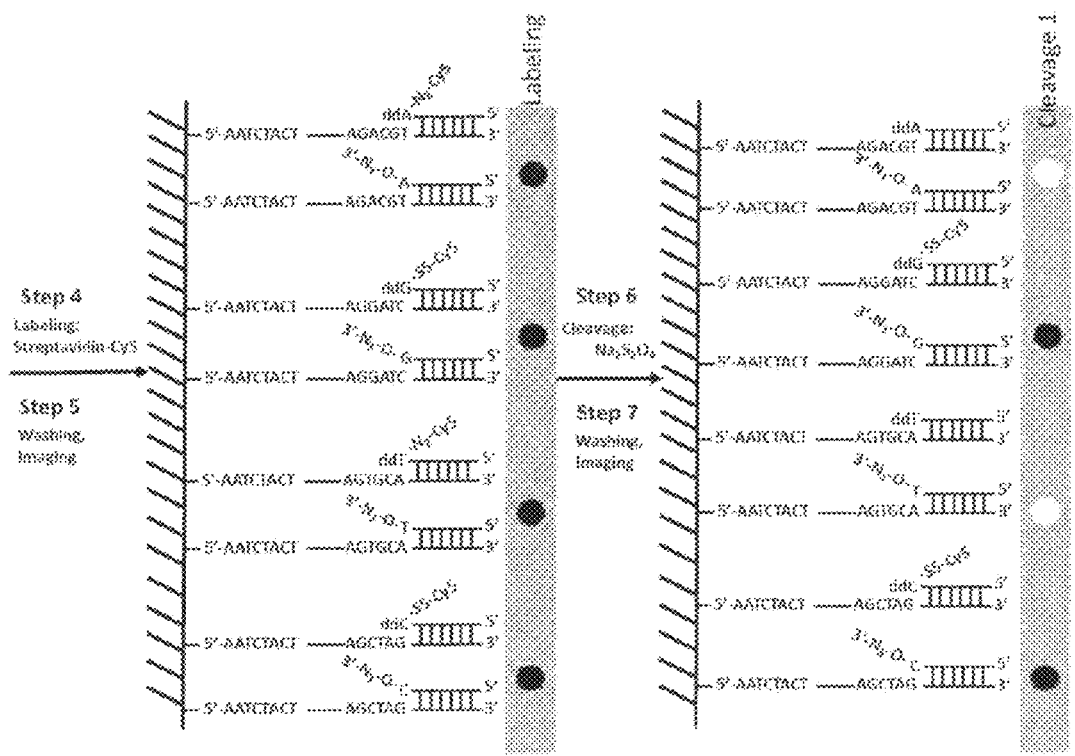
Figure 162C:
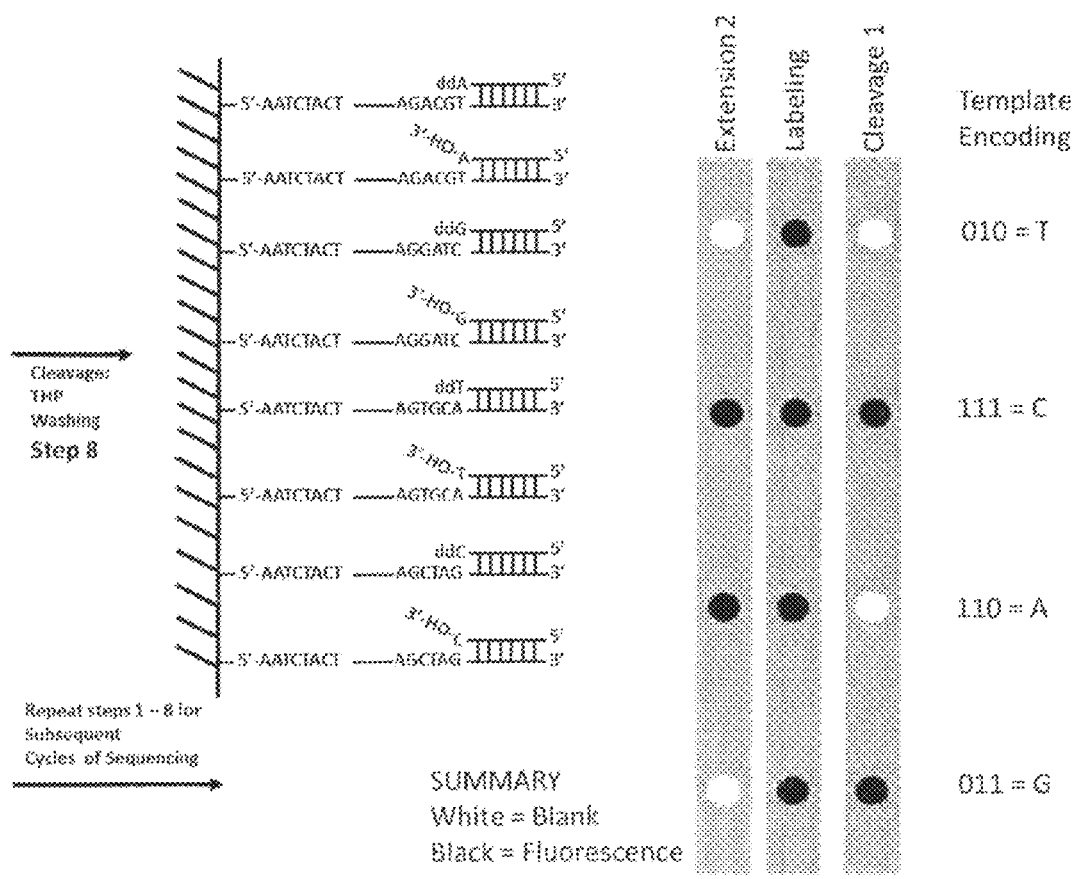

FIGS. 162A-162C: Schematic illustrating Single-color Sequencing by Synthesis Using Orthogonal Set of ddNTP Analogues, with All Combinations of Azo and SS Linkers and Biotin and Cy5.

FIGS. 163A-163F: Results for First Five Cycles of Single-color Sequencing by Synthesis with Slide-Immobilized Templates.

DETAILED DESCRIPTION

This invention provides a method of sequencing nucleic acid comprising:
 a) providing at least one nucleic acid template hybridized to a primer;
 b) extending the primer hybridized to said nucleic acid template with polymerase, and either:
  i) fluorescent labeled nucleotide analogues, wherein said fluorescently labeled nucleotide analogues have the label linked to the base via a cleavable linker and a blocking group on the 3'-hydroxyl group, wherein different nucleotides may have different anchors and different cleavable groups;
  ii) anchor labeled nucleotide analogues, wherein said anchor labeled nucleotide analogues have the anchor attached to the base via a cleavable linker and a blocking group on the 3'-hydroxyl group, wherein different nucleotides may have different anchors and different cleavable groups; or
  iii) a combination of both fluorescently and anchor labeled nucleotide analogues, wherein said fluorescently or anchor labeled nucleotide analogues have the label linked to the base via a cleavable linker and a blocking group on the 3'-hydroxyl group, wherein different nucleotides may have different cleavable groups;

c) optionally extending any unextended primer with 3' blocked nucleotides without any base modifications, and identifying the fluorescence signal due to incorporation of fluorescently nucleotide analogues;

d) optionally labeling anchor attached primer extension products with fluorescently labeled anchor binding molecules;

e) identifying newly generated fluorescence signals to partially or completely identify the incorporated nucleotides due to the labeling carried out in step d;

f) optionally repeating steps d and e;

g) optionally cleaving the label from fluorescently labeled nucleotides with a specific cleavable agent that cleaves one of the linkers but does not cleave the orthogonal linker;

h) identifying loss of fluorescence due to the cleavage carried out in step f to partially or completely identify the incorporated nucleotide;

i) optionally repeating steps g and h;

j) determining the specific nucleotide analogue incorporated by comparing the results obtained in steps c, e and h;

k) cleaving any remaining labels or anchors from the extended primers, at the same time restoring the 3'-hydroxyl groups; and l) iteratively carrying out steps a to k to obtain the sequence of the nucleic acid template, thereby sequencing the nucleic acid.

In further embodiments, the method comprises 1 label, 2 different labels, 3 different labels or 4 different labels. The invention also provides the instant method, wherein the labels are directly attached to the base via the cleavable linker. The invention also provides the instant method, wherein labels comprise dye clusters. The invention also provides the instant method, wherein labels comprise energy transfer donor dyes and acceptor dyes. The invention also provides the instant method comprising 1 anchor type, 2 different anchor types, 3 different anchor types or 4 different anchor types and an equal number of labeled anchor binding molecules. The invention also provides the instant method, wherein the anchors comprise biotin, TCO, DBCO and tetrazine and the labeled anchor binding molecules comprise streptavidin, tetrazine, azido and TCO respectively. The invention also provides the instant method, wherein the anchor binding molecules are labeled with fluorescent organic dyes or quantum dots. The invention also provides the instant method, wherein the fluorescent organic dye label is selected from a group of dyes comprising fluoresceins, rhodamines, cyanines, ATTO or Dyomics dyes. The invention also provides the instant method, wherein the anchors comprise anchor clusters.

The invention also provides the instant method, wherein:

a) the anchors or anchor clusters comprise a donor dye or an acceptor dye, b) the anchor binding molecule or anchor binding molecules comprise a donor dye or acceptor dye corresponding to the donor/acceptor dye on the anchor or anchor clusters, and c) attachment of the anchor or anchor cluster to the anchor binding molecule or anchor binding molecules results in energy transfer from donor dye to acceptor dye, wherein the donor may be a quantum dot.

The invention also provides the instant method comprising 1 cleavable linker type, 2 cleavable linker types, 3 cleavable linker types or 4 cleavable linker types.

The invention also provides the instant method, wherein the cleavable linker or cleavable linkers comprise an SS(DTM), an azo, an SS-azo, an allyl, a 2-nitrobenzyl, an azidomethyl, or azidomethyl derivative, and the cleaving agents comprise THP, sodium dithionite, Pd(0) and UV light (~340 nm) respectively.

The invention also provides the instant method, wherein there are four different labelled nucleotide analogues, each having a different label, and the identity of incorporated nucleotide is determined in step c. The invention also provides the instant method, wherein there are two different labelled nucleotide analogues, and wherein the incorporated nucleotide is determined from the results in steps c and e combined. The invention also provides the instant method, wherein there are two different labelled nucleotide analogues, and wherein the incorporated nucleotide is determined from the results in steps c and g combined. The invention also provides the instant method, wherein there is one dye labelled nucleotide analogue, and wherein the incorporated nucleotide is determined from the results in steps c, e and g combined.

The invention also provides a method of sequencing nucleic acid comprising:

a) providing at least one nucleic acid template hybridized to a primer;

b) extending the primer hybridized to said nucleic acid template with polymerase and a set of nucleotide analogues (A, C, G and T) carrying orthogonal sets of labels and anchors, the first nucleotide analogue with a fluorescent label directly attached to the base, the second with a different fluorescent label directly attached to the base, the third with an anchor moiety attached to the base, and the fourth with a different anchor moiety attached to the base, wherein said fluorescent or anchor labeled nucleotide analogues have the label linked to the base via the same type of cleavable linker and a blocking group with the same cleavable moiety on the 3'-hydroxyl position;

c) optionally extending any unextended primer with 3' blocked nucleotides without any base modifications, and identifying the fluorescence signal due to incorporation of fluorescently nucleotide analogues;

d) labeling primer extension products containing anchor moieties with fluorescently labeled anchor binding molecules, wherein the anchor binding molecules for attachment to the two different anchors contain the same two fluorescent labels as the nucleotide analogues in step b;

e) identifying newly generated fluorescence signals due to the labeling carried out in step d to determine the remaining two incorporated nucleotide analogues;

f) cleaving any remaining dyes and anchors from the primer extension products, and restoring the 3'-hydroxyl groups; and iteratively carrying out steps a to f to obtain the sequence of the nucleic acid template.

The invention also provides the instant method, wherein labels comprise dye clusters. The invention also provides the instant method, wherein labels comprise energy transfer donor dyes and acceptor dyes. The invention also provides the instant method, wherein the anchors comprise biotin, TCO, DBCO and tetrazine and the fluorescent labeled anchor binding molecules comprise streptavidin, tetrazine, azido and TCO respectively. The invention also provides the instant method, wherein the cleavable linkers comprise an SS(DTM), an azo, an SS-azo, an allyl, a 2-nitrobenzyl, an azidomethyl, or azidomethyl derivative, and the cleaving agents comprise THP, sodium dithionite, Pd(0) and UV light (~340 nm) respectively.

The invention also provides the instant method, wherein the anchor binding molecules are labeled with fluorescent organic dyes or quantum dots. The invention also provides the instant method, wherein the anchors comprise anchor clusters.

The invention also provides the instant method, wherein:
a) the anchors or anchor clusters comprise a donor dye or an acceptor dye,
b) the anchor binding molecule or anchor binding molecules comprise a donor dye or acceptor dye corresponding to the donor/acceptor dye on the anchor or anchor clusters, and
c) attachment of the anchor or anchor cluster to the anchor binding molecule or anchor binding molecules results in energy transfer from donor dye to acceptor dye, wherein the donor may be a quantum dot.

invention also provides A method of sequencing nucleic acid comprising:
a) providing a nucleic acid template hybridized to a primer;
b) extending the primer hybridized to said nucleic acid template with polymerase and an orthogonal set of fluorescently labeled nucleotide analogues (A, C, G and T), the first with a fluorescent dye directly attached to the base via a cleavable linker, the second with the same fluorescent dye directly attached to the base via a different type of cleavable linker, the third with a second dye directly attached to the base via the first type of cleavable linker, and the fourth with the second dye directly attached to the base via the second type of cleavable linker, wherein the cleavable moiety in the second cleavable linker can be cleaved under the same conditions as the cleavable blocking moiety at the 3'-hydroxyl position;
c) optionally extending any unextended primer with 3' blocked nucleotides without any base modifications, and identifying the fluorescence signal due to incorporation of fluorescently labeled nucleotide analogues to partially determine incorporation of two of the four nucleotides;
d) cleaving the dyes from fluorescently labeled nucleotides incorporated into the primer with a specific agent that cleaves the first type of linker;
e) identifying loss of fluorescence due to the cleavage carried out in step d;
f) determining the specific nucleotide analogue incorporated by comparing the results obtained in steps c and e;
g) cleaving any remaining dyes from the extended primers, at the same time restoring the 3'-hydroxyl groups; and
iteratively carrying out steps a to g to obtain the sequence of the nucleic acid template.

invention also provides the instant method, wherein the fluorescent label is selected from a group of dyes comprising fluoresceins, rhodamines, cyanines, ATTO or Dyomics dyes. The invention also provides the instant method, wherein the label comprises dye clusters. The invention also provides the instant method, wherein the label comprises energy transfer donor dyes and/or acceptor dyes.

The invention also provides the instant method, wherein the cleavable linkers comprise an SS(DTM), an azo, an SS-azo, an allyl, a 2-nitrobenzyl, an azidomethyl, or azidomethyl derivative, and the cleaving agents comprise THP, sodium dithionite, Pd(0) and UV light (~340 nm) respectively.

The invention also provides a method of sequencing nucleic acid comprising:
a) providing at least one nucleic acid template hybridized to a primer;
b) extending the primer hybridized to said nucleic acid template with polymerase and an orthogonal set of anchor labeled nucleotide analogues (A, C, G and T), the first with an anchor moiety directly attached to the base via a first type of cleavable linker, the second with the same anchor moiety directly attached to the base via a second type of cleavable linker, the third with a second anchor moiety directly attached to the base via the first type cleavable linker, and the fourth with the second anchor moiety directly attached to the base via the second type of cleavable linker, wherein the cleavable moiety in the second type of cleavable linker can be cleaved under the same conditions as the cleavable blocking moiety at the 3'-hydroxyl position;
c) optionally extending any unextended primer with 3' blocked nucleotides without any base modifications;
d) labeling primers extended with nucleotide analogues having the first anchor using a fluorescently labeled anchor binding molecule specific for the first anchor;
e) identifying fluorescence signal due to the labeling carried out in step d to partially determine 2 of the 4 incorporated nucleotide analogues;
f) labeling primers extended with nucleotide analogues having the second anchor using a fluorescently labeled anchor binding molecule specific for the second anchor, wherein the fluorescent label is the same label attached to the anchor binding molecule specific for the first anchor;
g) identifying newly generated fluorescence signal due to the labeling carried out in step f to partially determine the other 2 of the 4 incorporated nucleotide analogues;
h) cleaving the dyes and anchors from fluorescently labeled nucleotides with a specific cleavable agent that cleaves the first type of linker;
i) identifying loss of fluorescence due to the cleavage carried out in step h; thereby
j) determining the specific nucleotide analogue incorporated into the primer by comparing the results obtained in steps e, g and i;
k) cleaving any remaining dyes or anchors from the extended primers, at the same time restoring the 3'-hydroxyl groups; and
iteratively carrying out steps a to i to obtain the sequence of the nucleic acid template.

The invention also provides the instant method, wherein dyes comprise dye clusters. The invention also provides the instant method, wherein dyes comprise energy transfer donor dyes and acceptor dyes. The invention also provides the instant method, wherein the anchors comprise biotin, TCO, DBCO and tetrazine and the fluorescent labeled anchor binding molecules comprise streptavidin, tetrazine, azido and TCO respectively. The invention also provides the instant method, wherein the anchor binding molecules are labeled with organic dyes or quantum dots. The invention also provides the instant method, wherein the anchors comprise anchor clusters.

The invention also provides the instant method, wherein:
a) the anchors or anchor clusters comprise a donor dye or an acceptor dye, b) the anchor binding molecule or anchor binding molecules comprise a donor dye or acceptor dye corresponding to the donor/acceptor dye on the anchor or anchor clusters, and
c) attachment of the anchor or anchor cluster to the anchor binding molecule or anchor binding molecules results in energy transfer from donor dye to acceptor dye, wherein the donor may be a quantum dot.

The invention also provides the instant method, wherein the cleavable linkers comprise an SS(DTM), an azo, an SS-azo, an allyl, a 2-nitrobenzyl, an azidomethyl, or azidomethyl derivative, and the cleaving agents comprise THP, sodium dithionite, Pd(0) and UV light (~340 nm) respectively.

The invention also provides a method of sequencing nucleic acid comprising:
a) providing at least one nucleic acid template hybridized to a primer;
b) extending the primer hybridized to said nucleic acid template with polymerase and an orthogonal set of anchor labeled nucleotide analogues (A, C, G and T), the first with a dye directly attached to the base via a first type of cleavable linker, the second with the same dye directly attached to the base via a second type of cleavable linker, the third with an anchor moiety directly attached to the base via the first type of cleavable linker, and the fourth with the same anchor moiety directly attached to the base via the second type of cleavable linker, wherein the cleavable moiety in the second type of cleavable linker can be cleaved under the same conditions as the cleavable blocking moiety at the 3'-hydroxyl position;
c) optionally extending any unextended primer with 3' blocked nucleotides without any base modifications, and identifying fluorescence signals to partially determine two of the four nucleotide analogues;
d) labeling primers extended with nucleotide analogues having the anchor using a fluorescently labeled anchor binding molecule specific for that anchor;
e) identifying newly generated fluorescence due to the labeling carried out in step d to partially determine the other two of the four incorporated nucleotides;
f) cleaving the dyes and anchors from fluorescently labeled nucleotides with a specific cleavable agent that cleaves the first type of linker;
g) identifying loss of fluorescence due to the cleavage carried out in step f; thereby
h) determining the specific nucleotide analogue incorporated into the primer by comparing the results obtained in steps c, e and g;
i) cleaving any remaining dyes or anchors from the extended primers, at the same time restoring the 3'-hydroxyl groups; and
iteratively carrying out steps a to i to obtain the sequence of the nucleic acid template.

The invention also provides the instant method, wherein dyes comprise dye clusters. The invention also provides the instant method, wherein dyes comprise energy transfer donor dyes and acceptor dyes.

The invention also provides the instant method, wherein the anchors comprise biotin, TCO, DBCO and tetrazine and the fluorescent labeled anchor binding molecules comprise streptavidin, tetrazine, azido and TCO respectively. The invention also provides the instant method, wherein the anchor binding molecules are labeled with fluorescent organic dyes or quantum dots. The invention also provides the instant method, wherein the anchors comprise anchor clusters.

The invention also provides the instant method, wherein:
a) the anchors or anchor clusters comprise a donor dye or an acceptor dye,
b) the anchor binding molecule or anchor binding molecules comprise a donor dye or acceptor dye corresponding to the donor/acceptor dye on the anchor or anchor clusters, and
c) attachment of the anchor or anchor cluster to the anchor binding molecule or anchor binding molecules results in energy transfer from donor dye to acceptor dye, wherein the donor may be a quantum dot.

invention also provides the instant method, wherein the cleavable linkers comprise an SS(DTM), an azo, an SS-azo, an allyl, a 2-nitrobenzyl, an azidomethyl, or azidomethyl derivative, and the cleaving agents comprise THP, sodium dithionite, Pd(0) and UV light (~340 nm) respectively.

The invention also provides a dideoxynucleotide triphosphate (ddNTP) analogue having the structure:

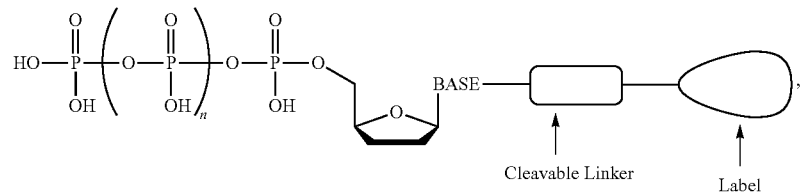

$n = 1$-$6$ wherein:
i) BASE comprises adenine, guanine, cytosine, thymine, uracil, hypoxanthine or analog thereof;
ii) cleavable linker an SS(DTM), an azo, an SS-azo, an allyl, a 2-nitrobenzyl, an azidomethyl, or azidomethyl derivative, and is attached to the base via 5 position of pyrimidines (C, U) or 7 position of purines (A, G);
iii) the cleavable linker between BASE and Label comprises polymeric molecule of varying length
iv) Label comprises a fluorescent dye, a cluster of fluorescent dyes, an anchor for dye attachment, and/or an anchor cluster for dye attachment The invention also provides the instant dideoxynucleotide triphosphate (ddNTP) analogue, wherein Label is an energy transfer dye or a cluster of energy transfer dyes having a corresponding donor or acceptor dye, wherein donor dye may be a quantum dot. The invention also provides the instant dideoxynucleotide triphosphate (ddNTP) analogue, wherein Label is an anchor, and the anchor comprises Biotin, DBCO, TCO, or Tetrazine, and wherein a corresponding anchor binding molecule comprises Streptavidin, Azide, TCO, or Tetrazine and further comprises a single dye or a cluster of a single dye, and wherein dye on the anchor binding molecule comprises an organic dye or a quantum dot.

The invention also provides a method for determining the identity of each of a series of consecutive nucleotide residues in a nucleic acid comprising:

a) contacting a plurality of the nucleic acid templates with (i) a dideoxynucleotide triphosphate (ddNTP) analogue described above, (ii) a deoxynucleotide triphosphate (dNTP) analogue having the structure:

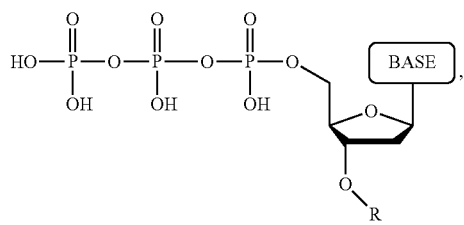

wherein BASE comprises adenine, guanine, cytosine, uracil, thymine, hypoxanthine or analogue thereof and wherein R is a cleavable chemical group, (iii) a nucleic acid polymerase and (iv) at least two identical primers each of which hybridizes with a separate nucleic acid of the plurality of nucleic acids, under conditions permitting a ddNTP analogue that is complementary to the consecutive nucleotide residue to be identified to form a phosphodiester bond with the 3' end of one of the primers and a dNTP analogue that is complementary to the consecutive nucleotide residue to be identified to form a phosphodiester bond with the 3' end of another of the primers;

b) identifying the fluorophore of the ddNTP analogue which has formed the phosphodiester bond thereby identifying the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

The invention also provides a nucleotide analogue having the structure:

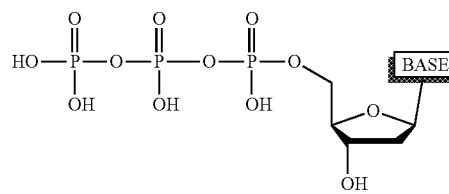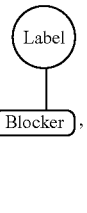

wherein, BASE comprises adenine, guanine, cytosine, thymine, uracil, hypoxanthine or analog thereof; Cleavable Linker comprises an SS(DTM), an azo, an SS-azo, an allyl, a 2-nitrobenzyl, an azidomethyl, or azidomethyl derivative; the attachment between BASE and Label comprises a polymeric molecule; Blocker is a nucleotide or oligonucleotide comprising 2-50 monomer units of abasic sugars or modified nucleosides or a combination thereof; and blocker is connected to the 5-position of pyrimidines (C, U) and 7-position of deazapurines (A, G, I) via a cleavable linker, wherein a Blocker is a molecule that after incorporation of the nucleotide analogue by a nucleotide polymerase, prevents further incorporation of additional nucleotides or nucleotide analogues into a primer strand;

Label comprises a fluorescent dye, a cluster of a fluorescent dye, an anchor for attachment of a fluorescent dye via an anchor binding molecule, or a cluster of an anchor for attachment of fluorescent dyes via anchor binding molecules, wherein Label is attached to the blocker.

The invention also provides the instant nucleotide analogue, wherein Label is selected from fluoresceins, rhodamines, cyanines, ATTO or Dyomics dyes. The invention also provides the instant nucleotide analogue, wherein Label comprises Cy3, Cy5, and ATTO 647N. The invention also provides the instant nucleotide analogue wherein Label is an energy transfer dye or a cluster of energy transfer dyes with a donor and acceptor dye, wherein the donor dye may be a quantum dot. The invention also provides the instant nucleotide analogue, wherein Label is an energy transfer dye, and the donor dye is Fluorescein, CyA, Cy3 and the acceptor dye is Rhodamine 110, R6G, TAMRA, ROX, Cy5, ATTO 647N, Alexa 647.

The invention also provides the instant nucleotide analogue, wherein Label is an anchor, and the anchor comprises Biotin, DBCO, TCO, or Tetrazine, and wherein the anchor binding molecule comprises Streptavidin, Azide, Tetrazine, or TCO and further comprises a single dye, a cluster of a single dyes, or energy transfer dyes. The invention also provides the instant nucleotide analogue, wherein the anchor binding molecule is labeled with an organic dye or a quantum dot.

The invention also provides the instant nucleotide analogue, wherein Cleavable Linker is DTM based. The invention also provides the instant nucleotide analogue, wherein Cleavable Linker is azo based.

The invention also provides a composition comprising four different types of the instant nucleotide analogue, wherein a different dye is attached to each of the four different nucleotide analogues. The invention also provides a composition comprising four different types of the instant nucleotide analogue, wherein two of the nucleotide analogues comprise a first dye and the remaining two nucleotide analogues comprise a second dye. The invention also provides a composition comprising four different types of the instant nucleotide analogue, wherein one type of dye is attached to each of the four nucleotides via the same cleavable linker. The invention also provides a composition comprising four different types of the instant nucleotide analogue, wherein one type of dye is attached to each of the four nucleotides via a different cleavable linker.

The invention also provides a method of stepwise sequencing of a nucleic acid comprising:
a) providing at least one nucleic acid template hybridized to a primer;
b) extending the primer hybridized to said nucleic acid template with polymerase and a fluorescently labeled nucleotide analogue disclosed above;
c) identifying primers extended with a fluorescently labeled nucleotide analogue to determine incorporation of the added nucleotide;
d) cleaving the dyes from the extended primers;
e) extending the primer hybridized to said nucleic acid template with polymerase and a fluorescently labeled nucleotide analogue disclosed above having a different base than the nucleotide analogue of step b);
f) identifying primers extended with a fluorescently labeled nucleotide analogue to determine incorporation the added nucleotide;
g) cleaving the dyes from the extended primers;
h) extending the primer hybridized to said nucleic acid template with polymerase and a fluorescently labeled nucleotide analogue disclosed above having a different base than the nucleotide analogue of steps b) and e);
i) identifying primers extended with the fluorescently labeled nucleotide analogue to determine incorporation the added nucleotide;
j) cleaving the dyes from the extended primers;
k) extending the primer hybridized to said nucleic acid template with polymerase and a fluorescently labeled nucleotide analogue disclosed above having a different base than the nucleotide analogue of steps b), e), and h);
l) identifying primers extended with a fluorescently labeled nucleotide analogue to determine incorporation the added nucleotide;
m) cleaving the dyes from the extended primers; and
iteratively carrying out steps a) to m) to obtain the sequence of the nucleic acid template.

The invention also provides a nucleotide analogue having the structure:

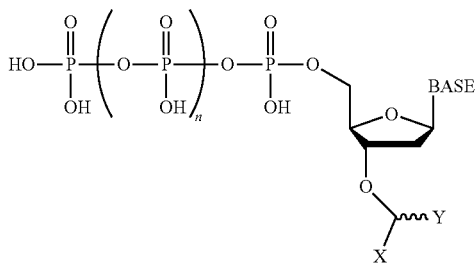

$n = 1\text{-}6$

X=Cleavable Trigger Moiety Y=Label, wherein, BASE comprises adenine, guanine, cytosine, thymine, uracil, hypoxanthine or analog thereof; X is a cleavable trigger moiety comprising SS(DTM), azo, alkenyl, 2-Nitrobenzyl, or azido; the wavy line to the Label (Y) comprises a polymeric molecule of various lengths; and Y is a Label comprising a fluorescent dye, a cluster of a fluorescent dye, an anchor moiety for binding of a fluorescent dye, or a cluster of an anchor moiety for binding of a fluorescent dye.

The invention also provides a method of sequencing a nucleic acid comprising:
a) providing at least one nucleic acid template hybridized to a primer;
b) extending the primer hybridized to said nucleic acid template with polymerase and a set of four different nucleotide analogues disclosed above each having the same dye attached to the 3' hydroxyl via a different type of trigger moiety;
c) optionally extending any unextended primer with 3' blocked nucleotides without any base modifications, and identifying primers extended with fluorescently labeled nucleotide analogues;
d) cleaving the fluorescently labeled nucleotide analogue with a specific agent that cleaves the first type of trigger, but does not restore the 3'-hydroxyl group;
e) identifying loss of fluorescence due to the cleavage carried out in step d;
f) determining the first type of specific nucleotide analogue incorporated;
g) cleaving the fluorescently labeled nucleotide analogue with a specific agent that cleaves the second type of trigger moiety, but does not restore the 3'-hydroxyl group;
h) identifying loss of fluorescence due to the cleavage carried out in step g;
i) determining the second type of specific nucleotide analogue incorporated;
j) cleaving the fluorescently labeled nucleotide analogue with a specific agent that cleaves the third type of trigger moiety, but does not restore the 3'-hydroxyl group;
k) identifying loss of fluorescence due to the cleavage carried out in step j;
l) thereby determining the third and by subtraction the fourth type of specific nucleotide analogue incorporated;
m) cleaving any remaining dyes or anchors from the extended primers, at the same time restoring the 3'-hydroxyl groups; and
iteratively carrying out steps a to m to obtain the sequence of the nucleic acid template.

The invention also provides a nucleotide analogue having the structure:

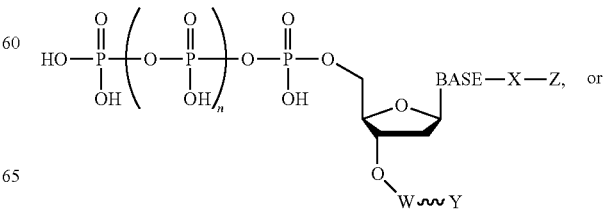

-continued

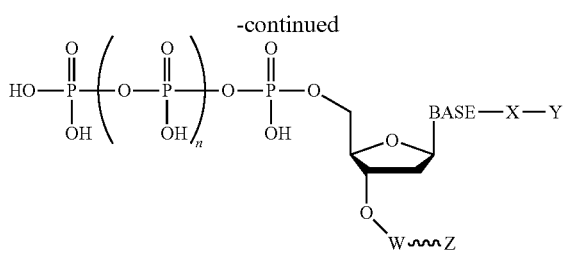

wherein, BASE comprises adenine, guanine, cytosine, thymine, uracil, hypoxanthine or analog thereof; X is a cleavable group comprising SS(DTM), an azo, an SS-azo, an allyl, a 2-nitrobenzyl, an azidomethyl, or azidomethyl derivative; W is a cleavable group comprising SS(DTM), an azo, an SS-azo, an allyl, a 2-nitrobenzyl, an azidomethyl, or azidomethyl derivative;
wherein X and W comprise the same or a different cleavable group;
Y is a label comprising a fluorescent dye, a cluster of a fluorescent dye, an anchor moiety for binding of a fluorescent dye, or a cluster of an anchor moiety for binding of a fluorescent dye; and
Z is an FRET donor or acceptor dye.

The invention also provides a method in which sequencing is performed according to the methods of Schemes XXIV-XXVIII with four types of the instant nucleotide analogues, wherein Z is a FRET donor or acceptor dye, Y is an anchor, and the anchor Y binding molecule is a FRET acceptor or donor dye compatible with Z.

The invention also provides the instant method, wherein the dye on the anchor binding molecule comprises a donor dye, and wherein the donor dye is a quantum dot.

The invention also provides a nucleotide analogue having the structure:

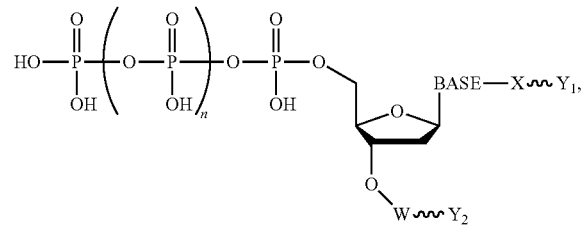

wherein, BASE comprises adenine, guanine, cytosine, thymine, uracil, hypoxanthine or analog thereof; X is a cleavable group comprising SS(DTM), an azo, an SS-azo, an allyl, a 2-nitrobenzyl, an azidomethyl, or azidomethyl derivative; W is a cleavable group comprising SS(DTM), an azo, an SS-azo, an allyl, a 2-nitrobenzyl, an azidomethyl, or azidomethyl derivative;
wherein X and W comprise the same or a different cleavable group; and
Y is a Label comprising a fluorescent dye, a cluster of a fluorescent dye, an anchor moiety for binding of a fluorescent dye, or a cluster of an anchor moiety for binding of a fluorescent dye.

The invention also provides a method in which sequencing is performed according to according to the methods of Schemes XXIV-XXVIII with four types of the instant nucleotide analogue, wherein $Y_1$ is an anchor or a cluster of anchors for attachment of one type of quantum dot via a specific anchor binding molecule and $Y_2$ is an anchor or a cluster of anchors for attachment of a second type of quantum dot via a second specific anchor binding molecule.

A nucleotide triphosphate analogue substantially as hereinabove described with reference to any one of the examples.

A composition comprising more than one nucleotide triphosphate analogue substantially as hereinabove described with reference to any one of the examples.

A dideoxynucleotide triphosphate analogue substantially as hereinabove described with reference to any one of the examples.

A composition comprising more than one dideoxynucleotide triphosphate substantially as hereinabove described with reference to any one of the examples.

A method of sequencing a nucleic acid substantially as hereinabove described with reference to any one of the examples.

A method of making a nucleotide triphosphate analogue or dideoxynucleotide triphosphate analogue substantially as hereinabove described with reference to any one of the examples.

A kit comprising one or more nucleotide triphosphate analogue or dideoxynucleotide triphosphate analogue substantially as hereinabove described with reference to any one of the examples.

While various embodiments of the invention are shown and described herein, it will be obvious to those skilled in the art that such embodiments are provided by way of example only. Numerous variations, changes, and substitutes may occur without departing from the disclosed invention. It should be understood that various alternatives to the embodiments of the invention described herein may be employed.

Terms

As used herein, and unless stated otherwise, each of the following terms shall have the definition set forth below.

| | |
|---|---|
| A | Adenine; |
| C | Cytosine; |
| G | Guanine; |
| T | Thymine; |
| U | Uracil; |
| DNA | Deoxyribonucleic acid; |
| RNA | Ribonucleic acid; |

"Nucleic acid" shall mean, unless otherwise specified, any nucleic acid molecule, including, without limitation, DNA, RNA and hybrids thereof. In an embodiment the nucleic acid bases that form nucleic acid molecules can be the bases A, C, G, T and U, as well as derivatives thereof.

"Derivatives" or "analogues" of these bases are well known in the art, and are exemplified in PCR Systems, Reagents and Consumables (Perkin Elmer Catalogue 1996-1997, Roche Molecular Systems, Inc., Branchburg, New Jersey, USA).

A "nucleotide residue" is a single nucleotide in the state it exists after being incorporated into, and thereby becoming a monomer of, a polynucleotide. Thus, a nucleotide residue is a nucleotide monomer of a polynucleotide, e.g. DNA, which is bound to an adjacent nucleotide monomer of the polynucleotide through a phosphodiester bond at the 3' position of its sugar and is bound to a second adjacent nucleotide monomer through its phosphate group, with the exceptions that (i) a 3' terminal nucleotide residue is only bound to one adjacent nucleotide monomer of the polynucleotide by a phosphodiester bond from its phosphate group, and (ii) a 5' terminal nucleotide residue is only bound to one adjacent nucleotide monomer of the polynucleotide by a phosphodiester bond from the 3' position of its sugar.

"Substrate" or "Surface" shall mean any suitable medium present in the solid phase to which a nucleic acid or an agent may be affixed. Non-limiting examples include chips, beads, nanopore structures and columns. In an embodiment the solid substrate can be present in a solution, including an aqueous solution, a gel, or a fluid.

"Hybridize" shall mean the annealing of one single-stranded nucleic acid to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York). As used herein, hybridization of a primer sequence, or of a DNA extension product, to another nucleic acid shall mean annealing sufficient such that the primer, or DNA extension product, respectively, is extendable by creation of a phosphodiester bond with an available nucleotide or nucleotide analog capable of forming a phosphodiester bond.

As used herein, unless otherwise specified, a base which is "unique" or "different from" another base or a recited list of bases shall mean that the base has a different structure from the other base or bases. For example, a base that is "unique" or "different from" adenine, thymine, and cytosine would include a base that is guanine or a base that is uracil.

As used herein, unless otherwise specified, a label or tag moiety which is "different" from the label or tag moiety of a referenced molecule means that the label or tag moiety has a different chemical structure from the chemical structure of the other/referenced label or tag moiety.

As used herein, unless otherwise specified, "primer" means an oligonucleotide that upon forming a duplex with a polynucleotide template, is capable of acting as a point of polymerase incorporation and extension from its 3' end along the template, thereby resulting in an extended duplex.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" includes groups having 1, 2, . . . , n−1 or n carbons in a linear or branched arrangement. For example, a "C1-C5 alkyl" includes groups having 1, 2, 3, 4, or 5 carbons in a linear or branched arrangement, and specifically includes methyl, ethyl, n-propyl, isopropyl, n-butyl, t-butyl, and pentyl.

As used herein, "alkenyl" refers to a non-aromatic hydrocarbon group, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl group having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon group straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl group having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

This patent application is divided into four sections, each focusing on nucleotide analogues with different characteristics. Examples of sequencing schemes may be found in each section. Though several similar schemes are found in multiple sections, some sections have unique schemes.

The two general nucleotide analogue structures presented in FIG. 1 cover most of the variants for Sections I-III. All the nucleotides can be of the variety shown in the top of FIG. 1, all the nucleotides can be of the variety shown in the bottom of FIG. 1, or mixtures of some of the top variety and some of the bottom variety may be used. Linker structures (between 3' OH and label, and between base and label) may include different lengths of polymers (e.g., PEG, alkanes, etc.). Triphosphates or polyphosphates can be used.

Nucleotide analogues comprise 3'-blocked structures (Sections I and IV) (R=OR' where R' can be different cleavable groups) for the type of sequencing by synthesis with nucleotide reversible terminators that are also found in the prior PCT applications (Ju et al WO 2017/058953A1; Ju et al WO2017/205336A1). These can have modifications on the base alone, the 3' group alone, or both. The modifications on the base can include a variety of cleavable linkers, a variety of dyes or dye clusters, and a variety of anchors or anchor clusters for subsequent attachment of dyes or dye clusters. The 3' position can be blocked with a variety of cleavable groups, and can be further attached to dyes or to anchors for subsequent attachment of dyes. In Section IV, so-called 3'-trigger nucleotides are described in which the bases may be modified as described above, but the 3' modification has two branches, with the smaller one containing one of a variety of cleavable groups and the longer one containing a variety of dyes or anchors. In this case, cleavage restores the 3'-OH along with removal of any 3' attached dyes or anchors.

For the hybrid sequencing approaches described in Section II, two sets of nucleotides are used, one set consisting of ddNTPs (R=H) with a variety of dyes or anchors attached to the bases via a variety of cleavable linkers, and the second set consisting of unlabeled nucleotide reversible terminators with any of a variety of 3'-blocking groups. For the approach described in Section III, a different style of nucleotide terminator analogue is used; these have 3'-OH groups (R=OH) but have a variety of blocking (extension inhibition) groups that permit addition of only one nucleotide analogue, along with a variety of dyes or anchors attached to the base via a variety of cleavable linkers. Further detailed examples and structures are provided later in each of the four sections. In addition, the triphosphate may be replaced with tetraphosphate, pentaphosphate, hexaphosphate or higher polyphosphates.

Shown in FIG. 2 are the general structures for the key nucleotide analogues used for SBS imaging in Section I. All the nucleotides can be of the variety shown in the top of FIG. 2, all the nucleotides can be of the variety shown in the bottom of FIG. 2, or mixtures of some of the top variety and some of the bottom variety may be used. Linker structures (between 3' OH or base and Label, may include different lengths of polymers (e.g., PEG, alkanes, etc.). Triphosphates or polyphosphates can be used.

Figure 3A:
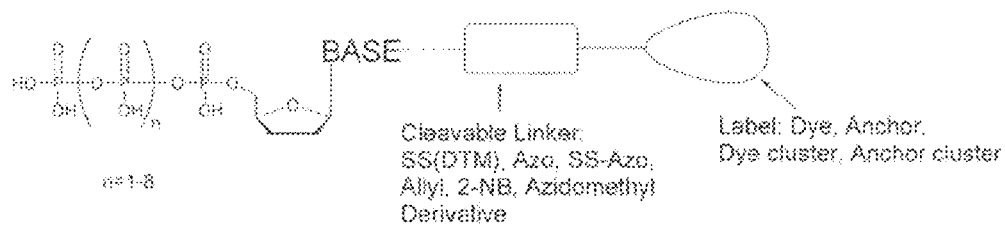
FIG. 3A: The general structure for the key nucleotide analogue used for SBS imaging in Section II.

Shown in FIG. 3A is the general structure for the key nucleotide analogue used for SBS imaging in Section II. In addition, since the following is a permanent terminator, a set of non-fluorescent reversible terminators is added at the same time to allow progressive sequencing by synthesis. Linker structures between base and label may include different lengths of polymers (e.g., PEG, alkanes, etc.). Triphosphates or polyphosphates can be used.

Figure 3B:
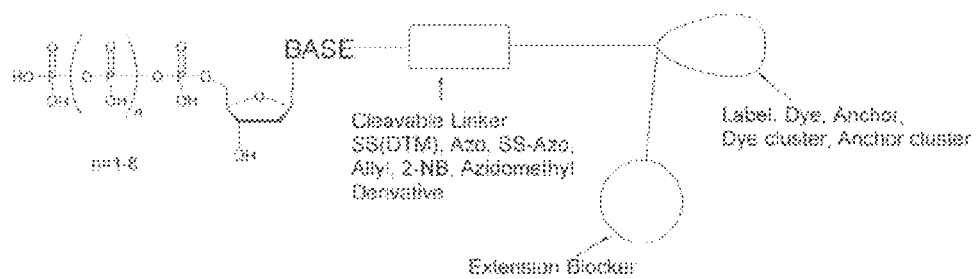
FIG. 3B: The general structure for the key nucleotide analogue used for SBS imaging in Section III.

Shown in FIG. 3B is the general structure for the key nucleotide analogue used for SBS imaging in Section III.

Figure 3C:
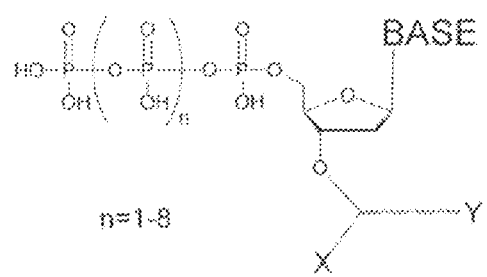
FIG. 3C: The general structure for the key nucleotide analogues used for SBS imaging in Section IV.

Shown in FIG. 3C is the general structure for the key nucleotide analogues used for SBS imaging in Section IV. Linker structures between 3' OH and label may include different lengths of polymers (e.g., PEG, alkanes, etc.). Triphosphates or polyphosphates can be used.

Figure 4:
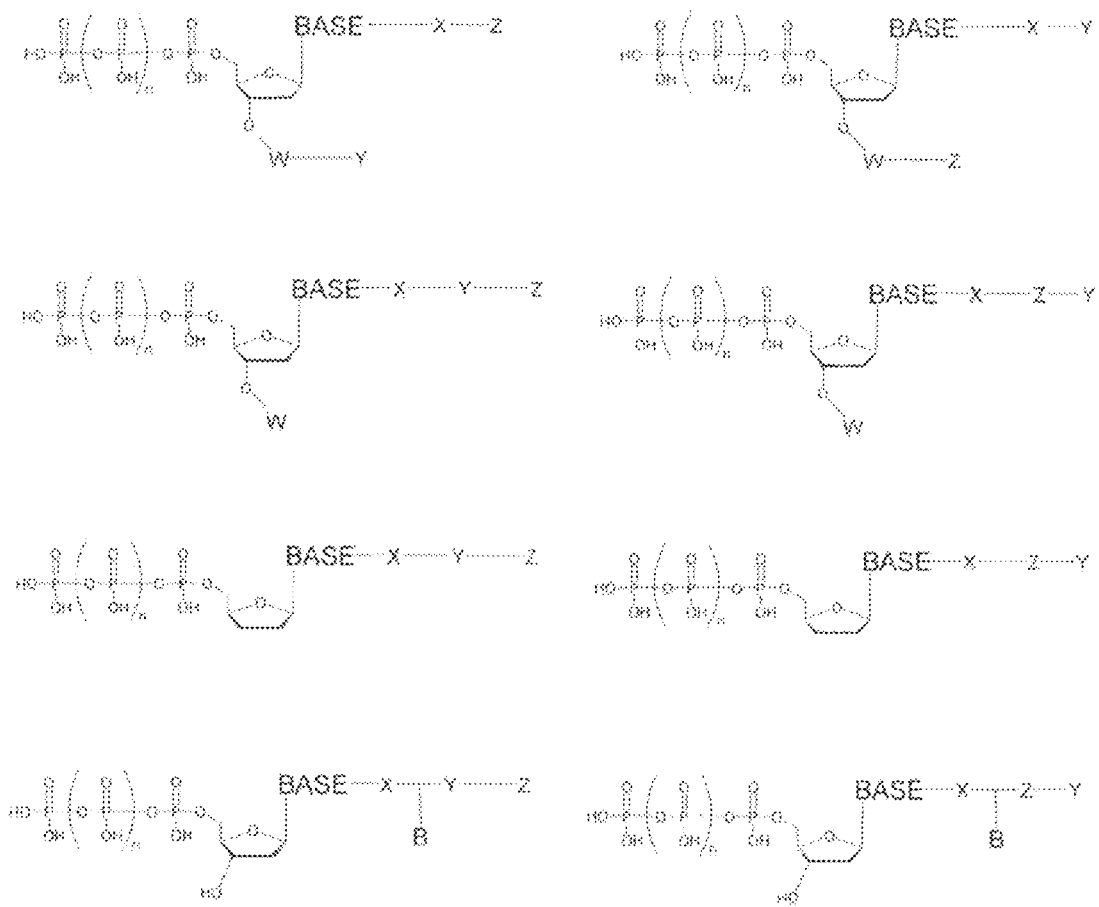
FIG. 4: An alternative class of molecules for Sections I-III in which energy transfer occurs between a donor and acceptor placed at various positions on the same nucleotide analogue.

An alternative class of molecules for Sections I-III in which energy transfer occurs between a donor and acceptor placed at various positions on the same nucleotide analogue is depicted in FIG. 4. In all these cases, if Z represents a FRET donor, the FRET acceptor will be attached to the anchor binding molecule that will attach to Y. If Z represents a FRET acceptor, the FRET donor will be attached to the anchor binding molecule that will attach to Y. FRET donors comprise organic dyes and quantum dots. Lengths of linkers will be designed to achieve maximal energy transfer without quenching. The same or different cleavable moieties may be placed at X and W. Triphosphates or polyphosphates can be used.

Within each of the four sections below, a variety of SBS schemes that take advantage of the above classes of nucleotide analogues are presented. In Sections I, III and IV, these schemes can be used with single template molecules and with ensembles of amplified templates. In Section II, because of the use of ddNTP analogues, only ensemble sequencing is described.

Most of the schemes in the four sections take advantage of orthogonal groups of cleavable groups, dyes, or anchors on nucleotide analogues, in which each of the four nucleotides has features orthogonal to the rest, e.g. orthogonal combinations of 2 dyes and 2 anchors, or 2 dyes and 2 cleavable linkers. The combinations allow 2-color (2 imaging steps per sequencing cycle) and even 1-color sequencing (3 imaging steps per cycle).

Throughout this application, most of the nucleotide analogues used in the various schemes contain dithiomethyl (DTM(SS)) blocking groups at the 3' O position and often contain cleavable DTM(SS) groups in the linkers between the base and the dye or anchor molecules. Previous methods have placed SS groups between the base and dye but after cleavage a free, reactive —SH group is formed which has to be capped with iodoacetamide before the second extension reaction can be carried out (Mitra et al 2003, Turcatti et al 2008). This limits the length of sequencing reads. The new DTM based linker between the base and the fluorophore disclosed in this application does not require capping of the resulting free SH group after cleavage with THP as the cleaved product instantaneously collapses to the stable OH group.

Section I: Nucleotide Analogues that have Disulfide Blocked 3'Position and Modifications on Base: Orthogonal Groups of Nucleotide Analogues The use of disulfide linker based nucleotides as reversible terminators for DNA sequencing has been previously described (Ju et al WO 2017/058953 A1; Ju et al WO2017/205336 A1). Herein disclosed are 12 novel SBS schemes using nucleotide analogues in which: (1) the 3' position of the nucleotide analogues is blocked by a dithiomethyl (DTM) moiety which can be cleaved specifically with tris(hydroxypropyl) phosphine (THP); and (2) either a fluorescent dye, or an anchor for subsequent attachment of a fluorescent dye, is linked to the base by an SS or other cleavable linker. In three of these schemes dye clusters or anchor clusters are used to enhance the signal for increased ease of single molecule sequencing.

Though the 3'-blocking group in all the examples shown in this section is t-butyl-dithiomethyl, other alkyl groups such as methyl-dithiomethyl or ethyl-dithiomethyl could also be used.

Wherever DTM is referred to in this patent application, it may refer to the dithiomethyl group or the various alkyl or other substituted dithiomethyl groups attached to the 3'-O position. Other blocking groups (azo, allyl, 2-nitrobenzyl, azidomethyl) may also be used, particularly if that group is present as the general cleavable group in all the linkers between the bases and dyes or anchors. In addition to nucleoside triphosphate analogues, nucleoside tetraphosphate, nucleoside pentaphosphate, nucleoside hexaphosphate and higher nucleoside polyphosphate analogues are feasible alternatives.

In the following schemes the Azo group is placed in linkers as an example of a second (non-DTM) cleavable linker; sodium dithionite is shown as an example cleaving agent (see FIGS. 124A-128B demonstrating the cleavage efficiency of sodium dithionite for the Azo group and the stability of SS bonds under these conditions). ATTO647N, Rox, and BodipyFL are used as examples of fluorophores; biotin or TCO are provided as examples of the anchors; and streptavidin or tetrazine are used as examples of the anchor binding molecules. However, a variety of other cleavable groups in the linker (e.g., allyl, 2-nitrobenzyl groups), cleavage agents (e.g., Pd(0), ~340 nm light), fluorophores, anchors (e.g., DBCO, $N_3$, tetrazine)*, and anchor binding molecules (e.g., $N_3$, DBCO, TCO)* are also feasible.

Fluorescent dyes can consist of single dye molecules, dye pairs that exhibit energy transfer, clusters of dyes attached at multiple positions of linear or branched polymers, and quantum dots. Though no examples are provided in this section, other labels may be used, e.g., non-fluorescent labels including Raman tags, and sets of tags that reduce ion current signals in nanopores to different extents, have different dwell times within the ion channel, or both.

Scheme I is a two-color SBS scheme that requires two detection steps. Schemes II and III are single-color schemes that require three detection steps to determine the incorporated nucleotide. Scheme IV is a one-color scheme using anchor and dye clusters and requiring three detection steps. Schemes V and VIA are two-color schemes using anchor and dye clusters and requiring three and two detection steps, respectively. Schemes VIB and VIC are 2-color schemes taking advantage of quantum dots (QDs) with anchors for QD labeling all present on the base. Schemes VID and VIE are 2-color schemes with quantum dots in which anchors for QD labeling are present on base and/or 3'-O position for different nucleotide analogues. Schemes VIIA and VIIB are one-color schemes taking advantage of energy transfer dyes, and each requiring three imaging steps.

Optional confirmatory imaging steps are included in some of these schemes. Chasing with unlabeled nucleotide analogues may be performed after adding the dye- or anchor-containing nucleotide analogues to guarantee that every DNA primer strand has been extended so as to avoid asynchronous reactions, and washing can be used between every step to remove the previous set of reagents and/or released dyes. The schemes can be used for ensemble or single molecule sequencing. In the case of ensemble sequencing, extension by a chase nucleotide analogue and the resulting absence of a signal for a subset of extended primers will still allow signals generated by the remaining primers extended with labeled nucleotide analogues to be observed. In the case of single molecule sequencing, a chase step is optional. In the case that chasing is used for single molecule sequencing, if a chase nucleotide analogue is incorporated into the growing DNA strand instead of the appropriate labeled nucleotide analogue, the base at that position will not be read, though the following base will be read in the appropriate cycle. Hence, the sequence will be accurate except at the known position where no signal was obtained.

Single Molecule Sequencing

As stated above, a number of the schemes described herein can be used for either ensemble or single molecule sequencing. In the case of single molecule fluorescent sequencing, two major concerns are sensitivity of the signal and background due to unincorporated fluorescent nucleotides or free fluorescent labeling molecules (e.g., anchor binding molecules bearing fluorophores). Special instrumentation such as total internal reflection fluorescence (TIRF) or stochastic optimal reconstruction microscopy (STORM) is utilized to detect single fluorescent molecules. TIRF microscopy, probably the most common of these, and the one used in Helicos BioSciences' single molecule sequencing approach, depends on the production of an evanescent wave at the surface of a glass slide which decays quickly with distance from the surface. Within the order of 100 nm from the surface, strong signals are obtained. Moreover, there is little background due to the fact that the majority of free fluorescent nucleotides or labeling molecules are not within that 100 nm window. Despite this, it is not possible to completely eliminate background. Similar principles occur with the Pacific Biosciences of California, Inc. zero mode waveguides (ZMWs) where the distance from the bottom of the 70 nm diameter wells are 100 nm. Thus, while most free fluorescent molecules (of 4 different colors) will be excluded, a small number will enter the ZMW where they may generate false positive signals.

At least two approaches are herein disclosed that can further impact single molecule sequencing using TIRF microscopy. In a first approach, to further enhance sensitivity, in some of the schemes below (Schemes IV-VIA), clusters of dyes or clusters of anchors for subsequent attachment of multiple dyes are used. In a second approach, that is directed more towards decreasing the likelihood of detecting background fluorescence, fluorescence resonance energy transfer between a donor and acceptor dye placed a short distance from each other is used (Scheme VIIA and VIIB). The combination of FRET with TIRF microscopy was reported previously using a Cy3 donor on one nucleotide and a Cy5 acceptor on a second nucleotide to achieve up to 5-base fingerprints (Braslavsky et al 2003). The Förster radius for typical fluorescent energy transfer is approximately 5 nm (between 1 and 10 nm). In aforementioned second approach, using energy transfer between a donor and acceptor on the same nucleotide, because the laser used to excite the donor dye is unable to directly excite the acceptor dye, free floating fluorescent acceptor molecules in the solution would have to be within just 1-10 nm to be seen as false signals. The likelihood of this is extremely low, meaning that only acceptor dyes purposely placed within ~5 nm of the donor dyes, either on the same stretch of a polymeric molecule attached directly to the nucleotide analogue or brought together when a donor dye directly attached to the nucleotide analogue with an anchor and an acceptor dye attached to the anchor binding molecule become conjugated.

Selection of the donor and acceptor dye is also critical. For example, a donor dye with a wide absorption window but a low fluorescence quantum yield can be used to increase the Stokes-shifted fluorescence emission of an acceptor dye (Hung et al 1996). For instance, it was shown that a CYA (cyanine dye) donor and a fluorescein or rhodamine derivative as acceptor are known to meet these conditions.

Further disclosed herein is an approach that can both increase signal, reduce background detection, and decrease the chance of missing an incorporation event, by having clusters of donor-acceptor dye pairs directly attached to the nucleotides (either in linear chains or dendrimeric conformations) or clusters of donor dyes and anchors for attachment of multiple acceptor dyes on anchor binding molecules (e.g., for Scheme VIIA). Potentially, this combined approach can be used to achieve single molecule SBS with state-of-the-art optical systems, with lower cost and footprint than TIRF microscopes.

Schemes Involving Single Dyes on Zach Nucleotide Analogue

Scheme I: Two-color SBS with two dyes and two cleavable linkers; imaging after incorporation and first cleavage. In Scheme I, an orthogonal set of nucleotide analogues, one with Dye1 attached to the base via an SS linkage, one with Dye1 attached to the base via an Azo linkage, one with Dye2 attached to the base via an SS linkage, and one with Dye2 attached to the base via an Azo linkage, is used. Imaging after addition of the four nucleotide analogues will indicate incorporation by either of two types of nucleotide analogues specifically. After cleavage of Azo linkers with sodium dithionite, imaging will reveal specifically which nucleotide analogue was incorporated. Cleavage with THP will then remove the remaining dyes and restore the 3'-OH group for subsequent sequencing cycles. In the example shown, Dye1 is Rox and Dye2 is BodipyFL. Other combinations of dyes and cleavable linkers can also be used.

Figure 5:
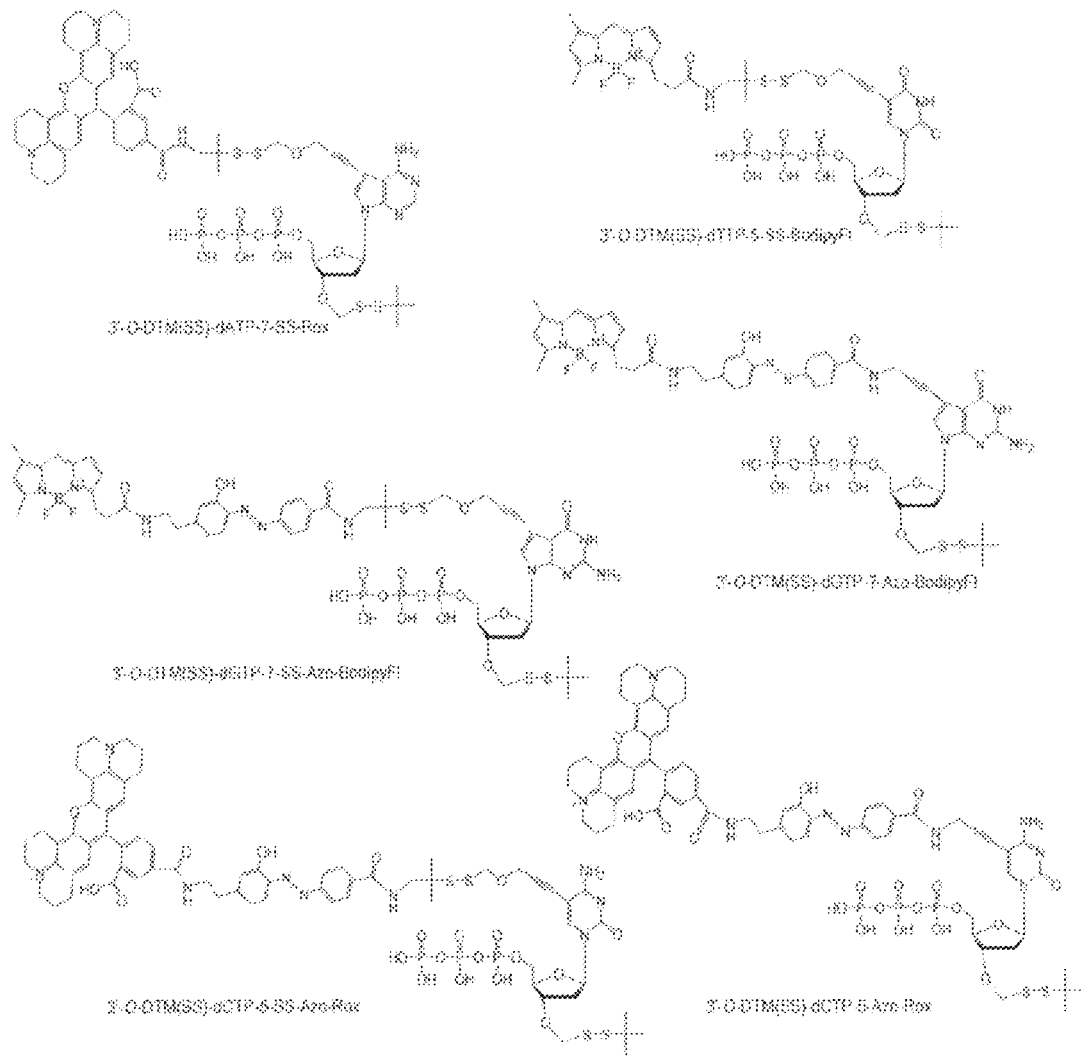
FIG. 5: 3'-O-SS(DTM)-dNTP-SS-Dyes (3'-O-SS-dATP-7-SS-Rox and 3'-O-SS-dUTP-5-SS-BodipyFL) and 3'-O-SS(DTM)-dNTP-SS-Azo-Dyes (3'-O-SS-dCTP-5-Azo-Rox or 3'-O-SS-dCTP-5-SS-Azo-Rox, and 3'-O-SS-dGTP-7-Azo-BodipyFL or 3'-O-SS-dGTP-7-SS-Azo-BodipyFL) for 2-color DNA SBS using approach delineated in Scheme I.

FIGS. 31A-31E contain a schematic for Scheme I using 3'-O-SS(DTM)-dNTP-SS-Dyes (3'-O-SS-dATP-7-SS-Rox, 3'-O-SS-dTTP-5-SS-BodipyFL) and 3'-O-SS(DTM)-dNTP-Azo-Dyes (3'-O-SS-dCTP-7-Azo-Rox, 3'-O-SS-dGTP-5-Azo-BodipyFL) to perform 2-color DNA SBS. Step 1, Addition of DNA polymerase and the four nucleotide analogues (3'-O-SS-dATP-7-SS-Rox, 3'-O-SS-dTTP-5-SS-BodipyFL, 3'-O-SS-dCTP-7-Azo-Rox and 3'-O-SS-dGTP-5-Azo-BodipyFL) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye. Step 3, after washing away the unincorporated dye labeled nucleotides, detection of the unique fluorescence signal from each of the fluorescent dyes on the DNA products allows the partial identification of the incorporated nucleotide for sequence determination: Rox signal indicates incorporation of either A or C, BodipyFL signal indicates incorporation of T or G. Step 4, cleavage of Azo linker by adding sodium dithionite ($Na_2S_2O_4$) to the elongated DNA strands results in removal of Rox from incorporated C and BodipyFL from incorporated G. Step 5, after washing away the cleaved dyes, a second round of detection of the unique fluorescence signal from each of the fluorescent dyes on the DNA products allows the identification of the incorporated nucleotide for sequence determination. Disappearance of Rox signal indicates incorporation of C, and disappearance of BodipyFL signal indicates incorporation of G. Remaining Rox signal indicates incorporation of A, and remaining BodipyFL signal indicates incorporation of T. Next, in Step 6, treatment of the DNA products with THP cleaves the SS linker, leading to the removal of the remaining fluorescent dye and the regeneration of a free 3'-OH group on the DNA extension product, which is ready for the next cycle of the DNA sequencing reaction. A schematic representation of fluorescence images is shown in FIG. 31Z. Hollow circles and triangles represent "no fluorescence signal" and filled circles and triangles represent "fluorescent signals at two different wavelengths". Similar schematics can be constructed for other 2-color SBS schemes in this section. Though not indicated in Scheme I, if desired, the presence of an additional SS linkage between the Azo group and the base results in the production of a shorter scar on the incorporated nucleotide after THP treatment which should result in longer reads. Structures of modified nucleotides used in this scheme are shown in FIG. 5.

Scheme II: One-color SBS with one dye, one anchor and two cleavable linkers; imaging after incorporation, labeling, and first cleavage. In Scheme II, an orthogonal set of nucleotide analogues, one with Dye1 attached to the base via an SS linkage, one with Dye1 attached to the base via an Azo linkage, one with Anchor1 attached to the base via an SS linkage, and one with Anchor1 attached to the base via an Azo linkage, is used. Imaging after addition of the four nucleotide analogues will indicate incorporation by either of two types of nucleotide analogues specifically. Imaging after labeling with Dye1 via an Anchor1-binding molecule will confirm incorporation by either of the other two types of nucleotide analogues specifically. (Imaging is optional but recommended at this step.) Finally, cleavage of the Azo linker with sodium dithionite will reveal specifically which nucleotide analogue was incorporated. Cleavage with THP will then remove the remaining dyes and restore the 3'-OH group for subsequent sequencing cycles. In the example shown, Dye1 is ATTO647N and Anchor1 is Biotin. Other combinations of dyes, anchors and cleavable linkers can also be used.

Figure 6:
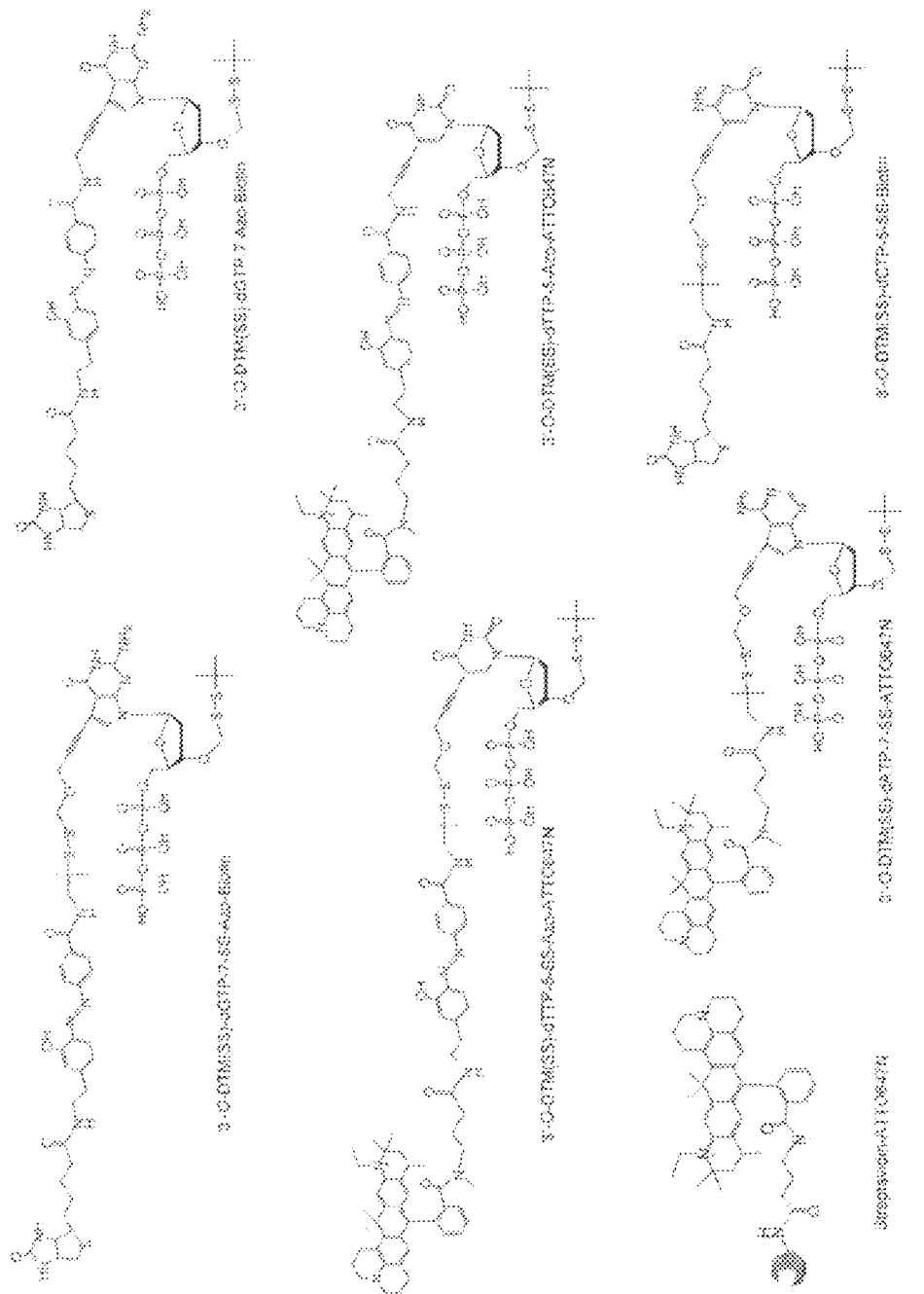
FIG. 6: 3'-O-SS(DTM)-dNTP-SS-Dye (3'-O-SS-dATP-7-SS-ATTO647N), 3'-O-SS(DTM)-dNTP-Azo-Dye (3'-O-SS-dTTP-5-Azo-ATTO647N or 3'-O-SS-dTTP-5-SS-Azo-ATTO647N), 3'-O-SS(DTM)-dNTP-SS-Anchor (3'-O-SS-dCTP-5-SS-Biotin), 3'-O-SS-dGTP-7-Azo-Anchor (3'-O-SS-dGTP-7-Azo-Biotin or 3'-O-SS-dGTP-7-SS-Azo-Biotin) and the corresponding Dye Labeled Binding Molecule (ATTO647N Labeled Streptavidin) for 1-color DNA SBS using approach delineated in Scheme II.

FIGS. 32A-32D contain a schematic for Scheme II using 3'-O-SS(DTM)-dNTP-SS-Dye (3'-O-SS-dATP-7-SS-ATTO647N), 3'-O-SS(DTM)-dNTP-Azo-Dye (3'-O-SS-dTTP-5-Azo-ATTO647N), 3'-O-SS(DTM)-dNTP-SS-Anchor (3'-O-SS-dCTP-5-SS-Biotin), 3'-O-SS(DTM)-dNTP-Azo-Anchor (3'-O-SS-dGTP-7-Azo-Biotin) and the corresponding Dye Labeled Binding Molecule (ATTO647N-labeled Streptavidin) to perform 1-color DNA SBS. Step 1, Addition of DNA polymerase and the four nucleotide analogues (3'-O-SS-dATP-7-SS-ATTO647N, 3'-O-SS-dTTP-5-Azo-ATTO647N, 3'-O-SS-dCTP-5-SS-Biotin and 3'-O-SS-dGTP-7-Azo-Biotin) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye or anchor. Step 3, after washing away the unincorporated dye labeled nucleotides and nucleotide terminators, detection of the fluorescence signal from each of the fluorescent dyes on the DNA products allows the partial identification of the incorporated nucleotide for sequence determination, the ATTO647N signal indicating incorporation of either A or T. Step 4, labeling with Streptavidin-ATTO647N. After washing away remaining free label, detection of new ATTO647N signal in Step 5 indicates incorporation of either C or G. Next, in Step 6, treatment of the DNA products with sodium dithionite cleaves the azo linker, leading to the removal of any fluorescent dye on G and T. Step 7, after washing away the cleaved dye, imaging is carried out. In this step, if it has already been determined that the incorporated nucleotide could be A or T, loss of fluorescence would reveal it to be T, while remaining fluorescence would reveal it to be A. Similarly, for signals previously determined as C or G, loss of fluorescence would indicate incorporation of G specifically while remaining fluorescence would indicate incorporation of C. Next, in Step 8, treatment of the DNA products with THP cleaves the SS linker, leading to the removal of the remaining fluorescent dye and the regeneration of a free 3'-OH group on the DNA extension product. After washing away THP, an optional imaging step (not shown) will confirm all dyes have been removed, in preparation for the next cycle of sequencing. A schematic representation of fluorescence images is shown at the bottom of Scheme II. Hollow circles represent "no fluorescence signal" and filled circles represent "fluorescence signal". Similar schematics can be constructed for other 1-color SBS schemes in this section. Though not indicated in Scheme II, if desired, the presence of an additional SS linkage between the Azo group and the base results in the production of a shorter scar on the incorporated nucleotide after THP treatment which should result in longer reads. Structures of modified nucleotides used in this scheme are shown in FIG. 6.

Scheme III: One-color SBS with two anchors and two cleavable linkers: imaging after each labeling step and after first cleavage. In Scheme III, an orthogonal set of nucleotide analogues, one with Anchor1 attached to the base via an SS linkage, one with Anchor1 attached to the base via an Azo linkage, one with Anchor2 attached to the base via an SS linkage, and one with Anchor2 attached to the base via an Azo linkage, is used. Incorporation is carried out. Then, imaging after the first labeling step with Dye1 attached to an Anchor1-binding molecule will indicate incorporation of either of two types of nucleotide analogues. Imaging after the second labeling step with Dye1 attached to an Anchor2-binding molecule will confirm incorporation of either of the other two types of nucleotide analogues. (Imaging is optional but recommended at this step.) Imaging after cleavage of the Azo linker with sodium dithionite will indicate the specific nucleotide analogue incorporated. Cleavage with THP will then remove the remaining dyes and restore the 3'-OH group for subsequent sequencing cycles. In the example shown, Dye1 is ATTO647N, Anchor1 is Biotin and Anchor2 is TCO. Other combinations of dyes, anchors and cleavable linkers can also be used.

In the case of 2-dye schemes, dyes are chosen that have well separated absorption and emission spectra. The 2-color and especially the 1-color schemes are designed to reduce the size, cost and complexity of the optical setup required.

While all the schemes presented use DNA templates and primers, 2-deoxynucleotide analogues and DNA polymerase, in principle the schemes can be adjusted to include appropriate templates, primers, and nucleotide analogues for RNA-dependent DNA polymerases as well as DNA- or RNA-dependent RNA polymerases.

Figure 7:
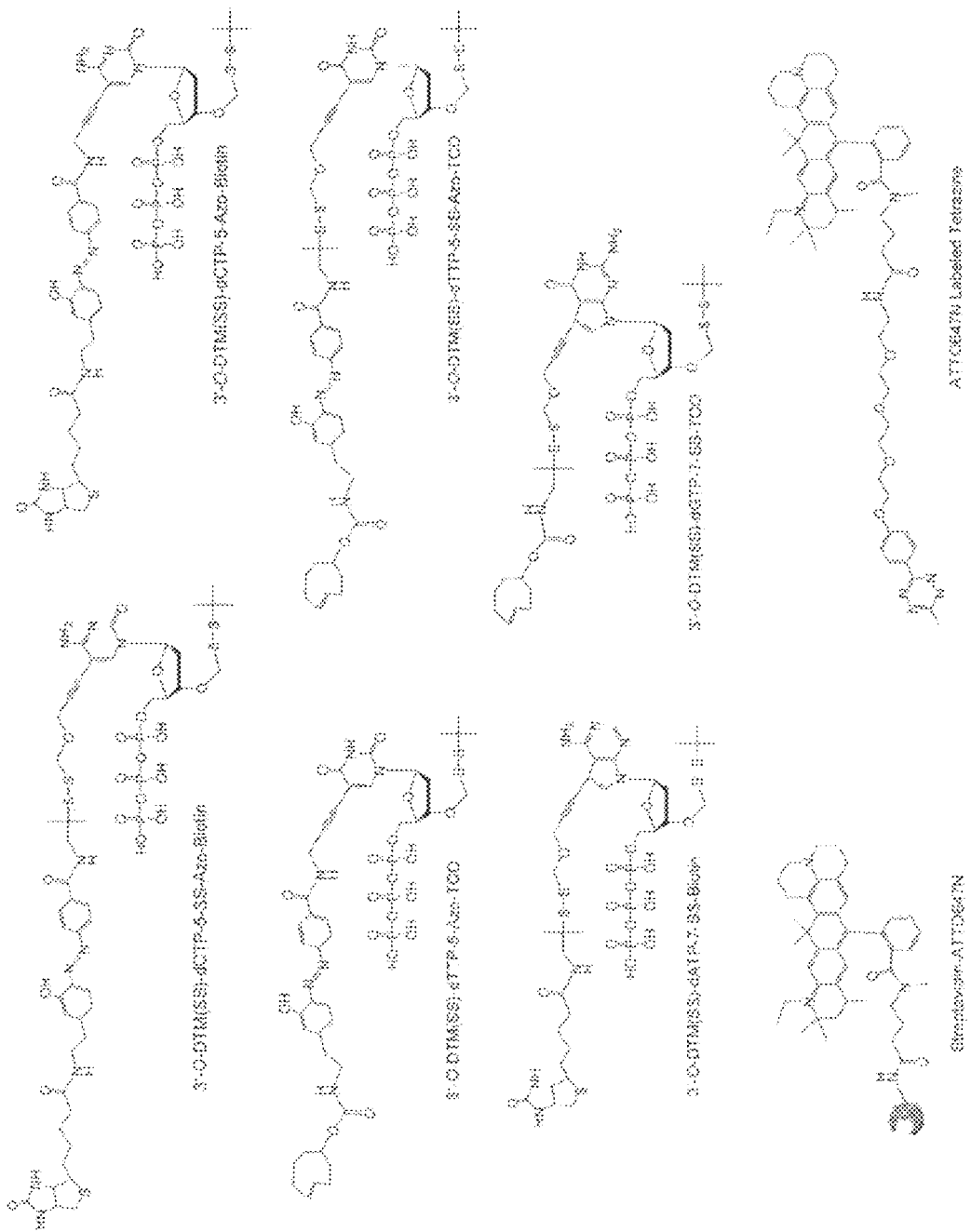
FIG. 7: 3'-O-SS(DTM)-dNTP-SS-Anchors (3'-O-SS-dATP-7-SS-Biotin and 3'-O-SS-dGTP-7-SS-TCO), 3'-O-SS(DTM)-dNTP-Azo-Anchors (3'-O-SS-dTTP-5-Azo-TCO or 3'-O-SS-dTTP-5-SS-Azo-TCO and 3'-O-SS-dCTP-5-Azo-Biotin or 3'-O-SS-dCTP-5-Azo-Biotin) and the corresponding Dye Labeled Binding Molecules (ATTO647N Labeled Streptavidin and ATTO647N Labeled Tetrazine) for 1-color DNA SBS using approach delineated in Scheme III.
Figure 8A:
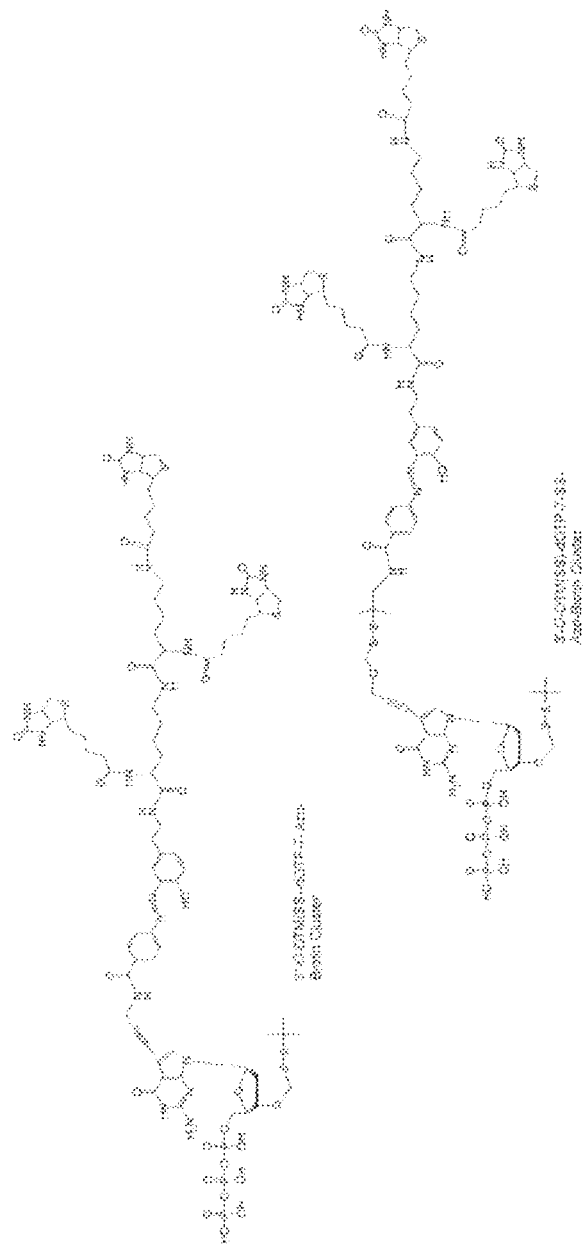
FIGS. 8A-8C: 3'-O-SS(DTM)-dNTP-SS-Anchor Cluster (3'-O-SS-dCTP-5-SS-Biotin Cluster), 3'-O-SS(DTM)-dNTP-Azo-Anchor Cluster (3'-O-SS-dGTP-7-Azo-Biotin Cluster or 3'-O-SS-dGTP-7-SS-Azo-Biotin Cluster), 3'-O-SS(DTM)-dNTP-SS-Dye Cluster (3'-O-SS-dATP-7-SS-ATTO647N Cluster) and 3'-O-SS(DTM)-dNTP-Azo-Dye Cluster (3'-O-SS-dTTP-5-Azo-ATTO647N or 3'-O-SS-dTTP-5-SS-Azo-ATTO647N) and the corresponding Dye Labeled Binding Molecules (ATTO 647N Labeled Streptavidin for 1-color DNA SBS using approach delineated in Scheme IV.
Figure 8B:
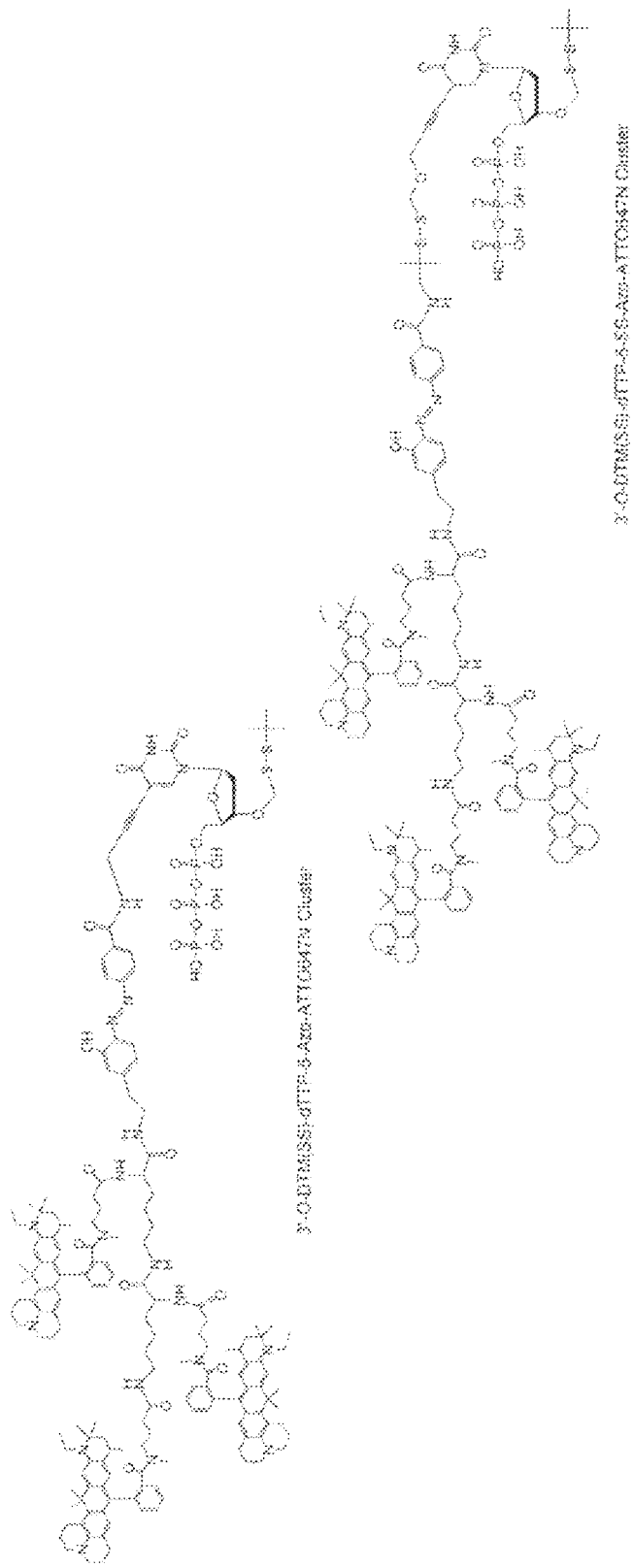
Figure 8C:
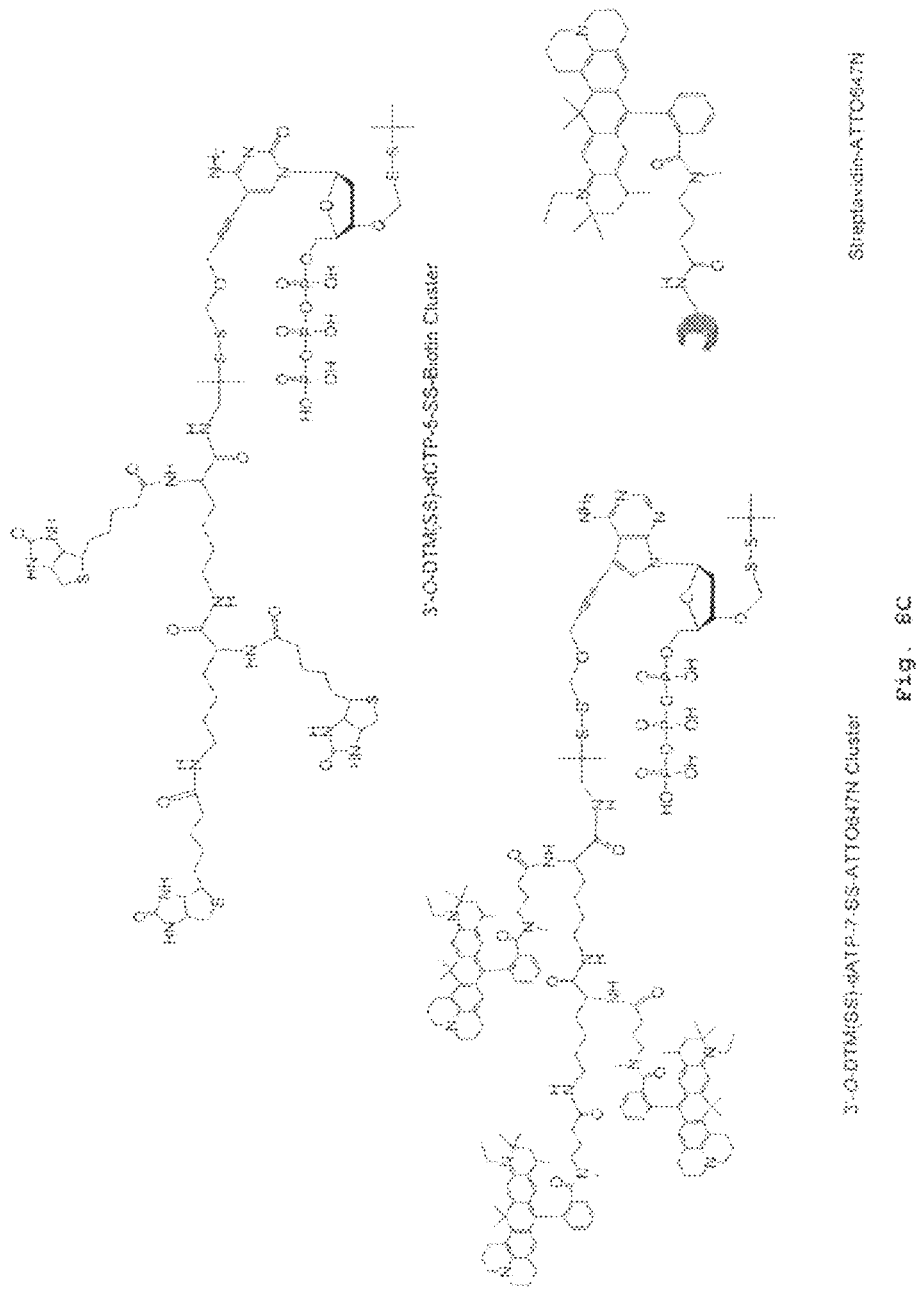

FIGS. 33A-33D contain a schematic showing Scheme III using 3'-O-SS(DTM)-dNTP-SS-Anchors (3'-O-SS-dATP-7-SS-Biotin, 3'-O-SS-dGTP-7-SS-TCO), 3'-O-SS(DTM)-dNTP-Azo-Anchors (3'-O-SS-dTTP-5-Azo-TCO, 3'-O-SS-dCTP-5-Azo-Biotin) and the corresponding Dye Labeled Binding Molecules (ATTO647N-labeled Streptavidin and ATTO647N-labeled Tetrazine) to perform 1-color DNA SBS. Step 1, Addition of DNA polymerase and the four nucleotide analogues (3'-O-SS-dATP-7-SS-Biotin, 3'-O-SS-dTTP-5-Azo-TCO, 3'-O-SS-dCTP-5-Azo-Biotin and 3'-O-SS-dGTP-7-SS-TCO) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the anchor labeled dNTPs in step 1. The growing DNA strands are terminated with one of the four anchor labeled nucleotide analogues (A, C, G, T) or the same one of the four nucleotide analogues (A, C, G, T) without anchor. Step 3, labeling with Streptavidin-ATTO647N. The dye will bind specifically to the A and C nucleotide analogues, but not the G and T analogues. Step 4, After washing away remaining free label and excess nucleotides, detection of new ATTO647N signal indicates incorporation of either A or C. Step 5, labeling with Tetrazine-ATTO647N. The dye will bind specifically to the G and T nucleotide analogues, but not the A and C analogues. Step 6, After washing away remaining free label and excess nucleotides, detection of new ATTO647N signal indicates incorporation of either G or T. Next, in Step 7, treatment of the DNA products with sodium dithionite cleaves the azo linker, leading to the removal of any fluorescent dye on T and C. Step 8, After washing away cleaved dye, imaging for the presence of ATTO647N fluorescence is carried out. In this step, if it has already been determined that the incorporated nucleotide could be A or C, loss of fluorescence would reveal it to be C, while remaining fluorescence would reveal it to be A. Similarly, for signals previously determined as G or T, loss of fluorescence would indicate incorporation of T specifically while remaining fluorescence would indicate incorporation of G. Next, in Step 9, treatment of the DNA products with THP cleaves the SS linker, leading to the removal of the remaining fluorescent dye and the regeneration of a free 3'-OH group on the DNA extension product. Step 10, after washing away THP, an optional imaging step will confirm all dyes have been removed, in preparation for the next cycle of sequencing. Though not indicated in Scheme III, if desired, the presence of an additional SS linkage between the Azo group and the base results in the production of a shorter scar on the incorporated nucleotide after THP treatment which should result in longer reads. Structures of modified nucleotides used in this scheme are shown in FIG. 7.

Schemes Involving Clusters of Dyes on Each Nucleotide Analogue

Scheme IV: One-color SBS with one dye cluster, one anchor cluster and two cleavable linkers; imaging after incorporation, labeling, and first cleavage. The only difference with Scheme II is that clusters of anchors (Anchor1 cluster) or clusters of dyes (Dye1 cluster) are attached to the base. In the labeling step, multiple dyes will bind to the anchor cluster. In the example shown, the Dye1 cluster is an ATTO647N cluster and the Anchor1 cluster is a Biotin cluster. Other combinations of dye clusters, anchor clusters and cleavable linkers can also be used.

Figure 34C:
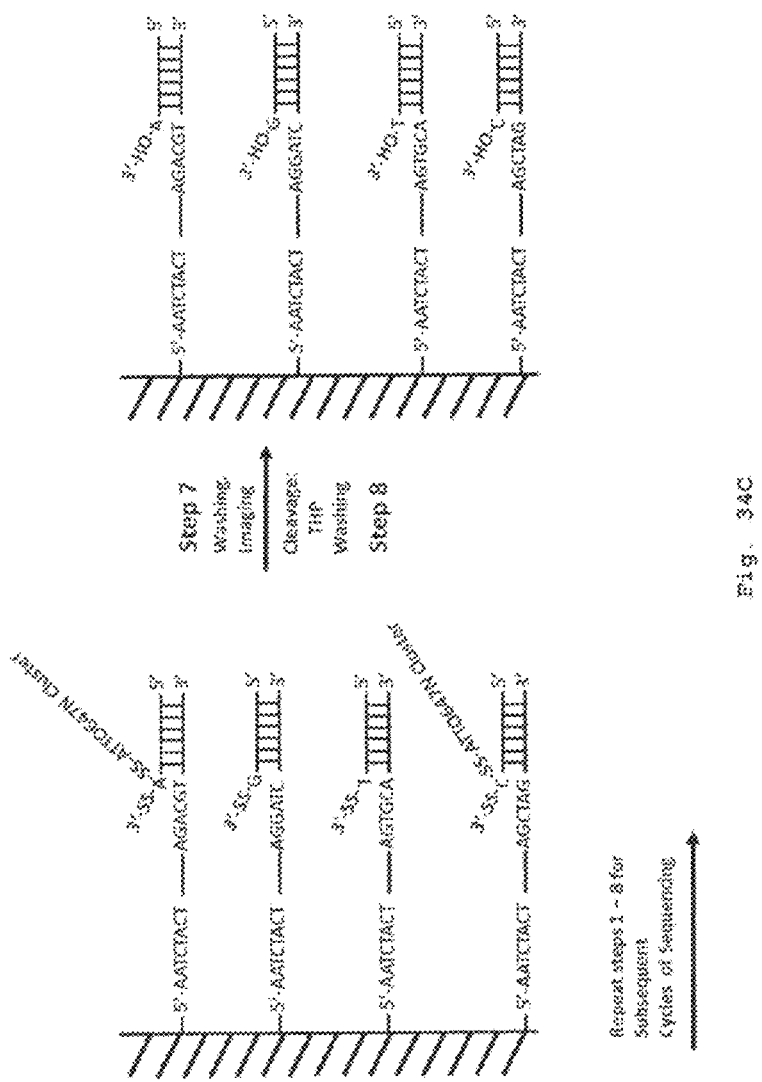
Figure 35A:
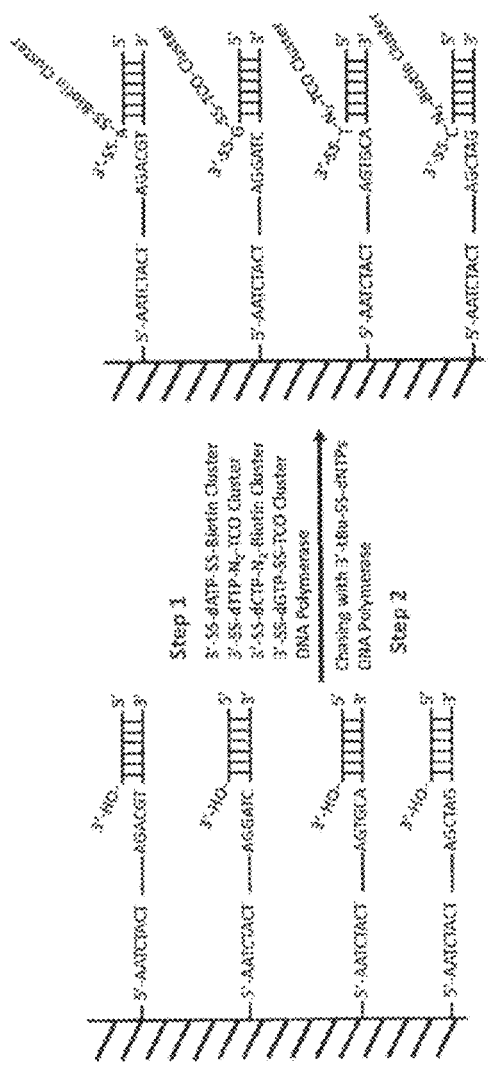
FIGS. 35A-35D: A schematic showing Scheme V using 3'-O-SS(DTM)-dNTP-SS-Anchor Clusters (3'-O-SS-dATP-7-SS-Biotin Cluster, 3'-O-SS-dGTP-7-SS-TCO Cluster), 3'-O-SS(DTM)-dNTP-Azo-Anchor Clusters (3'-O-SS-dCTP-5-Azo-Biotin Cluster, 3'-O-SS(DTM)-dTTP-5-Azo-TCO Cluster) and the corresponding Dye Labeled Binding Molecules (Rox-labeled Streptavidin and Alexa488-labeled Tetrazine) to perform 2-color DNA SBS.
Figure 35B:
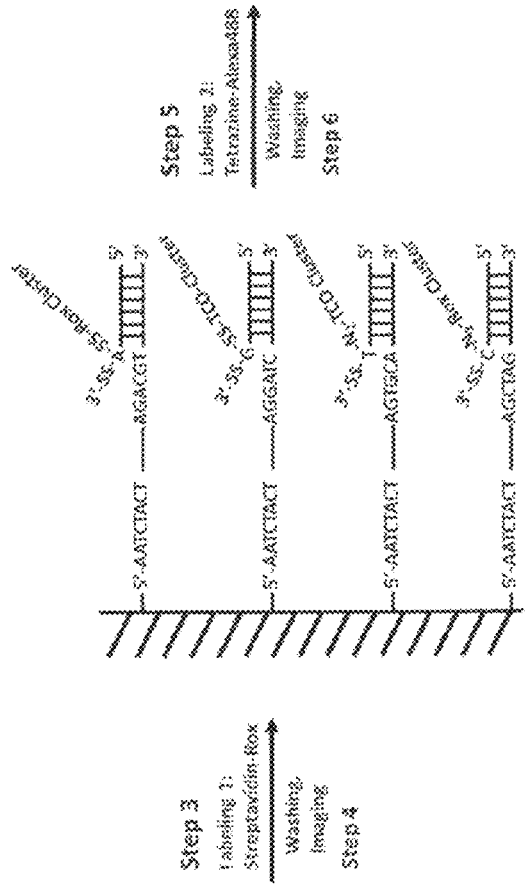
Figure 35C:
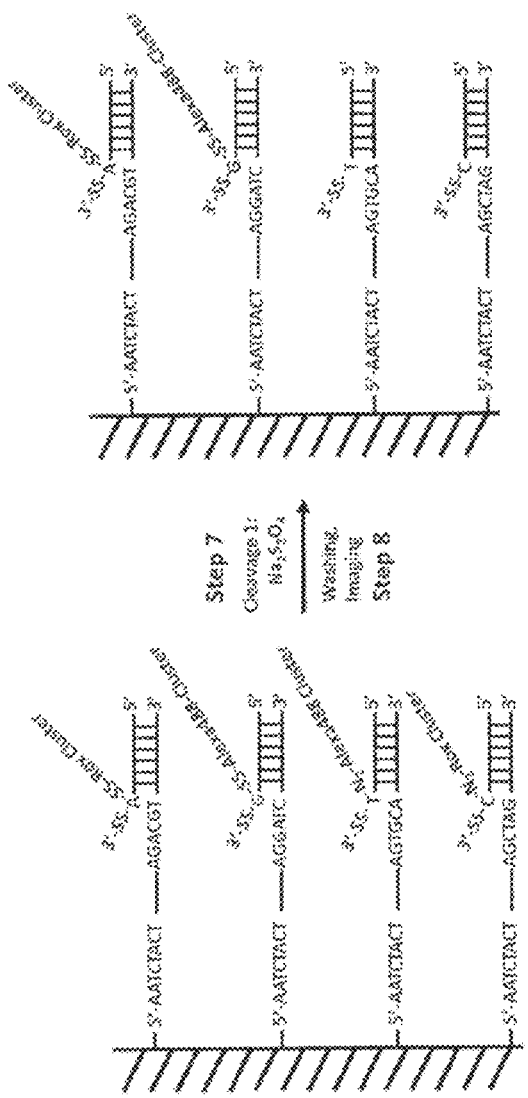
Figure 35D:
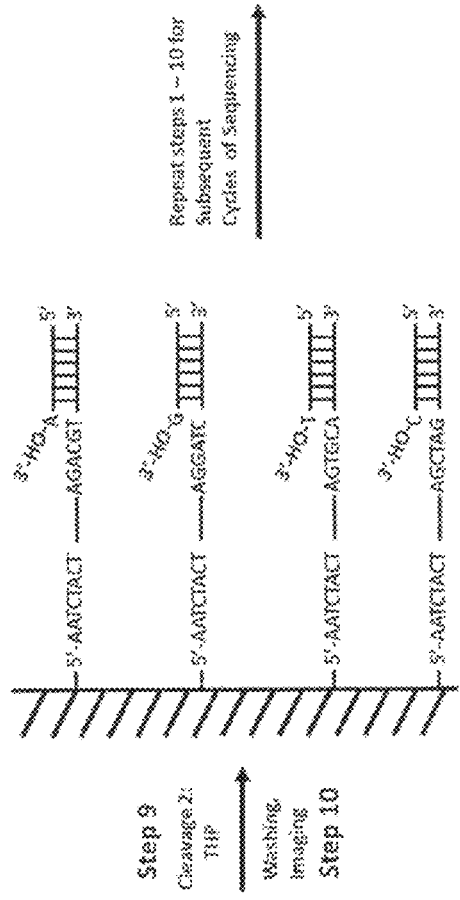

FIGS. 34A-34C contain a schematic showing Scheme IV using 3'-O-SS(DTM)-dNTP-SS-Dye Cluster (3'-O-SS-dATP-7-SS-ATTO647N Cluster), 3'-O-SS(DTM)-dNTP-Azo-Dye Cluster (3'-O-SS-dTTP-5-Azo-ATTO647N Cluster), 3'-O-SS(DTM)-dNTP-SS-Anchor Cluster (3'-O-SS-dCTP-5-SS-Biotin Cluster), 3'-O-SS(DTM)-dNTP-Azo-Anchor Cluster (3'-O-SS-dGTP-7-Azo-Biotin Cluster) and the corresponding Dye Labeled Binding Molecule (ATTO647N-labeled Streptavidin) to perform 1-color DNA SBS. Step 1, Addition of DNA polymerase and the four nucleotide analogues (3'-O-SS-dATP-7-SS-ATTO647N Cluster, 3'-O-SS-dTTP-5-Azo-ATTO647N Cluster, 3'-O-SS-dCTP-5-SS-Biotin Cluster, 3'-O-SS-dGTP-7-Azo-Biotin Cluster) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye cluster- or anchor cluster-labeled dNTPs in step 1. The growing DNA strands are terminated with one of the four dye cluster- or anchor cluster-labeled nucleotide analogues (A, C, G, T) or the same one of the four nucleotide analogues (A, C, G, T) without dye or anchor. Step 3, after washing away the unincorporated dye labeled nucleotides and nucleotide terminators, detection of the fluorescence signal from each of the fluorescent dyes on the DNA products allows the partial identification of the incorporated nucleotide analogue for sequence determination, the ATTO647N signal indicating incorporation of either A or T. Step 4, labeling with Streptavidin-ATTO647N. After washing away remaining free label, detection of new ATTO647N signal in Step 5 indicates incorporation of either C or G. Next, in Step 6, treatment of the DNA products with sodium dithionite cleaves the Azo linker, leading to the removal of any fluorescent dye on G and T. Step 7, after washing away the cleaved dye, imaging is carried out. In this step, if it has already been determined that the incorporated nucleotide analogue could be A or T, loss of fluorescence would reveal it to be T, while remaining fluorescence would reveal it to be A. Similarly, for signals previously determined as C or G, loss of fluorescence would indicate incorporation of G specifically while remaining fluorescence would indicate incorporation of C. Next, in Step 8, treatment of the DNA products with THP cleaves the SS linker, leading to the removal of the remaining fluorescent dye clusters and the regeneration of a free 3'-OH group on the DNA extension product. After washing away THP, an optional imaging step (not shown) will confirm all dyes have been removed, in preparation for the next cycle of sequencing. Though not indicated in Scheme IV, if desired, the presence of an additional SS linkage between the Azo group and the base results in the production of a shorter scar on the incorporated nucleotide after THP treatment which should result in longer reads. Structures of modified nucleotides used in this scheme are shown in FIG. 8.

Scheme V: Two-color SBS with two anchor clusters, 2 dyes, and two cleavable linkers: imaging after each labeling step and after first cleavage. Somewhat similar to Scheme III, but with one of two different dye clusters (Anchor1 cluster and Anchor2 cluster) attached to the base. In the labeling step, multiple dyes will bind to the anchor clusters. The presence of Dye1 fluorescence after the first labeling step will indicate two possible incorporated nucleotide analogues. The appearance of Dye2 fluorescence after the second labeling step will verify the incorporation of the other two types of nucleotide analogues. Imaging is optional but recommended at this step. Imaging after cleavage of the Azo linker with sodium dithionite will indicate the specific nucleotide analogue incorporated. Cleavage with THP will then remove the remaining dyes and restore the 3'-OH group for subsequent sequencing cycles. In this example, the Anchor1 cluster contains biotin, Anchor2 cluster contains TCO, Dye1 is Rox and Dye2 is Alexa488. Other combinations of dyes, anchors and cleavable linkers can also be used.

Figure 9A:
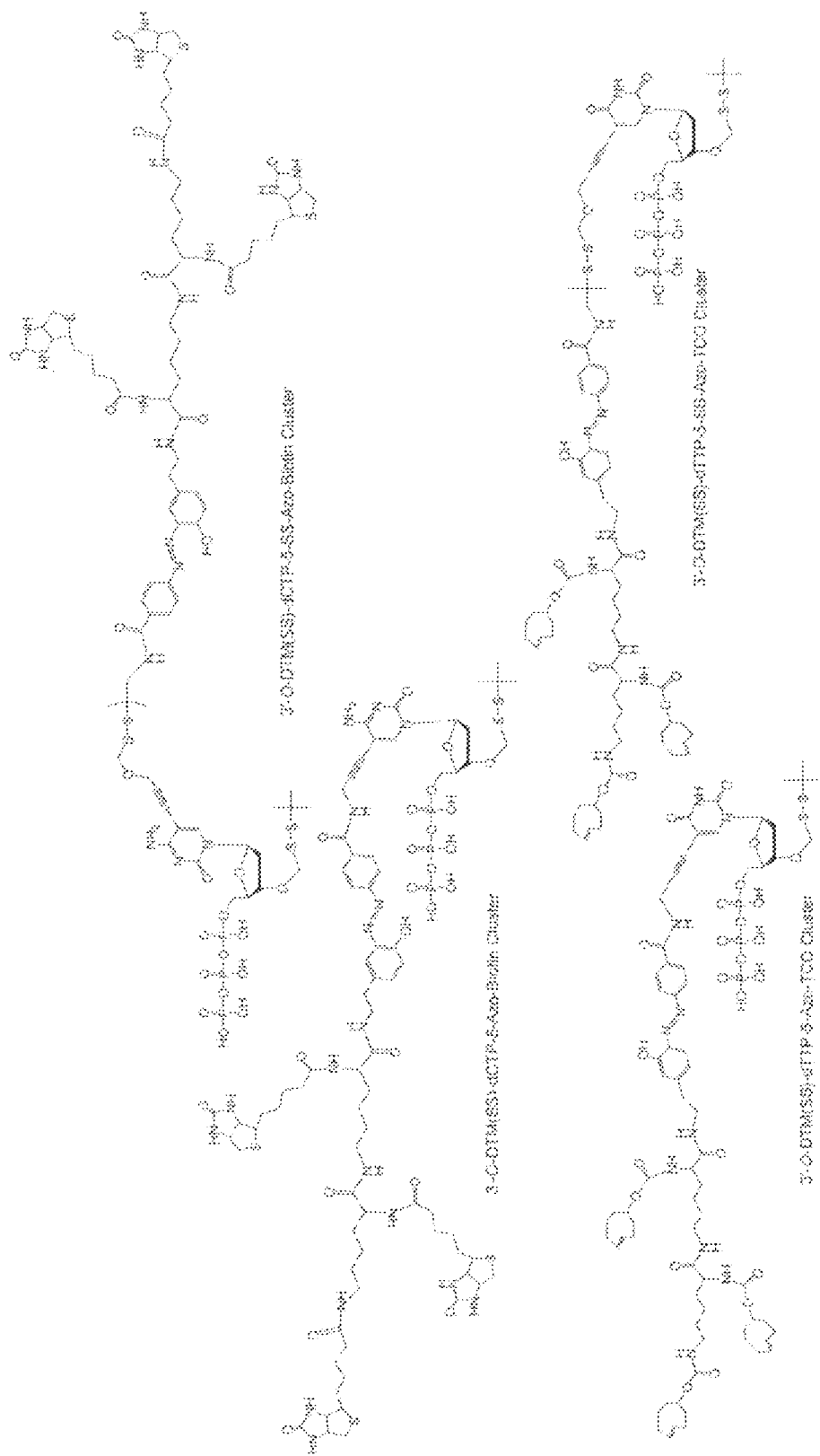
FIGS. 9A-9B: 3'-O-SS(DTM)-dNTP-SS-Anchor Cluster (3'-O-SS-dATP-7-SS-Biotin Cluster, 3'-O-SS-dGTP-7-SS-TCO Cluster) and 3'-O-SS(DTM)-dNTP-Azo-Anchor Cluster (3'-O-SS-dCTP-5-Azo-Biotin Cluster or 3'-O-SS-dCTP-5-SS-Azo-Biotin Cluster, 3'-O-SS-dTTP-5-Azo-TCO Cluster or 3'-O-SS-dTTP-5-SS-Azo-TCO Cluster) and the corresponding Dye Labeled Binding Molecules (Rox Labeled Streptavidin and Alexa488 labeled tetrazine) for 2-color DNA SBS using approach delineated in Scheme V.
Figure 9B:
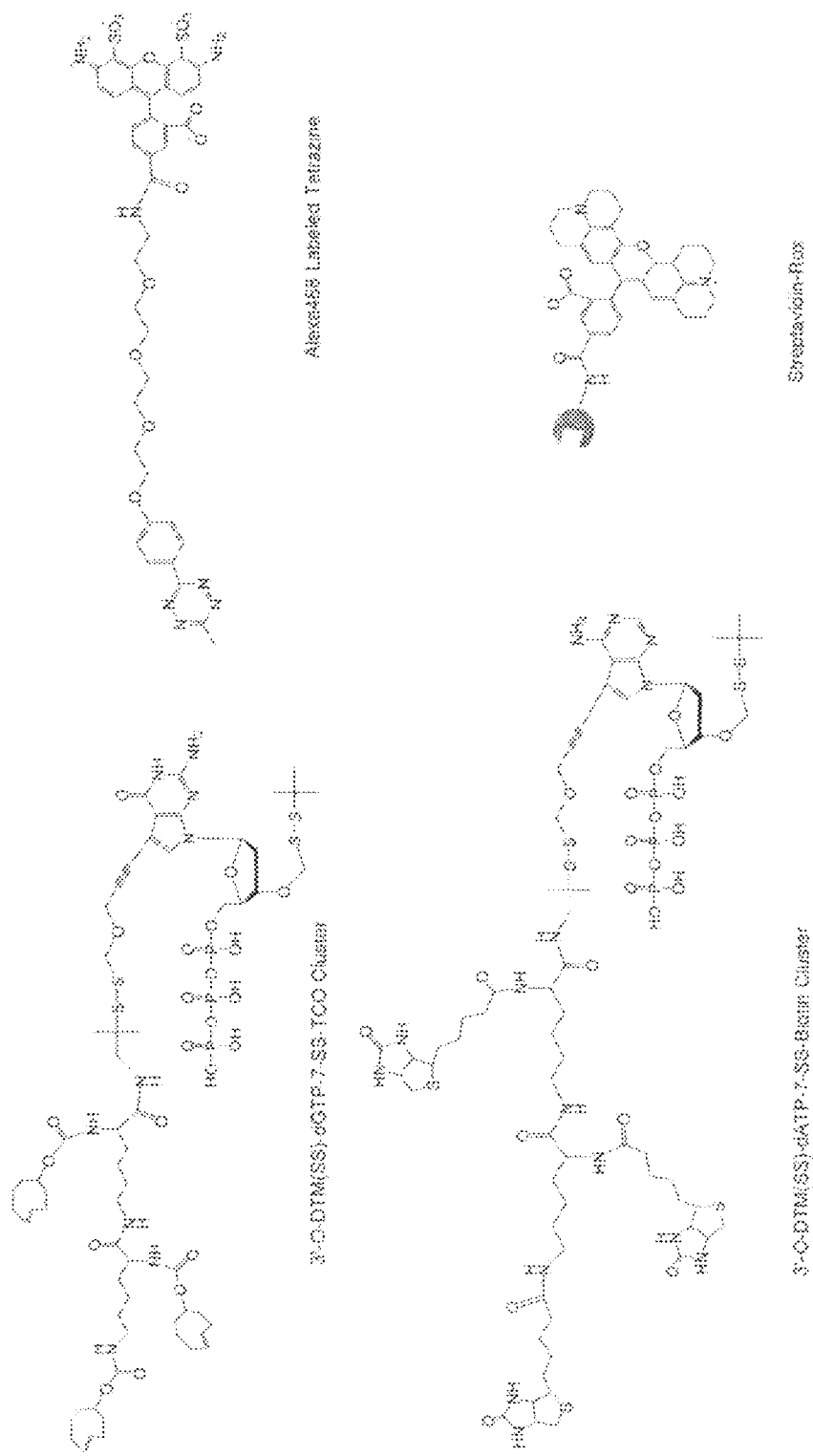

FIGS. 35A-35D contain a schematic showing Scheme V using 3'-O-SS(DTM)-dNTP-SS-Anchor Clusters (3'-O-SS-dATP-7-SS-Biotin Cluster, 3'-O-SS-dGTP-7-SS-TCO Cluster), 3'-O-SS(DTM)-dNTP-Azo-Anchor Clusters (3'-O-SS-dCTP-5-Azo-Biotin Cluster, 3'-O-SS(DTM)-dTTP-5-Azo-TCO Cluster) and the corresponding Dye Labeled Binding Molecules (Rox-labeled Streptavidin and Alexa488-labeled Tetrazine) to perform 2-color DNA SBS. Step 1, Addition of DNA polymerase and the four nucleotide analogues (3'-O-SS-dATP-7-SS-Biotin Cluster, 3'-O-SS-dTTP-5-Azo-TCO Cluster, 3'-O-SS-dCTP-5-Azo-Biotin Cluster and 3'-O-SS-dGTP-7-SS-TCO Cluster) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the anchor cluster labeled dNTPs in step 1. The growing DNA strands are terminated with one of the four anchor cluster labeled nucleotide analogues (A, C, G, T) or the same one of the four nucleotide analogues (A, C, G, T) without dye or anchor clusters. Step 3, labeling with Streptavidin-Rox. The dye will bind specifically to the A and C nucleotide analogues, but not the G and T analogues. Step 4, After washing away remaining free label and excess nucleotides, detection of new Rox signal indicates incorporation of either A or C. Step 5, labeling with Tetrazine-Alexa488. The dye will bind specifically to the G and T nucleotide analogues, but not the A and C analogues. Step 6, After washing away remaining free label and excess nucleotides, detection of new Alexa488 signal indicates incorporation of either G or T. Next, in Step 7, treatment of the DNA products with sodium dithionite cleaves the Azo linker, leading to the removal of any fluorescent dye on T and C. Step 8, After washing away cleaved dye clusters, imaging is carried out. In this step, if it has already been determined that the incorporated nucleotide could be A or C, loss of Rox fluorescence would reveal it to be C, while remaining Rox fluorescence would reveal it to be A. Similarly, for signals previously determined as G or T, loss of Alexa488 fluorescence would indicate incorporation of T specifically while remaining fluorescence would indicate incorporation of G. Next, in Step 9, treatment of the DNA products with THP cleaves the SS linker, leading to the removal of the remaining fluorescent dye clusters and the regeneration of a free 3'-OH group on the DNA extension product. Step 10, after washing away THP, an optional imaging step will confirm all dyes have been removed, in preparation for the next cycle of sequencing. Though not indicated in Scheme V, if desired, the presence of an additional SS linkage between the Azo group and the base results in the production of a shorter scar on the incorporated nucleotide after THP treatment which should result in longer reads. Structures of modified nucleotides used in this scheme are shown in FIG. 9.

Scheme VIA: Two-color SBS with two dye clusters, two anchor clusters and one cleavable linker: imaging after incorporation and labeling step. In Scheme VIA, Dye1 Cluster, Dye2 Cluster, Anchor1 Cluster and Anchor2 Cluster are attached to the four bases, respectively, all via an SS linkage. Incorporation is carried out. Imaging will indicate incorporation of two of the types of nucleotide analogues specifically. Next labeling is carried out with both Anchor1 and Anchor2 binding molecules attached to single copies of Dye1 and Dye2, respectively. Imaging will indicate incorporation of the other two types of nucleotide analogues specifically. Cleavage with THP will then remove the remaining dyes and restore the 3'-OH group for subsequent sequencing cycles. In the example clusters shown, Dye1 is Rox, Dye2 is BodipyFL, Anchor1 is Biotin and Anchor2 is TCO. Other combinations of dye clusters and anchor clusters can also be used.

The above approaches using dye and anchor clusters could be especially helpful for increasing sensitivity in the case of single molecule sequencing.

Figure 10A:
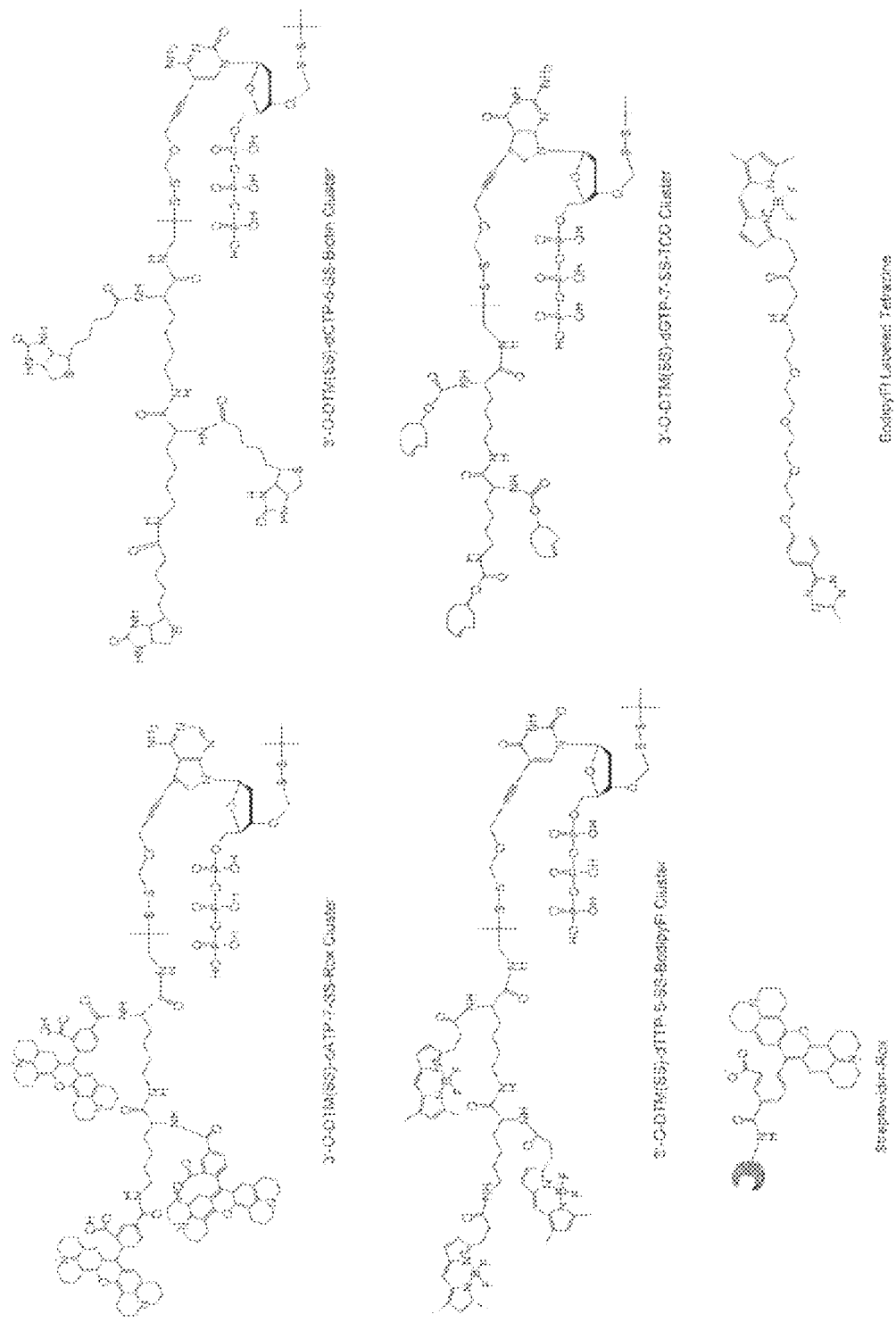
FIG. 10A: 3'-O-SS(DTM)-dNTP-SS-Dye Cluster (3'-O-SS-dATP-7-SS-Rox Cluster, 3'-O-SS-dTTP-5-SS-BodipyFL Cluster) and 3'-O-SS(DTM)-dNTP-SS-Anchor Cluster (3'-O-SS-dCTP-5-SS-Biotin Cluster, 3'-O-SS-dGTP-7-SS-TCO Cluster) and the corresponding Dye Labeled Binding Molecules (Rox Labeled Streptavidin and BodipyFL labeled tetrazine) for 2-color DNA SBS using approach delineated in Scheme VIA.
Figure 36A:
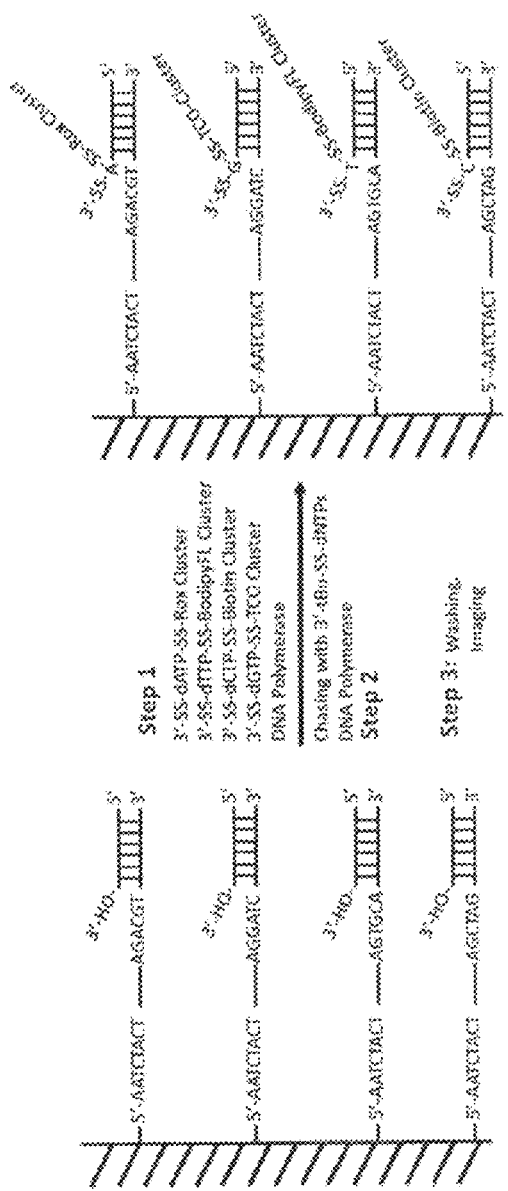
FIGS. 36A-36C: A schematic showing Scheme VIA using 3'-O-SS(DTM)-dNTP-SS-Dye Clusters (3'-O-SS-d ATP-7-SS-Rox Cluster, 3'-O-SS-dTTP-5-SS-BodipyFL Cluster), 3'-O-SS(DTM)-dNTP-SS-Anchor Clusters (3'-O-SS-dCTP-5-SS-Biotin Cluster, 3'-O-SS-dGTP-7-SS-TCO Cluster) and corresponding dye-labeled anchor binding molecules (Streptavidin-Rox, Tetrazine-BodipyFL) to perform 2-color DNA SBS.
Figure 36B:
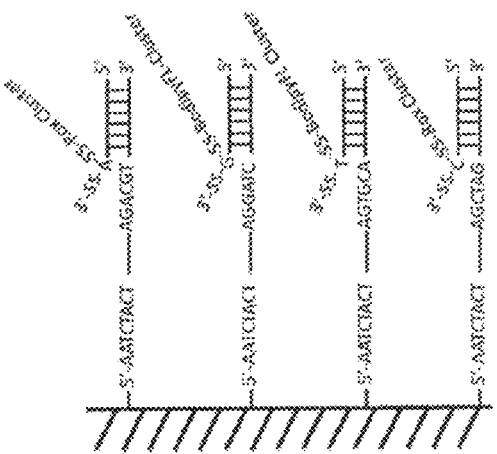
Figure 36C:
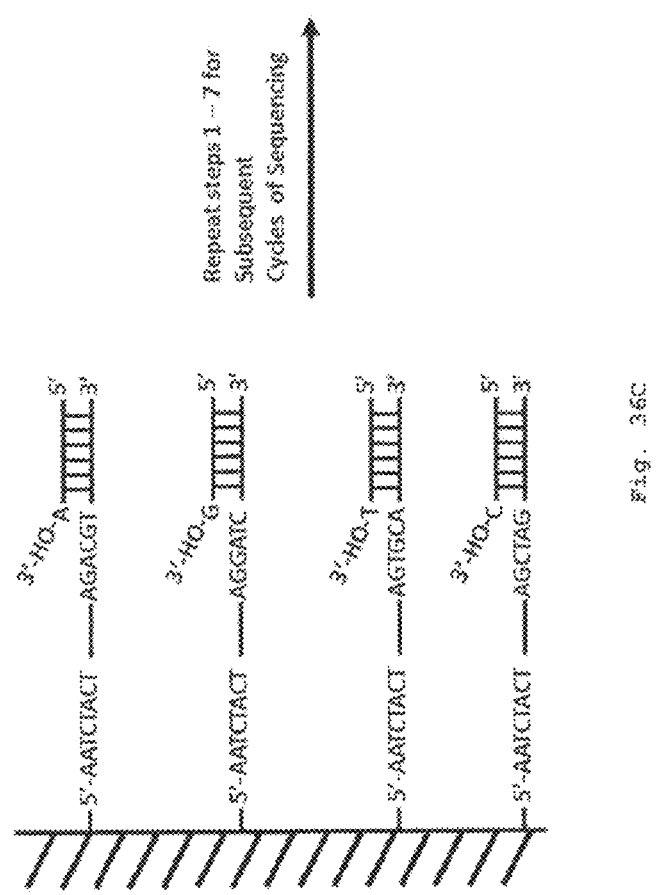

FIGS. 36A-36C contain a schematic showing Scheme VIA using 3'-O-SS(DTM)-dNTP-SS-Dye Clusters (3'-O-SS-dATP-7-SS-Rox Cluster, 3'-O-SS-dTTP-5-SS-BodipyFL Cluster), 3'-O-SS(DTM)-dNTP-SS-Anchor Clusters (3'-O-SS-dCTP-5-SS-Biotin Cluster, 3'-O-SS-dGTP-7-SS-TCO Cluster) and corresponding dye-labeled anchor binding molecules (Streptavidin-Rox, Tetrazine-BodipyFL) to perform 2-color DNA SBS. Step 1, Addition of DNA polymerase and the four nucleotide analogues (3'-O-SS-dATP-7-SS-Rox Cluster, 3'-O-SS-dTTP-5-SS-BodipyFL Cluster, 3'-O-SS-dCTP-5-SS-Biotin Cluster, 3'-O-SS-dGTP-7-SS-TCO Cluster) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the anchor cluster- or dye cluster-labeled dNTPs in step 1. The growing DNA strands are terminated with one of the four anchor cluster- or dye cluster-labeled nucleotide analogues (A, C, G, T) or the same one of the four nucleotide analogues (A, C, G, T) without dye or anchor cluster. Step 3, after washing away the unincorporated dye- or anchor-labeled nucleotides, detection of the unique fluorescence signal from each of the fluorescent dyes on the DNA products allows the identification of two of the incorporated nucleotide for sequence determination: Rox signal indicates incorporation of A, BodipyFL signal indicates incorporation of T. Step 4, labeling with Streptavidin-Rox molecules which will bind to the biotin anchor clusters and Tetrazine-BodipyFL molecules which will bind to the TCO anchor clusters. Step 5, after washing, a second round of detection of the unique fluorescence signal from each of the fluorescent dyes on the DNA products allows the identification of the remaining two incorporated nucleotides for sequence determination. A new Rox signal indicates incorporation of C; a new BodipyFL signal indicates incorporation of G. Next, in Step 6, treatment of the DNA products with THP cleaves the SS linker, leading to the removal of the remaining fluorescent dye clusters and the regeneration of a free 3'-OH group on the DNA extension product, which is ready for the next cycle of the DNA sequencing reaction. Step 7, after washing away THP, an optional imaging step will confirm all dyes have been removed, in preparation for the next cycle of sequencing. Though not indicated in Scheme VIA, if desired, the presence of an additional SS linkage between the Azo group and the base results in the production of a shorter scar on the incorporated nucleotide after THP treatment which should result in longer reads. Structures of modified nucleotides used in this scheme are shown in FIG. 10A.

Schemes Involving Quantum Dots

Scheme VIB: Two-color SB with two anchors, two varieties of quantum dots, and two cleavable linkers: imaging after labeling and cleavage. In Scheme VIB, the orthogonal set of nucleotide analogues consists of Anchor1 attached via an SS linkage, Anchor2 attached via an SS linkage, Anchor1 attached via an Azo linkage, and Anchor 2 attached via an Azo linkage each attached to a different base. Incorporation is carried out. Then Anchor1-Binding Molecule with Quantum Dot 1 (QD1) and Anchor2-Binding Molecule with QD2 are added. After imaging with excitation of both QDs by a single laser due to the broad adsorption spectra of quantum dots, appearance of QD1 fluorescence will limit the choice of incorporated nucleotide analogues to two possibilities and appearance of QD2 fluorescence will limit the choice of incorporated nucleotide analogues to the other two alternatives. Imaging, again with a single laser, after cleavage of the Azo linker with sodium dithionite will indicate the specific nucleotide analogue incorporated. Cleavage with THP will then remove the remaining QDs and restore the 3'-OH group for subsequent sequencing cycles. In the example shown, anchors are biotin and TCO, cleavable linkers are Azo and SS, and QD1 and QD2 are green and red emitters respectively, but other combinations of cleavable linkers, anchors and different QDs could also be used.

Figure 37C:
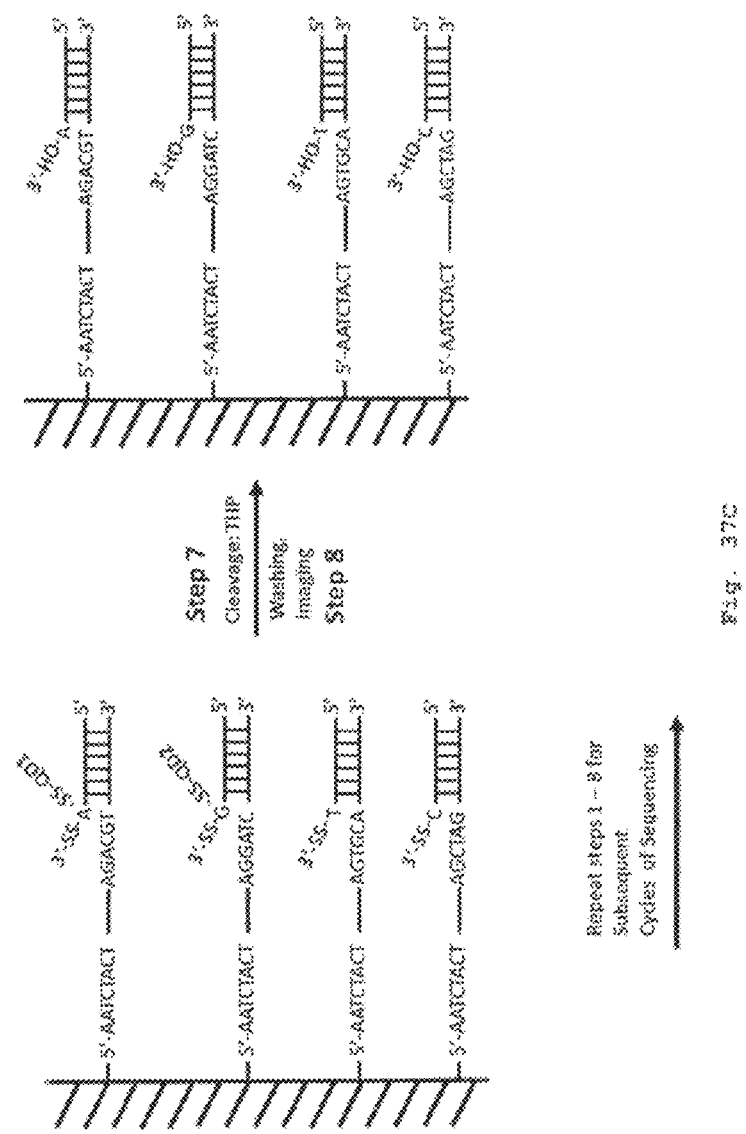
Figure 38A:
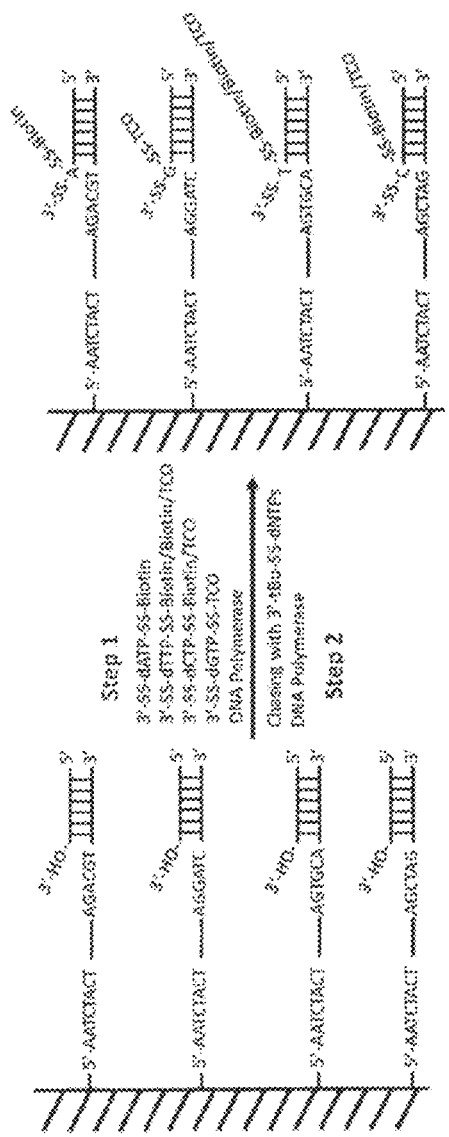
FIGS. 38A-38D: A schematic showing Scheme VIC using 3'-O-SS(DTM)-dNTP-SS-Anchors (3'-O-SS-dATP-7-SS-Biotin, 3'-O-SS-dGTP-7-SS-TCO, 3'-O-SS-dTTP-5-SS-Biotin/Biotin/TCO, 3'-O-SS-dCTP-5-SS-Biotin/TCO) and the corresponding Dye Labeled Binding Molecules (Quantum Dot 1 (Green)-labeled Streptavidin and Quantum Dot 2 (Red)-labeled Tetrazine) to perform 2-color DNA SBS.
Figure 38B:
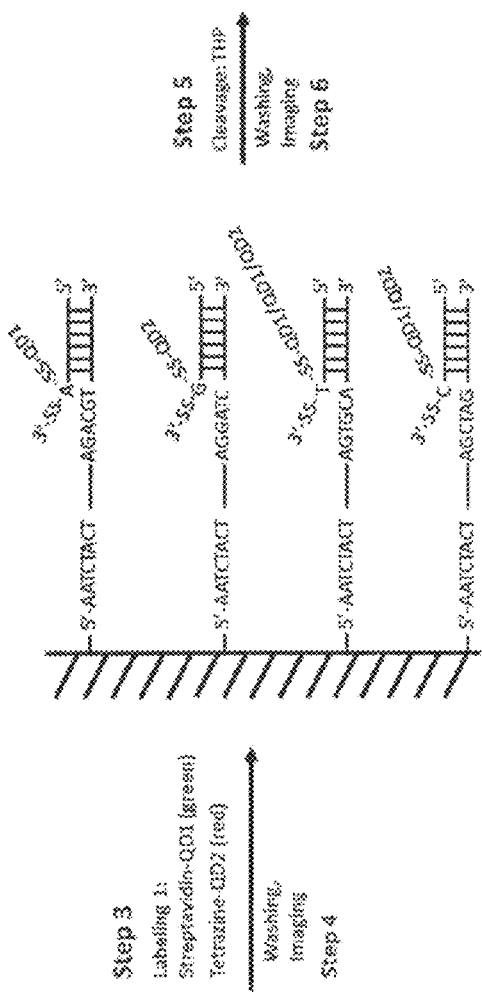
Figure 38C:
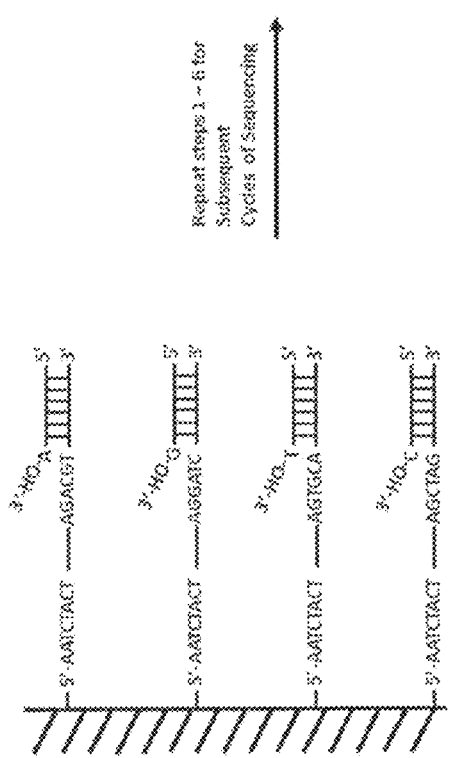
Figure 38D:
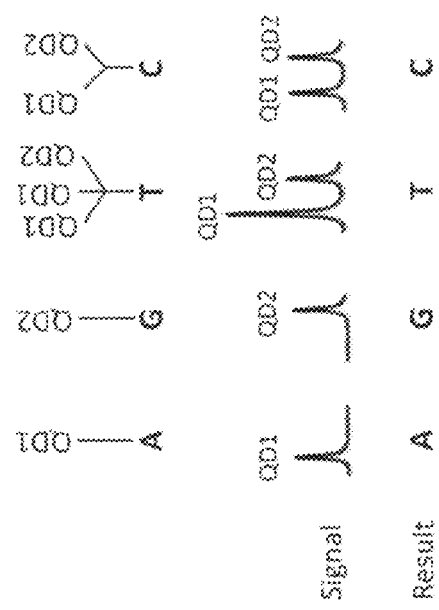

FIGS. 37A-37C contain a schematic showing Scheme VIB using 3'-O-SS(DTM)-dNTP-SS-Anchors (3'-O-SS-dATP-7-SS-Biotin, 3'-O-SS-dGTP-7-SS-TCO), 3'-O-SS (DTM)-dNTP-Azo-Anchors (3'-O-SS-dTTP-5-Azo-TCO, 3'-O-SS-dCTP-5-Azo-Biotin) and the corresponding Dye Labeled Binding Molecules (Quantum Dot 1 (Green)-labeled Streptavidin and Quantum Dot 2 (Red)-labeled Tetrazine) to perform 2-color DNA SBS. Step 1, Addition of DNA polymerase and the four nucleotide analogues (3'-O-SS-dATP-7-SS-Biotin, 3'-O-SS-dGTP-7-SS-TCO, 3'-O-SS-dTTP-5-Azo-TCO, 3'-O-SS-dCTP-5-Azo-Biotin) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyl-dithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the anchor labeled dNTPs in step 1. The growing DNA strands are terminated with one of the four anchor labeled nucleotide analogues (A, C, G, T) or the same one of the four nucleotide analogues (A, C, G, T) without anchor. Step 3, labeling with Streptavidin-QD1 and Tetrazine-QD2. QD1 will bind specifically to the A and C nucleotide analogues, while QD2 will bind to the G and T analogues. Step 4, After washing away remaining free label and excess nucleotides, detection of QD1 fluorescence will indicate incorporation of A or C; QD2 fluorescence will indicate incorporation of G or T. Next, in Step 5, treatment of the DNA products with sodium dithionite cleaves the azo linker, leading to the removal of QDs on T and C. Step 6, After washing away cleaved QDs, imaging for the presence of QD1 (green) and QD2 (red) fluorescence is carried out. In this step, if it has already been determined that the incorporated nucleotide could be A or C, loss of fluorescence would reveal it to be C, while remaining fluorescence would reveal it to be A. Similarly, for signals previously determined as G or T, loss of fluorescence would indicate incorporation of T specifically while remaining fluorescence would indicate incorporation of G. Next, in Step 7, treatment of the DNA products with THP cleaves the SS linker, leading to the removal of the remaining QDs and the regeneration of a free 3'-OH group on the DNA extension product. Step 8, after washing away THP, an optional imaging step will confirm all dyes have been removed, in preparation for the next cycle of sequencing. Though not indicated in Scheme VIB, if desired, the presence of an additional SS linkage between the Azo group and the base results in the production of a shorter scar on the incorporated nucleotide after THP treatment which should result in longer reads. Structures of modified nucleotides used in this scheme are shown in FIG. 10B.

Scheme VIC: Two-color SBS with two anchors in various ratios and two varieties of quantum dots: imaging after labeling. In Scheme VIC, the four nucleotide analogues are connected to either Anchor1, Anchor2, a 1:1 mixture of Anchor1:Anchor2, and a 2:1 mixture of Anchor1:Anchor2, all via an SS linker. After incorporation of all four nucleotide analogues, a labeling step is performed with Anchor1-Binding Molecule with QD1 and Anchor2-Binding Molecule with QD2. Imaging with excitation of both QDs by a single laser due to the broad adsorption spectra of quantum dots will reveal fluorescence due to QD1, fluorescence due to QD2, or intermediate fluorescence depending on the ratio of QD1 and QD2, indicating the specific nucleotide analogue incorporated. Cleavage with THP will then remove the remaining QDs and restore the 3'-OH group for subsequent sequencing cycles. In the example shown, anchors are biotin and TCO, and QD1 and QD2 are green and red emitters respectively, but other combinations of anchors and different QDs could also be used.

Figure 10C:
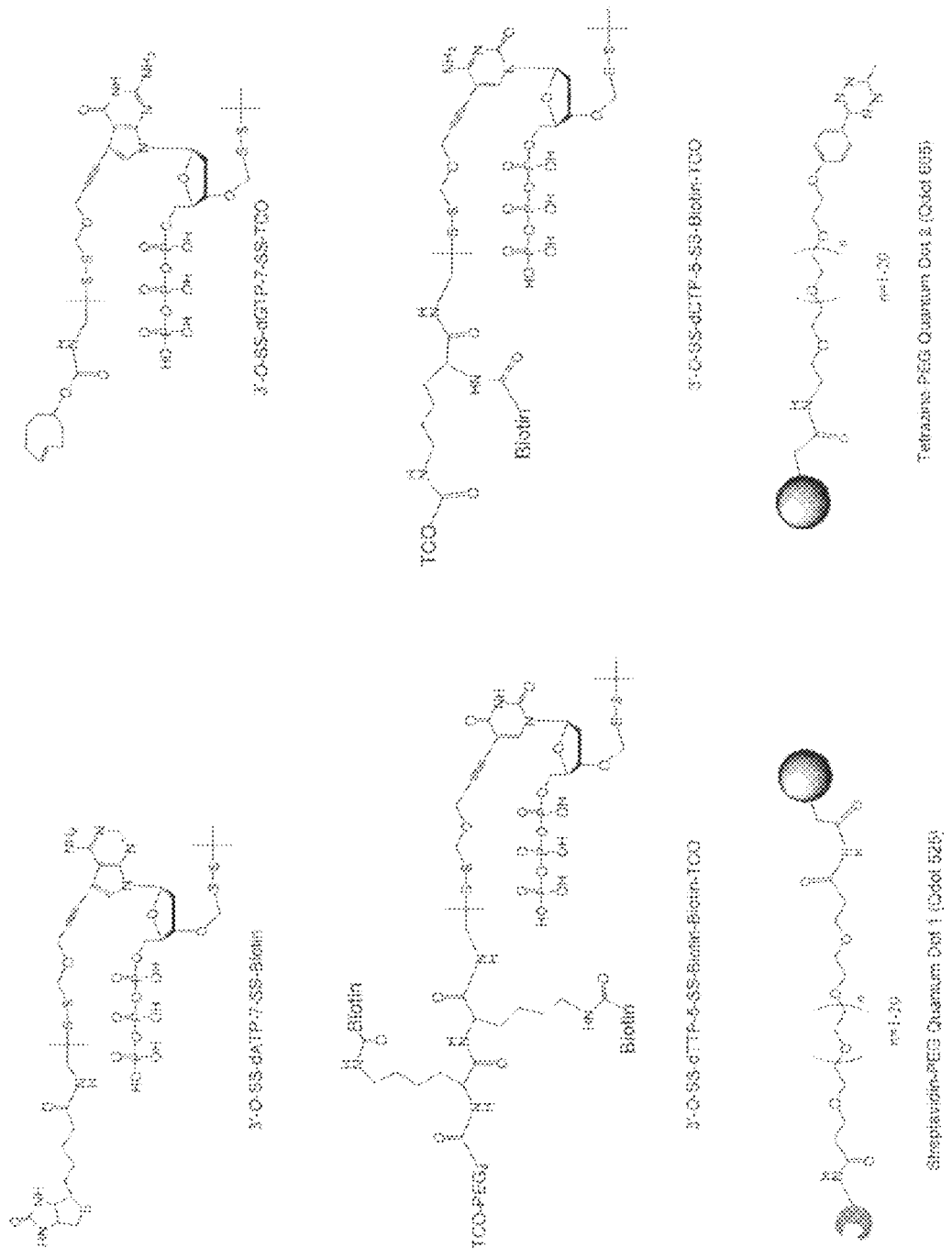
FIG. 10C: 3'-O-SS(DTM)-dNTP-SS-Anchors (3'-O-SS-dATP-7-SS-Biotin and 3'-O-SS-dGTP-7-SS-TCO), 3'-O-SS-dNTP-SS-Anchor-Cluster (3'-O-SS-dTTP-5-SS-Biotin-Biotin-TCO and 3'-O-SS-dCTP-5-SS-Biotin-TCO) and the corresponding Quantum Dot Labeled Binding Molecules (Qdot 525 Labeled Streptavidin and Qdot 605 Labeled Tetrazine) for one laser-2-color DNA SBS using quantum dots approach delineated in Scheme VIC.

FIGS. 38A-38D contain a schematic showing Scheme VIC using 3'-O-SS(DTM)-dNTP-SS-Anchors (3'-O-SSdATP-7-SS-Biotin, 3'-O-SS-dGTP-7-SS-TCO, 3'-O-SS-dTTP-5-SS-Biotin/Biotin/TCO, 3'-O-SS-dCTP-5-SS-Biotin/TCO) and the corresponding Dye Labeled Binding Molecules (Quantum Dot 1 (Green)-labeled Streptavidin and Quantum Dot 2 (Red)-labeled Tetrazine) to perform 2-color DNA SBS. Step 1, Addition of DNA polymerase and the four nucleotide analogues (3'-O-SS-dATP-7-SS-Biotin, 3'-O-SS-dGTP-7-SS-TCO, 3'-O-SS-dTTP-5-SS-Biotin/Biotin/TCO, 3'-O-SS-dCTP-5-SS-Biotin/TCO) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the anchor labeled dNTPs in step 1. The growing DNA strands are terminated with one of the four anchor labeled nucleotide analogues (A, C, G, T) or the same one of the four nucleotide analogues (A, C, G, T) without anchor. Step 3, labeling with Streptavidin-QD1 and Tetrazine-QD2. Only QD1 will bind to the A nucleotide analogue, only QD2 will bind to the G analogue, two molecules of QD1 and one molecule of QD2 will bind to the T analogue, and 1 molecule each of QD1 and QD2 will bind to the C analogue. Step 4, After washing away remaining free QDs and excess nucleotides, detection of QD1 fluorescence (green) will indicate incorporation of A, QD2 fluorescence (red) will indicate incorporation of G, an equal mixture of QD1 and QD2 fluorescence will indicate incorporation of C, and a 2:1 mixture of QD1:QD2 fluorescence will indicate incorporation of T. Next, in Step 5, treatment of the DNA products with THP cleaves the SS linker, leading to the removal of the QDs and the regeneration of a free 3'-OH group on the DNA extension product. Step 6, after washing away THP, an optional imaging step will confirm all QDs have been removed, in preparation for the next cycle of sequencing. A schematic representation of fluorescence spectra is shown at the bottom of Scheme VIC, indicating the ratiometric nature of this approach. Though not indicated in Scheme VIC, if desired, the presence of an additional SS linkage between the Azo group and the base results in the production of a shorter scar on the incorporated nucleotide after THP treatment which should result in longer reads. Structures of modified nucleotides used in this scheme are shown in FIG. 10C.

Scheme VID: Two-color SBS with two anchors, two varieties of quantum dots, and two cleavable linkers, where anchors are present at either or both base and 3' positions: imaging after labeling and cleavage. This scheme is identical in principle to Scheme VIB, except that anchors for attachment of quantum dots may be linked to the base, to the 3'-O position or to both the base and 3'-O position.

Figure 10D:
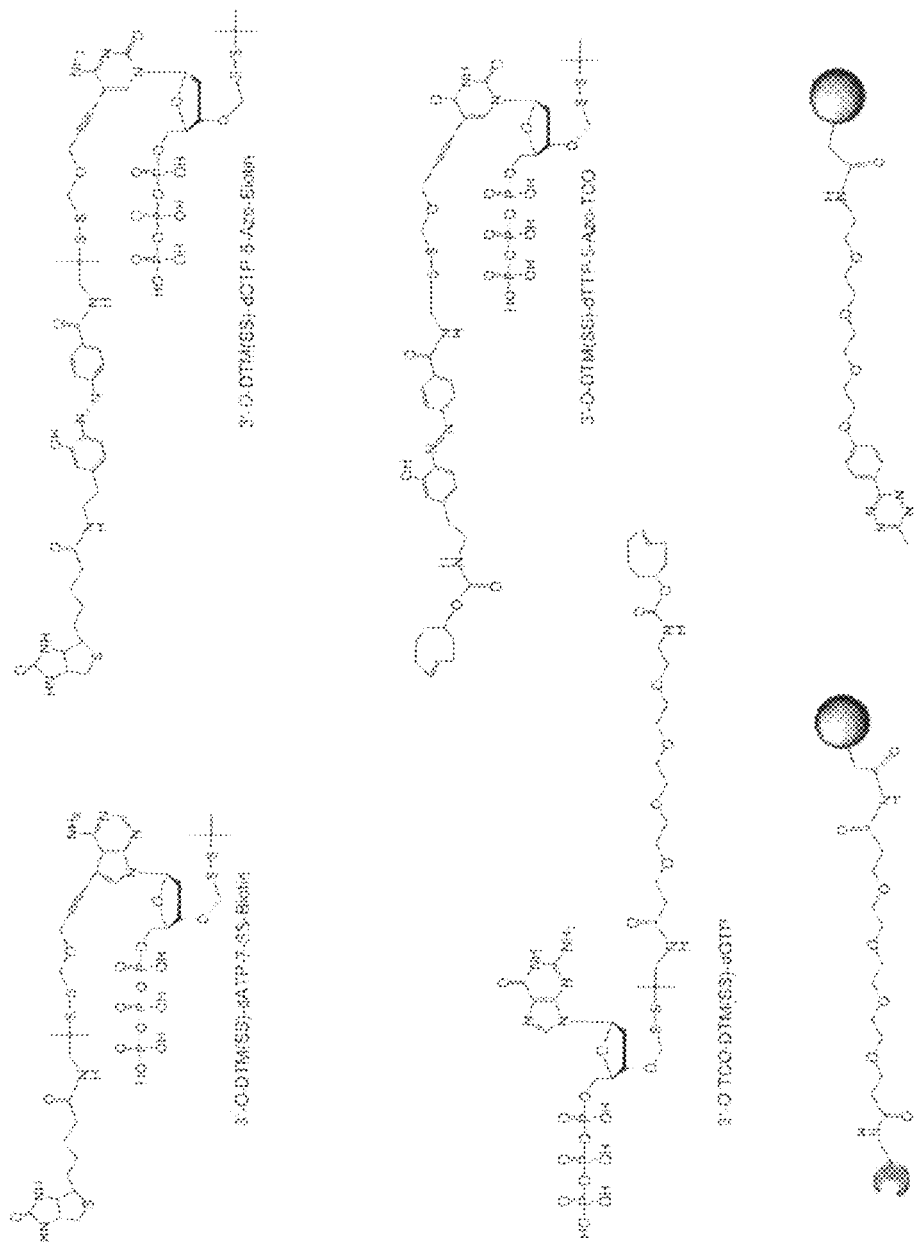
FIG. 10D: 3'-O-SS(DTM)-dNTP-SS-Anchors (3'-O-SS-dATP-7-SS-Biotin), 3'-O-SS(DTM)-dNTP-Azo-Anchors (3'-O-SS-dTTP-5-Azo-TCO and 3'-O-SS-dCTP-5-Azo-Biotin), 3'-O-Anchor-SS(DTM)-dNTP(3'-O-TCO-SS(DTM)-dGTP) and the corresponding Quantum Dot Labeled Binding Molecules (Qdot 605 Labeled Tetrazine and Qdot 525 Labeled Streptavidin) for 2-color DNA SBS using approach delineated in Scheme VID. Extended PEG linkers of various lengths may be placed on the Quantum Dot Labeled Binding Molecules as in FIG. 10C if desired.
Figure 39C:
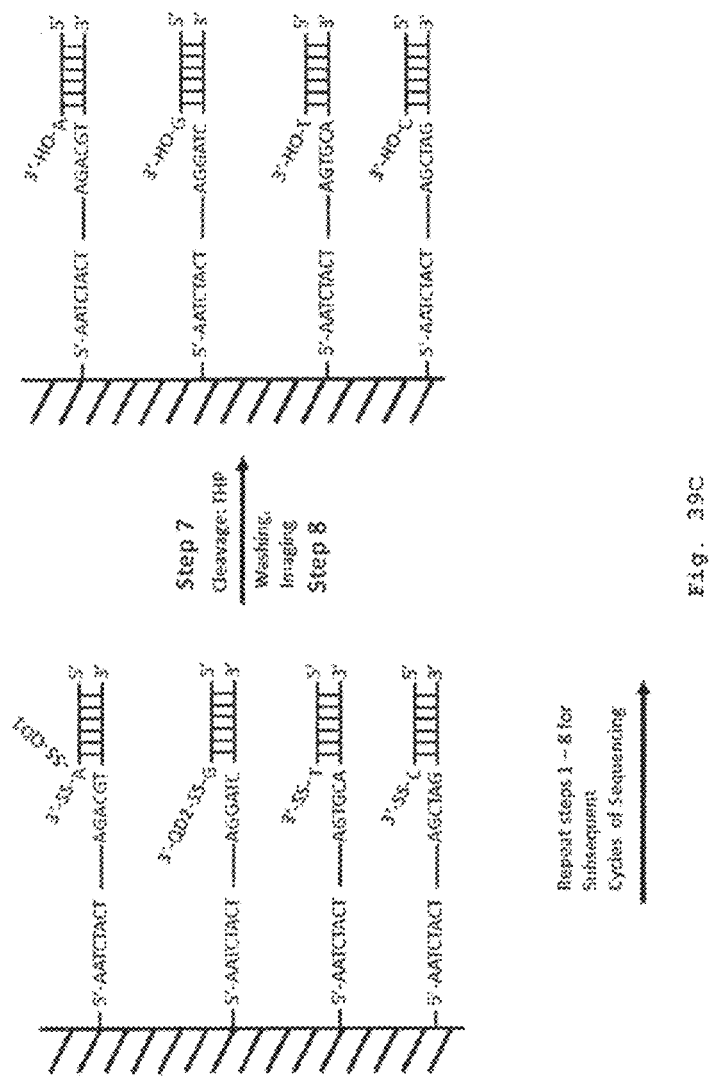

FIGS. 39A-39C contain a schematic showing Scheme VID using 3'-O-SS(DTM)-dNTP-SS-Anchor (3'-O-SS-dATP-7-SS-Biotin), 3'-O-SS(DTM)-dNTP-Azo-Anchors (3'-O-SS-dTTP-5-Azo-TCO, 3'-O-SS-dCTP-5-Azo-Biotin), 3'-O-Anchor-SS(DTM)-dNTP (3'-O-TCO-SS-dGTP), and the corresponding Dye Labeled Binding Molecules (Quantum Dot 1 (Green)-labeled Streptavidin and Quantum Dot 2 (Red)-labeled Tetrazine) to perform 2-color DNA SBS. Step 1, Addition of DNA polymerase and the four nucleotide analogues (3'-O-SS-dATP-7-SS-Biotin, 3'-O-SS-dTTP-5-Azo-TCO, 3'-O-SS-dCTP-5-Azo-Biotin, 3'-O-TCO-SS-dGTP) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the anchor labeled dNTPs in step 1. The growing DNA strands are terminated with one of the four anchor labeled nucleotide analogues (A, C, G, T) or the same one of the four nucleotide analogues (A, C, G, T) without anchor. Step 3, labeling with Streptavidin-QD1 and Tetrazine-QD2. QD1 will bind specifically to the A and C nucleotide analogues, while QD2 will bind to the G and T analogues. Step 4, After washing away remaining free label and excess nucleotides, detection of QD1 fluorescence will indicate incorporation of A or C; QD2 fluorescence will indicate incorporation of G or T. Next, in Step 5, treatment of the DNA products with sodium dithionite cleaves the azo linker, leading to the removal of QDs on T and C. Step 6, After washing away cleaved QDs, imaging for the presence of QD1 (green) and QD2 (red) fluorescence is carried out. In this step, if it has already been determined that the incorporated nucleotide could be A or C, loss of fluorescence would reveal it to be C, while remaining fluorescence would reveal it to be A. Similarly, for signals previously determined as G or T, loss of fluorescence would indicate incorporation of T specifically while remaining fluorescence would indicate incorporation of G. Next, in Step 7, treatment of the DNA products with THP cleaves the SS linker, leading to the removal of the remaining QD and the regeneration of a free 3'-OH group on the DNA extension product. Step 8, after washing away THP, an optional imaging step will confirm all QDs have been removed, in preparation for the next cycle of sequencing. Though not indicated in Scheme VID, if desired, the presence of an additional SS linkage between the Azo group and the base results in the production of a shorter scar on the incorporated nucleotide after THP treatment which should result in longer reads. Structures of modified nucleotides used in this scheme are shown in FIG. 10D.

Scheme VIE: Two-color SS with two anchors in various ratios and two varieties of quantum dots, where anchors are present at either or both base and 3' positions: imaging after labeling. This scheme is identical in principle to Scheme VIC, except that anchors for attachment of quantum dots may be linked to the base, to the 3'-O position or to both the base and 3'-O position.

Figure 10E:
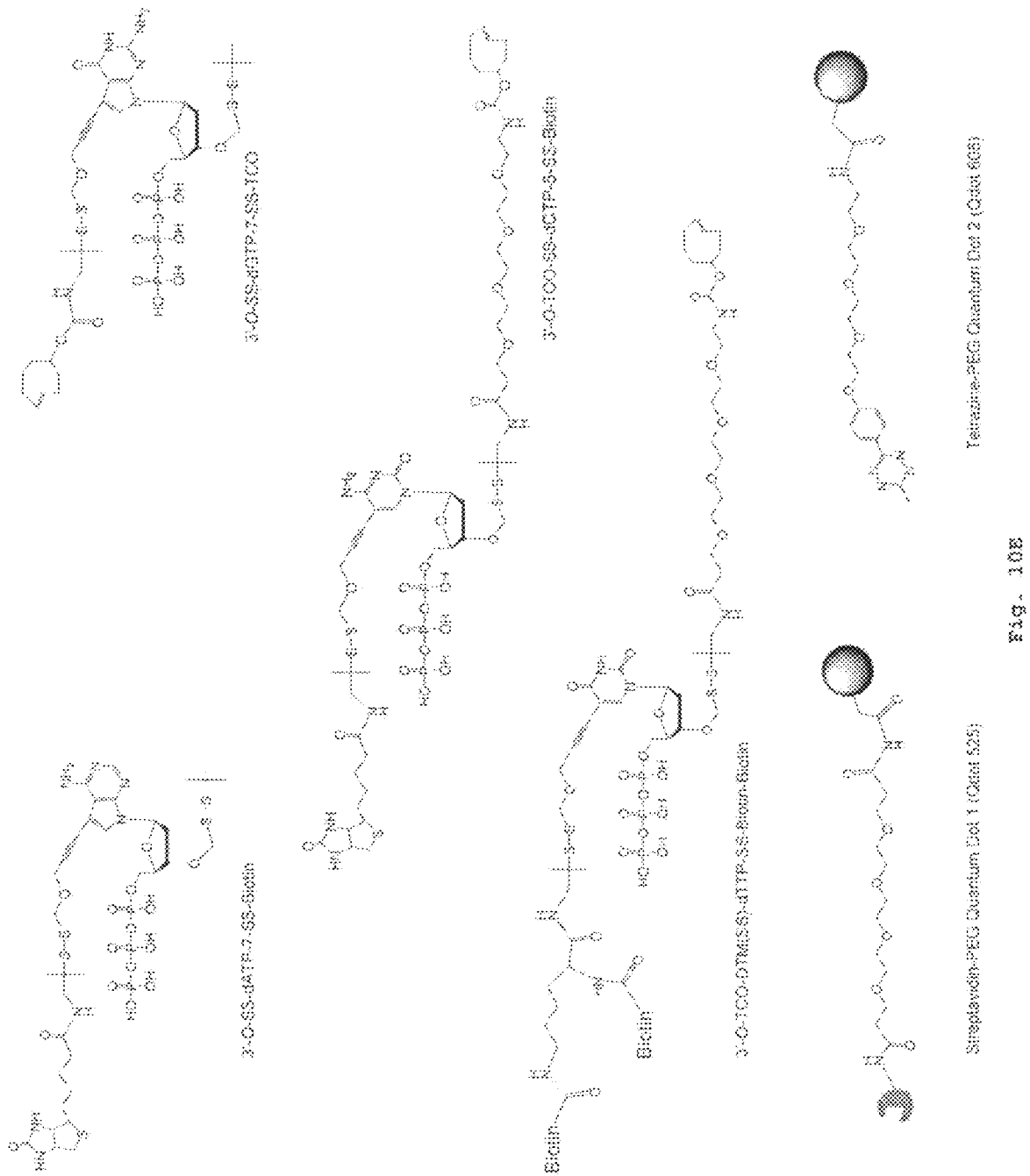
FIG. 10E: 3'-O-SS(DTM)-dNTP-SS-Anchors (3'-O-SS-dATP-7-SS-Biotin and 3'-O-SS-dGTP-7-SS-TCO), 3'-O-Anchor-SS(DTM)-dNTP-SS-Anchor-Cluster (3'-O-TCO-SS-dTTP-5-SS-Biotin-Biotin and 3'-O-TCO-SS-dCTP-5-SS-Biotin) and the corresponding Quantum Dot Labeled Binding Molecules (Qdot 605 Labeled Tetrazine and Qdot 525 Labeled Streptavidin) for one laser-2-color DNA SBS using approach delineated in Scheme VIE. Extended PEG linkers of various lengths may be placed on the Quantum Dot Labeled Binding Molecules as in FIG. 10C if desired.
Figure 40C:
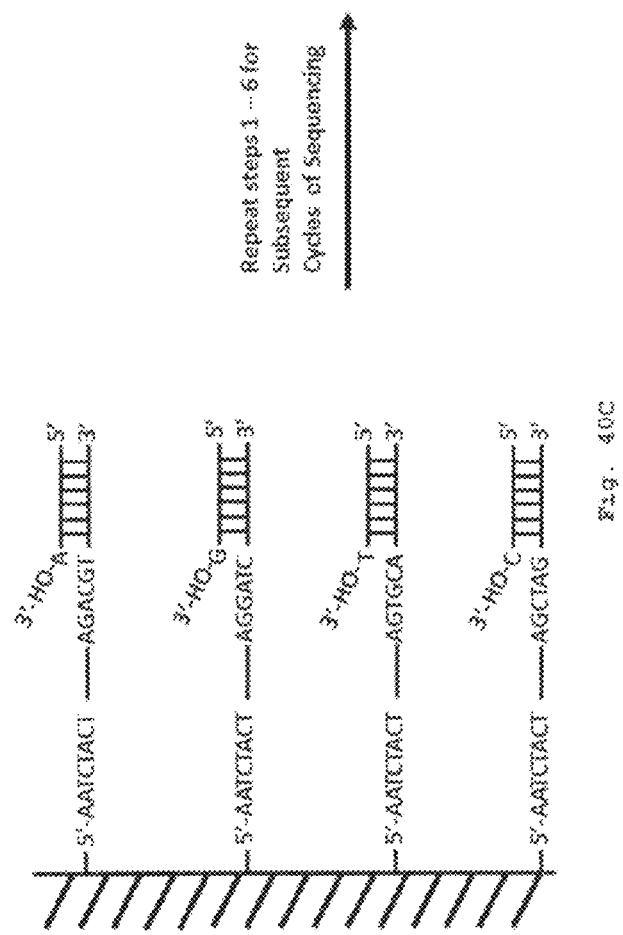

FIGS. 40A-40C contain a schematic showing Scheme VIE using 3'-O-SS(DTM)-dNTP-SS-Anchors (3'-O-SS-dATP-7-SS-Biotin, 3'-O-SS-dGTP-7-SS-TCO), 3'-O-Anchor-SS(DTM)-dNTP-SS-Anchors (3'-O-TCO-SS-dCTP-5-SS-Biotin, 3'-O-TCO-SS-dTTP-5-SS-Biotin/Biotin) and the corresponding Dye Labeled Binding Molecules (Quantum Dot 1 (Green)-labeled Streptavidin and Quantum Dot 2 (Red)-labeled Tetrazine) to perform 2-color DNA SBS. Step 1, Addition of DNA polymerase and the four nucleotide analogues (3'-O-SS-dATP-7-SS-Biotin, 3'-O-SS-dGTP-7-SS-TCO, 3'-O-TCO-SS-dCTP-5-SS-Biotin, 3'-O-TCO-SS-dTTP-5-SS-Biotin/Biotin) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the anchor labeled dNTPs in step 1. The growing DNA strands are terminated with one of the four anchor labeled nucleotide analogues (A, C, G, T) or the same-one of the four nucleotide analogues (A, C, G, T) without anchor. Step 3, labeling with Streptavidin-QD1 and Tetrazine-QD2. Only QD1 will bind to the A nucleotide analogue, only QD2 will bind to the G analogue, two molecules of QD1 and one molecule of QD2 will bind to the T analogue, and 1 molecule each of QD1 and QD2 will bind to the C analogue. Step 4, After washing away remaining free QDs and excess nucleotides, detection of QD1 fluorescence (green) will indicate incorporation of A, QD2 fluorescence (red) will indicate incorporation of G, an equal mixture of QD1 and QD2 fluorescence will indicate incorporation of C, and a 2:1 mixture of QD1:QD2 fluorescence will indicate incorporation of T. Next, in Step 5, treatment of the DNA products with THP cleaves the SS linker, leading to the removal of the QDs and the regeneration of a free 3'-OH group on the DNA extension product. Step 6, after washing away THP, an optional imaging step will confirm all QDs have been removed, in preparation for the next cycle of sequencing. A schematic representation of fluorescence spectra is shown at the bottom of Scheme VIC, indicating the ratiometric nature of this approach. Though not indicated in Scheme VIE, if desired, the presence of an additional SS linkage between the Azo group and the base results in the production of a shorter scar on the incorporated nucleotide after THP treatment which should result in longer reads. Structures of modified nucleotides used in this scheme are shown in FIG. 10E.

Schemes Involving Donor-Acceptor Pairs

Scheme VIIA: One-color SBS with two anchors, one donor-acceptor dye pair and two cleavable linkers: imaging after two labeling steps and after cleavage. In Scheme VII-A, the orthogonal set consists of Anchor1 containing DonorDye1 attached via an SS linkage, Anchor1 containing DonorDye1 attached via an Azo linkage, Anchor2 containing DonorDye1 attached via an SS linkage, and Anchor2 containing DonorDye1 attached via an Azo linkage each attached to a different base. Incorporation is carried out. Anchor1-Binding Molecule containing AcceptorDye1 is added. After imaging with excitation of DonorDye1, the appearance of fluorescence by AcceptorDye1 will indicate incorporation by two possible nucleotide analogues. Next Anchor2-Binding Molecule containing AcceptorDye1 is added. After imaging with excitation of DonorDye1, new appearance of fluorescence by AcceptorDye1 will indicate incorporation by the other two possible nucleotide analogues. Imaging after cleavage of the Azo linker with sodium dithionite will indicate the specific nucleotide analogue incorporated. Cleavage with THP will then remove the remaining dyes and restore the 3'-OH group for subsequent sequencing cycles. In the example shown, cleavable linkers are Azo and SS and DonorDye1 is Cy3 and AcceptorDye1 is Cy5, but other cleavable linkers (e.g., 2-nitrobenzyl or allyl) and other donor-acceptor pairs (e.g., CYA as donor with Rox or Cy3 as acceptor; FAM as donor with Rox as acceptor) could be used as well. The linker can be a long linear chain or dendrimer with 2 or more DonorDye1 molecules, in which case multiple acceptor dyes will be attached via the anchor-anchor binding molecule conjugation steps. This scheme would be particularly useful in the case of single molecule SBS as described above.

It should be recognized that the Donor Dye may be directly attached to the anchor molecule and the Acceptor Dye may be attached to the Anchor Binding Molecule as in the example shown. But the alternative arrangement, in which the Acceptor Dye is on the Anchor portion and the Donor Dye is on the Anchor Binding Molecule is just as reasonable, and in fact may have advantages. For instance, use of very large fluorescent structures, such as quantum dots (typically 10-50 nm semicolloidal nanocrystals) would preferentially be used in the labeling step. Quantum dots have advantages as FRET donors due to their broad absorption range allowing selection of an excitation wavelength that has no direct effect on the acceptor dye, very high brightness relative to organic fluorophores due to their very high extinction coefficients but similar quantum yields, tunability, stability and narrow bandwidth of the emission spectrum.

Scheme VIIB: One-color SBS with two anchors, one donor-acceptor dye pair and two cleavable linkers: imaging after two labeling steps and after cleavage. This scheme is practically identical to Scheme VIIA, except that the donor dye is attached to the base, while the anchors for attachment of the acceptor dye are present at the 3' position of the sugar. All the steps are performed in the same order as for Scheme VIIA. Careful design of the linkers on the base and 3' position will assure that the donor and acceptor dyes are within FRET distance of each other. While in this example, the Donor Dye is attached to the base and the Acceptor Dye is attached to the 3' position, the opposite positioning (Donor Dye at 3' and Acceptor Dye on base) is equally feasible.

Figure 12A:
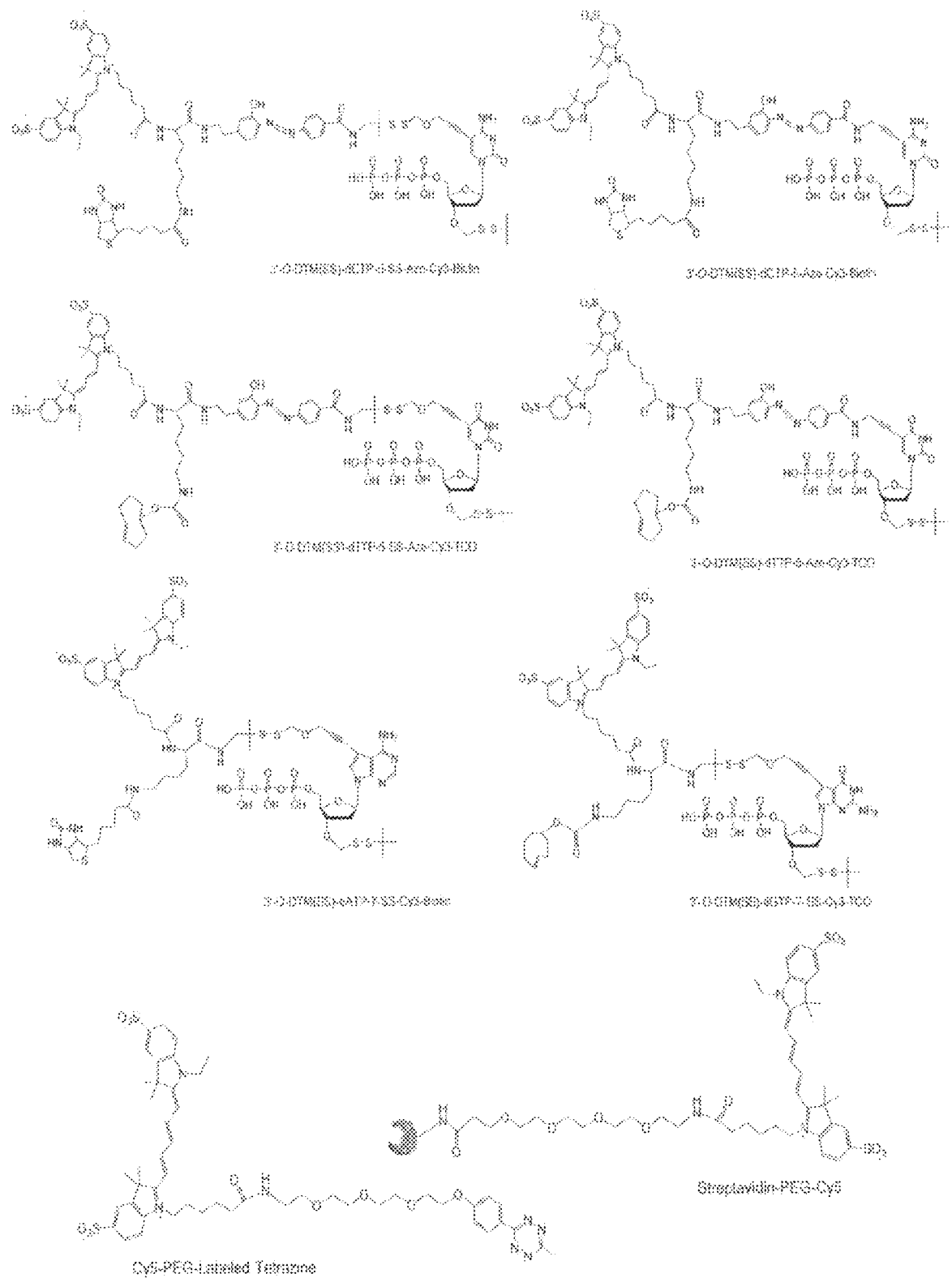
FIG. 12*k*: 3'-O-SS(DTM)-dNTP-SS-DonorDye-Anchors (3'-O-SS-dATP-7-SS-Cy3-Biotin and 3'-O-SS-dGTP-7-SS-Cy3-TCO), 3'-O-SS(DTM)-dNTP-DonorDye-Azo-Anchors (3'-O-SS-dTTP-5-Azo-Cy3-TCO or 3'-O-SS-dTTP-5-SS-Azo-Cy3-TCO and 3'-O-SS-dCTP-5-Azo-Cy3-Biotin or 3'-O-SS-dCTP-5-SS-Azo-Cy3-Biotin) and the corresponding Acceptor Dye Labeled Binding Molecules (Cy5 Labeled Streptavidin and Cy5 Labeled Tetrazine) for 1-color DNA SBS using approach delineated in Scheme VIIA. Though not shown in this figure, clusters of DonorDye-Anchors instead of a single copy of each may be placed on the nucleotide analogues.
FIGS. 12B-12C: 3'-O-Anchor-SS(DTM)-dNTP-Azo-DonorDye (3'-O-TCO-SS-dTTP-5-SS-Azo-Cy3, 3'-O-TCO-SS-dTTP-5-Azo-Cy3, 3'-O-Biotin-SS-dCTP-5-SS-Azo-Cy3 and 3'-O-SS-Biotin-dCTP-5-Azo-Cy3) 3'-O-Anchor-SS(DTM)-dNTP-SS-DonorDye (3'-O-Biotin-SS-dATP-7-SS-Cy3, 3'-O-TCO-SS-dGTP-7-SS-Cy3) and the corresponding Acceptor Dye Labeled Binding Molecules (Cy5 Labeled Streptavidin and Cy5 Labeled Tetrazine) for 1-color DNA SBS using approach delineated in Scheme VIIB. In this figure, the anchor molecules are attached to the SS linkage via formation of a triazole between an alkyne and an azide. Another option is attachment of the anchor to the SS bond through an amide bond between an amino group and an acid.
FIGS. 12D-12E: 3'-O-Anchor-SS(DTM)-dNTP-Azo-Acceptor Dye (3'-O-TCO-SS-dTTP-5-SS-Azo-Cy5, 3'-O-TCO-SS-dTTP-5-Azo-Cy5, 3'-O-Biotin-SS-dCTP-5-SS-Azo-Cy5 and 3'-O-SS-Biotin-dCTP-5-Azo-Cy5), 3'-O-Anchor-SS(DTM)-dNTP-SS-Acceptor Dye (3'-O-Biotin-SS-dATP-7-SS-Cy5, 3'-O-TCO-SS-dGTP-7-SS-Cy5) and the corresponding Donor Labeled Binding Molecules (Quantum Dot Labeled Streptavidin and Quantum Dot Labeled Tetrazine, or Cy3 Labeled Streptavidin and Cy3 Labeled Tetrazine) as alternate sets of molecules that can be used in the 1-color DNA SBS using approach delineated in Scheme VIIB. For instance, instead of using Cy3 as donor for Cy5, a QD can be used as the donor for Cy5. In this figure, the anchor molecules are attached to the SS linkage via formation of a triazole between an alkyne and an azide. Another option is attachment of the anchor to the SS bond through an amide bond between an amino group and an acid.
Figure 12B:
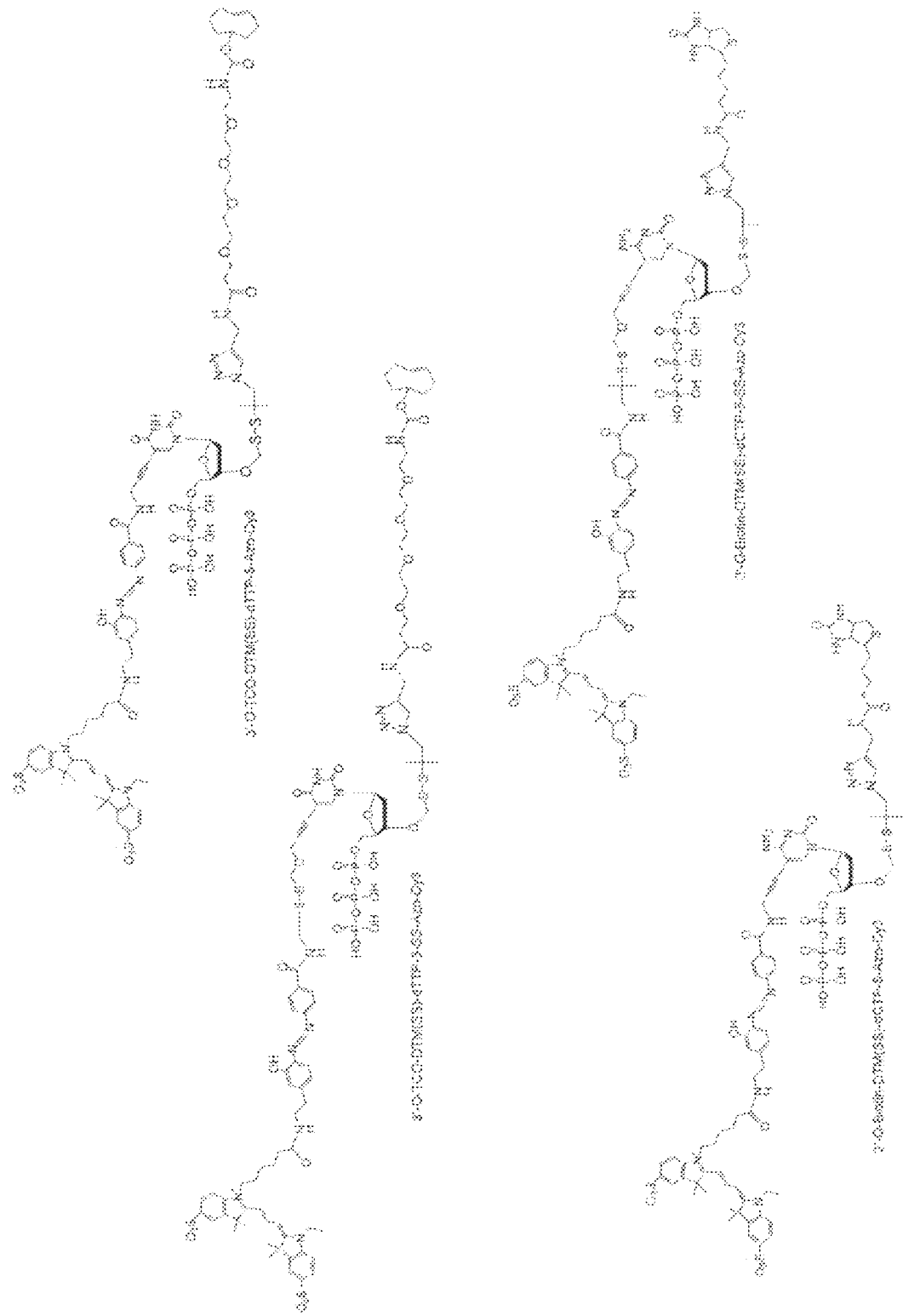
Figure 12C:
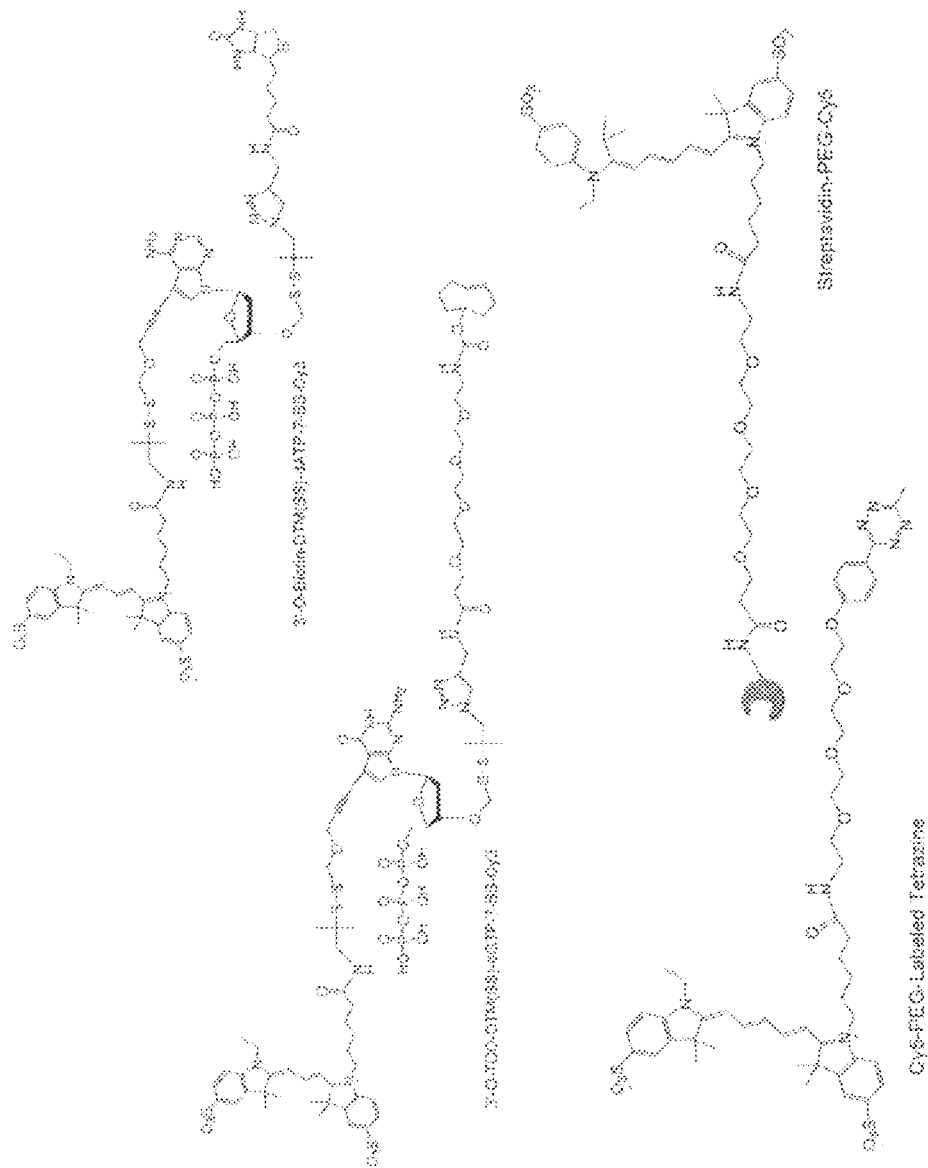
Figure 12D:
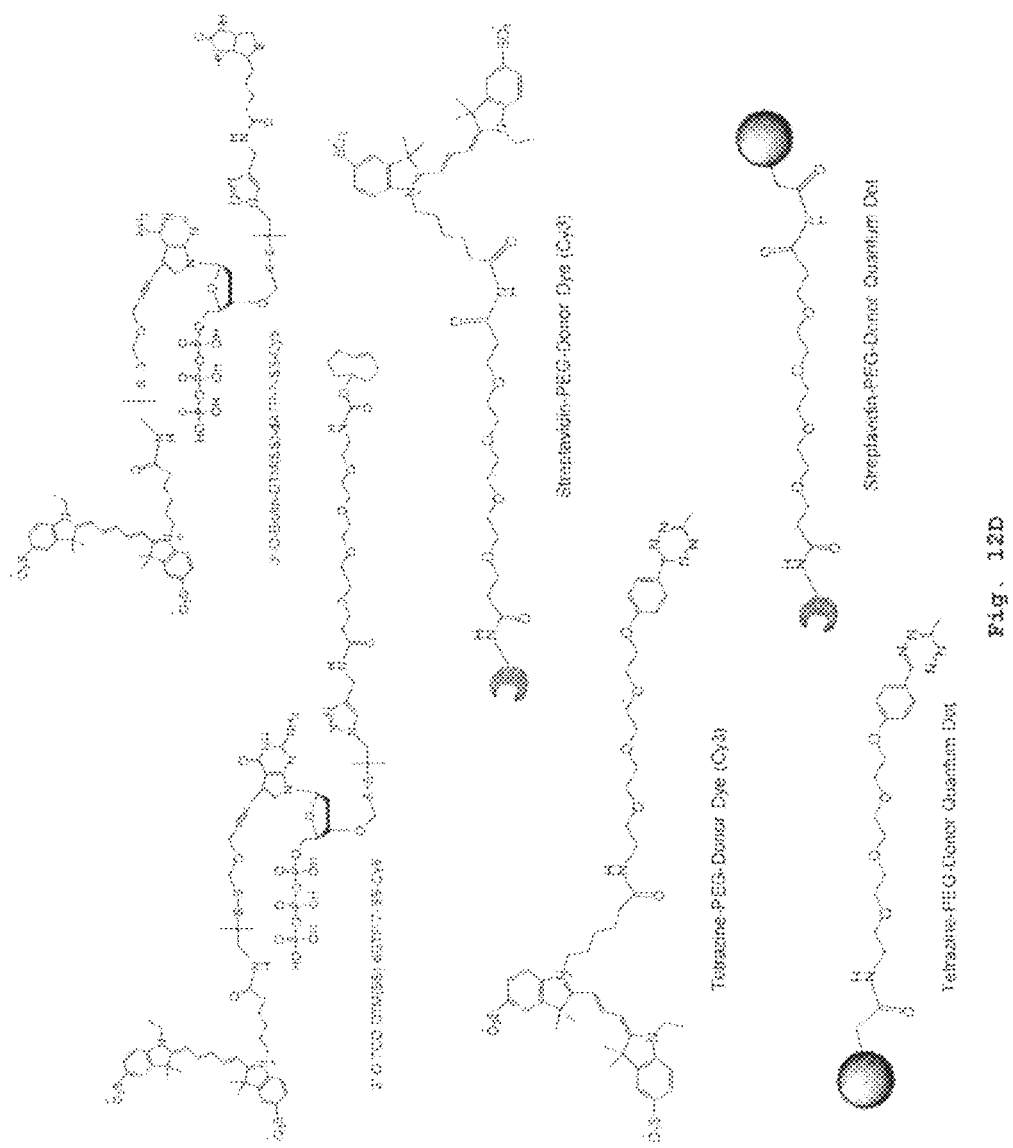
Figure 12B:
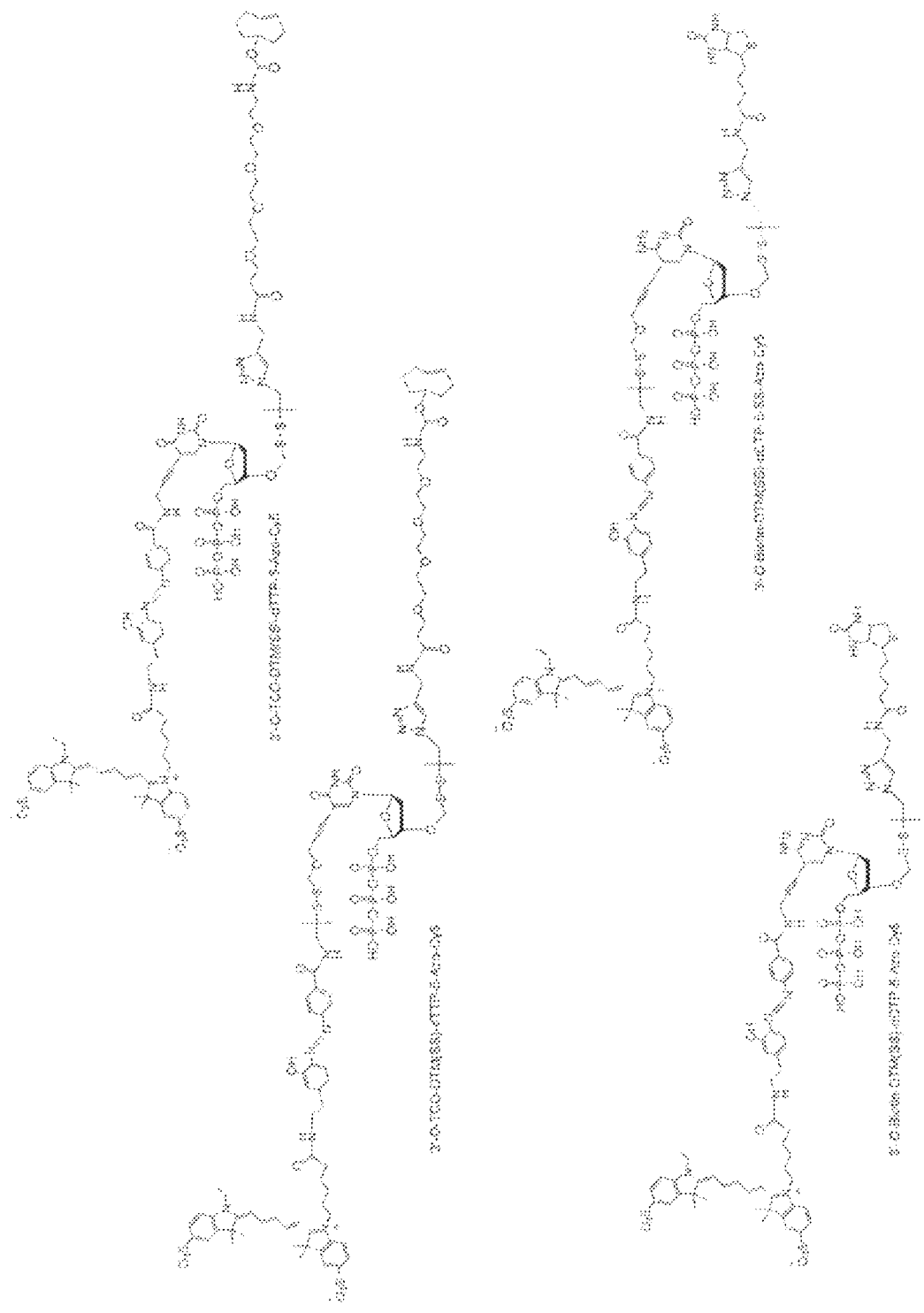
Figure 13:
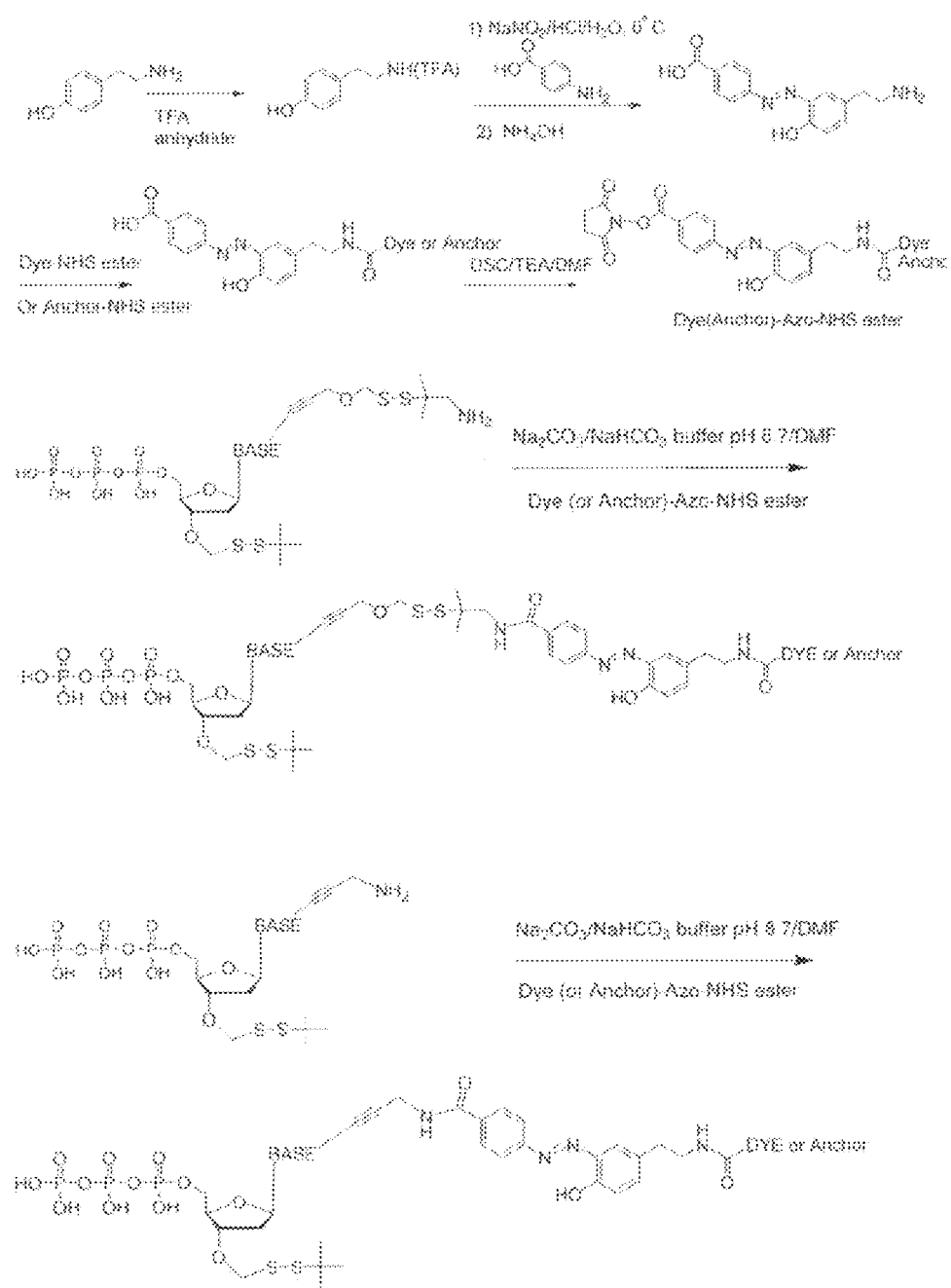
FIG. 13: General synthesis of 3'-O-SS-dNTP-Azo-Dye or -Anchor.
Figure 14A:
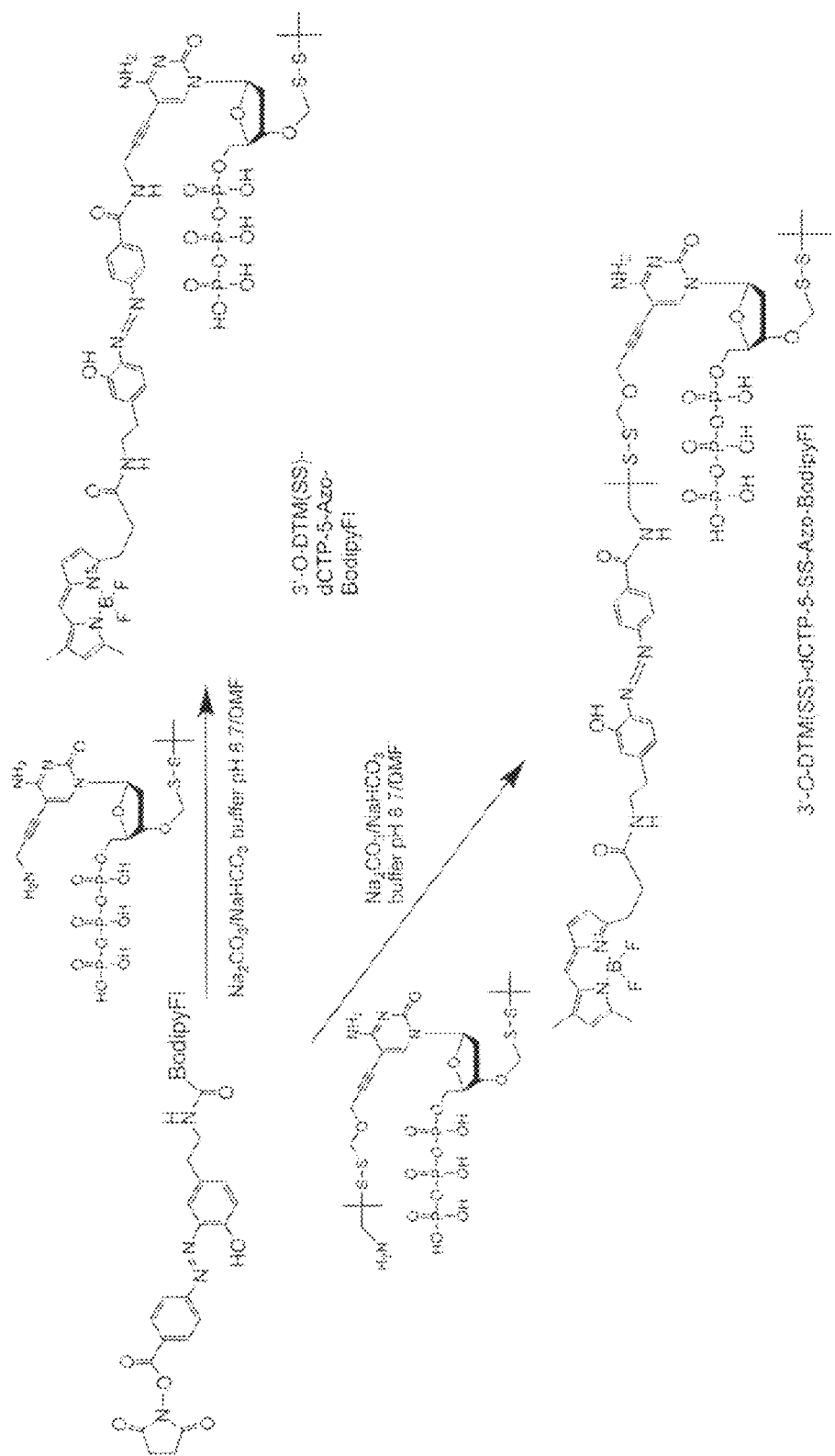
FIGS. 14A-14B: Synthesis of 3'-O-SS-dNTP-Azo-Dye: 3'-O-SS-dCTP-5-Azo-BodipyFL and 3'-O-SS-dGTP-7-Azo-Rox as examples.
Figure 14B:
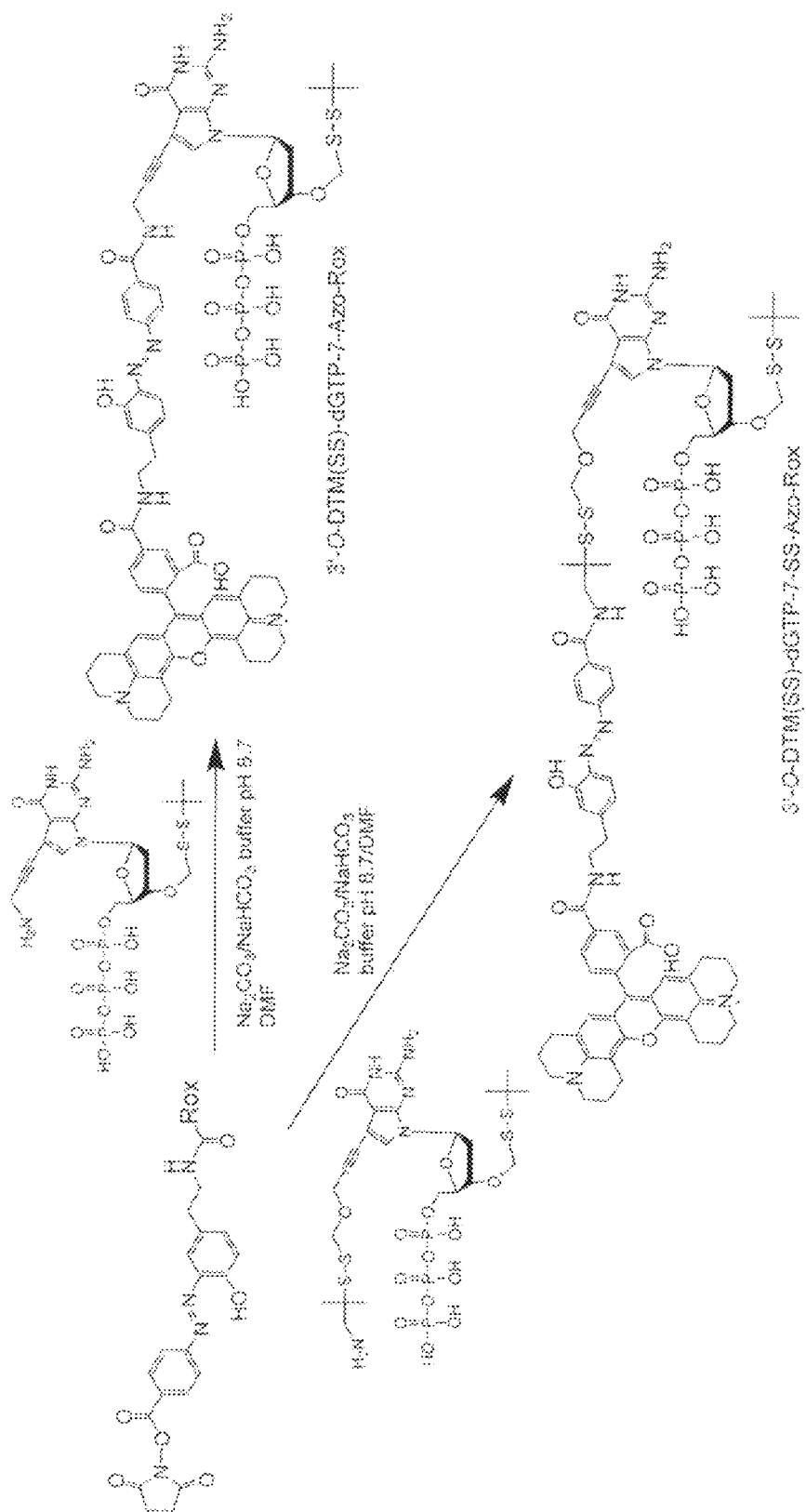
Figure 15A:
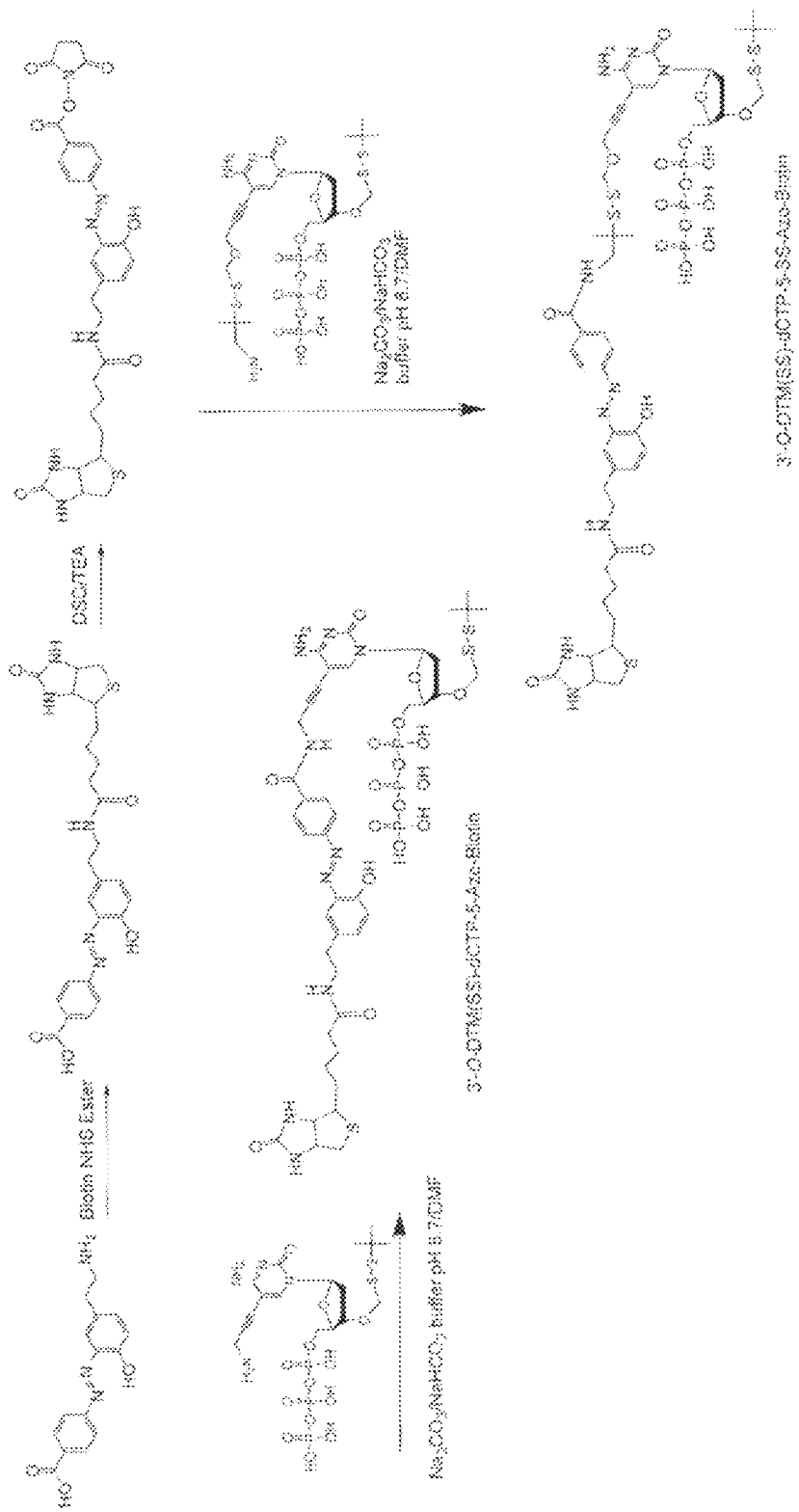
FIGS. 15A-15B: Synthesis of 3'-O-SS-dNTP-Azo-Anchor: 3'-O-SS-dCTP-5-Azo-Biotin and 3'-O-SS-dATP-7-Azo-TCO as examples.
Figure 15B:
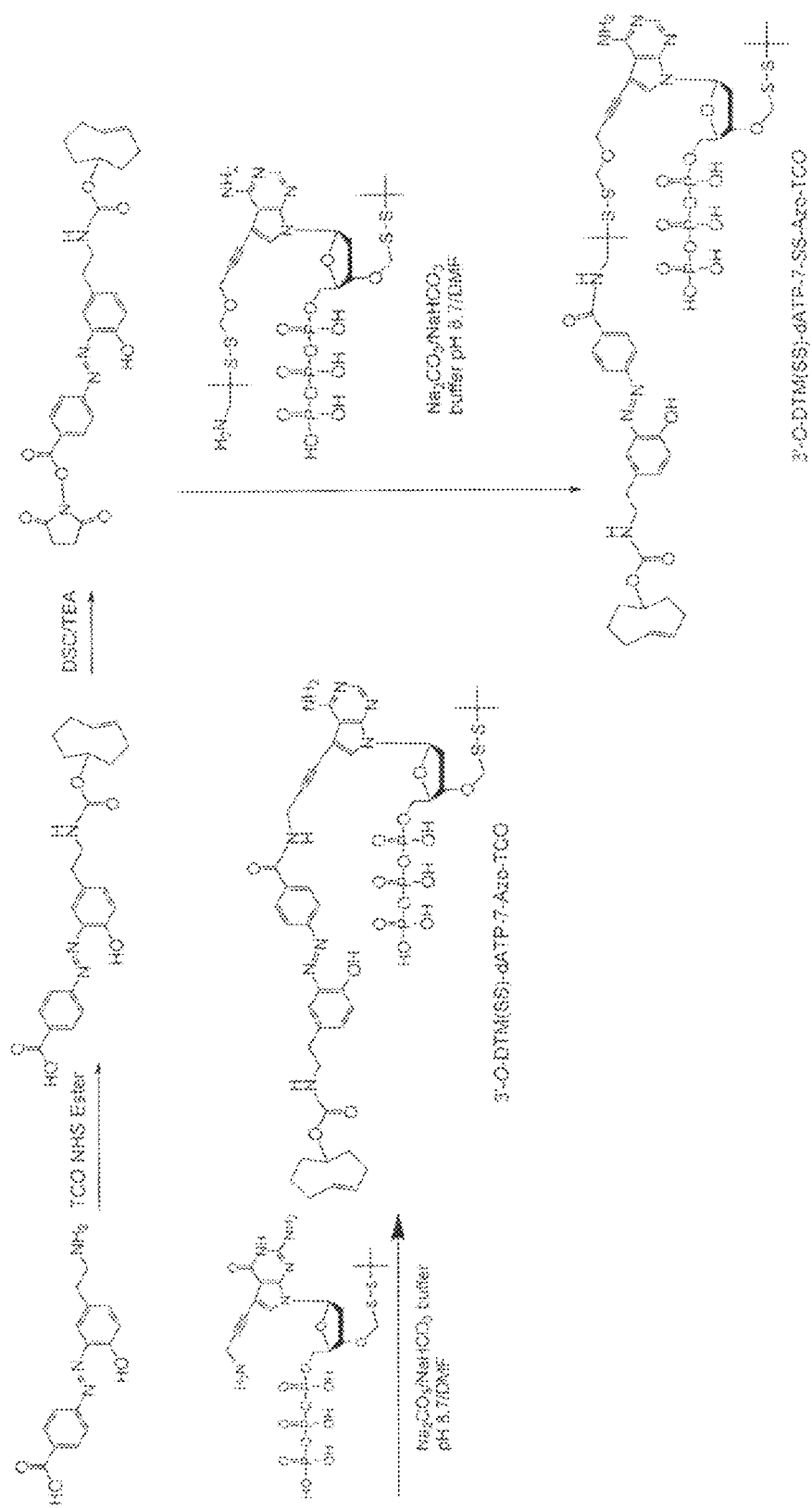
Figure 16:
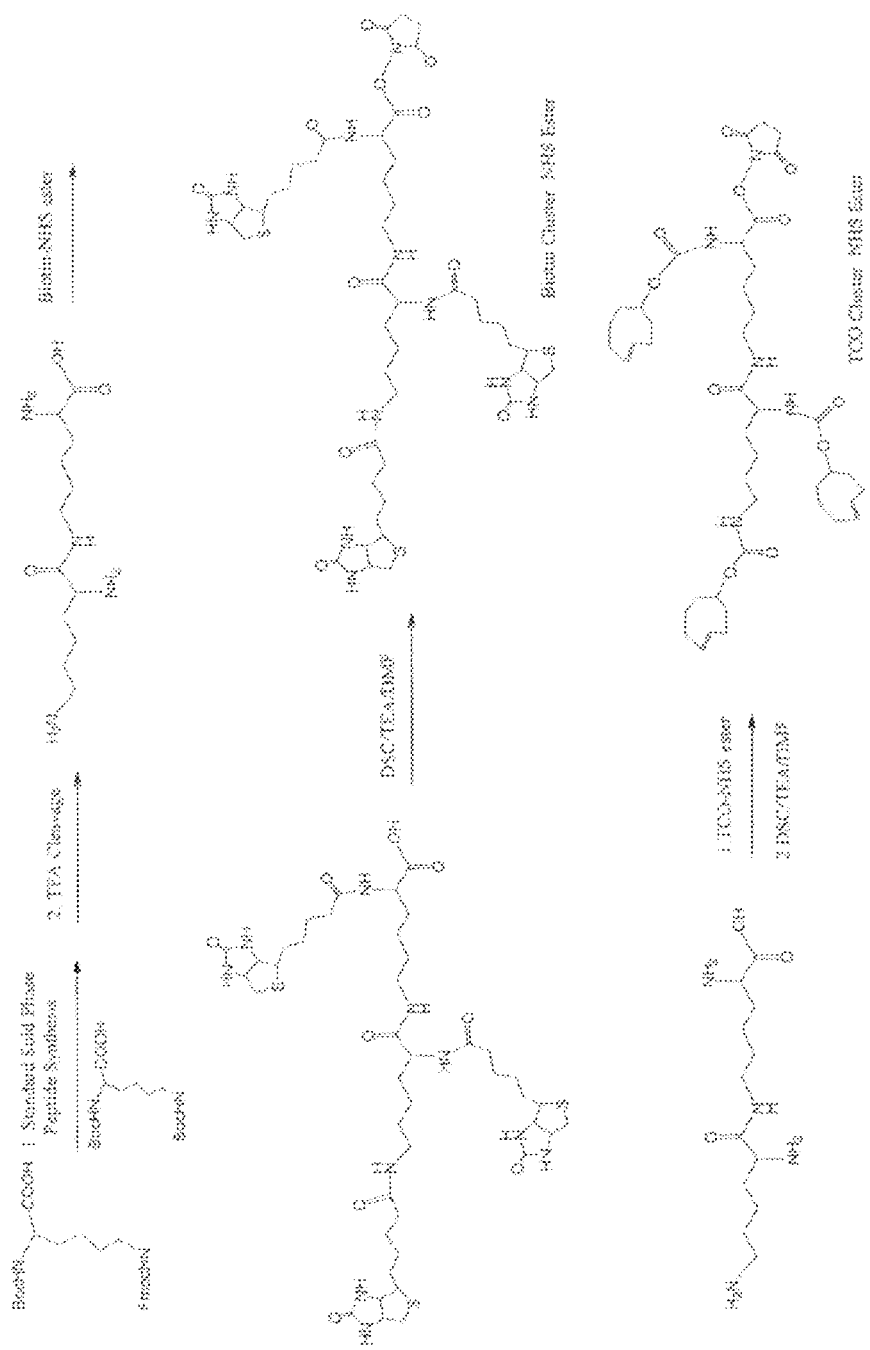
FIG. 16: Synthesis of Anchor molecule cluster NHS ester: Biotin cluster NHS ester and TCO cluster NHS ester as examples.
Figure 17:
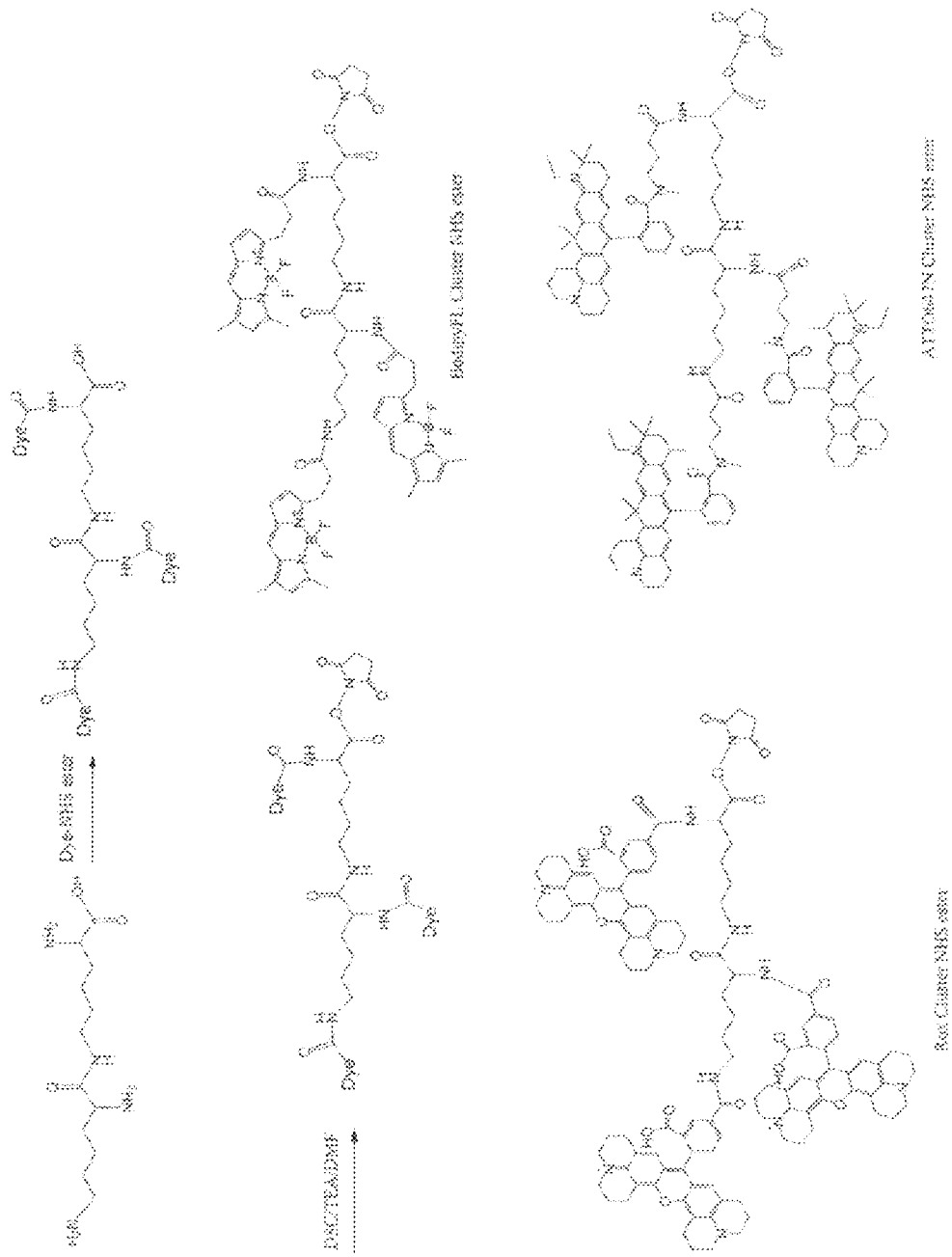
FIG. 17: Synthesis of Dye cluster NHS ester and example structures of BodipyFL cluster NHS ester, Rox cluster NHS ester and ATTO647N cluster NHS ester.
Figure 18:
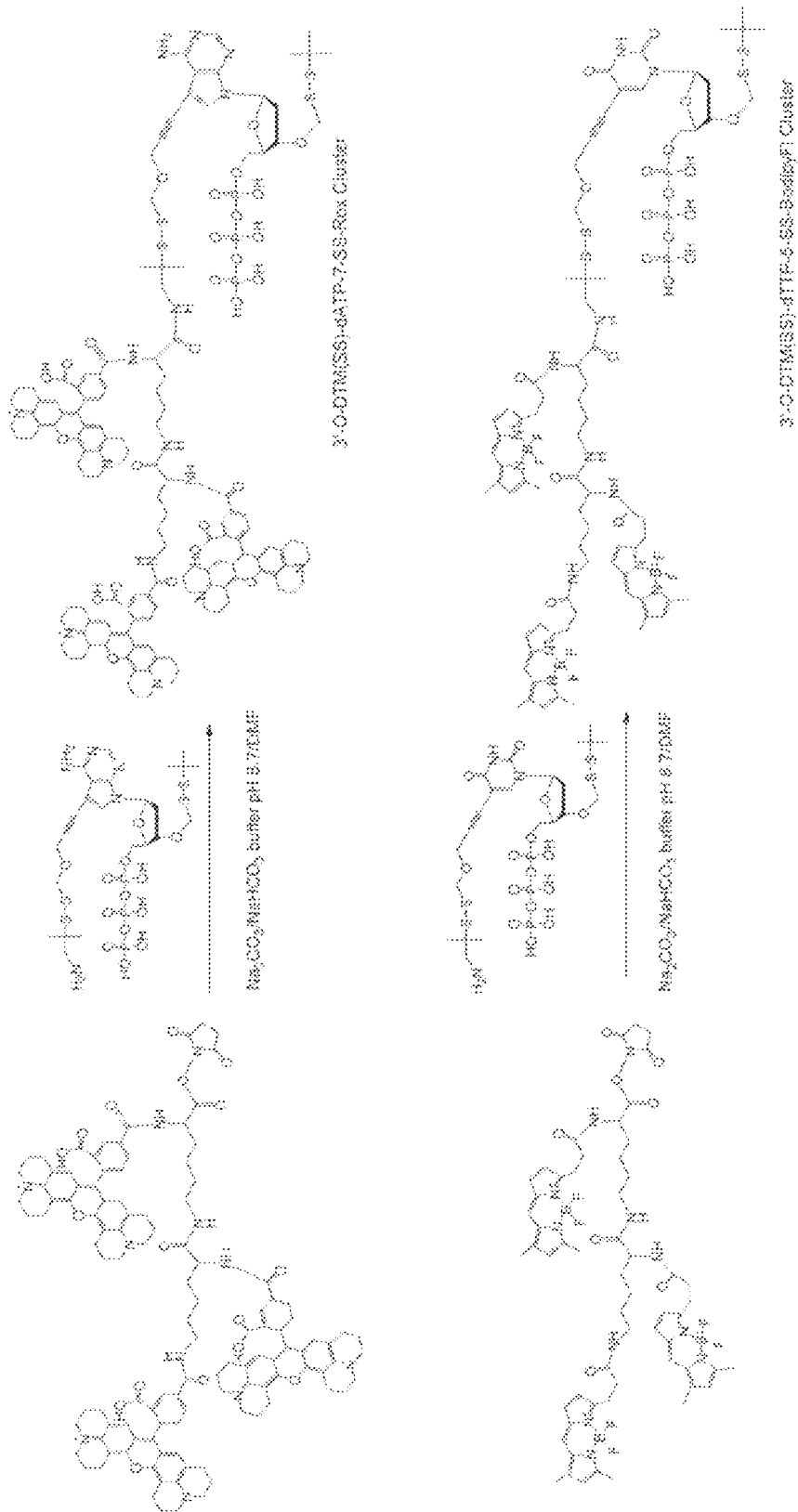
FIG. 18: Synthesis of 3'-O-DTM(SS)-dNTP-SS-Dye Cluster: 3'-O-DTM(SS)-dATP-7-SS-Rox Cluster and 3'-O-DTM(SS)-dTTP-5-SS-BodipyFL Cluster as examples.
Figure 19:
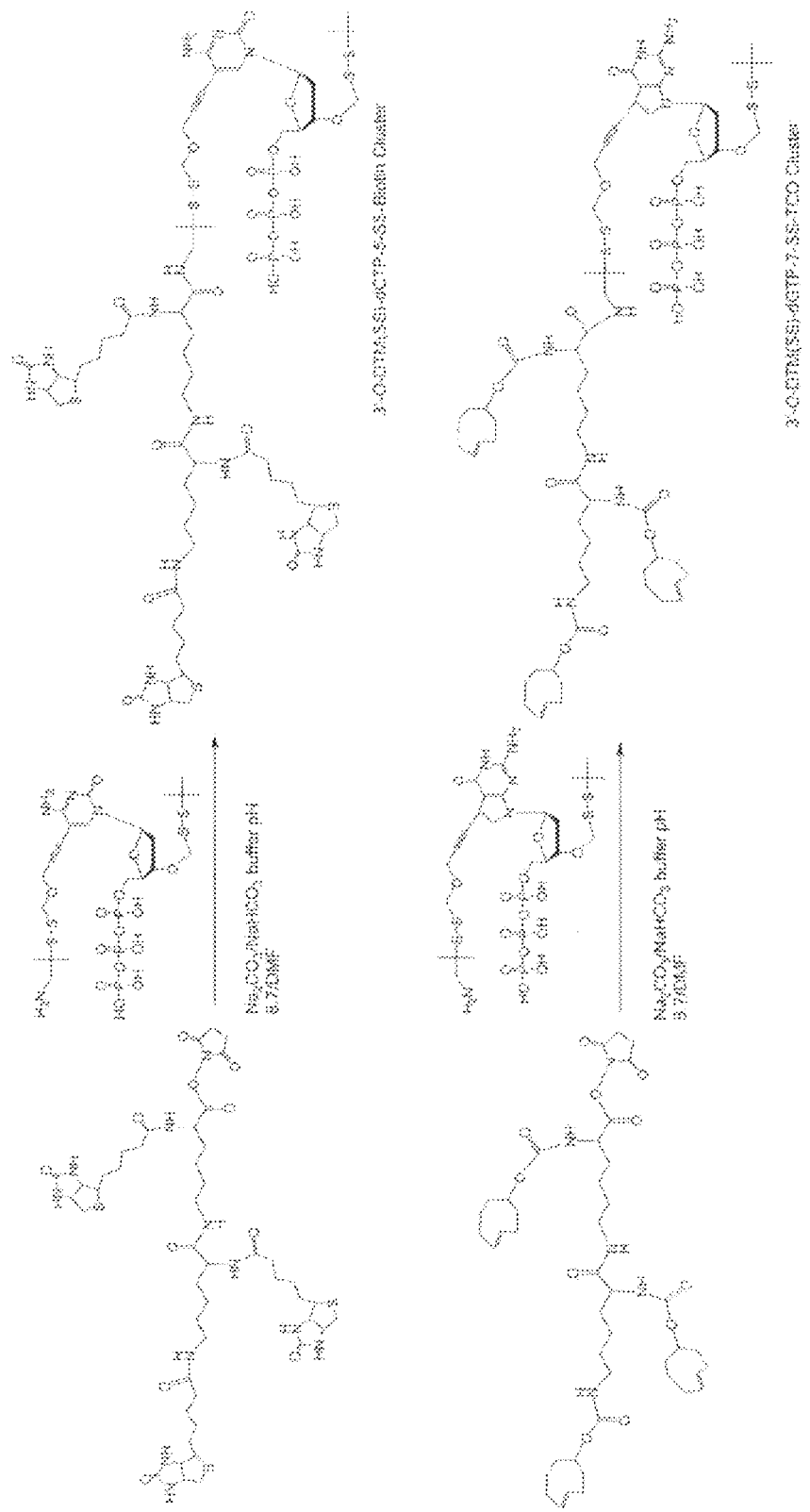
FIG. 19: Synthesis of 3'-O-DTM(SS)-dNTP-SS-Anchor Cluster: 3'-O-DTM(SS)-dCTP-5-SS-Biotin Cluster and 3'-O-DTM(SS)-dGTP-7-SS-TCO Cluster as examples.
Figure 20:
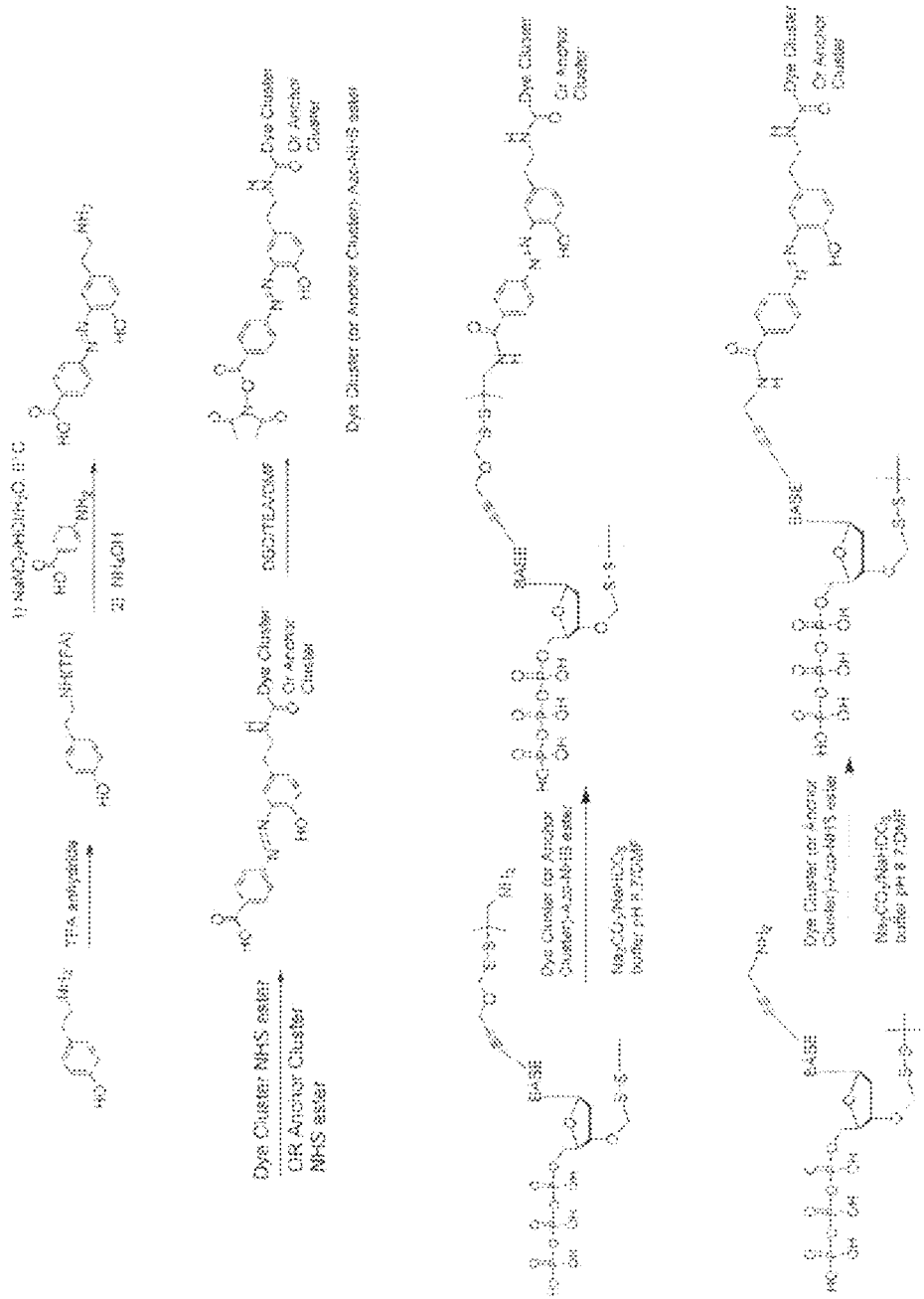
FIG. 20: General synthesis of 3'-O-DTM(SS)-dNTP-Azo-Dye or -Anchor Cluster.
Figure 21:
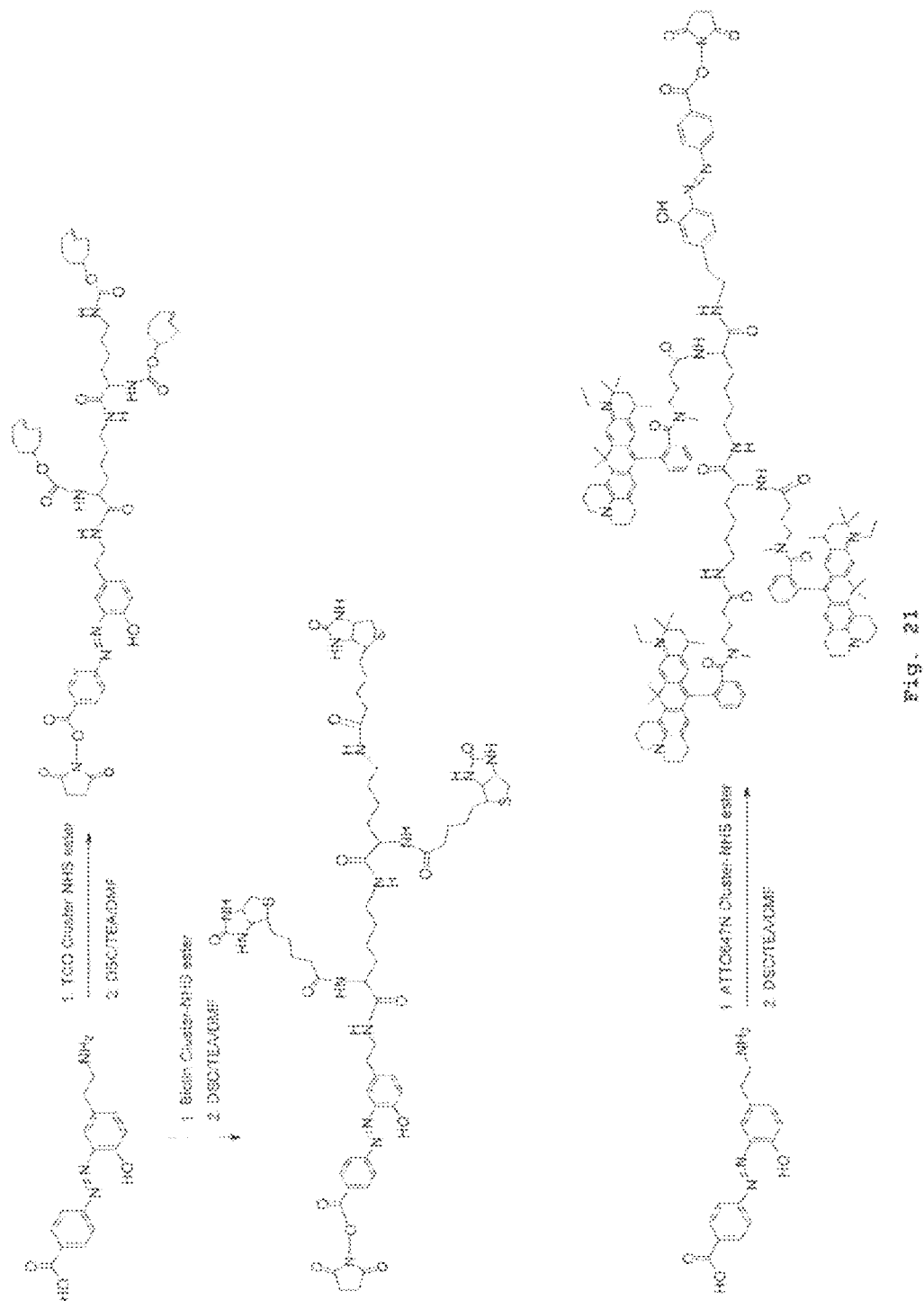
FIG. 21: Synthesis of Anchor or Dye Cluster-Azo-NHS ester: TCO-, Biotin- and ATTO647N-Azo NHS esters as examples.
Figure 22:
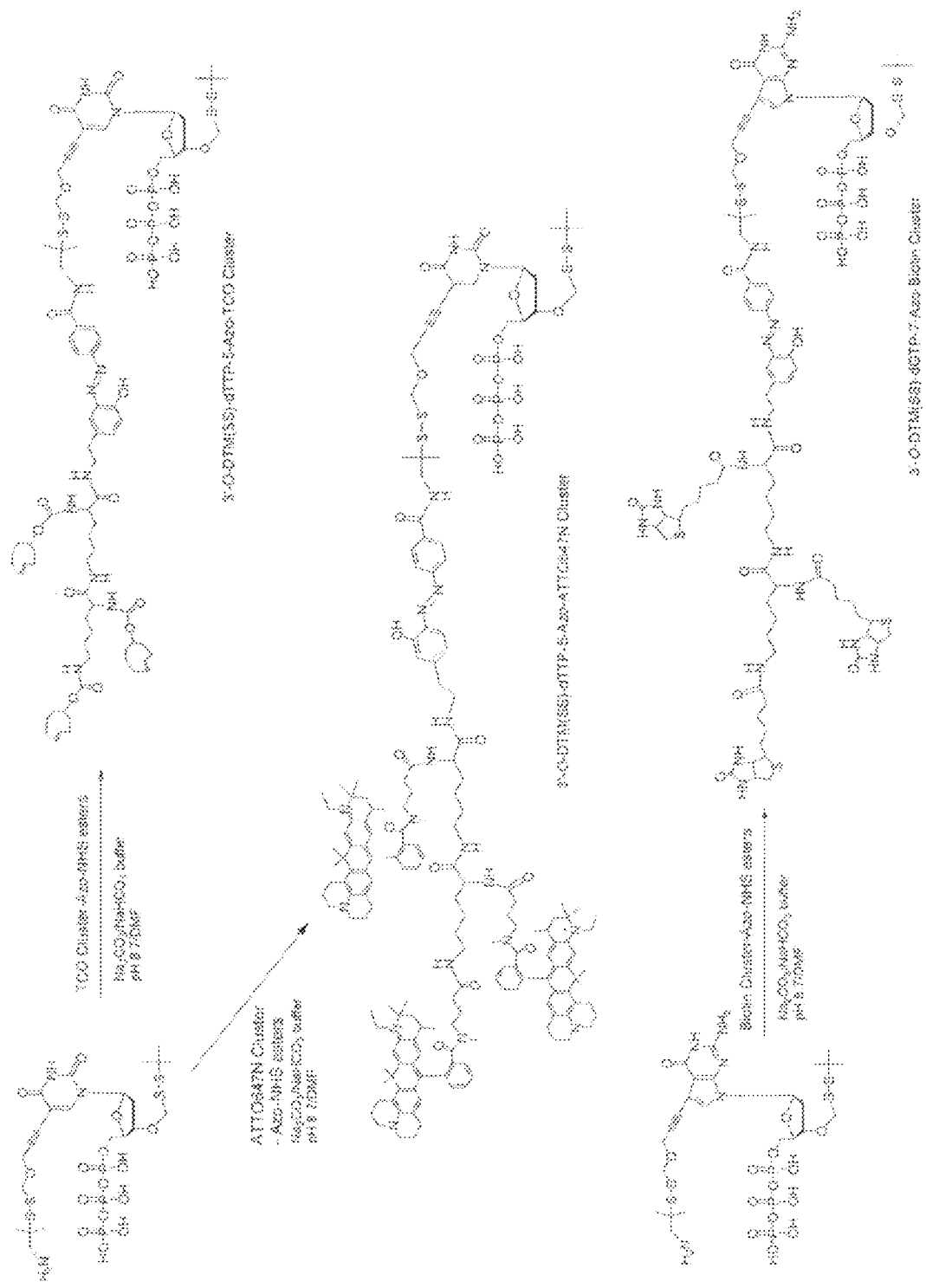
FIG. 22: Synthesis of 3'-O-DTM(SS)-dNTP-Azo-Dye or Anchor Cluster: 3'-O-DTM(SS)-dTTP-5-Azo-TCO Cluster, 3'-O-DTM(SS)-dTTP-5-Azo-ATTO647N Cluster and 3'-O-DTM(SS)-dGTP-7-Azo-Biotin Cluster as examples.
Figure 23A:
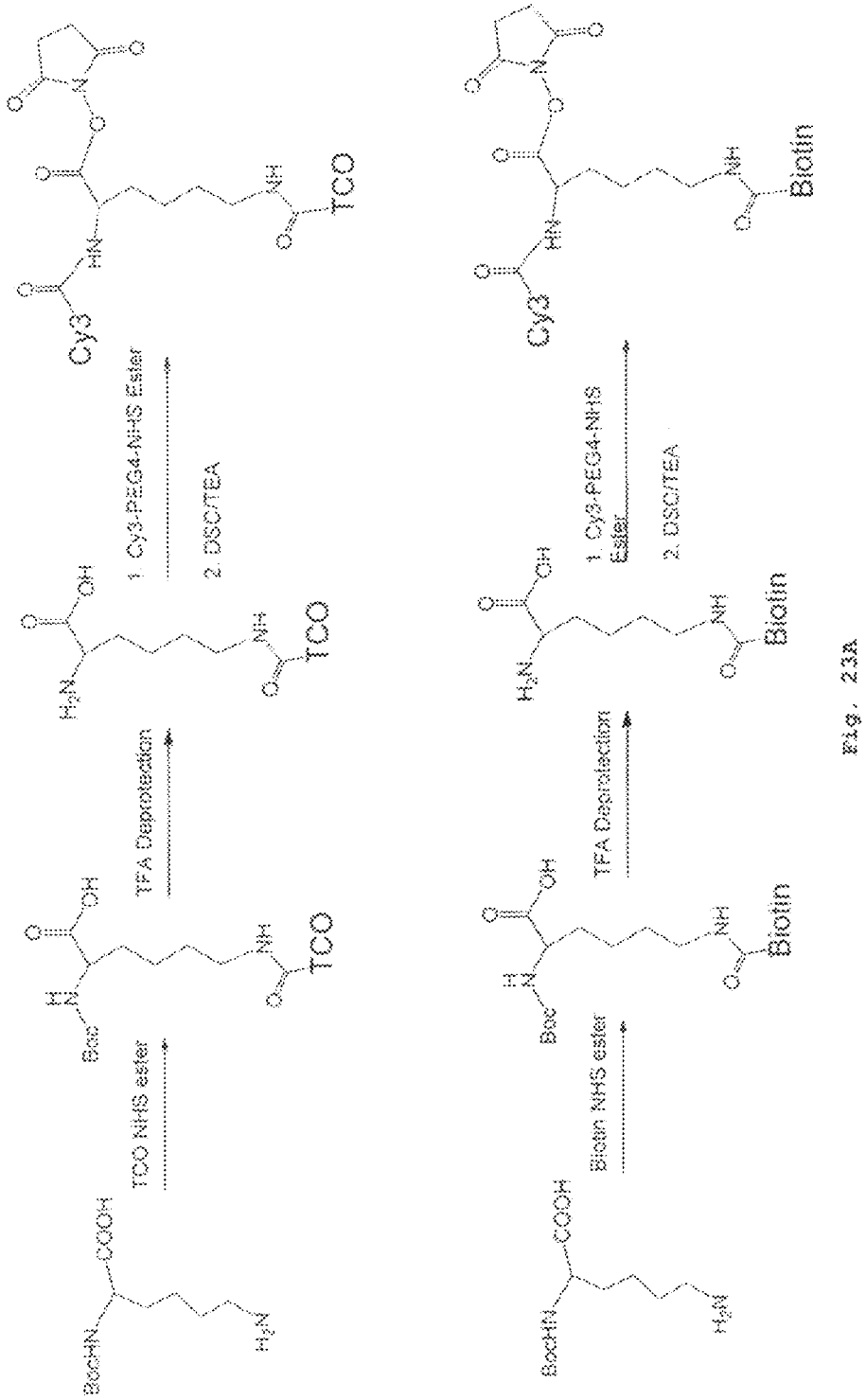
FIG. 23A: Synthesis of Donor Dye-Anchor-NHS ester, with Cy3-TCO-NHS ester and Cy3-Biotin-NHS ester as examples.
Figure 23B:
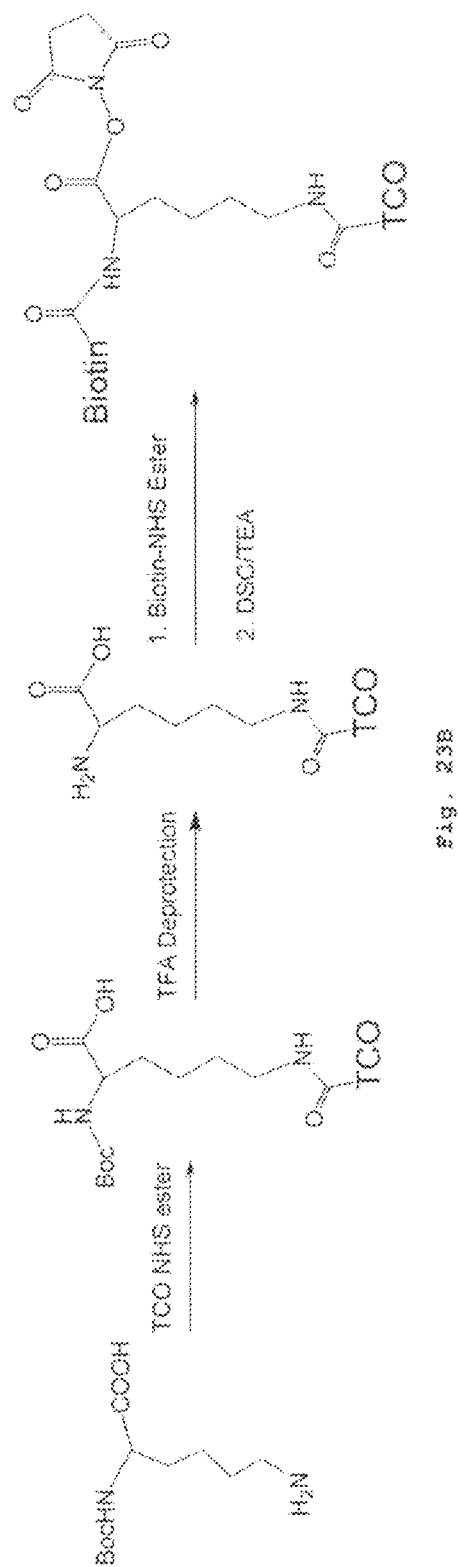
FIG. 23B: Synthesis of Two-Anchor-NHS ester (TCO-Biotin-NHS ester as example).
Figure 24A:
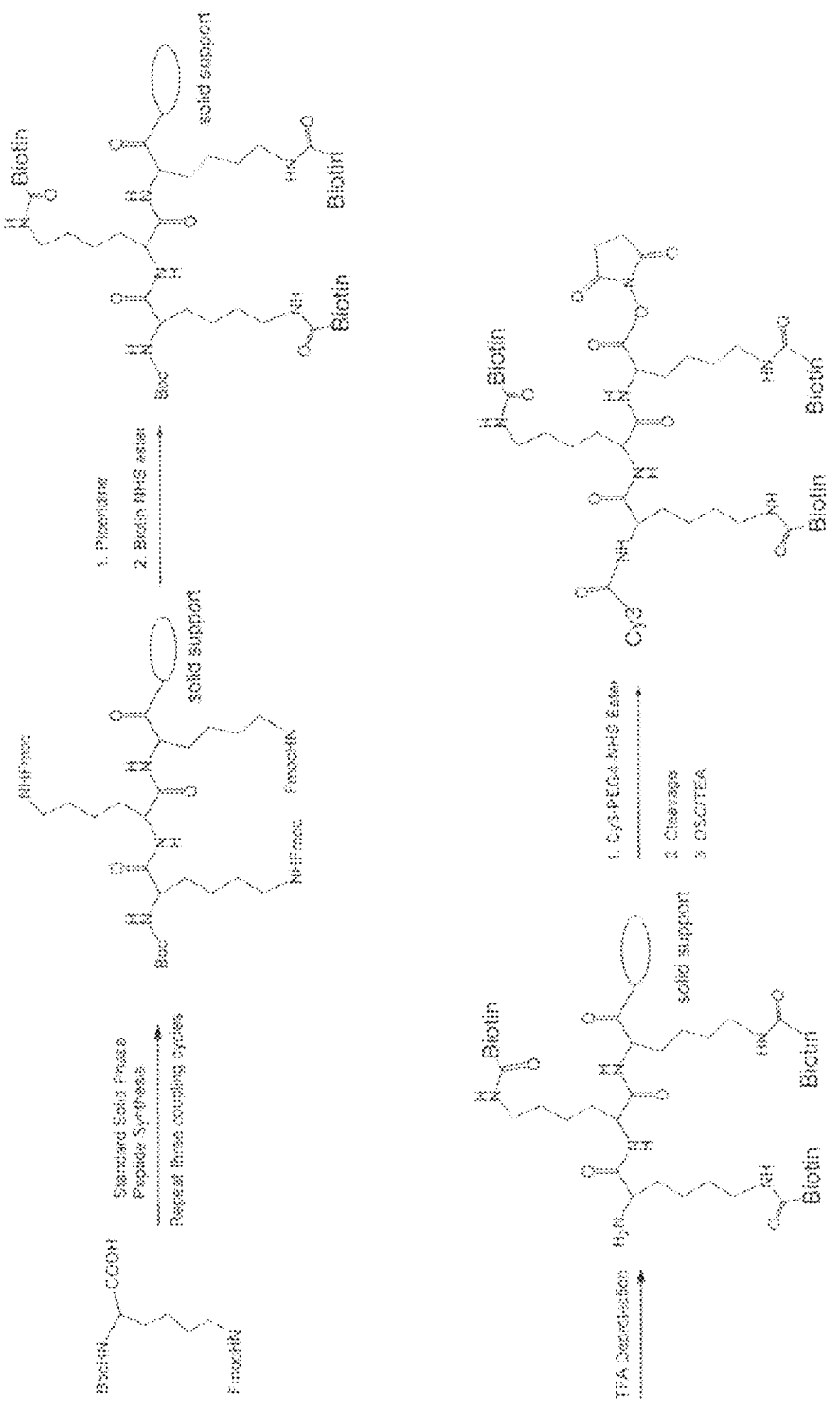
FIG. 24A: Synthesis of Donor Dye-Anchor Cluster-NHS ester, with Cy3-BiotinCluster-NHS ester as example.
Figure 24B:
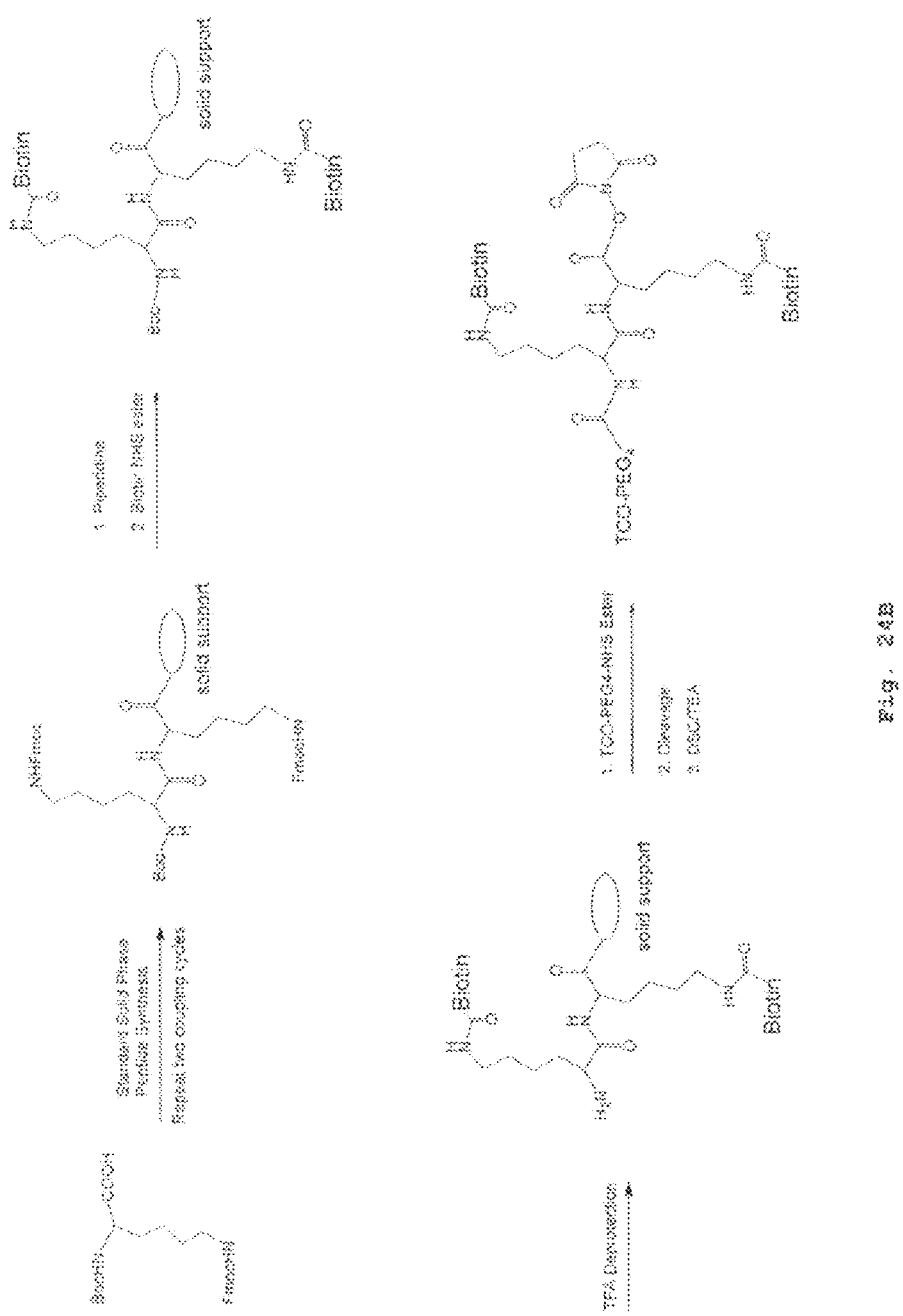
FIG. 24B: Synthesis of Three Anchor Cluster-NHS ester (Biotin-Biotin-TCO-NHS ester as example).
Figure 25:
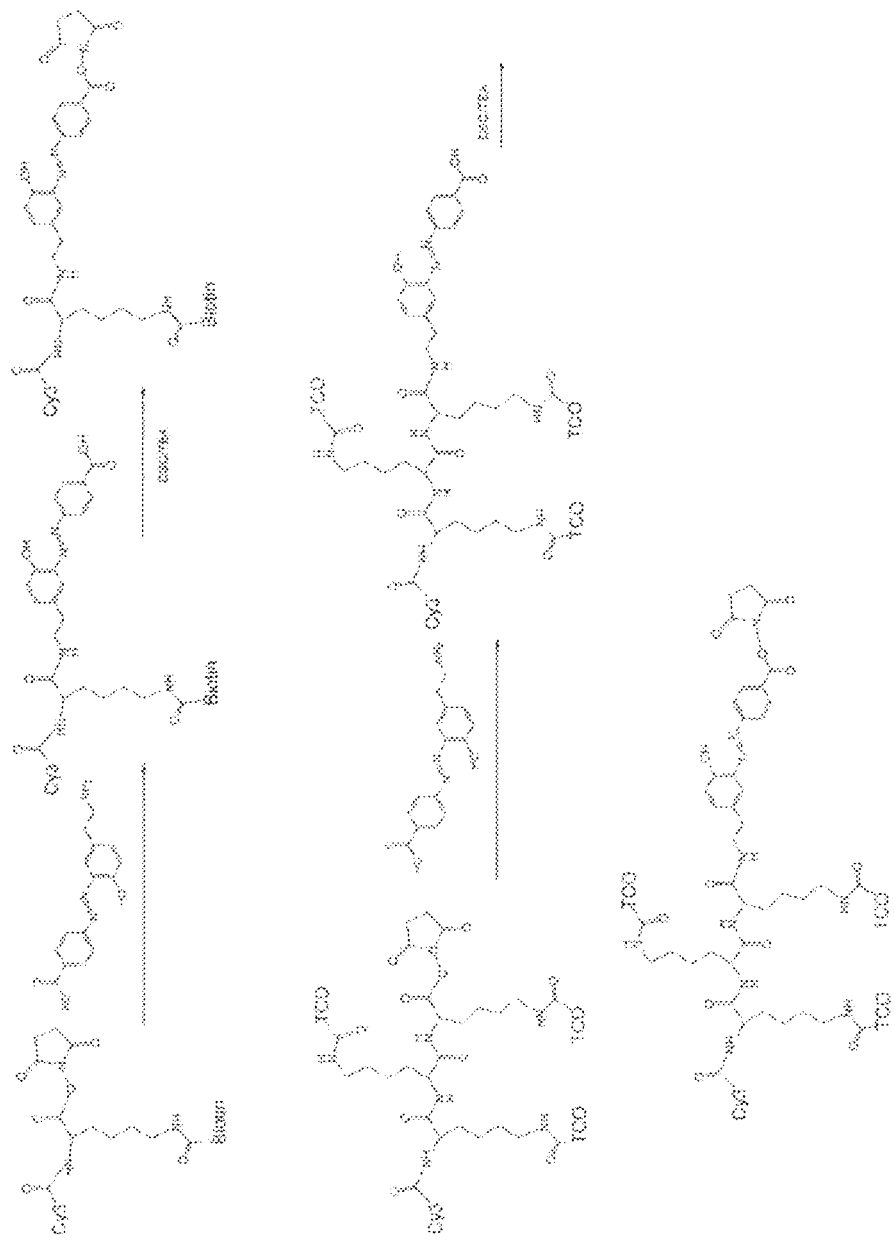
FIG. 25: Synthesis of Donor Dye-Anchor (or Anchor cluster)-Azolinker-NHS ester, with Cy3-Biotin-Azo-NHS ester and Cy3-TCO cluster-Azo-NHS esters as examples.
Figure 26:
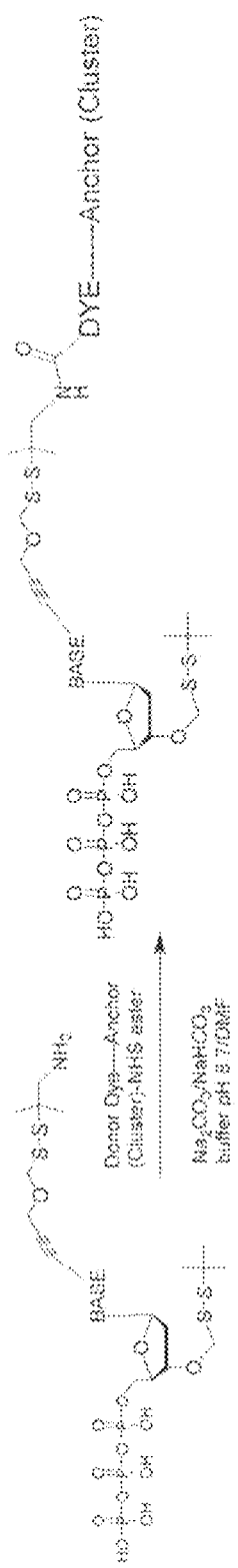
FIG. 26: General synthesis of 3'-O-SS-dNTP-Donor Dye-Anchor (or Anchor cluster).
Figure 27:
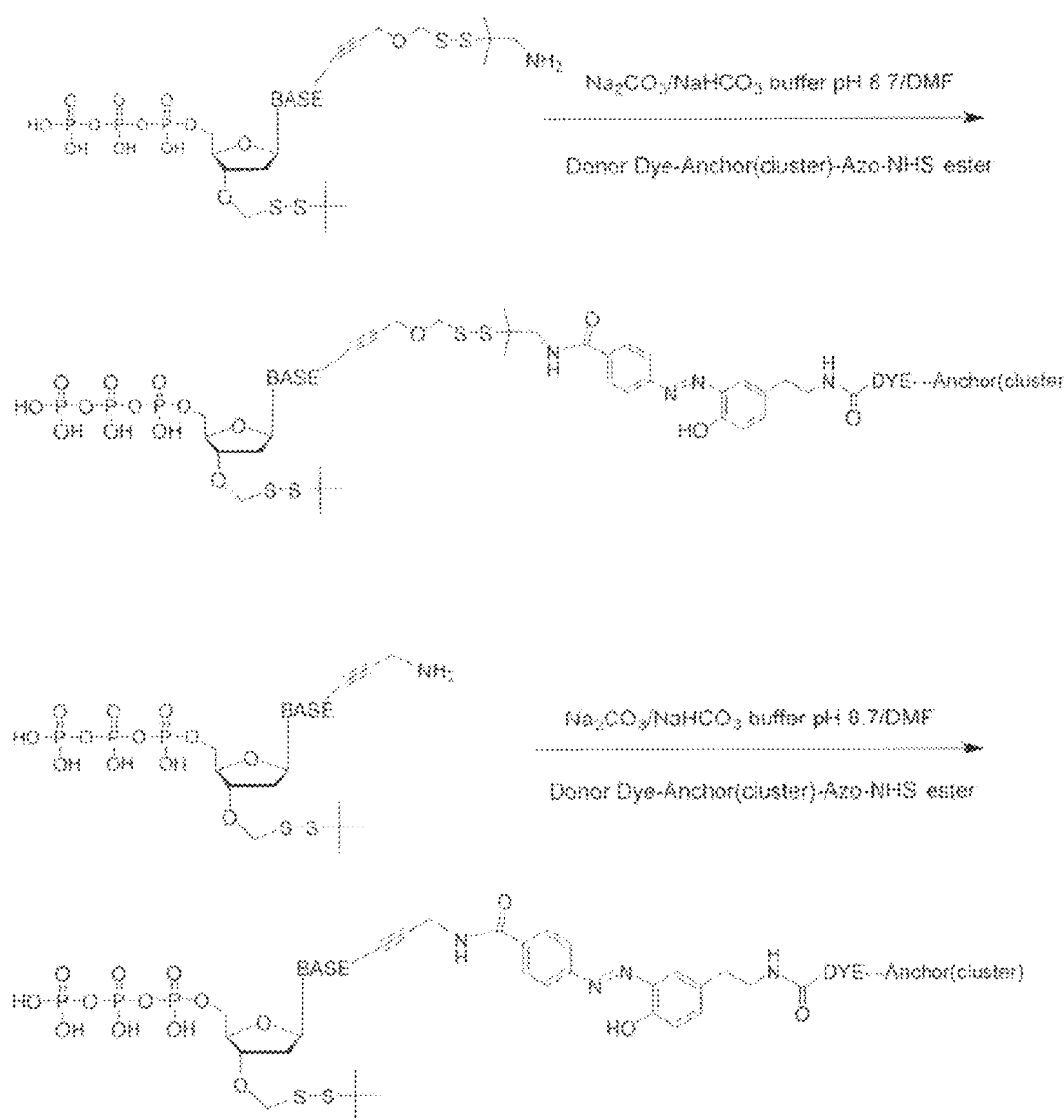
FIG. 27: General synthesis of 3'-O-SS-dNTP-Azo-Dye-Anchor (or -Anchor Cluster).
Figure 28:
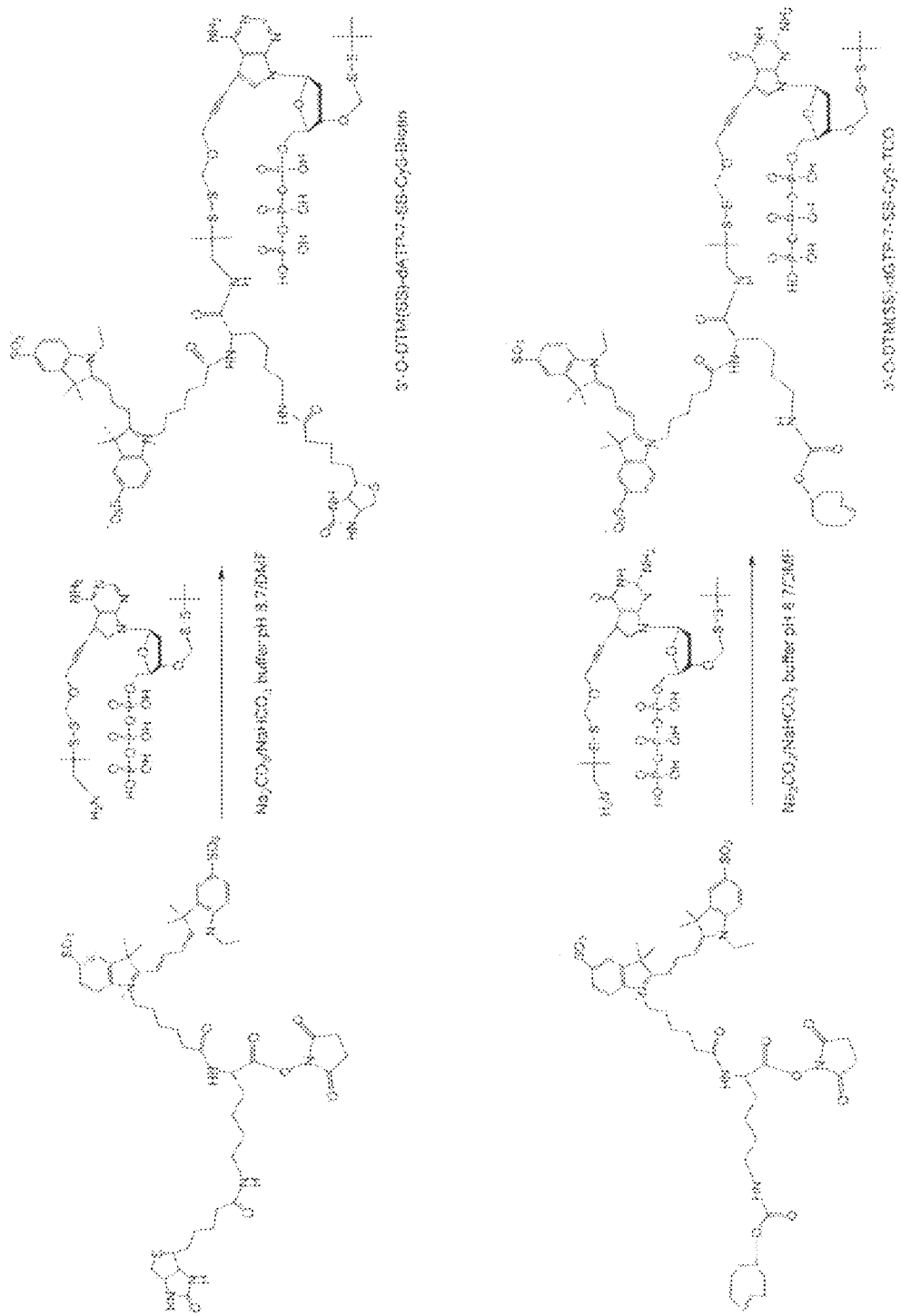
FIG. 28: Synthesis of 3'-O-DTM(SS)-dNTP-SS-Dye-Anchor: 3'-O-DTM(SS)-dATP-7-SS-Cy3-Biotin and 3'-O-DTM(SS)-dGTP-7-SS-Cy3-TCO as examples.
Figure 29A:
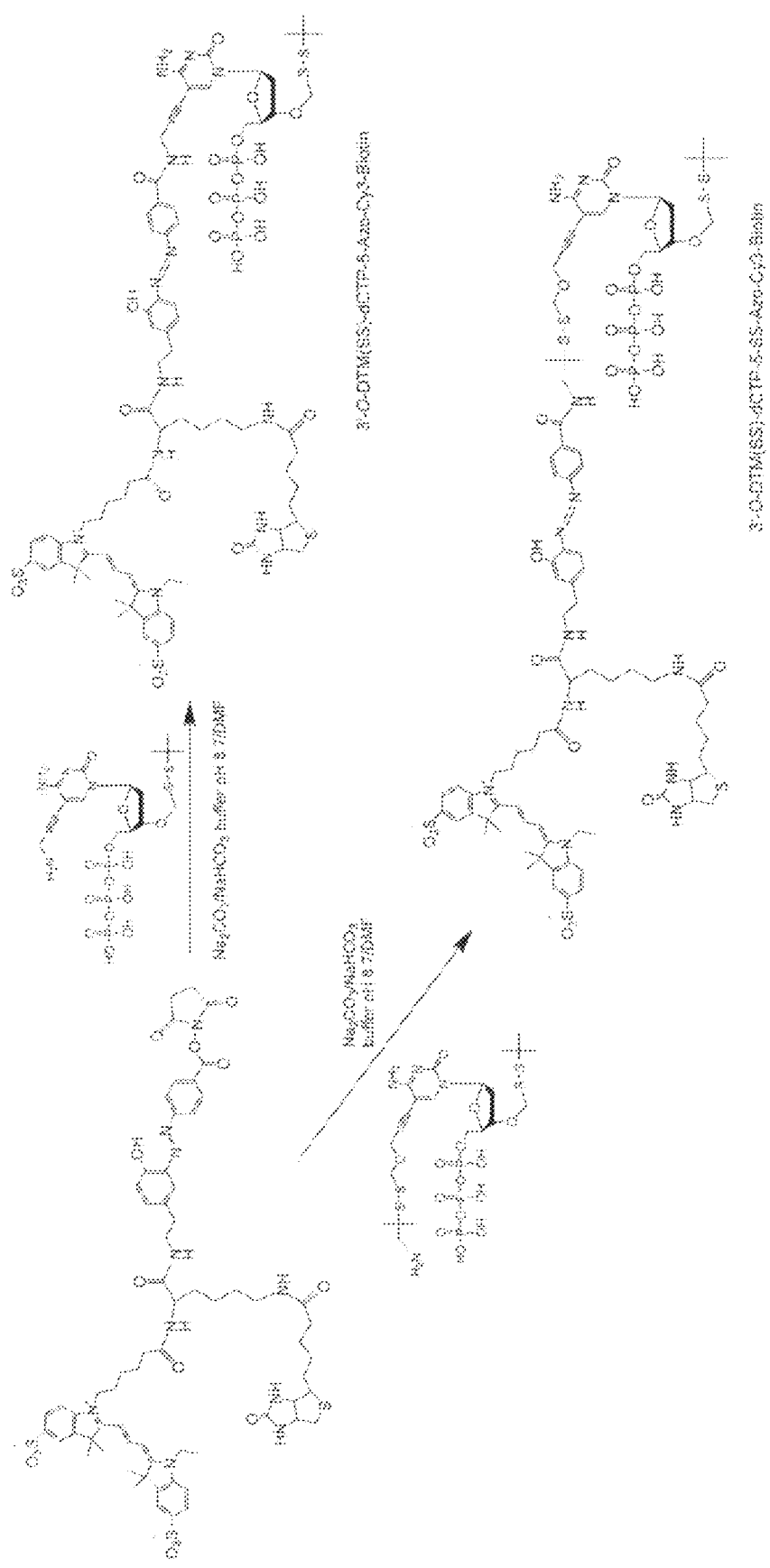
FIGS. 29A-29B: Synthesis of 3'-O-SS-dNTP-Azo-Dye-Anchor: 3'-O-SS-dCTP-5-Azo-Cy3-Biotin and 3'-O-SS-dTTP-5-Azo-Cy3-TCO as examples.
Figure 29B:
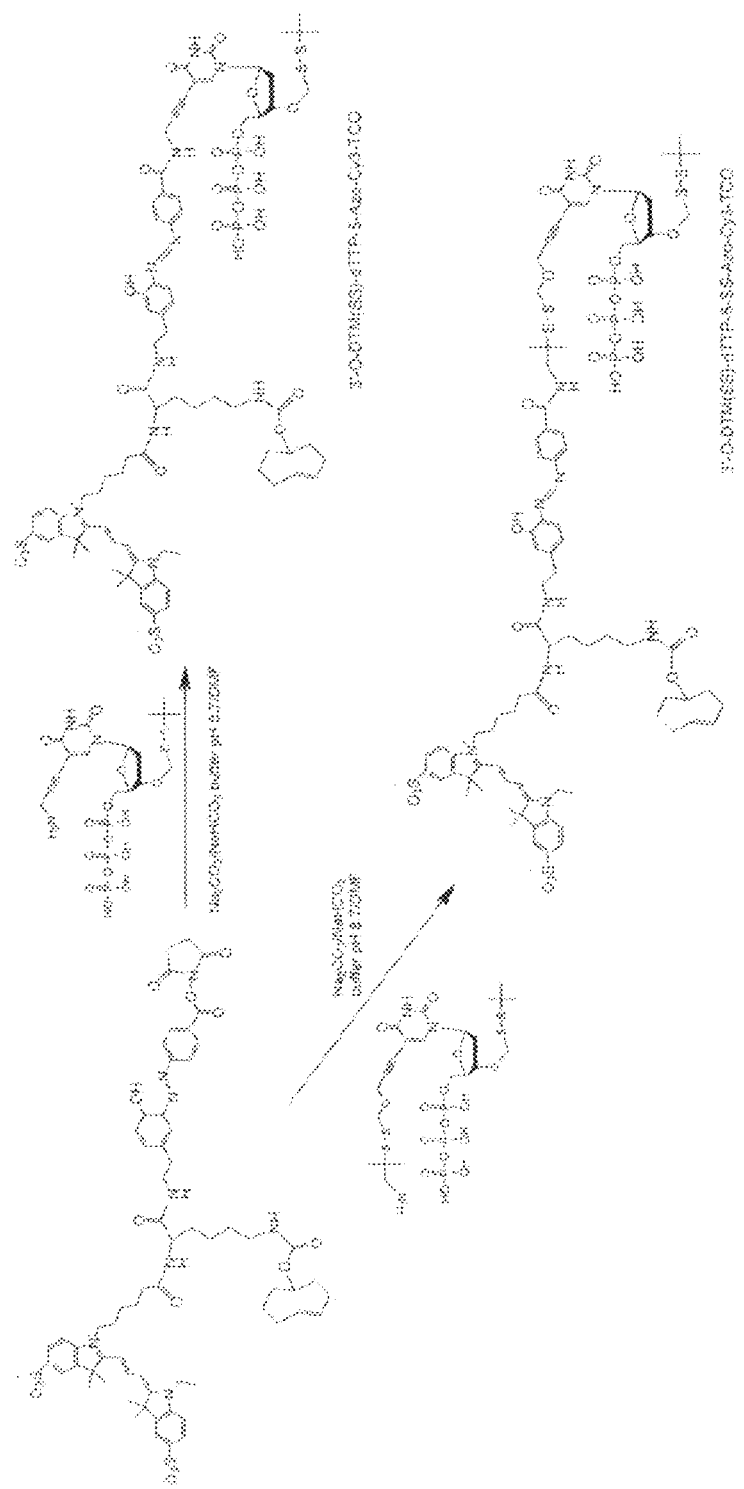
Figure 30A:
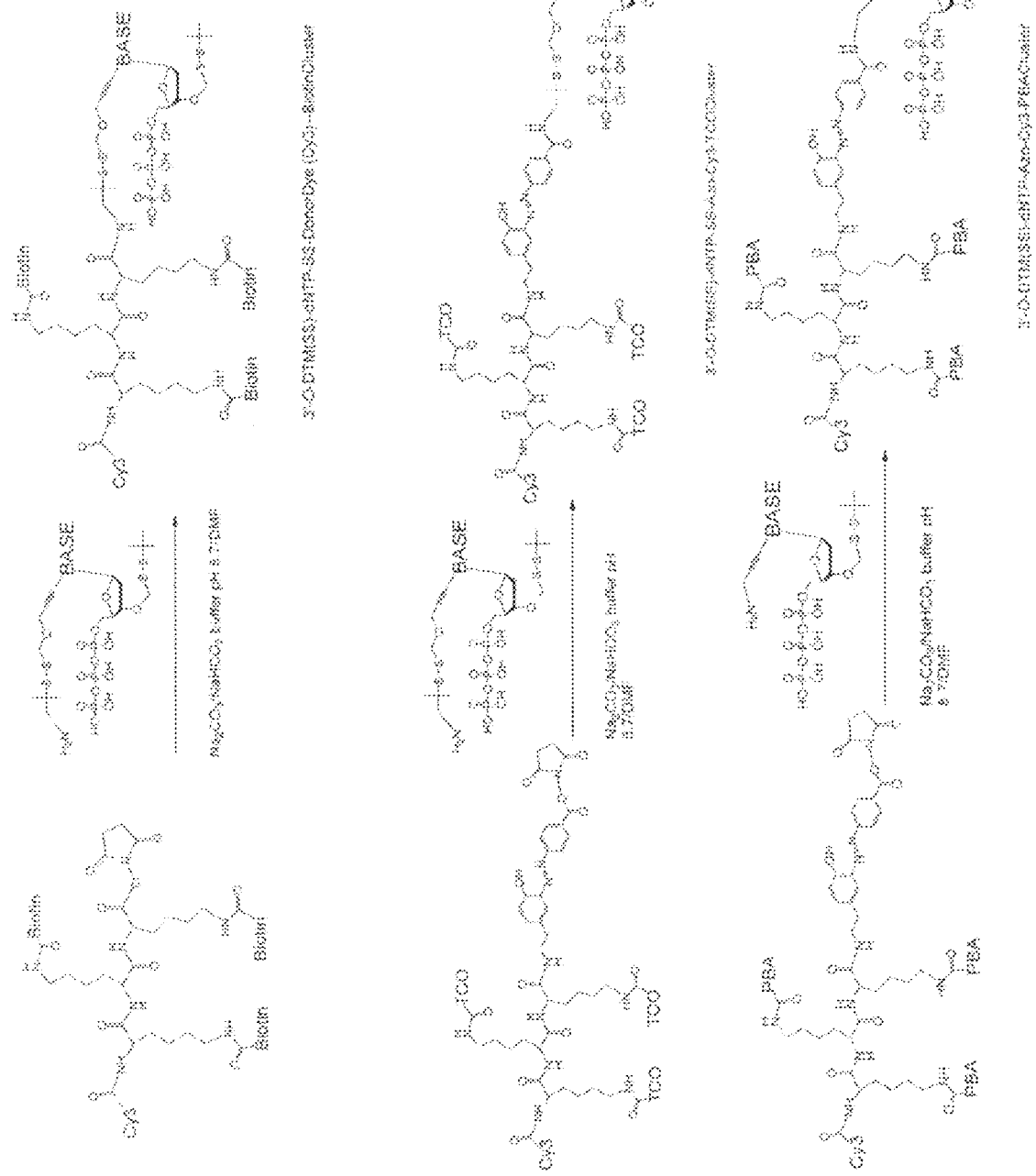
FIG. 30A: Example synthesis of 3'-O-DTM(SS)-dNTP-Cleavable Linker (SS or Azo as examples)-Donor Dye (Cy3 as example)-Anchor Clusters (Biotin, TCO or PBA).
Figure 30B:
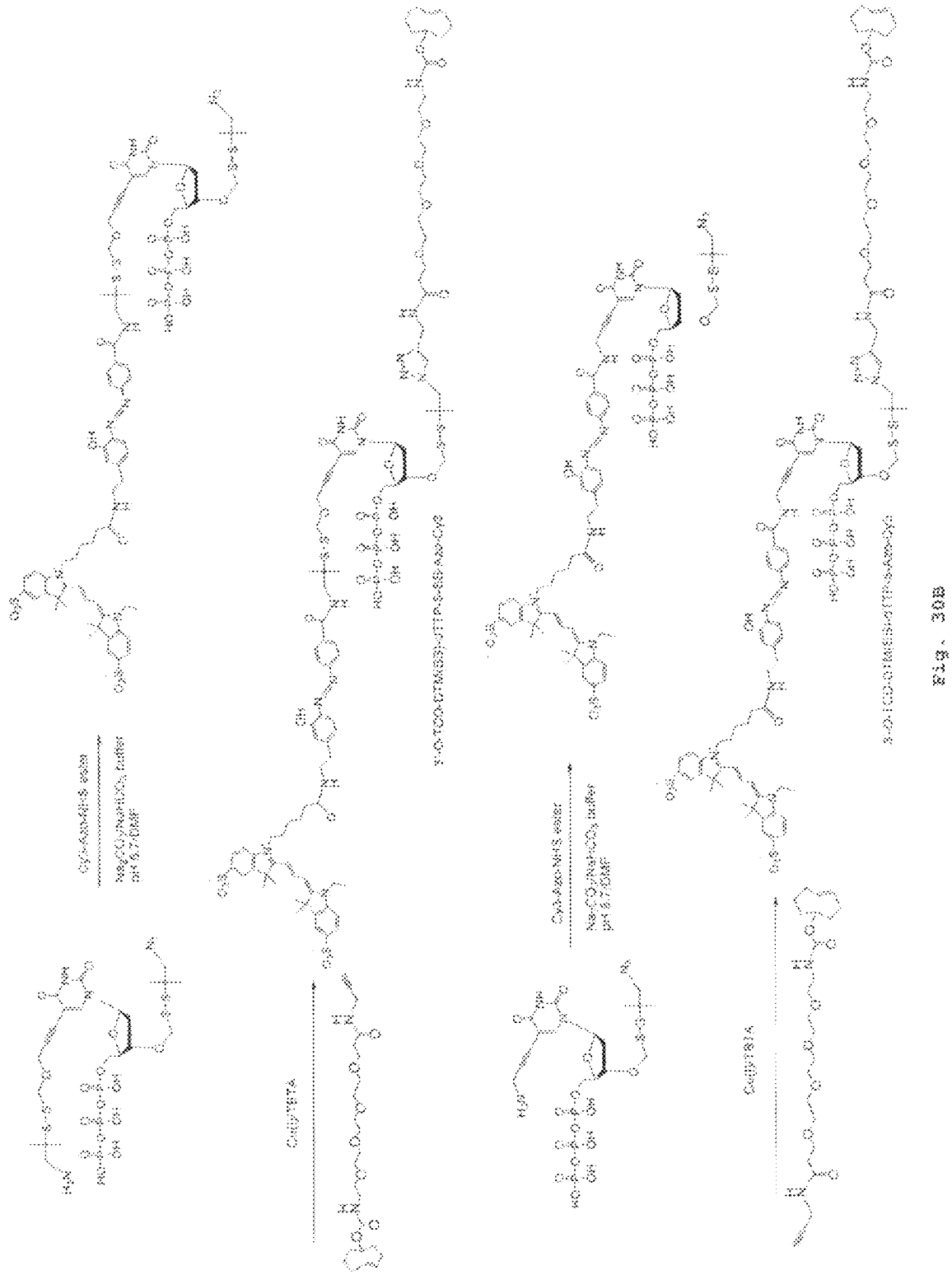
FIG. 30B: Synthesis of 3'-O-Anchor-SS(DTM)-dNTP-Azo-DonorDye (3'-O-TCO-SS-dTTP-5-SS-Azo-Cy3 and 3'-O-TCO-SS-dTTP-5-Azo-Cy3 as examples).
Figure 30C:
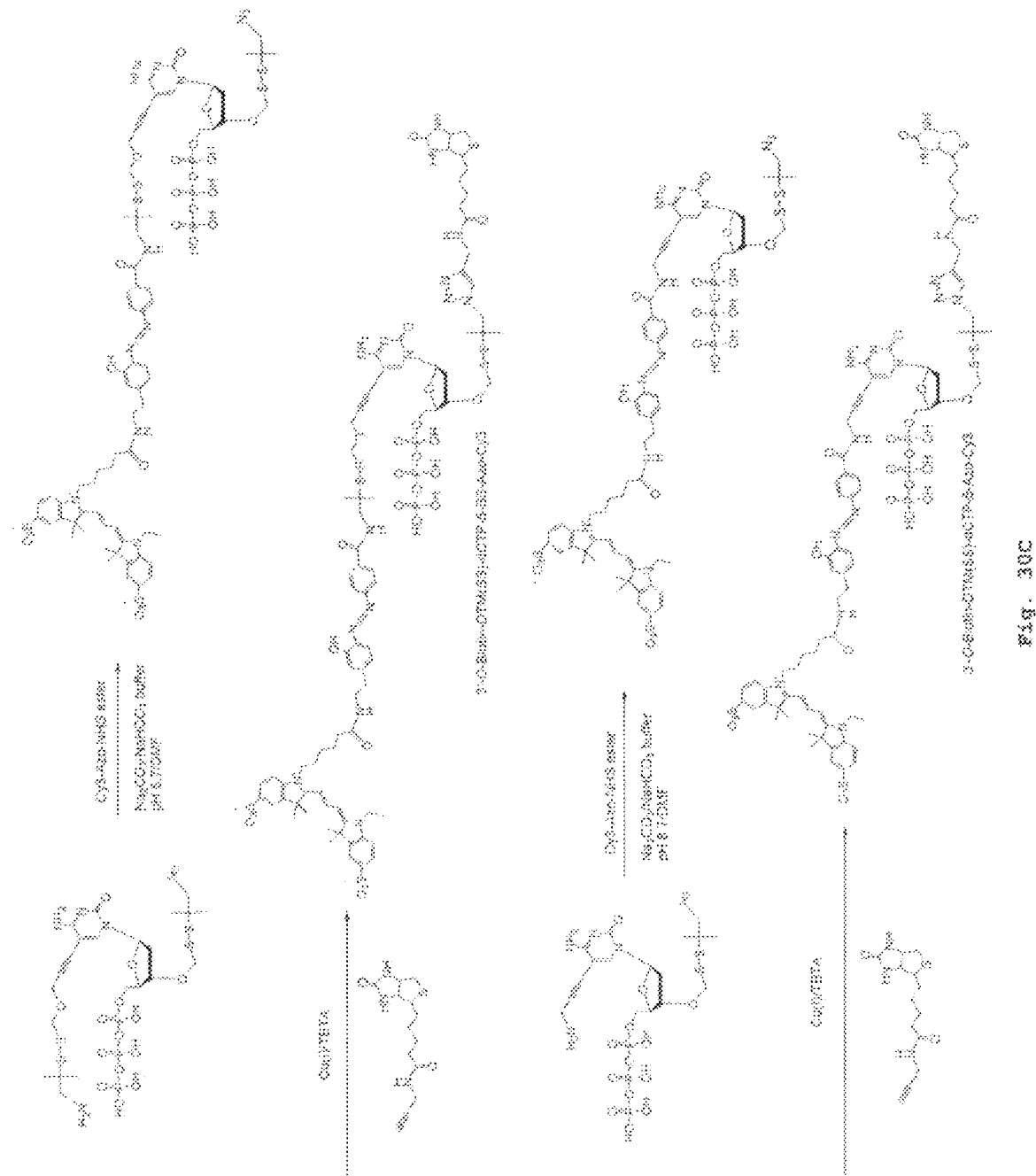
FIG. 30C: Synthesis of 3'-O-Anchor-SS(DTM)-dNTP-Azo-DonorDye (3'-O-Biotin-SS-dCTP-5-SS-Azo-Cy3 and 3'-O-Biotin-SS-dCTP-5-Azo-Cy3).
Figure 30D:
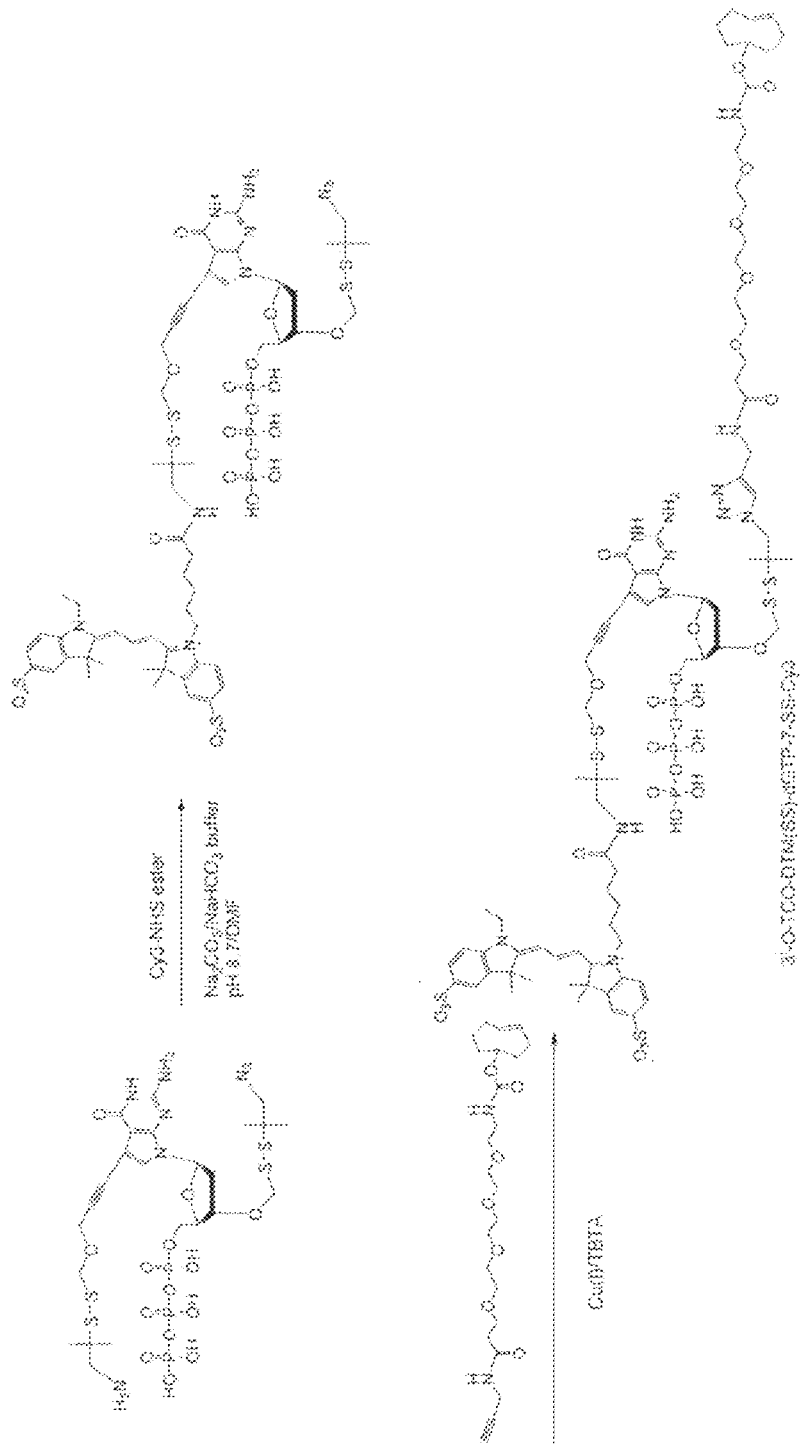
FIG. 30D-30Z: Synthesis of 3'-O-Anchor-SS(DTM)-dNTP-SS-DonorDye (3'-O-TCO-SS-dGTP-7-SS-Cy3, 3'-O-Biotin-SS-dATP-7-SS-Cy3 as examples).
Figure 30B:
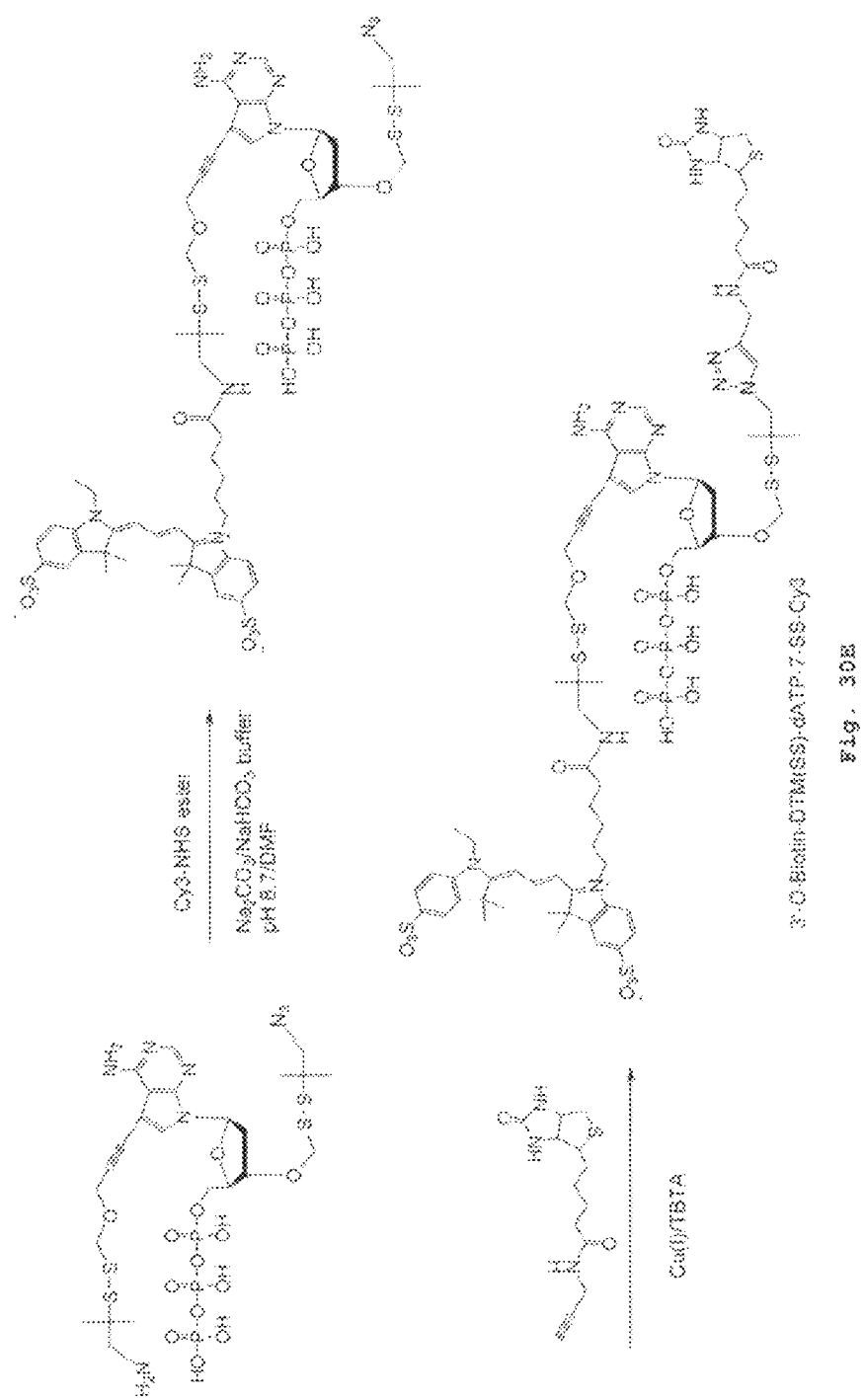
Figure 30F:
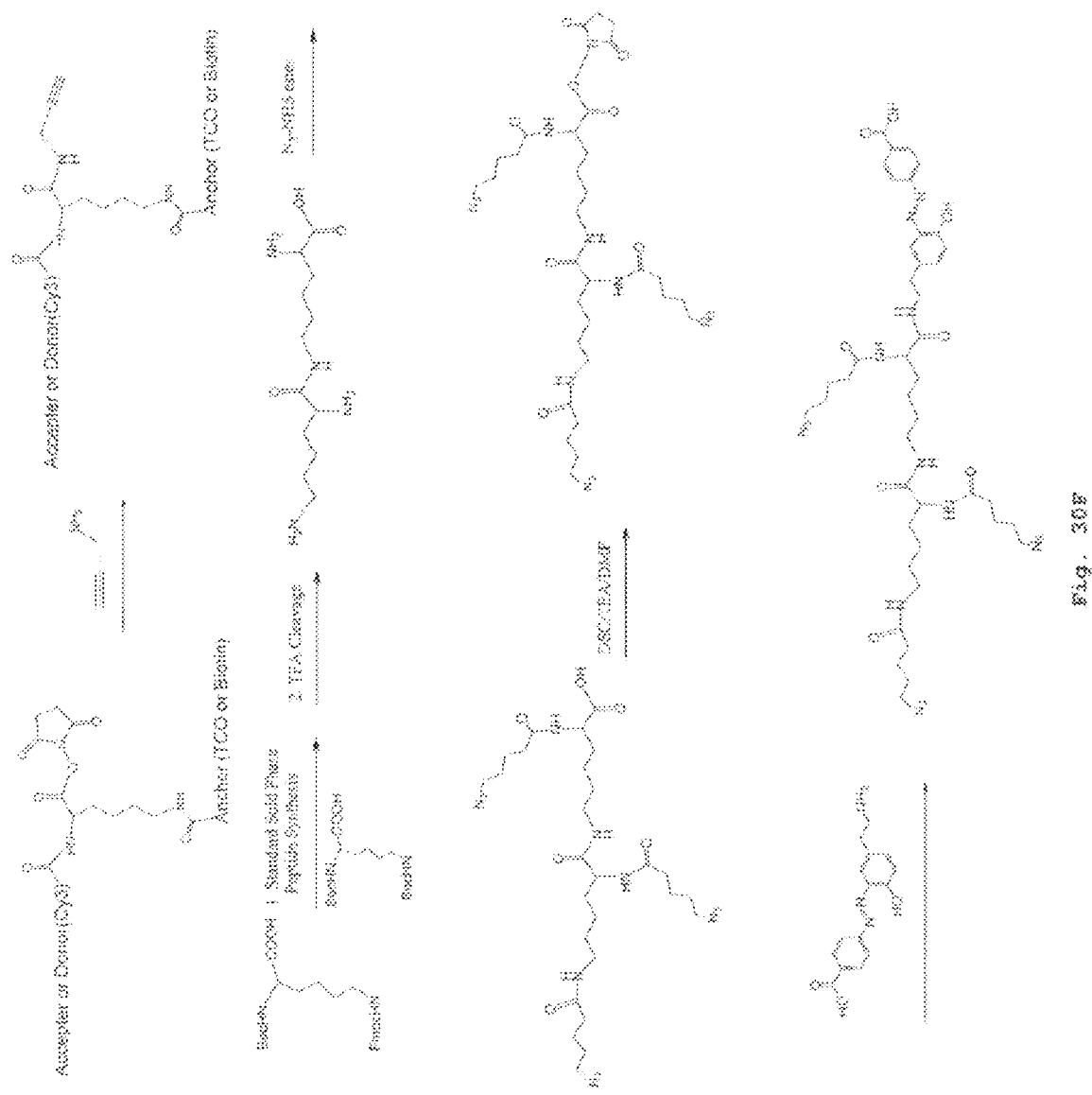
FIG. 30F: Synthesis of Dye (Donor or Acceptor)-Anchor-Alkyne, $N_3$ cluster Acid and $N_3$ cluster-Azo-Acid.
Figure 30G:
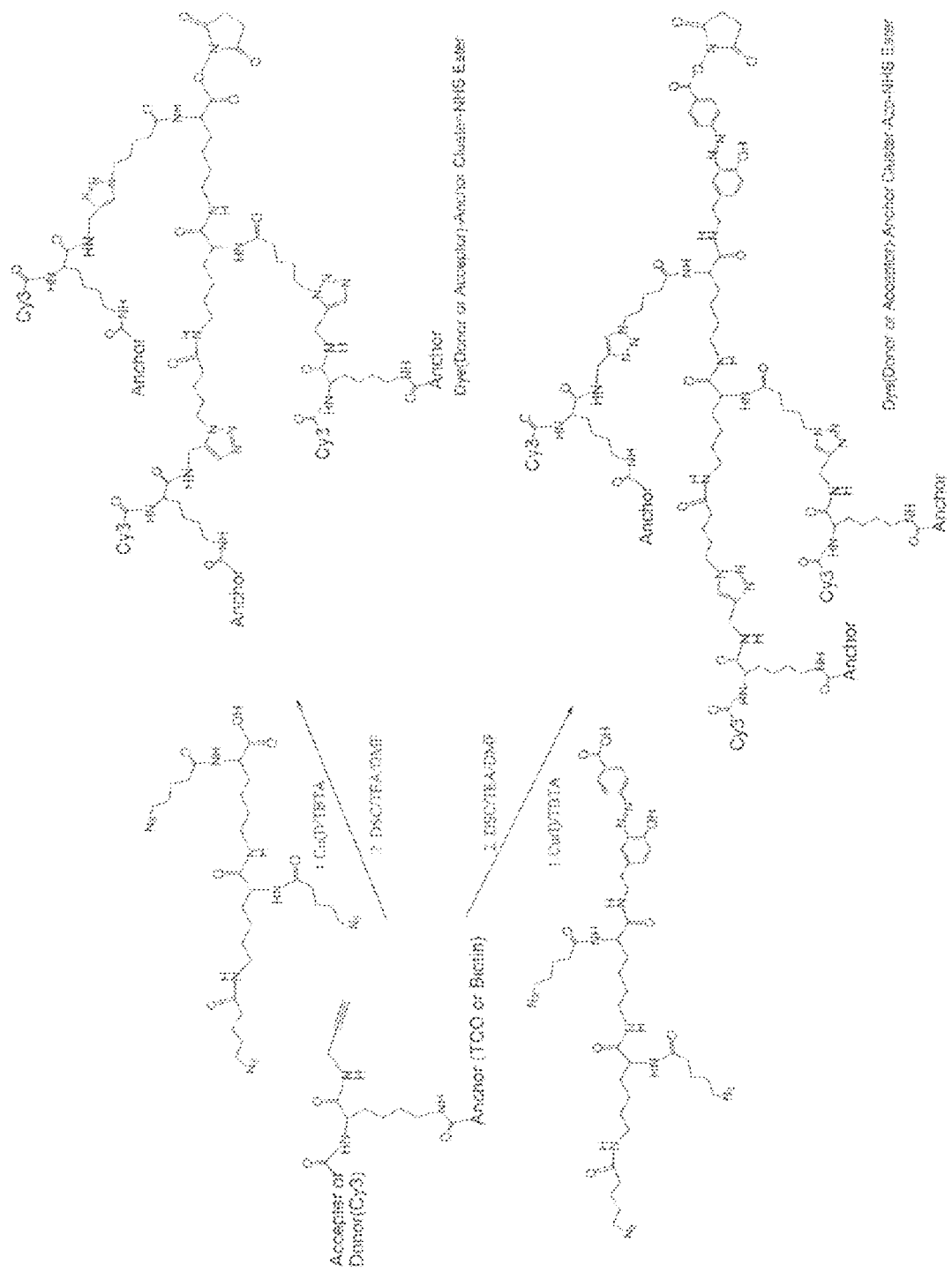
FIG. 30G: Synthesis of Dye (Donor or Acceptor)-Anchor Cluster-NHS Ester and Dye (Donor or Acceptor)-Anchor Cluster-Azo-NHS Ester.
Figure 30R:
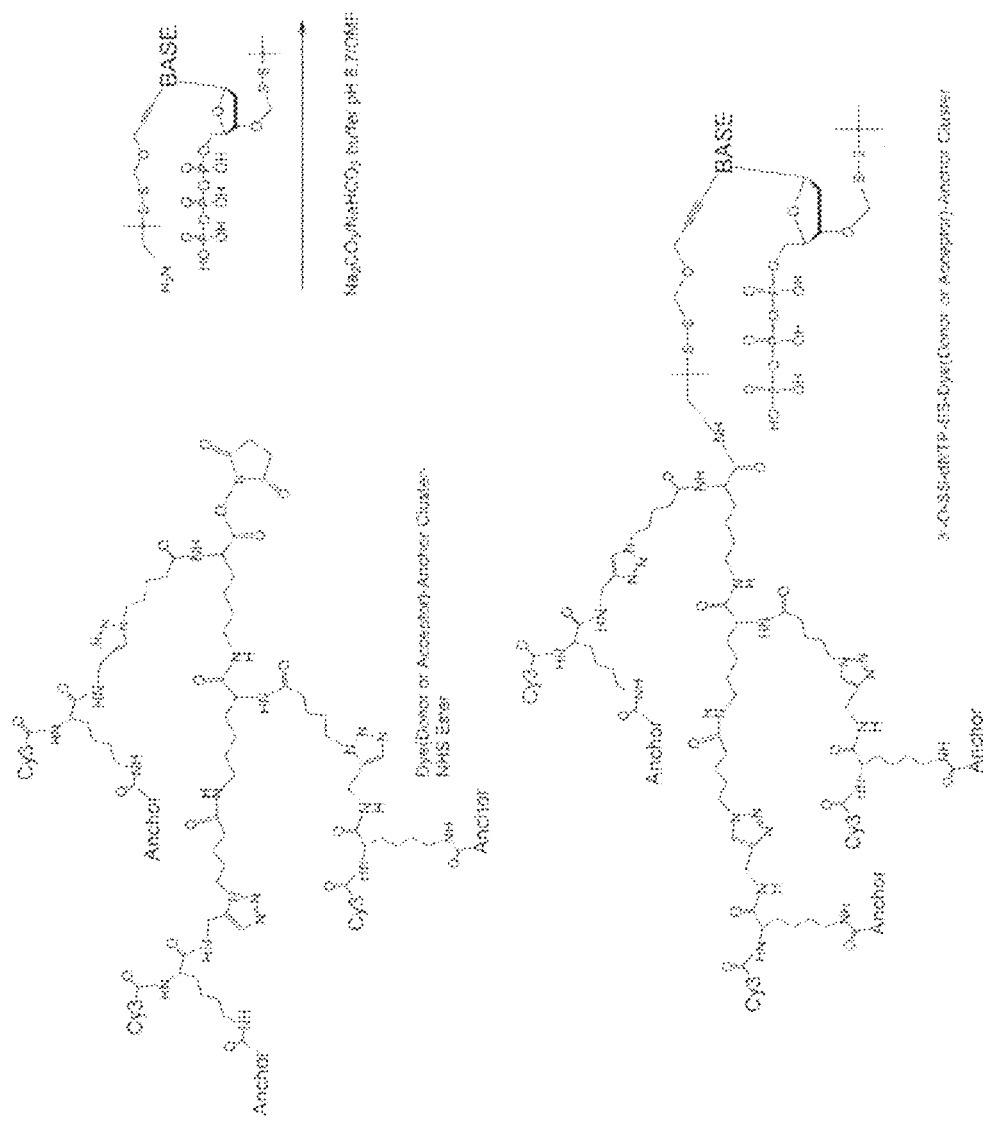
FIG. 30H: General synthesis of 3'-O-SS-dNTP-SS-Dye (Donor or Acceptor)-Anchor Cluster.
FIG. 30I: General synthesis of 3'-O-SS-dNTP-SS-Azo-Dye (Donor or Acceptor)-Anchor Cluster.
FIG. 30J: General synthesis of 3'-O-SS-dNTP-Azo-Dye (Donor or Acceptor)-Anchor Cluster.
FIG. 30K: General method for synthesis of Quantum Dot (QD) Labeled Binding Molecules (QD Labeled Tetrazine as example). Commercially available carboxylic acid modified QD can be coupled with tetrazine PEG amine to give QD labeled tetrazine.
Figure 30I:
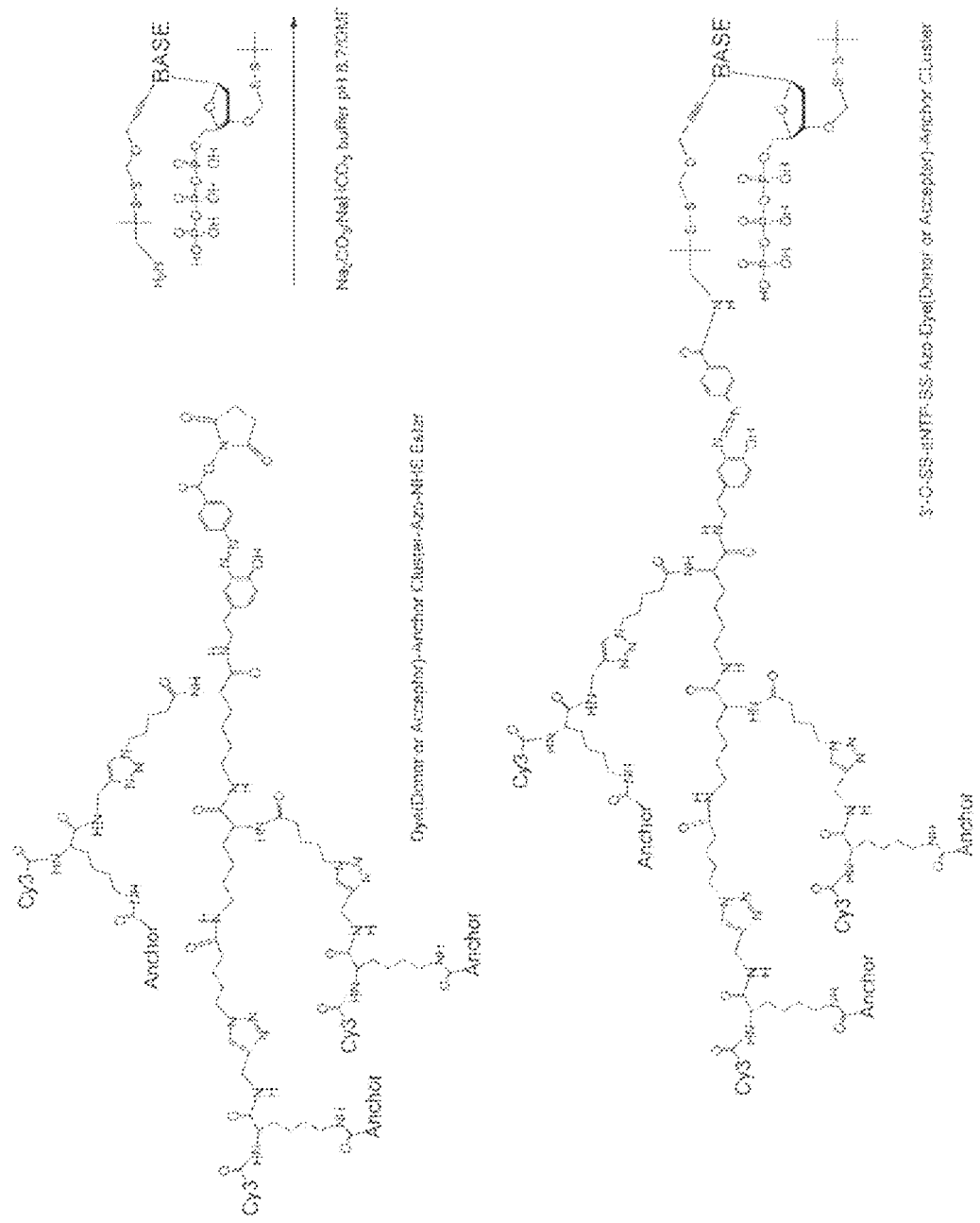
Figure 30J:
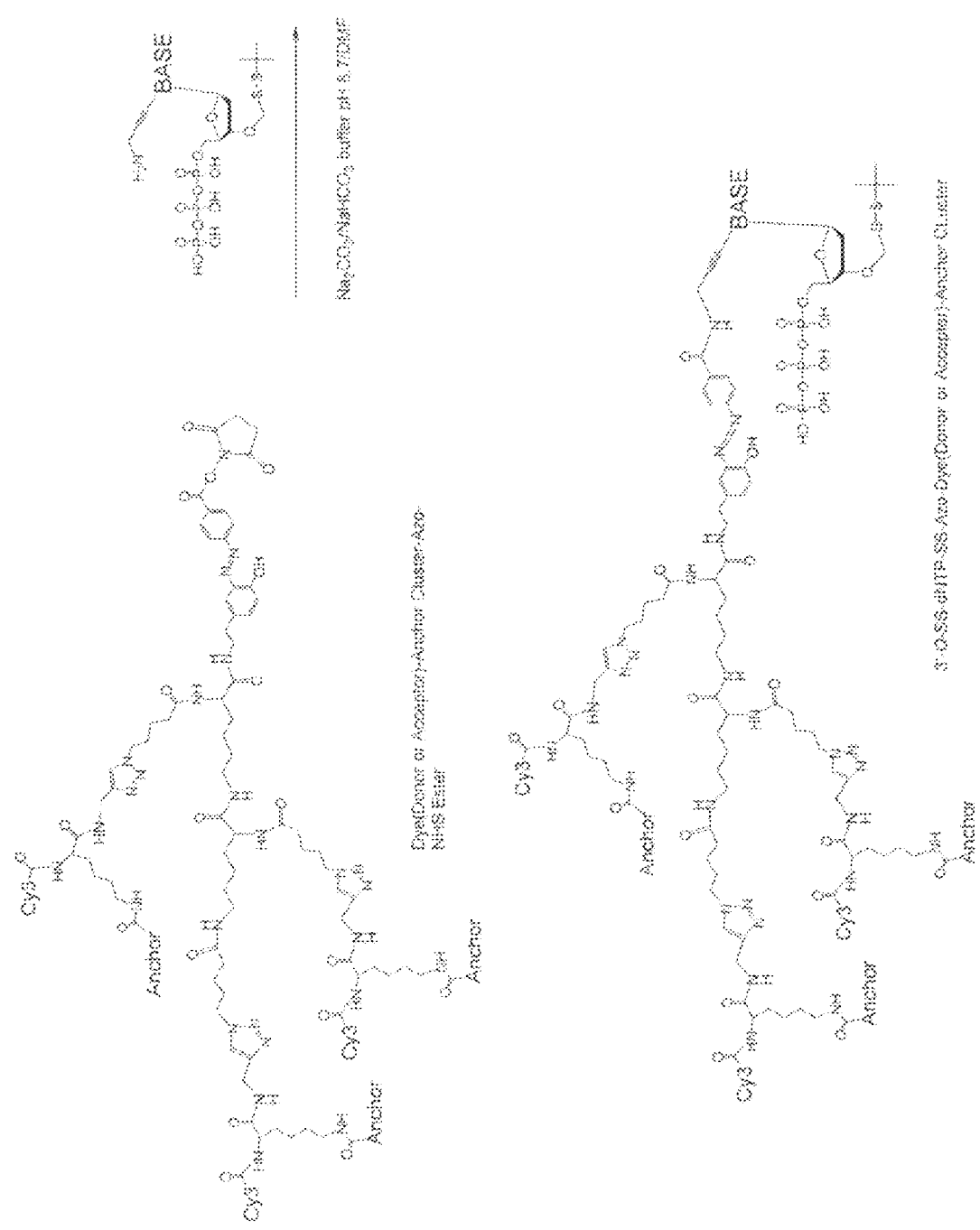
Figure 30X:
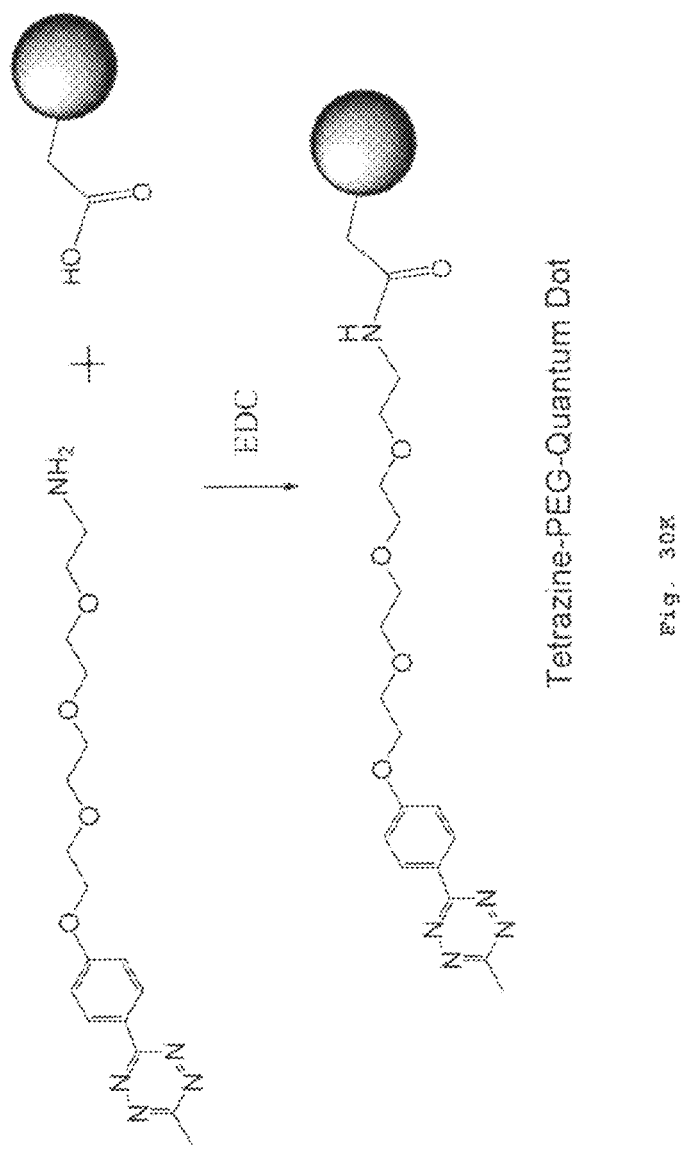
Figure 31C:
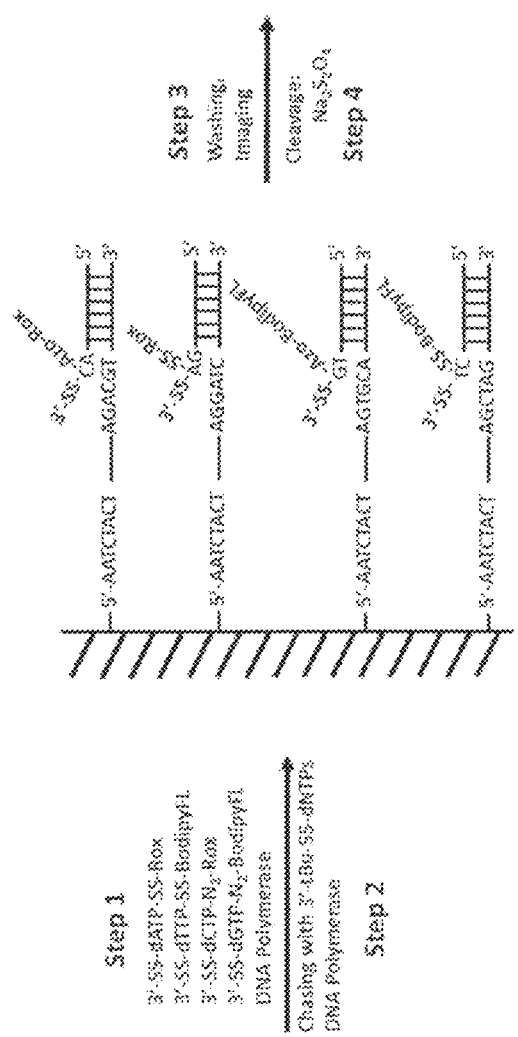
Figure 31D:
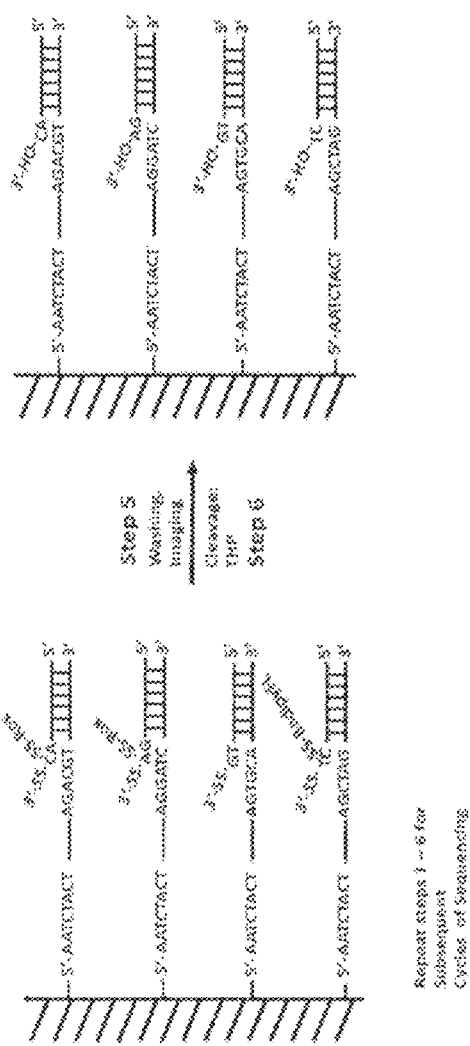
Figure 31E:
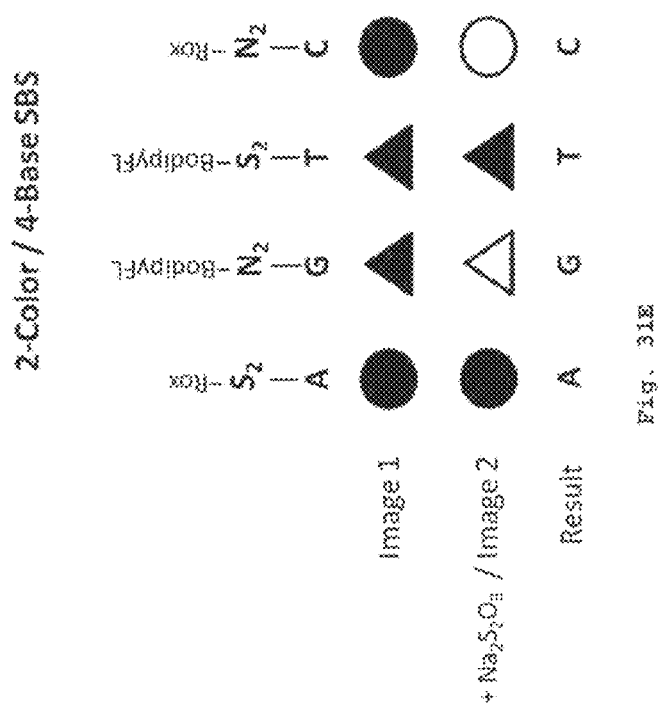
Figure 32C:
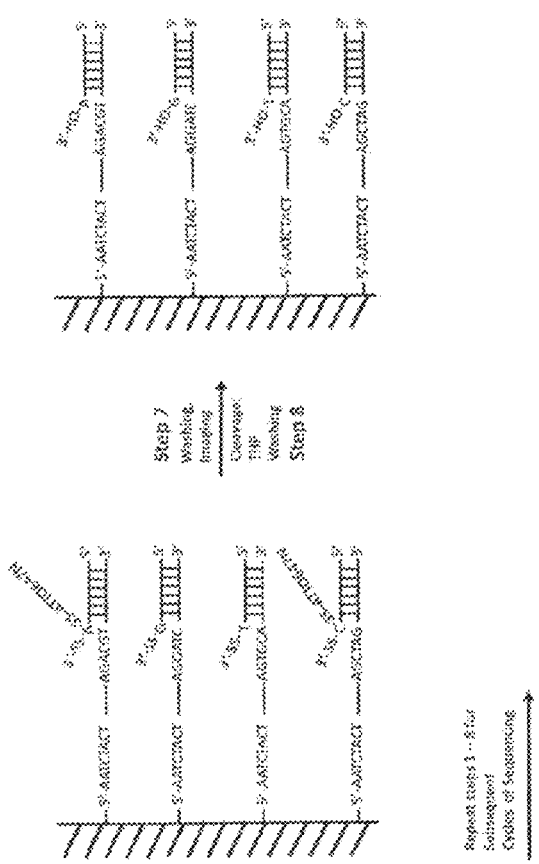
Figure 32D:
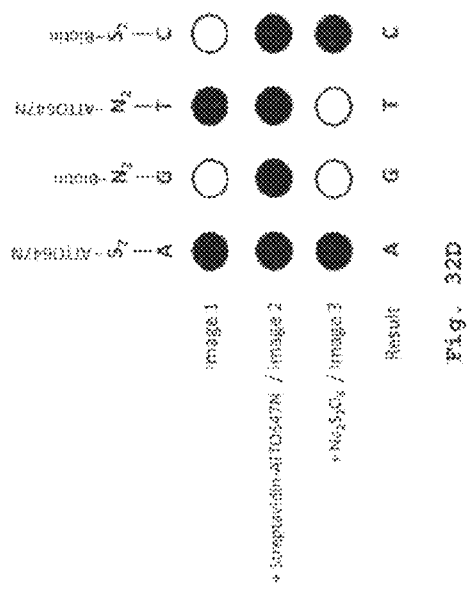
Figure 33A:
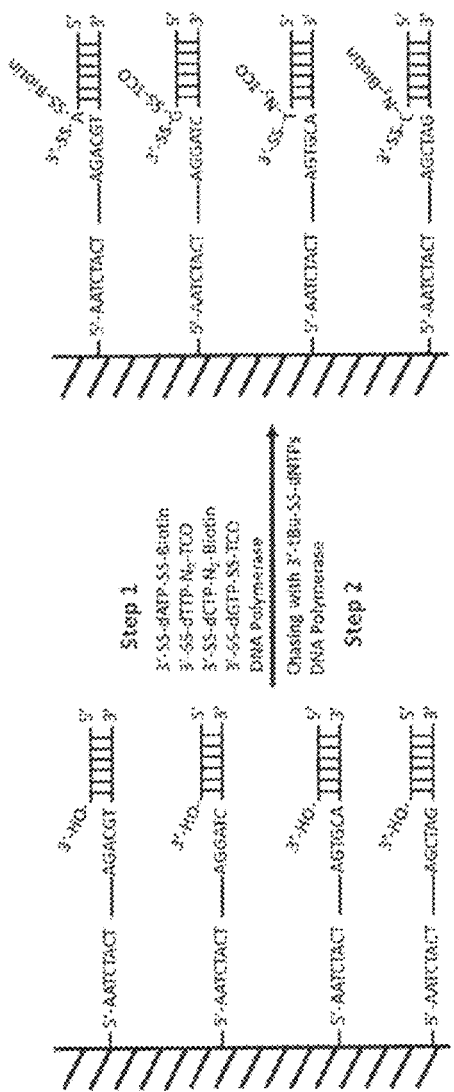
Figure 33B:
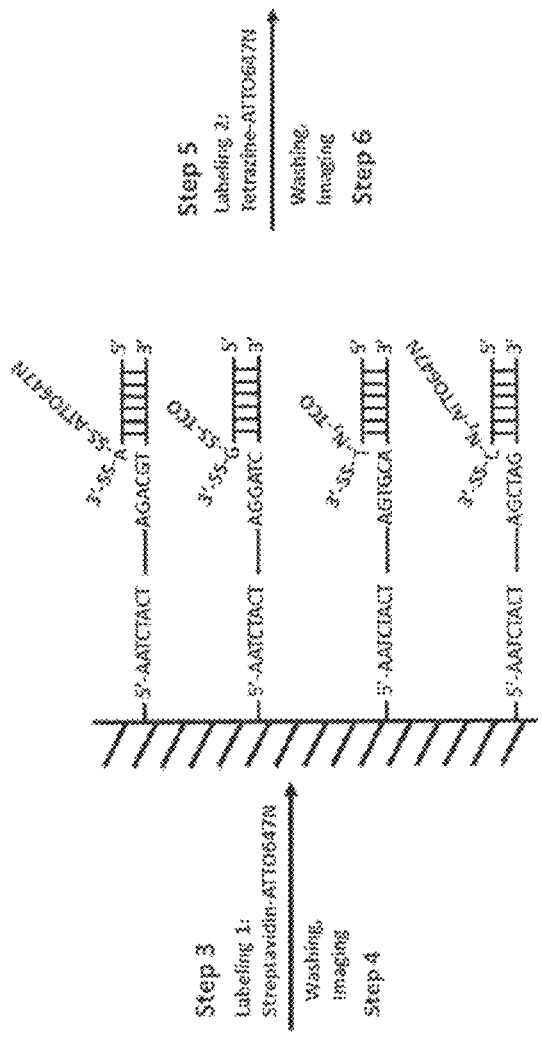

FIGS. 41A-41D contain a schematic showing Scheme VIIA using 3'-O-SS(DTM)-dNTP-SS-DonorDye-Anchors (3'-O-SS-dATP-7-SS-Cy3-Biotin, 3'-O-SS-dGTP-7-SS-Cy3-TCO), 3'-O-SS(DTM)-dNTP-Azo-DonorDye-Anchors (3'-O-SS-dTTP-5-Azo-Cy3-TCO, 3'-O-SS-dCTP-5-Azo-Cy3-Biotin) and the corresponding Dye Labeled Binding Molecules (Cy5-labeled Streptavidin and Cy5-labeled Tetrazine) to perform 1-color DNA SBS. Step 1, Addition of DNA polymerase and the four nucleotide analogues (3'-O-SS-dATP-7-SS-Cy3-Biotin, 3'-O-SS-dTTP-5-Azo-Cy3-TCO, 3'-O-SS-dCTP-5-Azo-Cy3-Biotin and 3'-O-SS-dGTP-7-SS-Cy3-TCO) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the anchor labeled dNTPs in step 1. The growing DNA strands are terminated with one of the four DonorDye-anchor labeled nucleotide analogues (A, C, G, T) or the same one of the four nucleotide analogues (A, C, G, T) without anchor. Step 3, labeling with Streptavidin-Cy5. The dye will bind specifically to the A and C nucleotide analogues, but not the G and T analogues. Step 4, After washing away remaining free label and excess nucleotides, detection of Cy5 signal after excitation of Cy3 indicates incorporation of either A or C. Step 5, labeling with Tetrazine-Cy5. The dye will bind specifically to the G and T nucleotide analogues, but not the A and C analogues. Step 6, After washing away remaining free label and excess nucleotides, detection of new Cy5 signal after excitation of Cy3 indicates incorporation of either G or T. Next, in Step 7, treatment of the DNA products with sodium dithionite cleaves the azo linker, leading to the removal of any donor-acceptor dye pairs on T and C. Step 8, After washing away cleaved dye, imaging for the presence of Cy5 fluorescence after excitation of Cy3 is carried out. In this step, if it has already been determined that the incorporated nucleotide could be A or C, loss of Cy5 fluorescence would reveal it to be C, while remaining fluorescence would reveal it to be A. Similarly, for signals previously determined as G or T, loss of Cy5 fluorescence would indicate incorporation of T specifically while remaining fluorescence would indicate incorporation of G. Next, in Step 9, treatment of the DNA products with THP cleaves the SS linker, leading to the removal of the remaining fluorescent dye and the regeneration of a free 3'-OH group on the DNA extension product. Step 10, after washing away THP, an optional imaging step will confirm all dyes have been removed, in preparation for the next cycle of sequencing. Though not indicated in Scheme VIIA, if desired, the presence of an additional SS linkage between the Azo group and the base results in the production of a shorter scar on the incorporated nucleotide after THP treatment which should result in longer reads. Structures of modified nucleotides used in this scheme are shown in FIG. 12A (with single anchors and donor dyes) but can include multiple anchors and donor dyes (see example synthetic scheme in FIG. 30A) as well. This can also include donor-anchor pair clusters connected to the base (structures and synthetic methods shown in FIGS. 26F-H. As with several other schemes, this scheme can be performed for either ensemble or single molecule SBS. Because of the energy transfer, with excitation of only the donor dye, and the fact that the acceptor is added via an anchor only after incorporation is complete, very little background fluorescence should be obtained. This would make this scheme particularly attractive for single molecule SBS.

Figure 11:
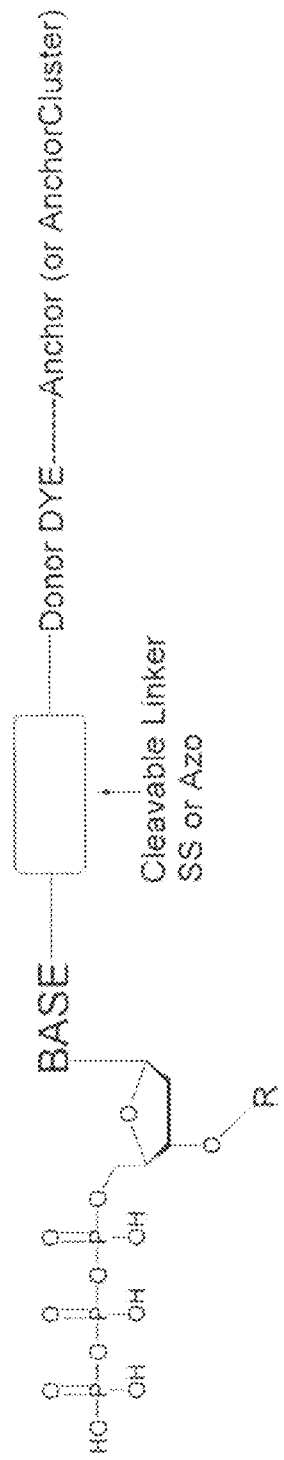
FIG. 11: General structure of nucleotide reversible terminator for fluorescence resonance energy transfer (FRET) based sequencing by synthesis.

Chemical structures of nucleotide analogues and other molecules for the various schemes are presented in FIGS. 5-10Z and 12A-12Z. A general structural scheme is presented in FIG. 11, and specific chemical schemes for the described molecules are presented in FIGS. 13-26.

Examples of additional possible anchors and anchor binding molecules (in some cases, these can be reversed, e.g., alkyne or cyclooctyne anchor and azide anchor binding molecule) can be found in Table 1:

TABLE 1

| Anchor | Anchor Binding Molecule |
| --- | --- |
| Azide | Alkyne; cyclooctyne |
| Tetrazine | Cyclooctene; Norbornene |
| Phenylboronic acid (PDBA) | Salicylhydroxamic acid (SHA) |
| Quadricyclane | Ni bis(dithiolene) |
| Norbornene | Nitrile oxide |

Section II: Hybrid Sequencing Using Dideoxynucleotides with Cleavable Linker and Dye on Base (Irreversible Terminators) and Unlabeled Nucleotide Analogues that have Disulfide Blocked 3'Positions (Reversible Terminators): Orthogonal Groups of Nucleotide Analogues The Ju laboratory (Guo et al. 2008 PNAS; Ju et al. US 2016/0024574 A1) described a method utilizing a combined set of 8 nucleotides: 4 of these were dideoxynucleotides with dyes attached to the base via cleavable linkers and the other 4 were unlabeled reversible terminators (3'-OH blocked). In this hybrid DNA sequencing by synthesis approach, while the majority of DNA molecules in an ensemble are extended by the unlabeled nucleotide reversible terminators (NRTs), a small portion are extended by the fluorescent ddNTPs to obtain a sufficient fluorescent signal to identify the base at that position, prior to cleavage of the dye. Although some members of the ensemble are lost in each round, by adjusting the ratio from mainly NRTs at the beginning to mainly fluorescent ddNTPs near the end, this approach was demonstrated to sequence several synthetic templates, achieving a length of 32 bases in a template containing a 5-base homopolymeric stretch. Disclosed herein is a general scheme (Scheme VIII) providing further details. In Guo et al, azidomethyl cleavable groups were used, though any specifically cleavable moiety could be utilized. In this section, the examples use SS blocking groups at the 3'-O position and SS, Azo and other cleavable groups in the linkers between base and dye or anchor.

By creating orthogonal or pseudo-orthogonal sets of fluorescent dideoxynucleotide analogues with different cleavable linkers, different dyes, or different anchors, all of the sequencing schemes presented in this application, including 4-color, 2-color and 1-color variants, can be modified to utilize fluorescent dideoxynucleotides (in combination with unlabeled reversible terminators). In this case, the unlabeled reversible terminators would be added together with the fluorescent dideoxynucleotides rather than in a separate chase step. Unlike some of the previous schemes with fluorescent reversible terminators which can be used for both ensemble and single molecule sequencing, this approach is restricted to ensemble sequencing.

Herein disclosed are a general scheme (Scheme VIII) and 11 additional SBS schemes (Schemes IX-XVII) using two sets of nucleotide analogues: (1) dideoxynucleotide analogues in which either a dye, or an anchor for subsequent attachment of a dye, is linked to the base by a DTM or other cleavable linker. In three of these schemes dye clusters or anchor clusters are used to enhance the signal; (2) deoxynucleotide analogues in which the 3' position of the nucleotide analogues is blocked by a dithiomethyl (DTM) moiety which can be cleaved specifically with THP; these will be referred to below as NRTs. In early rounds of SBS, very low ratios of labeled dideoxynucleotides:unlabeled NRTs are added; the ratio is gradually increased throughout the process; by the final rounds of SBS, the labeled dideoxynucleotides are present at higher concentrations than the unlabeled NRTs. Though there is a gradual loss in extendable growing strands over the course of the sequencing, assuming a starting ensemble of a million or more template copies, even if 3% of growing strands are labeled with the fluorescent-cleavable linker-ddNTPs in each sequencing cycle, at least 30 base long reads will be obtained, with strong enough specific signals even in the last few cycles. While the hybrid sequencing approach described in this section may be limited in terms of overall read length relative to the SBS schemes presented in other sections, it will provide more than sufficient sequence lengths for many diagnostic applications, including non-invasive DNA detection for trisomies, cancer, neurocellular damage, etc.

Though the 3'-blocking group in all the examples shown in this section is t-butyl-dithiomethyl, other alkyl groups, such as methyl-dithiomethyl or ethyl-dithiomethyl could also be used. Wherever DTM is referred to in this patent application, it may refer to the dithiomethyl group or the various alkyl or other substituted dithiomethyl groups attached to the 3'-O. Other 3'-blocking groups (allyl, 2-nitrobenzyl, azidomethyl) may also be used, particularly if that group is present as the general cleavable group in all the linkers between the bases and dyes or anchors on the dideoxynucleotides. In addition to nucleoside triphosphate analogues, nucleoside tetraphosphate, nucleoside pentaphosphate, nucleoside hexaphosphate and higher nucleoside polyphosphate analogues are feasible alternatives.

In the following schemes the Azo group is placed in linkers as an example of a second (non-DTM) cleavable linker; sodium dithionite is shown as an example cleaving agent (refer to FIGS. 124A-128B demonstrating the cleavage efficiency of sodium dithionite for the Azo group and the stability of SS bonds under these conditions). ATTO647N, Rox, and BodipyFL are used as examples of fluorophores; biotin or TCO are provided as examples of the anchors; and streptavidin or tetrazine are used as examples of the anchor binding molecules. However, a variety of other cleavable groups in the linker (e.g., allyl, 2-nitrobenzyl groups), cleavage agents (e.g., Pd(0), ~340 nm light), fluorophores, anchors (e.g., DBCO, $N_3$, tetrazine)*, and anchor binding molecules (e.g., $N_3$, DBCO, TCO)* are also feasible. Dyes can consist of single dye molecules, dye pairs that exhibit energy transfer, clusters of dyes attached at multiple positions of linear or branched polymers, or quantum dots (QDs). Though no examples are provided in this section, other labels may be used, e.g., non-fluorescent labels including Raman tags, and as described in the prior PCT, sets of tags that reduce ion current signals in nanopores to different extents, have different dwell times within the ion channel, or both.

General Scheme VIII shows results for two cycles of the hybrid sequencing by synthesis approach using only a single template (shown as 4 copies). This scheme is meant to demonstrate how either the ddNTP-Cleavable Linker-Dye/Anchor molecules or the same nucleotide reversible terminator can be incorporated. Further details are provided in the legend to Scheme VIII.

FIG. 66 contains a schematic showing the General Scheme VIII for hybrid sequencing using four ddNTP-Cleavable Linker-Dye nucleotide analogues and four nucleotide reversible terminators. In the example shown in FIG. 66, an SS cleavable linker between the dye and the base and a DTM 3' blocking group are used. For simplicity, only a single template is shown in this scheme. In Step 1, polymerase is added along with the four ddNTP-SS-Dye nucleotide analogues (ddATP-7-SS-Rox, ddTTP-5-SS-R6G, ddCTP-5-SS-Alexa488 and ddGTP-7-SS-Cy5), and the four 3'-tert-butyl-SS-dNTPs (3'-tert-butyl-SS-dATP, 3'-tert-butyl-SS-dTTP, 3'-tert-butyl-SS-dCTP and 3'-tert-butyl-SS-dGTP). The ratio of the ddNTP-SS-Dye nucleotide analogues and the nucleotide reversible terminators is such that in the vast majority of extension reactions, the reversible terminator will be incorporated, 3'-tert-butyl-SS-dATP in this example since the next base in the template strand is an A. Only a small subset (but enough to detect the specific fluorescent signal) of the growing DNA strands will be extended with the fluorescent ddNTP, ddATP-7-SS-Rox in this example. Step 2, after an optional chase step with the four 3'-tert-butyl-dNTPs, washing and imaging, Rox fluorescence will indicate incorporation of the ddA irreversible terminator; all ddA extended strands are lost to future sequencing cycles. Next, in Step 3, THP is added to cleave the SS group thereby releasing the dye, and at the same time to regenerate the 3'-OH groups on all the strands extended with the reversible terminators, readying them for the next round of sequencing. In the second cycle, in Step 1, the same set of 8 nucleotide analogues is added along with polymerase. Since C is the next available nucleotide in the template strand, all strands with a free terminal 3'-OH will be extended with either ddGTP-7-SS-Cy5 in the small minority of cases, and with 3'-tert-butyl-dGTP in the majority of cases. Step 2, after an optional chase step, Cy5 fluorescence will indicate incorporation of the ddGTP irreversible terminator; all ddG extended strands are lost to future sequencing cycles. Again, in Step 3, THP is added to cleave the SS group thereby releasing the dye, and at the same time to regenerate the 3'-OH groups on all the strands extended with the reversible terminators, readying them for the next round of sequencing. With the template shown, in subsequent cycles, G, T, C and T will be added. While only four copies of the template are shown here, in fact the ensemble of templates amplified clonally at a given position on the slide will contain a million or more copies. Thus, even if 3% of growing strands in the ensemble are lost in each round, it will be possible to sequence over 30 bases. Structures of modified nucleotides using in this scheme are shown in FIG. 48.

For the eleven remaining schemes (Schemes IX-XV, XVIA-C, XVII) the results for four different templates (two copies of each shown) as in other sections of this patent, with either incorporation of the ddNTP-Cleavable Linker-Dye/Anchor molecules or the 3'-reversibly blocked unlabeled terminators. Although only one example of an extended molecule with each of these nucleotide analogues is shown, the former would represent the minority of incorporation events (the unlabeled NRTs being incorporated in the majority of cases), but they are the only ones that can be detected by the fluorescent imaging steps. Further details are provided in the legends to those schemes.

Scheme IX is a two-color SBS scheme that requires two detection steps; Schemes X and XI are single-color schemes that require three detection steps to determine the incorporated nucleotide. Scheme XII is a one-color scheme using anchor and dye clusters and requiring three detection steps. Schemes XIII and XIV are two-color schemes using anchor and dye clusters and requiring three and two detection steps, respectively. Scheme XV is a 4-color scheme with one detection step and Scheme XVIA is a 4-color scheme with two detection steps. Schemes XVIB and XVIC are two-color schemes taking advantage of quantum dots. Scheme XVII is a one-color scheme that take advantage of energy transfer between a donor and acceptor dye. Optional confirmatory imaging steps are included in some of these schemes. Unlike with the previously described schemes, addition of unlabeled nucleotide analogues (NRTs) is performed at the same time the dye- or anchor-containing nucleotide analogues are added. This assures that only a small portion of the DNA molecules will be extended with the dye-labeled ddNTPs, which are irreversible terminators, while the majority will be extended with reversible terminators. Though this should also help to maintain the registry during sequencing reactions, an additional optional chase with the same reversible terminator can be performed to guarantee that every DNA primer strand has been extended so as to avoid asynchronous reactions. Washing is essential between every step to remove the previous set of reagents and/or released dyes.

One and Two-Color Schemes Involving Single Dyes on Each Dideoxynucleotide Analogue (Schemes IX-XI)

Scheme IX: Two-color SBS with two dyes and two cleavable linkers; imaging after incorporation and first cleavage. In Scheme IX, an orthogonal set of dideoxynucleotide analogues, one with Dye1 attached to the base via an SS linkage, one with Dye1 attached to the base via an Azo linkage, one with Dye2 attached to the base via an SS linkage, and one with Dye2 attached to the base via an Azo linkage, is used. The four NRTs are added at the same time. Imaging after addition of the eight nucleotide analogues will indicate incorporation by either of two types of dideoxynucleotide analogues specifically. After cleavage of Azo linkers with sodium dithionite, imaging will reveal specifically which dideoxynucleotide analogue was incorporated. Cleavage with THP will then remove the remaining dyes from the dideoxynucleotide analogues, which are unavailable for further reactions, and restore the 3'-OH group on the NRTs, which represent the vast majority of incorporation events for subsequent sequencing cycles. In the example shown, Dye1 is Rox and Dye2 is BodipyFL. Other combinations of dyes and cleavable linkers can also be used.

FIGS. 67A-67B contain a schematic showing Scheme IX using ddNTP-SS-Dyes (ddATP-7-SS-Rox, ddTTP-5-SS-BodipyFL), ddNTP-Azo-Dyes (ddGTP-7-Azo-BodipyFL, ddCTP-5-Azo-Rox), and 3'-O-SS-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS. Step 1, Addition of DNA polymerase and the eight nucleotide analogues (ddATP-7-SS-Rox, ddTTP-5-SS-BodipyFL, ddGTP-7-Azo-BodipyFL, ddCTP-5-Azo-Rox, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotide analogues in step 1. The growing DNA strands are terminated with one of the four dye labeled dideoxynucleotide analogues (A, C, G, T) or the same one of the four nucleotide reversible terminators (A, C, G, T) without dye. Step 3, after washing away the unincorporated nucleotides, detection of the unique fluorescence signal from each of the fluorescent dyes on the DNA products allows the partial identification of the incorporated dideoxynucleotide for sequence determination: Rox signal indicates incorporation of either ddA or ddC, BodipyFL signal indicates incorporation of ddT or ddG. Step 4, cleavage of Azo linker by adding sodium dithionite ($Na_2S_2O_4$) to the elongated DNA strands results in removal of Rox from incorporated ddC and BodipyFL from incorporated ddG. Step 5, after washing away the cleaved dyes, a second round of detection of the unique fluorescence signal from each of the fluorescent dyes on the DNA products allows the identification of the incorporated dideoxynucleotide for sequence determination. Disappearance of Rox signal indicates incorporation of ddC, and disappearance of BodipyFL signal indicates incorporation of ddG. Remaining Rox signal indicates incorporation of ddA, and remaining BodipyFL signal indicates incorporation of ddT. Next, in Step 6, treatment of the DNA products with THP cleaves the SS linker, leading to the removal of the remaining fluorescent dye on the subset of DNA molecules extended with ddNTPs and the regeneration of a free 3'-OH group on the majority of DNA molecules extended with NRTs, readying the extended DNA for the next cycle of the DNA sequencing reaction. A schematic showing the expected fluorescence at each imaging step is provided at the end of Scheme I. Similar schematics can be constructed for other 2-color SBS schemes in this section. Structures of modified nucleotides used in this scheme are shown in FIG. 42.

Scheme X: One-color SBS with one dye, one anchor and two cleavable linkers; imaging after incorporation, labeling, and first cleavage. In Scheme X, an orthogonal set of dideoxynucleotide analogues, one with Dye1 attached to the base via an SS linkage, one with Dye1 attached to the base via an Azo linkage, one with Anchor1 attached to the base via an SS linkage, and one with Anchor1 attached to the base via an Azo linkage, is used. The four NRTs are added at the same time. Imaging after addition of the eight nucleotide analogues will indicate incorporation by either of two types of dideoxynucleotide analogues specifically. Imaging after labeling with Dye1 via an Anchor1-binding molecule will confirm incorporation by either of the other two types of dideoxynucleotide analogues specifically. (Imaging is optional but recommended at this step.) Finally, cleavage of the Azo linker with sodium dithionite will reveal specifically which dideoxynucleotide analogue was incorporated. Cleavage with THP will then remove the remaining dyes from the dideoxynucleotide analogues, which are unavailable for further reactions, and restore the 3'-OH group on the NRTs, which represent the vast majority of incorporation events for subsequent sequencing cycles. In the example shown, Dye1 is ATTO647N and Anchor1 is Biotin. Other combinations of dyes, anchors and cleavable linkers can also be used.

FIGS. 68A-68C contain a schematic of Scheme X using ddNTP-SS-Dye (ddATP-7-SS-ATTO647N), ddNTP-Azo-Dye (ddTTP-5-Azo-ATTO647N), ddNTP-SS-Anchor (ddCTP-5-SS-Biotin), ddNTP-Azo-Anchor (3'-O-SS-dGTP-7-Azo-Biotin), the corresponding Dye Labeled Binding Molecule (ATTO647N-labeled Streptavidin), and 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS. Step 1, Addition of DNA polymerase, the four dideoxynucleotide analogues (3'-O-SS-dATP-7-SS-ATTO647N, 3'-O-SS-dTTP-5-Azo-ATTO647N, 3'-O-SS-dCTP-5-SS-Biotin and 3'-O-SS-dGTP-7-Azo-Biotin), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye labeled dNTPs in step 1. The growing DNA strands are terminated with one of the four dye labeled dideoxynucleotide analogues (ddA, ddC, ddG, ddT) or the same one of the four nucleotide reversible terminators (A, C, G, T) without dye or anchor. Step 3, after washing away the unincorporated nucleotides, detection of the fluorescence signal from each of the fluorescent dyes on the DNA products allows the partial identification of the incorporated dideoxynucleotide for sequence determination, the ATTO647N signal indicating incorporation of either ddA or ddT. Step 4, labeling with Streptavidin-ATTO647N. After washing away remaining free label, detection of new ATTO647N signal in Step 5 indicates incorporation of either ddC or ddG. Next, in Step 6, treatment of the DNA products with sodium dithionite cleaves the azo linker, leading to the removal of any fluorescent dye on ddG and ddT. Step 7, after washing away the cleaved dye, imaging is carried out. In this step, if it has been already determined that the incorporated nucleotide could be ddA or ddT, loss of fluorescence would reveal it to be ddT, while remaining fluorescence would reveal it to be ddA. Similarly, for signals previously determined as ddC or ddG, loss of fluorescence would indicate incorporation of ddG specifically while remaining fluorescence would indicate incorporation of ddC. Next, in Step 8, treatment of the DNA products with THP cleaves the SS linker, leading to the removal of the remaining fluorescent dye on the subset of DNA molecules extended with ddNTPs and the regeneration of a free 3'-OH group on the majority of DNA molecules extended with NRTs, readying the extended DNA for the next cycle of the DNA sequencing reaction. After washing away THP, an optional imaging step (not shown) will confirm all dyes have been removed, in preparation for the next cycle of sequencing. A schematic showing the expected fluorescence at each imaging step is provided at in FIG. 32D. Similar schematics can be constructed for other 1-color SBS schemes in this section. Structures of modified nucleotides used in this scheme are shown in FIG. 43.

Scheme XI: One-color SBS with two anchors and two cleavable linkers: imaging after each labeling step and after first cleavage. In Scheme XI, an orthogonal set of dideoxynucleotide analogues, one with Anchor1 attached to the base via an SS linkage, one with Anchor1 attached to the base via an Azo linkage, one with Anchor2 attached to the base via an SS linkage, and one with Anchor2 attached to the base via an Azo linkage, is used. The four NRTs are added at the same time and incorporation is carried out. Then, imaging after the first labeling step with Dye1 attached to an Anchor1-binding molecule will indicate incorporation of either of two types of dideoxynucleotide analogues. Imaging after the second labeling step with Dye1 attached to an Anchor2-binding molecule will confirm incorporation of either of the other two types of dideoxynucleotide analogues. (Imaging is optional but recommended at this step.) Imaging after cleavage of the Azo linker with sodium dithionite will indicate the specific dideoxynucleotide analogue incorporated. Cleavage with THP will then remove the remaining dyes from the dideoxynucleotide analogues, which are unavailable for further reactions, and restore the 3'-OH group on the NRTs, which represent the vast majority of incorporation events for subsequent sequencing cycles. In the example shown, Dye1 is ATTO647N, Anchor1 is Biotin and Anchor2 is TCO. Other combinations of dyes, anchors and cleavable linkers can also be used.

FIGS. 69A-69D contain a schematic showing Scheme XI using ddNTP-SS-Anchors (ddATP-7-SS-Biotin, ddGTP-7-SS-TCO), ddNTP-Azo-Anchors (ddTTP-5-Azo-TCO, ddCTP-5-Azo-Biotin), the corresponding Dye Labeled Binding Molecules (ATTO647N-labeled Streptavidin and ATTO647N-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS. Step 1, Addition of DNA polymerase and the eight nucleotide analogues (ddATP-7-SS-Biotin, ddGTP-7-SS-TCO, ddTTP-5-Azo-TCO, ddCTP-5-Azo-Biotin, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotide analogues in step 1. The growing DNA strands are terminated with one of the four anchor labeled dideoxynucleotide analogues (ddA, ddC, ddG, ddT) or the same one of the four nucleotide reversible terminators (A, C, G, T) without anchor. Step 3, labeling with Streptavidin-ATTO647N. The dye will bind specifically to the ddA and ddC nucleotide analogues, but not the ddG and ddT analogues. Step 4, After washing away remaining free label and excess nucleotides, detection of new ATTO647N signal indicates incorporation of either ddA or ddC. Step 5, labeling with Tetrazine-ATTO647N. The dye will bind specifically to the ddG and ddT nucleotide analogues, but not the ddA and ddC analogues. Step 6, After washing away remaining free label and excess nucleotides, detection of new ATTO647N signal indicates incorporation of either ddG or ddT. Next, in Step 7, treatment of the DNA products with sodium dithionite cleaves the azo linker, leading to the removal of any fluorescent dye on ddT and ddC. Step 8, After washing away cleaved dye, imaging for the presence of ATTO647N fluorescence is carried out. In this step, if it has already been determined that the incorporated nucleotide could be ddA or ddC, loss of fluorescence would reveal it to be ddC, while remaining fluorescence would reveal it to be ddA. Similarly, for signals previously determined as ddG or ddT, loss of fluorescence would indicate incorporation of ddT specifically while remaining fluorescence would indicate incorporation of ddG. Next, in Step 9, treatment of the DNA products with THP cleaves the SS linker, leading to the removal of the remaining fluorescent dye on the subset of DNA molecules extended with ddNTPs and the regeneration of a free 3'-OH group on the majority of DNA molecules extended with NRTs, readying the extended DNA for the next cycle of the DNA sequencing reaction. Step 10, after washing away THP, an optional imaging step will confirm all dyes have been removed, in preparation for the next cycle of sequencing. Structures of modified nucleotides used in this scheme are shown in FIG. 44.

In the case of 2-dye schemes, dyes are chosen that have well separated absorption and emission spectra. The 2-color and especially the 1-color schemes are designed to reduce the size, cost and complexity of the optical setup required.

While all the schemes presented use DNA templates and primers, dideoxynucleotide analogues, reversible terminators and DNA polymerase, in principle the schemes can be adjusted to include appropriate templates, primers, and nucleotide analogues for RNA-dependent DNA polymerases as well as DNA- or RNA-dependent RNA polymerases.

One and Two-Color Schemes Involving Clusters of Dyes on Each Nucleotide Analogue (Schemes XII-XIV)

Scheme XII: One-color SDS with one dye cluster, one anchor cluster and two cleavable linker clusters; imaging after Incorporation, labeling, and first cleavage. The only difference with Scheme IX is that clusters of anchors (Anchor1 cluster) or clusters of dyes (Dye1 cluster) are attached to the base of the dideoxynucleotide analogues. In the labeling step, multiple dyes will bind to the anchor cluster. In the example shown, the Dye1 cluster is an ATTO647N cluster and the Anchor1 cluster is a Biotin cluster. Other combinations of dye clusters, anchor clusters and cleavable linkers can also be used.

FIGS. 70A-70C contain a schematic showing Scheme XII using of ddNTP-SS-Dye Cluster (ddATP-7-SS-ATTO647N Cluster), ddNTP-Azo-Dye Cluster (ddTTP-5-Azo-ATTO647N Cluster), ddNTP-SS-Anchor Cluster (ddCTP-5-SS-Biotin Cluster), ddNTP-Azo-Anchor Cluster (ddGTP-7-Azo-Biotin Cluster), the corresponding Dye Labeled Binding Molecule (ATTO647N-labeled Streptavidin), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS. Step 1, Addition of DNA polymerase and the eight nucleotide analogues (ddATP-7-SS-ATTO647N Cluster, ddTTP-5-Azo-ATTO647N Cluster, ddCTP-5-SS-Biotin Cluster, ddGTP-7-Azo-Biotin Cluster, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotides in step 1. The growing DNA strands are terminated with one of the four dye cluster- or anchor cluster-labeled dideoxynucleotide analogues (ddA, ddC, ddG, ddT) or the same one of the four nucleotide reversible terminators (A, C, G, T) without dye or anchor. Step 3, after washing away the unincorporated dye labeled nucleotides, detection of the fluorescence signal from each of the fluorescent dyes on the DNA products allows the partial identification of the incorporated dideoxynucleotide analogue for sequence determination, the ATTO647N signal indicating incorporation of either ddA or ddT. Step 4, labeling with Streptavidin-ATTO647N. After washing away remaining free label, detection of new ATTO647N signal in Step 5 indicates incorporation of either ddC or ddG. Next, in Step 6, treatment of the DNA products with sodium dithionite cleaves the Azo linker, leading to the removal of any fluorescent dye on ddG and ddT. Step 7, after washing away the cleaved dye, imaging is carried out. In this step, if it has already been determined that the incorporated nucleotide analogue could be ddA or ddT, loss of fluorescence would reveal it to be ddT, while remaining fluorescence would reveal it to be ddA. Similarly, for signals previously determined as ddC or ddG, loss of fluorescence would indicate incorporation of ddG specifically while remaining fluorescence would indicate incorporation of ddC. Next, in Step a, treatment of the DNA products with THP cleaves the SS linker, leading to the removal of the remaining fluorescent dye on the subset of DNA molecules extended with ddNTPs and the regeneration of a free 3'-OH group on the majority of DNA molecules extended with NRTs, readying the extended DNA for the next cycle of the DNA sequencing reaction. After washing away THP, an optional imaging step (not shown) will confirm all dyes have been removed, in preparation for the next cycle of sequencing. Structures of modified nucleotides used in this scheme are shown in FIGS. 45A-45C.

Scheme XIII: Two-color SBS with two anchor clusters, 2 dyes, and two cleavable linkers: imaging after each labeling step and after first cleavage. Somewhat similar to Scheme X, but with one of two different dye clusters (Anchor1 cluster and Anchor2 cluster) attached to the base of the dideoxynucleotide analogues. In the labeling step, multiple dyes will bind to the anchor clusters. The presence of Dye1 after the first labeling step will indicate two possible incorporated dideoxynucleotide analogues. The appearance of Dye2 after the second labeling step will verify the incorporation of the other two types of dideoxynucleotide analogues. (Imaging is optional but recommended at this step.) Imaging after cleavage of the Azo linker with sodium dithionite will indicate the specific dideoxynucleotide analogue incorporated. Cleavage with THP will then remove the remaining dyes from the dideoxynucleotide analogues, which are unavailable for further reactions, and restore the 3'-OH group on the NRTs, which represent the vast majority of incorporation events for subsequent sequencing cycles. In this example, the Anchor1 cluster contains biotin, Anchor2 cluster contains TCO, Dye1 is Rox and Dye2 is Alexa488. Other combinations of dyes, anchors and cleavable linkers can also be used.

FIGS. 71A-71D contain a schematic showing Scheme XIII using ddNTP-SS-Anchor Clusters (ddATP-7-SS-Biotin Cluster, ddGTP-7-SS-TCO Cluster), ddNTP-Azo-Anchor Clusters (ddCTP-5-Azo-Biotin Cluster, ddTTP-5-Azo-TCO Cluster), the corresponding Dye Labeled Binding Molecules (Rox-labeled Streptavidin and Alexa488-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS. Step 1, Addition of DNA polymerase and the eight nucleotide analogues (ddATP-7-SS-Biotin Cluster, ddGTP-7-SS-TCO Cluster, ddCTP-5-Azo-Biotin Cluster, ddTTP-5-Azo-TCO Cluster, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotides in step 1. The growing DNA strands are terminated with one of the four anchor cluster labeled dideoxynucleotide analogues (ddA, ddC, ddG, ddT) or the same one of the four nucleotide reversible terminators (A, C, G, T) without dye or anchor clusters. Step 3, labeling with Streptavidin-Rox. The dye will bind specifically to the ddA and ddC nucleotide analogues, but not the ddG and ddT analogues. Step 4, After washing away remaining free label and excess nucleotides, detection of new Rox signal indicates incorporation of either ddA or ddC. Step 5, labeling with Tetrazine-Alexa488. The dye will bind specifically to the ddG and ddT nucleotide analogues, but not the ddA and ddC analogues. Step 6, After washing away remaining free label and excess nucleotides, detection of new Alexa488 signal indicates incorporation of either ddG or ddT. Next, in Step 7, treatment of the DNA products with sodium dithionite cleaves the Azo linker, leading to the removal of any fluorescent dye on ddT and ddC. Step 9, After washing away cleaved dye clusters, imaging is carried out. In this step, if it has already been determined that the incorporated nucleotide could be ddA or ddC, loss of Rox fluorescence would reveal it to be ddC, while remaining Rox fluorescence would reveal it to be ddA. Similarly, for signals previously determined as ddG or ddT, loss of Alexa488 fluorescence would indicate incorporation of ddT specifically while remaining fluorescence would indicate incorporation of ddG. Next, in Step 9, treatment of the DNA products with THP cleaves the SS linker, leading to the removal of the remaining fluorescent dye on the subset of DNA molecules extended with ddNTPs and the regeneration of a free 3'-OH group on the majority of DNA molecules extended with NRTs, readying the extended DNA for the next cycle of the DNA sequencing reaction. Step 10, after washing away THP, an optional imaging step will confirm all dyes have been removed, in preparation for the next cycle of sequencing. Structures of modified nucleotides used in this scheme are shown in FIGS. 461-46B.

Scheme XIV: Two-color SBS with two dye clusters, two anchor clusters and one cleavable linker: imaging after incorporation and labeling step. In Scheme XIV, Dye1 Cluster, Dye2 Cluster, Anchor1 Cluster and Anchor2 Cluster are attached to the four bases of the dideoxynucleotide analogues, respectively, all via an SS linkage. NRTs are added at the same time and incorporation is carried out. Imaging will indicate incorporation of two of the dideoxynucleotide analogues specifically. Next labeling is carried out with both Anchor1 and Anchor2 binding molecules attached to single molecules of Dye1 and Dye2, respectively. Imaging will indicate incorporation of the other two of the dideoxynucleotide analogues specifically. Cleavage with THP will then remove the remaining dyes from the dideoxynucleotide analogues, which are unavailable for further reactions, and restore the 3'-OH group on the NRTs, which represent the vast majority of incorporation events for subsequent sequencing cycles. In the example shown, Dye1 is Rox, Dye2 is BodipyFL, Anchor1 is Biotin and Anchor2 is TCO. Other combinations of dye clusters and anchor clusters can also be used.

FIGS. 72A-72C contain a schematic showing Scheme XIV using ddNTP-SS-Dye Clusters (ddATP-7-SS-Rox Cluster, dTTP-5-SS-BodipyFL Cluster), ddNTP-SS-Anchor Clusters (ddCTP-5-SS-Biotin Cluster, ddGTP-7-SS-TCO Cluster), corresponding dye-labeled anchor binding molecules (Streptavidin-Rox, Tetrazine-BodipyFL), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS. Step 1, Addition of DNA polymerase and the eight nucleotide analogues (ddATP-7-SS-Rox Cluster, dTTP-5-SS-BodipyFL Cluster, ddCTP-5-SS-Biotin Cluster, ddGTP-7-SS-TCO Cluster, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotide analogues in step 1. The growing DNA strands are terminated with one of the four anchor cluster- or dye cluster-labeled dideoxynucleotide analogues (ddA, ddC, ddG, ddT) or the same one of the four reversible terminators (A, C, G, T) without dye or anchor cluster. Step 3, after washing away the unincorporated nucleotides, detection of the unique fluorescence signal from each of the fluorescent dyes on the DNA products allows the identification of two of the incorporated dideoxynucleotides for sequence determination: Rox signal indicates incorporation of ddA, BodipyFL signal indicates incorporation of ddT. Step 4, labeling with Streptavidin-Rox molecules which will bind to the biotin anchor clusters and Tetrazine-BodipyFL molecules which will bind to the TCO anchor clusters. Step 5, after washing, a second round of detection of the unique fluorescence signal from each of the fluorescent dyes on the DNA products allows the identification of the remaining two incorporated dideoxynucleotides for sequence determination. A new Rox signal indicates incorporation of ddC; a new BodipyFL signal indicates incorporation of ddG. Next, in Step 6, treatment of the DNA products with THP cleaves the SS linker, leading to the removal of the fluorescent dye on the subset of DNA molecules extended with ddNTPs and the regeneration of a free 3'-OH group on the majority of DNA molecules extended with NRTs, readying the extended DNA for the next cycle of the DNA sequencing reaction. Step 7, after washing away THP, an optional imaging step will confirm all dyes have been removed, in preparation for the next cycle of sequencing. Structures of modified nucleotides used in this scheme are shown in FIG. 47.

Four-Color Schemes Involving Single Dyes on Each Dideoxynucleotide Analogue (Schemes XV and XVI):

Scheme XV: Hour-color SBS with four dyes directly attached to base: imaging after incorporation step. In Scheme XV, Dye 1, Dye2, Dye3 and Dye4 are attached to the four bases of the dideoxynucleotide analogues, respectively, all via an SS linkage. NRTs are added at the same time and incorporation is carried out. Imaging will indicate incorporation of each type of nucleotide analogue specifically. Cleavage with THP will then remove the remaining dyes from the dideoxynucleotide analogues, which are unavailable for further reactions, and restore the 3'-OH group on the NRTs, which represent the vast majority of incorporation events for subsequent sequencing cycles. In the example shown, Dye1 is Rox, Dye2 is R6G, Dye3 is Alexa488 and Dye4 is Cy5. Other combinations of dyes can also be used.

FIGS. 73A-73B contain a schematic showing Scheme XV using ddNTP-SS-Dyes (ddATP-7-SS-Rox, dTTP-5-SS-R6G, ddCTP-5-SS-Alexa488, ddGTP-7-SS-Cy5) and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 4-color DNA SBS. Step 1, Addition of DNA polymerase and the eight nucleotide analogues (ddATP-7-SS-Rox, dTTP-5-SS-BodipyFL, ddCTP-5-SS-Biotin, ddGTP-7-SS-TCO, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotide analogues in step 1. The growing DNA strands are terminated with one of the dye-labeled dideoxynucleotide analogues (ddA, ddC, ddG, ddT) or the same one of the four reversible terminators (A, C, G, T) without dye. Step 3, after washing away the unincorporated nucleotides, detection of the unique fluorescence signal from each of the fluorescent dyes on the DNA products allows the identification of the four incorporated dideoxynucleotides for sequence determination: Rox signal indicates incorporation of ddA; R6G signal indicates incorporation of ddT; Alexa488 signal indicates incorporation of ddC; Cy5 signal indicates incorporation of ddG. Next, in Step 4, treatment of the DNA products with THP cleaves the SS linker, leading to the removal of the fluorescent dye on the subset of DNA molecules extended with ddNTPs and the regeneration of a free 3'-OH group on the majority of DNA molecules extended with NRTs, readying the extended DNA for the next cycle of the DNA sequencing reaction. Structures of modified nucleotides used in this scheme are shown in FIG. 48.

Schema XVIA: Four-color BBS with four dyes and two anchors: imaging after incorporation and labeling step. In Scheme XVIA, Dye1, Dye2, Anchor1 and Anchor2 are attached to the four bases of the dideoxynucleotide analogues, respectively, all via an SS linkage. NRTs are added at the same time and incorporation is carried out. Imaging will indicate incorporation of two of the dideoxynucleotide analogues specifically. Next labeling is carried out with both Anchor1 and Anchor2 binding molecules attached to Dye1 and Dye2 respectively. Imaging will indicate incorporation of the other two of the dideoxynucleotide analogues specifically. Cleavage with THP will then remove the remaining dyes from the dideoxynucleotide analogues, which are unavailable for further reactions, and restore the 3'-OH group on the NRTs, which represent the vast majority of incorporation events for subsequent sequencing cycles. In the example shown, Dye1 is Rox, Dye2 is BodipyFL, Anchor1 is Biotin and Anchor2 is TCO. Other combinations of dyes and anchors can also be used.

In the case of 4-dye schemes, dyes are chosen that have well separated absorption and emission spectra.

FIG. 74A-74C contain a schematic showing Scheme XVIA using ddNTP-SS-Dye (ddATP-7-SS-Rox, dTTP-5-SS-BodipyFL), ddNTP-SS-Anchor (ddCTP-5-SS-Biotin, ddGTP-7-SS-TCO), corresponding dye-labeled anchor binding molecules (Streptavidin-TAMRA, Tetrazine-Cy5), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 4-color DNA SBS. Step 1, Addition of DNA polymerase and the eight nucleotide analogues (ddATP-7-SS-Rox, dTTP-5-SS-BodipyFL, ddCTP-5-SS-Biotin, ddGTP-7-SS-TCO, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotide analogues in step 1. The growing DNA strands are terminated with one of the four anchor- or dye-labeled dideoxynucleotide analogues (ddA, ddC, ddG, ddT) or the same one of the four reversible terminators (A, C, G, T) without dye or anchor. Step 3, after washing away the unincorporated nucleotides, detection of the unique fluorescence signal from each of the fluorescent dyes on the DNA products allows the identification of two of the incorporated dideoxynucleotides for sequence determination: Rox signal indicates incorporation of ddA, BodipyFL signal indicates incorporation of ddT. Step 4, labeling with Streptavidin-TAMRA molecules which will bind to the biotin and Tetrazine-Cy5 molecules which will bind to the TCO. Step 5, after washing, a second round of detection of the unique fluorescence signal from each of the fluorescent dyes on the DNA products allows the identification of the remaining two incorporated dideoxynucleotides for sequence determination. A TAMRA signal indicates incorporation of ddC; a Cy5 signal indicates incorporation of ddG. Next, in Step 6, treatment of the DNA products with THP cleaves the SS linker, leading to the removal of the fluorescent dye on the subset of DNA molecules extended with ddNTPs and the regeneration of a free 3'-OH group on the majority of DNA molecules extended with NRTs, readying the extended DNA for the next cycle of the DNA sequencing reaction. Step 7, after washing away THP, an optional imaging step will confirm all dyes have been removed, in preparation for the next cycle of sequencing. Structures of modified nucleotides used in this scheme are shown in FIG. 49A.

Schemes Involving Quantum Dots

Scheme XVIB: Two-color SBS with two anchors, two varieties of quantum dots, and two cleavable linkers: imaging after labeling and cleavage. In Scheme XVIB, the orthogonal set of dideoxynucleotide analogues consists of Anchor1 attached via an SS linkage, Anchor2 attached via an SS linkage, Anchor1 attached via an Azo linkage, and Anchor 2 attached via an Azo linkage each attached to a different base. Incorporation is carried out. Then Anchor1-Binding Molecule with Quantum Dot 1 (QD1) and Anchor2-Binding Molecule with QD2 are added. After imaging with excitation of both QDs After imaging with excitation of both QDs by a single laser due to the broad adsorption spectra of quantum dots, appearance of QD1 fluorescence will limit the choice of incorporated dideoxynucleotide analogues to two possibilities and appearance of QD2 fluorescence will limit the choice of incorporated dideoxynucleotide analogues to the other two alternatives. Imaging after cleavage of the Azo linker with sodium dithionite, again with a single laser, will indicate the specific dideoxynucleotide analogue incorporated. Cleavage with THP will then remove the remaining dyes and restore the 3'-OH group for subsequent sequencing cycles. In the example shown, anchors are biotin and TCO, cleavable linkers are Azo and SS, and QD1 and QD2 are green and red emitters respectively, but other combinations of cleavable linkers, anchors and different QDs could also be used.

FIGS. 75A-75C contain a schematic showing Scheme XVIB using 3'-O-SS(DTM)-dNTP-SS-Anchors (3'-O-SS-dATP-7-SS-Biotin, 3'-O-SS-dGTP-7-SS-TCO), 3'-O-SS(DTM)-dNTP-Azo-Anchors (3'-O-SS-dTTP-5-Azo-TCO, 3'-O-SS-dCTP-5-Azo-Biotin), the corresponding Dye Labeled Binding Molecules (Quantum Dot 1 (Green)-labeled Streptavidin and Quantum Dot 2 (Red)-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS. Step 1, Addition of DNA polymerase and the eight nucleotide analogues (3'-O-SS-dATP-7-SS-Biotin, 3'-O-SS-dGTP-7-SS-TCO, 3'-O-SS-dTTP-5-Azo-TCO, 3'-O-SS-dCTP-5-Azo-Biotin, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotide analogues in step 1. The growing DNA strands are terminated with one of the anchor-labeled dideoxynucleotide analogues (ddA, ddC, ddG, ddT) or the same one of the four reversible terminators (A, C, G, T) without anchor. Step 3, labeling with Streptavidin-QD1 and Tetrazine-QD2. QD1 will bind specifically to the A and C dideoxynucleotide analogues, while QD2 will bind to the G and T dideoxynucleotide analogues. Step 4, After washing away remaining free label and excess nucleotides, detection of QD1 fluorescence will indicate incorporation of A or C; QD2 fluorescence will indicate incorporation of G or T. Next, in Step 5, treatment of the DNA products with sodium dithionite cleaves the azo linker, leading to the removal of QDs on T and C. Step 6, After washing away cleaved QDs, imaging for the presence of QD1 (green) and QD2 (red) fluorescence is carried out. In this step, if it has already been determined that the incorporated dideoxynucleotide nucleotide could be A or C, loss of fluorescence would reveal it to be C, while remaining fluorescence would reveal it to be A. Similarly, for signals previously determined as G or T, loss of fluorescence would indicate incorporation of T specifically while remaining fluorescence would indicate incorporation of G. Next, in Step 7, treatment of the DNA products with THP cleaves the SS linker, leading to the removal of the remaining fluorescent QDs and the regeneration of a free 3'-OH group on the DNA extension product. Step 8, after washing away THP, an optional imaging step will confirm all dyes have been removed, in preparation for the next cycle of sequencing. Structures of modified nucleotides used in this scheme are shown in FIG. 49B.

Scheme XVIC: Two-color SBS with two anchors in various ratios and two varieties of quantum dots: imaging after labeling. In Scheme XVIC, the four dideoxynucleotide analogues are connected to either Anchor1, Anchor2, a 1:1 mixture of Anchor1:Anchor2, and a 2:1 mixture of Anchor1: Anchor2, all via an SS linker. After incorporation of all four nucleotide analogues, a labeling step is performed with Anchor1-Binding Molecule with QD1 and Anchor2-Binding Molecule with QD2. Imaging with excitation of both QDs by a single laser due to the broad adsorption spectra of quantum dots will reveal fluorescence due to QD1, fluorescence due to QD2, or intermediate fluorescence depending on the ratio of QD1 and QD2, indicating the specific dideoxynucleotide analogue incorporated. Cleavage with THP will then remove the remaining dyes and restore the 3'-OH group for subsequent sequencing cycles. In the example shown, anchors are biotin and TCO, and QD1 and QD2 are green and red emitters respectively, but other combinations of anchors and different QDs could also be used.

FIGS. 76A-76C contain a schematic showing Scheme XVIC using 3'-O-SS(DTM)-dNTP-SS-Anchors (3'-O-SS-dATP-7-SS-Biotin, 3'-O-SS-dGTP-7-SS-TCO, 3'-O-SS-dTTP-5-SS-Biotin/Biotin/TCO, 3'-O-SS-dCTP-5-SS-Biotin/TCO), the corresponding Dye Labeled Binding Molecules (Quantum Dot 1 (Green)-labeled Streptavidin and Quantum Dot 2 (Red)-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS. Step 1, Addition of DNA polymerase and the eight nucleotide analogues (3'-O-SS-dATP-7-SS-Biotin, 3'-O-SS-dGTP-7-SS-TCO, 3'-O-SS-dTTP-5-SS-Biotin/Biotin/TCO, 3'-O-SS-dCTP-5-SS-Biotin/TCO, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotide analogues in step 1. The growing DNA strands are terminated with one of the anchor-labeled dideoxynucleotide analogues (ddA, ddC, ddG, ddT) or the same one of the four reversible terminators (A, C, G, T) without anchor. Step 3, labeling with Streptavidin-QD1 and Tetrazine-QD2. Only QD1 will bind to the A dideoxynucleotide analogue, only QD2 will bind to the G dideoxynucleotide analogue, one copy each of QD1 and QD2 will bind to the C analogue, and 2 copies of QD1 and 1 copy of QD2 will bind to the T analogue. Step 4, After washing away remaining free QDs and excess nucleotides, imaging will be carried out with excitation of both QD1 and QD2 simultaneously. Detection of QD1 (green) fluorescence will indicate incorporation of A, QD2 (red) fluorescence will indicate incorporation of G, an equal ratio of QD1 and QD2 fluorescence will indicate incorporation of C, and a 2:1 ratio of QD1:QD2 fluorescence will indicate incorporation of G. Next, in Step 5, treatment of the DNA products with THP cleaves the SS linker, leading to the removal of the fluorescent QDs and the regeneration of a free 3'-OH group on the DNA extension product. Step 8, after washing away THP, an optional imaging step will confirm all QDs have been removed, in preparation for the next cycle of sequencing. A schematic showing expected fluorescence spectra for this scheme would be similar to that presented at the bottom of Scheme VIC, indicating the ratiometric nature of this approach. Structures of modified nucleotides used in this scheme are shown in FIG. 49C.

Schemes Involving Donor-Acceptor Pair

Scheme XVII: One-color SBS with two anchors, one donor-acceptor dye pair and two cleavable linkers: imaging after two labeling steps and after cleavage. In Scheme XVII, Anchor1 containing DonorDye1 attached via an SS linkage, Anchor1 containing DonorDye1 attached via an Azo linkage, Anchor2 containing DonorDye1 attached via an SS linkage, and Anchor2 containing DonorDye1 attached via an Azo linkage are each linked to a different base. Incorporation is carried out with the four ddNTPs and the four NRTs. Anchor1-Binding Molecule containing AcceptorDye1 is added. After imaging with excitation of DonorDye1, the appearance of fluorescence by AcceptorDye1 will indicate incorporation by two possible nucleotide analogues. Next Anchor2-Binding Molecule containing AcceptorDye1 is added. After imaging with excitation of DonorDye1, new appearance of fluorescence by AcceptorDye1 will indicate incorporation by the other two possible nucleotide analogues. Imaging after cleavage of the Azo linker with sodium dithionite will indicate the specific nucleotide analogue incorporated. Cleavage with THP will then remove the remaining dyes and restore the 3'-OH group for subsequent sequencing cycles. In the example shown, cleavable linkers are Azo and SS and DonorDye1 is Cy3 and AcceptorDye1 is Cy5, but other cleavable linkers (e.g., 2NB or allyl) and other donor-acceptor pairs (e.g., CYA as donor with Rox or Cy3 as acceptor; FAM as donor with Rox as acceptor) could be used as well. The linker may be a long linear molecule or dendrimer with 2 or more donor dyes attached, in which case multiple acceptor dyes will be attached via the anchor-anchor binding molecule conjugation steps.

FIGS. 77A-77D contain a schematic showing Scheme XVII using ddNTP-SS-DonorDye-Anchors (ddATP-7-SS-Cy3-Biotin, ddGTP-7-SS-Cy3-TCO), ddNTP-Azo-Anchors (ddTTP-5-Azo-Cy3-TCO, ddCTP-5-Azo-Cy3-Biotin), the corresponding Dye Labeled Binding Molecules (Cy5-labeled Streptavidin and Cy5-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS. Step 1, Addition of DNA polymerase and the eight nucleotide analogues (ddATP-7-SS-Cy3-Biotin, ddGTP-7-SS-Cy3-TCO, ddTTP-5-Azo-Cy3-TCO, ddCTP-5-Azo-Cy3-Biotin, 3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Optional Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the nucleotide analogues in step 1. The growing DNA strands are terminated with one of the four DonorDye-anchor-labeled dideoxynucleotide analogues (ddA, ddC, ddG, ddT) or the same one of the four reversible terminators (A, C, G, T) without DonorDye-anchor. Step 3, labeling with Streptavidin-Cy5. The dye will bind specifically to the A and C nucleotide analogues, but not the G and T analogues. Step 4, After washing away remaining free label and excess nucleotides, detection of Cy5 signal after excitation of Cy3 indicates incorporation of either A or C. Step 5, labeling with Tetrazine-Cy5. The dye will bind specifically to the G and T nucleotide analogues, but not the A and C analogues. Step 6, After washing away remaining free label and excess nucleotides, detection of new Cy5 signal after excitation of Cy3 indicates incorporation of either G or T. Next, in Step 7, treatment of the DNA products with sodium dithionite cleaves the azo linker, leading to the removal of fluorescent donor-acceptor dye pairs on T and C. Step 8, After washing away cleaved dye, imaging for the presence of Cy5 fluorescence after excitation of Cy3 is carried out. In this step, if it has already been determined that the incorporated nucleotide could be A or C, loss of fluorescence would reveal it to be C, while remaining fluorescence would reveal it to be A. Similarly, for signals previously determined as G or T, loss of fluorescence would indicate incorporation of T specifically while remaining fluorescence would indicate incorporation of G. Next, in Step 9, treatment of the DNA products with THP cleaves the SS linker, leading to the removal of the fluorescent donor-acceptor dye pair on the subset of DNA molecules extended with ddNTPs and the regeneration of a free 3'-OH group on the majority of DNA molecules extended with NRTs, readying the extended DNA for the next cycle of the DNA sequencing reaction. Step 10, after washing away THP, an optional imaging step will confirm all dyes have been removed, in preparation for the next cycle of sequencing. Structures of modified nucleotides used in this scheme are shown in FIGS. 51A-51B (with single anchors and donor dyes) but multiple anchors and donor dyes can be installed on these nucleotide analogues as well (see synthetic scheme in FIGS. 65K-65D). The nucleotide analogues can also have multiple donor-anchor pair clusters attached to the base via SS or azo linkers (see structures and synthetic schemes in FIGS. 65B-D.

It should be recognized that the Donor Dye may be directly attached to the anchor molecule and the Acceptor Dye may be attached to the Anchor Binding Molecule as in the example shown. But the alternative arrangement, in which the Acceptor Dye is on the Anchor portion and the Donor Dye is on the Anchor Binding Molecule is just as reasonable, and in fact may have advantages. For instance, use of very large fluorescent structures, such as quantum dots (typically 10-50 nm semicolloidal nanocrystals) would preferentially be used in the labeling step. Quantum dots have advantages as FRET donors due to their broad absorption range allowing selection of an excitation wavelength that has no direct effect on the acceptor dye, very high brightness due to their very high extinction coefficients but similar quantum yields to organic fluors, tunability, stability and narrow bandwidth of the emission spectrum.

Chemical structures of nucleotide analogues and other molecules for the various schemes are presented in FIGS. 42-51. Published structures from the group of propargyl groups linked to ddNTPs are provided in FIG. 52, and specific chemical synthesis schemes for the described molecules are presented in FIGS. 53-65.

Examples of additional possible anchors and anchor binding molecules (in some cases, these can be reversed, e.g., alkyne or cyclooctyne anchor and azide anchor binding molecule) can be found in Table 2:

TABLE 2

| Anchor | Anchor Binding Molecule |
| --- | --- |
| Azide | Alkyne; cyclooctyne |
| Tetrazine | Cyclooctene; Norbornene |
| Phenylboronic acid (PBA) | Salicylhydroxamic acid (SHA) |
| Quadricyclane | Ni bis(dithiolene) |
| Norbornene | Nitrile oxide |

Section III: Nucleotide Analogues with 3'-OH and Modifications on Base that Prevent Second Nucleotide Addition The Helicos BioSciences Corporation (Bowers et al. 2009) reported on the use of virtual terminators that could be incorporated into DNA, as assessed by their low but sufficient $k_{Pol}/K_D$ ratios even with Klenow exo-DNA polymerase, good fidelity, and preferential incorporation of the first nucleotide over a second nucleotide, even in homopolymer stretches, as assessed by $k_1/k_2$ ratios as high as 10'. The virtual terminators consist of nucleotides with no blocking groups at the 3' position but which have a dye attached to the 5 position of pyrimidine bases or the 7 position of purine bases via a cleavable linker. The dye is in turn linked, directly or indirectly, to an inhibitor molecule such as a nucleotide with a phosphate group at each of its 3' and 5' positions. In the Helicos system, these virtual terminators (A, C, G and T) all have the same fluorophore, to accommodate single-color single-molecule SBS.

For use as virtual terminators, NRTs with unprotected 3'-OH and a cleavable disulfide linker attached between the base and fluorescent dye has been reported (Turcotti et al 2008). However, after DNA polymerase catalyzed extension reaction on the primer/template and imaging the incorporated base, the cleavage of the disulfide linkage generates a free reactive —SH group which has to be capped with iodoacetamide before the second extension reaction can be carried out. This capping step not only adds an extra step in the process but also limits the addition of multiple nucleotides in a row because of the long remnant tail on the nucleotide base moiety. With this approach the sequencing read length is limited to only 10 bases (Turcotti et al 2008). Other disulfide-based approaches require a similar capping reaction to render the free SH group unreactive (Mitra et al 2003).

For the long read SBS strategy it is preferable that the cleavable linker is stable during the sequencing reactions, requires less manipulations and does not leave a long tail on the base after the cleavage reaction. Herein described are nucleotide analogues containing a 3'-O-DTM group and a cleavable DTM linker between the base and dye or anchor. These nucleotide analogues are good terminators and substrates for DNA polymerase in a solution-phase DNA extension reaction and that both the fluorophore and the 3'-O-DTM group can be removed with high efficiency in a single step in aqueous solution. The new DTM based linker between the base and the fluorophore after cleavage with THP does not require capping of the resulting free SH group as the cleaved product instantaneously collapses to the stable OH group. In this section describes, in part, the DTM linker along with a free 3'-OH in some of nucleotide analogues of the invention herein disclosed. Depending on the SBS scheme, other cleavable groups, such as Azo, will be present in the linkers of other nucleotide analogues.

Disclosed herein are two types of nucleotides with modifications on the base that may serve as terminators. The use of 3'-OH nucleotides with dyes attached to the base (the 5-position of pyrimidines or the 7 position of purines) via photocleavable linkers for use in stepwise sequencing by synthesis has been previously disclosed (Seo et al 2005). Herein disclosed are general and specific structures in FIGS. 78, 80-93 and some example synthetic schemes in FIGS. 94-96.

Recently sets of nucleotides consisting of long tags attached to the terminal phosphate of a polyphosphate (Kumar & Sood 2006) for nanopore-based sequencing by synthesis (Kumar et al 2012, Fuller et al 2016, Ju et al 2007 U.S. Pat. No. 8,889,348 B2, Ju et al 2013 (EP 2652153 A2 (WO 2012/083249 A2)) or attached to the base have been developed. The latter tags, which were originally developed for single-molecule electronic single base extension reactions (Ju et al WO 2016/154215 A1) with nanopore detection, typically consist of a linker, an optional fluorescent label, and a long (~30 base long) oligonucleotide tag with a capped end. Examples are shown in FIG. 79. FIG. 143 demonstrates their efficient incorporation into growing DNA strands using various enzymes. In particular, ThermoSequenase easily incorporates these nucleotides, at about the same efficiency as unmodified ddNTPs (FIG. 144).

For these to serve in an equivalent way to virtual terminators, several modifications would have to be introduced. Rather than a dideoxynucleotide, as shown in FIG. 79, a deoxynucleotide with an unblocked 3'-OH would be utilized. The linker would have a cleavable moiety (e.g., disulfide, azo, 2-nitrobenzyl, allyl, azidomethyl, etc.). In some cases, the tags, including one or more identical fluorescent dyes, would be directly attached to the dNTP via the cleavable linker. In other cases, the cleavable linker will be attached to an anchor molecule (e.g., biotin, TCO), which could be attached to the tag including fluorescent dyes via an anchor binding molecule (e.g., streptavidin, tetrazine). If the tag is a polynucleotide chain, the last nucleotide in the tag may have a free 3'-OH group, 3' phosphate or other group. If the last nucleotide is not attached to the penultimate nucleotide by a phosphodiester bond, but rather attached via its base, the 5' position on the terminal nucleotide may have a phosphate or other modification. Single dye clusters could be used to enhance sensitivity. One of these dyes could be attached to the bases of a subset, for example 2-4, of the nucleotides in the tag (see examples in FIGS. 85-88).

Similarly, multiple instances of anchors for subsequent attachment of dyes can be attached to the polymer chains (see example in FIG. 89A). Other variations can be envisioned, such as placing flexible linkers, such as PEG or alkane chains, between the ultimate and penultimate nucleotides in the tag. Further, the oligonucleotide tag could be replaced by a polysaccharide, peptide or other polymeric molecule. The key point is that such bulky groups attached to the bases, while having a minimal effect on incorporation of the first base, should strongly inhibit subsequent incorporation due to steric hindrance, competition for binding of subsequent nucleotides, or other factors.

Herein disclosed is the design of orthogonal or pseudo-orthogonal sets of these 3'-OH containing tagged nucleotide analogues bearing different cleavable linkers, different dyes, or different anchors in their tags and blocking groups. With such design variations, essentially all of the sequencing schemes, including 4-color, 2-color and 1-color variants, presented throughout this application could incorporate this type of "virtual" terminator in place of the nucleotide reversible terminators bearing reversible 3'-blocking groups. For the Helicos instrument, for instance, the one-color approach using Cy5 or ATTO647N as the dye moiety on the base (either directly attached to the base via a cleavable linker, or attached to an anchor-binding molecule for labeling of an anchor which is itself attached to the base via a cleavable linker) will be the design of choice. For other platforms, one or more than one dye can be used.

Herein disclosed are 7 additional SBS schemes using nucleotide analogues in which 3'-OH terminators, as described above, are used. Combinations of dyes, anchors, and cleavable linkers other than those presented in these schemes can also be used. Other labels may be used, e.g., non-fluorescent labels including Raman tags, and as described in the prior PCT, sets of tags that reduce ion current signals in nanopores to different extents, have different dwell times within the ion channel, or both.

In the following schemes the Azo group is placed in linkers as an example of a second orthogonal (non-DTM) cleavable linker; sodium dithionite is shown as an example cleaving agent (refer to FIGS. 124A-128B demonstrating the cleavage efficiency of sodium dithionite for the Azo group); ATTO647N, Rox, TAMRA and BodipyFL are used as examples of fluorophores; biotin is provided as an example of the anchors; and streptavidin is used as an example of the anchor binding molecules. However, a variety of other cleavable groups in the linker (e.g., allyl, 2-nitrobenzyl groups), cleavage agents (e.g., Pd(0), 340 nm light), fluorophores, anchors (e.g., TCO, DBCO, $N_3$, tetrazine)*, and anchor binding molecules (e.g., tetrazine, $N_3$, DBCO, TCO)* are also feasible. Dyes can consist of single dye molecules, dye pairs that exhibit energy transfer, clusters of dyes attached at multiple positions of linear or branched polymers, or quantum dots (QDs). In addition to nucleoside triphosphate analogues, nucleoside tetraphosphate, nucleoside pentaphosphate, nucleoside hexaphosphate and higher nucleoside polyphosphate analogues are feasible alternatives.

Scheme XVIII is a one-color scheme in which each of the four nucleotide analogues is added individually in step-by-step fashion. In the remaining schemes, all four nucleotide analogues are added together. Scheme XIX is a one-color scheme that requires four detection steps. Scheme XX is a single-color SBS scheme that requires three detection steps to determine the incorporated nucleotide. Scheme XXI is a two-color scheme that requires three detection steps to determine the incorporated nucleotide. Scheme XXIIA is a four-color scheme. Schemes XXIIB and XXIIC are two-color schemes that take advantage of quantum dots. Scheme XXIII is a one-color scheme that takes advantage of energy transfer between a donor and acceptor dye.

Chasing with unlabeled nucleotide reversible terminator analogues is performed after adding the dye- or anchor-containing nucleotide analogues to guarantee that every DNA primer strand has been extended so as to avoid asynchronous reactions, and washing is essential between every step to remove the previous set of reagents and/or released dyes. The schemes can be used for ensemble or single molecule sequencing. Chase steps with nucleotide reversible terminators are shown in all schemes except Scheme XVIII, though such a step could be included within Scheme XVIII as well. The purpose of the chase is to maintain phasing in parallel sequencing reactions. In the case of ensemble sequencing, extension by a chase nucleotide analogue and the resulting absence of a signal for a subset of extended primers will still allow signals generated by the remaining primers extended with labeled nucleotide analogues to be observed. In the case of single molecule sequencing, a chase is optional. In the case that chasing is used for single molecule sequencing, if a chase nucleotide analogue is incorporated into the growing DNA strand instead of the appropriate labeled nucleotide analogue, the base at that position will not be read, though the following base will be read in the appropriate cycle. Hence, the sequence will be accurate except at the known position where no signal was obtained. Though the chase step is helpful, a potential concern is that the 3'-SS(DTM) nucleotides (NRTs) could attach non-specifically to available sites such as phosphate groups in the extended tags on the labeled nucleotide analogues, and thereby be prevented from incorporating into the growing chain. This can be controlled by using appropriate concentrations of the NRTs.

Single Molecule Sequencing

As stated above, a number of the schemes to be described below can be used for either ensemble or single molecule sequencing. In the case of single molecule fluorescent sequencing, two major concerns are sensitivity of the signal and background due to unincorporated fluorescent nucleotides or free fluorescent labeling molecules (e.g., anchor binding molecules bearing fluorophores). Special instrumentation such as total internal reflection fluorescence (TIRF) or stochastic optimal reconstruction microscopy (STORM) is utilized to detect single fluorescent molecules. TIRF microscopy, probably the most common of these, and the one used by Helicos for their single molecule sequencing approach, depends on the production of an evanescent wave at the surface of a glass slide which decays quickly with distance from the surface. Within the order of 100 nm from the surface, strong signals are obtained. Moreover, there is little background signal interference due to the fact that the majority of free fluorescent nucleotides or labeling molecules are not within that 100 nm window. Despite this, it is not possible to completely eliminate background signal interference. Similar principles occur with Pacific Biosciences zero mode waveguides (ZMWs) where the distance from the bottom of the 70 nm diameter wells are 100 nm. Thus, while most free fluorescent molecules (of 4 different colors) will be excluded, a small number will enter the ZMW where they may generate false positive signals.

Two approaches that can further impact single molecule sequencing using TIRF microscopy are herein disclosed. To further enhance sensitivity, in some of the schemes below (Schemes XVIII-XXII), clusters of dyes or clusters of anchors for subsequent attachment of multiple dyes can be used (FIGS. 85-89D). In a second approach geared more toward decreasing the likelihood of detecting background fluorescence, fluorescence resonance energy transfer between a donor and acceptor dye placed a short distance from each other is used (Scheme XXIII). The combination of FRET with TIRF microscopy was reported previously using a Cy3 donor on one nucleotide and a Cy5 acceptor on a second nucleotide to achieve up to 5-base fingerprints (Braslavsky et al 2003). The Förster radius for typical fluorescent energy transfer is approximately 5 nm (between 1 and 10 nm). In the methods disclosed herein using energy transfer between a donor and acceptor on the same nucleotide, because the laser used to excite the donor dye is unable to directly excite the acceptor dye, free floating fluorescent acceptor molecules in the solution would have to be within just 1-10 nm to be seen as false signals. The likelihood of this is extremely low, meaning that only acceptor dyes purposely placed within 5 nm of the donor dyes, either on the same stretch of a polymeric molecule attached directly to the nucleotide analogue or brought together when a donor dye directly attached to the nucleotide analogue with an anchor and an acceptor dye attached to the anchor binding molecule become conjugated.

Selection of the donor and acceptor dye is also critical. For example, a donor dye with a wide absorption window but a low fluorescence quantum yield can be used to increase the Stokes-shifted fluorescence emission of an acceptor dye (Hung et al 1996). It has been shown that a CYA donor and a fluorescein or rhodamine derivative as acceptor meet these conditions.

Herein disclosed is also an approach that can both increase signal, reduce background detection, and decrease the chance of missing an incorporation event by having clusters of donor-acceptor dye pairs directly attached to the nucleotides (either in linear chains or dendrimeric conformations) or clusters of donor dyes and anchors for attachment of multiple acceptor dyes on anchor binding molecules (Scheme XXIII using compounds with structures such as those in FIG. 93A-93C) Potentially, this combined approach can be used to achieve single molecule SBS with state-of-the-art optical systems, with lower cost and footprint than TIRF microscopes.

Scheme XVIII: One-color SBS with Stepwise Addition of 3'-OH Terminators. Scheme XVIII is a one-color SBS scheme in which each of the four 3'-OH terminators (A, C, G and T) bears the same dye (ATTO647N in the example shown), the same blocker (3'-phosphate modified dTMP in the example), and the same cleavable linker (SS) in the example). This scheme would be used in a stepwise scheme of nucleotide addition, such as the approach used by Helicos. Each cycle consists of incorporation, washing, imaging and cleavage with THP. Thus, if the next available bases in the template strand are T, G, A, A, and the 3'-OH terminators are added in the order A, C, G, T, in the first cycle the A will be incorporated and imaging will reveal the incorporation event. After washing away the nucleotides, the SS group is cleaved to simultaneously remove the dye and the blocker. Since the next 3'-OH terminator added is a C, it will be incorporated. After washing, imaging and cleavage, a G is added, but since this is not complementary to the next available base (A) in the template strand, it will not be incorporated and no fluorescence will be observed after washing and imaging. Since there was no incorporation, the cleavage reaction may be skipped. The process continues with addition of T, which will be incorporated and read. Since it acts as a terminator, the following T will not be observed until 4 more cycles have occurred. The procedure will be repeated to continue sequencing the template strand.

FIG. 97 contains a schematic showing Scheme XVIII using four dNTP-SS-Blocker-Dye molecules (dATP-SS-Blocker-ATTO647N, dCTP-SS-Blocker-ATTO647N, dGTP-SS-Blocker-ATTO647N, dTTP-SS-Blocker-ATTO647N) for single-color step-by-step sequencing. Nucleotides are added one at a time. In each sequencing cycle, after the incorporation step, washing and imaging are carried out to reveal whether a nucleotide was incorporated. Then THP or TCEP treatment is used to remove the blocker and dye, and washing and imaging are performed to make sure all the dye has been removed. Structures of the molecules used in this scheme are presented in FIG. 80.

Scheme XIX: One-color SBS with Simultaneous Addition of All Four 3'-OH Terminators and Consecutive Cleavage Reactions. Scheme XIX is also a one-color SBS scheme, in which each of the four virtual terminators bears the same dye (ATTO647N in the example shown) and blocker (3'-phosphate modified dTMP in the example) but each has a different cleavable linker (azo, allyl, 2-nitrobenzyl, and SS) in the example). Only one of the four 3'-OH terminators will be incorporated, the one complementary to the base of the next available nucleotide in the template strand. Treatment with 4 consecutive cleavage agents (sodium dithionite, Pd(0), 340 nm light, and THP) will be performed with washing and imaging between each cleavage. Loss of fluorescence following a given cleavage will indicate the nucleotide that was incorporated.

FIG. 98 contains a schematic showing Scheme XIX using dNTP-Cleavable Linker-Blocker-Dyes (dATP-Allyl-Blocker-ATTO647N, dTTP-SS-Blocker-ATTO647N, dCTP-Azo-Blocker-ATTO647N, dGTP-2-Nitrobenzyl-Blocker-ATTO647N) and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS. Step 1, Addition of DNA polymerase and the four nucleotide analogues (dATP-Allyl-Blocker-ATTO647N, dTTP-SS-Blocker-ATTO647N, dCTP-Azo-Blocker-ATTO647N, dGTP-2-Nitrobenzyl-Blocker-ATTO647N) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye. Step 3, after washing away the unincorporated dye labeled nucleotides, detection of the unique fluorescence signal confirms incorporation, but does not indicate which nucleotide was incorporated. Step 4, cleavage of Allyl linker by adding Pd(0) to the elongated DNA strands results in removal of ATTO647N from incorporated A. Step 5, after washing away the cleaved dyes, a second round of imaging is performed. Loss of ATTO647N signal indicates incorporation of A. Step 6, cleavage of Azo linker by adding sodium dithionite ($Na_2S_2O_4$) to the elongated DNA strands results in removal of ATTO647N from incorporated C. Step 7, after washing away the cleaved dyes, a third round of imaging is performed. Loss of ATTO647N signal indicates incorporation of C. Step 8, cleavage of 2-nitrobenzyl linker by treating the elongated DNA strands with 340 nm light results in removal of ATTO647N from incorporated G. Step 9, after washing away the cleaved dyes, a fourth round of imaging is performed. Loss of ATTO647N signal indicates incorporation of G. Step 10, cleavage of SS linker by adding THP to the elongated DNA strands results in removal of ATTO647N from incorporated T and also restores the 3'-OH group on any growing strands extended with a 3'-O-SS (DTM)-dNTP. Step 11, after washing away the cleaved dyes, a final round of imaging is performed. Loss of ATTO647N signal confirms incorporation of T. The DNA products are ready for the next cycle of the DNA sequencing reaction. Structures of nucleotides used in this scheme are presented in FIG. 81.

Scheme XX: One-color SBS with Simultaneous Addition of Two 3'-OH Terminators with the Same Dyes and Two 3'-OH Terminators with the Same Anchors. Scheme XX is a 1-color SBS scheme, that requires three imaging steps, after incorporation, after labeling and after the specific cleavage step. Imaging after incorporation reveals the incorporation of either of two types of nucleotides, the labeling step reveals incorporation of either of the other two types of nucleotides, and the first cleavage reaction resolves which nucleotide was incorporated specifically. The final cleavage reaction restores the system for the next sequencing cycle.

Figure 99A:
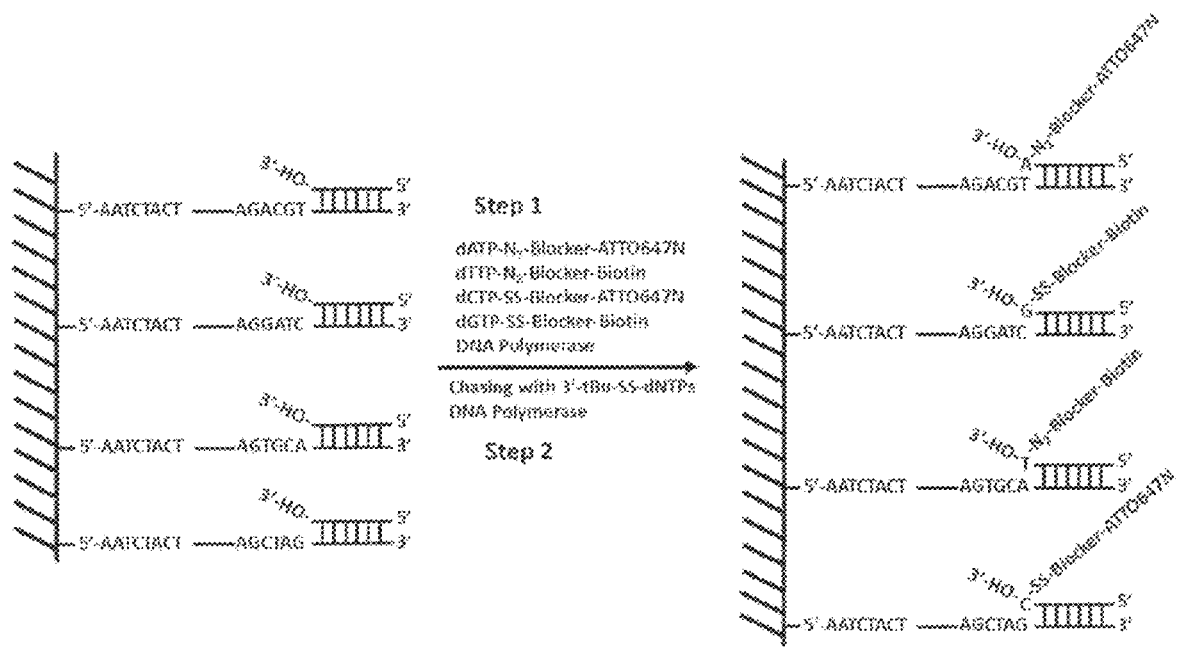
Figure 99B:
Figure 99C:
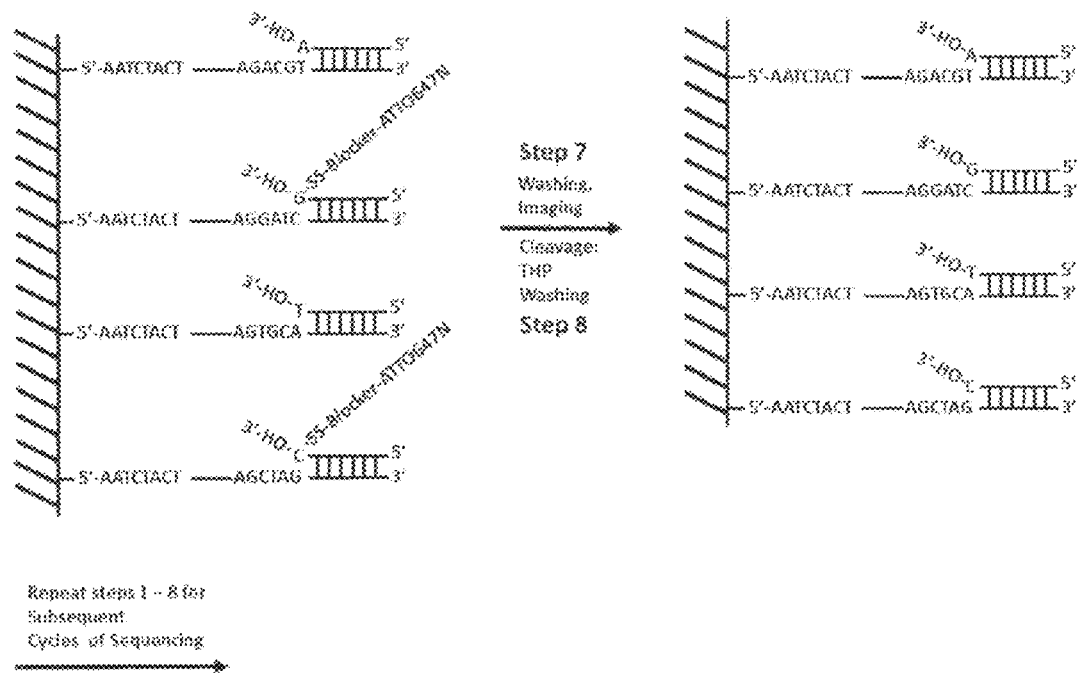
Figure 99D:
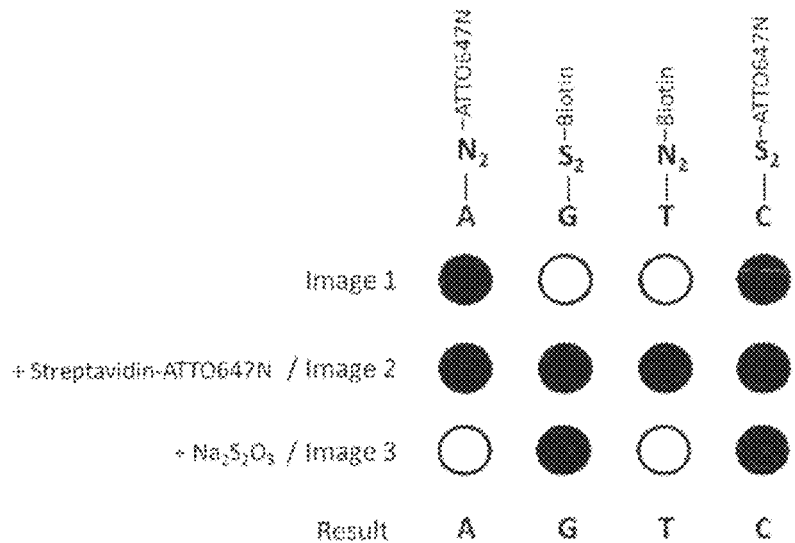

FIGS. 99A-99D contain a schematic showing Scheme XX using dNTP-Cleavable Linker-Blocker-Dyes (dATP-Azo-Blocker-ATTO647N, dCTP-SS-Blocker-ATTO647N), dNTP-Cleavable Linker-Blocker-Anchors (dTTP-Azo-Blocker-Biotin and dGTP-SS-Blocker-Biotin), the corresponding dye labeled Anchor Binding Molecule (Streptavidin-ATTO647N), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 1-color DNA SBS. Step 1, Addition of DNA polymerase, the two dNTP-Cleavable Linker-Blocker-Dyes (dATP-Azo-Blocker-ATTO647N, dCTP-SS-Blocker-ATTO647N) and the two dNTP-Cleavable Linker-Blocker-Anchors (dTTP-Azo-Blocker-Biotin and dGTP-SS-Blocker-Biotin) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye or anchor labeled dNTPs in step 1. The growing DNA strands are terminated with either of the two dye labeled nucleotide analogues (A, C), either of the two anchor containing nucleotide analogues (G, T) or the same one of the four nucleotide analogues (A, C, G, T) without dye or anchor. Step 3, after washing away the unincorporated nucleotides, detection of an ATTO647N signal indicates incorporation by A or C. Step 4, addition of Streptavidin-ATTO647N which will label the biotin anchor-containing molecules (G and T). Step 5, after washing, imaging is carried out. Newly appearing ATTO647N fluorescence indicates incorporation by G or T. Step 6, cleavage of Azo linker by adding sodium dithionite ($Na_2S_2O_4$) to the elongated DNA strands results in removal of ATTO647N from incorporated A or T. Step 7, after washing away the cleaved dyes, a third round of imaging is performed. Loss of ATTO647N signal that appeared after the initial incorporation indicates incorporation of A; loss of ATTO647N signal that appeared only after the labeling reaction indicates incorporation of T. If signal was present after incorporation and is still present after cleavage, a C was incorporated. If signal appeared after labeling and is still present after cleavage, a G was added. Next, in Step 8, treatment of the DNA products with THP cleaves the SS linker, leading to the removal of the remaining fluorescent dyes. After washing away THP, an optional imaging step (not shown) will confirm all dyes have been removed, in preparation for the next cycle of sequencing. A schematic representation of fluorescence images is shown in FIG. 99D. Hollow circles represent "no fluorescence signal" and filled circles represent "fluorescence signal". Similar schematics can be constructed for other 1-color SBS schemes in this section. Structures of nucleotides and anchor binding molecules used in this scheme are presented in FIG. 82.

Scheme XXI: Two-color SBS with Two 3'-OR Terminators Bearing Two Different Dyes and Two 3'-OH Terminators Bearing Two Different Anchors. Scheme XXI is a two-color method that requires two imaging steps, after incorporation and after the specific cleavage reaction. Incorporation reveals the incorporation of either of two types of nucleotides; the optional labeling step reveals incorporation of either of the other two types of nucleotides, and the first cleavage reaction resolves which nucleotide was incorporated specifically. The final cleavage reaction restores the system for the next sequencing cycle.

FIGS. 100A-100C contain a schematic showing Scheme XXI using dNTP-SS-Blocker-Dyes (dATP-SS-Blocker-Rox, dTTP-SS-Blocker-ATTO647N), dNTP-SS-Blocker-Anchors (dCTP-SS-Blocker-Biotin and dGTP-SS-Blocker-TCO), the corresponding Dye-labeled Anchor Binding Molecules (Streptavidin-Rox and Tetrazine-ATTO647N), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS. Step 1, Addition of DNA polymerase, the two dNTP-SS-Blocker-Dyes (dATP-SS-Blocker-Rox, dTTP-SS-Blocker-ATTO647N), and the two dNTP-SS-Blocker-Anchors (dCTP-SS-Blocker-Biotin and dGTP-SS-Blocker-TCO), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye or anchor labeled dNTPs in step 1. The growing DNA strands are terminated with either of the two dye labeled nucleotide analogues (A, T), either of the two anchor containing nucleotide analogues (C, G) or the same one of the four nucleotide analogues (A, C, G, T) without dye or anchor. Step 3, after washing away the unincorporated nucleotides, detection of a Rox signal indicates incorporation by A; detection of an ATTO647N signal indicates incorporation by T. Step 4, addition of Streptavidin-Rox which will label the biotin anchor-containing nucleotide analogue (C) and Tetrazine-ATTO647N, which will label the TCO anchor-containing nucleotide analogue (G). Step 5, after washing, imaging is carried out. Newly appearing Rox fluorescence indicates incorporation by C; newly appearing ATTO647N fluorescence indicates incorporation by G. Next, in Step 6, treatment of the DNA products with THP cleaves the SS linker, leading to the removal of the remaining fluorescent dyes. After washing away THP, an optional imaging step (Step 7) will confirm all dyes have been removed, in preparation for the next cycle of sequencing. A schematic representation of fluorescence images is shown in FIG. 100C. Hollow circles and triangles represent "no fluorescence signal" and filled circles and triangles represent "fluorescent signals at two different wavelengths". Similar schematics can be constructed for other 2-color SBS schemes in this section. Structures of nucleotides used in this scheme are presented in FIG. 83.

Scheme XXIIA: Four-color SBS with Simultaneous Addition of All Four 3'-OH Terminators. Scheme XXIIA is a 4-color SBS scheme, in which each of the four 3'-OH terminators bears a different dye (BodipyFL, TAMRA, Rox and ATTO647N in the example), but the same blocker (3'-phosphate modified TMP) and the same cleavable group in the linker (SS). In the simplest version of this scheme, a single imaging after incorporation and washing will reveal the nucleotide analogue incorporated. Cleavage with THP will remove the dye and blocker, in preparation for the next cycle of sequencing.

FIG. 101 contains a schematic showing Scheme XXIIA using dNTP-SS-Blocker-Dyes (dATP-SS-Blocker-Rox, dTTP-SS-Blocker-BodipyFL, dCTP-SS-Blocker-TAMRA and dGTP-SS-Blocker-ATTO647N) and the four 3'-O-SS (DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 4-color DNA SBS. Step 1, Addition of DNA polymerase and the four dNTP-SS-Blocker-Dyes (dATP-SS-Blocker-Rox, dTTP-S-Blocker-BodipyFL, dCTP-SS-Blocker-TAMRA and dGTP-SS-Blocker-ATTO647N) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye. Step 3, after washing away the unincorporated nucleotides, detection of a Rox signal indicates incorporation by A; detection of a BodipyFL signal indicates incorporation by T; detection of a TAMRA signal indicates incorporation by C; detection of an ATTO647N signal indicates incorporation by G. Next, in Step 4, treatment of the DNA products with THP cleaves the SS linker, leading to the removal of the remaining fluorescent dyes. After washing away THP, an optional imaging step (Step 5) will confirm all dyes have been removed, in preparation for the next cycle of sequencing. Structures of nucleotides used in this scheme are presented in FIG. 84.

Schemes Involving Quantum Dots

Scheme XXIIB: Two-color SBS with two anchors, two varieties of quantum dots, and two cleavable linkers: imaging after labeling and cleavage. In Scheme XXIIB, the orthogonal set of 3'-OH terminators consists of Anchor1 attached via an SS linkage, Anchor2 attached via an SS linkage, Anchor1 attached via an Azo linkage, and Anchor2 attached via an Azo linkage each attached to a different base. Incorporation is carried out. Then Anchor1-Binding Molecule with Quantum Dot 1 (QD1) and Anchor2-Binding Molecule with QD2 are added. After imaging with excitation of both QDs by a single laser due to the broad adsorption spectra of quantum dots, appearance of QD1 fluorescence will limit the choice of incorporated 3'-OH terminators to two possibilities and appearance of QD2 fluorescence will limit the choice of incorporated 3'-OH terminators to the other two alternatives. Imaging, again with a single laser, after cleavage of the Azo linker with sodium dithionite will indicate the specific 3'-OH terminator incorporated. Cleavage with THP will then remove the remaining dyes and restore the 3'-OH group for subsequent sequencing cycles. In the example shown in FIGS. 102A-102C, anchors are biotin and TCO, cleavable linkers are Azo and SS, and QD1 and QD2 are green and red emitters respectively, but other combinations of cleavable linkers, anchors and different QDs could also be used.

FIGS. 102A-102C contain a schematic showing Scheme XXIIB using dNTP-SS-Blocker-Anchors (dATP-SS-Blocker-Biotin, dGTP-SS-Blocker-TCO), dNTP-Azo-Blocker-Anchors (dTTP-Azo-Blocker-TCO, dCTP-Azo-Blocker-Biotin), the corresponding Dye Labeled Binding Molecules (Quantum Dot 1 (Green)-labeled Streptavidin and Quantum Dot 2 (Red)-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS. Step 1, Addition of DNA polymerase and the four nucleotide analogues (dATP-SS-Blocker-Biotin, dGTP-SS-Blocker-TCO, dTTP-Azo-Blocker-TCO, dCTP-Azo-Blocker-Biotin) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye labeled dNTPs in step 1. The growing DNA strands are terminated with one of the four anchor labeled nucleotide analogues (A, C, G, T) or the same one of the four nucleotide analogues (A, C, G, T) without anchor. Step 3, labeling with Streptavidin-QD1 and Tetrazine-QD2. QD1 will bind specifically to the A and C deoxynucleotide analogues, while QD2 will bind to the G and T deoxynucleotide analogues. Step 4, After washing away remaining free label and excess nucleotides, detection of QD1 fluorescence will indicate incorporation of A or C; QD2 fluorescence will indicate incorporation of G or T. Next, in Step 5, treatment of the DNA products with sodium dithionite cleaves the azo linker, leading to the removal of QDs and blockers on T and C nucleotide analogues. Step 6, After washing away cleaved QDs, imaging for the presence of QD1 (green) and QD2 (red) fluorescence is carried out. In this step, if it has already been determined that the incorporated deoxynucleotide could be A or C, loss of fluorescence would reveal it to be C, while remaining fluorescence would reveal it to be A. Similarly, for signals previously determined as G or T, loss of fluorescence would indicate incorporation of T specifically while remaining fluorescence would indicate incorporation of G. Next, in Step 7, treatment of the DNA products with THP cleaves the SS linker, leading to the removal of the remaining fluorescent QDs and blockers and the regeneration of a free 3'-OH group on the DNA extension product. Step 8, after washing away THP, an optional imaging step will confirm all dyes have been removed, in preparation for the next cycle of sequencing. Though not indicated in Scheme XXIIB, if desired, the presence of an additional SS linkage between the Azo group and the base results in the production of a shorter scar on the incorporated nucleotide after THP treatment which should result in longer reads. Structures of modified nucleotides used in this scheme are shown in FIG. 89B.

Scheme XXIIC: Two-color BS with two anchors in various ratios and two varieties of quantum dots: imaging after labeling. In Scheme XXIIC, the four 3'-OH terminators are connected to either Anchor1, Anchor2, a 1:1 mixture of Anchor1:Anchor2, and a 2:1 mixture of Anchor1:Anchor2, all via an SS linker. After incorporation of all four 3'-OH terminators, a labeling step is performed with Anchor1-Binding Molecule with QD1 and Anchor2-Binding Molecule with QD2. Imaging with excitation of both QDs by a single laser due to the broad adsorption spectra of quantum dots will reveal fluorescence due to QD1, fluorescence due to QD2, or intermediate fluorescence depending on the ratio of QD1 and QD2, indicating the specific 3'-OH terminator incorporated. Cleavage with THP will then remove the remaining dyes and restore the 3'-OH group for subsequent sequencing cycles. In the example shown, anchors are biotin and TCO, and QD1 and QD2 are green and red emitters respectively, but other combinations of anchors and different QDs could also be used.

FIG. 103 contains a schematic showing Scheme XXIIC using dNTP-SS-Blocker-Anchors (dATP-SS-Blocker-Biotin, dGTP-SS-Blocker-TCO, dTTP-SS-Blocker-Biotin/Biotin/TCO, dCTP-SS-Blocker-Biotin/TCO), the corresponding Dye Labeled Binding Molecules (Quantum Dot 1 (Green)-labeled Streptavidin and Quantum Dot 2 (Red)-labeled Tetrazine), and the four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to perform 2-color DNA SBS. Step 1, Addition of DNA polymerase and the four nucleotide analogues (dATP-SS-Blocker-Biotin, dGTP-SS-Blocker-TCO, dTTP-SS-Blocker-Biotin/Biotin/TCO, dCTP-SS-Blocker-Biotin/TCO) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl (SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the dye labeled dNTPs in step 1. The growing DNA strands are terminated with one of the four anchor labeled nucleotide analogues (A, C, G, T) or the same one of the four nucleotide analogues (A, C, G, T) without anchor. Step 3, labeling with Streptavidin-QD1 and Tetrazine-QD2. Only QD1 will bind to the A dideoxynucleotide analogue, only QD2 will bind to the G dideoxynucleotide analogue, one copy each of QD1 and QD2 will bind to the C analogue, and 2 copies of QD1 and 1 copy of QD2 will bind to the T analogue. Step 4, After washing away remaining free QDs and excess nucleotides, imaging will be carried out with excitation of both QD1 and QD2 simultaneously. Detection of QD1 (green) fluorescence will indicate incorporation of A, QD2 (red) fluorescence will indicate incorporation of G, an equal ratio of QD1 and QD2 fluorescence will indicate incorporation of C, and a 2:1 ratio of QD1:QD2 fluorescence will indicate incorporation of G. Next, in Step 5, treatment of the DNA products with THP cleaves the SS linker, leading to the removal of the fluorescent QDs and the regeneration of a free 3'-OH group on the DNA extension product. Step 8, after washing away THP, an optional imaging step will confirm all QDs have been removed, in preparation for the next cycle of sequencing. Though not indicated in Scheme XXIIC, if desired, the presence of an additional SS linkage between the Azo group and the base results in the production of a shorter scar on the incorporated nucleotide after THP treatment which should result in longer reads. Structures of modified nucleotides used in this scheme are shown in FIGS. 89C-89D.

Schemes Involving Donor-Acceptor Pair

Scheme XXIII: One-color SBS with two anchors, one donor-acceptor dye pair and two cleavable linkers: imaging after two labeling steps and after cleavage. In Scheme XXIII, Anchor1 containing DonorDye1 attached via an SS linkage, Anchor1 containing DonorDye1 attached via an Azo linkage, Anchor2 containing DonorDye1 attached via an SS linkage, and Anchor2 containing DonorDye1 attached via an Azo linkage are each linked to a different base. Incorporation is carried out. Anchor1-Binding Molecule containing AcceptorDye1 is added. After imaging with excitation of DonorDye1, the appearance of fluorescence by AcceptorDye1 will indicate incorporation by two possible nucleotide analogues. Next Anchor2-Binding Molecule containing AcceptorDye1 is added. After imaging with excitation of DonorDye1, new appearance of fluorescence by AcceptorDye1 will indicate incorporation by the other two possible nucleotide analogues. Imaging after cleavage of the Azo linker with sodium dithionite will indicate the specific nucleotide analogue incorporated. Cleavage with THP will then remove the remaining dyes and restore the 3'-OH group for subsequent sequencing cycles. In the example shown, cleavable linkers are Azo and SS and DonorDye1 is Cy3 and AcceptorDye1 is Cy5, but other cleavable linkers (e.g., 2NB or allyl) and other donor-acceptor pairs (e.g., CYA as donor with Rox or Cy3 as acceptor; FAM as donor with Rox as acceptor) could be used as well. The linker-blocker may be a linear molecule or dendrimer with 2 or more donor dyes attached, in which case multiple acceptor dyes will be attached via the anchor-anchor binding molecule conjugation steps.

FIGS. 104A-104D contain a schematic showing Scheme XXIII using dNTP-SS-Blocker-DonorDye-Anchors (3'-O-SS-dATP-7-SS-Blocker-Cy3-Biotin, 3'-O-SS-dGTP-7-SS-Blocker-Cy3-TCO), 3'-O-SS(DTM)-dNTP-Azo-Blocker-Cy3-Anchors (3'-O-SS-dTTP-5-Azo-Blocker-Cy3-TCO, 3'-O-SS-dCTP-5-Azo-Blocker-Cy3-Biotin), the corresponding Dye Labeled Binding Molecules (Cy5-labeled Streptavidin and Cy5-labeled Tetrazine), and the four 3'-O-SS (DTM)-dNTPs (3'-O-t-Butyldithiomethyl(SS)-dATP, 3'-O-t-Butyldithiomethyl(SS)-dCTP, 3'-O-t-Butyldithiomethyl (SS)-dTTP and 3'-O-t-Butyldithiomethyl(SS)-dGTP) to perform 1-color DNA SBS. Step 1, Addition of DNA polymerase and the four nucleotide analogues (3'-O-SS-dATP-7-SS-Blocker-Cy3-Biotin, 3'-O-SS-dGTP-7-SS-Blocker-Cy3-TCO, 3'-O-SS-dTTP-5-Azo-Blocker-Cy3-TCO, 3'-O-SS-dCTP-5-Azo-Blocker-Cy3-Biotin) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the subset of growing DNA strands that were not extended with any of the Blocker-DonorDye containing Anchor dNTPs in step 1. The growing DNA strands are terminated with one of the four Blocker-DonorDye-Anchor labeled nucleotide analogues (A, C, G, T) or the same one of the four nucleotide analogues (A, C, G, T) without dye. Step 3, labeling with Streptavidin-Cy5. The dye will bind specifically to the A and C nucleotide analogues, but not the G and T analogues. Step 4, After washing away remaining free label and excess nucleotides, detection of Cy5 signal after excitation of Cy3 indicates incorporation of either A or C. Step 5, labeling with Tetrazine-Cy5. The dye will bind specifically to the G and T nucleotide analogues, but not the A and C analogues. Step 6, After washing away remaining free label and excess nucleotides, detection of new Cy5 signal after excitation of Cy3 indicates incorporation of either G or T. Next, in Step 7, treatment of the DNA products with sodium dithionite cleaves the azo linker, leading to the removal of any blockers and donor-acceptor dye pairs on T and C. Step, After washing away cleaved dye, imaging for the presence of Cy5 fluorescence after excitation of Cy3 is carried out. In this step, if it has already been determined that the incorporated nucleotide could be A or C, loss of Cy5 fluorescence would reveal it to be C, while remaining fluorescence would reveal it to be A. Similarly, for signals previously determined as G or T, loss of Cy5 fluorescence would indicate incorporation of T specifically while remaining fluorescence would indicate incorporation of G. Next, in Step 9, treatment of the DNA products with THP cleaves the SS linker, leading to the removal of the remaining blocker and Cy3-Cy5 dye pairs. Step 10, after washing away THP, an optional imaging step will confirm all dyes have been removed, in preparation for the next cycle of sequencing. Though not indicated in FIGS. 104A-104D, if desired, the presence of an additional SS linkage between the Azo group and the base results in the production of a shorter scar on the incorporated nucleotide after THP treatment which should result in longer reads. Structures of modified nucleotides used in this scheme are shown in FIGS. 90-92D (with single anchors and donor dyes) and FIGS. 93A-93C (with 2 or more anchors and donor dyes). Multiple donor-anchor pair clusters attached to the base can also be used to amplify the energy transfer signal (FIGS. 93A-93C show example structures).

It should be recognized that the Donor Dye may be directly attached to the anchor molecule and the Acceptor Dye may be attached to the Anchor Binding Molecule as in the example shown. But the alternative arrangement, in which the Acceptor Dye is on the Anchor portion and the Donor Dye is on the Anchor Binding Molecule is just as reasonable, and in fact may have advantages. For instance, use of very large fluorescent structures, such as quantum dots (typically 10-50 nm semicolloidal nanocrystals) would preferentially be used in the labeling step. Quantum dots have advantages as FRET donors due to their broad absorption range allowing selection of an excitation wavelength that has no direct effect on the acceptor dye, very high brightness relative to organic fluors due to their very high extinction coefficients but similar quantum yields, tunability, stability and narrow bandwidth of the emission spectrum.

Section IV: "Trigger" Molecules: Breached Linkers with Cleavable Moiety on One Branch and Anchors or Dyes on Other Branch Herein disclosed is the novel use of reversible terminators in which the 3'-OH group of the nucleotide analogue is blocked by a branched molecule to carry out DNA (or RNA) sequencing by synthesis. The shorter branch (branch 1) consists of a cleavable moiety, while the other branch (branch 2) is attached directly to a fluorescent dye or other label, or else to an anchor for subsequent post-incorporation binding of a fluorescent or other label via an anchor-specific binding molecule. Cleavage of the cleavable moiety on branch 1 leads to removal of branch 2 with its associated directly or secondarily linked label and at the same time restores the 3'-OH group for subsequent rounds of SBS. Because of their ability to simultaneously cause removal of both branches, such cleavable moieties are referred to herein as "triggers".

The use of a trigger molecule with an azidomethyl based trigger has been disclosed previously (Ju et al 2017 U.S. Pat. No. 9,624,539). Examples of triggering cleavable groups that can be positioned to serve as triggers include allyl, 2-nitrobenzyl (2NB), azo (N2) and dithiomethyl (DTM) groups. These can be cleaved, respectively, by Pd(0), 340 nm light, sodium dithionite, and a reducing agent such as TCEP, THP or DTT, under conditions that are efficient and not harmful to DNA.

Examples of anchors include biotin, TCO, and azide ($N_3$); associated anchor binding molecules are streptavidin, tetrazine and dibenzylcyclooctyne (DBCO). Other anchors and anchor binding molecule combinations are included in the table immediately following this section.

In the case of 2-dye schemes, dyes are chosen that have well separated absorption and emission spectra. The 2-color and especially the 1-color designs are preferred, in order to reduce the size and cost of the optical set-up.

In addition to nucleoside triphosphate analogues, nucleoside tetraphosphate, nucleoside pentaphosphate, nucleoside hexaphosphate and higher nucleoside polyphosphate analogues are feasible alternatives.

Herein are disclosed several examples of SBS schemes taking advantage of nucleotide analogues with cleavable triggers. In the examples presented herein, for ease of presentation, all four of the (deoxy)nucleotide analogues (A, C, G and T/U) possess a cleavable trigger. However, these schemes can work equally well, when one, two or three of the nucleotide analogues has a non-branched structure, or even if the anchor/dye is attached to the base on one, two or three of the nucleotide analogues. A unifying principle is that at least one of the nucleotide analogues bears the branched cleavable 3'-OH blocking group and label/anchor. Because all the modifications shown are at the 3'-O position of the sugar, relatively small dyes (Rox and BodipyFL) and anchors (biotin and TCO) have been selected for use in the examples herein disclosed. Similar schemes have been presented previously (Ju et al WO 2017/058953 A1, Ju et al WO 2017/205336 A1), but with standard cleavable linkers instead of the cleavable trigger-based linkers presented here. Other schemes, such as Section I of this application, can also be adapted to include these cleavage triggering molecules.

Scheme XXIV is a four-color scheme that requires imaging after incorporation and labeling to specifically identify the incorporated nucleotide analogue, Schemes XXV and XXVI are two-color schemes: imaging is required after incorporation and labeling in Scheme XXV and after labeling and the first cleavage step in Scheme XXVI. Schemes XXVII and XXVIII are one-color schemes. Scheme XXVII requires imaging after each of three cleavage steps, while Scheme XXVIII requires imaging after incorporation and after a first cleavage step. Optional confirmatory imaging steps are included in some of these schemes. As with all the previously described schemes, chasing with unlabeled nucleotide analogues is performed after adding the dye- or anchor-containing nucleotide analogues to guarantee that every DNA primer strand has been extended so as to avoid asynchronous reactions, and washing is essential between every step to remove the previous set of reagents and/or released dyes. While all the schemes presented use DNA templates and primers, 2-deoxynucleotide analogues and DNA polymerase, in principle the schemes can be taken to include appropriate templates, primers, and nucleotide analogues for RNA-dependent DNA polymerases as well as DNA- or RNA-dependent RNA polymerases.

Scheme XXIV: Pour-color SBS with 1 cleavable trigger molecule, two anchors and four dyes. In Scheme XXIV, incorporation is performed with one nucleotide analogue containing Dye1 directly attached to Trigger1 (DTM in the example), one nucleotide analogue containing Dye2 directly attached to Trigger1, one nucleotide with Anchor1 (biotin in the example) attached to Trigger1 and one nucleotide with Anchor2 (TCO in the example) attached to Trigger1 to identify two of the types of nucleotides specifically. Then labeling is carried out with Dye3-labeled Anchor1-specific binding molecule (streptavidin in the example) and Dye4-labeled Anchor2-specific binding molecule (tetrazine in the example) to identify the remaining two types of nucleotides specifically. Cleavage of the trigger moiety with, for example, THP, will remove the remaining dyes and restore the 3'-OH group for subsequent sequencing cycles. In the example, Dye1 is Rox, Dye2 is BodipyFL, Dye3 is Cy5 and Dye4 is R6G. Other combinations of dyes, anchors and cleavable trigger linkers can also be used. While in theory four different dyes could directly be attached to the four nucleotides, eliminating the use of anchors, the approach delineated here permits four relatively small chemical groups to be added (Rox, BodipyFL, biotin and TCO), so as not to impede incorporation of the nucleotide analogue.

FIG. 119 contains a schematic showing Scheme XXIV using 3'-O-Dye-SS(DTM)Trigger-dNTPs (3'-O-Rox-$PEG_4$-SS(DTM)Trigger-dATP, 3'-O-BodipyFL-$PEG_4$-SS(DTM) Trigger-dGTP), 3'-O-Anchor-SS(DTM)Trigger-dNTPs (3'-O-Biotin-SS(DTM)Trigger-dTTP, 3'-O-TCO-SS(DTM) Trigger-dCTP) and associated Dye-labeled Anchor Binding Molecules (Cy5-labeled Streptavidin, R6G-labeled Tetrazine) to perform four-color SBS. Step 1, addition of DNA polymerase and the four 3'-O-Dye/Anchor-SS(DTM)-dNTPs (3'-O-Rox-PEG$_4$-SS(DTM)Trigger-dATP, 3'-O-BodipyFL-PEG$_4$-SS(DTM)Trigger-dGTP, 3'-O-Biotin-SS(DTM)Trigger-dTTP and 3'-O-TCO-SS(DTM)Trigger-dCTP) to the immobilized primed DNA template enables the incorporation of the complementary nucleotide analogue to the growing DNA strand to terminate DNA synthesis; Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS(DTM)-nucleotide analogue to a subset of growing DNA strands that were not extended with any of the dye or anchor linked dNTPs in step 1; Step 3, Incubation with Cy5-labeled Streptavidin and R6G-labeled Tetrazine; Step 4, After washing away unincorporated nucleotide analogues and excess labeled anchor binding molecules, imaging is performed; the presence of a Rox signal indicates incorporation of A, a BodipyFL signal indicates incorporation of G, a Cy5 signal indicates incorporation of T, and an R6G signal indicates incorporation of C; Step 5, Cleavage of the disulfide bond is conducted with DTT, TCEP, or THP to remove the dye and regenerate free 3'-OH on all the DNA extension products, which are ready for subsequent cycles of SBS. After washing away the cleavage agent, steps 1 to 5 are repeated to continue subsequent cycles of 4-color DNA SBS. Structures of modified nucleotides used in this scheme are shown in FIG. 105.

Scheme XXV: Two-color SBS with 1 cleavable trigger molecule, two anchors and two dyes. In Scheme XXV, incorporation is performed with one nucleotide analogue containing Dye1 directly attached to Trigger1 (DTM in the example), one nucleotide analogue containing Dye2 directly attached to Trigger1, one nucleotide analogue containing Anchor1 (biotin in this example) attached to Trigger1, and one nucleotide analogue containing Anchor2 (TCO in this example) attached to Trigger1 to identify two of the types of nucleotides specifically. Then labeling is carried out with Dye1-labeled Anchor1-specific binding molecule (streptavidin in the example) and Dye2-labeled Anchor2-specific binding molecule (tetrazine in the example) to identify the remaining two types of nucleotides specifically. Cleavage of the trigger moiety with, for example, THP, will remove the remaining dyes and restore the 3'-OH group for subsequent sequencing cycles. In the example, Dye1 is Rox and Dye2 is BodipyFL. Other combinations of dyes, anchors and cleavable trigger linkers can also be used. In essence, Schemes XXIV and XXV are identical except that only two dyes are used in the latter.

FIG. 120 contains a schematic showing Scheme XXV using 3'-O-Dye-SS(DTM)Trigger-dNTPs (3'-O-Rox-PEG$_4$-SS(DTM)Trigger-dATP, 3'-O-BodipyFL-PEG$_4$-SS(DTM)Trigger-dGTP), 3'-O-Anchor-SS(DTM)Trigger-dNTPs (3'-O-Biotin-SS(DTM)Trigger-dTTP, 3'-O-TCO-SS(DTM)Trigger-dCTP) and associated Dye-labeled Anchor Binding Molecules (Rox-labeled Streptavidin, BodipyFL-labeled Tetrazine) to perform two-color SBS. Step 1, addition of DNA polymerase and the four 3'-O-Dye/Anchor-SS(DTM)-dNTPs (3'-O-Rox-PEG$_4$-SS (DTM) Trigger-dATP, 3'-O-BodipyFL-PEG$_4$-SS(DTM)Trigger-dGTP, 3'-O-Biotin-SS(DTM)Trigger-dTTP and 3'-O-TCO-SS(DTM)Trigger-dCTP) to the immobilized primed DNA template enables the incorporation of the complementary nucleotide analogue to the growing DNA strand to terminate DNA synthesis; Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS(DTM)-nucleotide analogue to a subset of growing DNA strands that were not extended with any of the dye or anchor linked dNTPs in step 1; Step 3, After washing away unincorporated nucleotide analogues, imaging is carried out. Presence of a Rox signal will indicate incorporation of A; presence of a BodipyFL signal will indicate incorporation of G. Step 4, Incubation with Rox-labeled Streptavidin and BodipyFL-labeled Tetrazine; Step 5, After washing away excess labeled anchor binding molecules, imaging is performed; the presence of a new Rox signal indicates incorporation of T; the presence of a new BodipyFL signal indicates incorporation of C; Step 6, Cleavage of the disulfide bond is conducted with DTT, TCEP, or THP to remove the dye and regenerate free 3'-OH on all the DNA extension products, which are ready for subsequent cycles of SBS. After washing away the cleavage agent, steps 1 to 6 are repeated to continue subsequent cycles of 2-color DNA SBS. Structures of modified nucleotides used in this scheme are shown in FIG. 106.

Scheme XVI: Two-color SBS with 2 cleavable trigger molecules, 2 anchors and 2 dyes. In Scheme XXVI, incorporation is carried out with an orthogonal set of nucleotide analogues, the first with Anchor1 (biotin in this example) attached to Trigger1 (Azo in this example), the second with Anchor1 attached to Trigger 2 (DTM in this example), the third with Anchor 2 (TCO in this example) attached to Trigger1 and the fourth with Anchor2 attached to Trigger2. Next labeling is carried out with Dye1-labeled Anchor1-binding molecule (streptavidin in the example) and Dye2-labeled Anchor2-binding molecule (tetrazine in the example). At this point, imaging will reveal one of two alternative types of nucleotides having been incorporated, but not which one specifically. A second round of imaging after cleavage of Trigger1 with sodium dithionite will indicate which types of nucleotide was incorporated specifically. Finally, cleavage of Trigger2 with THP will remove the remaining dyes and restore the 3'-OH group for subsequent sequencing cycles. In the example, Dye1 is Rox and Dye2 is BodipyFL. Other combinations of dyes, anchors and cleavable trigger linkers can also be used. Whereas Scheme XXV, also a two-color SBS scheme, requires imaging after the incorporation and labeling steps, Scheme XXVI requires imaging after the labeling and first cleavage steps.

FIGS. 121A-121C contain a schematic showing Scheme XXVI using 3'-O-Anchor-SS(DTM)Trigger-dNTPs (3'-O-Biotin-SS(DTM)Trigger-dTTP, 3'-O-TCO-SS(DTM)Trigger-dGTP), 3'-O-Anchor-AzoTrigger-dNTPs (3'-O-Biotin-AzoTrigger-dATP, 3'-O-TCO-AzoTrigger-dCTP) and associated Dye-labeled Anchor Binding Molecules (Rox-labeled Streptavidin, BodipyFL-labeled Tetrazine) to perform two-color SBS. Step 1, addition of DNA polymerase and the four 3'-O-Anchor-linked-dNTPs (3'-O-Biotin-SS(DTM)Trigger-dTTP, 3'-O-TCO-SS(DTM)Trigger-dGTP, 3'-O-Biotin-AzoTrigger-dATP, and 3'-O-TCO-AzoTrigger-dCTP) to the immobilized primed DNA template enables the incorporation of the complementary nucleotide analogue to the growing DNA strand to terminate DNA synthesis; Step 2, Chase: addition of DNA polymerase and four 3'-O-SS(DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS(DTM)-nucleotide analogue to a subset of growing DNA strands that were not extended with any of the anchor linked dNTPs in step 1; Step 3, Incubation with Rox-labeled Streptavidin and BodipyFL-PEG$_4$-labeled Tetrazine. Step 4, After washing away unincorporated nucleotide analogues and excess dye labeled anchor binding molecules, imaging is carried out. Presence of a Rox signal will indicate incorporation of either A or T; presence of a BodipyFL signal will indicate incorporation of a G or C. Step 5, Addition of sodium dithionite to cleave the Azo trigger, and simultaneously restore the 3'-OH on any primers extended with A or C; Step 6, After washing away excess labeled anchor binding molecules, imaging is performed; loss of a Rox signal indicates incorporation of A, a remaining Rox signal indicates incorporation by T; similarly loss of a BodipyFL signal indicates incorporation by C, a remaining BodipyFL signal indicates incorporation by G. Step 7, Cleavage of the disulfide bond is conducted with DTT, TCEP, or THP to remove any remaining dye on primers extended with G or T, and regenerate free 3'-OH on all the DNA extension products, which are ready for subsequent cycles of SBS. After washing away the cleavage agent, steps 1 to 7 are repeated to continue subsequent cycles of 2-color DNA SBS. Structures of modified nucleotides used in this scheme are shown in 107.

Scheme XXVII: One-color SBS with 4 cleavable trigger molecules and one dye. In Scheme XXVII, incorporation is carried out with one nucleotide analogue containing Dye1 attached to Trigger1 (Azo in this example), one nucleotide analogue containing Dye1 attached to Trigger2 (Allyl in this example), one nucleotide analogue containing Dye1 attached to Trigger3 (2NB in this example) and one nucleotide analogue containing Dye1 attached to Trigger4 (DTM in this example). An optional but recommended imaging step is carried out after incorporation to ensure that a nucleotide has been incorporated. Then cleavage reactions are carried out to remove dyes one by one, at the same time restoring 3'-OH groups. In the example shown in FIGS. 122A-122C, the cleavage agents are sodium dithionite, Pd(0), 340 nm light and THP respectively. Imaging after each of the first 3 cleavage steps will indicate specifically which type of nucleotide analogue was incorporated. In the example, Dye1 is Rox.

FIGS. 122A-122C contain a schematic showing Scheme XXVII using 3'-O-Dye-SS(DTM)Trigger-dNTP (3'-O-Rox-PEG$_4$-SS(DTM)Trigger-dCTP), 3'-O-Dye-AzoTrigger-dNTP (3'-O-Rox-PEG$_4$-AzoTrigger-dGTP), 3'-O-Dye-AllylTrigger-dNTP (3'-O-Rox-PEG$_4$-AllylTrigger-dATP), and 3'-O-Dye-2NBTrigger-dNTP (3'-O-Rox-PEG$_4$-2NBTrigger-dTTP) to perform one-color SBS. Step 1, addition of DNA polymerase and the four 3'-O-Dye-linked-Cleavable Trigger-dNTP analogues (3'-O-Rox-PEG$_4$-SS(DTM)Trigger-dCTP, 3'-O-Rox-PEG$_4$-AzoTrigger-dGTP, 3'-O-Rox-PEG$_4$-AllylTrigger-dATP and 3'-O-Rox-PEG$_4$-2NBTrigger-dTTP) to the immobilized primed DNA template enables the incorporation of the complementary nucleotide analogue to the growing DNA strand to terminate DNA synthesis; Step 2, Chase: addition of DNA polymerase and four 3'-O-SS (DTM)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS(DTM)-nucleotide analogue to a subset of growing DNA strands that were not extended with any of the dye linked dNTP analogues in step 1; Step 3 (optional), after washing to remove any unincorporated nucleotide analogues, imaging will indicate incorporation of one of the four nucleotides non-specifically. Step 4, treatment with sodium dithionite is performed to cleave Azo linker, triggering at the same time restoration of the 3'-OH on DNA molecules extended with G. Step 5, After washing away unincorporated nucleotide analogues, imaging is carried out. Loss of the Rox signal will indicate incorporation of G; Step 6, treatment with Pd(0) is performed to cleave Allyl linkers, triggering at the same time restoration of the 3'-OH on DNA molecules extended with A. Step 7, After washing away unincorporated nucleotide analogues, imaging is carried out. Loss of the Rox signal will indicate incorporation of A. Step 8, exposure to 340 nm light is used to cleave 2-nitrobenzyl (2NB) linkers, triggering at the same time restoration of the 3'-OH on DNA molecules extended with T. Step 9, After washing away unincorporated nucleotide analogues, imaging is carried out. Loss of the Rox signal will indicate incorporation of T. Step 10, Cleavage of the disulfide bond is conducted with DTT, TCEP, or THP to remove any remaining dye on primers and restore the 3'-OH on any DNA molecules extended with C. The extension products are now ready for subsequent cycles of SBS. After washing away the cleavage agent, steps 1 to 10 are repeated to continue subsequent cycles of single-color DNA SBS. Structures of modified nucleotides used in this scheme are shown in FIG. 108.

Scheme XXVIII: One-color SBS with 2 cleavable trigger molecules, one anchor and one dye. In Scheme XXVIII, incorporation is carried out with an orthogonal set of nucleotide analogues, one with Dye1 attached directly to Trigger1 (Azo in this example), one with Dye1 attached directly to Trigger2 (DTM in this example), one with Anchor1 (biotin in this example) attached to Trigger1, and one with Anchor1 attached to Trigger 2, after which imaging is performed to identify incorporation by two of the types of nucleotide analogues non-specifically. Next, labeling is carried out with Dye1-labeled Anchor1-specific binding molecule (streptavidin in this example) followed by an optional but recommended imaging step to reveal incorporation by the remaining two types of nucleotide analogues non-specifically. Treatment with sodium dithionite to cleave Trigger1 followed by imaging will reveal which nucleotide was incorporated specifically. Finally, cleavage of Trigger2 with THP will remove any remaining dyes and restore the 3'-OH group for subsequent sequencing cycles. In the example, Dye1 is Rox. Whereas Scheme XXVII, also a one-color SBS scheme, requires imaging after each of three cleavage steps, Scheme XXVIII requires imaging after the incorporation and first cleavage steps.

FIGS. 123A-123C contain a schematic showing Scheme XXVIII using 3'-O-Dye-SS(DTM)Trigger-dNTP (3'-O-Rox-PEG$_4$-SS(DTM)Trigger-dATP), 3'-O-Dye-AzoTrigger-dNTP (3'-O-Rox-PEG$_4$-AzoTrigger-dGTP), 3'-O-Anchor-SS(DTM)Trigger-dNTP (3'-O-Biotin-SS(DTM)Trigger-dTTP), 3'-O-Anchor-AzoTrigger-dNTP (3'-O-Biotin-AzoTrigger-dCTP) and appropriate Dye-labeled Anchor Binding Molecule (Rox-labeled Streptavidin) to perform one-color SBS. Step 1, addition of DNA polymerase and the four 3'-O-Dye/Anchor-linked-Cleavable Trigger-dNTP analogues (3'-O-Rox-PEG$_4$-SS(DTM)Trigger-dATP, 3'-O-Rox-PEG$_4$-AzoTrigger-dGTP, 3'-O-Biotin-SS(DTM)Trigger-dTTP, 3'-O-Biotin-AzoTrigger-dCTP) to the immobilized primed DNA template enables the incorporation of the complementary nucleotide analogue to the growing DNA strand to terminate DNA synthesis; Step 2, Chase: addition of DNA polymerase and four 3'-O-SS(DTM)-dNTPs (3'-O-t-Butyldithiomethyl(SS)-dATP, 3'-O-t-Butyldithiomethyl (SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS(DTM)-nucleotide analogue to a subset of growing DNA strands that were not extended with any of the dye linked dNTP analogues in step 1; Step 3, after washing to remove any unincorporated nucleotide analogues, imaging will indicate incorporation of either A or G non-specifically. Step 4, incubation with Rox-labeled Streptavidin. Step 5, After washing away excess labeled anchor binding molecule, imaging is carried out. Appearance of a new Rox signal will indicate incorporation of either C or T non-specifically; Step 6, cleavage with sodium dithionite to cleave the Azo linkage on G or C, simultaneously restoring the 3' OH on DNA molecules extended with G or C. Step 7, after washing to remove excess cleavage agent, imaging is carried out. If it was determined that A or G was incorporated in Step 3, loss of Rox signal will indicate incorporation of G, while retention of signal will indicate incorporation of A. Similarly, if it was determined in step 5 that either C or T was incorporated, loss of Rox signal will indicate incorporation of C, while retention of signal will indicate incorporation of T. Step B, Cleavage of the disulfide bond is conducted with DTT, TCEP, or THP to remove any remaining dye on primers and restore the 3'-OH on any DNA molecules extended with A or T. The extension products are now ready for subsequent cycles of SBS. After washing away the cleavage agent, steps 1 to 8 are repeated to continue subsequent cycles of single-color DNA SBS. Structures of modified nucleotides used in this scheme are shown in FIG. 108.

It should be understood from the foregoing that, while particular implementations have been illustrated and described, various modifications can be made thereto and are contemplated herein. For example, other variants of the schemes herein disclosed are possible: e.g., (a) some cleavable linkers can be trigger molecules while others can be routine cleavable linkers (unbranched); (b) hybrid approach in which trigger cleavable linkers for one, two or three nucleotide analogues are at the 3' position and standard cleavable linkers for the remaining nucleotide analogues are attached to the base. Particularly in instances where anchors are used, the labels attached to the anchor binding molecules can include energy transfer dyes, non-fluorescent labels including Raman tags and as described in the prior PCT, sets of tags that reduce ion current signals in nanopores to different extents, have different dwell times within the ion channel, or both.

Chemical structures of nucleotide analogues and other molecules for the various schemes are presented in FIGS. 105-109. Chemical synthesis schemes for the described molecules are presented in FIGS. 110-118.

Examples of additional possible anchors and anchor binding molecules (in some cases, these can be reversed, e.g., alkyne or cyclooctyne anchor and azide anchor binding molecule) can be found in Table 3:

TABLE 3

| Anchor | Anchor Binding Molecule |
| --- | --- |
| Azide | Alkyne; cyclooctyne |
| Tetrazine | Cyclooctene; Norbornene |
| Phenylboronic acid (PBA) | Salicylhydroxamic acid (SHA) |
| Quadricyclane | Ni bis(dithiolene) |
| Norbornene | Nitrile oxide |

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

All combinations of the various elements described herein are within the scope of the invention. All sub-combinations of the various elements described herein are also within the scope of the invention.

This invention will be better understood by reference to the Experimental Details which follow, but those skilled in the art will readily appreciate that the specific experiments are only illustrative of the invention as described more fully in the claims which follow thereafter. Every embodiment and feature described in the application should be understood to be interchangeable and combinable with every with embodiment contained within.

EXPERIMENTAL DETAILS

Example 1: Cleavage Compatibility of SS Linker and Azo Linker

For the two-color SBS method to work sufficiently, the disulfide linker needs to be intact upon treating with sodium dithionite to cleave the azo linker. It was previously reported that the azo linker can be cleaved in 10 mM $Na_2S_2O_4$ in less than 5 min at room temperature (Yang et al 2010).

Disclosed herein are the results of a compatibility test was performed using 3'-O-SS-dATP-SS-Rox (cal: MW1344.36 Da, observed 1345.61) as model compound. 2 µl of 0.1 mM 3'-O-SS-dATP-SS-Rox was treated with 100 µL of freshly made 25 mM $Na_2S_2O_4$ (in PBS buffer [pH 7.4]) and the mixture was kept shaking for 30 min at 37° C. Then desalination was carried out with a ZipTip, and the product was subjected to MALDI TOF MS measurement. The resulting peak is shown as 1347.37 Da indicating integrity of 3'-O-SS-dATP-SS-Rox in the present of $Na_2S_2O_4$ and no cleavage or degradation was observed (FIGS. 124A-124B). The result proves that the disulfide linker is stable at much higher concentration of sodium dithionite and at longer reaction time than necessary to cleave the Azo linker.

An additional compatibility test was conducted on 3'-SS-dC extended ssDNA. The single base extension experiment was carried out by adding 20 pmol Exon 8 template, 60 pmol primer (M.W. 5144), 2 mM $MnCl_2$ and 2 U Therminator 9 polymerase in 20 µl 1×Pol buffer in each PCR reaction tube which were subject to PCR thermocycles (65° C. for 30" 45° C. for 30", 38 cycles). After completion of the incorporation, $NaS_2O_4$ solution was added to the reaction tube to a final concentration of 20 mM and incubated at room temperature for 40 min. Then the reaction mixture was treated with a Clean & Concentrator column to purify ssDNA. The resulting oligonucleotide was subject to MALDI-TOF MS measurement. The results showed that 3'-SS-dC was incorporated to the 5144 primer, yielding an incorporation product with an MS peak of 5559 Da without $NaS_2O_4$ treatment. The single base extended oligonucleotide after $NaS_2O_4$ treatment also showed the same MS peak of 5559 Da and no extra cleavage peak was found. The results demonstrated that both DNA and the SS linkage remained intact upon $NaS_2O_4$ treatment to cleave the Azo liker. Thus, the combination of an azo and a disulfide linker is feasible for orthogonal cleavage and two-color and one-color SBS.

Example 2: Sodium Dithionite Cleavage Conditions for a DNA Primer AzoLinker Biotin Conjugate Many of the nucleotide analogues throughout this patent application have Azo-containing linkers between the base and the dye or anchor molecule. Sodium dithionite can be used to cleave the azo bond (Yang et al 2010). A separate system using an Azo-containing linker between an oligodeoxynucleotide and biotin was used to determine the best conditions for carrying out dithionite cleavage. The larger goal of this study was to develop a method for capturing and then releasing DNA from streptavidin beads without the need for breaking the biotin-streptavidin bond, a process which is not very efficient under conditions that are gentle enough to use for DNA, proteins and other organic molecules. Thus, this is meant to be a general enrichment method. The synthesis of the biotin-Azo linker-DNA compound and sodium dithionite conditions resulting in complete cleavage of the Azo bond is disclosed herein.

1. Synthesis of biotin-PEG4-AzoLinker-DNA. Synthesis of biotin-PEG4-AzoLinker NHS ester was carried out as shown in FIG. 125. Biotin-PEG4-NHS ester was reacted with amino azolinker benzoic acid yielding biotin-azolinker-benzoic acid, which was further converted to biotin azolinker NHS ester by treatment with DSC. Amino modified 18mer oligonucleotide was then treated with biotin azolinker NHS ester resulting in DNA Primer-AzoLinker-Biotin Conjugate (FIG. 126). The expected DNA Azo biotin conjugate was purified by HPLC and dried in preparation for experimental testing.
2. Cleavage Tests of DNA Primer-AzoLinker-Biotin Conjugate (FIG. 127). Upon treatment with $Na_2S_2O_4$, the Azo linker will be cleaved and DNA can be released from the biotin. A variety of cleavage conditions were tested to optimize the cleavage time and temperature for the desired biological applications. (For instance, if the biotinylated oligonucleotide is a primer, it can be used to enrich for ternary complexes of polymerase, primer, template and nucleotide for Nanopore SBS.) A stock solution (1M) of $Na_2S_2O_4$ was prepared in 1×PBS buffer (pH 7.4), then between 1.25 µl and 5 µl $Na_2S_2O_4$ stock solution (1M) was added to DNA solution (21-32 µl) and made up with PBS buffer to a final volume of 50 µl. The cleavage reaction mixtures were incubated at different temperatures and for different lengths of time. The lowest working concentration of the $Na_2S_2O_4$ cleavage agent for quantitative cleavage was found to be 25 mM. Time and temperature conditions were screened at this concentration, as follows.

Condition 1: $Na_2S_2O_4$: 25 mM, Temperature: RT, Time: 30 min results in approximately 80% Cleavage 1.25 µl 1M $Na_2S_2O_4$, DNA 32 µl (300 ng/µl), 5 µl 10×PBS in 50 µl Condition 2: $Na_2S_2O_4$: 25 mM, Temperature: 30° C., Time: 15 min results in 100% Cleavage 1.25 µl 1M $Na_2S_2O_4$, DNA 21 µl (300 ng/µl), 5 µl 10×PBS in 50 µl Condition 3: $Na_2S_2O_4$: 25 mM, Temperature: 37° C., Time: 0.5 min results in 100% Cleavage 1.25 µl 1M Na2S2O4, DNA 32 µl (300 ng/µl), 5 µl 10×PBS in 50 µl HPLC was used to monitor the cleavage results. FIG. 128A indicates the HPLC profile prior to cleavage and FIG. 128 indicates the profile following cleavage. Under Conditions 2 and 3 above, there is no remaining trace of the initial Primer-Azo Linker-Biotin molecule. A new peak appears with a shorter retention time, indicative of the cleaved product.

Example 3: Single-Color Fluorescent Sequencing by Synthesis (SBS) Using 3'-OH Blocked Nucleotide Reversible Terminators (NRTs), One Anchor and Two Cleavable Linkers In this one-color SBS scheme, in the style of Scheme II shown in FIGS. 32A-32D, and described in greater detail herein above, four nucleotide analogues were required: one NRT with Dye attached to the base via Cleavable Linker 1, one NRT with Dye attached to the base via Cleavable Linker 2, one NRT with Anchor attached to the base via Cleavable Linker 1, and one NRT with Anchor attached to the base via Cleavable Linker 2; the generalized structures of these nucleotides are presented in FIG. 129. The general design of the scheme used is displayed in FIG. 130. The scheme consists of an extension with the four NRTs, labeling with an anchor-binding molecule bearing the same Dye, cleavage of Cleavable Linker 2, and finally cleavage of Cleavable Linker 1 (which also restores the 3'-OH group). If the NRT with Dye and Cleavable Linker 1 is incorporated, it will show fluorescence after the extension step and retain this fluorescence until the second cleavage step is completed. If the NRT with Dye and Cleavable Linker 2 is incorporated, fluorescence will be seen after the extension step and will be lost after the first cleavage step. If the NRT with Anchor and Cleavable Linker 1 is incorporated, fluorescence will not be seen until after the labeling step and will not be lost until after the second cleavage step. If the NRT with Anchor and Cleavable Linker 2 is incorporated, fluorescence will not be seen until after the labeling step and will be lost after the first cleavage step.

With a digital readout in which 1 represents the appearance of significantly above background fluorescence and 0 represents only background fluorescence, the following three imaging steps can be considered: (1) after extension; (2) after labeling; and (3) after first cleavage. Thus, the first NRT will display a pattern of 111, the second NRT will display a pattern of 110, the third NRT will display a pattern of 011, and the fourth NRT will display a pattern of 010. These four unique codes will thus allow base-calling.

Technically the imaging after the labeling step is not essential as it is only confirmatory, with the unique coding patterns 11, 10, 01 and 00 being obtained from just the imaging after extension and first cleavage steps. Imaging after the second cleavage is also not essential for base calling since all four nucleotides will display background fluorescence (0) at this point.

In this example, the four NRT analogues having the structures illustrated in FIG. 131 were synthesized and characterized: (1) 3'-O-t-Butyl-SS(DTM)-dTTP-PEG4-Azo-Cy5; (2) 3'-O-t-Butyl-SS(DTM)-dGTP-SS-Cy5; (3) 3'-O-t-Butyl-SS(DTM)-dATP-PEG4-Azo-Biotin; and (4) 3'-O-t-Butyl-SS(DTM)-dCTP-SS-Biotin. The labeling molecule was Streptavidin-Cy5.

Example 3a: Synthesis of 3'-O-t-Butyl-SS(DTM)-dTTP-PEG4-Azo-Cy5 (FIG. 132)

The azo linker was prepared from the starting materials tyramine and 4-aminobenzoic acid. After protecting the amino group on tyramine with TFA and nitrosylation of 4-aminobenzoic acid to form a diazonium salt, these compounds were coupled to form an azo compound which was then coupled to a PEG4 linker. This is the stable form of the azo linker that can be stored for attachment to various nucleotide analogues. In this case, it was converted to an NHS ester and coupled to 3'-O-t-butyl-SS-dTTP-propargyl-NH2. After removal of the TFA group, the resulting compound was coupled to Sulfo-Cyanine5-NHS ester to produce the desired compound. A detailed description of the method is presented below. A MALDI-TOF MS trace to confirm synthesis of the correct molecule is presented in FIG. 133.

3. Protection of amino group on tyramine: Tyramine and 4-aminobenzoic acid are used as the starting materials for synthesis of the azo-benzene-based linker. The amino group on the tyramine was initially protected as trifluoroacetamide (A1). Tyramine (500 mg, 3.65 mmol) was suspended in 5 mL of dichloromethane (DCM). Trifluoroacetic anhydride (761 µL, 5.47 mmol) and pyridine (587.3 µL, 7.3 mmol) were added to the suspension which was stirred at room temperature overnight. The reaction was monitored by TLC (DCM:MeOH=10:1) until completion. 10 mL of saturated NaHCO3 solution was added to the reaction mixture to stop the reaction, followed by extraction with DCM (5×50 mL). All organic layers were combined, dried over Na2SO4 and concentrated under vacuum. The residue was purified by flash column chromatography. 760 mg of A1 was obtained, which was characterized by 1H-NMR.

4. Coupling reaction of diazonium salt to form azo compound (A2): The nitrosylation of a primary aromatic amine with sodium nitrite and strong acid (hydrochloric acid) at 0° C. leads to a diazonium salt. The nitrosonium ion from sodium nitrite dissociation is attacked by the amino group on 4-aminobenzoic acid to form the diazonium salt. The diazonium salt is an intermediate for the preparation of the azo-compound through the azo coupling. The hydroxyl group on the aromatic compound is a strong para, ortho directing substituent: substitution occurs on the ortho position of phenol while the para position is blocked.

4-Aminobenzoic acid (895 mg, 6.53 mmol) was suspended in 25 mL 6 M HCl and cooled in an ice bath. NaNO2 (1.13 g, 16.3 mmole) was added slowly and the suspension was stirred at 0° C. for 40 minutes. The trifluoro-N-(2-(hydroxy-phenyl)-ethyl)-acetamide (A1) (761 mg, 3.27 mmol) was dissolved in 32 mL 1:1 tetrahydrofuran (THF): saturated aq. NaHCO3 solution and cooled in an ice bath. The above prepared diazonium salt solution was added portion-wise at 0° C. while stirring. The pH was monitored and kept basic by adding K2CO3 as needed. The reaction mixture was warmed to room temp. and stirred overnight. The mixture turned dark red. Afterwards, THF was removed in vacuo and the pH was adjusted to 2 using 2 M HCl. The reaction mixture was extracted with ethyl acetate (3×50 mL) and the extracts were combined and washed with 1 M HCl (30 mL) and brine (30 mL), then dried over MgSO4 and concentrated in vacuo. The residue was purified twice by flash column chromatography (DCM:MeOH=10:1) and compound A2 was obtained (360 mg, 0.9 mmol) as an orange solid. The product was characterized by 1H NMR and HRMS (C17H14F3N3O4: 381.09 Da, found: 381.1 Da).

Addition of PEG4 linker to the amino group of the azo linker (A4): TFA-NH-Azo-COOH, A2, (38 mg, 99.73 pmol) was dissolved in DMF. To the dissolved solution N'N-dicyclohexylcarbodiimide, DCC (23.048 mg, 111.706 pmol), N-hydroxysuccinimide (17.22 mg, 149.6 pmol) and 4-dimethylaminopyridine, DMAP (12.184 mg, 99.73 pmol) were added. The reaction was monitored by thin layer chromatography. When the NHS ester analog, A3, conversion reached 50%, amine-PEG4-COOH (17.61 mg, 66.486 pmol) that was pre-dissolved in DMF was added to the reaction mixture. The reaction was kept stirring at 35° C. overnight. Compound A4 was purified using reverse-phase HPLC (HFIP buffer and MeOH) and characterized by HRMS (C28H36F3N4O9: 628.24 Da, found ESI+: 629.24 Da).

Conjugation of PEG4-Azo linker to propargyl linker on modified nucleotide (A5): To the DMF dissolved TFA-Azo-PEG4-COOH, A4, (1.75 mg, 2.785 pmol), N, N'-disuccinimidyl carbonate, DSC (0.856 mg, 3.34 pmol) and 4 µL of DIPEA were added. The reaction was monitored by TLC. 3'-O-t-butyl-SS-dTTP-PEG4-Azo-propargyl-NH2 dissolved in NaHCO3/Na2CO3 buffer (pH 8.6) was added into the reaction mixture after half an hour of stirring at 35° C. The reaction was run overnight. The afforded product A5, 3'-O-t-butyl-SS-dTTP-PEG4-Azo-TFA, was desalted through a C18 column followed by reverse-phase HPLC purification (HFIP buffer and MeOH). Compound A5 was characterized by MALDI TOF MS+ (C45H61F3N7O22P3S2: 1265.25 Da, found 1265.25 Da).

Linking of fluorescent dye Cyanine 5 to the amino group of the modified nucleotide (A7): The regeneration of the amino group on compound A5, 3'-O-t-butyl-SS-dTTP-PEG4-Azo-TFA (0.5 mg, 0.395 □mol), was performed by removing the trifluoroacetate group in 300 µL ammonium hydroxide. The reaction was stirred at 30° C. for 5 hours. The major peak at 1175 Da (calc'd: 1169.27) in the MALDI TOF MS spectrum reflected the successful deprotection of the amino group (A6). To the dissolved compound A6 (~0.5 mg, 0.395 µmol) in NaHCO3/Na2CO3 buffer, sulfo-cyanine5-NHS ester (1.29 mg, 1.66 µmol), which was pre-dissolved in DMF, was added. The reaction mixture was stirred overnight at 37° C. with exclusion of light and purified using reverse-phase HPLC. MALDI-TOF MS confirmed the formation of compound A7 indicated by a major peak at 1794.4 Da (calc'd: 1794.45 Da).

Figure 134C:
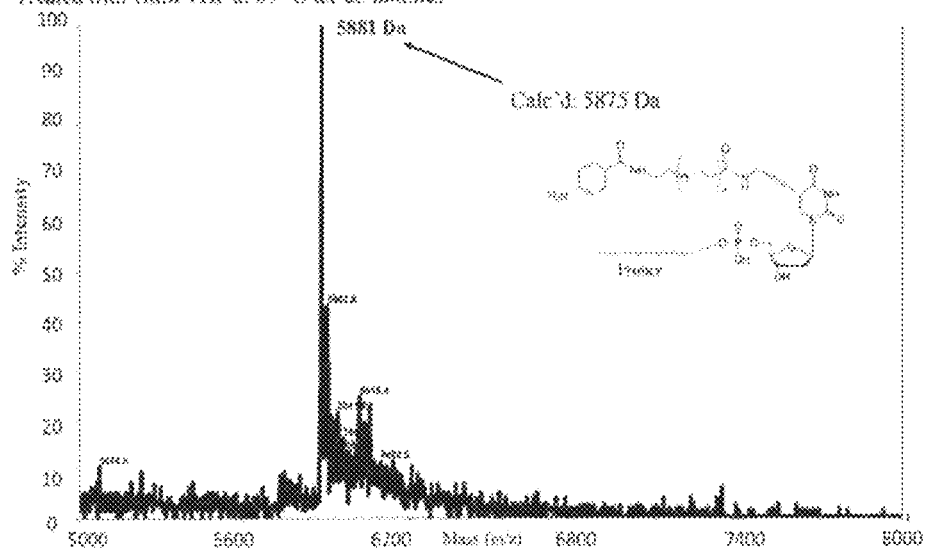

Example 3b: Single Base Incorporation for 3'-O-t-butyl-SS-dTTP-PEG4-Azo-Cy5, Azo Linker Cleavage Results for the Extended Primer 3'-O-t-butyl-SS-dTTP-PEG4-Azo-Cy5, and Disulfide Cleavage Reaction for Extended Primer by 3'-O-t-butyl-SS-dTTP-PEG4-Azo-Cy5 (FIGS. 134A-134C)

A single base DNA extension reaction (SBE) was performed with 3'-O-SS (DTM)-dTTP-PEG4-Azo-Cy5, using a primer (5'-GATAGGACTCATCACCA-3' [SEQ ID 1]) and a synthetic DNA template (5'-GAAGGAGACACGC-GGCCAGAGAGGGTCCTGTCCGTGTTTGTGCGTG-GAGTTCGACAAGGCAGGGTCAT CTAATGGTGAT-GAGTCCTATCCTTTTCTCTTCGTTCTCCGT-3' [SEQ ID 2]) based on a portion of exon 8 of the human p53 gene as follows. The bold letters in the template represent the extension position for the primers. 2 µL of 10× concentrated buffer, 1 µL of primer, E8TT (MW: 5163, 100 µM), 3 µL of Exon 8 template (20 µM), 1 µL of nucleotide (3'-O-t-butyl-SS-dTTP-PEG4-Azo-Cy5, 432 µM), 1 µL of Terminator IX DNA Polymerase, T9 (10 U/λ) and 12 µL of dH2O were combined in a total volume of 20 µL. The reaction consisted of 38 cycles at 65° C. for 30 seconds and 45° C. for 30 seconds. Single base extension was confirmed by MALDI-TOF MS as indicated by the major peak at 6791.8 Da (calc'd, 6782.4 Da) in the spectrum. No primer peak (5163 Da) was observed indicating that essentially all the primer was extended and the incorporation rate was 100%.

As seen in FIG. 134A, the primer strand is extended essentially 100% efficiency (no primer peak is visible) (reaction details are provided in detailed methods below). Moreover, the t-butyl-SS-methyl group is an effective blocker since, despite the presence of two A's in a row in the template, only a single base extension reaction takes place.

The azo cleavage reaction was performed on single base extended primer (E8TT+3'-O-t-butyl-SS-dTMP-PEG4-Azo-Cy5, 6782.4 Da). A 1M stock solution of Na2S2O4 was prepared in 1×PBS buffer (pH 7.4). 1.25 µL Na2S2O4 solution was added to the extended primer solution (20 µL, 32 µM) along with 28.75 µL of 1×PBS buffer. The reaction mixtures were incubated and stirred at 37° C. for 20 min. Afterwards, reaction mixtures were purified with a ZipTip and concentrated using a Speed Vac. The size of the cleaved extended primer was characterized by MALDI-TOF MS as 6009.44 Da (calc'd: 6008.9 Da). The treatment with 25 mM sodium dithionite at 37° C. for 20 minutes lead to complete cleavage of the linker (complete loss of extended primer peak) as shown in FIG. 134B.

Tris(hydroxypropyl)phosphine (THP) (1 µL, 1 mM) was added to the azo cleaved extended primer (9 µL, 15 µM) (E8TT+3'-O-t-butyl-SS-dTMP-PEG4-aniline, 6009.44 Da). The reaction was maintained at 65° C. for 25 min. After the spin column-based nucleic acid purification (ZymoPURE Oligo Clean & Concentrator), the product was confirmed by MALDI-TOF MS: 5881.4 Da (calc'd: 5874.9 Da). As shown in FIG. 134C, the treatment with 1 mM THP for 5 minutes at 65° C. removed the blocking group with high efficiency.

Example 3c: Synthesis of 3'-O-t-Butyl-SS(DTM)-dATP-PEG4-Azo-Biotin (FIG. 135)

The synthesis begins with the NHS ester of the linker in Example 3a and 3'-O-t-butyl-SS-dATP-propargyl-NH2 and is carried out in an identical way to Example 3a except that in the last coupling step Biotin-NHS ester is used. A detailed description of the method is presented below. A MALDI-TOF MS trace to confirm synthesis of the correct molecule is presented in Figure FIG. 136.

5. Protection of amino group on tyramine: Tyramine and 4-aminobenzoic acid are used as the starting materials for synthesis of the azo-benzene-based linker. The amino group on the tyramine was initially protected as trifluoroacetamide (A1). Tyramine (500 mg, 3.65 mmol) was suspended in 5 mL of dichloromethane (DCM). Trifluoroacetic anhydride (761 µL, 5.47 mmol) and pyridine (587.3 µL, 7.3 mmol) were added to the suspension which was stirred at room temperature overnight. The reaction was monitored by TLC (DCM: MeOH=10:1) until completion. 10 mL of saturated NaHCO$_3$ solution was added to the reaction mixture to stop the reaction, followed by extraction with DCM (5×50 mL). All organic layers were combined, dried over Na$_2$SO$_4$ and concentrated under vacuum. The residue was purified by flash column chromatography. 760 mg of A1 was obtained, which was characterized by $^1$H-NMR.

6. Coupling reaction of diazonium salt to form azo compound (A2): The nitrosylation of a primary aromatic amine with sodium nitrite and strong acid (hydrochloric acid) at 0° C. leads to a diazonium salt. The nitrosonium ion from sodium nitrite dissociation is attacked by the amino group on 4-aminobenzoic acid to form the diazonium salt. The diazonium salt is an intermediate for the preparation of the azo-compound through the azo coupling. The hydroxyl group on the aromatic compound is a strong para, ortho directing substituent: substitution occurs on the ortho position of phenol while the para position is blocked.

4-Aminobenzoic acid (895 mg, 6.53 mmol) was suspended in 25 mL 6 M HCl and cooled in an ice bath. NaNO$_2$ (1.13 g, 16.3 mmole) was added slowly and the suspension was stirred at 0° C. for 40 minutes. The trifluoro-N-(2-(hydroxy-phenyl)-ethyl)-acetamide (A1) (761 mg, 3.27 mmol) was dissolved in 32 mL 1:1 tetrahydrofuran (THF): saturated aq. NaHCO$_3$ solution and cooled in an ice bath. The above prepared diazonium salt solution was added portion-wise at 0° C. while stirring. The pH was monitored and kept basic by adding K$_2$CO$_3$ as needed. The reaction mixture was warmed to room temp. and stirred overnight. The mixture turned dark red. Afterwards, THF was removed in vacuo and the pH was adjusted to 2 using 2 M HCl. The reaction mixture was extracted with ethyl acetate (3×50 mL) and the extracts were combined and washed with 1 M HCl (30 mL) and brine (30 mL), then dried over MgSO4 and concentrated in vacuo. The residue was purified twice by flash column chromatography (DCM:MeOH=10:1) and compound A2 was obtained (360 mg, 0.9 mmol) as an orange solid. The product was characterized by 1H NMR and HRMS (C$_{17}$H$_{14}$F$_3$N$_3$O$_4$: 381.09 Da, found: 381.1 Da).

3. Addition of PEG4 linker to the amino group of the azo linker (A4): TFA-NH-Azo-COOH, A2, (38 mg, 99.73 µmol) was dissolved in DMF. To the dissolved solution N'N-dicyclohexylcarbodiimide, DCC (23.048 mg, 111.706 µmol), N-hydroxysuccinimide (17.22 mg, 149.6 µmol) and 4-dimethylaminopyridine, DMAP (12.184 mg, 99.73 µmol) were added. The reaction was monitored by thin layer chromatography. When the NHS ester analog, A3, conversion reached 50%, amine-PEG$_4$-COOH (17.61 mg, 66.486 µmol) that was pre-dissolved in DMF was added to the reaction mixture. The reaction was kept stirring at 35° C. overnight. Compound A4 was purified using reverse-phase HPLC (HFIP buffer and MeOH) and characterized by HRMS (C$_{28}$H$_{36}$F$_3$N$_4$O$_9$: 628.24 Da, found ESI$^+$: 629.24 Da).

Conjugation of PEG$_4$-Azo linker to propargyl linker on modified nucleotide (A5): To the DMF dissolved TFA-Azo-PEG$_4$-COOH, A4, (14.71 mg, 23.4 µmol), N, N'-disuccinimidyl carbonate, DSC (7.2 mg, 28 µmol) and 8 µL of DIPEA were added. The reaction was monitored by TLC. 3'-O-t-butyl-SS-dATP-propargyl-NH2 (1 mg, 1.47 µmol) dissolved in NaHCO$_3$/Na$_2$CO$_3$ buffer (pH 8.5) was added into the reaction mixture after half an hour of stirring at 35° C. The reaction was run overnight. The afforded product A5, 3'-O-t-butyl-SS-dATP-PEG$_4$-Azo-TFA, was purified through an anion exchange column on DEAE-Sephadex A-25 at room temperature using a gradient of TEAB (pH 8.0; 0.1-1.0 M), then followed by reverse-phase HPLC purification (HFIP buffer and MeOH). Compound A5 was characterized by MALDI TOF MS$^+$ (C$_{47}$H$_{63}$F$_3$N$_9$O$_{20}$P$_3$S2: 1288.28 Da, found 1288.23 Da).

Linking of Biotin to the amino group of the modified nucleotide (A7): The regeneration of the amino group on compound A5, 3'-O-t-butyl-SS-dATP-PEG$_4$-Azo-TFA (0.51 mg, 0.428 µmol), was performed by removing the trifluoroacetate group in 300 µL ammonium hydroxide. The reaction was stirred at 25° C. for 3 hours. The major peak at 1197.2 Da (calc'd: 1191.3) in the MALDI TOF MS spectrum reflected the successful deprotection of the amino group (A6). To the dissolved compound A6 (~0.51 mg, 0.428 µmol) in NaHCO$_3$/Na$_2$CO$_3$ buffer, sulfo-Biotin-NHS ester (1.898 mg, 4.28 µmol), which was pre-dissolved in DMF, was added. The reaction mixture was stirred overnight at 25° C. with exclusion of light and purified using first a C18 column followed by reverse-phase HPLC purification. MALDI-TOF MS confirmed the formation of compound A7 indicated by a peak at 1417.3 Da (calc'd: 1417.3 Da).

Example 3d: Single Base Extension for 3'-O-t-butyl-SS-dATP-PEG$_4$-Azo-Biotin and Cleavage of Azo linker for 3'-O-t-butyl-SS-dATP-PEG$_4$-Azo-Biotin extended primer (FIGS. 137A-137B)

Synthesized 3'-O-t-butyl-SS-dATP-PEG$_4$-Azo-Biotin was used to perform a single-base extension reaction. The primer E8AA-6084 (5'-TAGATGACCCTGCCTTGTCG-3' at 6084 Da), exon 8 template (see sequence above) and Therminator IX DNA polymerase (T9) were added along with the modified nucleotides. In the 3'-O-t-butyl-SS-dATP-PEG$_4$-Azo-Biotin (A7) incorporation reaction, the primer was extended to 7327.4 Da (expected, 7326.3 Da). No primer peak was detected using MALDI TOF MS after 38 cycles of reaction. The incorporation result suggests that Therminator IX DNA polymerase can recognize the synthesized azo-bearing nucleotide and incorporate it onto the primer with excellent efficiency.

As seen in FIG. 137A, the primer strand is extended with essentially 100% efficiency (no primer peak is visible) (reaction details are provided in detailed methods below). Moreover, the t-butyl-SS-methyl group is an effective blocker since, despite the presence of two T's in a row in the template, only a single base extension reaction takes place.

Single base extended primers (6084ExAA+3'-O-t-butyl-SS-dAMP-PEG$_4$-Azo-Biotin, 7327.4 Da) was treated with 25 mM sodium dithionite in 1×PBS buffer. After stirring at 37° C. for 10 min, the extended primer was confirmed to be cleaved by MALDI TOF MS. The azo cleaved product reflects a molecular weight of 6951.1 Da which agrees with the expected value of 6952.3 Da. As shown in FIG. 137B, the initial extended primer peak (7327.4 Da) was not observed in the spectrum which demonstrates that the azobenzene linker bearing nucleotides can be cleaved efficiently with Na$_2$S$_2$O$_4$ solution during one-color SBS.

Example 3e: Synthesis of 3'-O-t-Butyl-SS(DTM)-dGTP-SS-Cy5 and 3'-O-t-Butyl-SS(DTM)-dCTP-SS-Biotin 3'-O-t-Butyl-SS(DTM)-dNTP-SS-NH2 compounds were prepared and their attachment to either Sulfo-Cyanine5-NHS ester or Biotin-NHS ester is carried out exactly as in Examples 3a and 3c. MALDI-TOF MS traces to confirm synthesis of the correct molecules are presented in FIGS. 138-139.

Example 3f: Single-color Sequencing by Synthesis Using Orthogonal Set of Nucleotide Reversible Terminators, with All Combinations of Azo and SS Linkers and Biotin and Cy5 (FIGS. 140A-140C)

3'-O-DTM(SS)-dNTP-Cleavable Linker-Dyes (3'-O-DTM(SS)-dTTP-Azo-Cy5, 3'-O-DTM(SS)-dGTP-SS-Cy5), 3'-O-DTM(SS)-dNTP-Cleavable Linker-Anchors (3'-O-DTM(SS)-dATP-Azo-Biotin, 3'-O-DTM(SS)-dCTP-SS-Biotin), and Anchor Binding Molecule-Dye (Streptavidin-Cy5) were used to perform 1-color DNA SBS in accordance with the schematic found in FIGS. 140A-140C. Step 1, Addition of DNA polymerase and the four nucleotide analogues (3'-O-DTM(SS)-dTTP-Azo-Cy5, 3'-O-DTM(SS)-dGTP-SS-Cy5, 3'-O-DTM(SS)-dATP-Azo-Biotin, 3'-O-DTM(SS)-dCTP-SS-Biotin) to the immobilized primed DNA template enables the incorporation of the complementary nucleotide analogue to the growing DNA strand to terminate DNA synthesis. Step 2, Chase: addition of the DNA polymerase and four 3'-O-SS(DTM)-dNTPs (3'-O-DTM(SS)-dATP, 3'-O-DTM(SS)-dCTP, 3'-O-DTM(SS)-dTTP and 3'-O-DTM(SS)-dGTP) to the immobilized primed DNA template enables the incorporation of the complementary 3'-O-SS-nucleotide analogue to the subset of growing DNA strands that were not extended with any of the dye labeled dNTPs in step 1. The growing DNA strands are terminated with one of the four dye labeled nucleotide analogues (A, C, G, T) or the same one of the four nucleotide analogues (A, C, G, T) without dye. Step 3, after washing away the unincorporated dye labeled nucleotides, an imaging step is performed. A positive signal will indicate incorporation of either T or G. Step 4, labeling with streptavidin-Cy5 is carried out to attach Cy5 to A and C. Step 5, after washing away the unused labeling reagents, a second imaging step is performed. Gain of Cy5 signal indicates incorporation of A or C. Step 6, cleavage of Azo linker by adding sodium dithionite (Na$_2$S$_2$O$_4$) to the elongated DNA strands results in removal of Cy5 from incorporated A and T. Step 7, after washing away the cleaved dyes, a third round of imaging is performed. Loss of Cy5 signal indicates incorporation of T in the case of previous determination that either G or T were incorporated, and incorporation of A in the case where it was previously determining that either A or C were incorporated. Step 8, cleavage of SS linker by adding THP to the elongated DNA strands results in removal of any remaining dyes (on C and G) and also restores the 3'-OH group on any growing strands extended with a 3'-O-SS (DTM)-dNTP in the chase step. Step 9, after washing away the cleaved dyes, an optional final round of imaging is performed. The DNA products are ready for the next cycle of the DNA sequencing reaction. Structures of nucleotides used in this scheme are presented in FIG. 131. In the imaging cartoons at each step, black indicates a positive Cy5 signal and white a negative signal. Note that the encoding in the summary cartoon at the end indicates the template sequence, not the incorporated nucleotides.

Results for First Cycle of Single-Color Sequencing by Synthesis with Slide-Immobilized Templates (FIG. 142):

Each cycle consisted of the steps indicated in FIGS. 130 and 140A-140C, which utilized the nucleotide analogues and labeling molecules shown in FIG. 132, with the templates arranged as shown in FIG. 141. Results are shown here for the top four areas of FIG. 142.

First, extension is carried out with the four 3'-O-DTM (SS)-dNTPs bearing SS or Azo Linkers and Biotin or Cy5 using Therminator IX polymerase. The resulting image shown at the top left shows high signal intensity averages for the two areas at left (3,907 and 3,266 au) and background signals for the two areas at right (690 and 590 au). Since only the T and G dNTP analogues had Cy5, the left areas must display indicate incorporation of either T or G, and the right areas incorporation of either A or C. After labeling with Cy5-streptavidin, the images shown at lower left are obtained with all four areas now showing high signal intensities (3,931, 3,346, 2,306 and 2,357; note that signal intensities should be compared during the same imaging step to account for step-specific losses). Next, cleavage of the Azo linker with sodium dithionite is carried out resulting in the image at lower right. The middle two areas retain high average signal intensity (2,647 and 1,781 au), while the left and right areas now have background fluorescence intensity (581 and 1,285 au). Since only the A and T dNTP analogues had Azo linkers, this defines the incorporation in the four areas as T, G, C and A from left to right. Finally, cleavage of the SS linkers and removal of the blocking groups on any incorporated dNTP analogues is carried out in preparation for the second SBS cycle. The results obtained are exactly what would be expected, given the sequences of the four templates. The digital codes (1 for a positive signal and 0 for a background signal) associated with the first 3 imaging steps in each cycle are used to identify the incorporated nucleotide analogue. Thus 010 denotes A, 011 denotes C, 111 denotes G and 110 denotes T in this example.

Example 4: Polymer Tagged ddNTPs

Oligonucleotide polymers were conjugated to the 5-position of pyrimidines (C and U) and 7-position of purines (A and G). To synthesize these molecules, first, 5-proparglyamino-ddNTPs for C/U and 7-proparglyamino-ddNTPs for A/G were extended with amino caproic acid-N hydroxysuccinimide (NHS) ester to install an amino extended chain on the ddNTPs as described by Duthie et al (2002). The products were purified by reverse phase HPLC. In order to attach polymer tags using a click chemistry approach, based on a cycloaddition reaction between an alkyne and an azide, an azido group was introduced by reacting the extended ddNTPs with azidobutyric acid-NHS ester. The reaction mixture was stirred overnight at room temperature and purified by HPLC using 0.1 M triethylammonium acetate (TEAC) buffer (pH 7.5) and an acetonitrile gradient to provide azido extended ddNTPs. Each 5'-hexynyl-oligonucleotide tag (custom synthesized by TriLink, 500 nmol in 200 µl $H_2O$) was reacted with the corresponding ddNTP-$N_3$ nucleotide (750 nmol) followed by the addition of copper bromide (50 µl, 0.1 M solution in 3:1 DMSO/t-BuOH) and tris[(1-benzyl-1H-1,2,3-triazol-4-yl)methyl]amine (TBTA) (100 µl, 0.1 M solution in 3:1 DMSO/t-BuOH). The reaction mixture was stirred at 40° C. for 16 hr and purified by HPLC using 0.1 M TEAC buffer (pH 7.5) and an acetonitrile gradient and the final products were characterized by MALDI-TOF MS analysis.

Synthesis of Cleavable linker-Blocker-Dye-dNTPs and Cleavable linker-Blocker-ET Dyes: The synthesis of deoxynucleoside-5'-triphosphates with a Cleavable Linker-Blocker moiety-Dye attached to the 5-position of pyrimidines (C and U) and 7-position of 7-deazapurines (A and G) is shown in FIGS. 90-91. 5(7)-Iodo-2'-deoxynucleosides are reacted with a cleavable linker (Ju et al (2016) WO2016/154215 A1) in the presence of triphenylphosphine Pd(0), CuI and triethylamine in anhydrous DMF. The resulting nucleoside is triphosphorylated and hydrolyzed with $NH_4OH$ to remove the amino protective group. These amino-terminated cleavable linker attached dNTPs are further reacted with azidobutyric acid-NHS ester to provide $N_3$-terminated dNTPs and purified by HPLC.

The Blocker nucleotide(s) which has an alkynyl group at the 5'-end is synthesized on a DNA synthesizer using standard phosphoramidite chemistry (FIGS. 90-91). After dye attachment to the alkynyl terminated Blocker nucleotide(s), it is reacted with the azido-terminated dNTP described above. For FRET, an ET dye cassette with one or more donor or acceptor dyes, or anchor and donor dyes can be synthesized using standard phosphoramidite chemistry (Ju et al 1996) (FIG. 96).

Screening several DNA polymerases for incorporation of the polymer tagged ddNTPs: In search of a polymerase that can recognize and incorporate polymer tagged ddNTP analogues, five DNA polymerases (Therminator II, Therminator III, Klenow, Sequenase 2.0 and Thermo Sequenase) that are known to have the ability to incorporate modified ddNTPs were screened for SBE with self-primed looped templates and different ratios of the polymer tagged ddNTP relative to the templates. Sequences of these templates are as follows: 5'-CGCGGCGCGGTTCCGCGCCGCGAGCT-3' [SEQ ID 3] for T and 5'-CGCGGCGCGGTTCCGCGCCGCGGCTA-3' [SEQ ID 4] for C. The reactions were performed at 37° C. for 1 hour in a 20 µL volume containing 1 µM template, 4 units of Thermo Sequenase (Affymetrix) and 20 or 30 µM tagged ddNTPs. Reactions with 5 units of Klenow(exo-) (New England Biolabs), 13 units of Sequenase 2.0 (Affymetrix), or 4 units of Therminator II or III (NEB) having the same concentration of the template and the tagged ddNTPs were also investigated. The extension products were analyzed by 8M urea 15% polyacrylamide gel electrophoresis. Results are shown in FIG. 143, which indicates their especially high ability to be incorporated by Thermo Sequenase.

Kinetic Measurements of Nucleotide Activity Using a Fluorogenic Assay

Extension reactions were prepared with the primer, Thermo Sequenase, dCTP and various dilutions of ddCTP or tagged ddCTP. First, a series of SBE reactions were carried out with final ddCTP concentrations ranging from 0 to 10 µM at a concentration of dCTP of 10 µM and 0.3 pH of labeled primer. Under these conditions, the primer is extended by the incorporation of dCTP until it encounters ddCTP incorporation. Next, the same experiments were performed in the presence of the polymer tagged ddCTP at concentrations ranging from 0 to 5 µM with 5 µM dCTP and 0.3 µM labeled primer. Fluorescence intensity was measured on a SpectraMax3 Microplate Reader (Molecular Devices, LLC). The results are provided in FIG. 144, which demonstrates that Thermo Sequenase can incorporate a ddCTP analogue containing a very long modification on its base as efficiently as a regular ddCTP.

Example 5: Single-Color Fluorescent Sequencing by Synthesis (SBS) Using Hybrid Approach with Unlabeled NRTs and Fluorescent ddNTPs, One Anchor and Two Cleavable Linkers In this one-color SBS scheme, in the style of Scheme X described hereinabove, eight nucleotide analogues are required: the four 3'-O-azidomethyl NRTs and four ddNTP analogues, one with Dye attached to the base via Cleavable Linker 1, one with Dye attached to the base via Cleavable Linker 2, one with Anchor attached to the base via Cleavable Linker 1, and one with Anchor attached to the base via Cleavable Linker 2. The generalized structures of these nucleotides are presented in FIG. 145 (note their similarity to those in FIG. 129). The general design is displayed in FIG. 146 (again, note similarity to the scheme presented in FIG. 130), and consists of extension with the four NRTs, labeling with an anchor-binding molecule bearing the same Dye, cleavage of Cleavable Linker 2, and finally cleavage of Cleavable Linker 1 (which also restores the 3'-OH group). If the ddNTP analogue with Dye and Cleavable Linker 1 is incorporated, it will show fluorescence after the extension step and retain this fluorescence until the second cleavage step is completed. If the ddNTP analogue with Dye and Cleavable Linker 2 is incorporated, fluorescence will be seen after the extension step and will be lost after the first cleavage step. If the ddNTP analogue with Anchor and Cleavable Linker 1 is incorporated, fluorescence will not be seen until after the labeling step and will not be lost until after the second cleavage step. If the ddNTP analogue with Anchor and Cleavable Linker 2 is incorporated, fluorescence will not be seen until after the labeling step and will be lost after the first cleavage step.

With a digital readout in which 1 represents the appearance of significantly above background fluorescence and 0 represents only background fluorescence, consider the following three imaging steps are considered: after extension, after labeling, and after first cleavage. Thus, the first ddNTP analogue will display a pattern of 111, the second ddNTP analogue will display a pattern of 110, the third ddNTP analogue will display a pattern of 011, and the fourth ddNTP analogue will display a pattern of 010. These four unique codes will thus allow base-calling. Technically the imaging after the labeling step is not essential for base calling as it is only confirmatory, with the unique coding patterns 11, 10, 01 and 00 being obtained from just the imaging after extension and first cleavage steps. Imaging after the second cleavage is also not essential since all four nucleotides will display background fluorescence (0) at this point. As will be described, the azidomethyl dNTPs can be added (1) together with the labeled ddNTPs but at a much higher ratio; (2) after the labeled ddNTPs in a chase step even if they were included in the prior mixture of 8 nucleotide analogues; or (3) in an incubation step prior to the extension with labeled ddNTPs. The results for this third option are illustrated below.

In this example, in addition to the four 3'-O-azidomethyl dNTPs, the following four ddNTP analogues, with the structures illustrated in FIG. 147A, were synthesized and characterized: (1) ddTTP-5-Azo-Cy5; (2) ddGTP-7-SS-Cy5; (3) ddATP-7-Azo-Biotin; and (4) ddCTP-5-SS-Biotin. The labeling molecule was Streptavidin-Cy5. However, ddNTPs with dyes other than Cy5, anchors other than biotin (examples listed in Provisional Application) and cleavable groups other than SS and Azo (examples also listed in the Provisional Application) could be used with this approach.

Example 5a: Synthesis of an Azo-Benzene Based Linker (TFA-Azo-NHS Ester) for Use in Synthesizing NRTs (1) and (3) (FIG. 148)

Briefly, a series of condensation reactions beginning with tyramine and a TFA-protected aminohexanoic acid NHS ester, followed by attachment of 4-aminobenzoic acid and TFA-NHS, was carried out to form the Azo-benzene based linker. A detailed description of the synthesis is provided below.

To a solution of Tyramine (2 g, 14.6 mmol) in 8 mL anhydrous DMF was added TFA protected amino hexanoic acid-NHS ester (22.0 mmol) and diisopropyl ethylamine (30 mmol). The resulting mixture was stirred at room temperature overnight. The reaction was monitored by TLC (DCM:MeOH=10:1) for completion, diluted with water and extracted with DCM (3×50 mL). All organic layers were combined, dried over $Na_2SO_4$ and concentrated under vacuum. The residue was purified by flash column chromatography (silica gel: 5%-10% MeOH/DCM) to furnish the six carbon chain extended tyramine with TFA protection on amino group as an off-white solid (3.5 g).

4-Aminobenzoic acid (298 mg, 2.18 mmol) was suspended in 9 mL 6 M HCl and cooled in an ice bath. NaNO2 (0.38 g, 5.43 mmole) was added slowly and the suspension was stirred at 0° C. for 40 minutes, allowing for formation of diazonium salt. The TFA-C6-tyramine (377 mg, 1.09 nmol) was dissolved in 11 mL 1:1 tetrahydrofuran (THF): saturated aq. $NaHCO_3$ solution and cooled in an ice bath. The above prepared diazonium salt solution was added to TFA-C6-tyramine portion-wise at 0° C. while stirring. The pH was monitored and kept basic by adding $NaHCO_3$ as needed. The reaction mixture was warmed to room temp and stirred overnight. The mixture, which turned brownish red, was filtered to remove solids and washed with 1M HCl (3×25 ml). THF was removed in vacuo and the mixture was extracted with ethyl acetate (3×50 mL). The extracts were combined and washed with 1 M HCl (30 mL) and brine (30 mL), dried over MgSO4 and concentrated in vacuo. The residue was purified by flash column chromatography (DCM:MeOH=10:1) to provide TFA-Azo linker-Acid (188 mg) as an orange solid. The product was characterized by HRMS ($C_{23}H_{25}F_3N_4O_5$: 494.18 Da, found: 494.20 Da).

TFA-Azo linker-Acid (100 mg) was dissolved in DCM/Pyridine (3 ml, 2:1, v/v) and 5 eq. of TFA-NHS was added. After stirring for 2 hours at room temperature, the solvent was evaporated and diluted with 20 ml DCM and washed with water (2×20 ml). The organic layer was dried over anhydrous $Na_2SO_4$, concentrated under vacuum and purified on a silica gel column using 5% MeOH/DCM to yield the expected TFA-Azo linker-NHS ester.

Example 5b: Synthesis of ddUTP-5-Azo-Cy5 (FIG. 149)

Briefly, the linker from Example 3a is coupled to ddTTP-pentyl-propargyl-$NH_2$. After removal of the TFA group, the resulting compound is coupled to Sulfo-Cyanine5-NHS ester to produce the desired compound. A detailed description of the synthesis is provided below. A MALDI-TOF MS trace to confirm synthesis of the correct molecule is presented in FIG. 150.

To the solution of 1l-ddUTP (2 µmol) which was dissolved in $NaHCO_3/Na_2CO_3$ buffer (pH 8.8), 200 µl of Azo Linker NHS ester (10 mg in DMF) was added. The reaction mixture was stirred for 4 hours at r.t., then the reaction mixture was applied to a DEAE A-25 ion exchange column (2 ml). The column was eluded with a gradient of TEAC buffer (pH 8.0) from 0.1M to 1 M. The fractions containing Azo linker labeled ddUTP were collected and dried. To the resulting Azo linker labeled ddUTP, 0.8 ml of concentrated ammonium hydroxide was added and the solution stirred for 4 hours. The reaction mixture was then dried (speed vac), the resulting residue product, Amino-Azo linker labeled ddUTP, was re-dissolved in 400 µl of $NaHCO_3/Na_2CO_3$ buffer (pH 8.8) and Cy5 NHS (5 mg) in 400 µl of DMF was added. The mixture was stirred overnight at r.t., concentrated to a volume of 300 µl and applied to a silica gel column (2 ml), which was eluted with DCM/MeOH (4:1, v/v), then i-Propanol/Ammonia/Water (5:4:1, v/v). The fraction containing Cy5 labeled Azo-ddTTP was concentrated to dryness and subjected to a C18 reverse-phase HPLC purification using gradient elution: B (MeOH) 0-67% in 40 min in A (HFIP buffer). The product peak was collected, dried and characterized by MALDI TOF MS+ (calculated for ddUTP-5-Azo-Cy5: 1621.5 Da, found 1622.5 Da).

Example 5c: Synthesis of ddATP-7-Azo-Biotin (FIG. 151)

The synthesis begins with the linker in Example 5a and ddATP-pentyl-propargyl-NH2 and is carried out in an identical way to Example 5b except that in the last coupling step Biotin-NHS ester is used. A detailed description of the synthesis is provided below. A MALDI-TOF MS trace to confirm synthesis of the correct molecule is presented in FIG. 152.

To the solution of 11-ddATP (2 μmol) which was dissolved in $NaHCO_3/Na_2CO_3$ buffer (pH 8.8), 200 μl of Azo Linker NHS ester (10 mg in DMF) was added. The reaction mixture was stirred for 4 hours at r.t., then the reaction mixture was applied to a DEAE A-25 ion exchange column (2 ml). The column was eluted with a gradient of TEAC buffer (pH 8.0) from 0.1M to 1 M. The fractions containing Azo linker labeled ddATP was collected and dried. To the resulting Azo linker labeled ddATP, 0.8 ml of concentrated ammonium hydroxide was added and the solution stirred for 4 hours. The reaction mixture was then dried (speed vac), the resulting residue product Amino-Azo linker labeled ddATP was re-dissolved in 400 μl of NaHCO3/Na2CO3 buffer (pH 8.8) and Biotin NHS (5 mg) in 400 μl of DMF was added. The mixture was stirred overnight at r.t., concentrated to a volume of 300 μl and applied to a silica gel column (2 ml), which was eluted with DCM/MeOH (4:1, v/v), then i-Propanol/Ammonia/Water (5:4:1, v/v). The fraction containing Biotin labeled Azo-ddATP was concentrated to dryness and subjected to a C18 reverse-phase HPLC purification using gradient elution: B (MeOH) 0-67% in 40 min in A (HFIP buffer). The product peak was collected, dried and characterized by MALDI TOF MS+(calculated for ddATP-7-Azo-Biotin: 1246.4 Da, found 1242.1 Da).

Example 5d: Synthesis of SS-Based Linker (TFA-SS-NHS Ester) for Use in Synthesizing ddNTPs (2) and (4) (FIG. 153)

Propargyl-SS-NH(TFA) (330 mg, 1.096 mmol), synthesized using established procedures (see Scheme E2S5, top two rows), was dissolved in 3 ml DMF. CuBr (0.1 eq., 15.63 mg, 0.01 mmol) and TBTA (116.31 mg, 0.02 mmol) were dissolved in 1 ml DMSO-t-ButOH (3/1, v/v), 200 μl of CuBr-TBTA solution was added to the SS linker solution, then azido-propanoic acid (315 mg, 2.4 mmol) dissolved in 0.5 ml of DMF was added into the reaction mixture. The resulting mixture was stirred overnight at r.t. The solvent was evaporated under vacuum, and ethyl acetate (3 ml) was added to re-suspend the reaction mixture, which was subjected to silica gel column purification using gradient elution with ethyl acetate/hexane (50/50), ethyl acetate then ethyl acetate/MeOH (50/1). The expected product fraction was collected and dried, yielding (TFA)NH-SS-NHS linker-Acid. MS measurement for C13H19F3N404S2 (M/Z 416.08); found 417 (APCI-MS, M+1) and 416 (APCI-MS, M−1). The resulting TFA-SS linker-Acid (95 mg) was dissolved in DCM/Pyridine (1:4, v/v) and 5 eq. of TFA-NHS was added. After stirring for 2 hours at room temperature, the solvent and pyridine was evaporated and to the residue 20 ml ethyl acetate was added. The organic phase was washed with water (4×10 ml) and then dried over anhydrous Na2SO4. Removal of ethyl acetate under vacuum yields the expected (TFA)NH-SS-linker-NHS ester.

Example 5e: Synthesis of ddGTP-7-SS-Cy5 (FIG. 154)

Briefly, the linker from Example 5d is coupled to ddGTP-pentyl-propargyl NH2. After removal of the TFA group, the resulting compound is coupled to Sulfo-Cyanine5-NHS ester to produce the desired compound. A detailed description of the synthesis is provided below. A MALDI-TOF MS trace to confirm synthesis of the correct molecule is presented in FIG. 155.

To the solution of 11-ddGTP (2 μmol) which was dissolved in NaHCO3/Na2CO3 buffer (pH 8.8), 200 μl of (TFA)NH-SS-linker-NHS (10 mg in DMF) was added. The reaction mixture was stirred for 4 hours at r.t., then applied to a DEAE A-25 ion exchange column (2 ml). The column was eluted with a gradient of TEAC buffer (pH 8.0) from 0.1M to 1 M. The fractions containing (TFA)NH-SS linker labeled ddGTP were collected and dried. To the resulting (TFA)NH-SS linker labeled ddGTP, 0.8 ml of concentrated ammonium hydroxide was added and the solution stirred for 2 hours. The reaction mixture was then dried (speed vac). The resulting residue product Amino-SS linker labeled ddGTP was re-dissolved in 300 μl of NaHCO3/Na2CO3 buffer (pH 8.8) and Cy5-NHS (5 mg) in 300 μl of DMF was added. The mixture was stirred overnight at r.t., then concentrated to a volume of 300 μl and applied to a DEAE A-25 ion exchange column (2 ml), which was eluted with a gradient of TEAC buffer (pH 8.0) from 0.1M to 1 M. The fraction containing Cy5 labeled SS-ddGTP was concentrated to dryness and subjected to a C18 reverse-phase HPLC purification using gradient elution: B (MeOH) 0-67% in 40 min in A (HFIP buffer). The product peak was collected, dried and characterized by MALDI TOF MS+ (calculated for ddGTP-7-SS-Cy5: 1595.4 Da, found 1596.6 Da).

Example 5f: Synthesis of ddCTP-5-SS-Biotin (FIG. 156)

The synthesis begins with the linker in Example 2d and, ddCTP-pentyl-propargyl-$NH_2$ and is carried out in an identical way to Example 5e except that in the last coupling step Biotin-NHS ester is used. A detailed description of the synthesis is provided below. A MALDI-TOF MS trace to confirm synthesis of the correct molecule is presented in FIG. 157.

To the solution of 11-ddCTP (2 umol) which was dissolved in NaHCO3/Na2CO3 buffer (pH 8.8), 200 μl of (TFA)NH-SS-linker-NHS (10 mg in DMF) was added. The reaction mixture was stirred for 4 hours at r.t., then the reaction mixture was applied to a DEAE A-25 ion exchange column (2 ml). The column was eluted with a gradient of TEAC buffer (pH 8.0) from 0.1M to 1 M. The fractions containing (TFA)NH-SS-linker labeled ddCTP were collected and dried. To the resulting (TFA)NH-SS linker labeled ddCTP, 0.8 ml of concentrated ammonium hydroxide was added and the solution stirred for 2 hours. The reaction mixture was then dried (speed vac). The resulting residue product Amino-SS linker labeled ddCTP was re-dissolved in 300 μl of NaHCO3/Na2CO3 buffer (pH 8.8) and Biotin-NHS (6 mg) in 300 μl of DMF was added. The mixture was stirred overnight at r.t., then concentrated to a volume of 300 μl and applied to a DEAE A-25 ion exchange column (2 ml), which was eluted with a gradient of TEAC buffer (pH 8.0) from 0.1M to 1 M. The fraction containing Biotin labeled SS-ddCTP was concentrated to dryness and subjected to a C18 reverse-phase HPLC purification using gradient elution: B (MeOH) 0-67% in 40 min in A (HFIP buffer). The product peak was collected, dried and characterized by MALDI TOF MS+(calculated for ddCTP-5-SS-Biotin: 1145.2 Da, found 1149.9 Da).

Example 5g: Highly Efficient Incorporation and Cleavage of ddTTP-5-Azo-Cy5 (FIG. 158)

As seen in the left panel of FIG. 158, the primer strand is extended with essentially 100% efficiency (no primer peak is visible) (the details are provided below). Treatment with 25 mM sodium dithionite at 45° C. for 1 minute leads to complete cleavage of the linker (complete loss of extended primer peak) as shown in the right panel of FIG. 158.

Example 5h: Highly Efficient Incorporation and Cleavage of ddATP-7-Azo-Biotin (FIG. 159)

As seen in the left panel of FIG. 159, the primer strand is extended with essentially 100% efficiency (no primer peak is visible) (the details are provided below). Treatment with 25 mM sodium dithionite at 45° C. for 1 minute leads to complete cleavage of the linker (complete loss of extended primer peak) as shown in the right panel of FIG. 159.

Example 5I: Highly Efficient Incorporation and Cleavage of ddGTP-7-SS-Cy5 (FIG. 160)

As seen in the left panel of FIG. 160, the primer strand is extended with essentially 100% efficiency (no primer peak is visible) (the details are provided below). Treatment with THP (details also provided below) leads to complete cleavage of the linker (complete loss of extended primer peak) as shown in the right panel of FIG. 160.

Example 5j: Highly Efficient Incorporation and Cleavage of ddCTP-5 SS-Biotin (FIG. 161)

As seen in the left panel of FIG. 161, the primer strand is extended with essentially 100% efficiency (no primer peak is visible) (the details are provided below). Treatment with THP (details also provided below) leads to complete cleavage of the linker (complete loss of extended primer peak) as shown in the right panel of FIG. 161.

Methods for Examples 5g-5j

The template used for ddATP-7-Azo-Biotin, ddCTP-5-SS-Biotin, and ddTTP-5-Azo-Cy5 was 5'-GAAGGA-GACACGCGGCCAGAGAGGGTCCTGTCCGTGTTTGTG CGTGGAGTTCGACAAGGCAGGGTCATCTAATGGT-GATGAGTCCTATCCTTTTCTCTTCGTTCTCCGT-3' [SEQ ID 5]. The primers used for these ddATP, ddCTP and ddTTP analogues were 5'-TAGATGACCCTGCCTTGTCG-3' [SEQ ID 6], 5'-TCTCTGGCCGCGTGTCT-3' [SEQ ID 7] and 5'-GATAGGACTCATCACCA-3' [SEQ ID 8], respectively. The bold A, G and T letters in the template strand are the complementary positions for these three single base extended primers.

The template used for ddGTP-7-SS-Cy5 was 5'-TACC-CGGAGGCCAAGTACGGCGGGTACGTCCTTGA-CAATGTGTACATCAACATCACCTACCACCATGT CAGTCTCGGTTGGATCCTCTATTGTGTCCGGG-3' [SEQ ID 9] and the primer used for this ddGTP analogue was 5'-GTTGATGTACACATTGTCAA-3' [SEQ ID 10]. The bold C in the template strand is the complementary position for this single base extended primer.

Extension reactions consisted of 3 µl template (60 µM), 1 µl primer (100 µM), 2 µl of one of the above ddNTP analogues (100 µM), 2 µl 10× Thermo Pol Buffer, 1 µl Terminator IX DNA polymerase (10 unit/µl) and 11 µl water. Extension was performed in a thermal cycler and consisted of 1 min denaturation at 65° C., followed by 38 cycles of 30 sec at 65° C., 30 sec at 45° C. and 30 sec at 65° C., with a final 3 min extension at 72° C., and storage at 4° C. Desalting was carried out using Oligo Clean & Concentrator (Zymo Research) according to the manufacturer's instructions prior to checking results of polymerase reaction by MALDI-TOF-MS.

Sodium dithionite cleavage reactions were performed using a buffer consisting of 6 µl 10×PBS pH 7.4, 6 µl freshly prepared 250 mM Na2S2O4, 48 µl water at 37° C. for 10 min.

THP cleavage reactions were performed using a buffer consisting of 6 µl THP (50 mM), 6 µl NaCl (200 mM), 12 µl sodium borate (0.1M, pH9), 36 µl water at 65° C. for 10 min.

Example 5k: Preparation of Template-Containing Slides (FIG. 141)

A description of the attachment of template loop primers to the slide is provided below.

The 5'-amino-modified self-priming template DNA (see FIG. 141 for sequences of the looped primer templates and their arrangement on the slide) was dissolved in 50 mM sodium phosphate buffer, pH 9.0 at a concentration of 30 µM and spotted on NHS ester-derivatized CodeLink slides (Surmodics Inc., MN) using a SpotArray 72 microarray printing robot (PerkinElmer, MA). After the completion of spotting, the slides were incubated overnight in a humid chamber containing a solution of saturated sodium chloride at 37° C. to immobilize the DNA. Following immobilization, unreacted NHS ester groups were quenched by incubating the slides in a solution of 50 mM 3-amino-1-propanol in 100 mM tris-HCl buffer, pH 9.0 for 2 hours at ambient temperature. Finally, the slides were briefly rinsed in boiling water, air-dried under compressed air and stored desiccated in a dark container until further use.

Example 5l: Successful Fluorescent SBS Using Hybrid Approach with Unlabeled NRTs and Fluorescent ddNTP Analogues Bearing Either a Dye or Anchor and One of Two Possible Cleavable Linkers Between the Base and Dye or Anchor (FIGS. 162A-162C and FIGS. 163A-163F)

FIGS. 162A-162C contain a schematic showing the use of ddNTP-Cleavable Linker-Dyes (ddGTP-7-SS-Cy5, ddTTP-5-Azo-Cy5), ddNTP-Cleavable Linker-Anchors (ddCTP-5-SS-Biotin, ddATP-7-Azo-Biotin), 3'-O-azidomethyl dNTPs (3'-O-azidomethyl-dATP, 3'-O-azidomethyl-dCTP, 3'-O-azidomethyl-dGTP, 3'-O-azidomethyl-dTTP), and Anchor Binding Molecule-Dye (Streptavidin-Cy5) to perform 1-color DNA SBS. Step 1, Addition of Therminator IX DNA polymerase and the four reversible terminators (3'-O-azidomethyl-dATP, 3'-O-azidomethyl-dCTP, 3'-O-azidomethyl-dGTP, 3'-O-azidomethyl-dTTP) to the immobilized primed DNA template enables the incorporation of the complementary nucleotide analogue to the majority of growing DNA strands (>90%) to terminate DNA synthesis. Step 2, addition of Thermo Sequenase and ddNTP analogues (ddGTP-7-SS-Cy5, ddTTP-5-Azo-Cy5, ddCTP-5-SS-Biotin, ddATP-7-Azo-Biotin) to extend most of the remaining immobilized primed DNA templates. After this step, the growing DNA strands are terminated with one of the four dye or anchor labeled dideoxynucleotide analogues (A, C, G, T) or the same one of the four 3'-blocked reversible terminator nucleotide analogues (A, C, G, T) without dye. Step 3, after washing away the unincorporated nucleotides, an imaging step is performed. A positive signal will indicate incorporation of either ddT or ddG. Step 4, labeling with streptavidin-Cy5 is carried out to attach Cy5 to ddA and ddC. Step 5, after washing away the unused labeling reagents, a second round of imaging is performed. Gain of Cy5 signal indicates incorporation of ddA or ddC. Step 6, cleavage of Azo linker by adding sodium dithionite ($Na_2S_2O_4$) to the elongated DNA strands results in removal of Cy5 from incorporated ddA and ddT. Step 7, after washing away the cleaved dyes, a third round of imaging is performed. Loss of Cy5 signal indicates incorporation of ddT in the case of previous determination that either ddG or ddT were incorporated, and incorporation of ddA in the case where it was previously determined that either ddA or ddC were incorporated. Step 8, cleavage of SS linker by adding THP to the elongated DNA strands results in removal of any remaining dyes (on ddC and ddG) and also restores the 3'-OH group on any growing strands extended with a 3'-O-azidomethyl-dNTPs in the first step. After washing away the cleaved dyes, an optional final round of imaging is performed. The DNA products are ready for the next cycle of the DNA sequencing reaction. Structures of nucleotides used in this scheme are presented in FIGS. 147A-147B. In FIGS. 162A-162C at each step, black indicates a positive Cy5 signal and white a negative signal. Note that the encoding in the summary cartoon at the end indicates the template sequence, not the incorporated nucleotides.

The following solution (solution A) was prepared for the first extension: 5 µl 100 µM 3'-O-N3-dATP, 5 µl 100 µM 3'-O-N3-dCTP, 3 µl 100 µM 3'-O-N3-dGTP, 5 µl 100 µM 3'-O-N3-dTTP, and 82 µl water. For the actual extension 35 µl Solution A, 6 µl 1 unit/µl Therminator IX, 6 µl 10× ThermoPol Buffer (200 mM Tris-HCl, 100 mM (NH4)2SO4, 100 mM KCl, 20 mM MgSO4, 1% Triton-X-100, pH 8.8) and 13 µl water was prepared and the 60 µl solution was placed within a chamber covering all eight spotted areas of the slide for 5 minutes at 65° C. Thus, the approximate final concentrations of the 3'-azidomethyl dNTPs were ~2.5 µM for the A, C and T analogues and ~1.5 µM for the G analogue.

After the incubation, the slides were washed by dipping in a solution of 1×PBS pH 7.4, 0.1% Tween 20 for 5 min at 37° C. and rinsed thoroughly with water. After drying, slides were scanned for Cy5 fluorescence (633 nm laser and emission window centering around 670 nm) and the intensity averaged over each spotted area, where each area had hundreds of spots of the same template, as described in FIG. 141.

The following solution (solution B) was prepared for the second extension: 2 µl 2 µM ddATP-7-Azo-Biotin, 2 µl 2 µM ddCTP-5-SS-Biotin, 5 µl 20 µM ddGTP-5-SS-Cy5, and 1 µl 2 µM ddTTP-5-Azo-Cy5. For the actual extension, 5 µl Solution B, 1 µl 4 unit/µl Thermo Sequenase, 6 µl 10× Buffer (260 mM Tris-HCl, pH 9.5, 65 mM MgCl2), and 48 µl water was prepared and 60 µl of this solution was added to the DNA on the slide for 5 min at 65° C. as described for the first extension. The final concentrations for the four ddNTP analogues were ~30 nM for ddATP-7-Azo-Biotin and ddCTP-5-SS-Biotin, ~80 nM for ddGTP-5-SS-Cy5 and ~15 nM for ddTTP-5-Azo-Cy5. Thus, the ratios of the azidomethyl dNTPs in the first extension and the ddNTP analogues in the second extension were ~80× for A and C, ~20× for G and ~150× for T.

After the incubation, the slides were washed, rinsed, dried and scanned exactly as above.

For labeling, the slides were incubated at 37° C. for 10 min with a 60 µl solution consisting of 5 µl of 2 µM streptavidin-Cy5, 6 µl of 10×PBS, pH 7.4, and 49 µl of water. The slides were washed, rinsed, dried and scanned as above.

The first cleavage was carried out on the slide using 60 µl of a solution consisting of 6 µl 250 mM Na2S2O4, 6 µl 10×PBS pH 7.4, and 48 µl water for 5 min at 45° C. After the incubation, the slides were washed, rinsed, dried and scanned exactly as above.

The second cleavage was carried out on the slide using 60 µl of a solution consisting of 6 µl 50 mM THP, 6 µl 200 mM NaCl, 12 µl 100 mM Sodium Borate (pH 9), and 36 µl water for 5 min at 65° C. After the incubation, the slides were washed, rinsed, dried and scanned exactly as above.

Figure 163A:
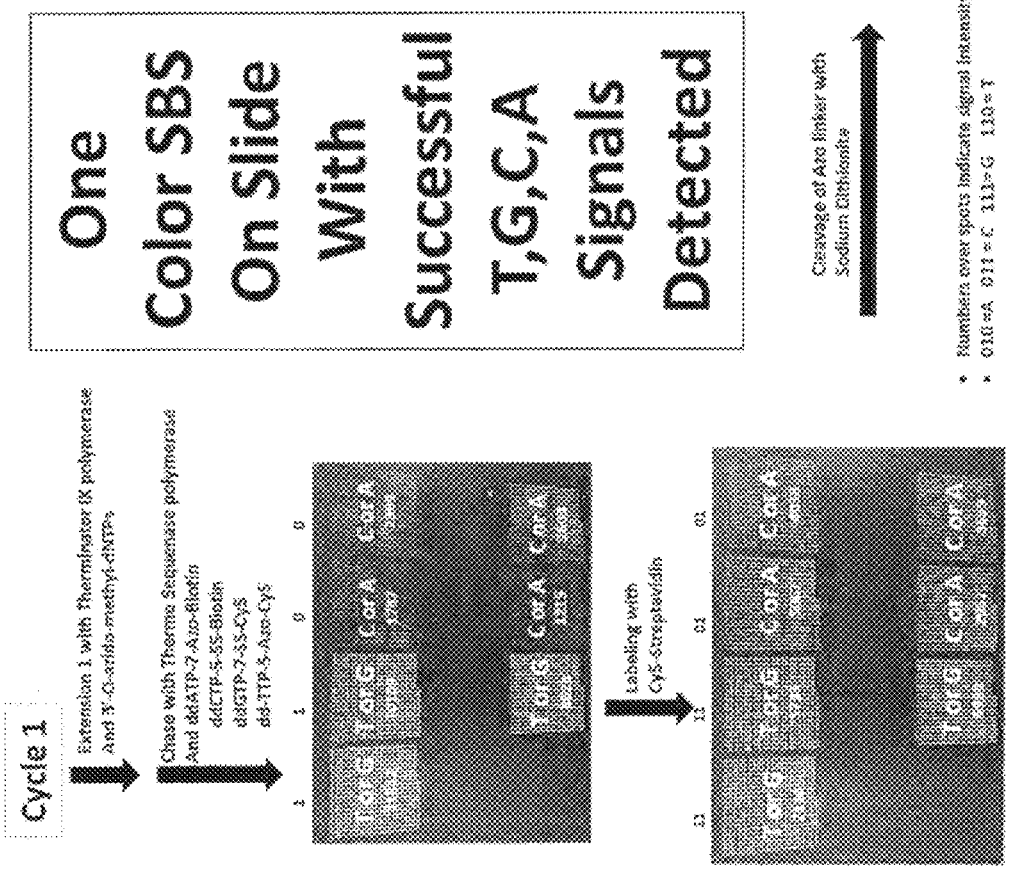
Figure 163B:
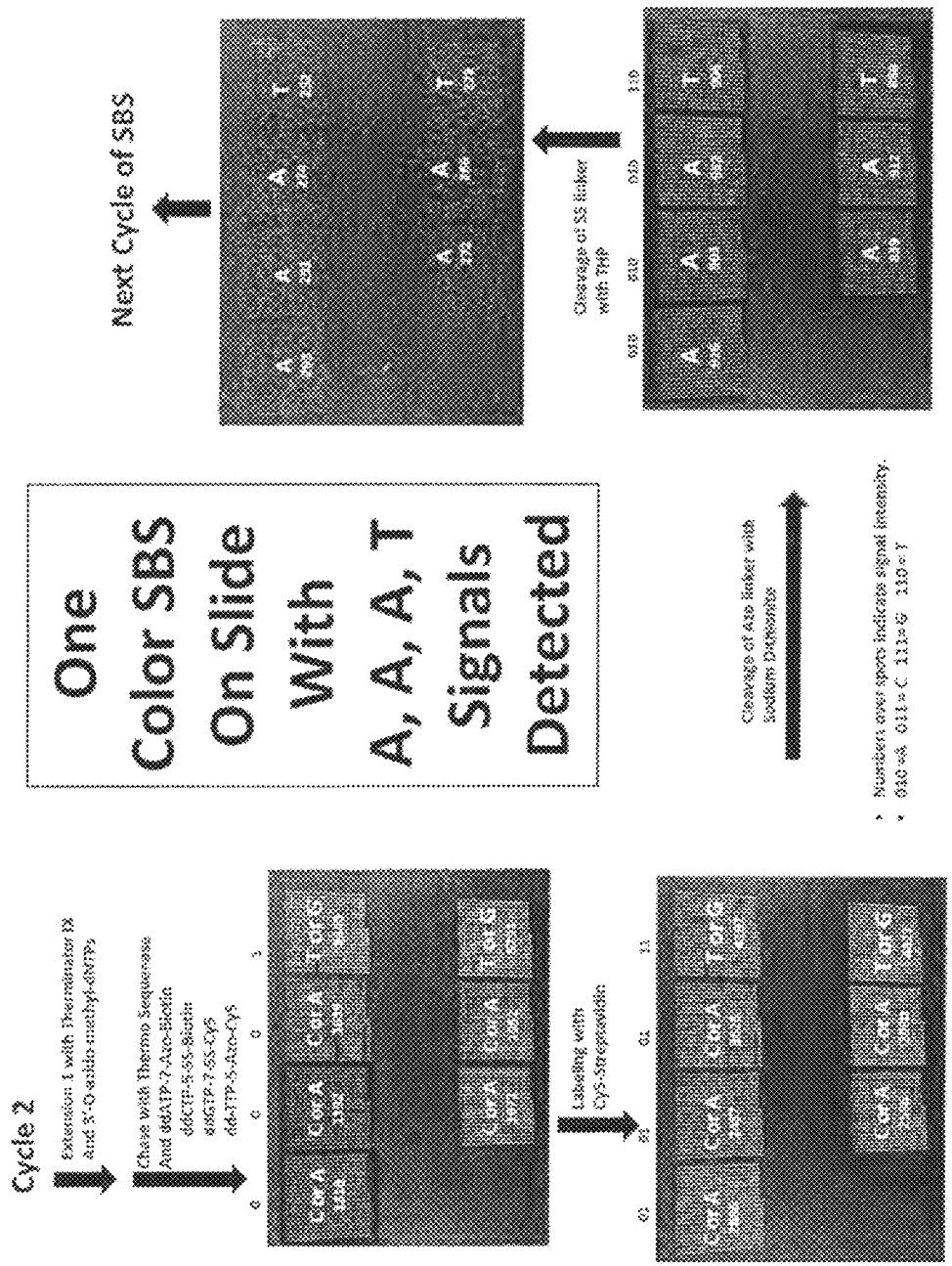
Figure 163C:
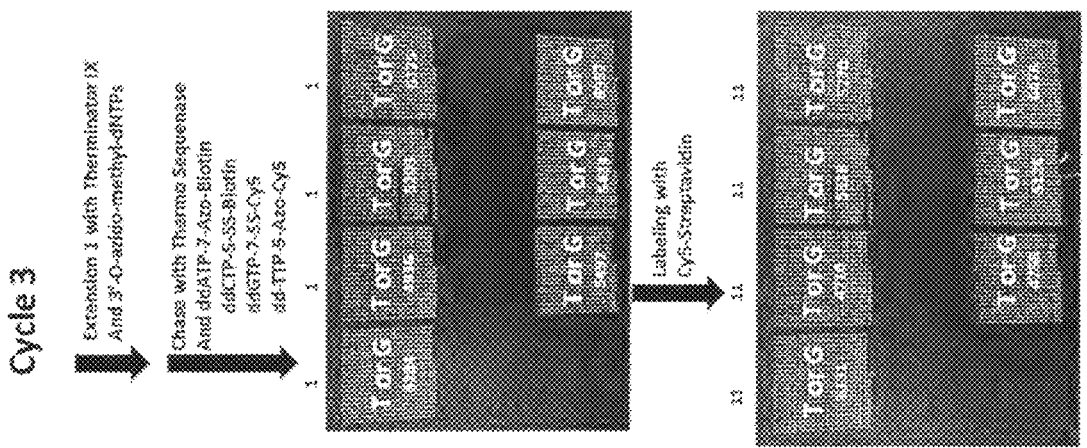
Figure 163B:
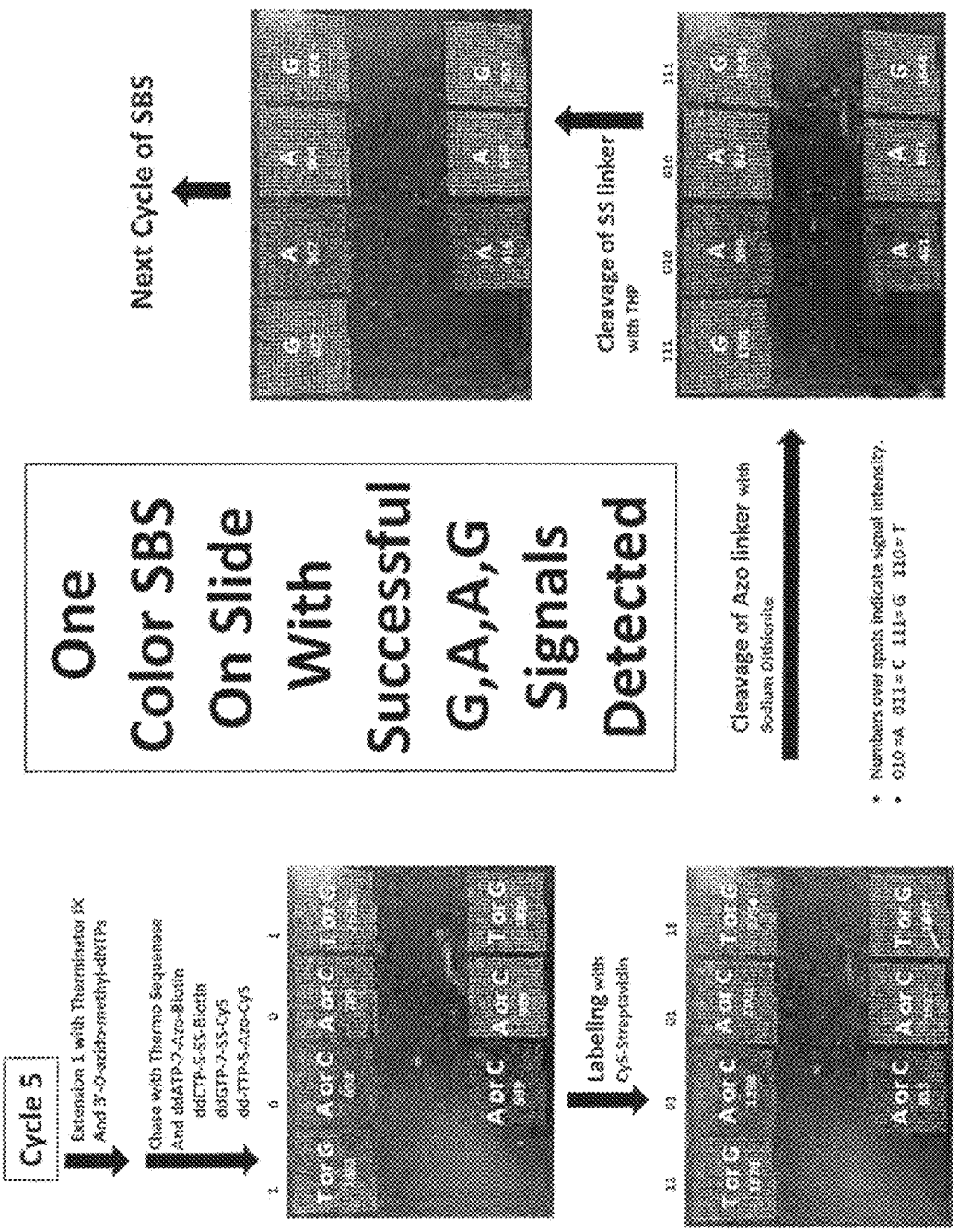
Figure 163F:
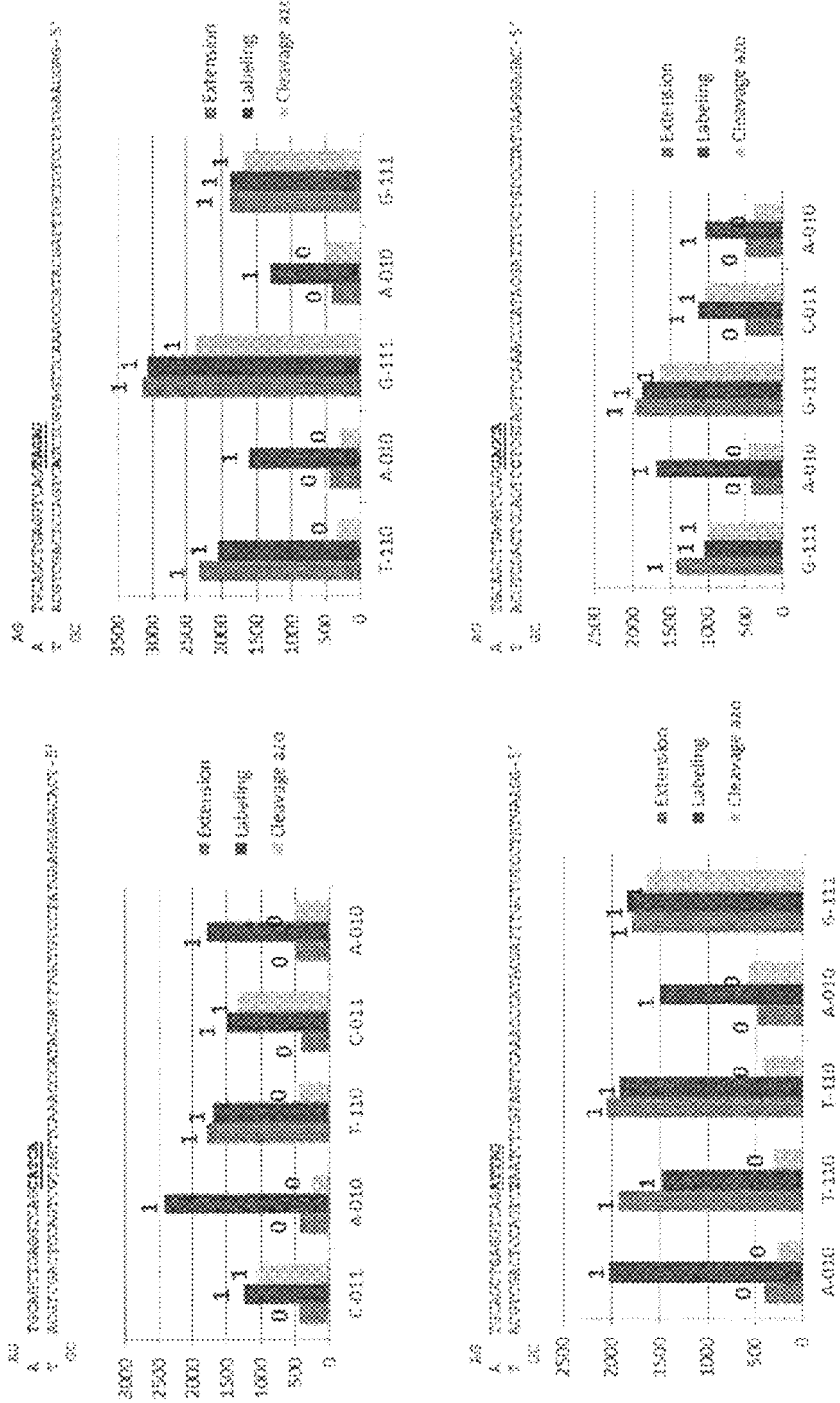

Results for First Five Cycles of Single-color Sequencing by Synthesis with Slide-Immobilized Templates. The first cycle results are shown in FIG. 163A with subsequent cycles in FIGS. 163B-163E. The results for all five cycles are summarized in the bar graphs presented in FIG. 163F. Taking as an example cycle 1 (FIG. 163A), and focusing on the upper four areas, extension is carried out first with the four 3'-O-azidomethyl dNTPs using Therminator IX polymerase, and then with the four ddNTP analogues using Thermo Sequenase. The resulting image shown at the top left shows high signal intensity averages for the two areas at left (11,812 and 10,109 au) and background signals for the two areas at right (1,787 and 2,399 au). Since only the T and G ddNTP analogues had Cy5, the left areas must display indicate incorporation of either T or G, and the right areas incorporation of either A or C. After labeling with Cy5-streptavidin, the images shown at lower left are obtained with all four areas now showing high signal intensities (7,114, 5,733, 5,062 and 4,038; note that signal intensities should be compared during the same imaging step to account for step-specific losses). Next, cleavage of the Azo linker with sodium dithionite is carried out resulting in the image at lower right. Only the middle two areas retain high average signal intensity (4,160 and 4,260 au), while the left and right areas now have background fluorescence intensity (570 and 947 au). Since only the A and T ddNTP analogues had Azo linkers, this defines the incorporation in the four areas as T, G, C and A from left to right. Finally, cleavage of the SS linkers and removal of the blocking groups on any incorporated 3'-O-azidomethyl dNTPs results in background fluorescence in all four areas (304, 379, 286 and 261 au). Similar analysis indicates incorporation of A, A, A and T in the four upper areas (from left to right) for Cycle 2 (FIG. 163B), G, G, T and T for Cycle 3 (FIG. 163C), A, C, C and A for Cycle 4 (FIG. 163D), and G, A, A and G for Cycle 5 (FIG. 163E). These results are exactly what would be expected, given the sequences of the four templates. In FIG. 163F, the same data is graphed. This clarifies the distinction between positive and background signals, as well as use of digital codes (1 for positive, 0 for background) in the first 3 imaging steps in each cycle for calling incorporation of A (010), C (011), G (111) and T (110). Please note that in FIGS. 163A-163V, the encoding refers to the incorporated nucleotide, which is complementary to the template encoding.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

REFERENCES

Bowers, J., Mitchell, J., Beer, E., Buzby, P. R., Causey, M., Efcavitch, J. W., Jarosz, M., Krzymanska-Olejnik, E., Kung, L., Lipson, D., Lowman, G. M., Marappan, S., McInerney, P., Platt, A., Roy, A., Siddiqi, S. M., Steinmann, K., Thompson, J. F. (2009) Virtual terminator nucleotides for next-generation DNA sequencing. *Nature Meth* 6:593-595.

Braslavsky I, Hebert B, Kartalov E, Quake S R (2003) Sequence information can be obtained from single DNA molecules. *Proc Natl Acad Sci USA* 100:3960-3964.

Duthie R S, Kalve I M, Samols S B, Hamilton S, Livshin I, Khot M, Nampali S, Kumar S, Fuller C W (2002) Novel cyanine dye-labeled dideoxynucleoside triphosphates for DNA sequencing. *Bioconj Chem* 13:699-706.

Fuller C, Kumar S, et al (2016) Real-time single molecule electronic DNA sequencing by synthesis using tagged-nucleotides on Genia chip. *Proc Natl Acad Sci USA* 113:5233-5238.

Guo J, Xu N, Li Z, Zhang S, Wu J, Ki, D H, Marma M S, Meng Q, Cao H, Li X, Shi S, Yu L, Kalachikov S, Russo J J, Turro N J, Ju J (2008) Four-color DNA sequencing with 3'-O-modified nucleotide reversible terminators and chemically cleavable fluorescent dideoxynucleotides. *Proc Natl Acad Sci USA*. 105: 914-950.

Hobbs F W Jr, Trainor G L (1992) U.S. Pat. No. 5,151,507 A. Alkynylamino-nucleotides.

Hung S-C, Ju J, Mathies R A, Glazer A N (1996) Cyanine dyes with high absorption cross section as donor chromophores in energy transfer primers. *Anal Biochem* 243: 15-27.

Ju J (2007) DNA sequencing by nanopore using modified nucleotides. U.S. Pat. No. 8,889,348 B2, US 20090298072 A1.

Ju J, Chen X, Li X, Li Z, Hsieh M-K, Chien M, Shi S, Ren J, Guo C, Kumar S, Russo J J, Tao C, Jockusch S, Kalachikov S (2017) WO 2017/205336 A1. Nucleotide derivatives and methods of use thereof.

Ju J, Cho Y, Kumar S, Kalachikov S, Tao C, Chien M, Russo J J (2016) WO 2016/154215 A1. Polymer tagged nucleotides for single molecule electronic SNP assay.

Ju J, Glazer A N, Mathies R A (1996) Cassette labeling for facile construction of energy transfer fluorescent primers. *Nucleic Acids Res* 24:1144-1148.

Ju J, Kim D H, Guo J, Meng Q, Li Z, Cao H (2016) US 2016/0024574 A1. DNA sequencing with non-fluorescent nucleotide reversible terminators and cleavable label modified nucleotide terminators.

Ju J, Kumar S, Li Z, Tao C, Chien M, Russo J J, Kalachikov S, Shepard K, Rosenstein J K (2013) DNA sequencing by synthesis using modified nucleotides and nanopore detection. EP 2652153 A2 (WO 2012083249 A2)

Ju J, Li X, Chen X, Li Z, Kumar S, Shi S, Guo C, Ren J, Hsieh M-K, Chien M, Tao C, Erturk E, Kalachikov S, Russo J J (2017) WO 2017/058953 A1. Design and synthesis of novel disulfide linker based nucleotides as reversible terminators for DNA sequencing by synthesis.

Ju J, Wu J, Li Z (2017) U.S. Pat. No. 9,624,539. DNA sequencing by synthesis using Raman and Infrared spectroscopy detection.

Kumar S, Sood A (2006) *Labeled Nucleoside Polyphosphates*. U.S. Pat. No. 7,041,812

Kumar S, Tao C, Chien M, Hellner B, Balijepalli A, Robertson J W F, Li Z, Russo J J, Reiner J E, Kasianowicz J, Ju J (2012) PEG-Labeled Nucleotides and Nanopore Detection for Single Molecule DNA Sequencing by Synthesis. *Scientific Reports* 2, 684.

Mitra R D, Shendure J, Olejnik J, Edyta Krzymanska O, Church G M (2003) Fluorescent in situ sequencing on polymerase colonies. *Anal Biochem* 320:55-65.

Seo, T S, Bai X, Kim D H, Meng Q, Shi S, Ruparel H, Li Z, Turro N J, Ju J (2005) Four-color DNA sequencing by synthesis on a chip using photocleavable fluorescent nucleotides. *Proc Natl Acad Sci USA* 102:5926-5931.

Turcatti G, Romieu A, Fedurco M, Tairi A-P (2008) A new class of reversible fluorescent nucleotides: synthesis and optimization as reversible terminators for DNA sequencing by synthesis. *Nucleic Acids Res* 36:e25.

Yang Y Y, Grammel M, Raghavan A S, Charron G, Hang H C (2010) Comparative analysis of cleavable azobenzene-based affinity tags for biorthogonal chemical proteomics. *Chem Biol* 17:1212-1222.

What is claimed is:

1. A method of sequencing nucleic acid comprising:
   a) providing at least one nucleic acid template hybridized to a primer;
   b) extending the primer hybridized to said nucleic acid template with a polymerase, and a set of nucleotide analogues selected from the group consisting of:
      i) a set of fluorescently labeled nucleotide analogues, wherein said fluorescently labeled nucleotide analogues have a fluorescent label linked to the base via a cleavable linker and a blocking group on the 3'-hydroxyl position, wherein different fluorescently labeled nucleotide analogues in the set may have different fluorescent labels and different cleavable linkers;
      ii) a set of anchor labeled nucleotide analogues, wherein said anchor labeled nucleotide analogues have an anchor attached to the base via a cleavable linker and a blocking group on the 3'-hydroxyl position, wherein different anchor labeled nucleotide analogues in the set may have different anchors and different cleavable linkers; and
      iii) a set comprising a combination of both fluorescently and anchor labeled nucleotide analogues, wherein said fluorescently or anchor labeled nucleotide analogues have the fluorescent or anchor label linked to the base via a cleavable linker and a blocking group on the 3'-hydroxyl position, wherein different nucleotide analogues in the set may have different fluorescent labels, anchors, and/or cleavable linkers;
   c) extending any unextended primer with another set of nucleotide analogues having a blocking group on the 3'-hydroxyl position without any base modifications, and if the set of nucleotide analogues in step b) has one or more fluorescently labeled nucleotide analogues, identifying one or more fluorescence signals due to incorporation of one or more fluorescently labeled nucleotide analogues;
   d) if the set of nucleotide analogues in step b) comprises anchor labeled nucleotide analogues:
      (i) labeling the anchor labeled nucleotide analogues with one or more corresponding fluorescently or quantum dot labeled anchor binding molecules;
      (ii) identifying newly generated fluorescence signals to thereby partially or completely identify the incorporated nucleotide analogues due to the labeling carried out in step d) (i); and
      (iii) if not all of the anchor labeled nucleotide analogues in step a) are labeled in step d) (i), repeating steps d) (i) and d) (ii);
   e) cleaving one or more of the fluorescent labels from one or more of the fluorescently labeled nucleotide analogues in step b) or one or more of the fluorescently or quantum dot labeled anchor binding molecules in step d) (i) with a specific cleavable agent that cleaves one type of the cleavable linkers, wherein the specific cleavable agent does not cleave the blocking group on the 3'-hydroxyl position of the nucleotide analogues;
   f) identifying loss of fluorescence signals due to the cleavage carried out in step e) to partially or completely identify the incorporated nucleotide analogues;
   g) if not all of the fluorescent labels from fluorescently labeled nucleotide analogues in step b) or the fluorescently or quantum dot labeled anchor binding molecules from step d) (i) are cleaved, repeating steps e) and f) with a different cleavable agent;
   h) determining the specific nucleotide analogue incorporated by comparing the results obtained in steps c, d) (ii) and f);
   i) cleaving any remaining fluorescent labels or anchors from the extended primer, at the same time cleaving the blocking group on the 3'-hydroxyl position of the incorporated nucleotide analogue to restore a 3'-hydroxyl group; and
   j) iteratively carrying out steps a) to i) to obtain the sequence of the nucleic acid template, thereby sequencing the nucleic acid;
wherein the set of nucleotide analogues in step b)ii) comprises four nucleotide analogues, wherein the first nucleotide analogue has a first type of anchor moiety attached to the base via a first type of cleavable linker, the second nucleotide analogue has a second type of anchor moiety attached to the base via the first type of cleavable linker, the third nucleotide analogue has the second type of anchor moiety attached to the base via a second type of cleavable linker, and the fourth nucleotide analogue has the first type of anchor moiety attached to the base via the second type of cleavable linker.

2. The method of claim 1, wherein the fluorescently or quantum dot labeled anchor binding molecules comprise streptavidin, tetrazine, azido or TCO.

3. The method of claim 1, wherein the first and/or second type of anchor moiety of the anchor labeled nucleotide analogues further comprises anchor clusters.

4. The method of claim 1, wherein
(a) the first and second type of anchor moieties comprise biotin, TCO, DBCO or tetrazine;
(b) the first and second type of cleavable linkers comprise an SS (DTM), an azo, an SS-azo, an allyl, a 2-nitrobenzyl, an azidomethyl, or azidomethyl derivative;
(c) the specific cleaving agents in step e) comprises THP, sodium dithionite, Pd(0); or UV light; and/or
(d) the fluorescently or quantum dot labeled anchor binding molecules are labeled with a fluorescent organic dye or a fluorescent transfer dye, wherein the fluorescent organic dye is selected from a group consisting of fluorescein, rhodamine, cyanine, ATTO or Dyomic dyes, wherein the fluorescent transfer dye consists of a donor dye and a acceptor dye, wherein the donor dye is fluorescein, CyA or Cy3 and the acceptor dye is Rhodamine 110, R6G, TAMRA, ROX, Cy5, ATTO 647N or Alexa 647.

5. The method of claim 4, wherein
(a) the first and second type of anchor moieties are biotin and TCO;
(b) the first and second type of cleavable linkers are SS (DTM) and an azo;
(c) the specific cleaving agents in step e) are THP and sodium dithionite; and/or
(d) two quantum dot labeled anchor binding molecules are used in step d) (i); wherein one quantum dot labeled anchor binding molecule is labeled with streptavidin and another is labeled with tetrazine.

6. The method of claim 5, wherein the set of nucleotide analogues in step b) comprises

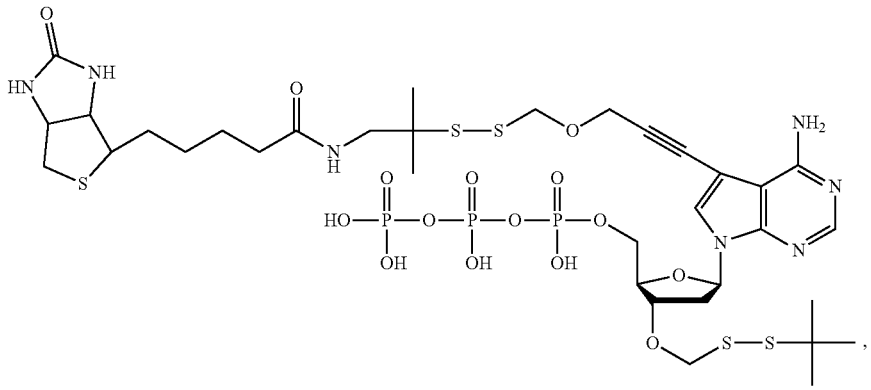

3'-O-DTM(SS)-dATP-7-SS-Biotin

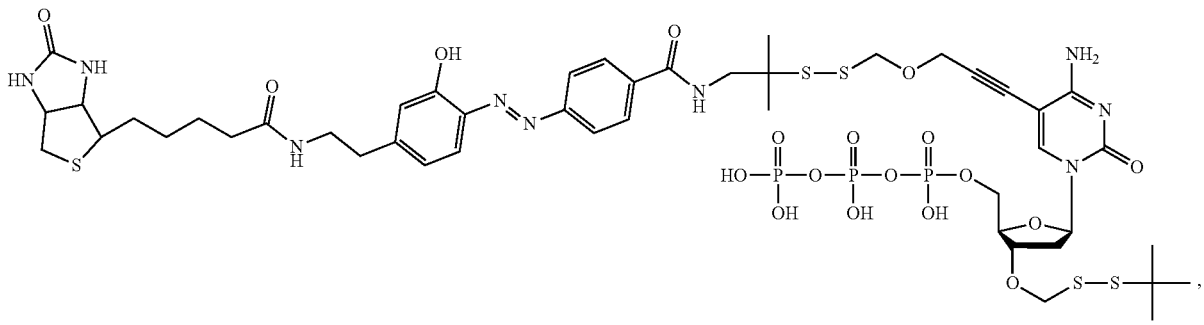

3'-O-DTM(SS)-dCTP-5-Azo-Biotin

-continued

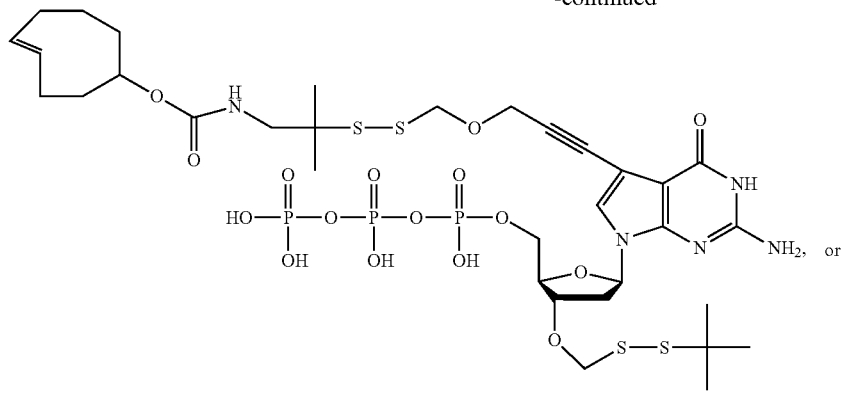

3′-O-DTM(SS)-dGTP-7-SS-TCO

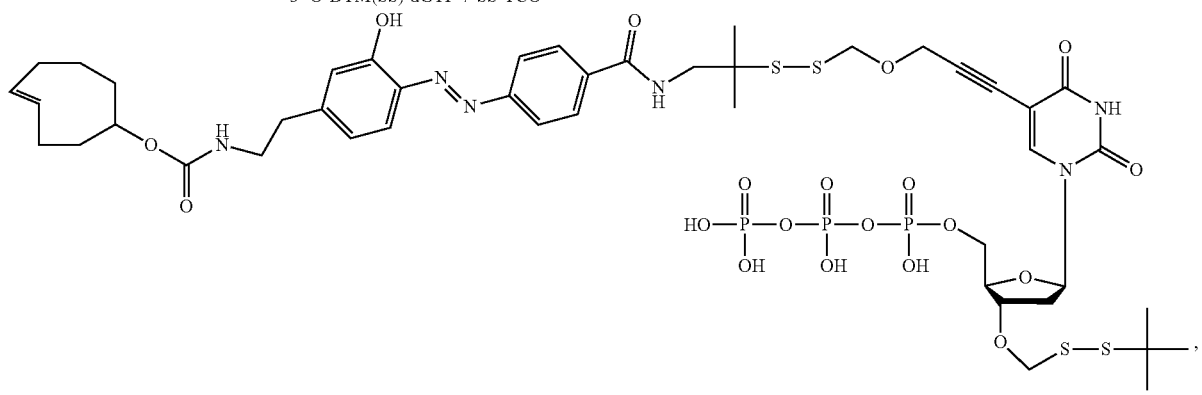

3′-O-DTM(SS)-dTTP-5-Azo-TCO and the quantum dot labeled anchor binding molecules are

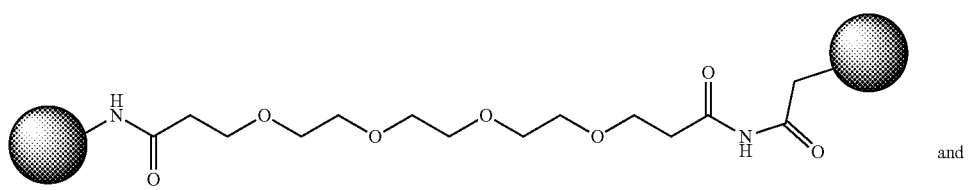

Streptavidin-PEG Quantum Dot 1 (Qdot 525)

and

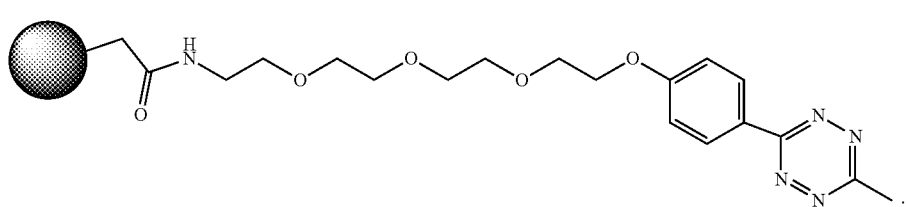

Tetrazine-PEG Quantum Dot 2 (Qdot 605)

7. The method of claim 1, wherein:
a) the first and second type of anchor moieties further comprise a first and second type of anchor clusters, wherein the first and second type of anchor clusters comprise biotin clusters, TCO clusters, DBCO clusters or tetrazine clusters.

8. The method of claim 7, wherein:
a) the first and second type of anchor clusters are biotin clusters and TCO clusters;

b) the first and second type of cleavable linker are an SS (DTM) and an azo;

c) the specific cleaving agents in step e) are THP and sodium dithionite; and/or d) two fluorescently labeled anchor binding molecules are used in step d) (i); wherein one fluorescently labeled anchor binding molecule is labeled with Rox and another is labeled with Alexa488.

9. The method of claim 8, wherein the set of nucleotide analogues in step b) comprises
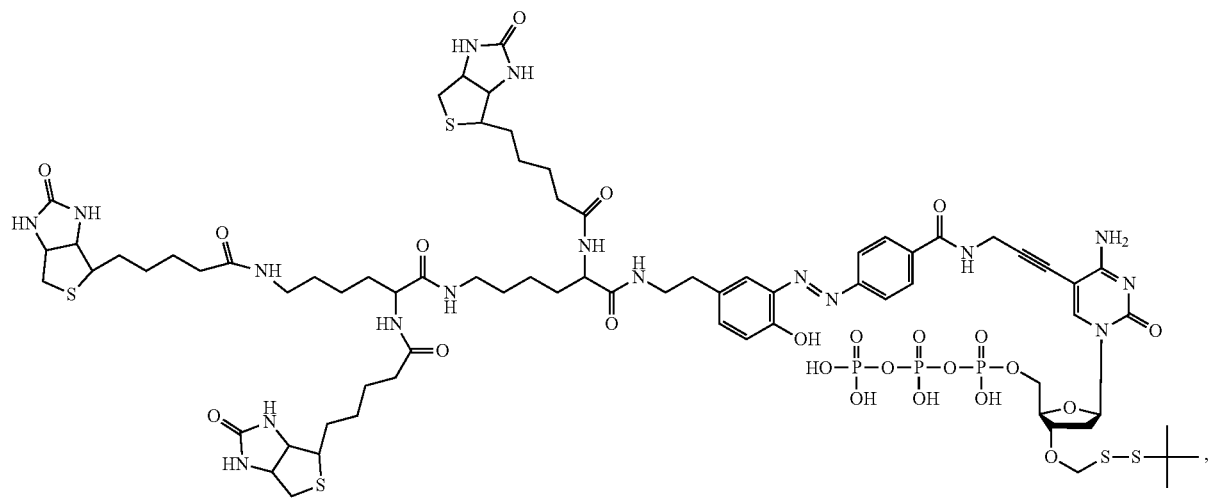
3′-O-DTM(SS)-dCTP-5-Azo-Biotin Cluster
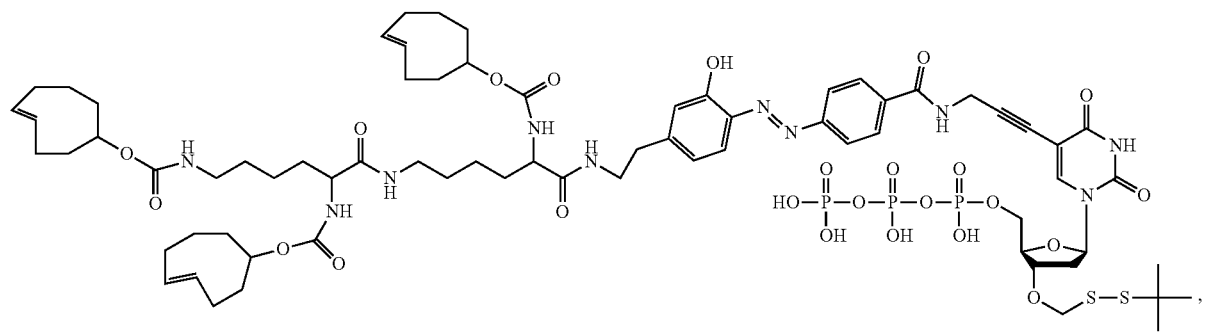
3′-O-DTM(SS)-dTTP-5-Azo-TCO Cluster
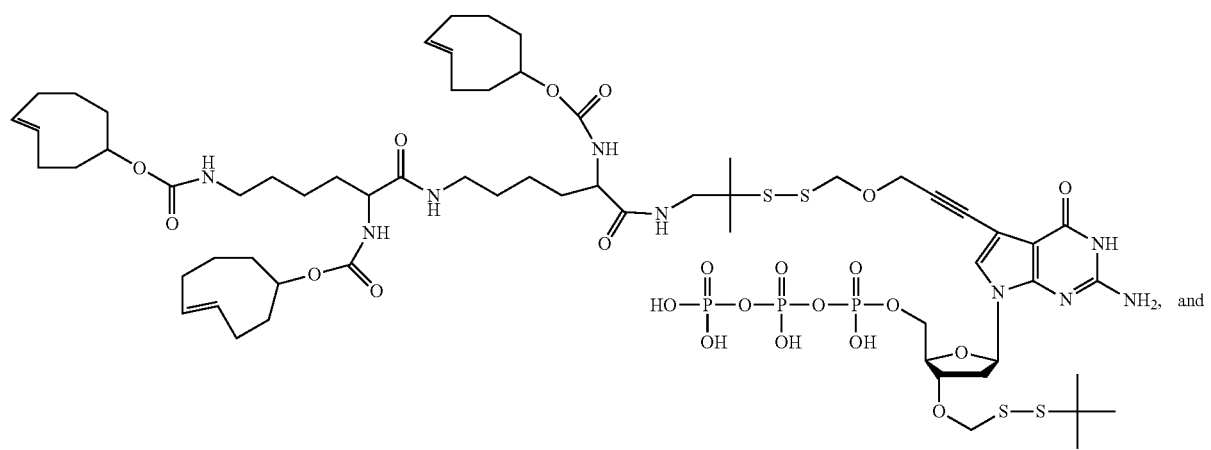
3′-O-DTM(SS)-dGTP-7-SS-TCO Cluster -continued
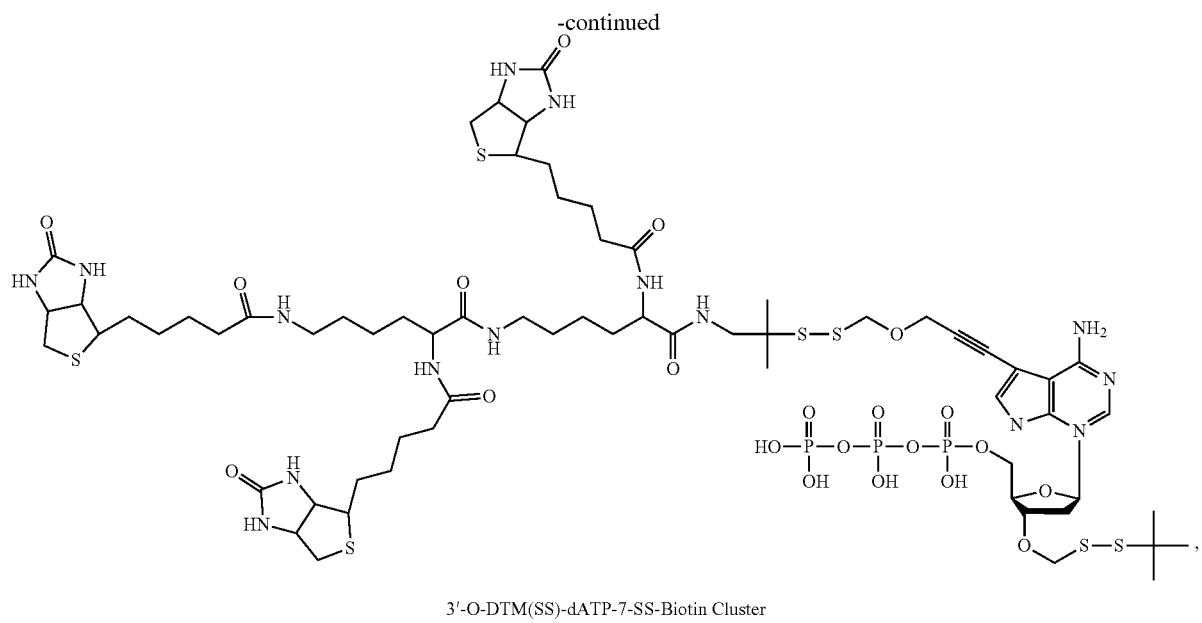
3′-O-DTM(SS)-dATP-7-SS-Biotin Cluster
and the fluorescently labeled anchor binding molecules are
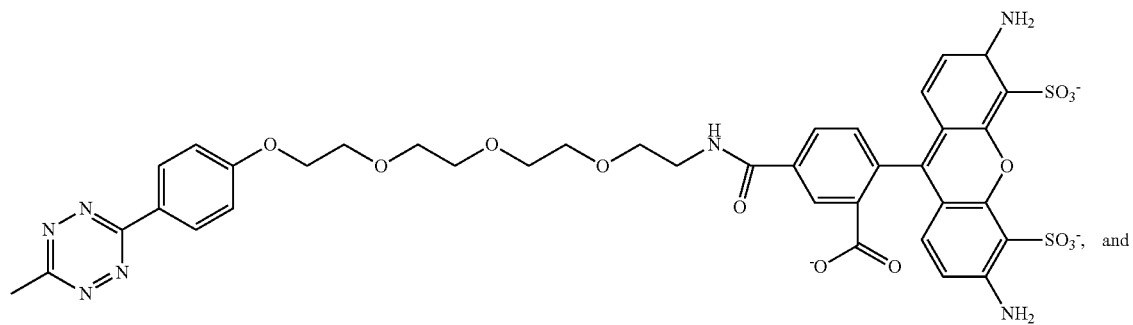
Alexa488 Labeled Tetrazine
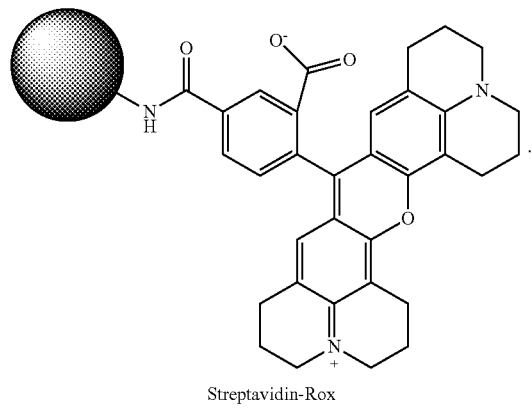
Streptavidin-Rox 10. A method of sequencing nucleic acid comprising:
a) providing at least one nucleic acid template hybridized to a primer;
b) extending the primer hybridized to said nucleic acid template with a polymerase, and a set of nucleotide analogues selected from the group consisting of:
  i) a set of fluorescently labeled nucleotide analogues, wherein said fluorescently labeled nucleotide analogues have a fluorescent label linked to the base via a cleavable linker and a blocking group on the 3'-hydroxyl position, wherein different fluorescently labeled nucleotide analogues in the set may have different fluorescent labels and different cleavable linkers;
  ii) a set of anchor labeled nucleotide analogues, wherein said anchor labeled nucleotide analogues have an anchor attached to the base via a cleavable linker and a blocking group on the 3'-hydroxyl position, wherein different anchor labeled nucleotide analogues in the set may have different anchors and different cleavable linkers; and
  iii) a set comprising a combination of both fluorescently and anchor labeled nucleotide analogues, wherein said fluorescently or anchor labeled nucleotide analogues have the fluorescent or anchor label linked to the base via a cleavable linker and a blocking group on the 3'-hydroxyl position, wherein different nucleotide analogues in the set may have different fluorescent labels, anchors, and/or cleavable linkers;
c) extending any unextended primer with another set of nucleotide analogues having a blocking group on the 3'-hydroxyl position without any base modifications, and if the set of nucleotide analogues in step b) has one or more fluorescently labeled nucleotide analogues, identifying one or more fluorescence signals due to incorporation of one or more fluorescently labeled nucleotide analogues;
d) if the set of nucleotide analogues in step b) comprises anchor labeled nucleotide analogues:
  (i) labeling the anchor labeled nucleotide analogues with one or more corresponding fluorescently or quantum dot labeled anchor binding molecules;
  (ii) identifying newly generated fluorescence signals to thereby partially or completely identify the incorporated nucleotide analogues due to the labeling carried out in step d) (i); and
  (iii) if not all of the anchor labeled nucleotide analogues in step a) are labeled in step d) (i), repeating steps d) (i) and d) (ii);
e) cleaving one or more of the fluorescent labels from one or more of the fluorescently labeled nucleotide analogues in step b) or one or more of the fluorescently or quantum dot labeled anchor binding molecules in step d) (i) with a specific cleavable agent that cleaves one type of the cleavable linkers, wherein the specific cleavable agent does not cleave the blocking group on the 3'-hydroxyl position of the nucleotide analogues;
f) identifying loss of fluorescence signals due to the cleavage carried out in step e) to partially or completely identify the incorporated nucleotide analogues;
g) if not all of the fluorescent labels from fluorescently labeled nucleotide analogues in step b) or the fluorescently or quantum dot labeled anchor binding molecules from step d) (i) are cleaved, repeating steps e) and f) with a different cleavable agent;
h) determining the specific nucleotide analogue incorporated by comparing the results obtained in steps c, d) (ii) and f);
i) cleaving any remaining anchors from the extended primer, at the same time cleaving the blocking group on the 3'-hydroxyl position of the incorporated nucleotide analogue to restore a 3'-hydroxyl group; and
j) iteratively carrying out steps a) to i) to obtain the sequence of the nucleic acid template,
thereby sequencing the nucleic acid; wherein the set of nucleotide analogues in step b) ii) comprises four nucleotide analogues, wherein the first nucleotide analogue has a fluorescent dye attached to the base via a first type of cleavable linker, the second nucleotide analogue has the same fluorescent dye as first nucleotide analogue attached to the base via a second type of cleavable linker, the third nucleotide analogue has an anchor moiety attached to the base via the first type of cleavable linker, and the fourth nucleotide analogue has same anchor moiety as the third nucleotide analogue attached to the base via the second type of cleavable linker.

11. The method of claim 10, wherein
(a) the fluorescent dye comprises fluorescein, rhodamine, cyanine, ATTO or Dyomics dye;
(b) the anchor moiety comprises biotin, TCO, DBCO or tetrazine;
(c) the first and second type of cleavable linkers comprise an SS (DTM), an azo, an SS-azo, an allyl, a 2-nitrobenzyl, an azidomethyl, or azidomethyl derivative;
(d) the specific cleaving agents in step e) comprises THP, sodium dithionite, Pd(0); or UV light; and/or
(e) the fluorescently or quantum dot labeled anchor binding molecules are labeled with a fluorescent organic dye or a fluorescent transfer dye, wherein the fluorescent organic dye is selected from a group consisting of fluorescein, rhodamine, cyanine, ATTO or Dyomic dyes, wherein the fluorescent transfer dye consists of a donor dye and a acceptor dye, wherein the donor dye is fluorescein, CyA or Cy3 and the acceptor dye is Rhodamine 110, R6G, TAMRA, ROX, Cy5, ATTO 647N or Alexa 647.

12. The method of claim 11, wherein
(a) the fluorescent dye is ATTO;
(b) the anchor moiety is biotin;
(c) the first and second types of cleavable linker are an SS (DTM) linker and an azo linker;
(d) the specific cleaving agents in step e) are THP and sodium dithionite; and/or
(e) one fluorescently labeled anchor binding molecule is used in step d) (i); wherein the fluorescent labeled anchor binding molecule is labeled with ATTO.

13. The method of claim 12, wherein the set of nucleotide analogues in step b) comprises
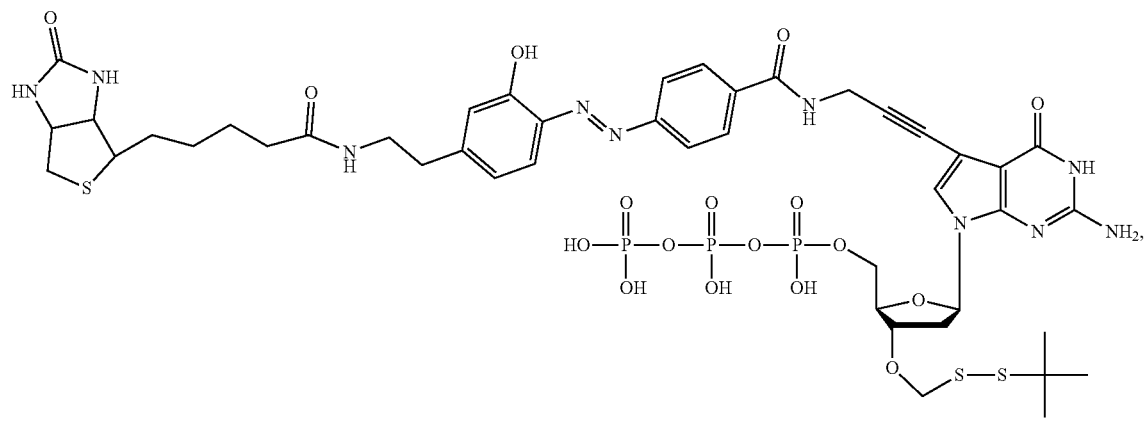
3′-O-DTM(SS)-dGTP-7-Azo-Biotin
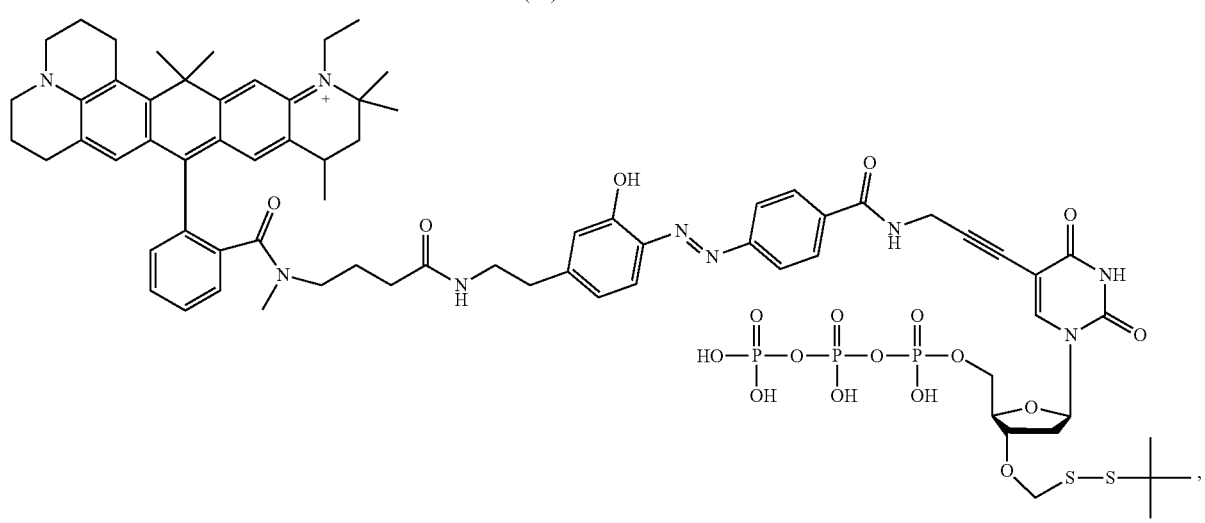
3′-O-DTM(SS)-dTTP-5-Azo-ATTO647N
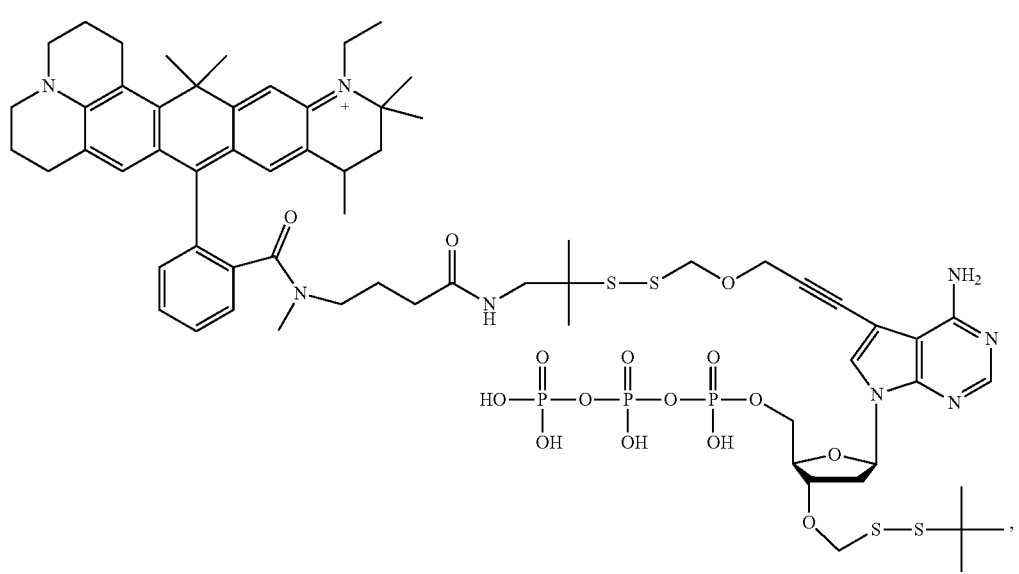
3′-O-DTM(SS)-dATP-7-SS-ATTO647N -continued

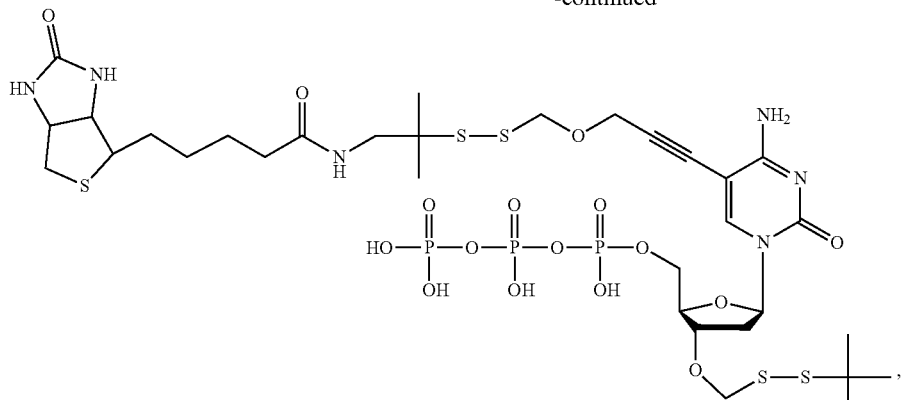

3′-O-DTM(SS)-dCTP-5-SS-Biotin and the fluorescently labeled anchor binding molecule is

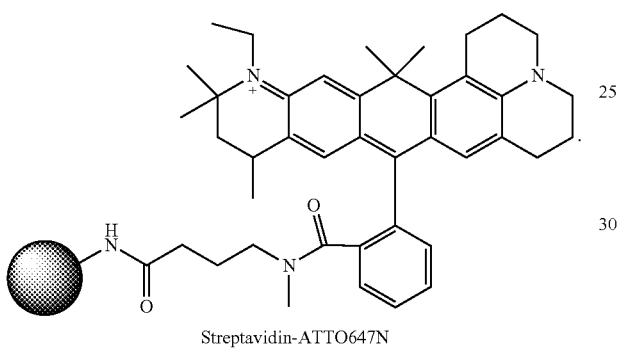

Streptavidin-ATTO647N

14. The method of claim 11, wherein
(a) the fluorescent dye is Cy5;
(b) the anchor moiety is biotin;
(c) the first and second types of cleavable linker are an SS (DTM) linker and an azo linker;
(d) the specific cleaving agents in step e) are THP and sodium dithionite; and/or
(e) one fluorescent labeled anchor binding molecule is used in step d) (i); wherein the fluorescent labeled anchor binding molecule is labeled with Cy5.

15. The method of claim 14, wherein the set of nucleotide analogues in step b) comprises

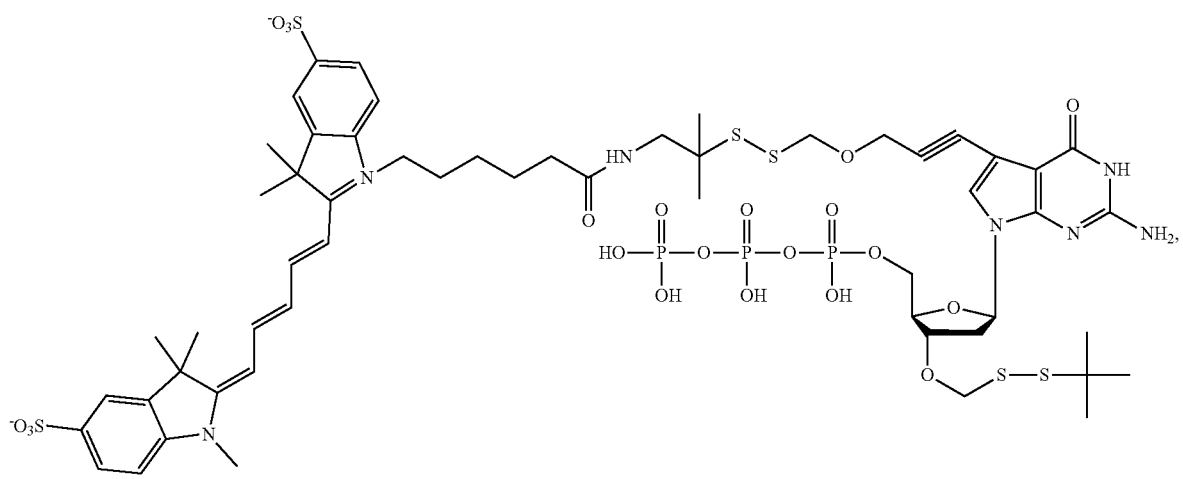

3′-O-t-butyl-SS-dGTP-SS-Cy5

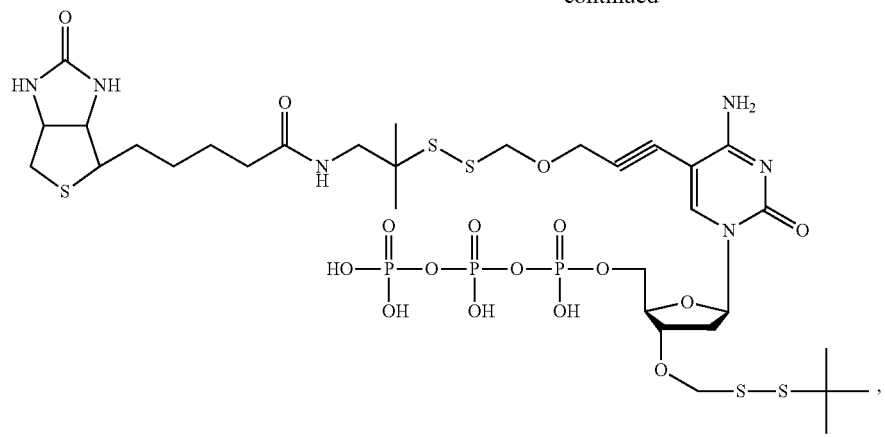
3'-O-t-butyl-SS-dCTP-SS-Biotin
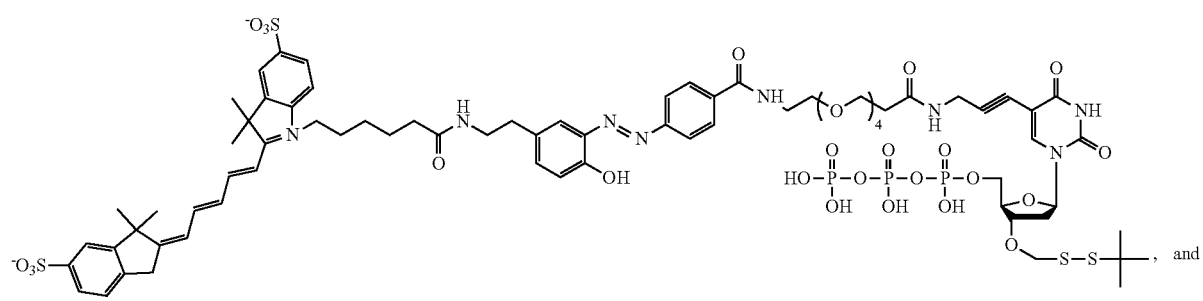
3'-O-t-butyl-SS-dTTP-PEG₄-Azo-Cy5
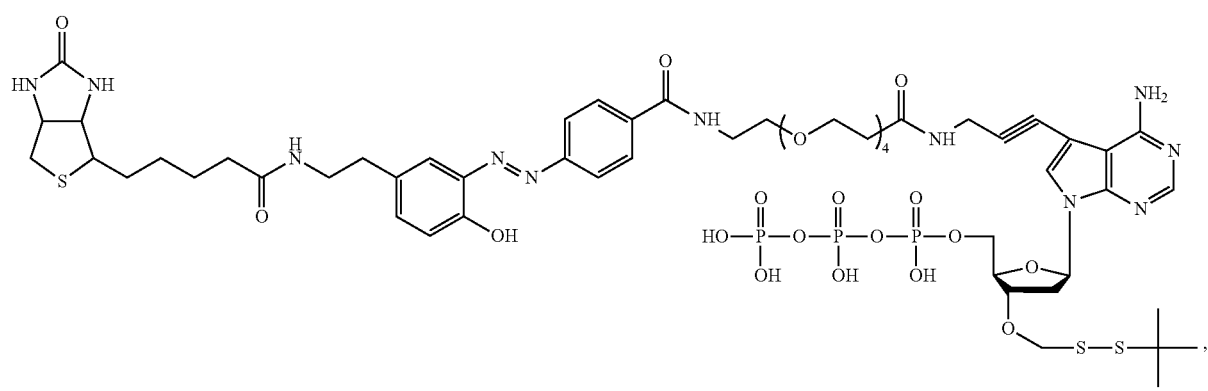
3'-O-t-butyl-SS-dATP-PEG₄-Azo-Biotin and the fluorescent labeled anchor binding molecule is

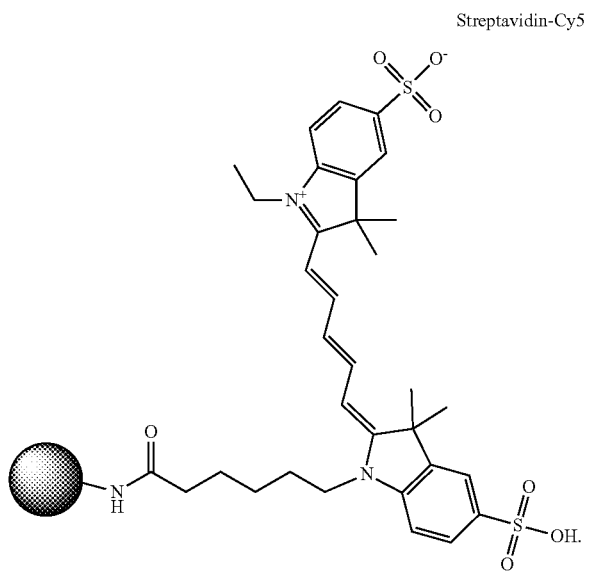 [SMILES: CC[N+]1=C(/C=C/C=C/C=C2/N(CCCCCC(=O)NC)c3ccc(S(=O)(=O)O)cc3C2(C)C)C(C)(C)c2cc(S(=O)(=O)[O-])ccc21]

Streptavidin-Cy5

16. A method of sequencing nucleic acid comprising:
a) providing at least one nucleic acid template hybridized to a primer;
b) extending the primer hybridized to said nucleic acid template with a polymerase, and a set of nucleotide analogues selected from the group consisting of:
   i) a set of fluorescently labeled nucleotide analogues, wherein said fluorescently labeled nucleotide analogues have a fluorescent label linked to the base via a cleavable linker and a blocking group on the 3'-hydroxyl position, wherein different fluorescently labeled nucleotide analogues in the set may have different fluorescent labels and different cleavable linkers;
   ii) a set of anchor labeled nucleotide analogues, wherein said anchor labeled nucleotide analogues have an anchor attached to the base via a cleavable linker and a blocking group on the 3'-hydroxyl position, wherein different anchor labeled nucleotide analogues in the set may have different anchors and different cleavable linkers; and
   iii) a set comprising a combination of both fluorescently and anchor labeled nucleotide analogues, wherein said fluorescently or anchor labeled nucleotide analogues have the fluorescent or anchor label linked to the base via a cleavable linker and a blocking group on the 3'-hydroxyl position, wherein different nucleotide analogues in the set may have different fluorescent labels, anchors, and/or cleavable linkers;
c) extending any unextended primer with another set of nucleotide analogues having a blocking group on the 3'-hydroxyl position without any base modifications, and if the set of nucleotide analogues in step b) has one or more fluorescently labeled nucleotide analogues, identifying one or more fluorescence signals due to incorporation of one or more fluorescently labeled nucleotide analogues;
d) if the set of nucleotide analogues in step b) comprises anchor labeled nucleotide analogues:
   (i) labeling the anchor labeled nucleotide analogues with one or more corresponding fluorescently or quantum dot labeled anchor binding molecules;
   (ii) identifying newly generated fluorescence signals to thereby partially or completely identify the incorporated nucleotide analogues due to the labeling carried out in step d) (i); and
   (iii) if not all of the anchor labeled nucleotide analogues in step a) are labeled in step d) (i), repeating steps d) (i) and d) (ii);
e) cleaving one or more of the fluorescent labels from one or more of the fluorescently labeled nucleotide analogues in step b) or one or more of the fluorescently or quantum dot labeled anchor binding molecules in step d) (i) with a specific cleavable agent that cleaves one type of the cleavable linkers, wherein the specific cleavable agent does not cleave the blocking group on the 3'-hydroxyl position of the nucleotide analogues;
f) identifying loss of fluorescence signals due to the cleavage carried out in step e) to partially or completely identify the incorporated nucleotide analogues;
g) if not all of the fluorescent labels from fluorescently labeled nucleotide analogues in step b) or the fluorescently or quantum dot labeled anchor binding molecules from step d) (i) are cleaved, repeating steps e) and f) with a different cleavable agent;
h) determining the specific nucleotide analogue incorporated by comparing the results obtained in steps c, d) (ii) and f);
i) cleaving any remaining fluorescent labels or anchors from the extended primer, at the same time cleaving the blocking group on the 3'-hydroxyl position of the incorporated nucleotide analogue to restore a 3'-hydroxyl group; and
j) iteratively carrying out steps a) to i) to obtain the sequence of the nucleic acid template,
thereby sequencing the nucleic acid; wherein the set of nucleotide analogues in step b) ii) comprises four nucleotide analogues; wherein the first nucleotide analogue has a first type of anchor moiety attached to the base via a cleavable linker, the second nucleotide analogue has a second type of anchor moiety attached to the base via the cleavable linker, the third nucleotide analogue has a first mixture of the first type and the second type of anchor moieties attached to the base via the cleavable linker, and the fourth nucleotide analogue has a second mixture of the first type and the second type of anchor moieties attached to the base via the cleavable linker; wherein the ratio between the first and the second type anchor moiety in the first mixture is different from the ratio in the second mixture.

17. The method of claim 16, wherein
(a) the ratio between the first and the second type anchor moiety in the first mixture is 1:1; and/or the ratio between the first and the second type anchor moiety in the second mixture is 2:1;
(b) the first and second type of anchor moieties comprise biotin, TCO, DBCO or tetrazine;
(c) the cleavable linker comprises an SS (DTM), an azo, an SS-azo, an allyl, a 2-nitrobenzyl, an azidomethyl, or azidomethyl derivative;
(d) the specific cleaving agents in step e) comprises THP, sodium dithionite, Pd(0); or UV light; and/or
(e) the fluorescently or quantum dot labeled anchor binding molecules are labeled with a fluorescent organic dye or a fluorescent transfer dye, wherein the fluorescent organic dye is selected from a group consisting of fluorescein, rhodamine, cyanine, ATTO or Dyomic dyes, wherein the fluorescent transfer dye consists of a donor dye and a acceptor dye, wherein the donor dye is fluorescein, CyA or Cy3 and the acceptor dye is Rhodamine 110, R6G, TAMRA, ROX, Cy5, ATTO 647N or Alexa 647.

18. The method of claim 17, wherein
(a) the first and second type of anchor moieties are biotin and TCO;
(b) the cleavable linker is an SS (DTM) linker;
(c) the specific cleaving agent in step e) is THP; and/or
(d) two quantum dot labeled anchor binding molecules are used in step d) (i), wherein one quantum dot labeled anchor binding molecule is labeled with streptavidin and another is labeled with tetrazine.

19. The method of claim 18, wherein the set of nucleotide analogues in step b) comprises

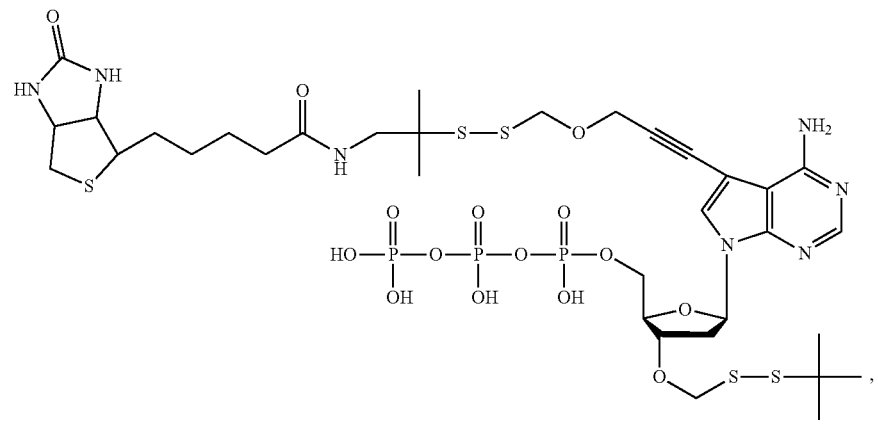

3'-O-SS-dATP-7-SS-Biotin

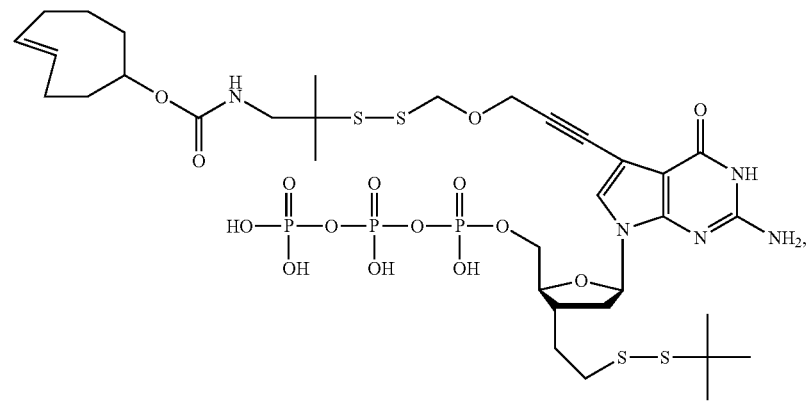

3'-O-SS-dGTP-7-SS-TCO

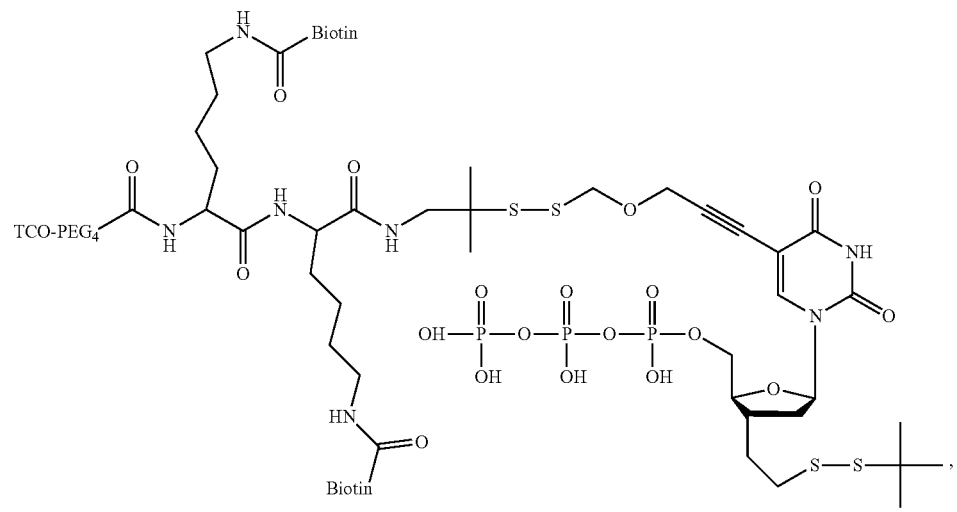

3'-O-SS-dTTP-5-SS-Biotin-Biotin-TCO

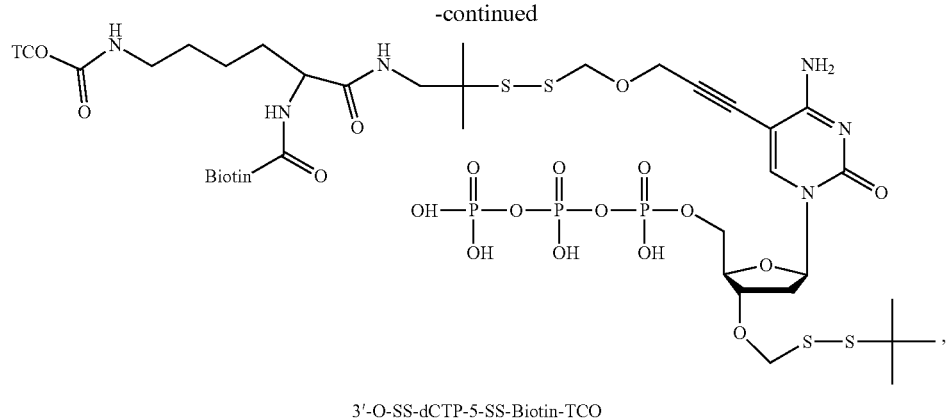

3'-O-SS-dCTP-5-SS-Biotin-TCO and wherein the fluorescent labeled anchor binding molecules are

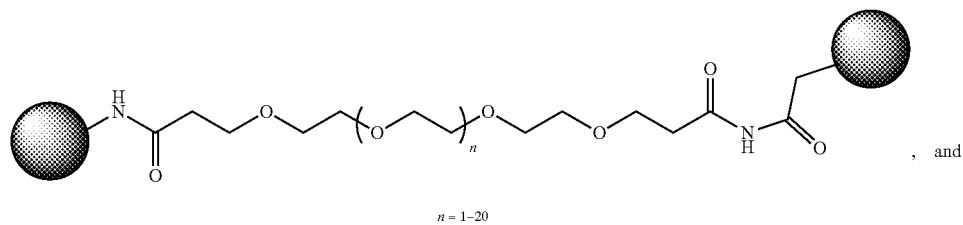

Streptavidin-PEG Quantum Dot 1 (Qdot 525)

$n = 1–20$

, and

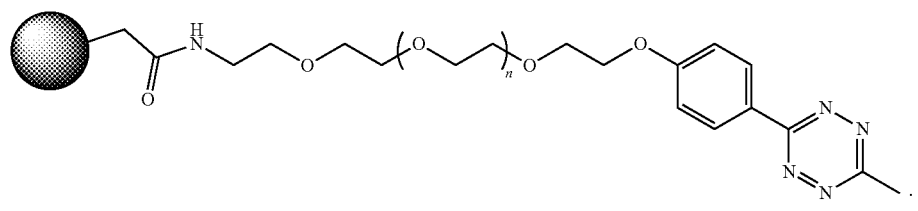

Tetrazine-PEG Quantum Dot 2 (Qdot 605)

$n = 1–20$

20. The method of claim 3, wherein:
a) the anchor or the anchor clusters comprise a donor dye or an acceptor dye,
b) the fluorescently or quantum dot labeled anchor binding molecules in step d) (i) comprise a donor dye which corresponds to an acceptor dye on the anchor or anchor clusters, or comprise an acceptor dye which corresponds to the donor dye on the anchor or anchor clusters, and/or
c) the labeling of the anchor labeled nucleotide analogues having anchor or anchor clusters with the fluorescently or quantum dot labeled anchor binding molecules results in energy transfer from a donor dye on the anchor or anchor clusters to a corresponding acceptor dye on the fluorescently or quantum dot labeled anchor binding molecules, or a donor dye on the fluorescently or quantum dot labeled anchor binding molecules to a corresponding acceptor dye on the anchor or anchor clusters, wherein the donor dye is the quantum dot.

21. The method of claim 7, wherein:
a) the first and second type of cleavable linkers comprises an SS (DTM), an azo, an SS-azo, an allyl, a 2-nitrobenzyl, an azidomethyl, or azidomethyl derivative;
b) the specific cleaving agents in step e) comprises THP, sodium dithionite, Pd(0); or UV light; and/or
c) the fluorescently or quantum dot labeled anchor binding molecules are labeled with a fluorescent organic dye or a fluorescent transfer dye, wherein the fluorescent organic dye is selected from a group consisting of fluorescein, rhodamine, cyanine, ATTO or Dyomic dyes, wherein the fluorescent transfer dye consists of a donor dye and a acceptor dye, wherein the donor dye is fluorescein, CyA or Cy3 and the acceptor dye is Rhodamine 110, R6G, TAMRA, ROX, Cy5, ATTO 647N or Alexa 647.

* * * * *